US012774286B2

(12) United States Patent
Kim et al.

(10) Patent No.: US 12,774,286 B2
(45) Date of Patent: Oct. 27, 2026

(54) COMPOUND AND ORGANIC LIGHT EMITTING DEVICE COMPRISING THE SAME

(71) Applicant: LG CHEM, LTD., Seoul (KR)

(72) Inventors: Minjun Kim, Daejeon (KR); Dong Hoon Lee, Daejeon (KR); Sang Duk Suh, Daejeon (KR); Young Seok Kim, Daejeon (KR); Kyung Seok Jeong, Daejeon (KR); Da Jung Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1101 days.

(21) Appl. No.: 17/801,611

(22) PCT Filed: Apr. 14, 2021

(86) PCT No.: PCT/KR2021/004694
§ 371 (c)(1),
(2) Date: Aug. 23, 2022

(87) PCT Pub. No.: WO2021/210911
PCT Pub. Date: Oct. 21, 2021

(65) Prior Publication Data

US 2023/0174544 A1 Jun. 8, 2023

(30) Foreign Application Priority Data

Apr. 14, 2020 (KR) ........................ 10-2020-0045516
Apr. 13, 2021 (KR) ........................ 10-2021-0048060

(51) Int. Cl.
*C07D 491/048* (2006.01)
*H10K 50/11* (2023.01)
*H10K 85/60* (2023.01)

(52) U.S. Cl.
CPC ......... *C07D 491/048* (2013.01); *H10K 50/11* (2023.02); *H10K 85/615* (2023.02); (Continued)

(58) Field of Classification Search
None
See application file for complete search history.

(56) References Cited

U.S. PATENT DOCUMENTS

2004/0251816 A1 12/2004 Leo et al.
2015/0171336 A1 6/2015 Park et al.
(Continued)

FOREIGN PATENT DOCUMENTS

CN 107253954 10/2017
CN 109912610 A 6/2019
(Continued)

OTHER PUBLICATIONS

Machine English translation of Cao et al. (CN 109912610 A). Sep. 9, 2025.*

*Primary Examiner* — Jay Yang
(74) *Attorney, Agent, or Firm* — Bryan Cave Leighton Paisner LLP

(57) ABSTRACT

A compound of Chemical Formula 1:

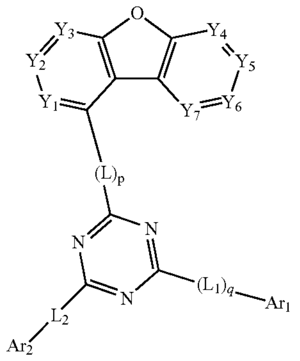

$Y_1$ to $Y_5$ are independently N, C—H, C-D, or C-L'-R; L' is a bond or a substituted or unsubstituted $C_{6-60}$ arylene; R is a substituted or unsubstituted $C_{6-60}$ aryl or $C_{2-60}$ heteroaryl containing one or more of N, O and S, provided that R is not 9-phenylcarbazolyl; $Y_6$ and $Y_7$ are independently N, C—H, or C-D; at least one of $Y_1$ to $Y_7$ is N; L is a bond, or a substituted or unsubstituted $C_{6-60}$ arylene or $C_{2-60}$ heteroarylene containing one or
(Continued)

more of N, O and S; $L_1$ and $L_2$ are independently a bond or a substituted or unsubstituted $C_{6-60}$ arylene; $Ar_1$ and $Ar_2$ are independently a substituted or unsubstituted $C_{6-60}$ aryl or $C_{2-60}$ heteroaryl containing any one or more of N, O and S, and p and q are independently 0 to 2, and an organic light-emitting device including the same.

11 Claims, 1 Drawing Sheet

(52) U.S. Cl.
CPC ......... *H10K 85/622* (2023.02); *H10K 85/654* (2023.02); *H10K 85/657* (2023.02); *H10K 85/6572* (2023.02); *H10K 85/6574* (2023.02); *H10K 85/6576* (2023.02)

(56) References Cited

U.S. PATENT DOCUMENTS

| | | | |
|---|---|---|---|
| 2015/0207082 | A1 | 7/2015 | Dyatkin et al. |
| 2015/0349268 | A1 | 12/2015 | Zeng et al. |
| 2016/0329502 | A1 | 11/2016 | Dyatkin et al. |
| 2017/0309829 | A1 | 10/2017 | Jung et al. |
| 2018/0319776 | A1 | 11/2018 | Cha et al. |
| 2019/0248804 | A1 | 8/2019 | Wolleb et al. |
| 2019/0337397 | A1 | 11/2019 | Park |
| 2020/0020865 | A1 | 1/2020 | Otsu et al. |
| 2021/0143337 | A1 | 5/2021 | Kim et al. |

FOREIGN PATENT DOCUMENTS

| | | | |
|---|---|---|---|
| JP | 2008-074939 | | 4/2008 |
| JP | 2019-110102 | | 7/2019 |
| KR | 10-2000-0051826 | | 8/2000 |
| KR | 10-2013-0091888 | | 8/2013 |
| KR | 10-2014-0079306 | | 6/2014 |
| KR | 10-2014-0145355 | | 12/2014 |
| KR | 10-2017-0056431 | | 5/2017 |
| KR | 10-2019-0076375 | | 7/2019 |
| KR | 10-2019-0076376 | | 7/2019 |
| KR | 10-2019-0127582 | | 11/2019 |
| KR | 10-2020-0015495 | | 2/2020 |
| WO | 2003-012890 | A2 | 2/2003 |
| WO | 2016-208865 | | 12/2016 |
| WO | 2017-039067 | | 3/2017 |
| WO | 2018-043761 | | 3/2018 |
| | 107253954 | | |
| WO | 2018-079459 | | 5/2018 |
| WO | 2018-230969 | | 12/2018 |
| WO | 2019-194209 | | 10/2019 |
| WO | 2019-212287 | A1 | 11/2019 |

* cited by examiner

【FIG. 1】
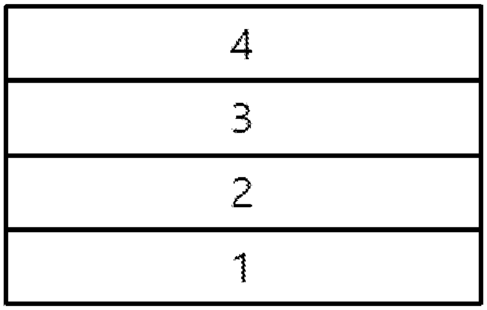
【FIG. 2】
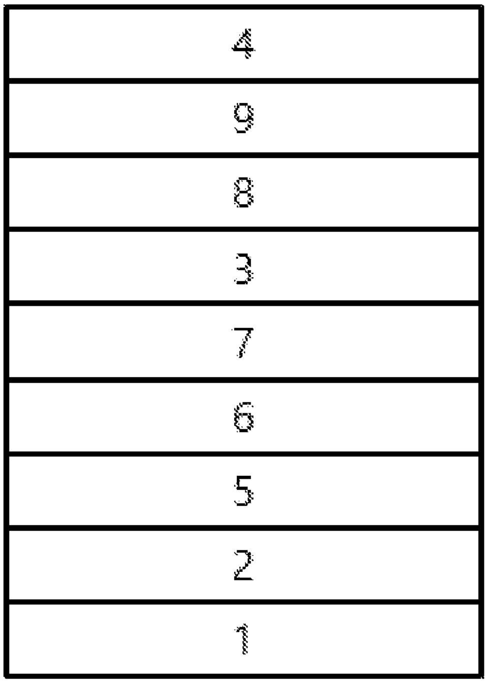

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2021/004694 filed on Apr. 14, 2021, which claims the benefit of Korean Patent Application No. 10-2020-0045516 filed on Apr. 14, 2020 and Korean Patent Application No. 10-2021-0048060 filed on Apr. 13, 2021 in the Korean Intellectual Property Office, the disclosures of which are incorporated herein by reference in their entirety.

TECHNICAL FIELD

The present disclosure relates to a novel compound and an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuous need to develop a new material for the organic material used in the organic light emitting device as described above.

PRIOR ART LITERATURE

Patent Literature (Patent Literature 0001) Korean Unexamined Patent Publication No. 10-2000-0051826

BRIEF DESCRIPTION

Technical Problem

It is an object of the present disclosure to provide a novel compound and an organic light emitting device comprising the same.

Technical Solution

According to an aspect of the present disclosure, provided is a compound of Chemical Formula 1:

[Chemical Formula 1]

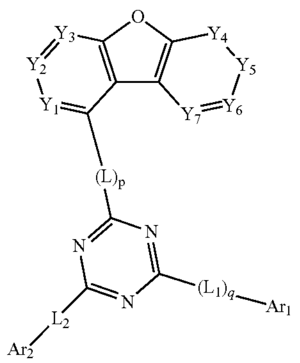

wherein, in Chemical Formula 1:

$Y_1$ to $Y_5$ are each independently N, C—H, C-D, or C-L'-R;

L' is a single bond or a substituted or unsubstituted $C_{6-60}$ arylene;

R is a substituted or unsubstituted $C_{6-60}$ aryl or a substituted or unsubstituted $C_{2-60}$ heteroaryl containing any one or more heteroatoms selected from the group consisting of N, O and S, provided that R is not 9-phenylcarbazolyl;

$Y_6$ and $Y_7$ are each independently N, C—H, or C-D;

at least one of $Y_1$ to $Y_7$ is N;

L is a single bond, a substituted or unsubstituted $C_{6-60}$ arylene, or a substituted or unsubstituted $C_{2-60}$ heteroarylene containing any one or more heteroatoms selected from the group consisting of N, O and S;

$L_1$ and $L_2$ are each independently a single bond or a substituted or unsubstituted $C_{6-60}$ arylene;

$Ar_1$ and $Ar_2$ are each independently a substituted or unsubstituted $C_{6-60}$ aryl or a substituted or unsubstituted $C_{2-60}$ heteroaryl containing any one or more heteroatoms selected from the group consisting of N, O and S; and p and q are each independently an integer of 0 to 2.

According to another aspect of the present disclosure, provided is an organic light emitting device comprising: a first electrode; a second electrode that is provided opposite to the first electrode; and a light emitting layer that is provided between the first electrode and the second electrode, wherein the light emitting layer comprises the compound of Chemical Formula 1.

Advantageous Effects

The above-mentioned compound of Chemical Formula 1 is used as a material of an organic material layer in an organic light emitting device, and thus, can improve the efficiency, achieve low driving voltage and/or improve lifetime characteristics in the organic light emitting device.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, an electron blocking layer 7, a light emitting layer 3, a hole blocking layer 8, an electron injection and transport layer 9, and a cathode 4.

DETAILED DESCRIPTION

Hereinafter, embodiments of the present disclosure will be described in more detail to facilitate understanding of the invention.

Definition of Terms

As used herein, the notation

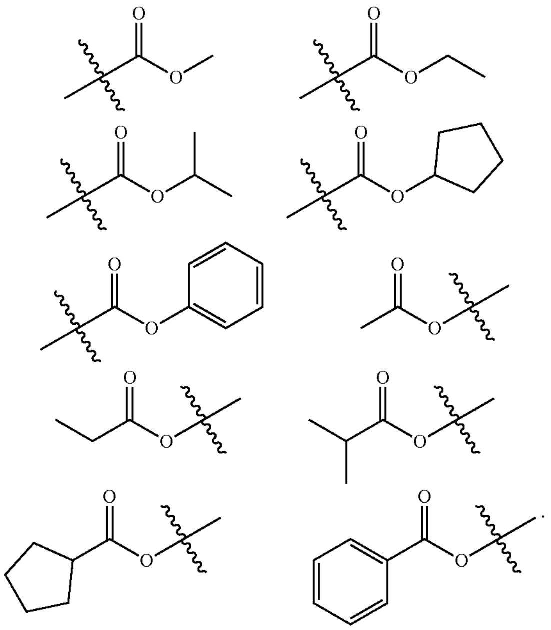

and  mean a bond linked to another substituent group, and "D" means deuterium.

As used herein, the term "substituted or unsubstituted" means being unsubstituted or substituted with one or more substituents selected from the group consisting of deuterium, a halogen group, a cyano group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heteroaryl containing at least one of N, O and S atoms, or being unsubstituted or substituted with a substituent to which two or more substituents of the above-exemplified substituents are linked. For example, "a substituent in which two or more substituents are linked" can be a biphenyl group. Namely, a biphenyl group can be an aryl group, or it can also be interpreted as a substituent in which two phenyl groups are linked.

In the present disclosure, the carbon number of a carbonyl group is not particularly limited, but is preferably 1 to 40.

Specifically, the carbonyl group can be a group having the following structural formulas, but is not limited thereto:

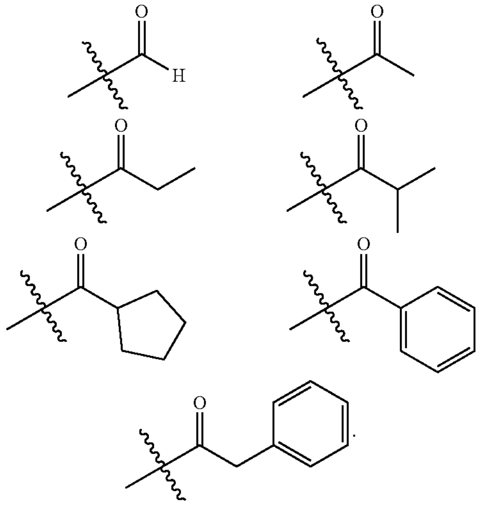

In the present disclosure, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a group having the following structural formulas, but is not limited thereto:

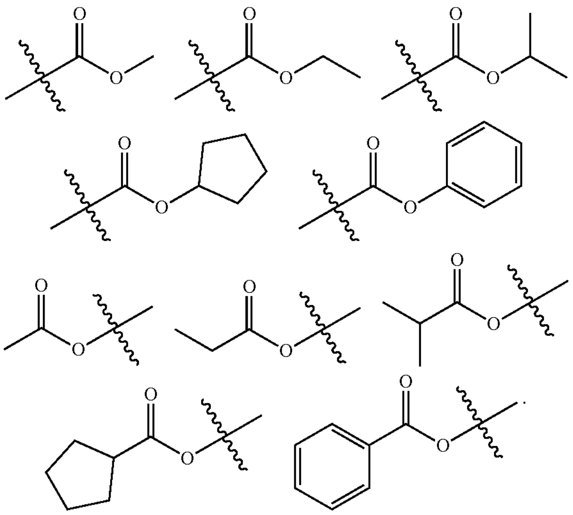

In the present disclosure, the carbon number of an imide group is not particularly limited, but is preferably 1 to 25. Specifically, the imide group can be a group having the following structural formulas, but is not limited thereto:

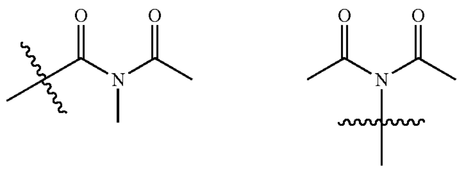

-continued

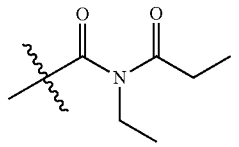

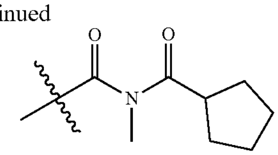

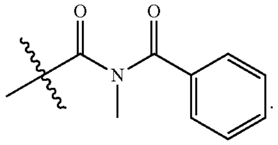

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present disclosure, a boron group specifically includes a dimethylboron group, a triethylboron group, a t-butylmethylboron group, a triphenylboron group, and a phenylboron group, but is not limited thereto.

In the present disclosure, examples of a halogen group include fluorine, chlorine, bromine, or iodine.

In the present disclosure, the alkyl group can be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methyl-hexyl, and the like, but are not limited thereto.

In the present disclosure, the alkenyl group can be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it can be a monocyclic aryl group or a polycyclic aryl group. According to one embodiment, the carbon number of the aryl group is 6 to 30. According to one embodiment, the carbon number of the aryl group is 6 to 20. The aryl group can be a phenyl group, a biphenylyl group, a terphenylyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, a fluorenyl group, or the like, but is not limited thereto.

In the present disclosure, the fluorenyl group can be substituted, and two substituents can be linked with each other to form a spiro structure. In the case where the fluorenyl group is substituted,

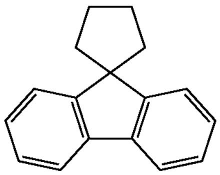

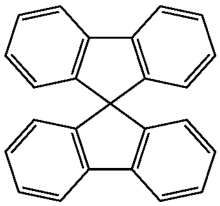

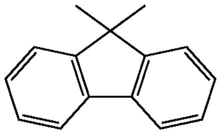

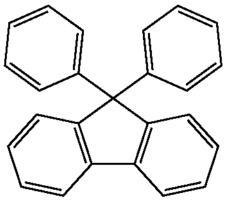

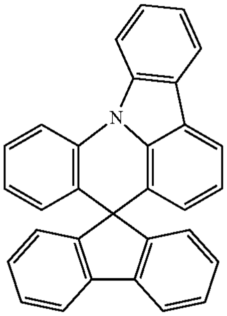

and the like can be formed.

In the present disclosure, a heteroaryl is a heteroaryl containing at least one of O, N, Si and S as a heteroatom, and the carbon number thereof is not particularly limited, but is preferably 2 to 60. Examples of the heteroaryl include xanthene, thioxanthene, a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group, the arylamine group and the arylsilyl group is the same as the above-mentioned examples of the aryl group. In the present disclosure, the alkyl group in the aralkyl group, the alkylaryl group and the alkylamine group is the same as the above-mentioned examples of the alkyl group. In the present disclosure, the heteroaryl in the heteroarylamine can be applied to the above-mentioned description of the heteroaryl. In the present disclosure, the alkenyl group in the aralkenyl group is the same as the above-mentioned examples of the alkenyl group. In the present disclosure, the above-mentioned description of the aryl group can be applied except that the arylene is a divalent group. In the present disclosure, the above-mentioned description of the heteroaryl can be applied except that the heteroarylene is a divalent group. In the present disclosure, the above-mentioned description of the aryl group or cycloalkyl group can be applied except that the hydrocarbon ring is not a monovalent group but formed by combining two substituent groups. In the present disclosure, the aforementioned description of the heteroaryl can be applied, except that the heterocyclic ring is not a monovalent group but formed by combining two substituent groups.

In the present disclosure, the term "deuterated or substituted with deuterium" means that at least one usable hydrogen in each chemical formula or substituent group is replaced by deuterium. In one example, being at least 10% deuterated in each formula means that at least 10% of the usable hydrogen is replaced by deuterium. In one example, each chemical formula can be at least 20%, at least 30%, at least 40%, at least 50%, at least 60%, at least 70%, at least 80%, at least 90%, or 100% deuterated.

(Compound)

The present disclosure provides the compound of Chemical Formula 1.

The compound of Chemical Formula 1 has a core structure in which a triazinyl group is substituted on the 1$^{st}$ carbon in dibenzofuran, and at least one of the 2nd carbon, 3rd carbon, 4th carbon, 6th carbon, 7th carbon, 8th carbon and 9th carbon is substituted with a "nitrogen atom". In particular, the compound has a feature that it has no substituent other than deuterium at the 8th and 9th carbon atoms of the core, and 9-phenylcarbazolyl is excluded from "R" which is a substituent that can be optionally substituted.

In this case, the structure of the 9-phenylcarbazolyl group excluded from R is as follows:

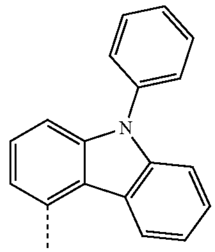

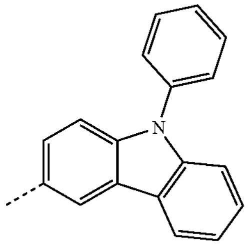

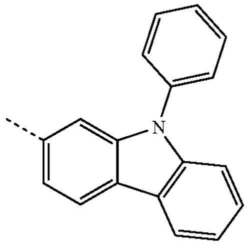

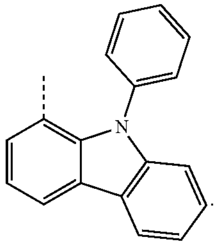

Further, the organic light emitting device employing the compound can exhibit excellent energy transfer characteristics and stability, as compared with the organic light emitting device employing a compound in which a triazinyl group is substituted at another position of the core, a compound in which $Y_6$ and $Y_7$ in Chemical Formula 1 are not C—H or C-D, that is, are substituted with a substituent other than deuterium, or a compound in which R in Chemical Formula 1 is 9-phenylcarbazolyl. Therefore, the organic light emitting device employing the compound can exhibit device characteristics in which luminous efficiency and lifetime are simultaneously improved, as compared with an organic light emitting device employing a compound having no such structure.

In Chemical Formula 1, at least one of $Y_1$ to $Y_7$, specifically, one or two of $Y_1$ to $Y_7$ can be N.

Preferably, one of $Y_1$ to $Y_7$ can be N.

Specifically, one of $Y_1$ to $Y_5$ is N, and the rest are each independently C—H, C-D, or C-L'-R, and $Y_6$ and $Y_7$ can be each independently C—H or C-D.

More specifically, one of $Y_1$ to $Y_5$ is N, and the rest are each independently C—H, or C-D, and $Y_6$ and $Y_7$ are each independently C—H or C-D; or one of $Y_1$ to $Y_5$ is N, one of the rest is C-L'-R, and the rest are each independently C—H, or C-D, and $Y_6$ and $Y_7$ can be each independently C—H or C-D.

Alternatively, $Y_1$ to $Y_5$ are each independently C—H, C-D, or C-L'-R, and one of $Y_6$ and $Y_7$ can be N, and the other can be C—H or C-D.

More specifically, $Y_1$ to $Y_5$ are each independently C—H, or C-D, one of $Y_6$ and $Y_7$ is N and the other is C—H or C-D; or one of $Y_1$ to $Y_5$ is C-L'-R, and the rest are each independently C—H or C-D, and one of $Y_6$ and $Y_7$ can be N, and the other can be C—H or C-D.

Alternatively, $Y_1$ to $Y_5$ are each independently C—H, or C-D, and one of $Y_6$ and $Y_7$ is N and the other is C—H, or C-D; or one of $Y_1$ to $Y_3$ and $Y_5$ is C-L'-R, the rest are each independently C—H, or C-D, $Y_5$ is C—H, or C-D, and one of $Y_6$ and $Y_7$ can be N, and the other can be C—H or C-D.

Further, in Chemical Formula 1, L' can be a single bond or a $C_{6-20}$ arylene that is unsubstituted or substituted with deuterium.

Specifically, L' can be a single bond, phenylene that is unsubstituted or substituted with deuterium, or naphthylene that is unsubstituted or substituted with deuterium.

For example, L' is a single bond,

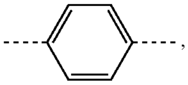

, or

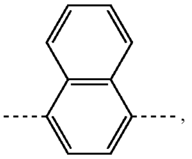

, but is not limited thereto.

Further, in Chemical Formula 1, R is a $C_{6-60}$ aryl, or a $C_{2-20}$ heteroaryl containing any one heteroatom selected from the group consisting of N, O and S, provided that R is not 9-phenylcarbazolyl, where R can be unsubstituted or substituted with one or more, for example, one or two substituents selected from the group consisting of deuterium, $C_{1-10}$ alkyl and $C_{6-20}$ aryl.

Specifically, R is any one structure selected from the group consisting of the following:

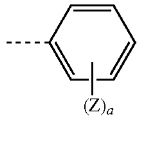

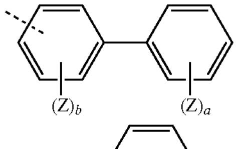

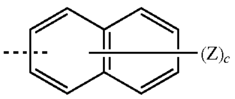

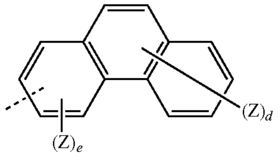

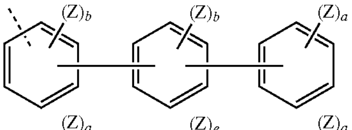

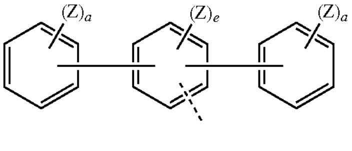

-continued

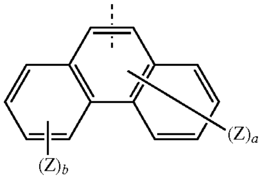

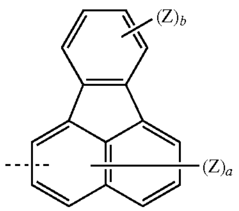

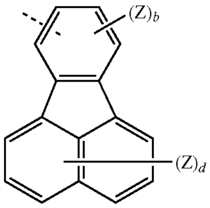

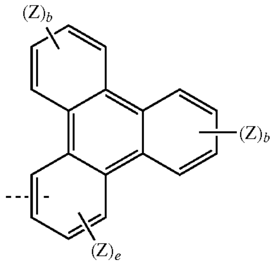

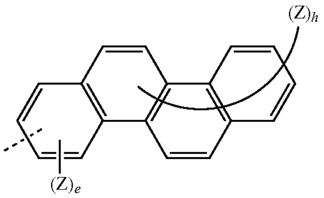

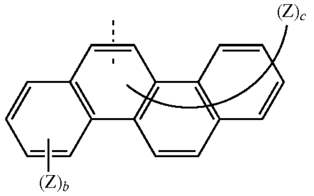

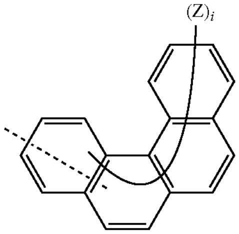

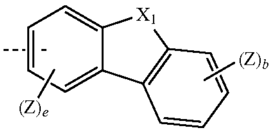

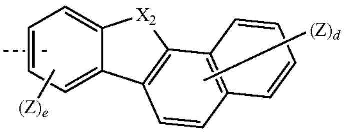

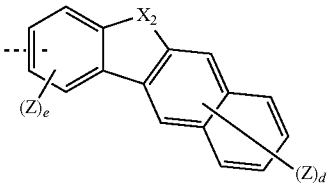

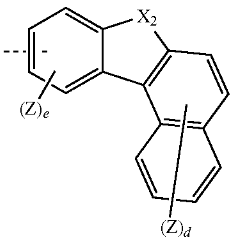

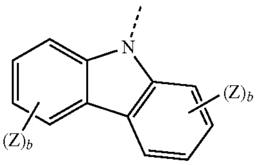

-continued

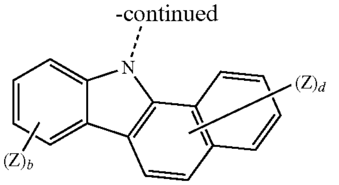

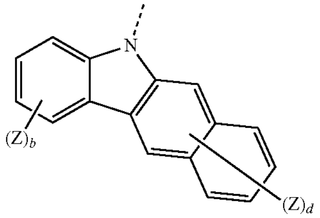

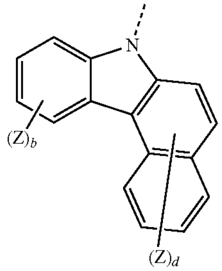

wherein:

$X_1$ is O or S;

$X_2$ is O, S, or N(phenyl);

each Z is independently deuterium (D), $C_{1-10}$ alkyl, or $C_{6-20}$ aryl;

each a is independently an integer of 0 to 5;

each b is independently an integer of 0 to 4;

each c is independently an integer of 0 to 7;

each d is independently an integer of 0 to 6;

each e is independently an integer of 0 to 3;

h is an integer of 0 to 8; and i is an integer of 0 to 11.

For example, R can be any one structure selected from the group consisting of the following, but is not limited thereto:

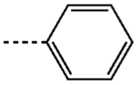

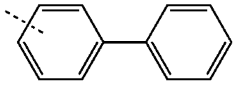

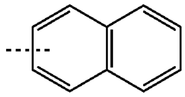

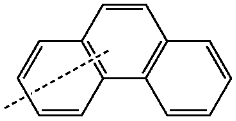

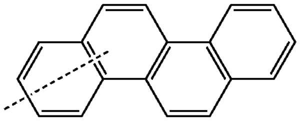

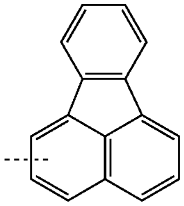

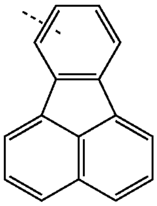

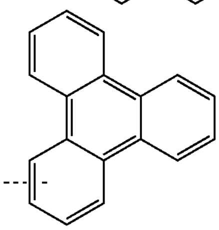

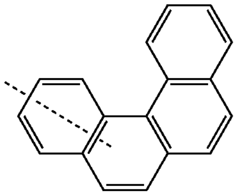

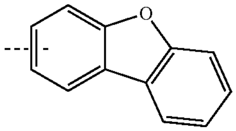

-continued

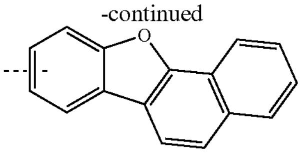

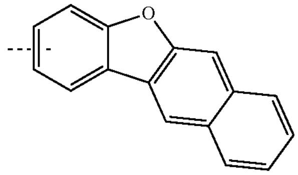

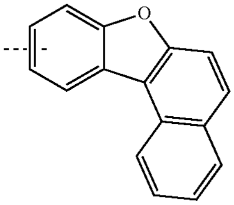

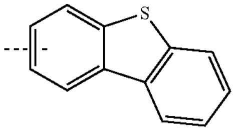

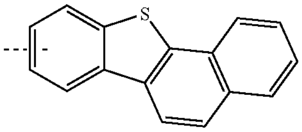

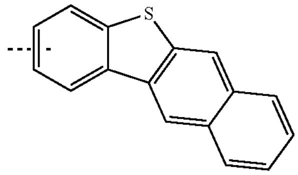

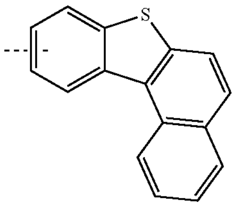

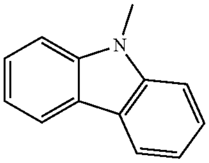

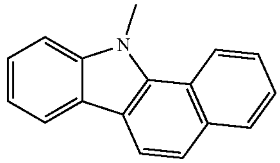

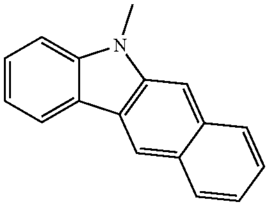

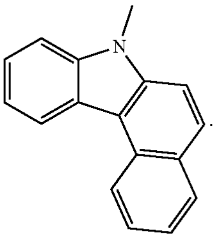

.

Further, in Chemical Formula 1, L can be a single bond or a $C_{6-20}$ arylene unsubstituted or substituted with deuterium.

Specifically, L can be a single bond, phenylene that is unsubstituted or substituted with deuterium, or naphthylene that is unsubstituted or substituted with deuterium.

More specifically, L can be a single bond or any one structure selected from the group consisting of the following:

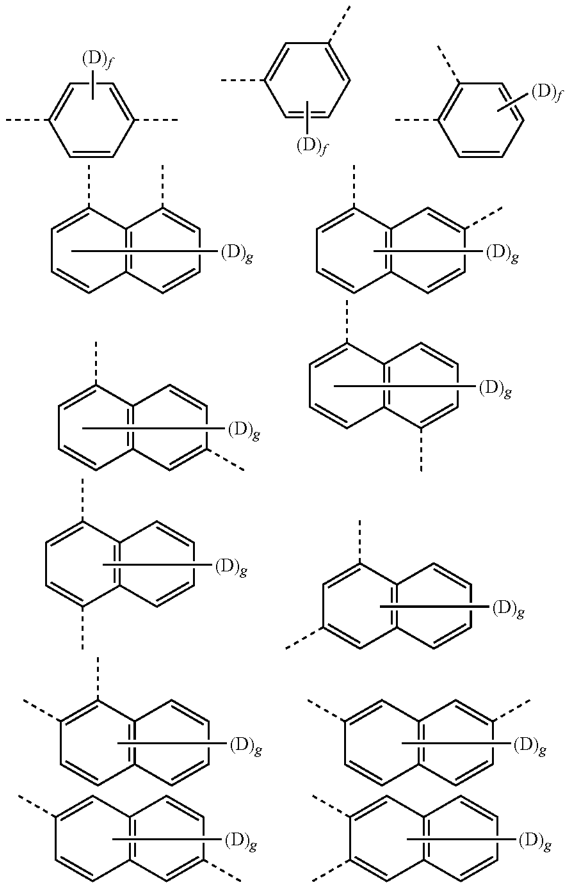

wherein:

D means deuterium;

each f is independently an integer of 0 to 4; and each g is independently an integer of 0 to 6.

For example, L can be a single bond, or any one structure selected from the group consisting of the following:

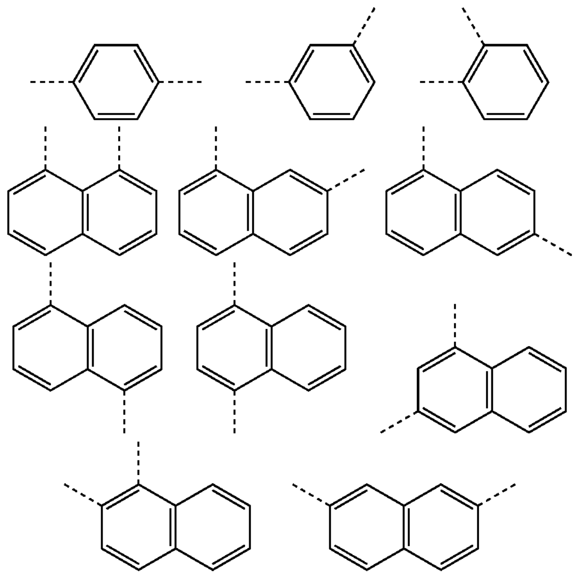

-continued

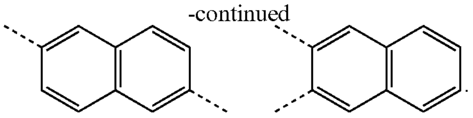

Further, in Chemical Formula 1, $L_1$ and $L_2$ can be each independently a single bond or a $C_{6-20}$ arylene unsubstituted or substituted with deuterium.

Specifically, $L_1$ and $L_2$ can be each independently a single bond, phenylene that is unsubstituted or substituted with deuterium, biphenyldiyl that is unsubstituted or substituted with deuterium, or naphthylene that is unsubstituted or substituted with deuterium.

And, one of $L_1$ and $L_2$ can be a single bond.

Further, p, which means the number of L, is 0, 1, or 2, and when p is 2, the two Ls are identical to or different from each other. And, q, which means the number of $L_1$, is 0, 1, or 2, and when q is 2, the two L is are identical to or different from each other.

In this case, p+q can be 0, 1, 2, or 3.

Further, in Chemical Formula 1, $Ar_1$ and $Ar_2$ are each independently a $C_{6-20}$ aryl or a $C_{2-20}$ heteroaryl containing one heteroatom selected from the group consisting of N, O and S, where $Ar_1$ and $Ar_2$ can be unsubstituted or substituted with one or more substituents selected from the group consisting of deuterium, a $C_{1-10}$ alkyl and a $C_{6-20}$ aryl.

Specifically, $Ar_1$ and $Ar_2$ are each independently phenyl, biphenylyl, terphenylyl, naphthyl, phenanthryl, chrysenyl, benzo[c]phenanthrenyl, fluoranthenyl, dibenzofuranyl, dibenzothiophenyl, benzonaphthofuranyl, benzonaphthothiophenyl, carbazolyl, or benzocarbazolyl, where $Ar_1$ and $Ar_2$ can be unsubstituted or substituted with one or more, for example, one or two substituents selected from the group consisting of deuterium, $C_{1-10}$ alkyl and $C_{6-20}$ aryl.

Specifically, one of $Ar_1$ and $Ar_2$ can be phenyl, biphenylyl, or naphthyl.

For example, one of $Ar_1$ and $Ar_2$ can be

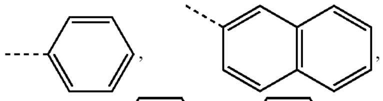

or

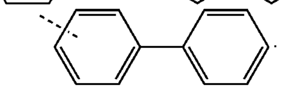

Also, in Chemical Formula 1, $Ar_1$ and $Ar_2$ can be identical to or different from each other.

When $Ar_1$ and $Ar_2$ are identical, both $Ar_1$ and $Ar_2$ can be

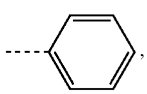

or

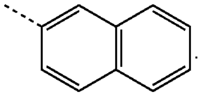

Alternatively, both $Ar_1$ and $Ar_2$ may not be

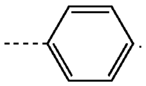

Further, in Chemical Formula 1, $L_1$ is a single bond, and $L_2$ is a single bond,

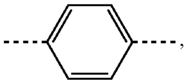, or 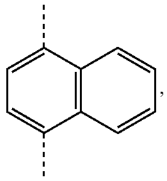, and one of $Ar_1$ and $Ar_2$ can be phenyl, naphthyl, or biphenylyl, and the rest can be phenyl, biphenylyl, terphenylyl, naphthyl, phenanthryl, chrycenyl, benzo[c]phenanthrenyl, fluoranthenyl, dibenzofuranyl, dibenzothiophenyl, benzonaphthofuranyl, benzonaphthothiophenyl, carbazolyl, or benzocarbazolyl.

Meanwhile, the compound can be any one of the following Chemical Formulas 1-1 to 1-7:

1-1

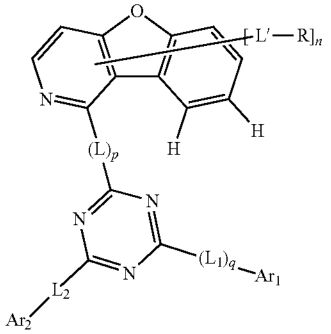

1-2

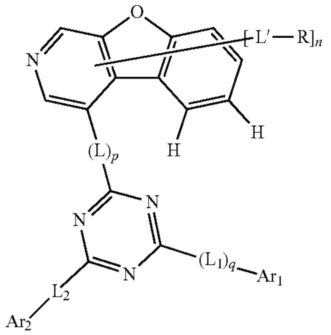

1-3

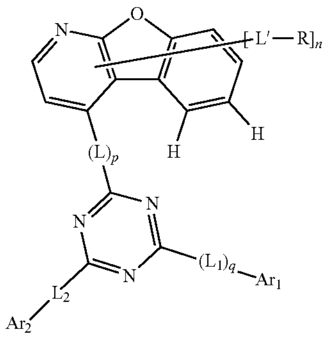

-continued 1-4

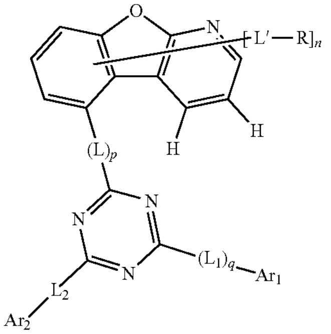

1-5

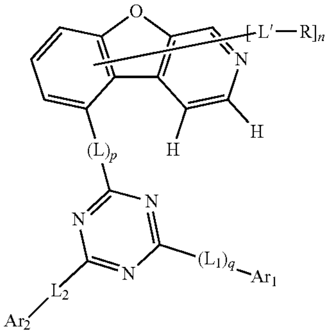

1-6

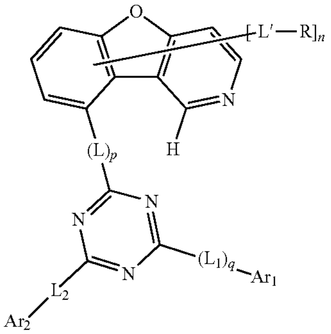

1-7

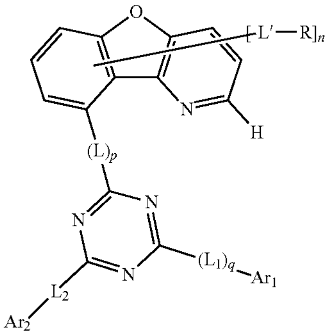

wherein, in Chemical Formulas 1-1 to 1-7:

n is 0 or 1; and

L, L', R, $L_1$, $L_2$, p, q, $Ar_1$ and $Ar_2$ are as defined in Chemical Formula 1.

At this time, in Chemical Formula 1-1, when n is 1, the bonding position of the substituent

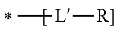

is any one of carbon at position *a, carbon at position *b, carbon at position *c, and carbon at position *d, and the notation "*" in

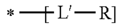

means a bonding position to any one of carbon at position *a, carbon at position *b, carbon at position *c, and carbon at position *d:

[Chemical Formula 1-1]

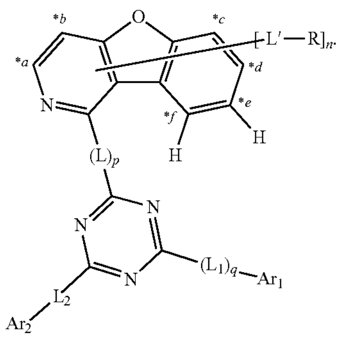

That is, in Chemical Formula 1-1, the substituent

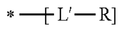

means that it can be bonded to any one of carbon at position *a, carbon at position *b, carbon at position *c, and carbon at position *d and cannot be bonded to carbon at position *e and carbon at position *f.

The bonding positions of the substituent

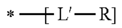

in Chemical Formulas 1-2 to 1-7 can also be understood in the same manner as in Chemical Formula 1-1.

As an example, the compound is any one compound selected from the group consisting of the following compounds:

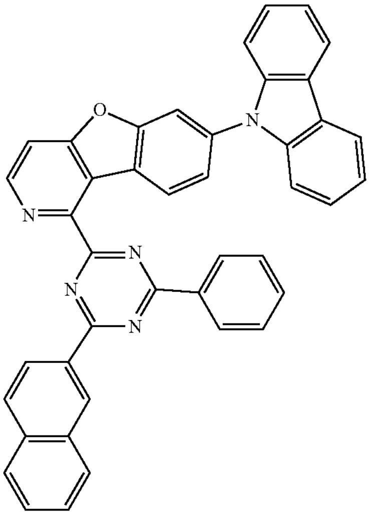

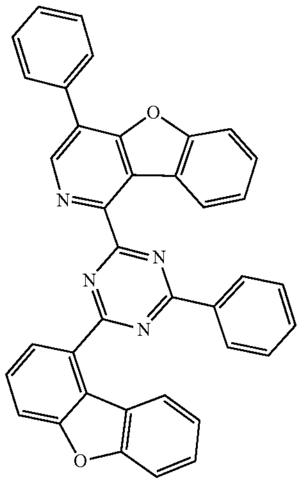

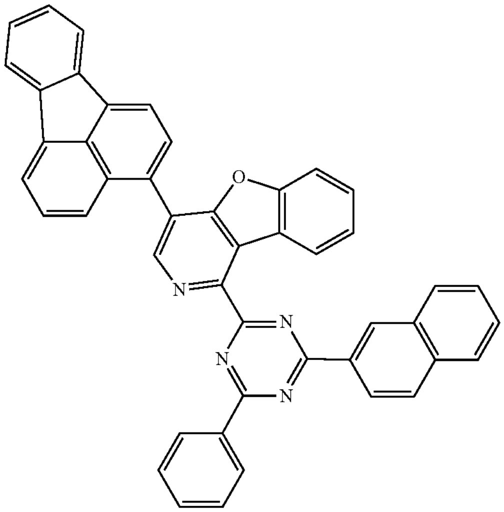

-continued
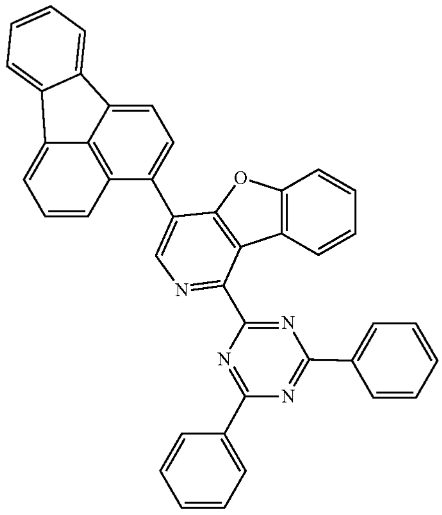
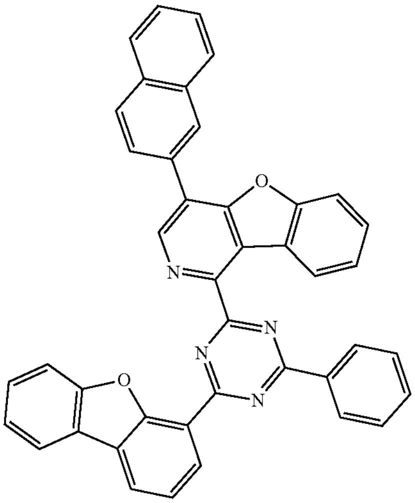
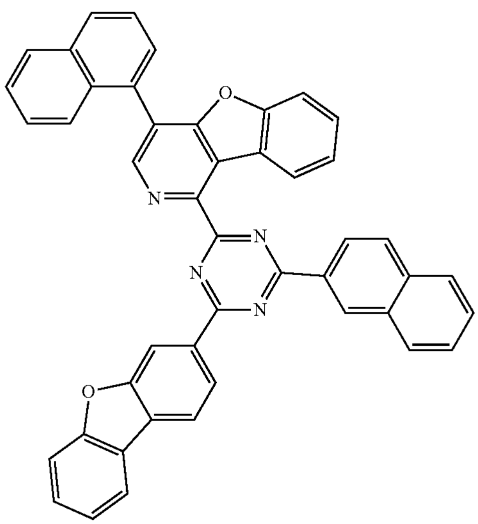
-continued
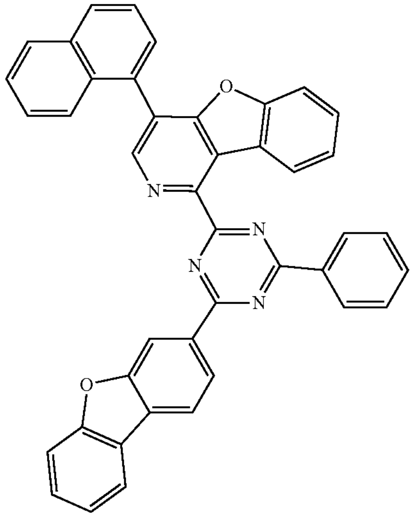
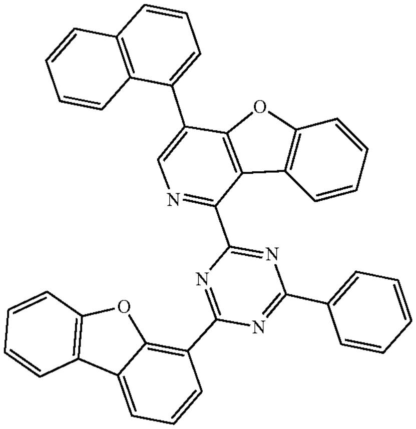
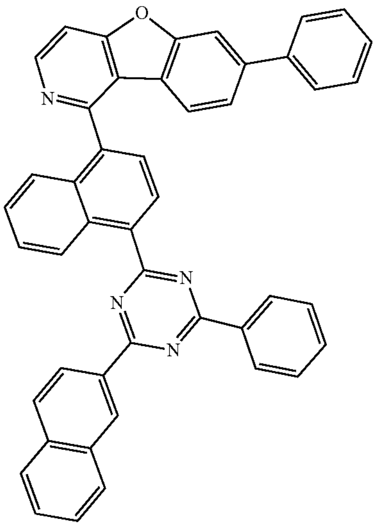

-continued
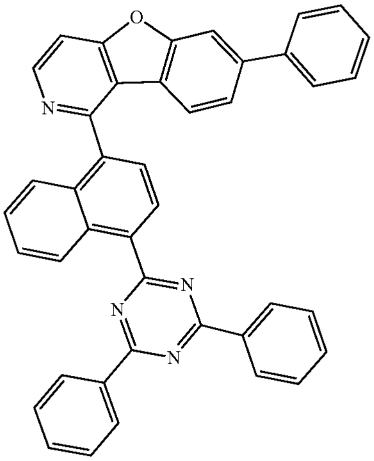
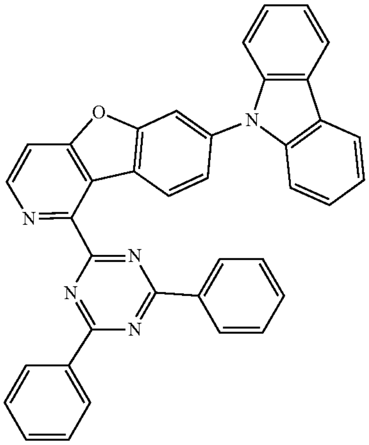
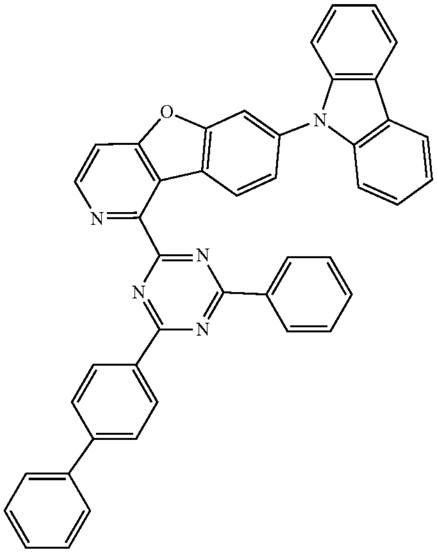
-continued
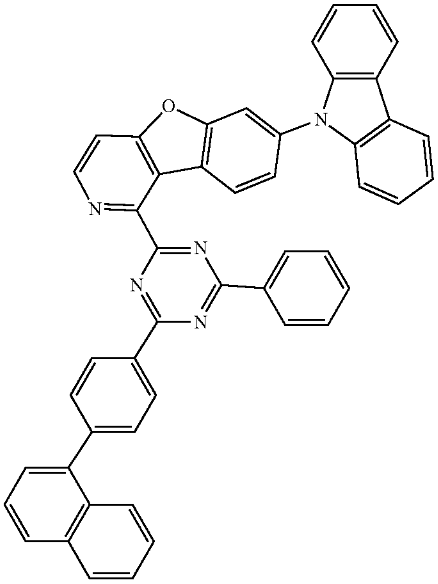
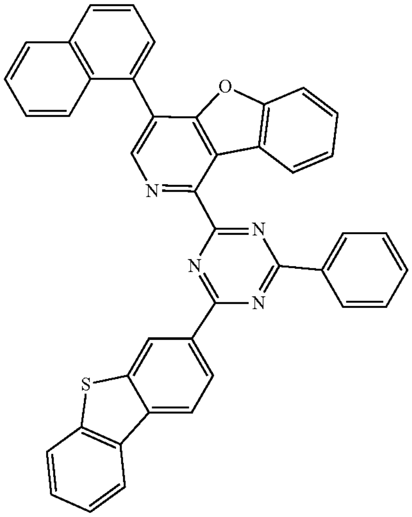
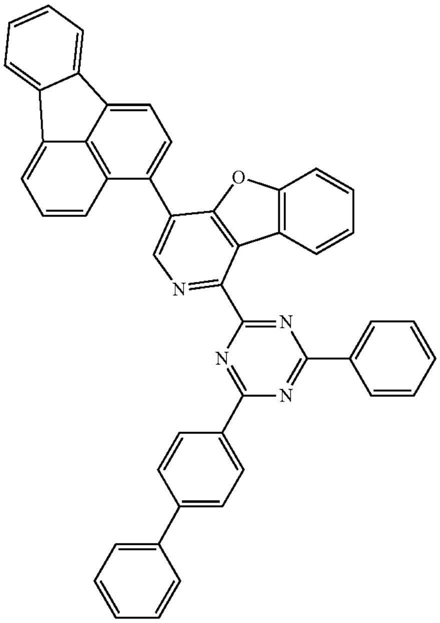

-continued
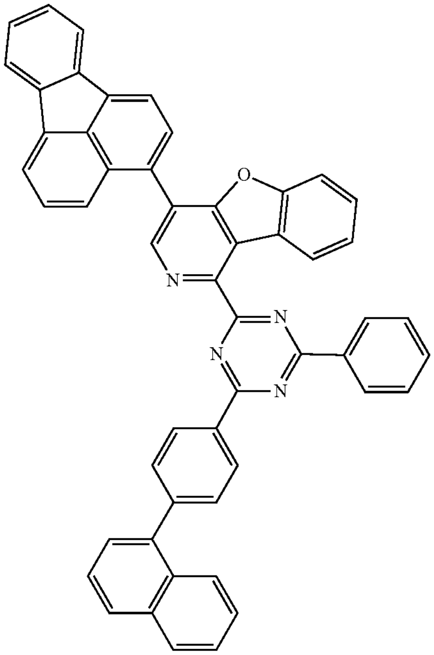
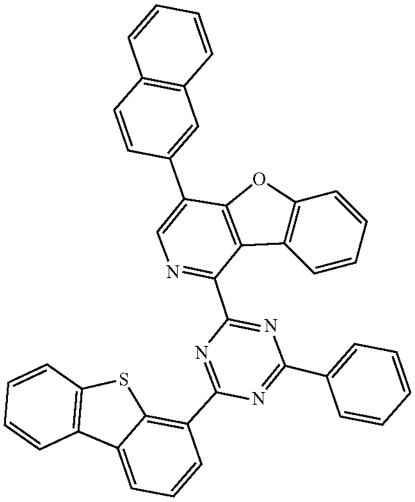
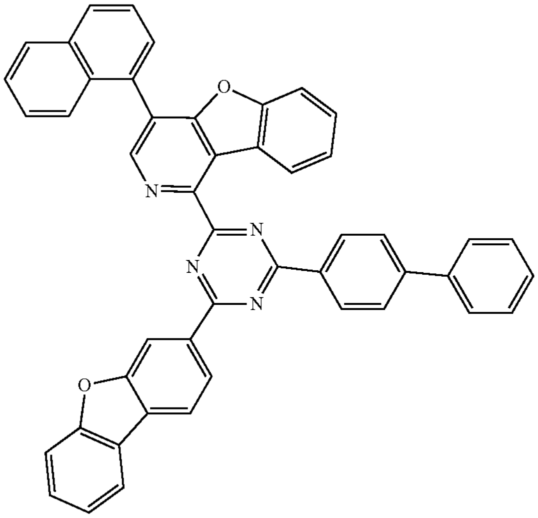
-continued
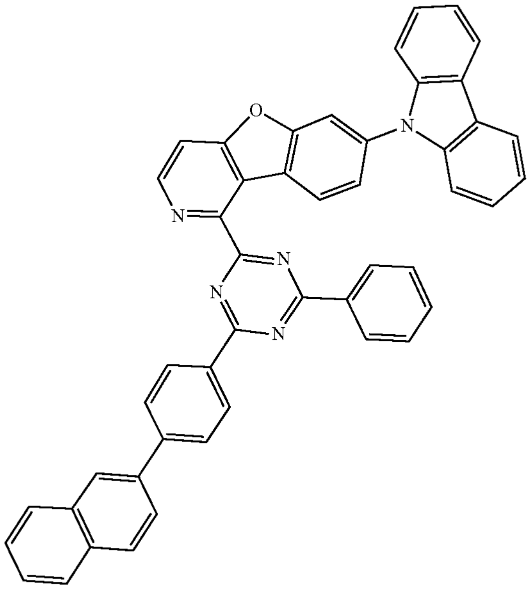
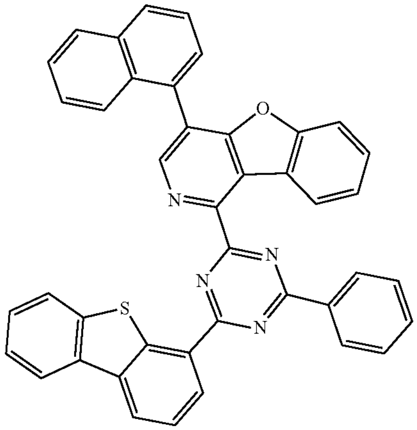
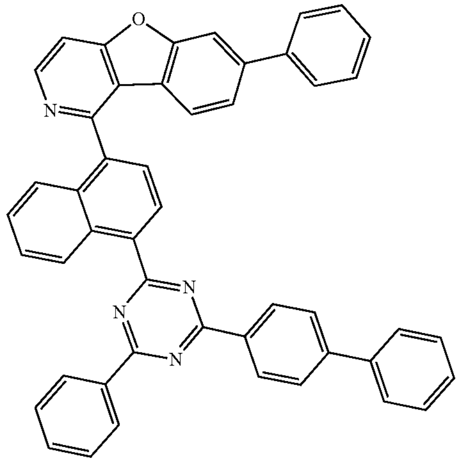

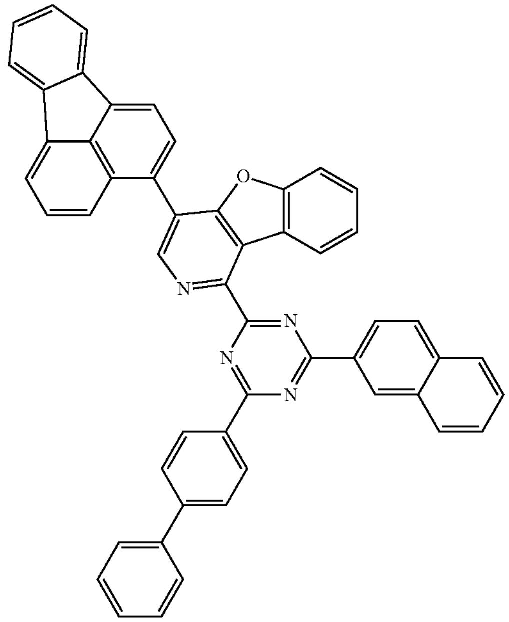
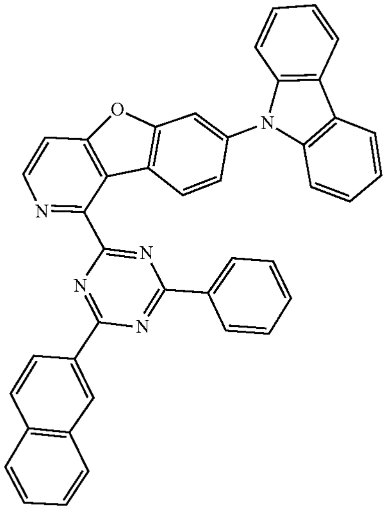
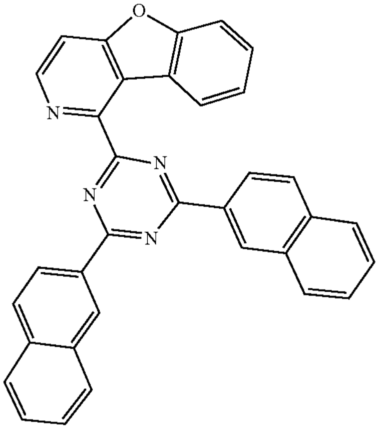
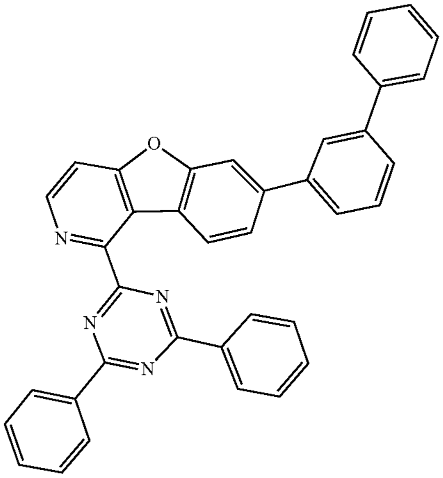
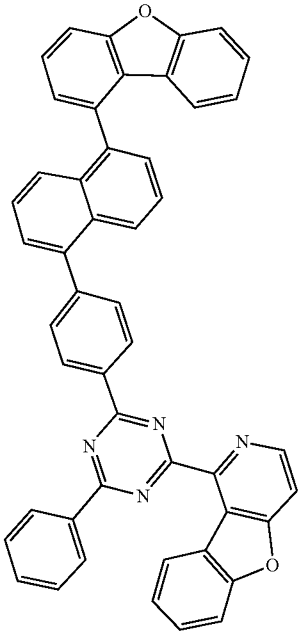
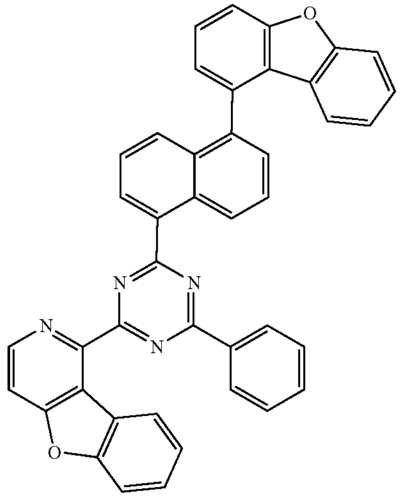

-continued
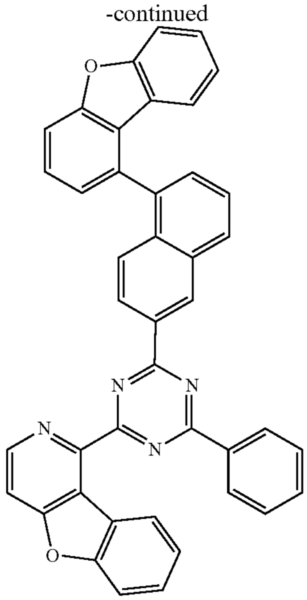
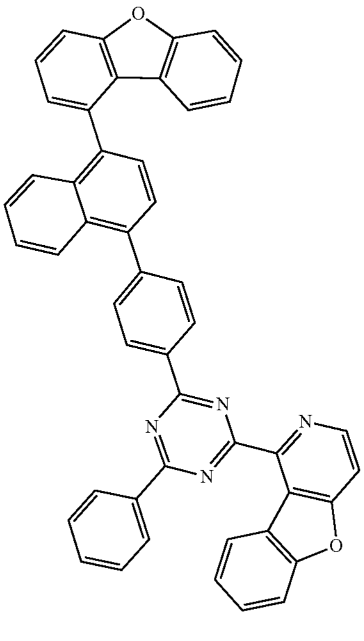
-continued
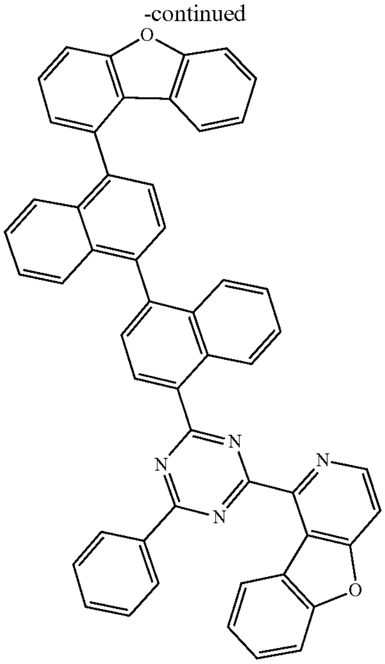
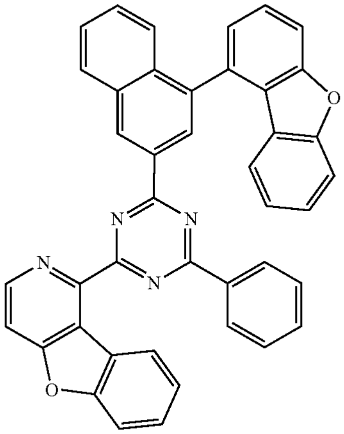
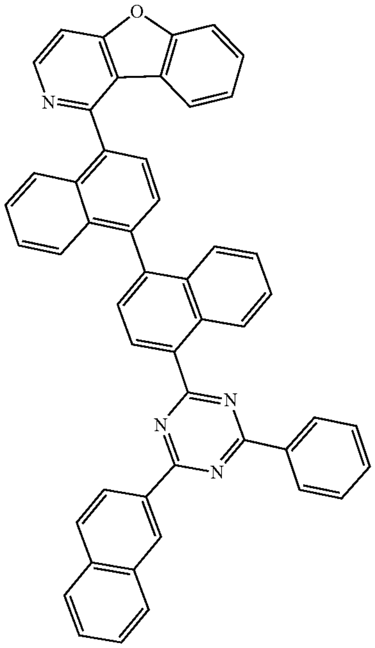

-continued
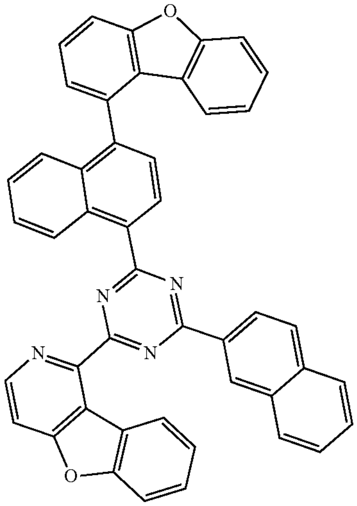
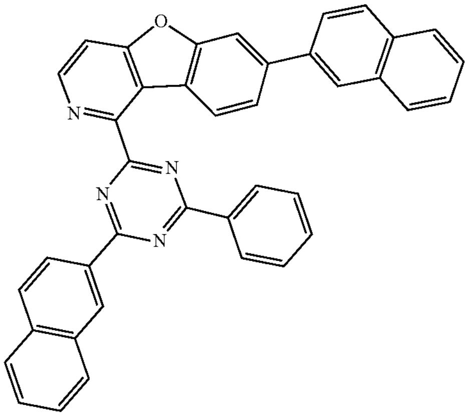
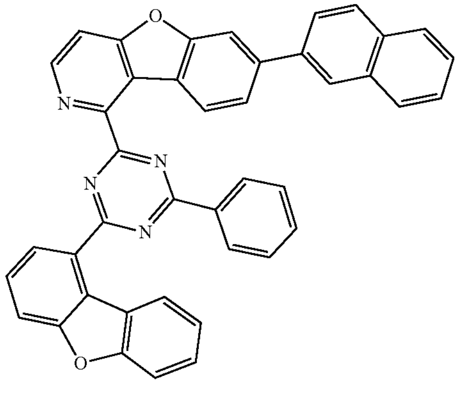
-continued
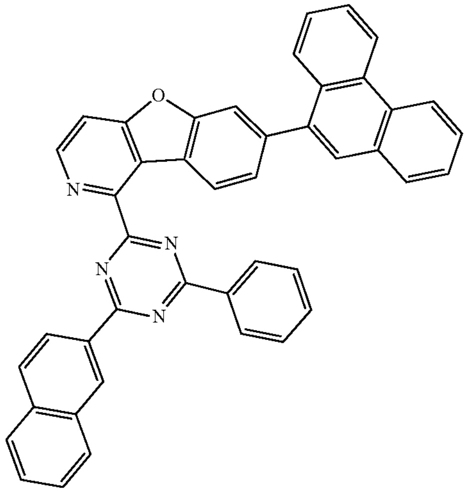
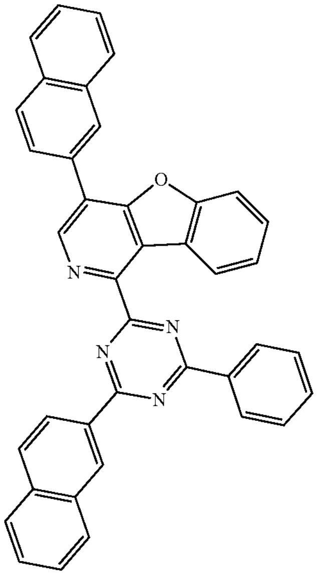
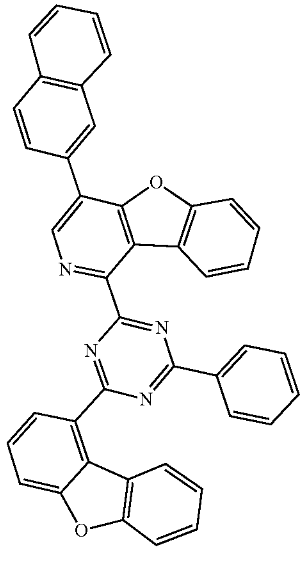

-continued
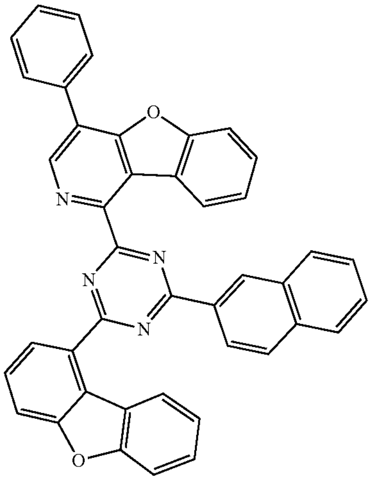
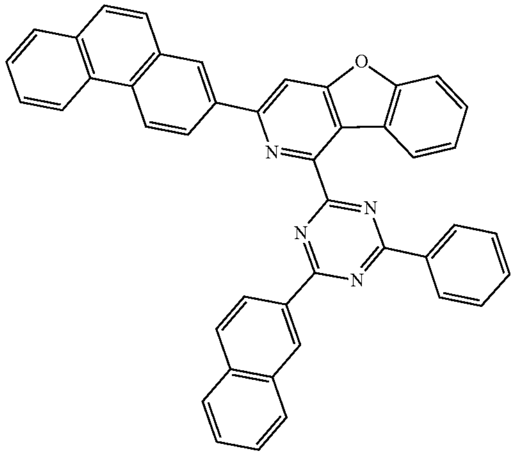
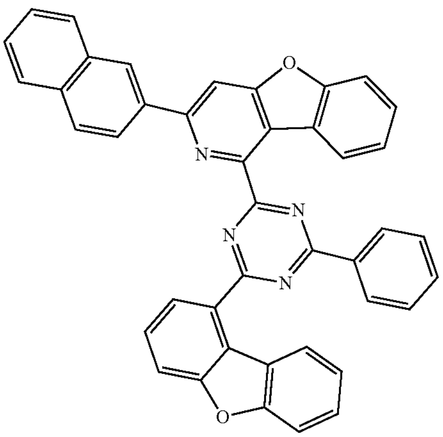
-continued
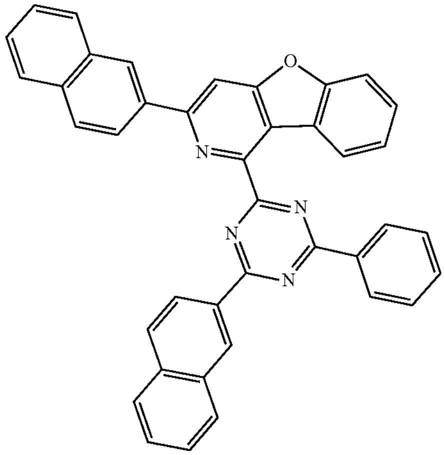
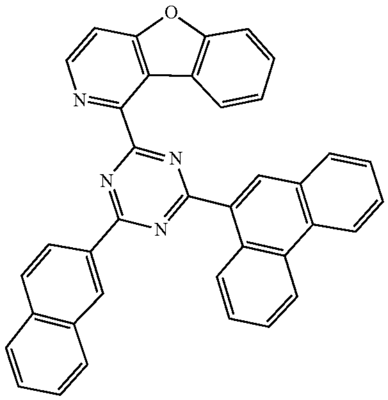
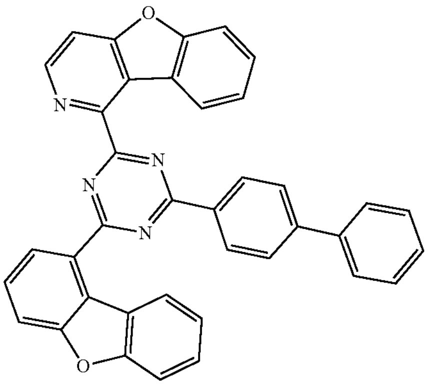
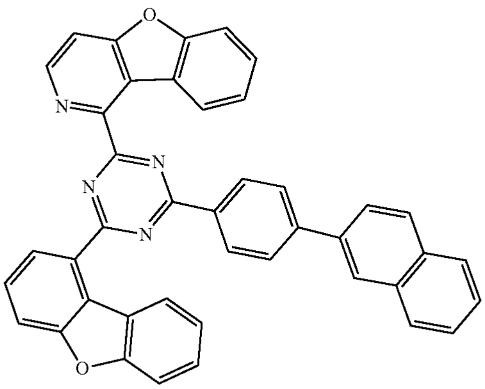

-continued
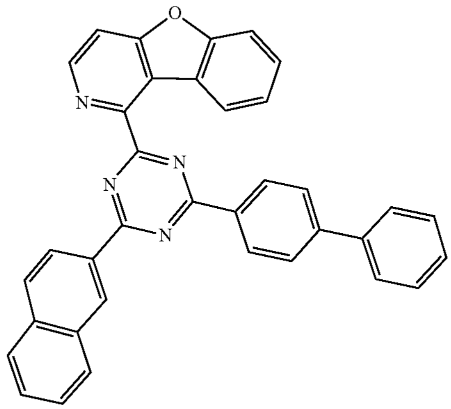
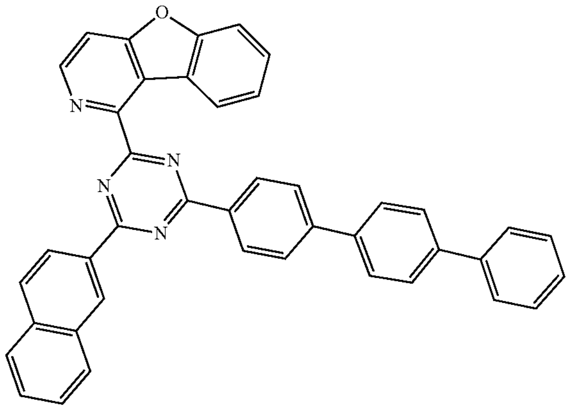
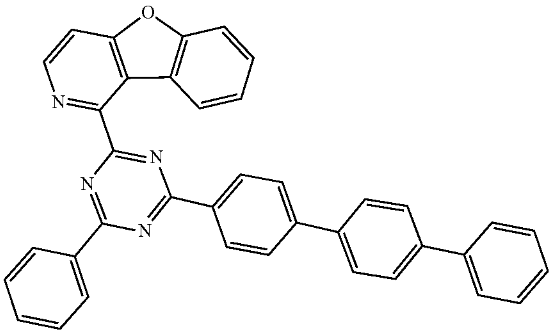
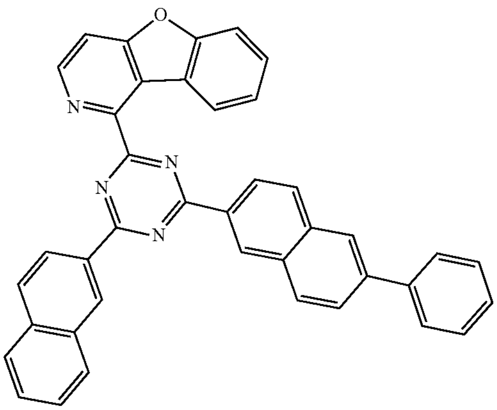
-continued
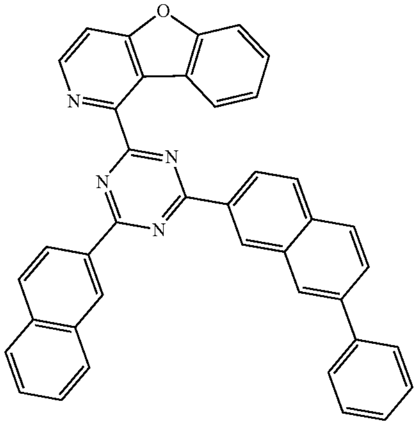
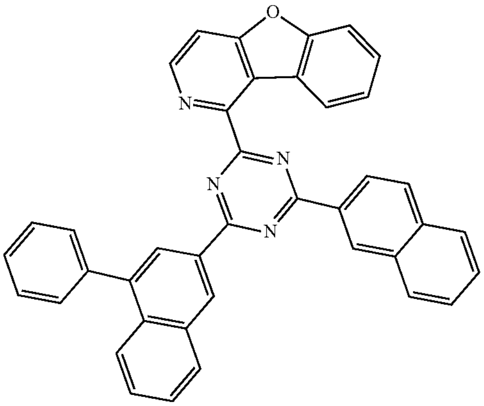
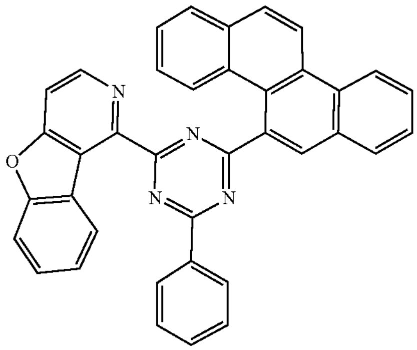
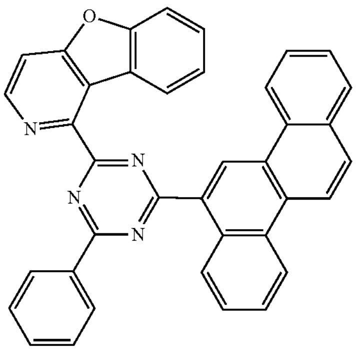

-continued
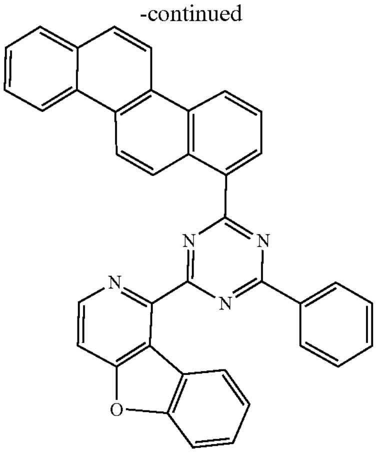
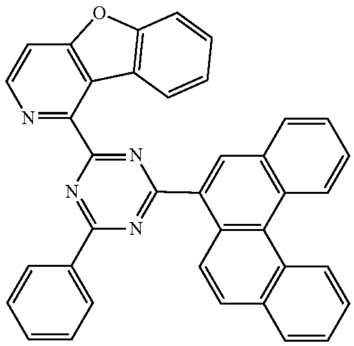
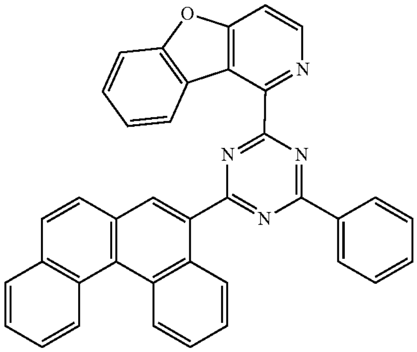
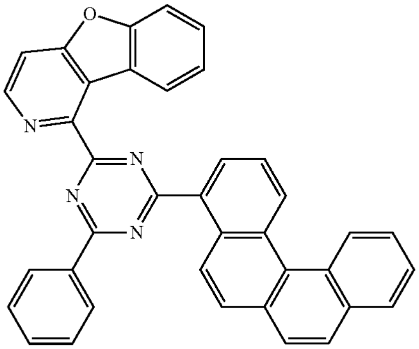
-continued
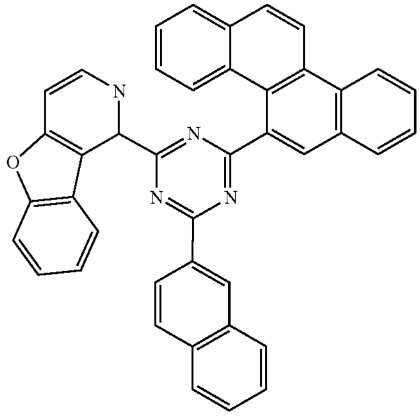
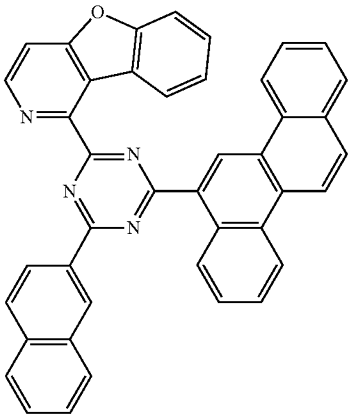
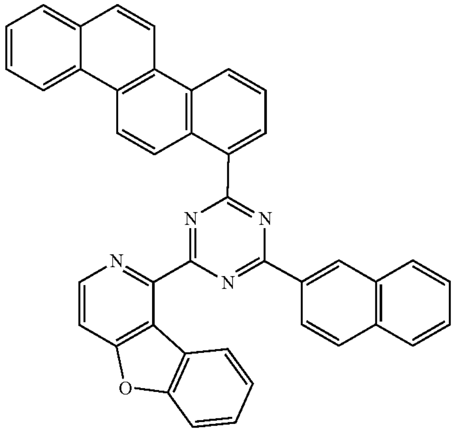
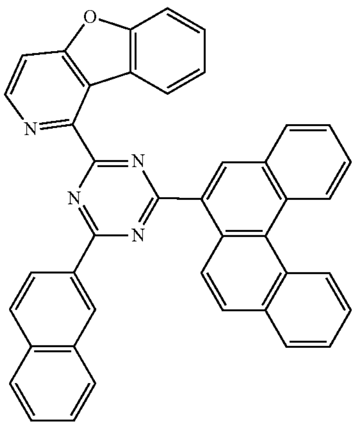

-continued
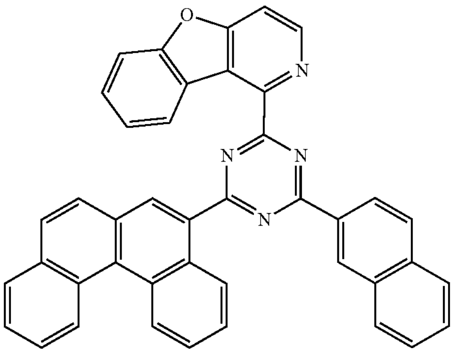
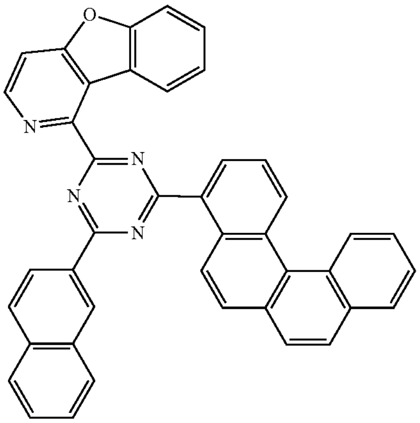
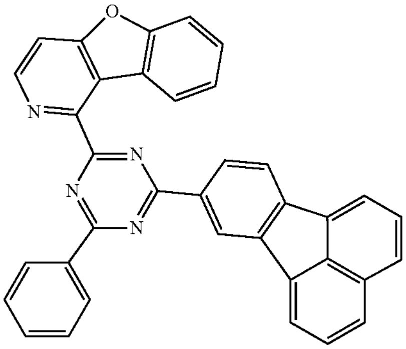
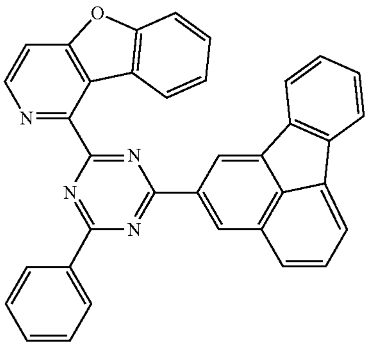
-continued
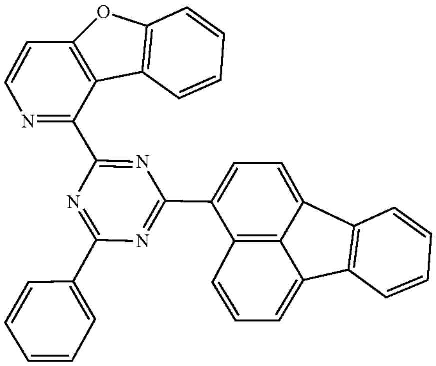
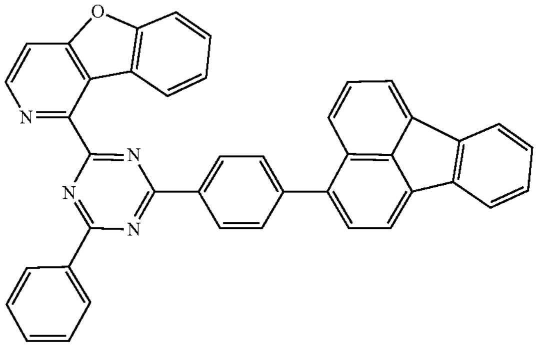
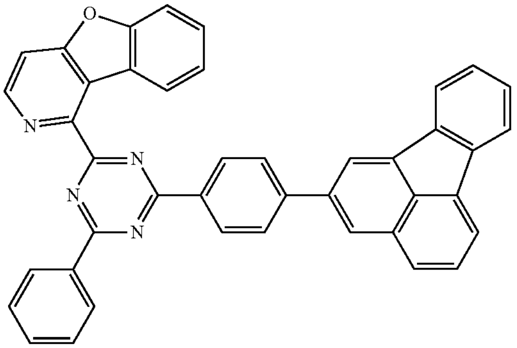
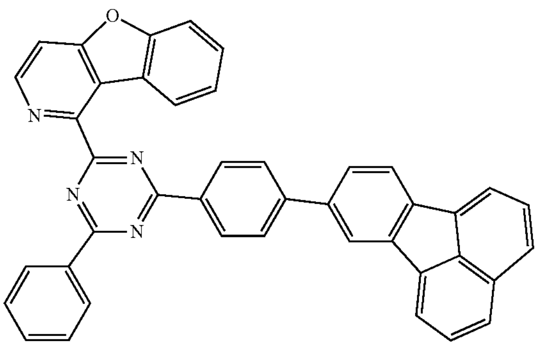

-continued
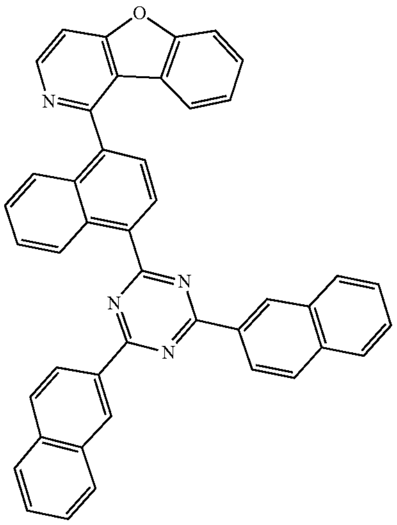
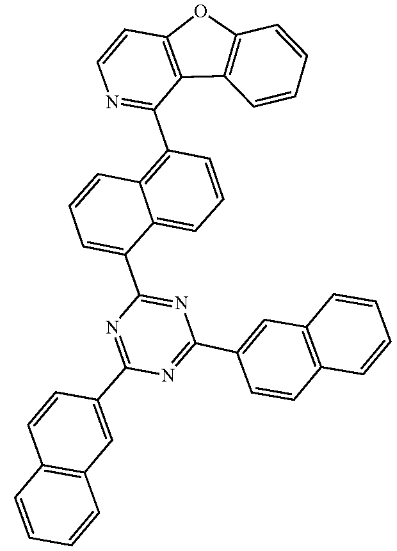
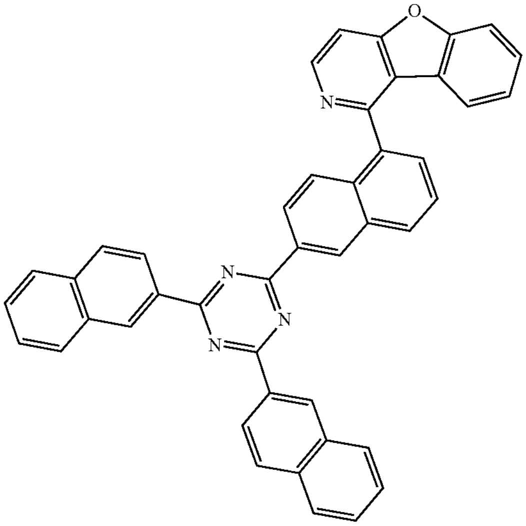
-continued
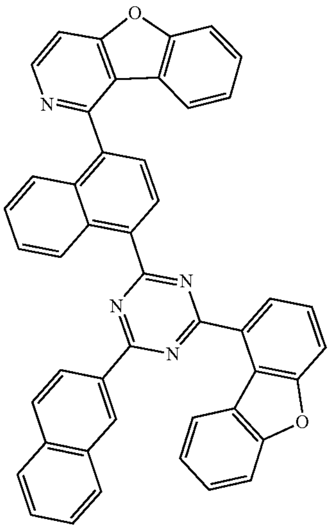
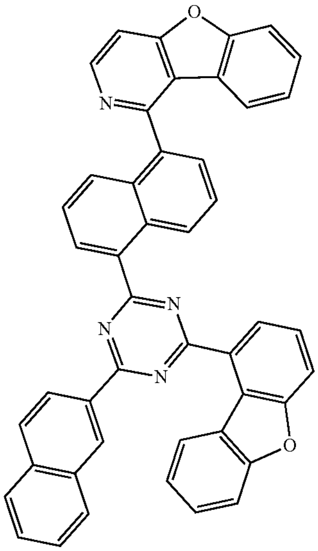
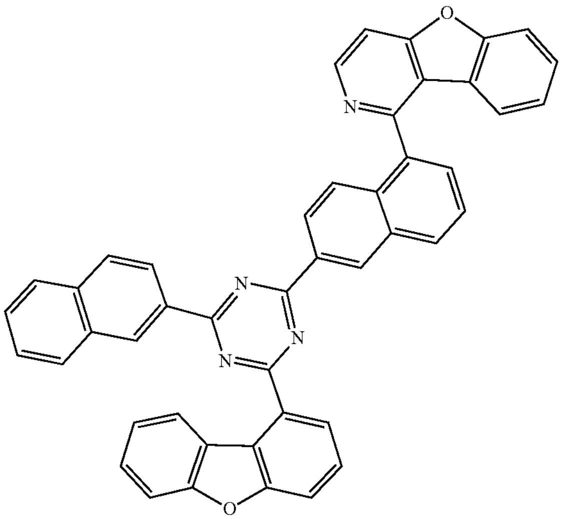

-continued
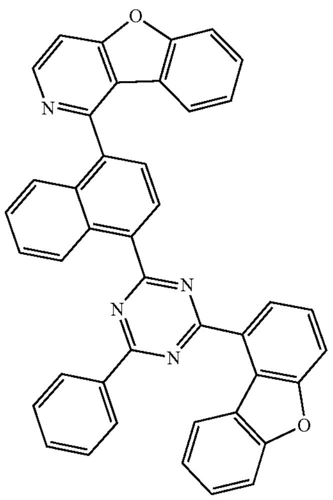
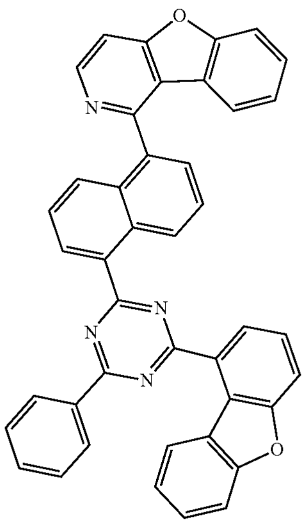
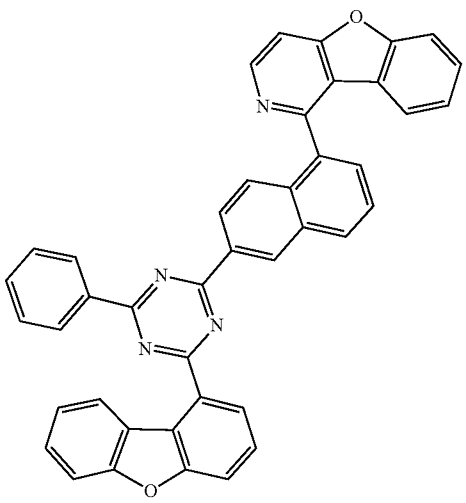
-continued
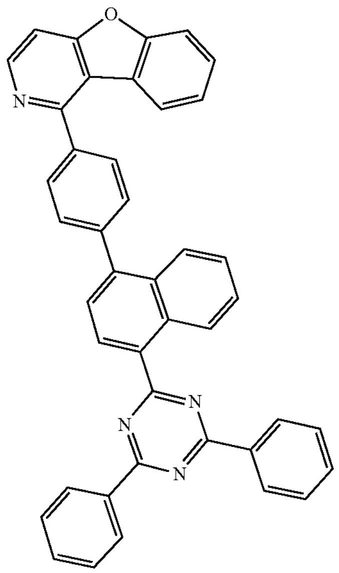
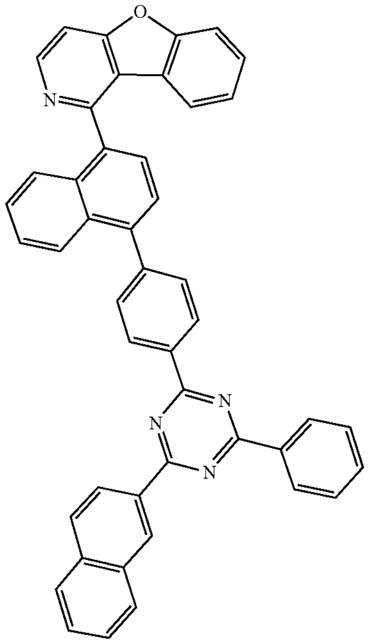
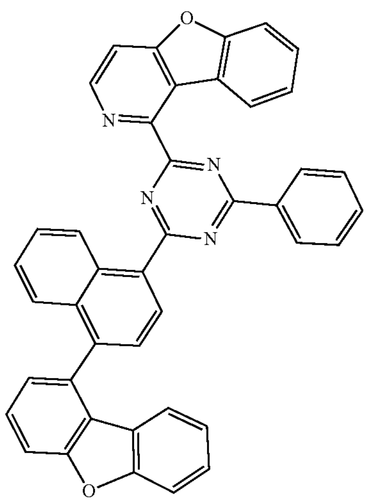

-continued
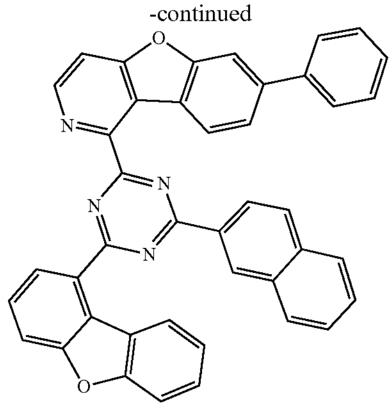
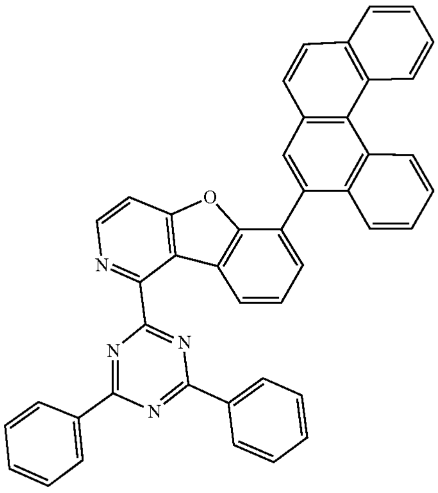
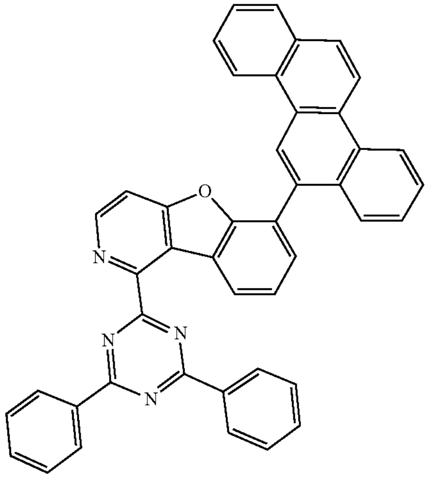
-continued
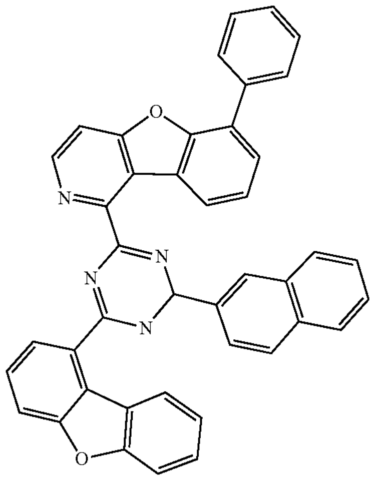
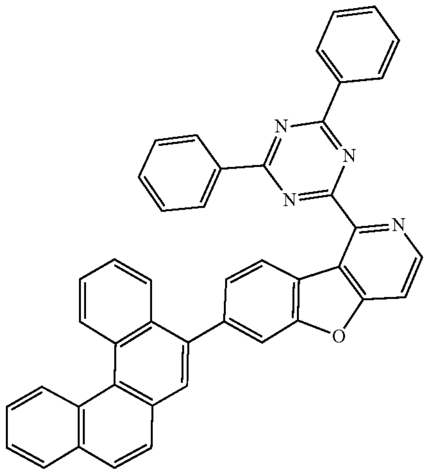
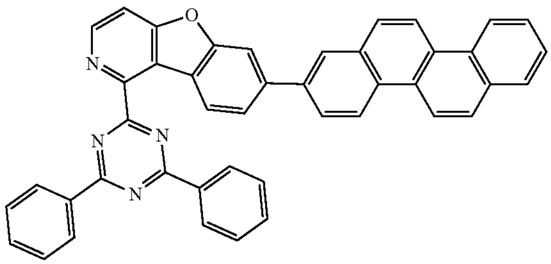
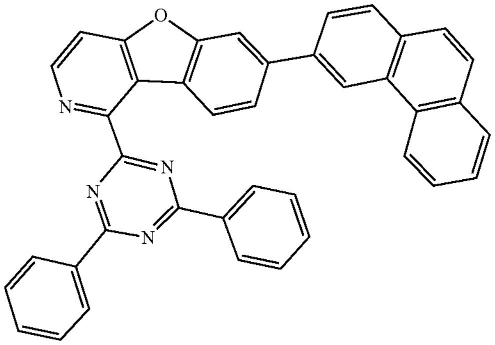

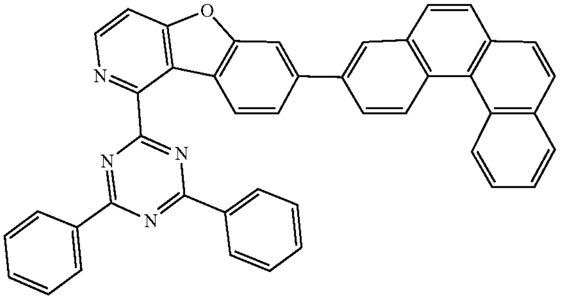
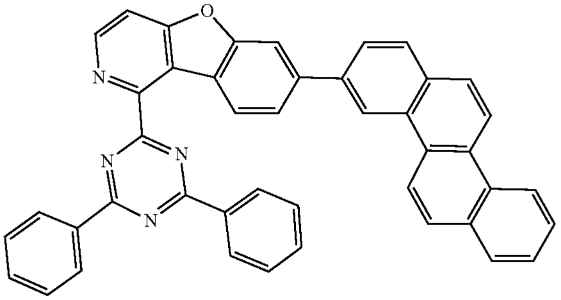
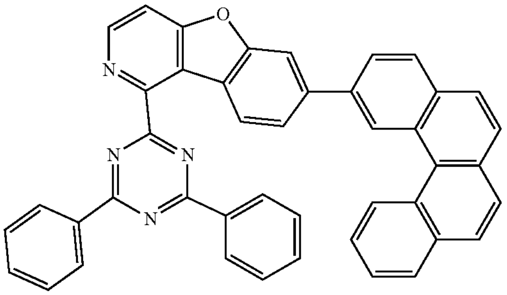
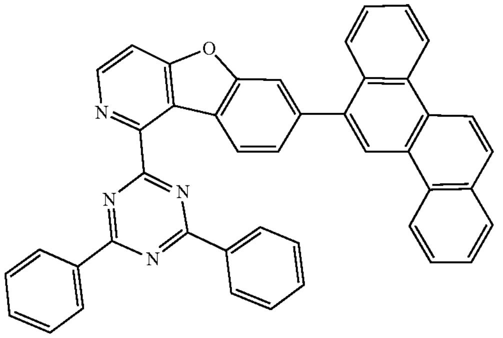
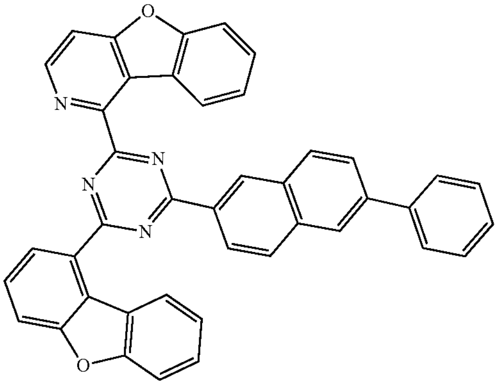
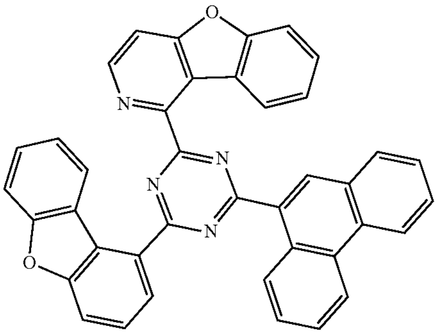
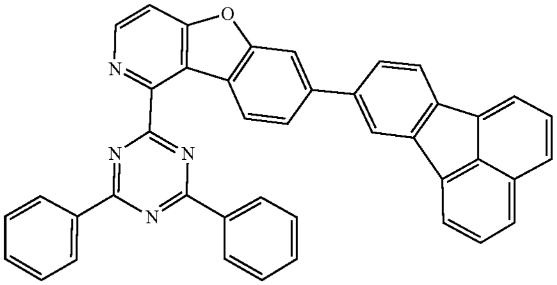
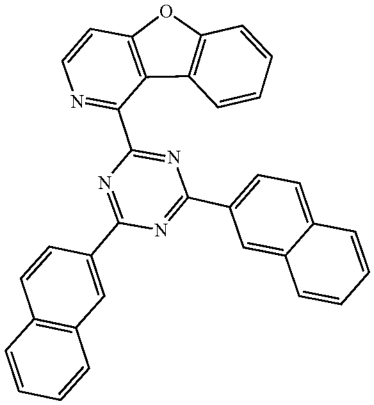
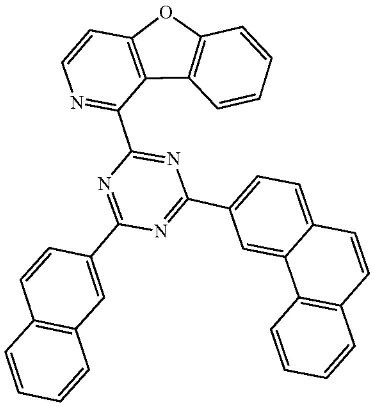

-continued
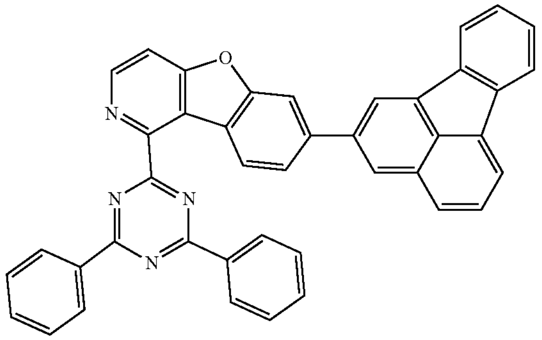
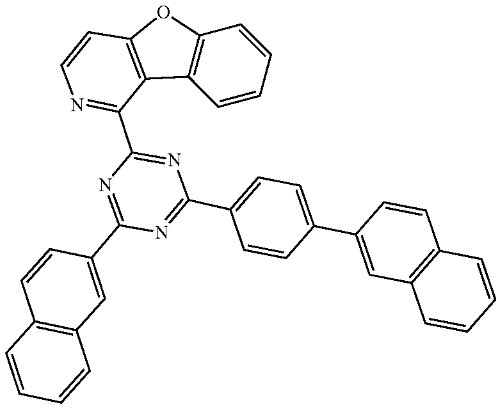
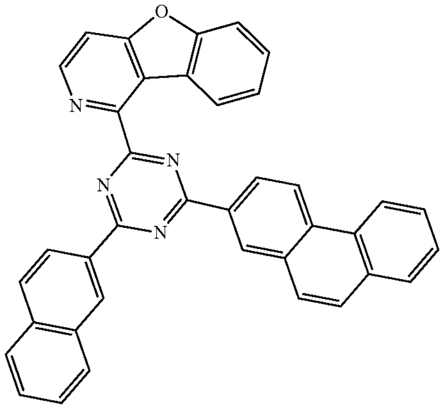
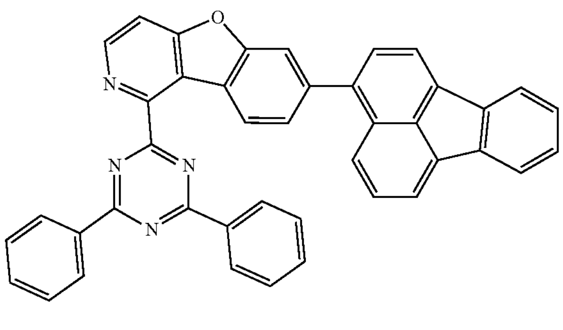
-continued
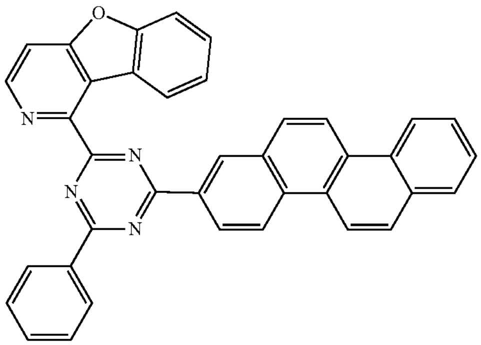
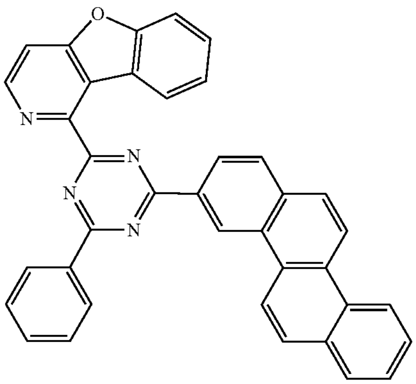
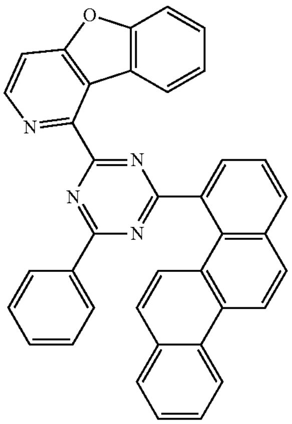
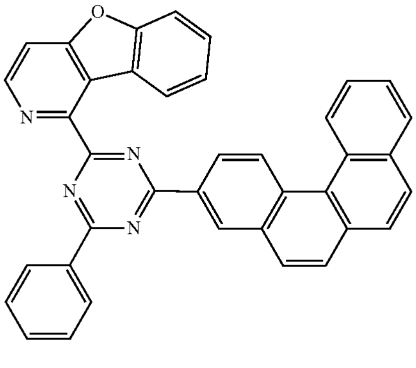

-continued
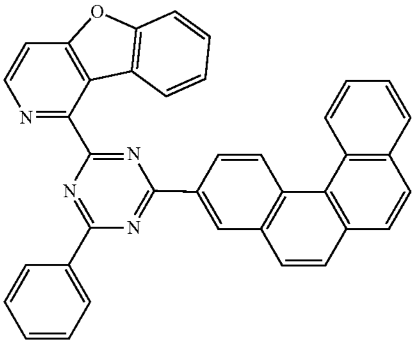
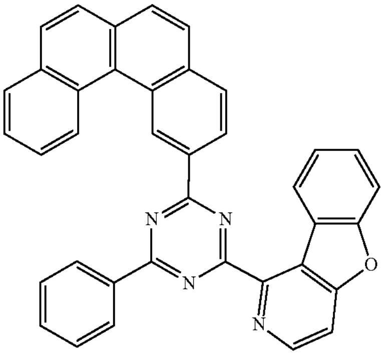
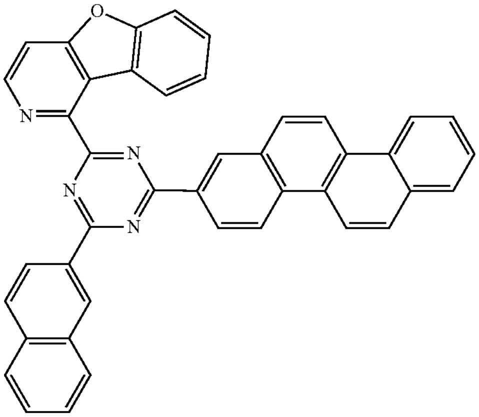
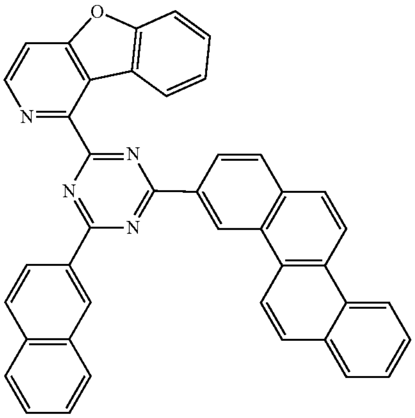
-continued
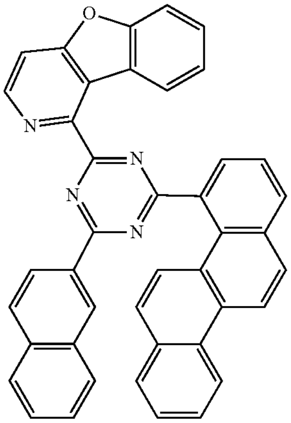
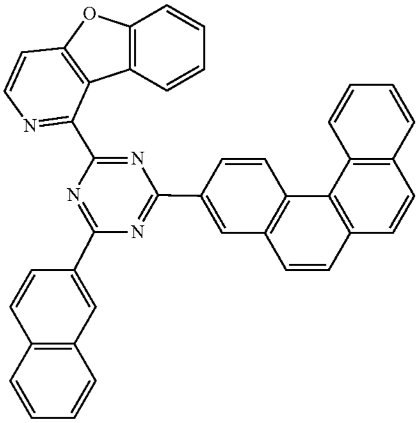
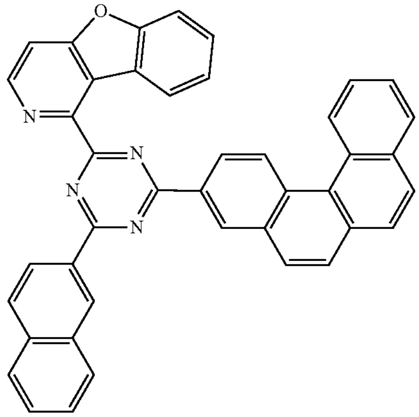
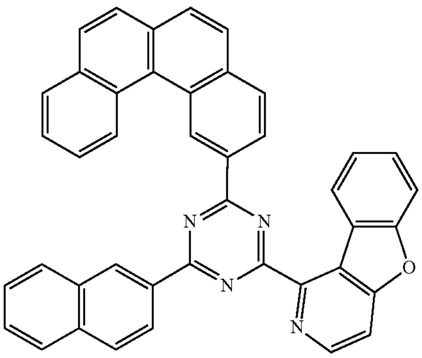

-continued
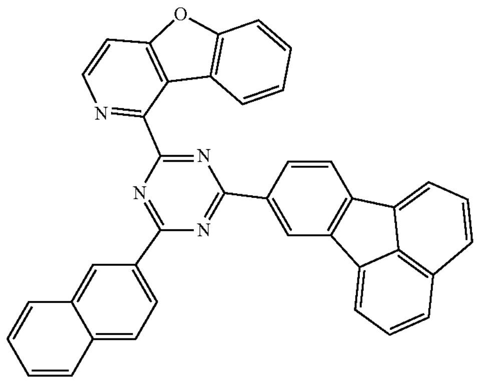
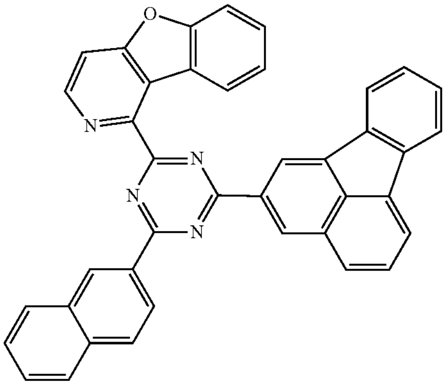
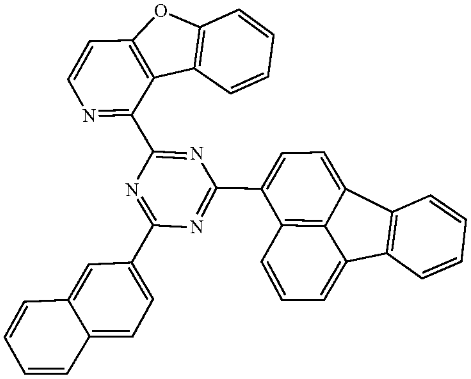
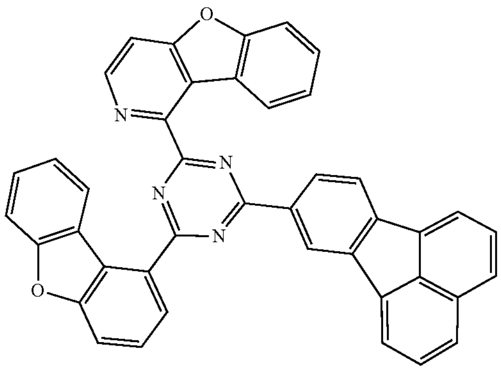
-continued
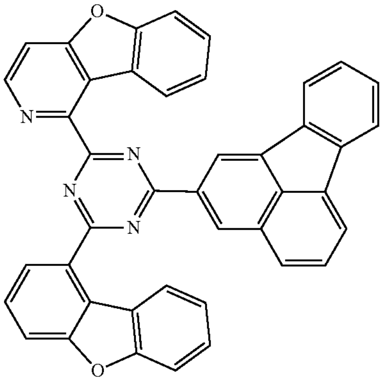
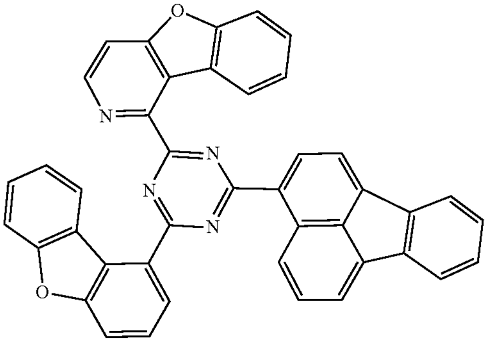
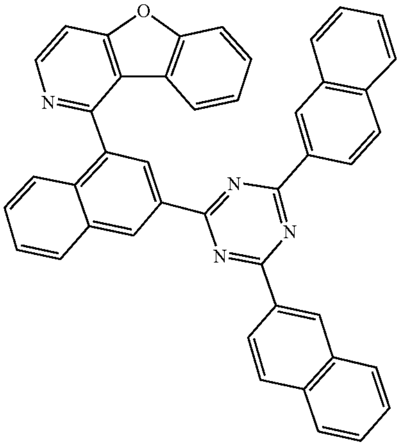
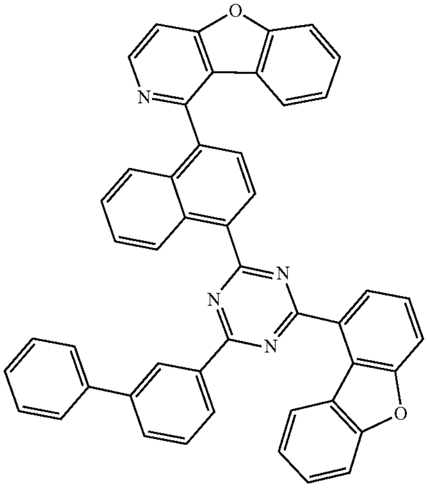

-continued
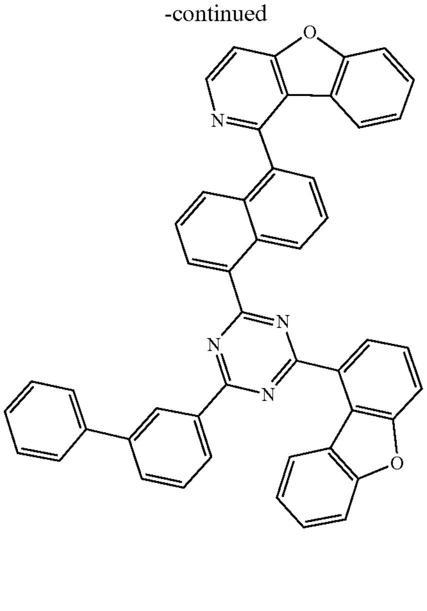
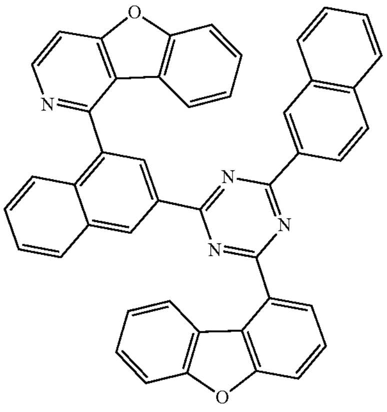
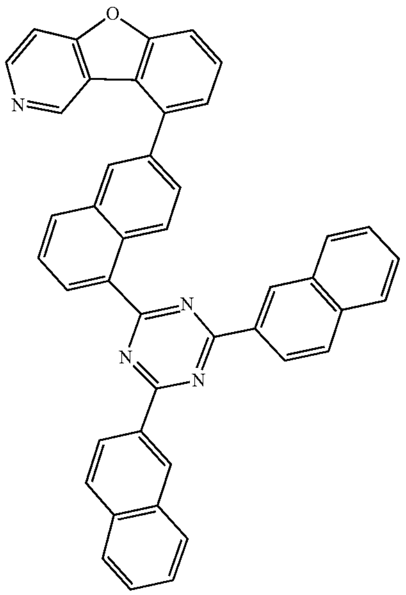
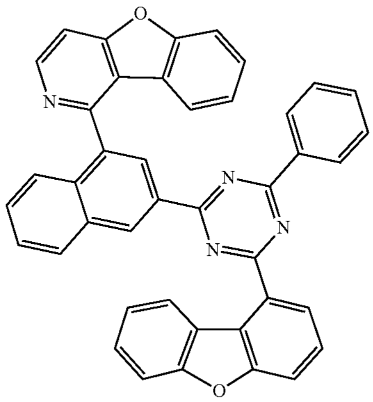
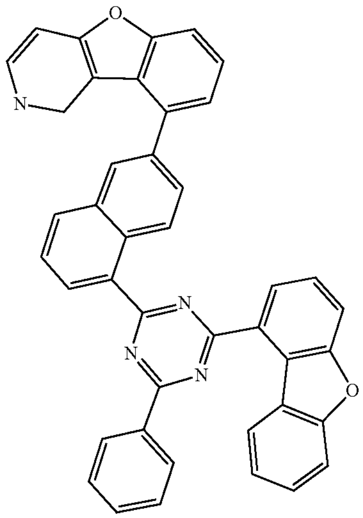
-continued
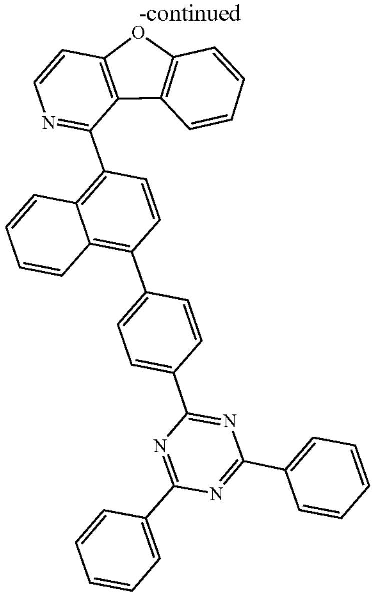

-continued
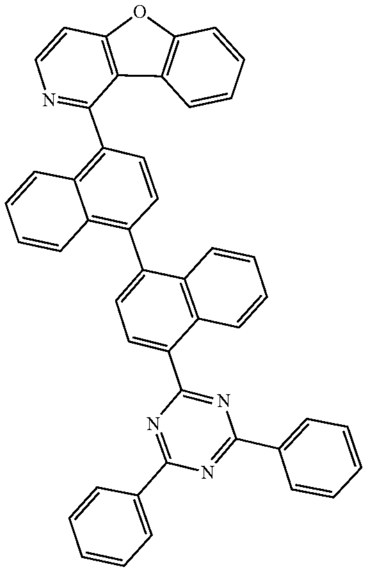
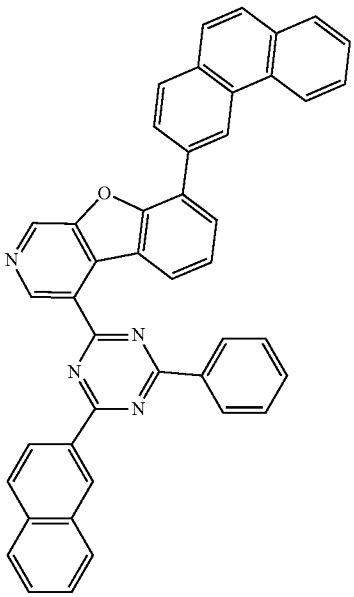
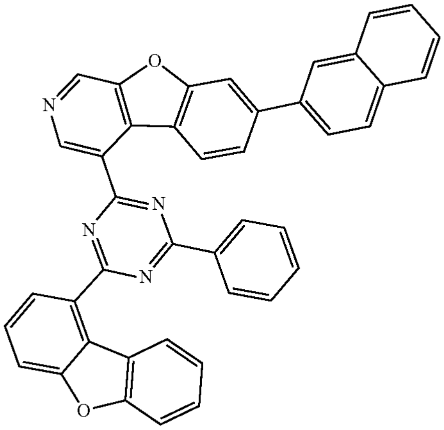
-continued
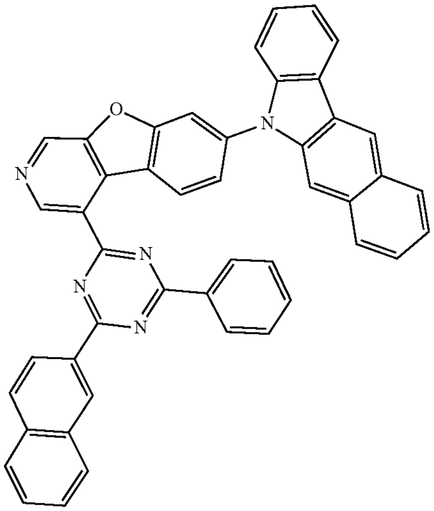
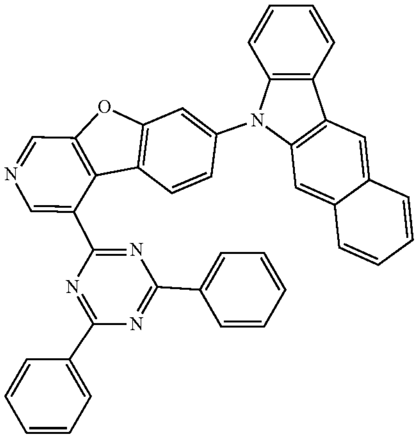
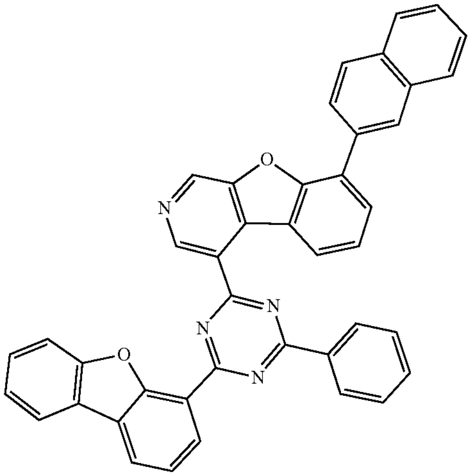

-continued
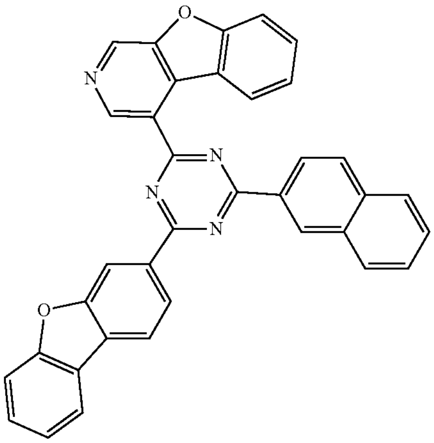
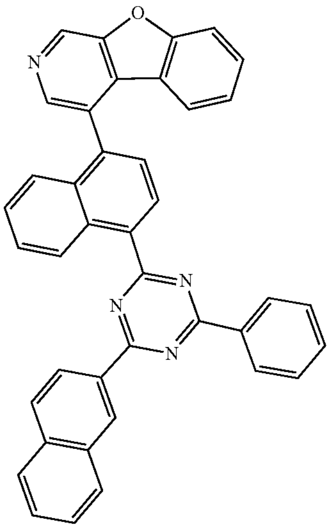
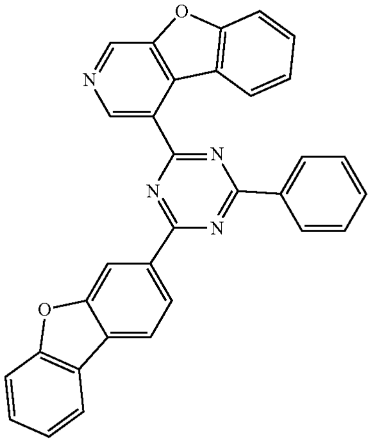
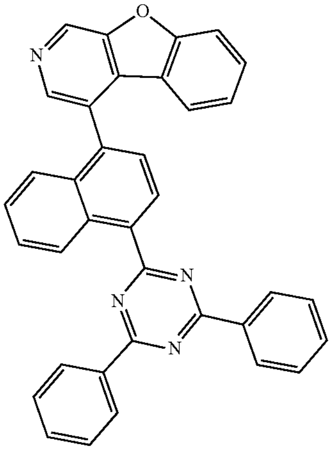
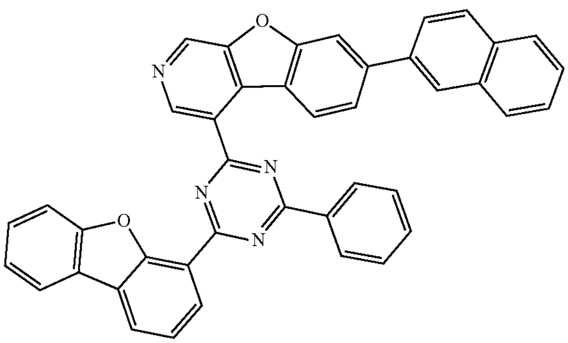
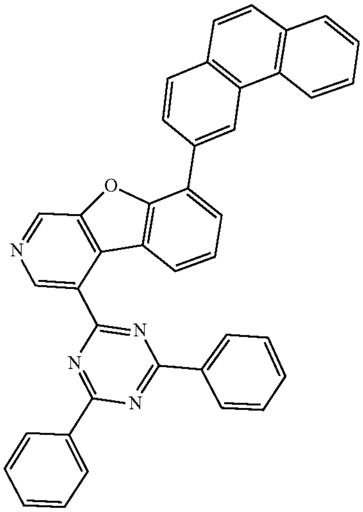
-continued -continued
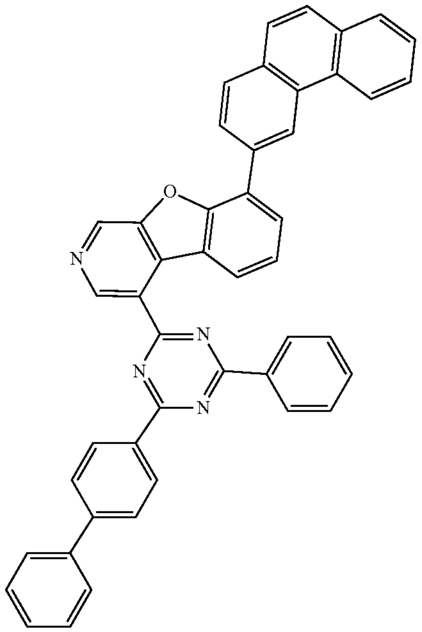
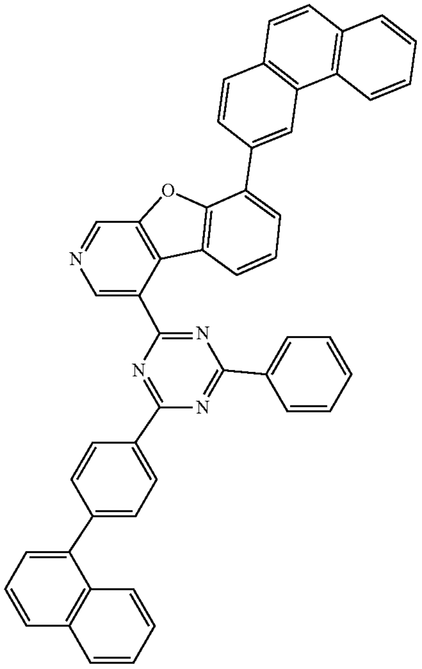
-continued
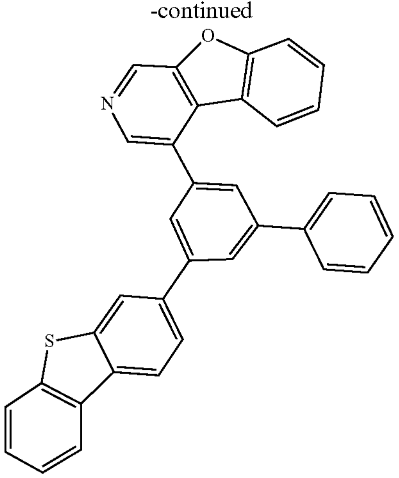
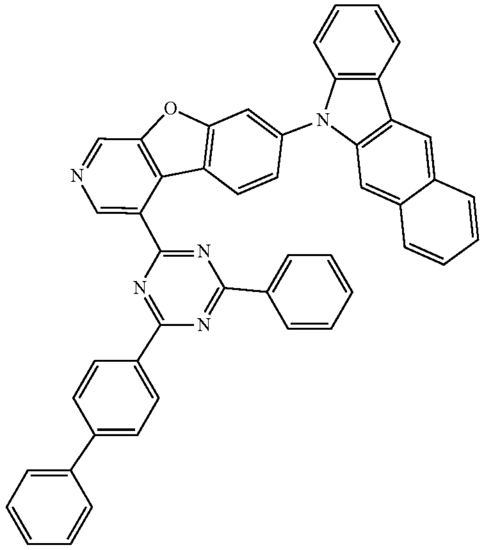
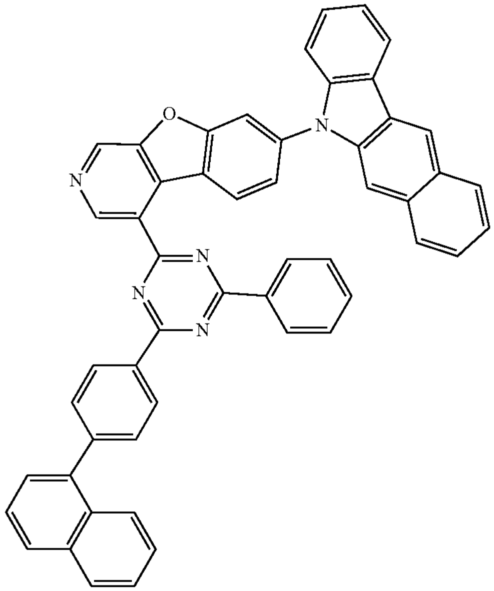

-continued
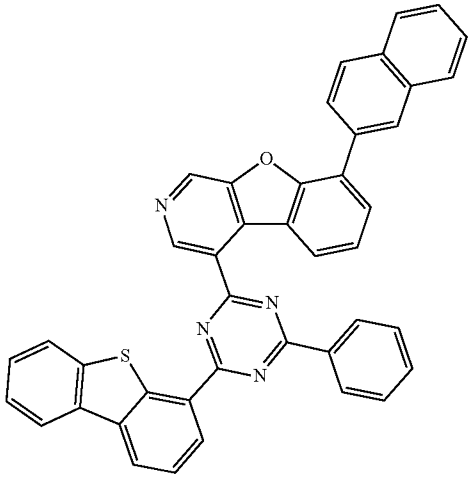
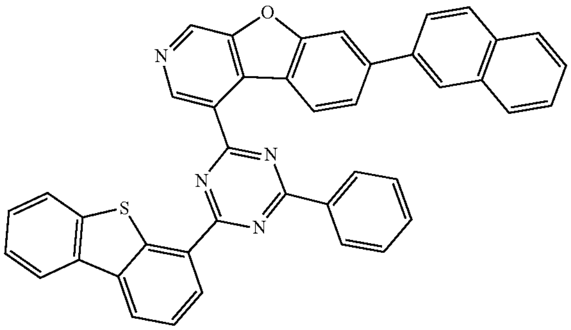
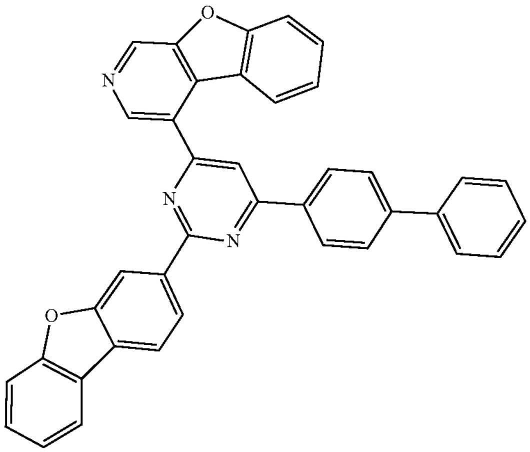
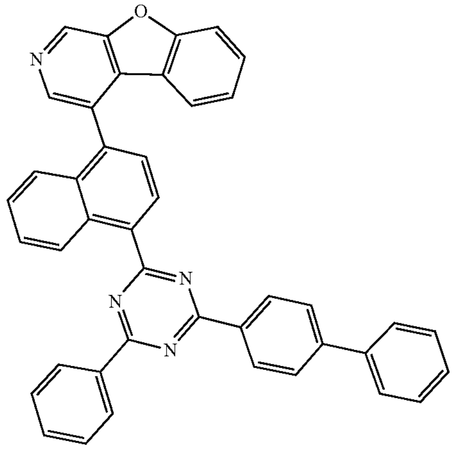
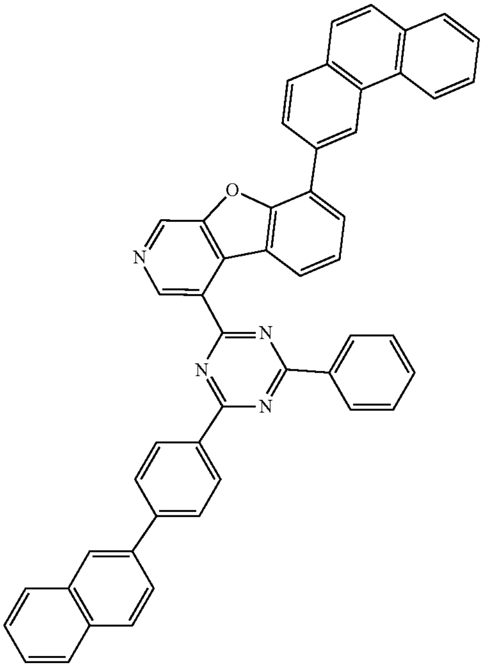
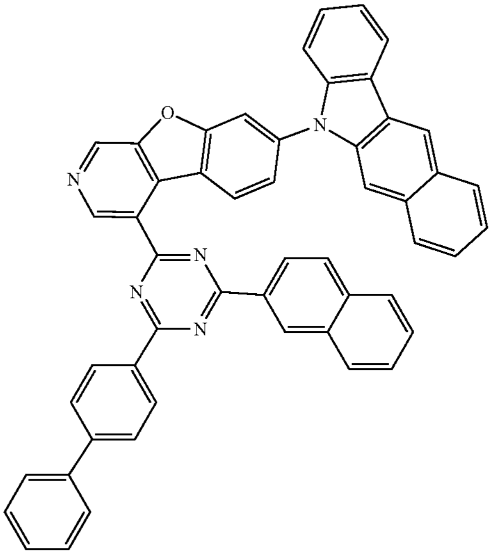
-continued -continued
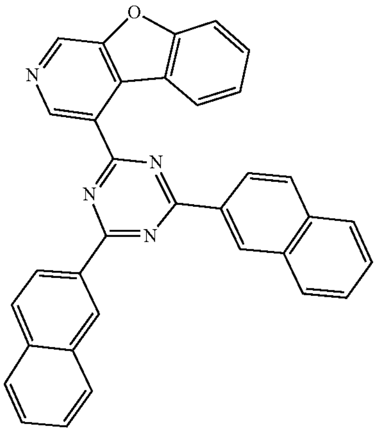
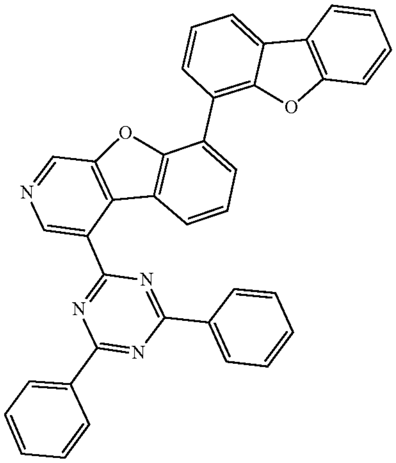
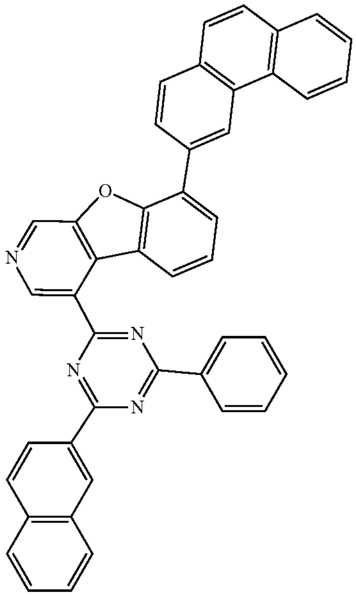
-continued
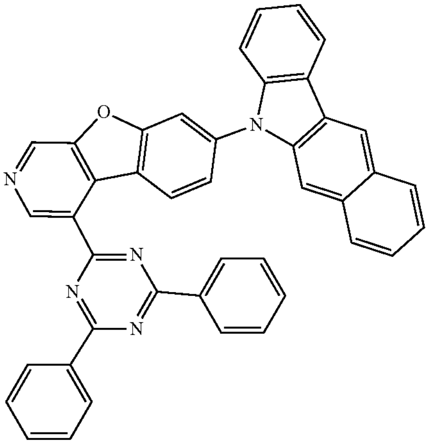
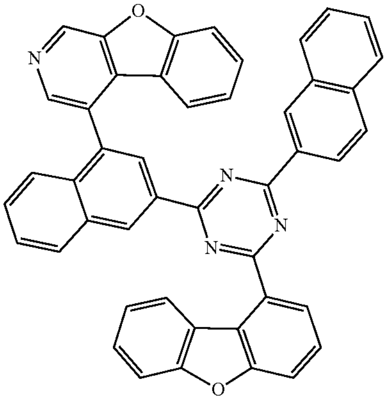
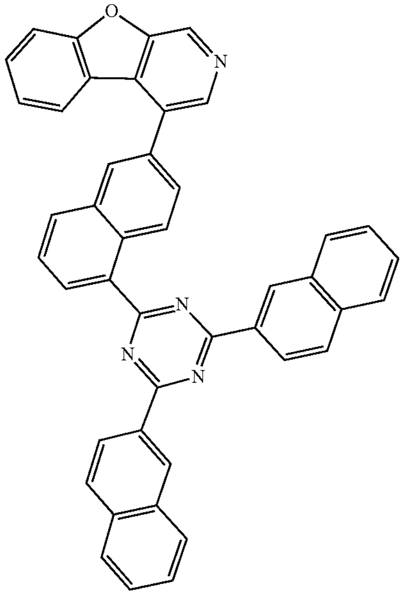

-continued
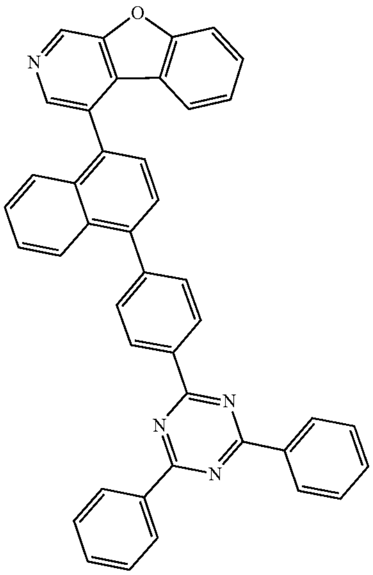
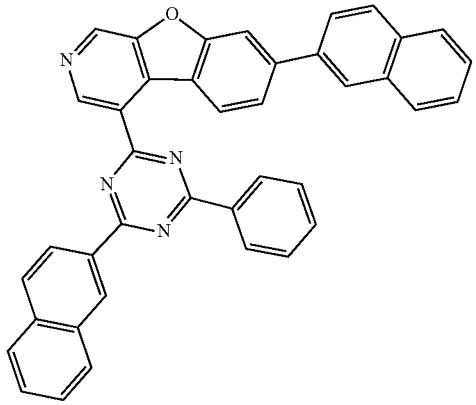
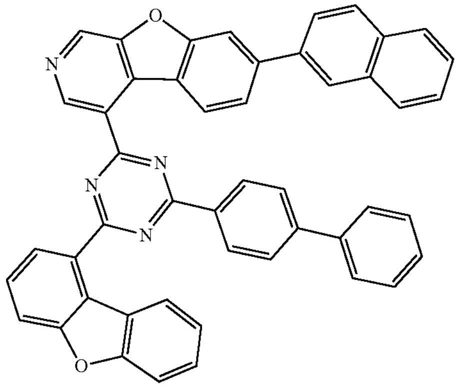
-continued
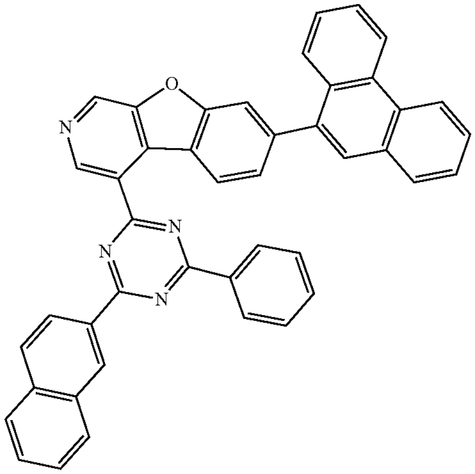
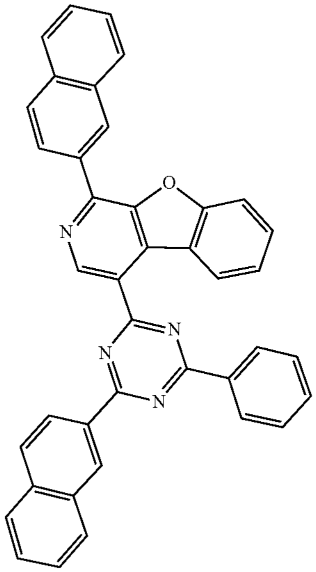
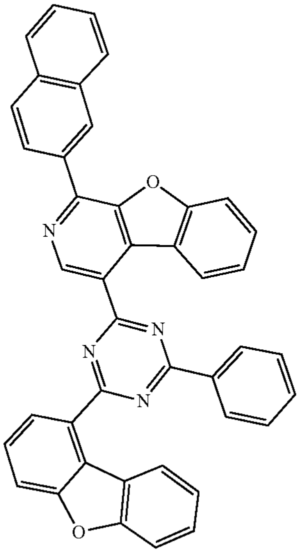

-continued
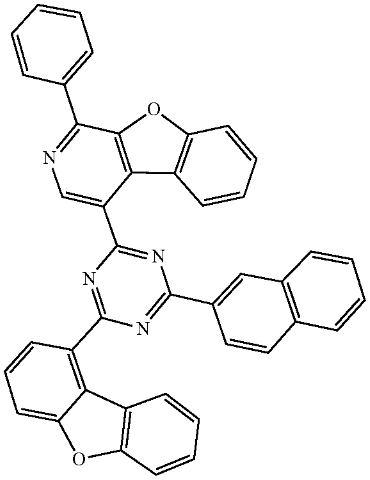
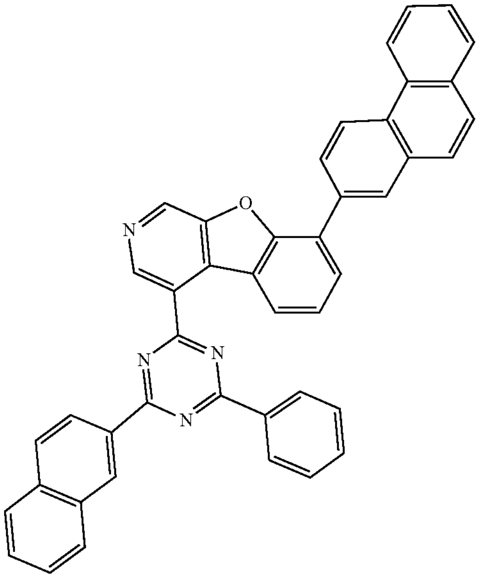
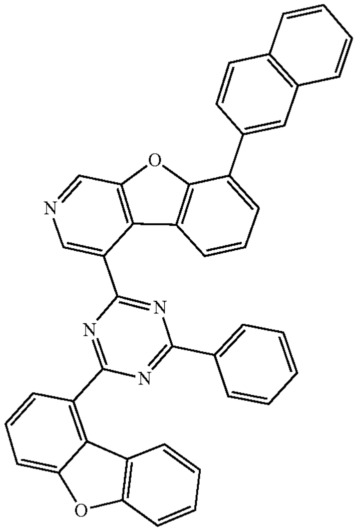
-continued
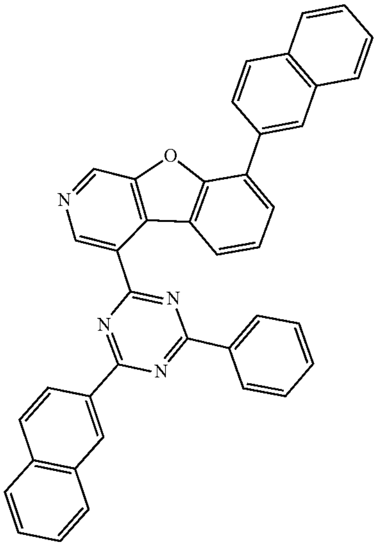
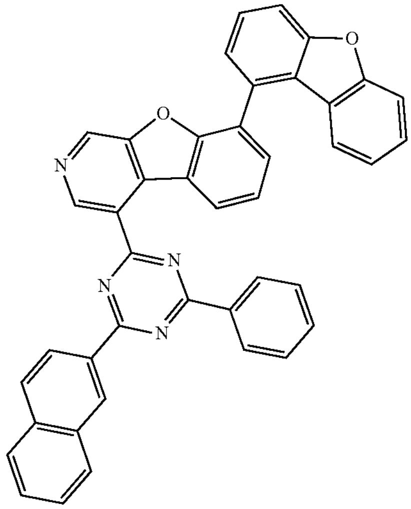
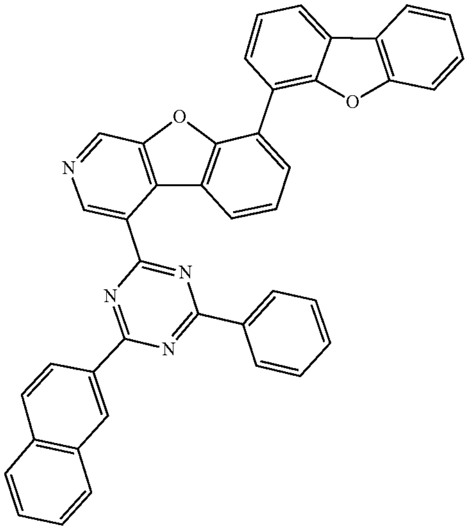

-continued
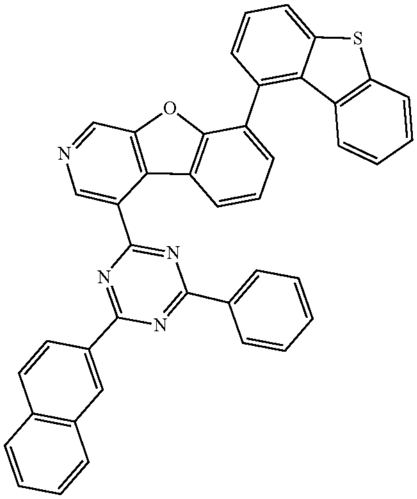 [SMILES: c1ccc(-c2nc(-c3ccc4ccccc4c3)nc(-c3cncc4oc5c(-c6cccc7sc8ccccc8c67)cccc5c34)n2)cc1]
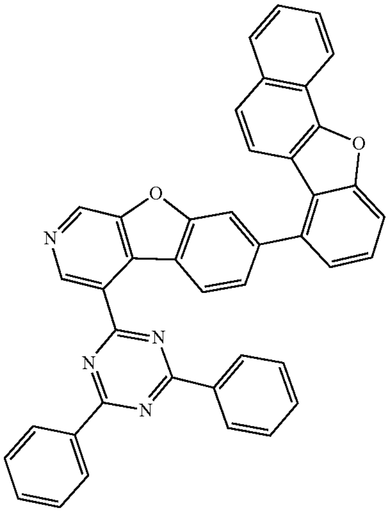
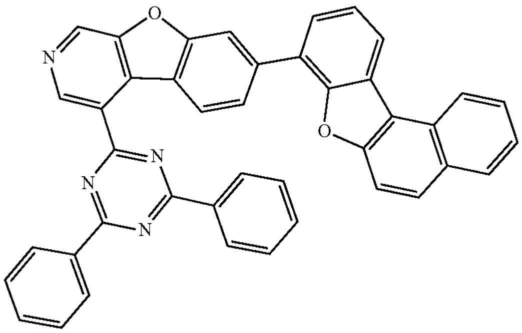
-continued
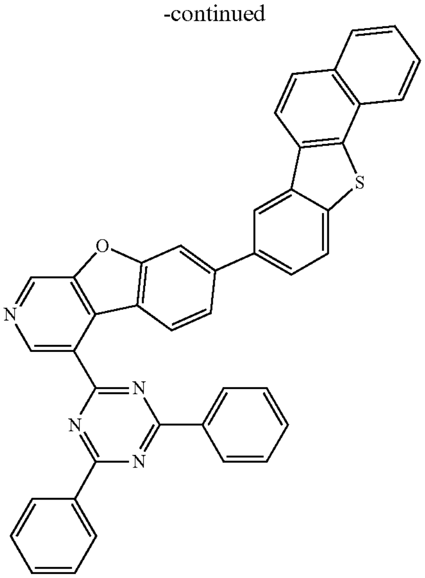
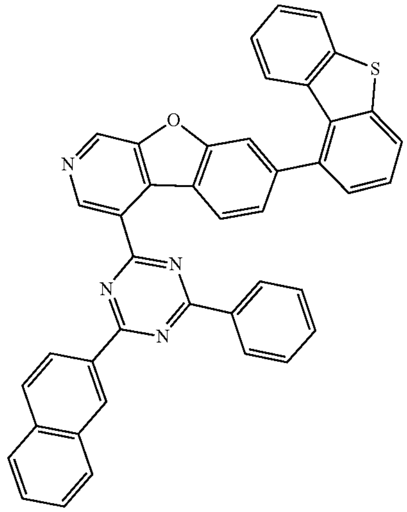
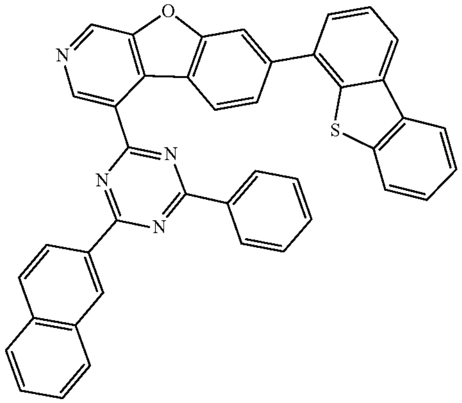

-continued
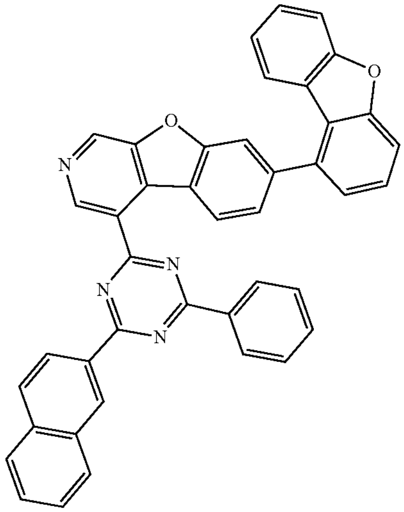
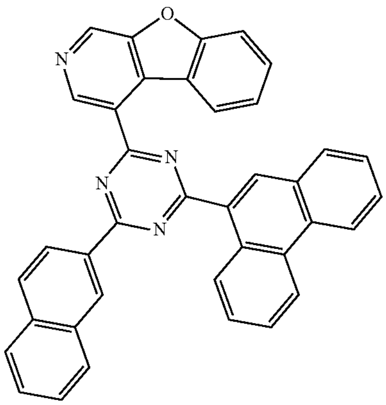
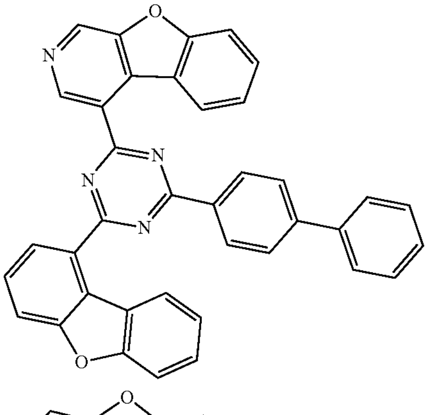
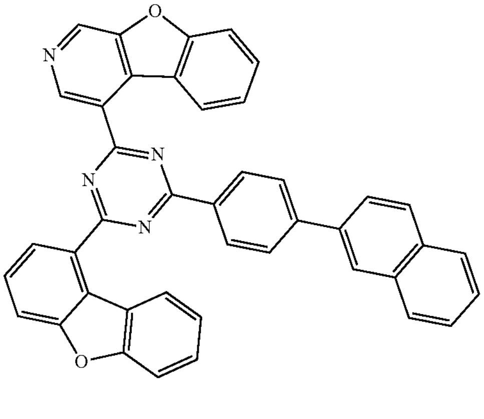
-continued
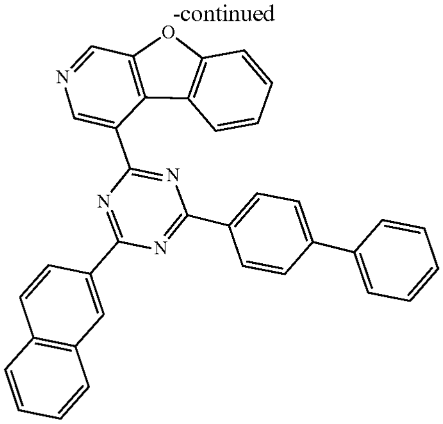
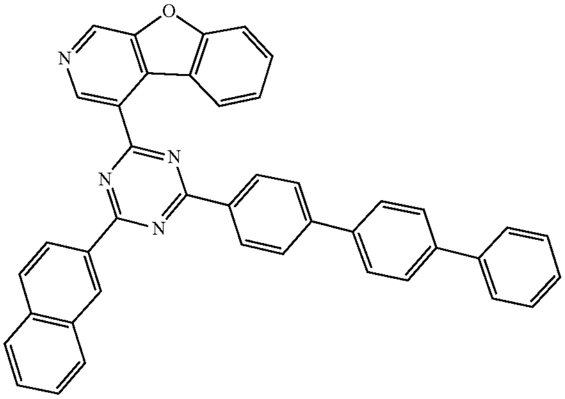
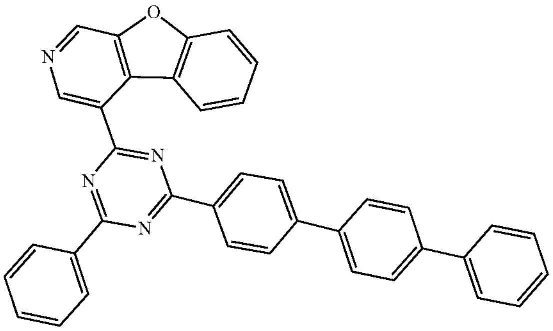
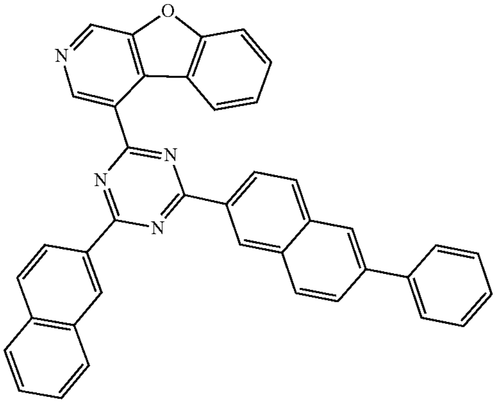

-continued
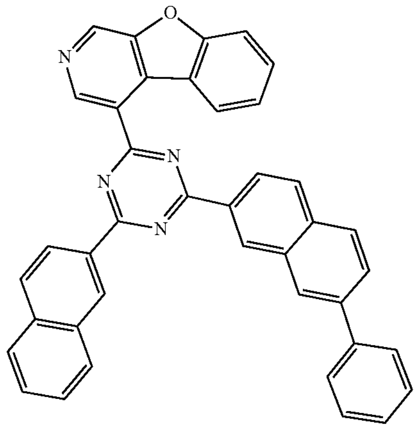
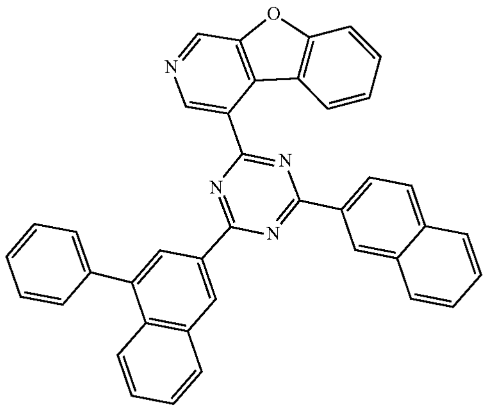
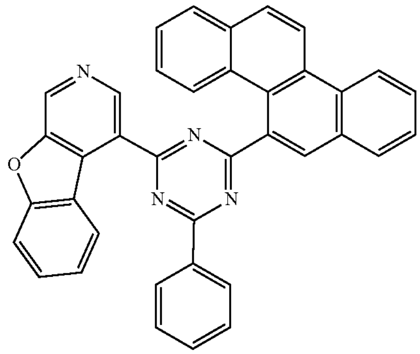
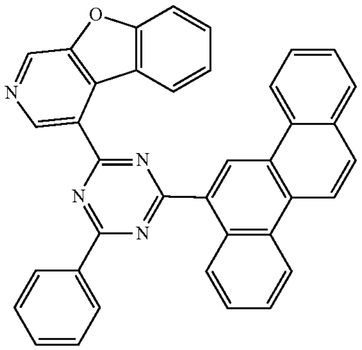
-continued
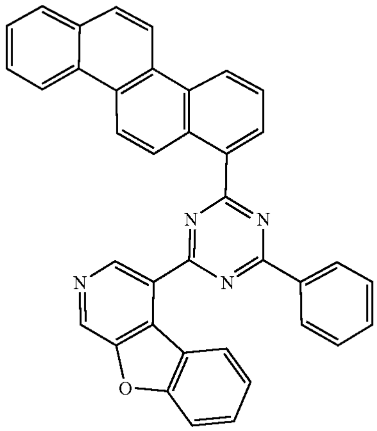
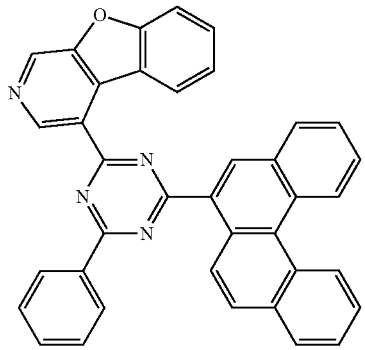
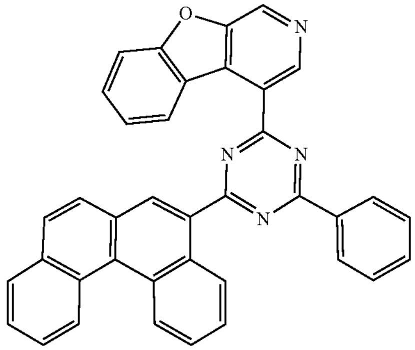
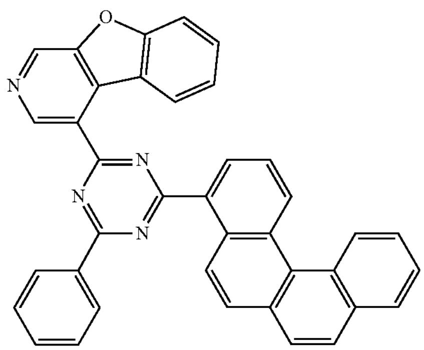

-continued
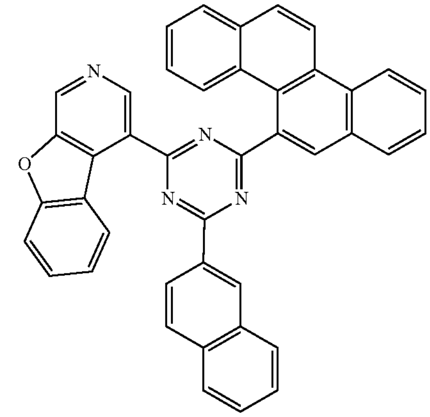
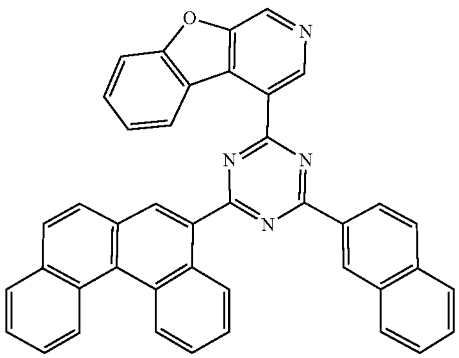
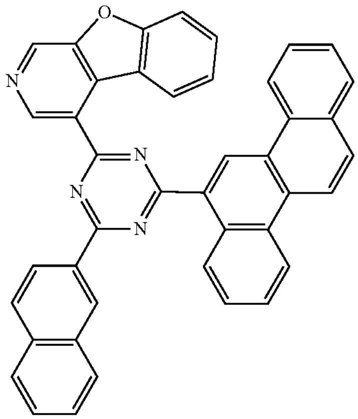
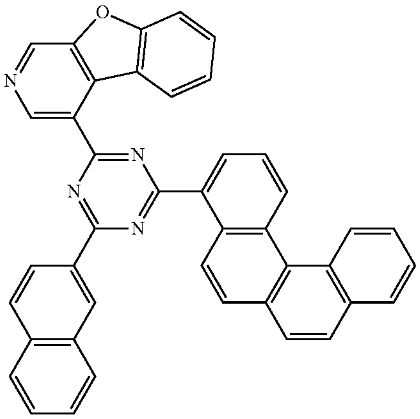
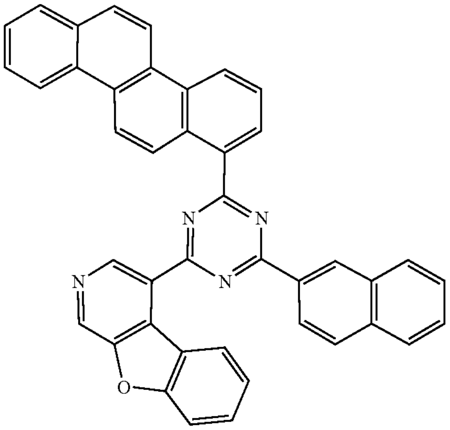
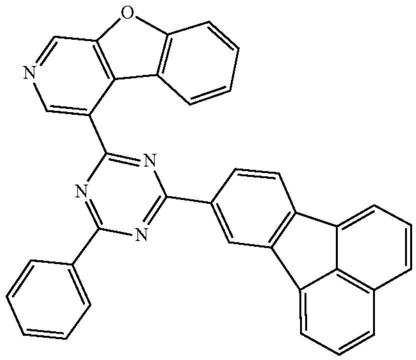
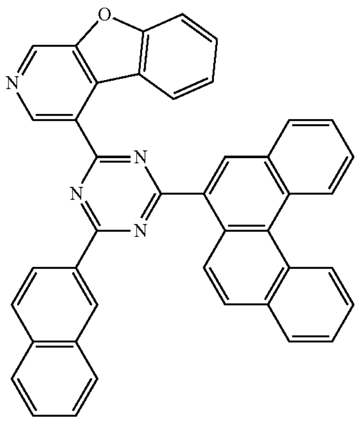
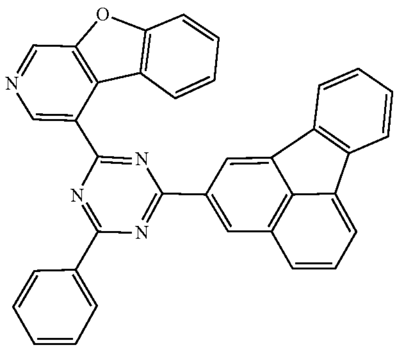
-continued -continued
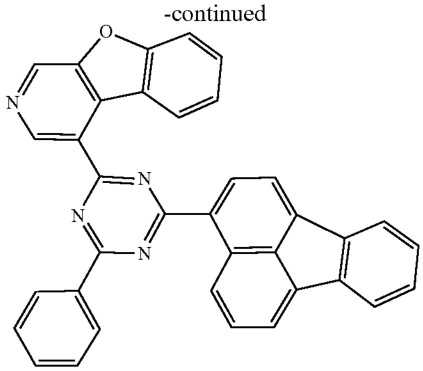
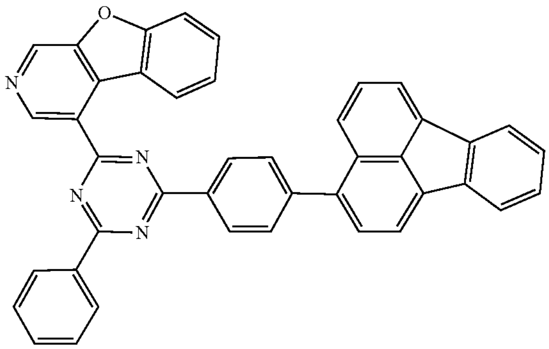
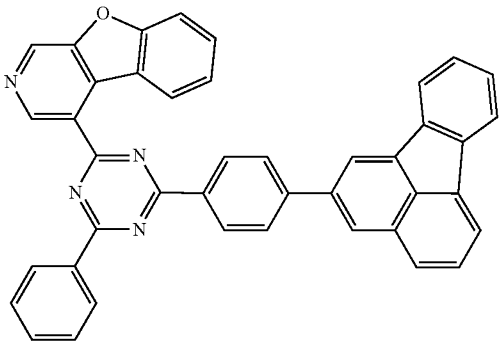
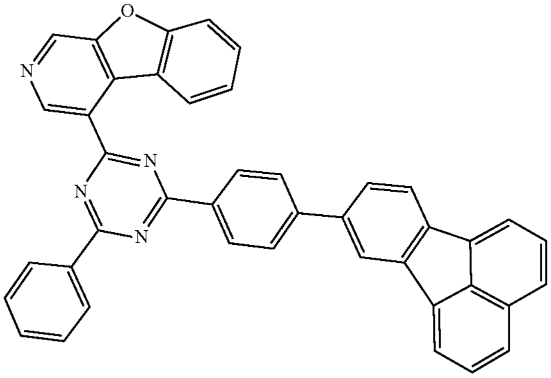
-continued
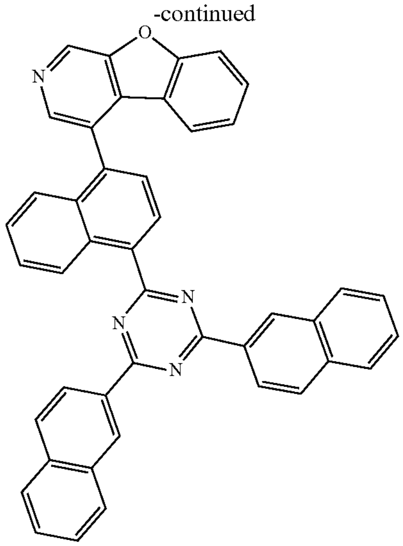
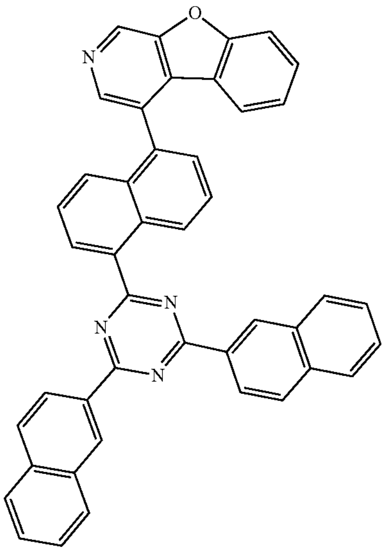
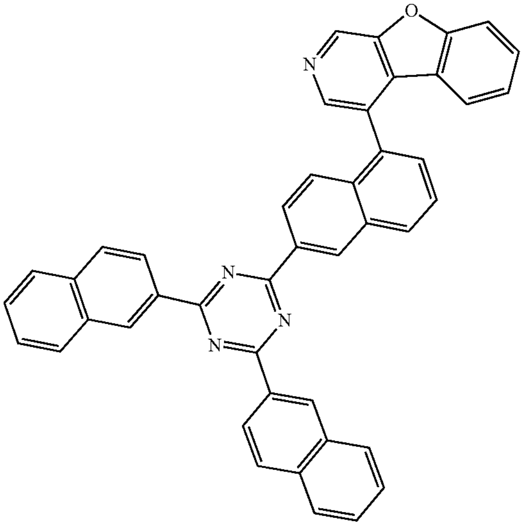

-continued
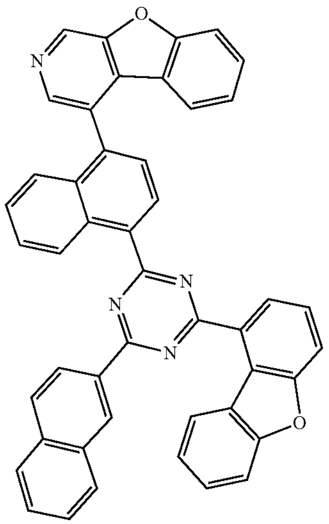
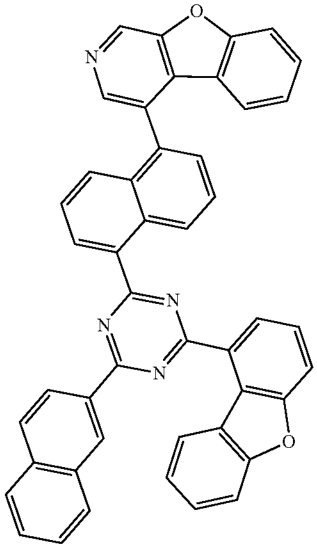
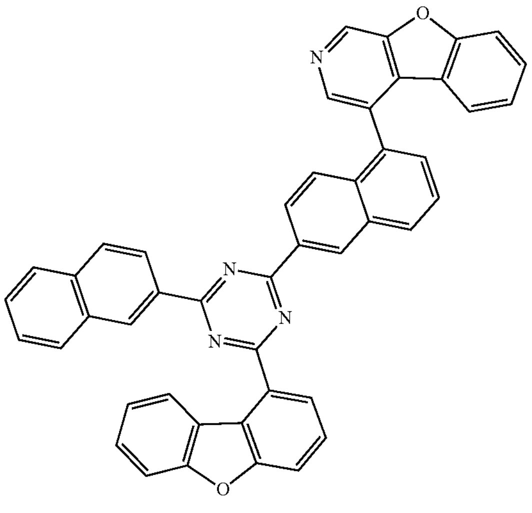
-continued
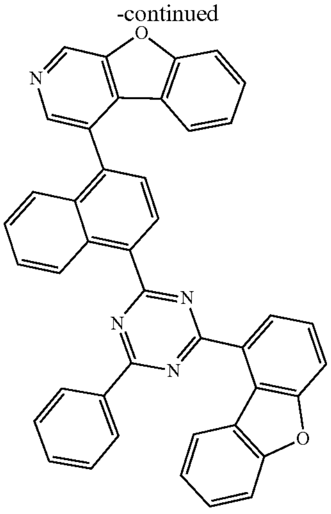
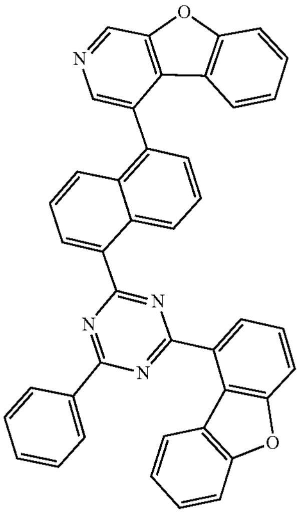
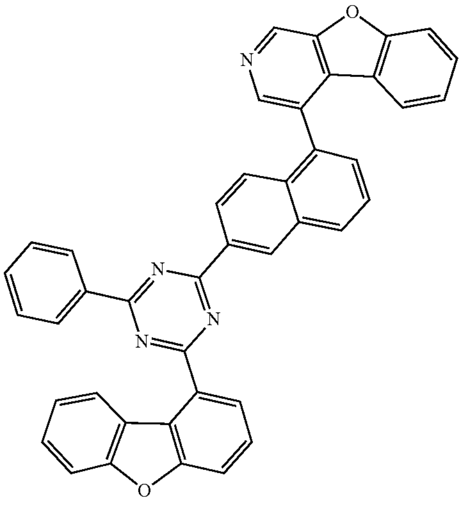

-continued
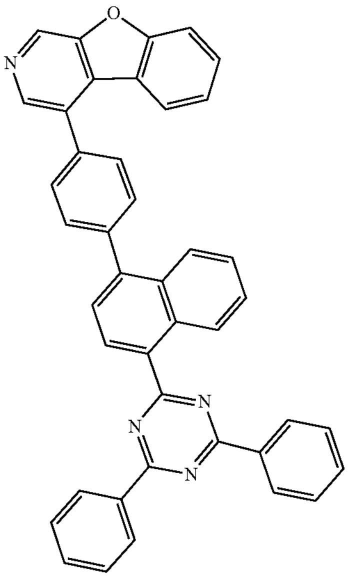
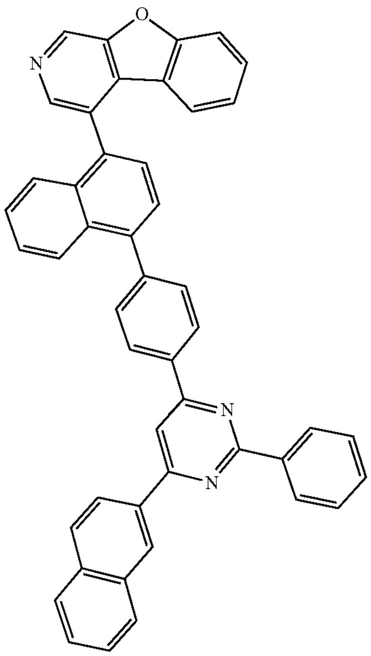
-continued
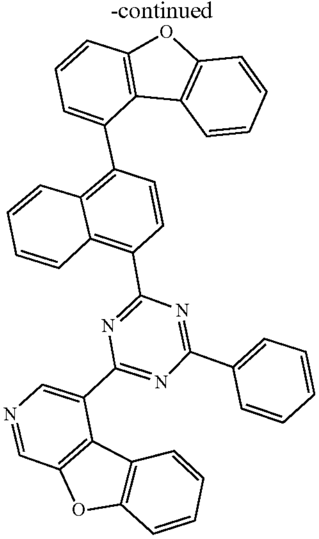
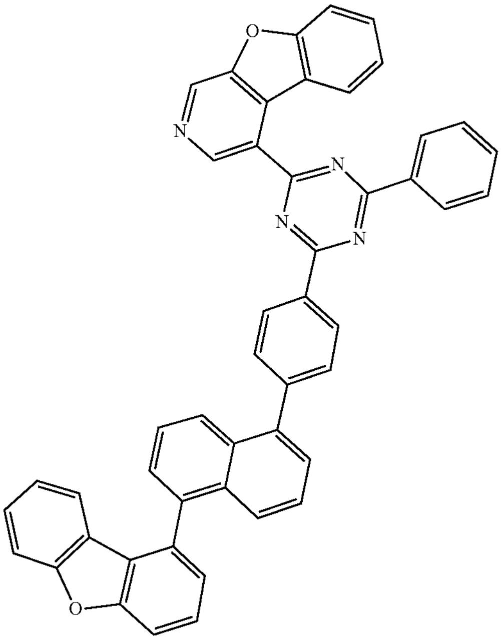
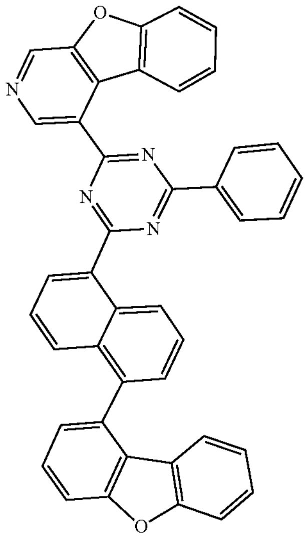

-continued
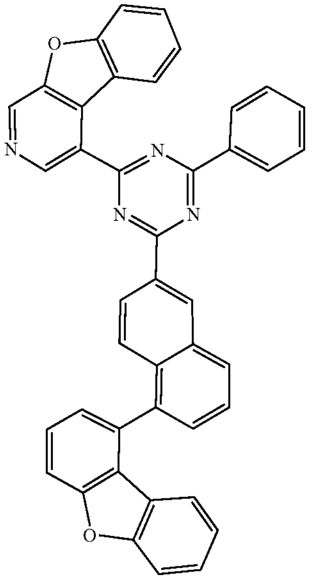
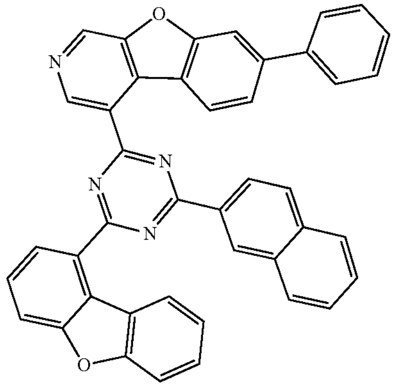
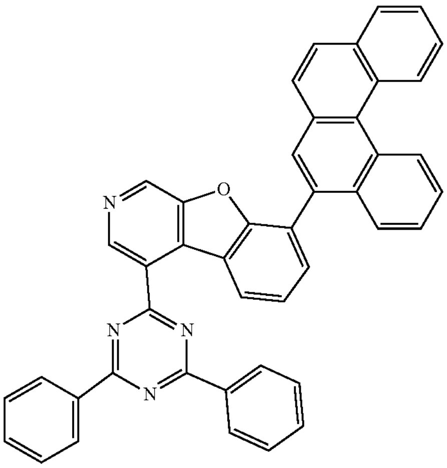
-continued
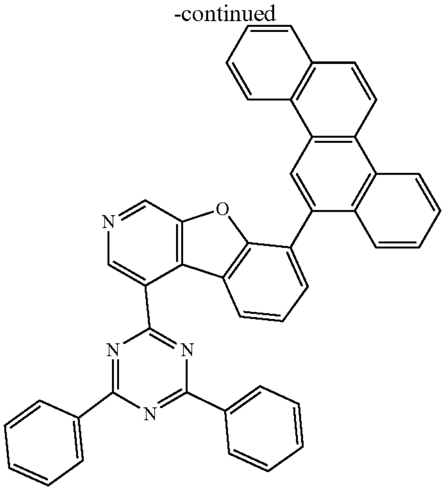
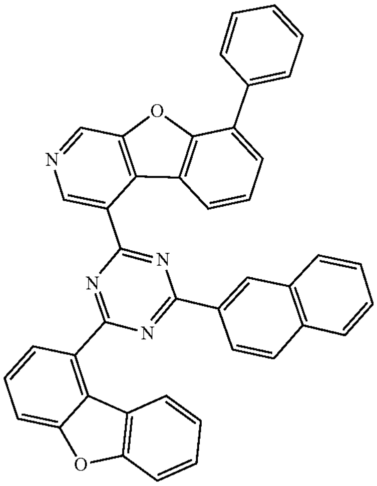
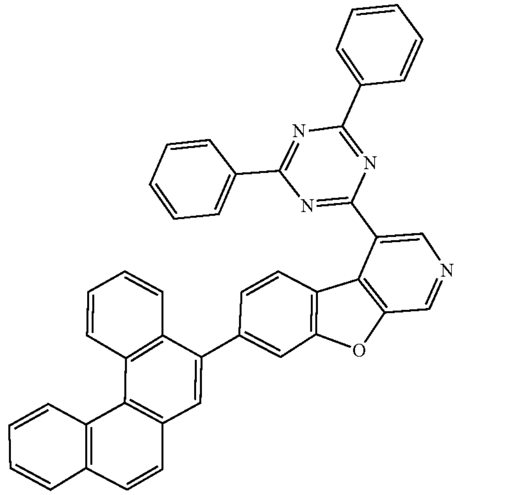
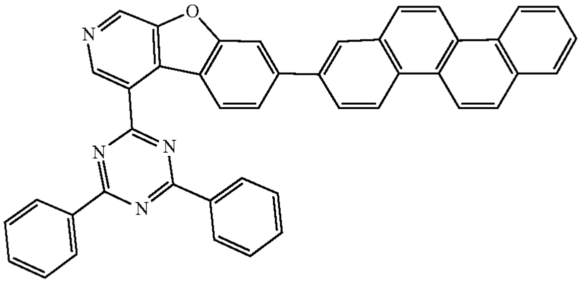

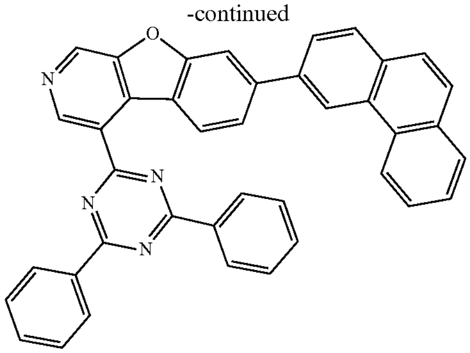
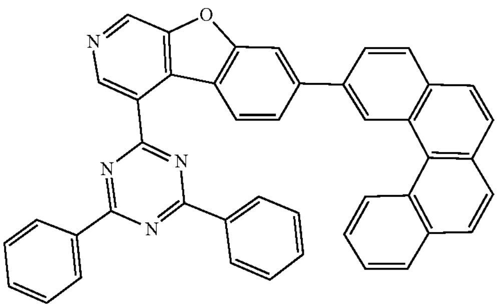
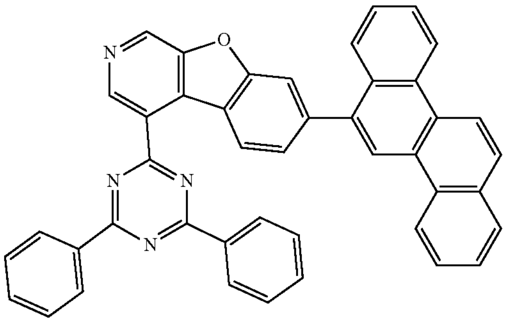
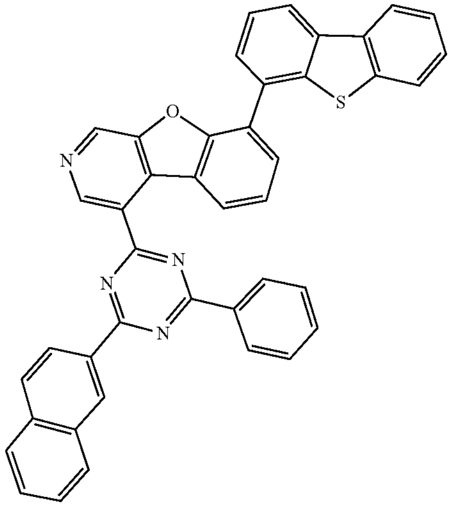
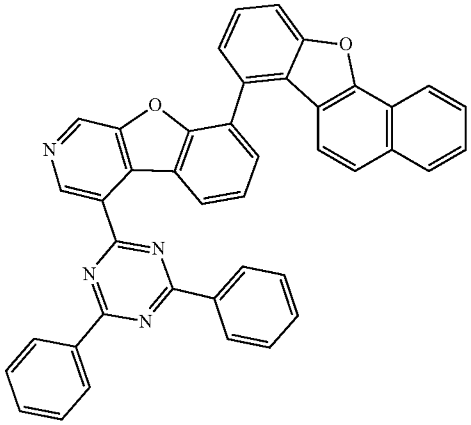
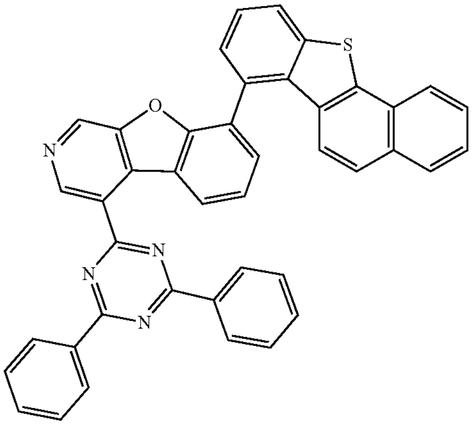
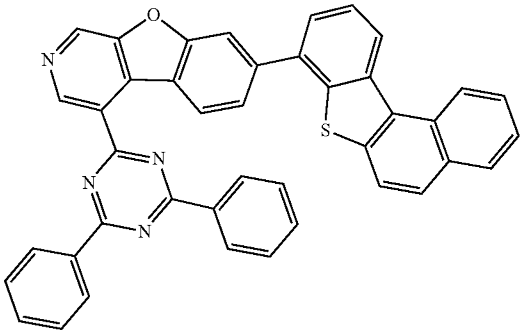
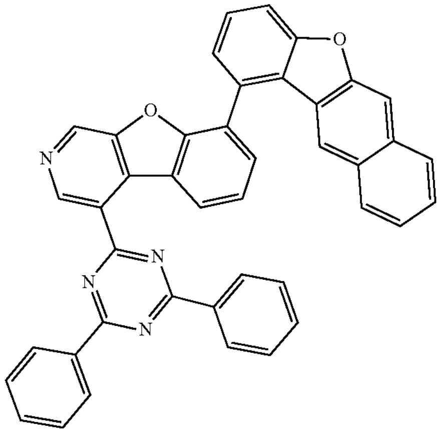

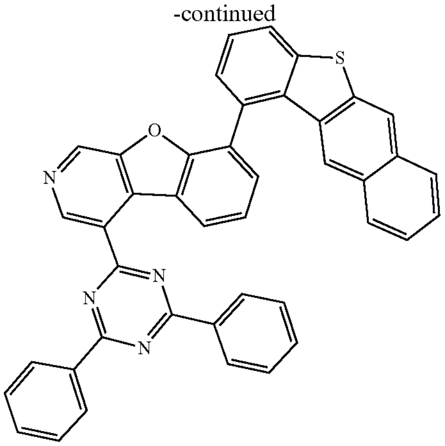
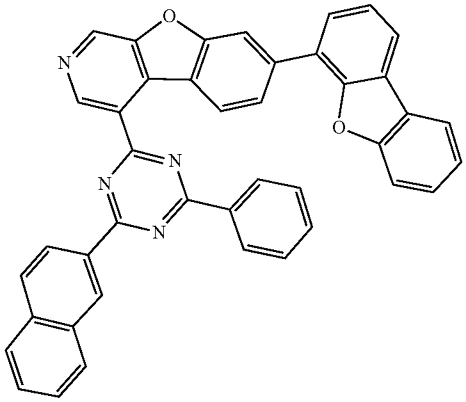
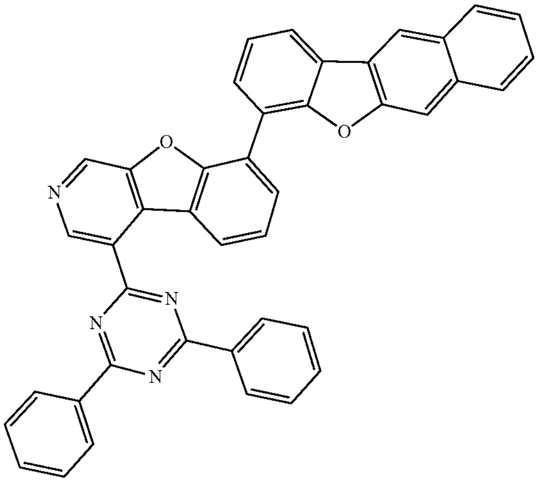
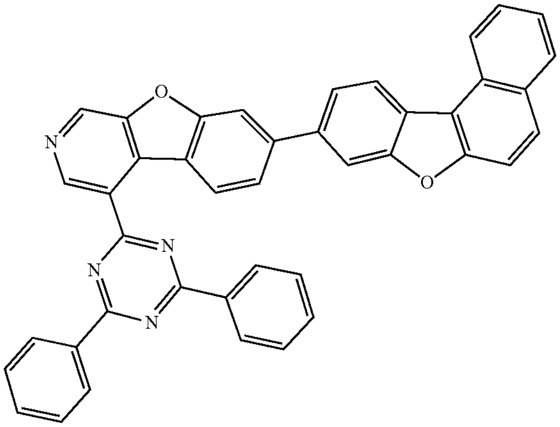
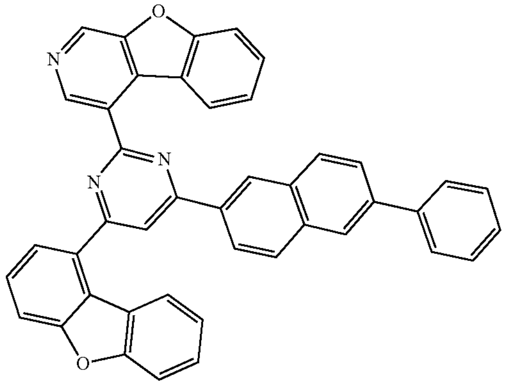
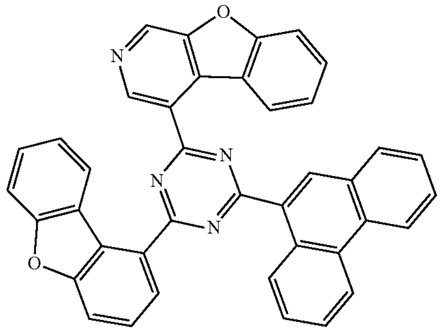
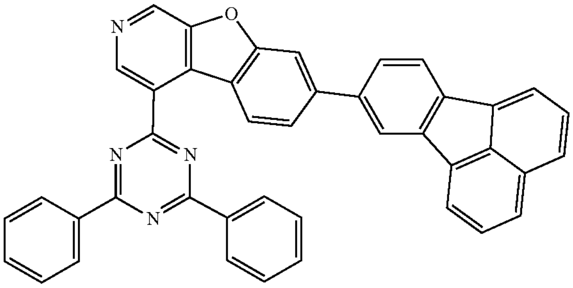
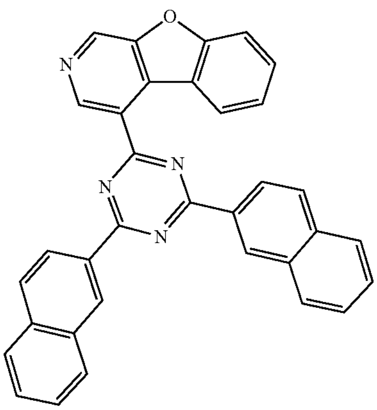

-continued
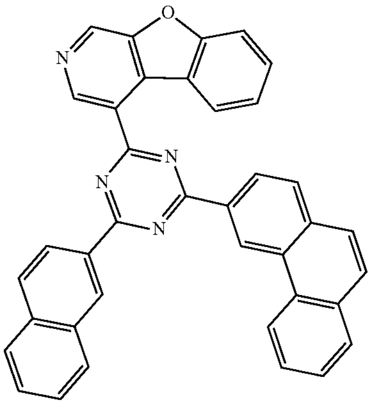
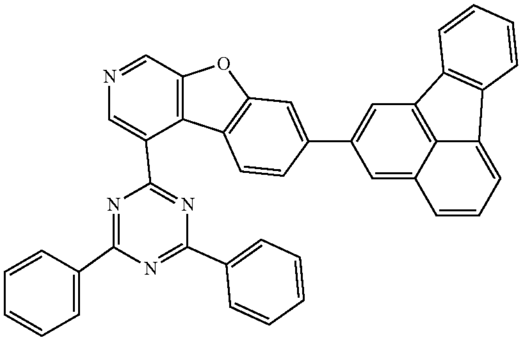
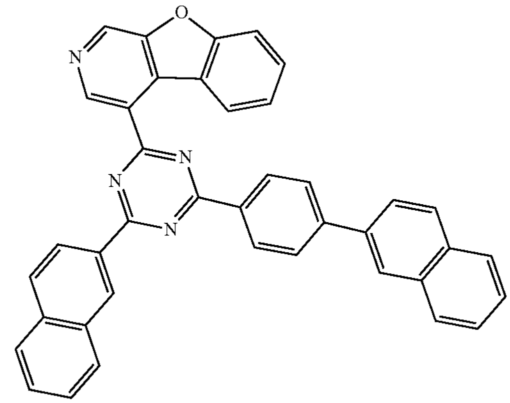
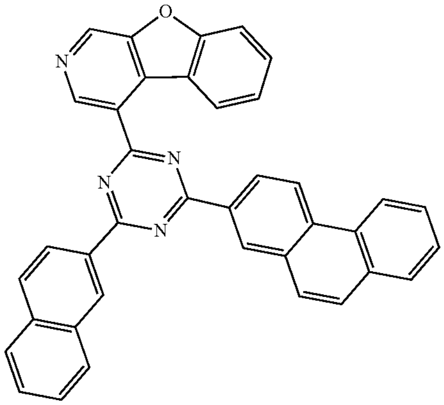
-continued
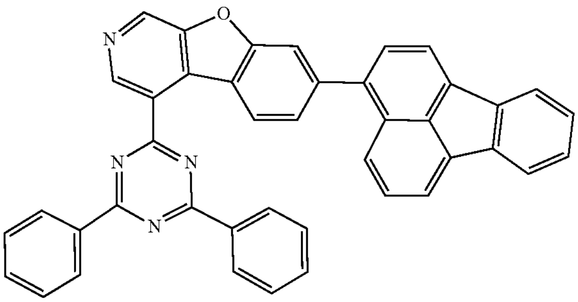
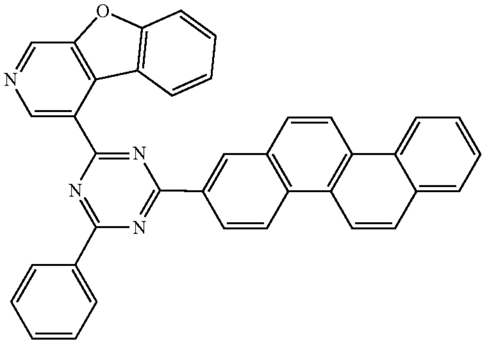
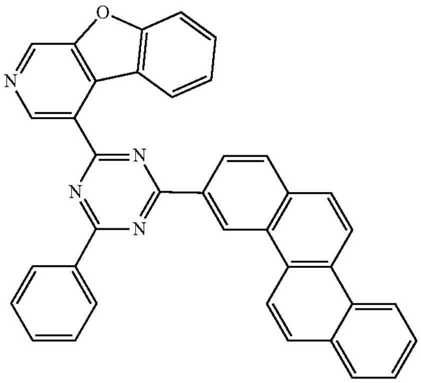
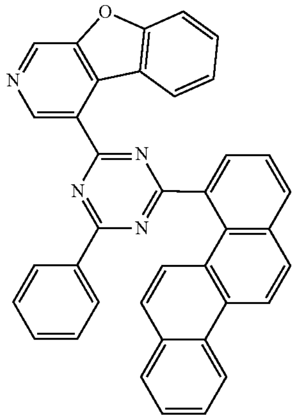

-continued
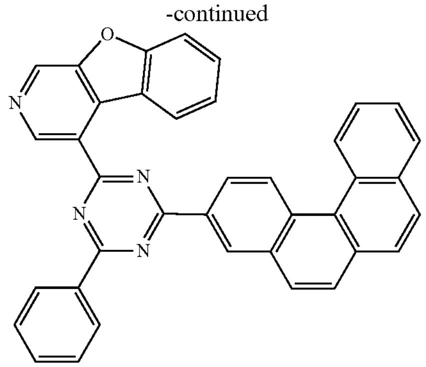
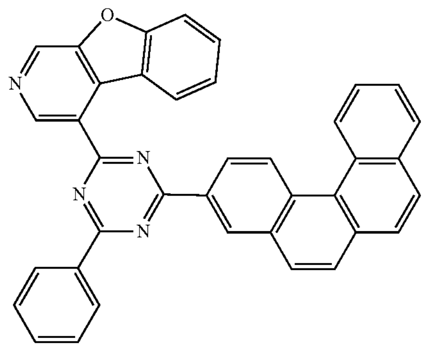
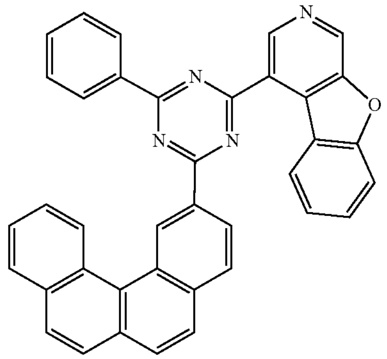
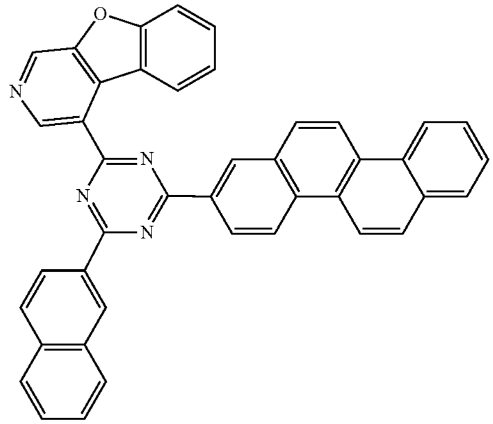
-continued
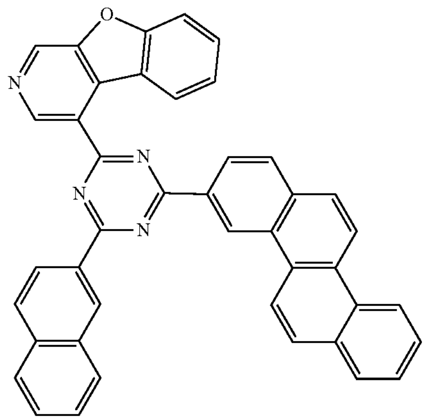
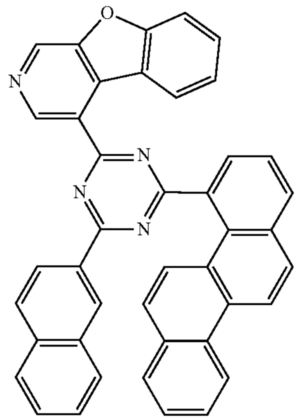
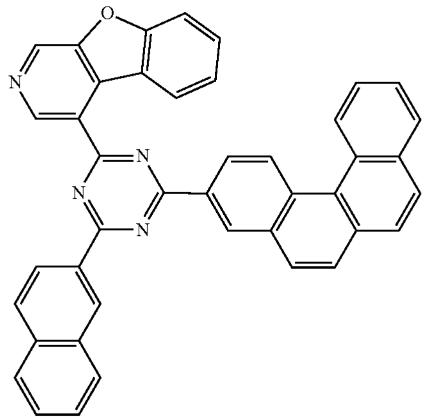
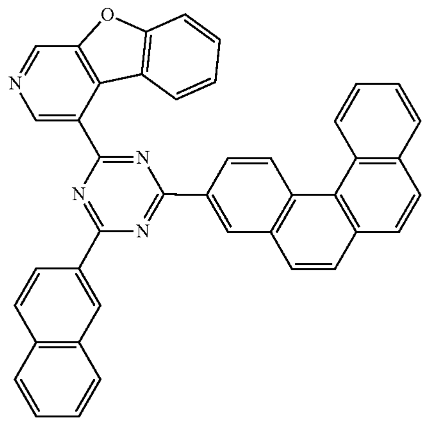

-continued
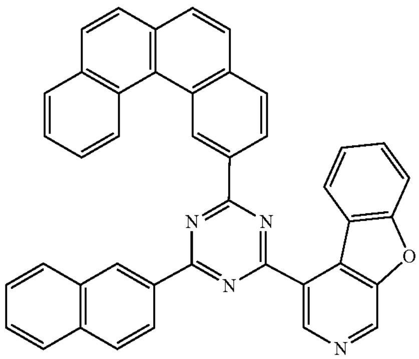
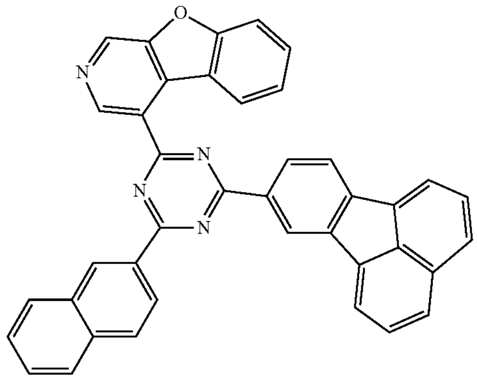
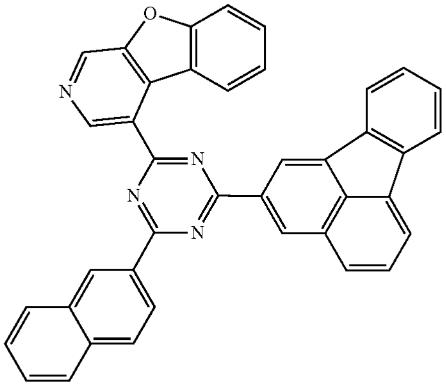
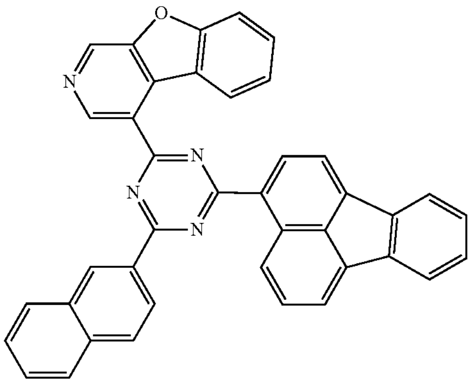
-continued
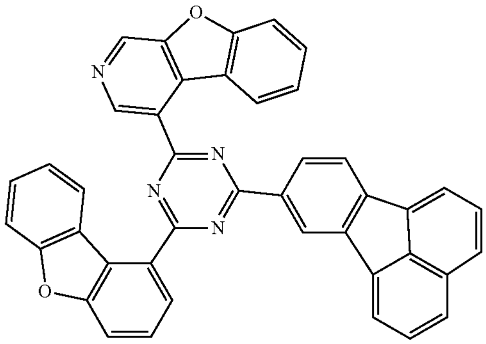
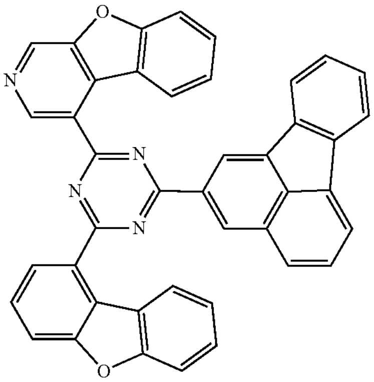
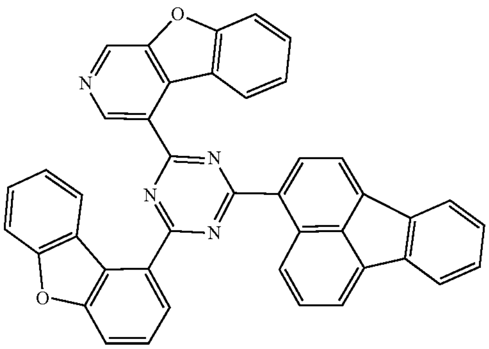
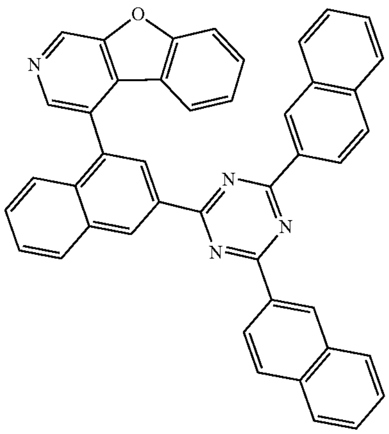

-continued
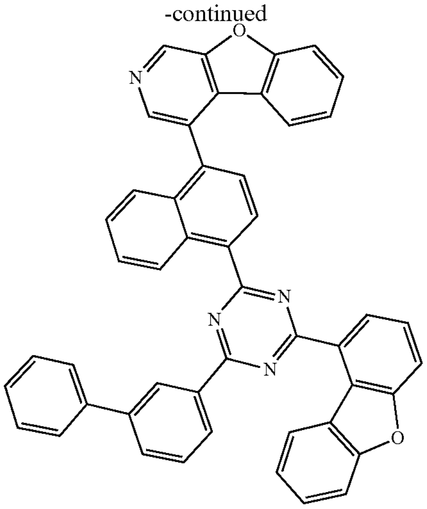
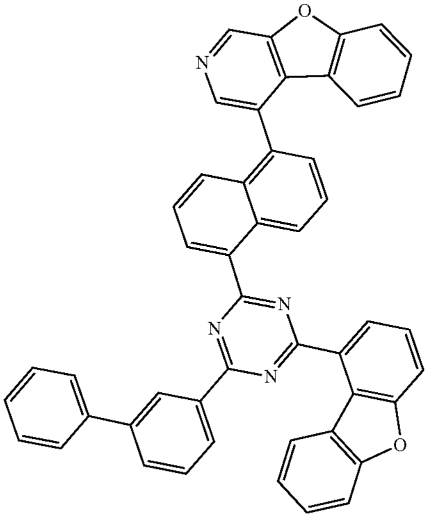
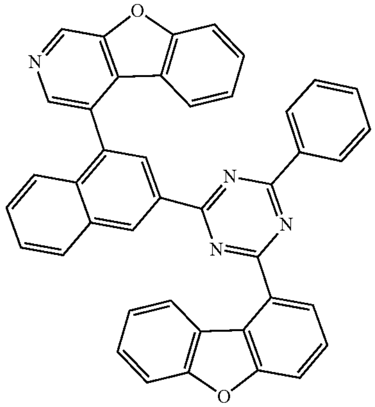
-continued
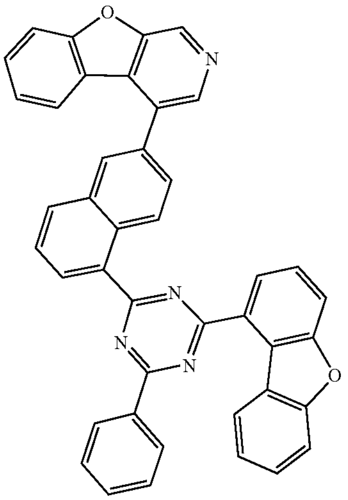
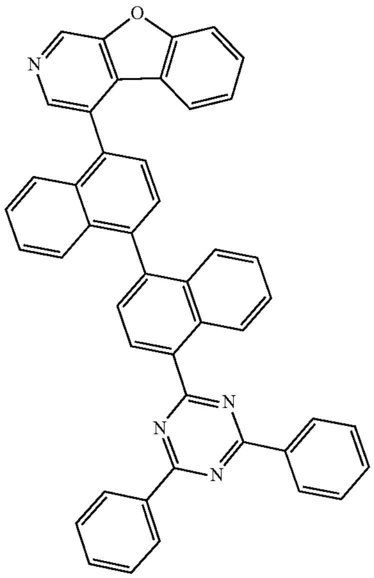
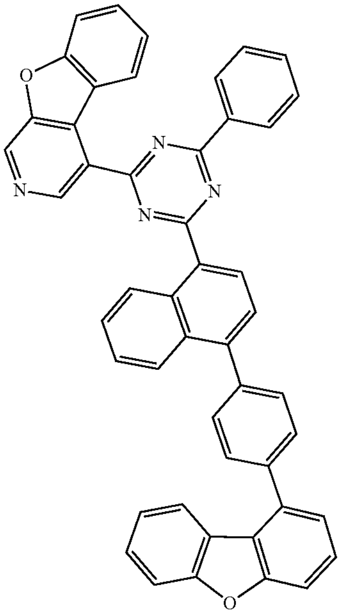

-continued
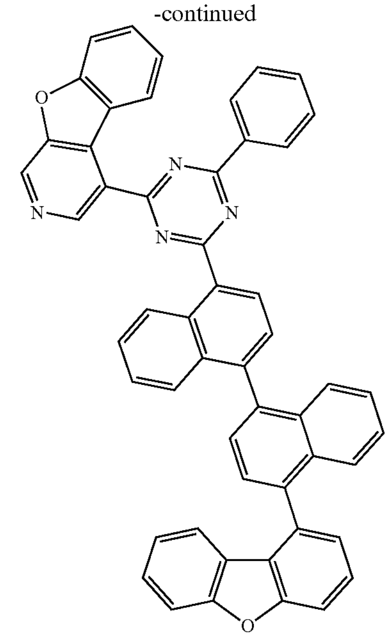
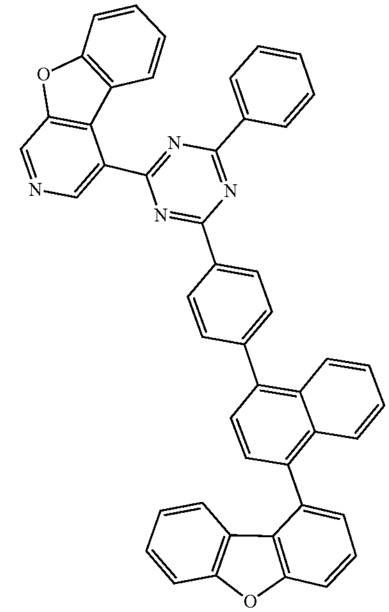
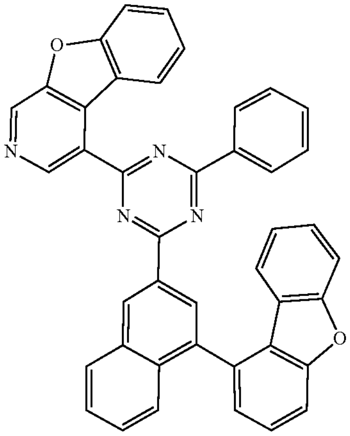
-continued
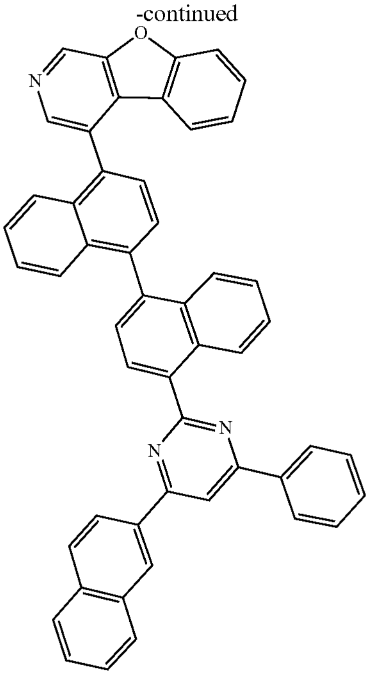
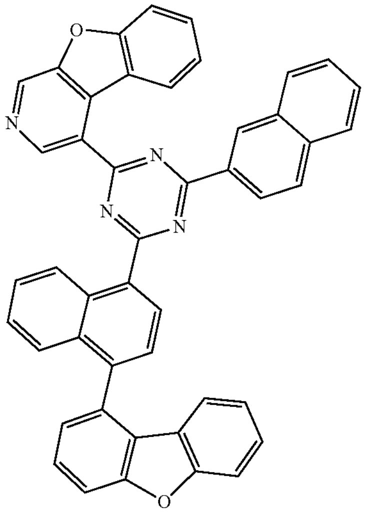
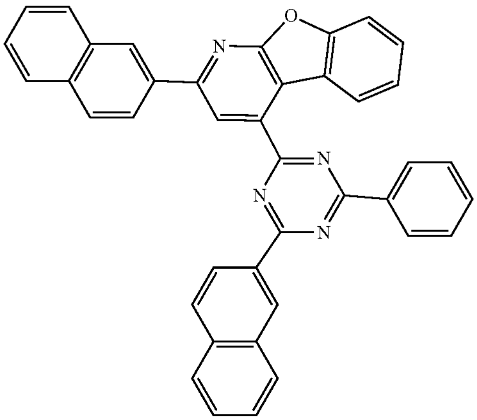

-continued
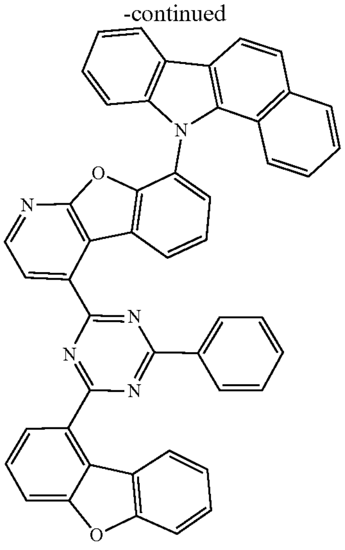
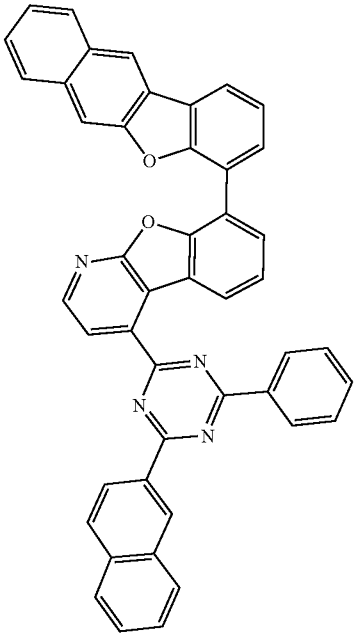
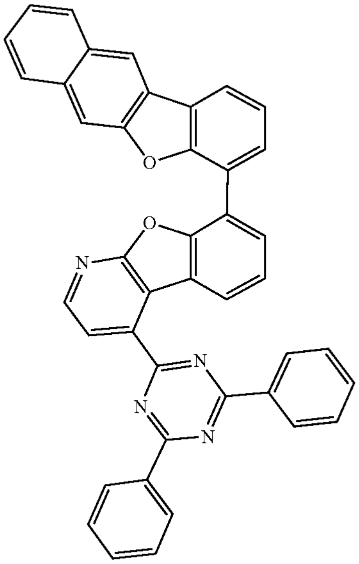
-continued
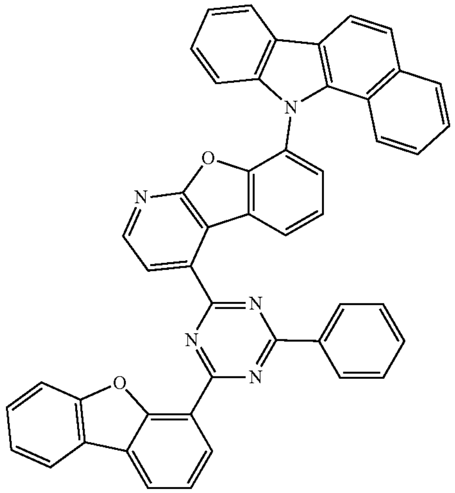
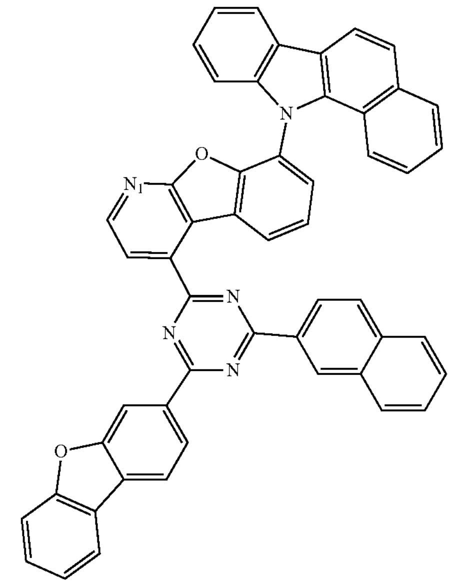
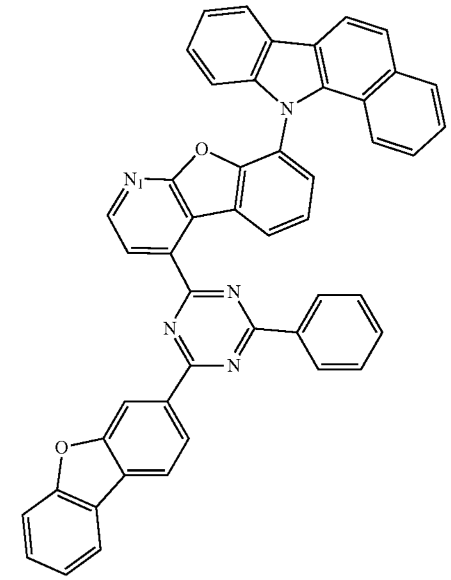

-continued
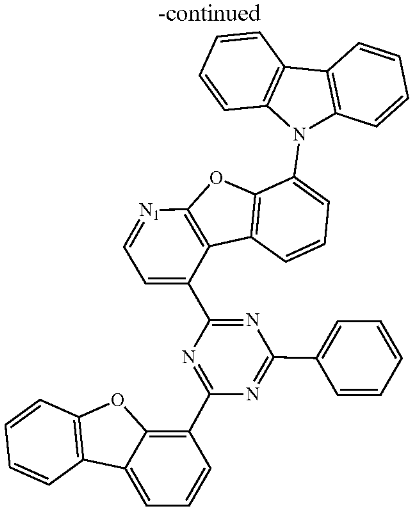
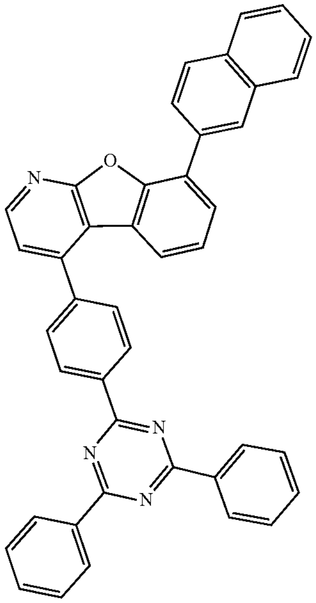
-continued
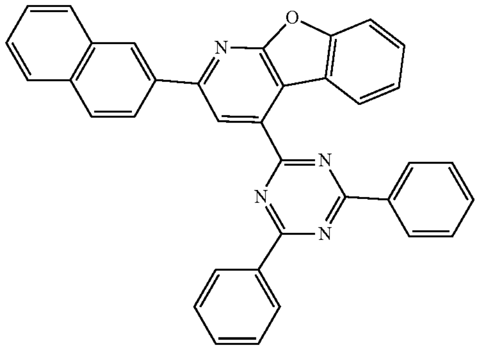
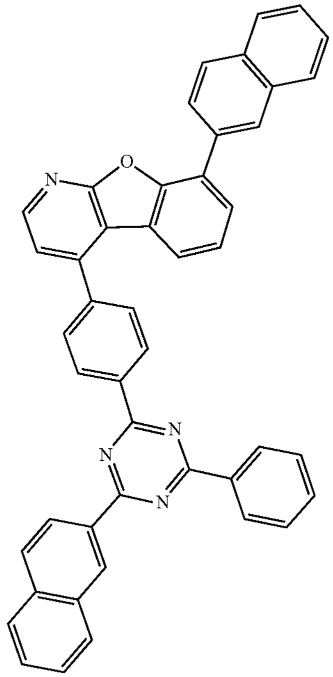
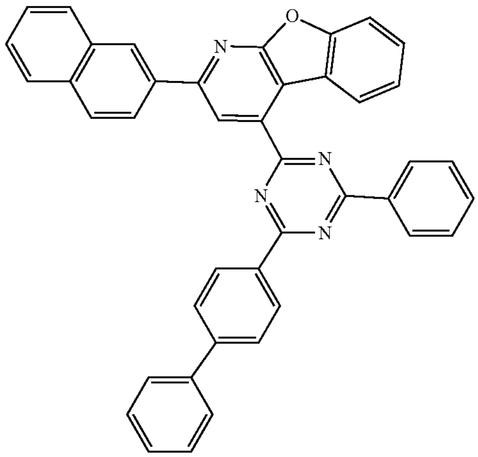

-continued
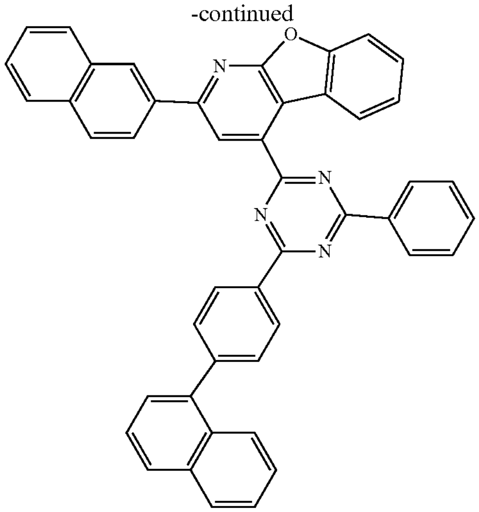
-continued
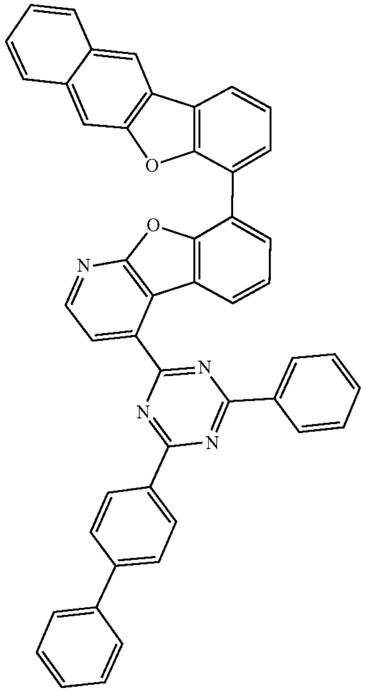
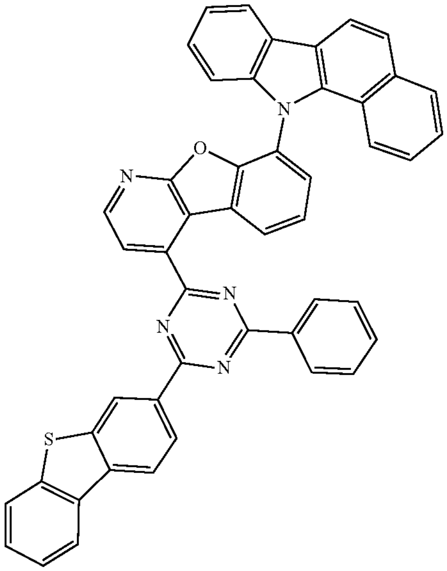
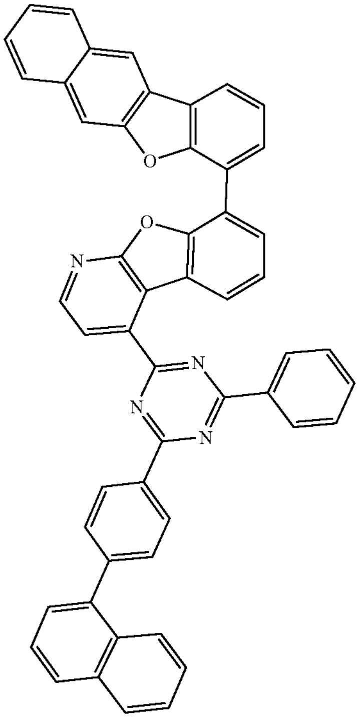

-continued
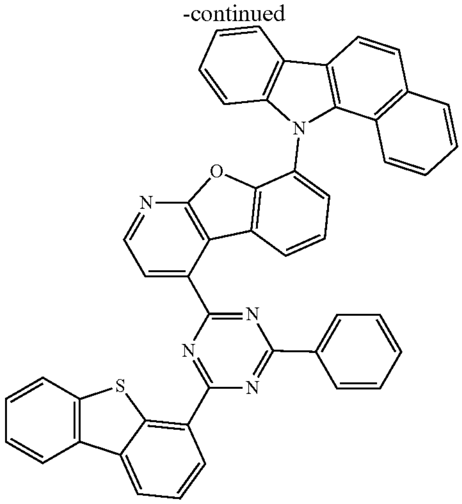
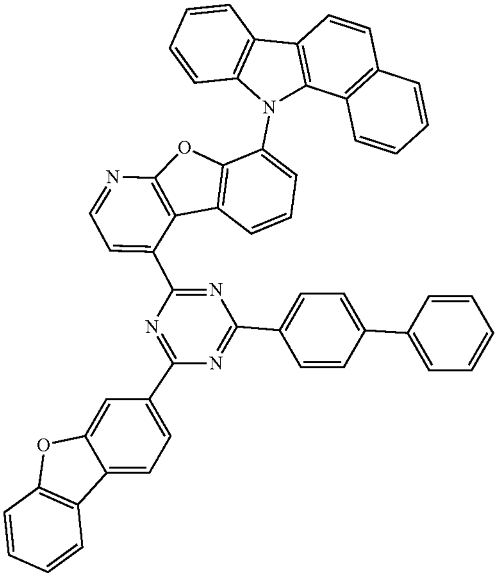
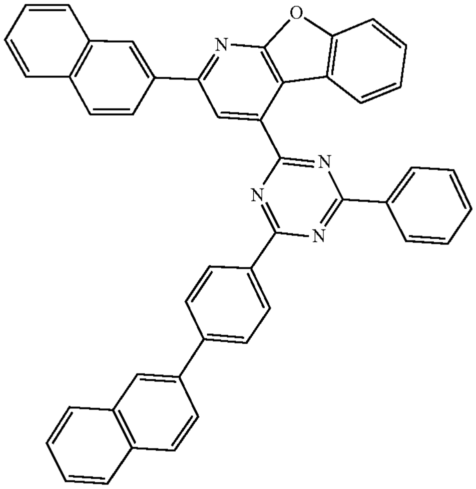
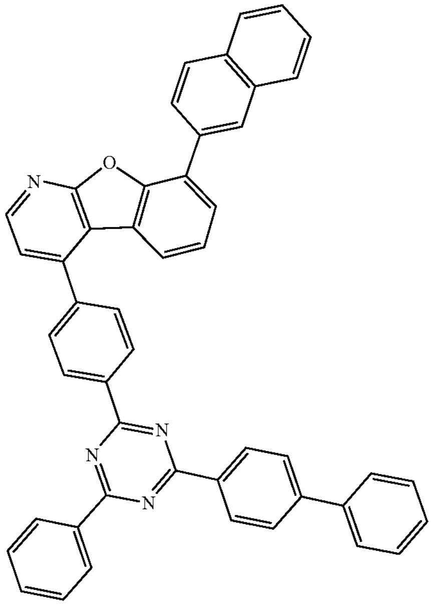
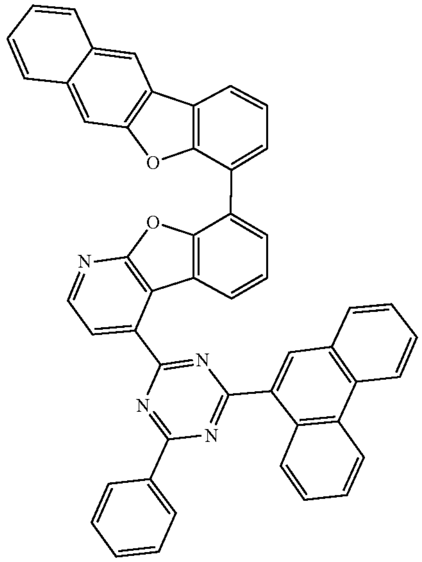
-continued
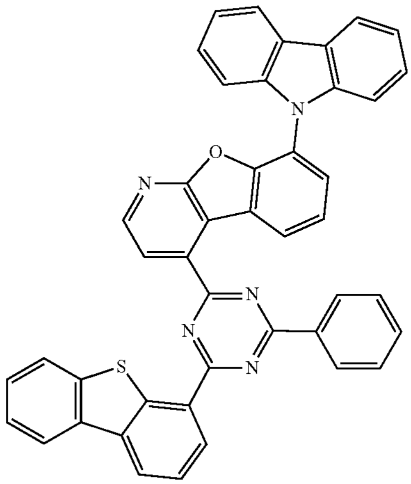

-continued
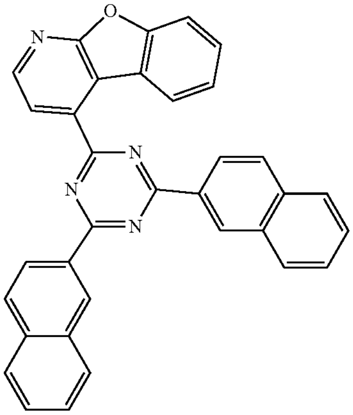
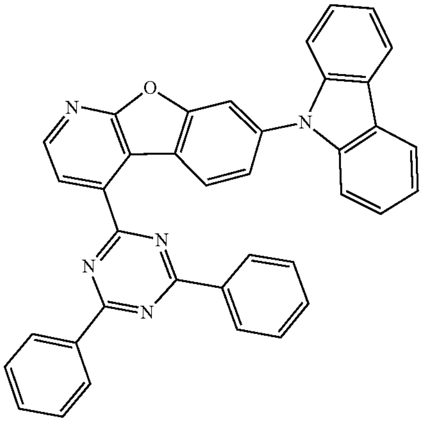
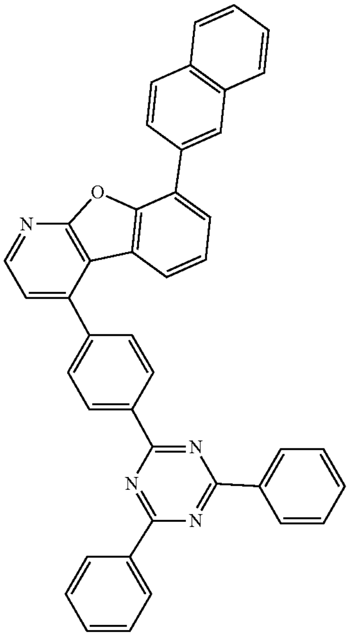
-continued
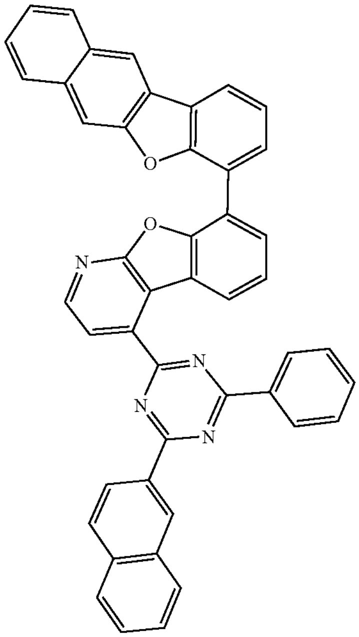
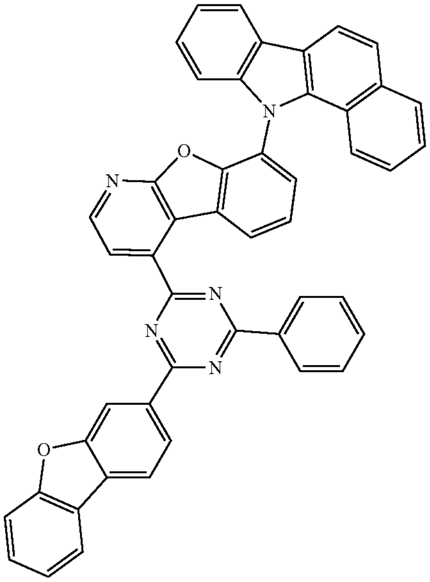
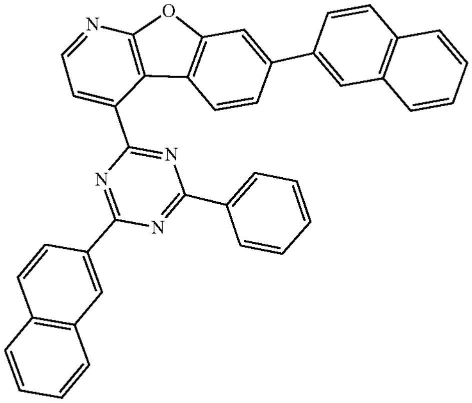

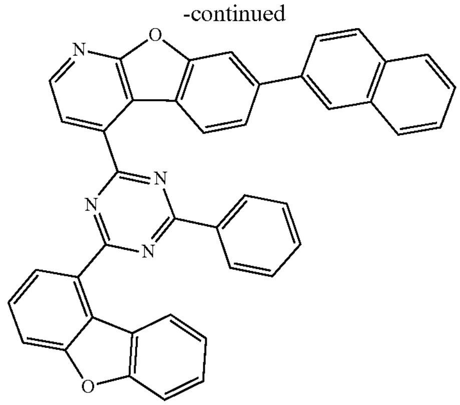
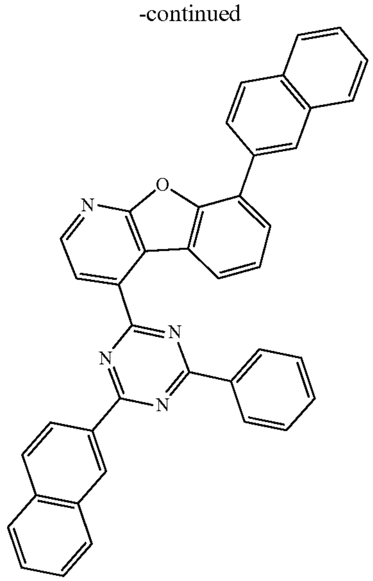
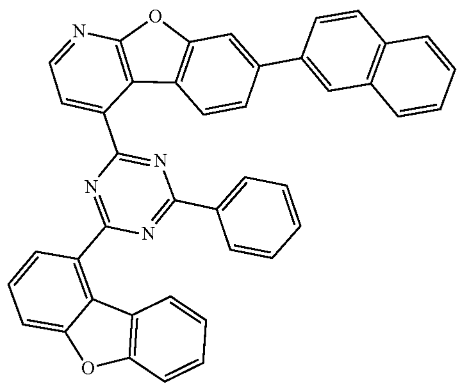
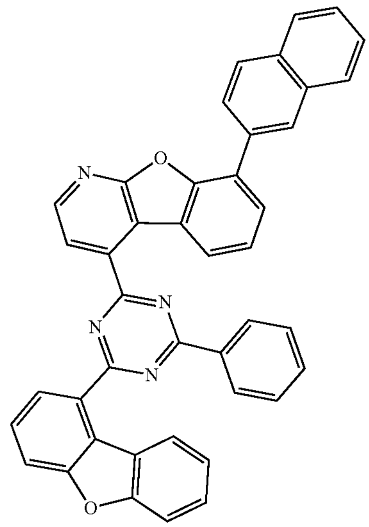
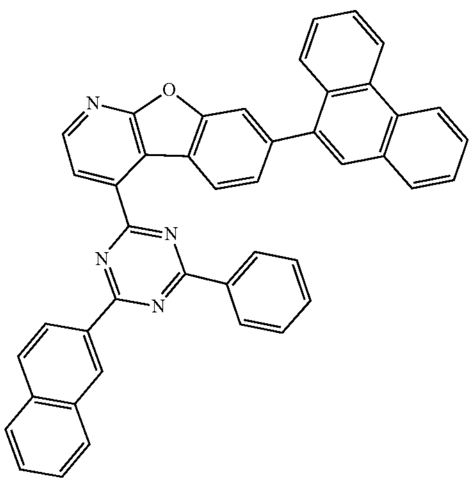
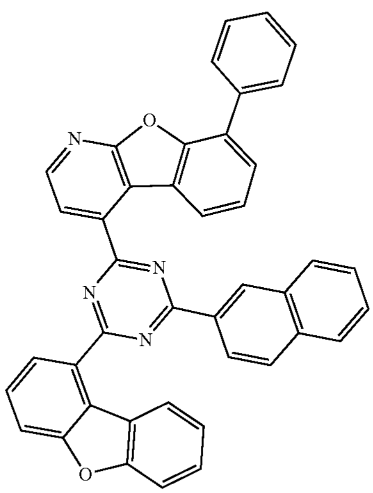

-continued
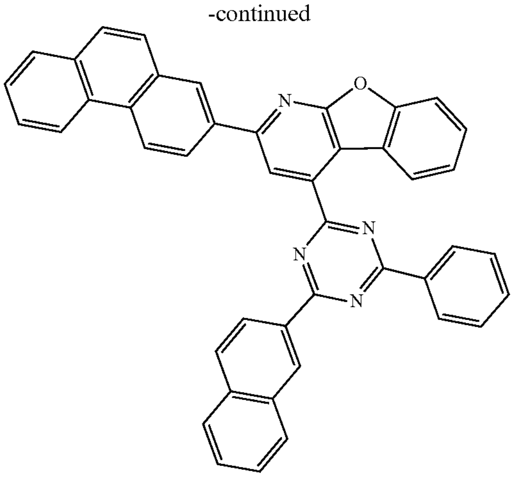
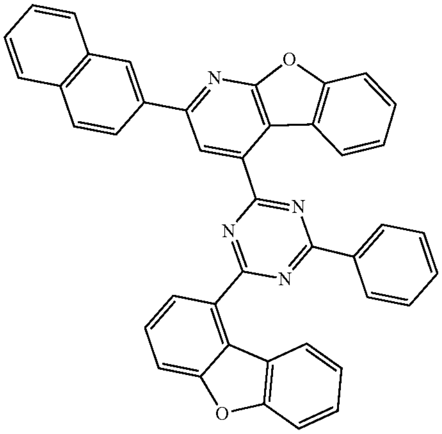
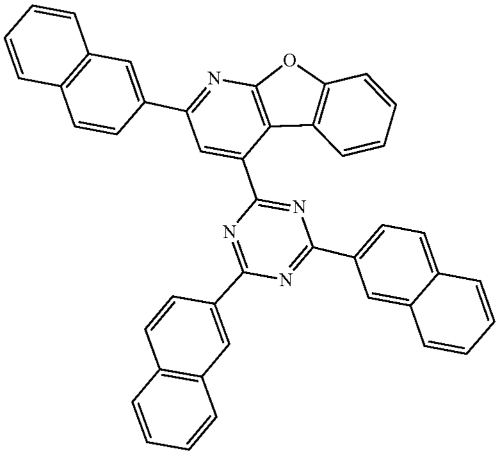
-continued
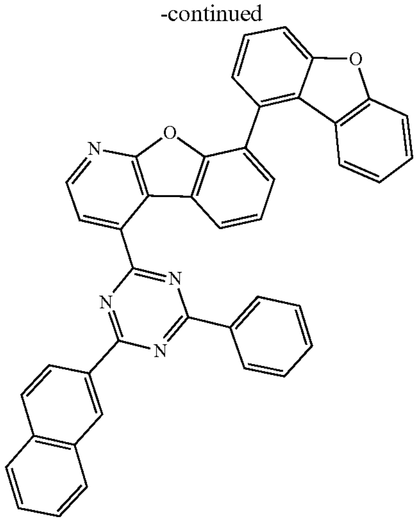
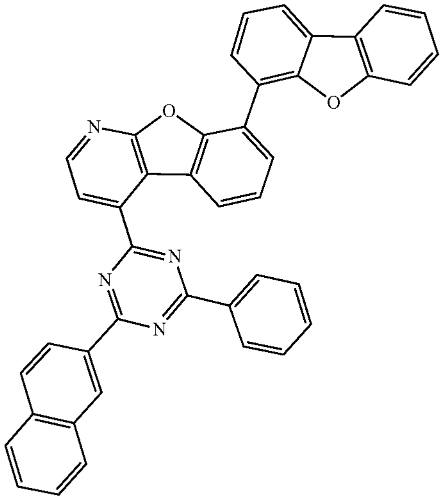
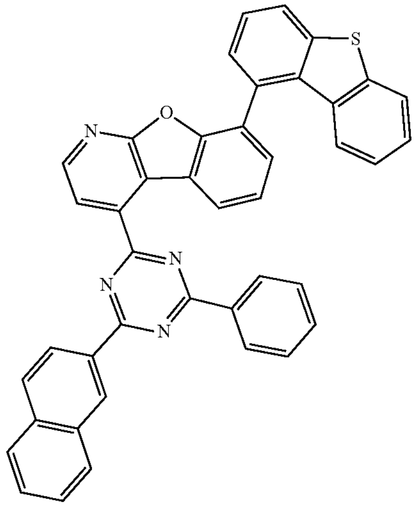

-continued
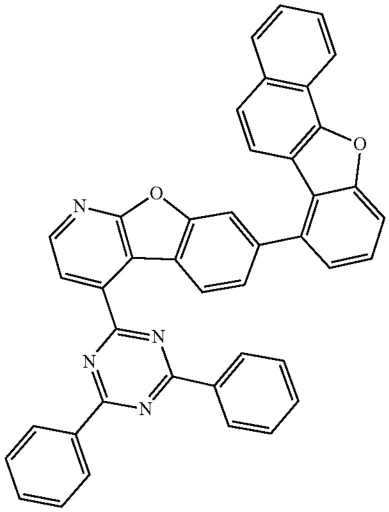
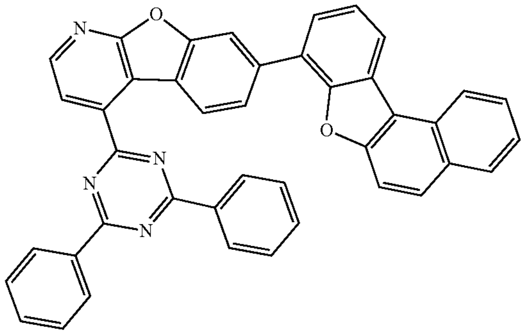
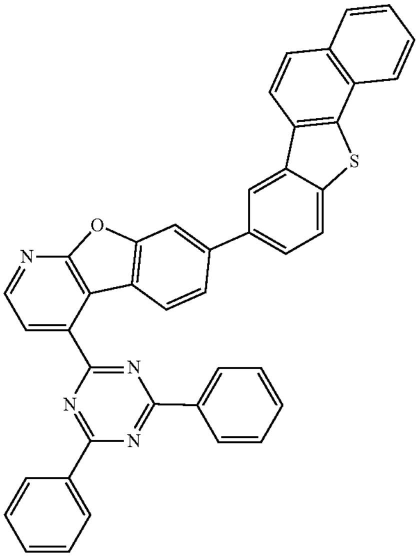
-continued
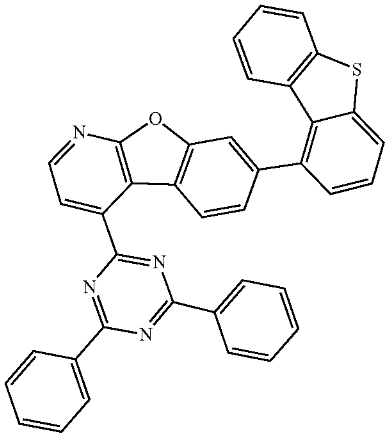
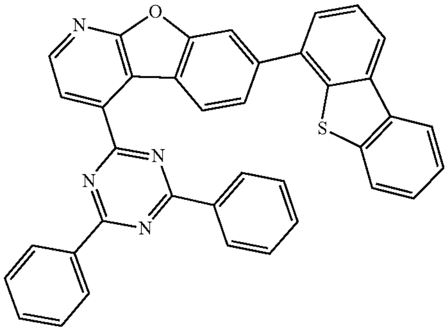
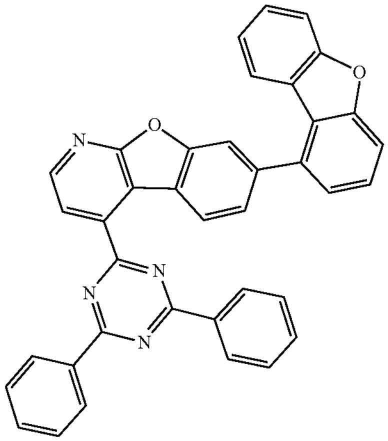
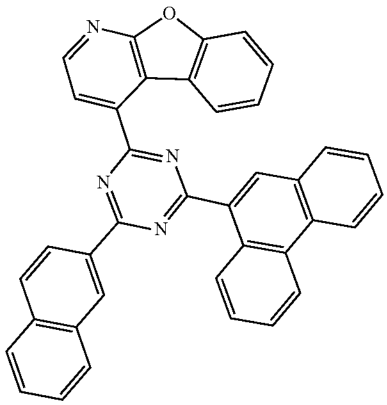

-continued
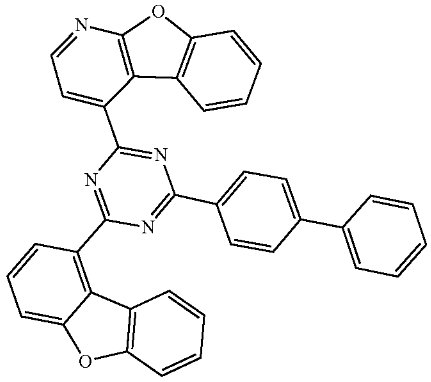
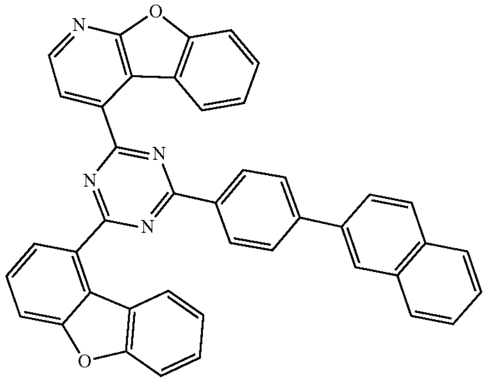
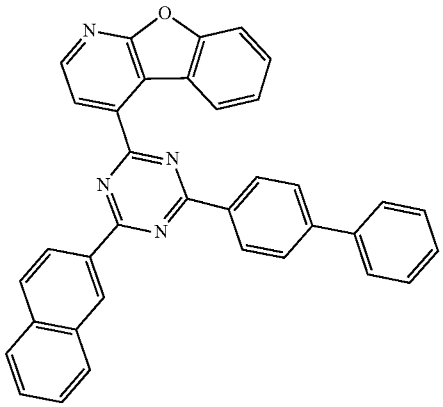
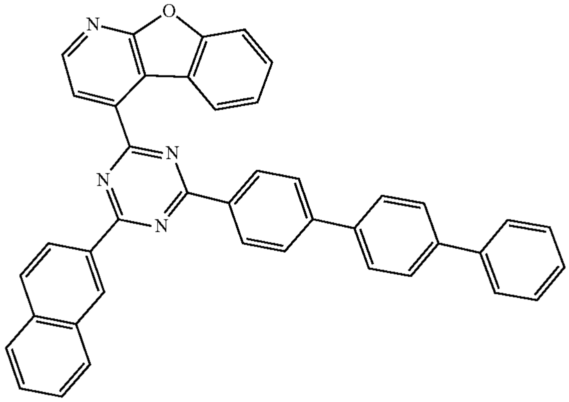
-continued
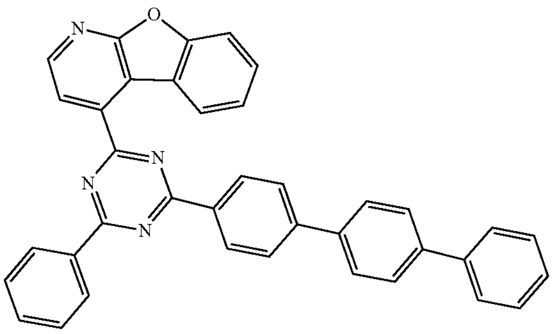 [SMILES: c1ccc(-c2ccc(-c3ccc(-c4nc(-c5ccccc5)nc(-c5ccnc6oc7ccccc7c56)n4)cc3)cc2)cc1]
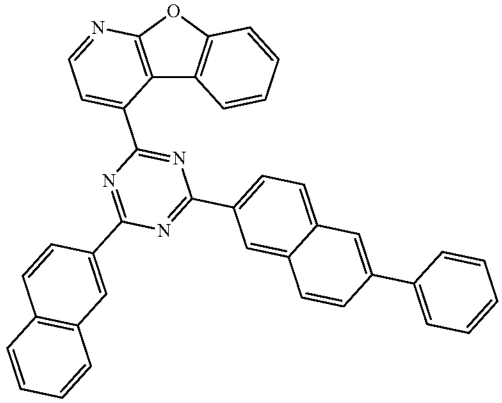
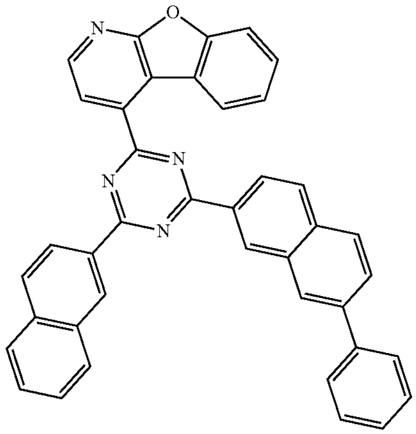
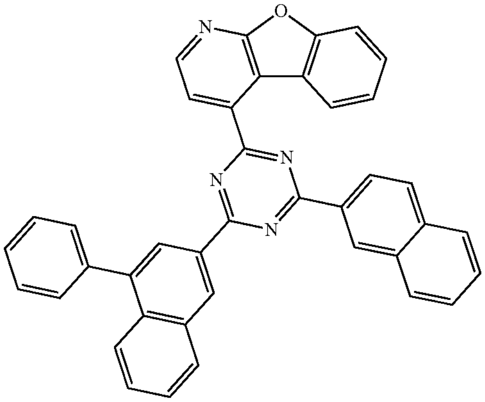

-continued
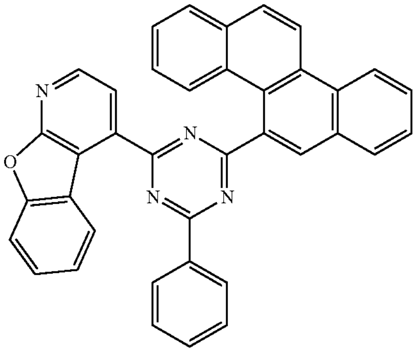
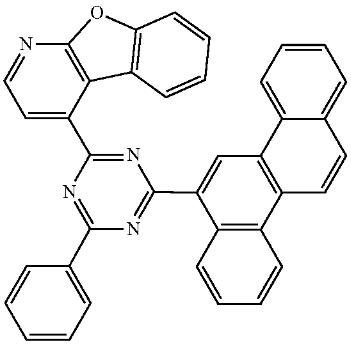
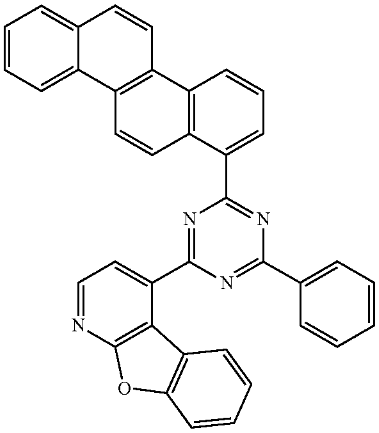
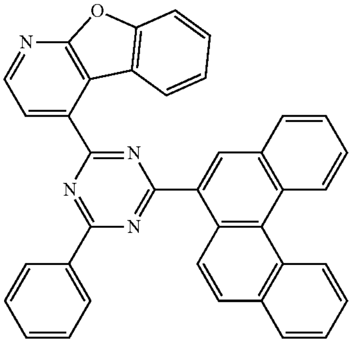
-continued
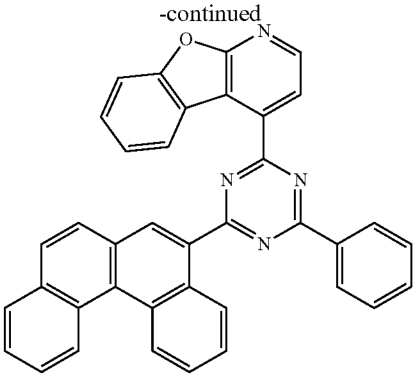
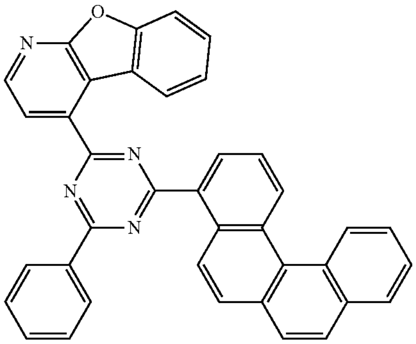
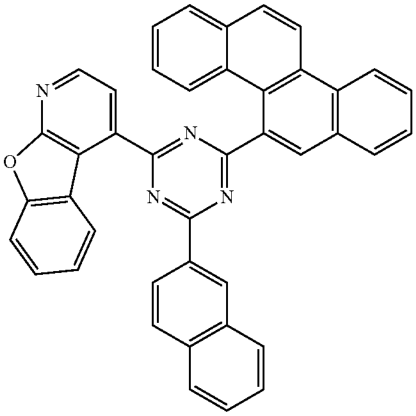
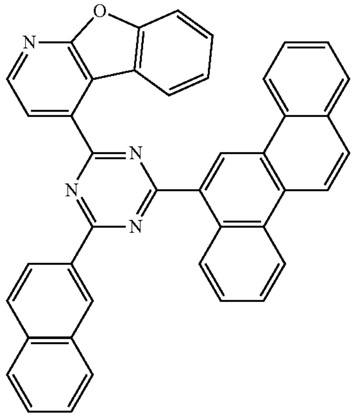

-continued
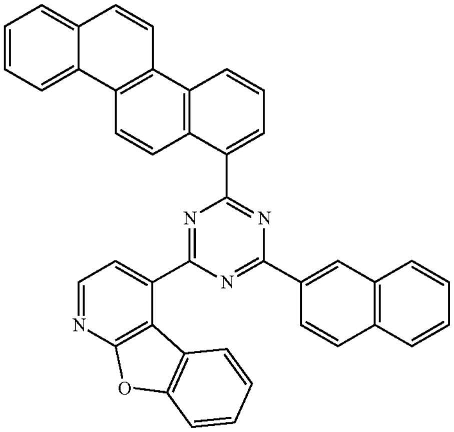
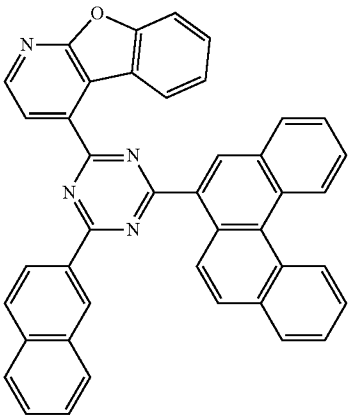
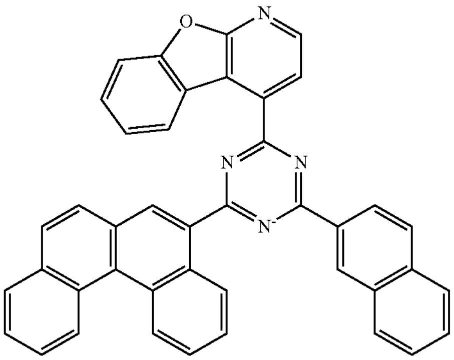
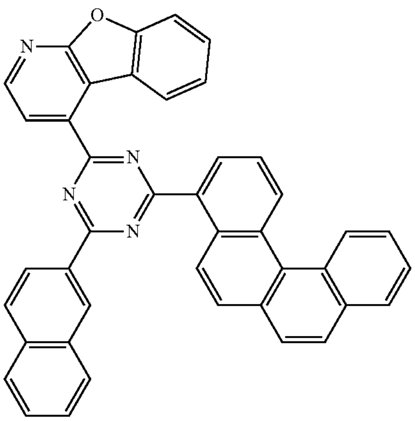
-continued
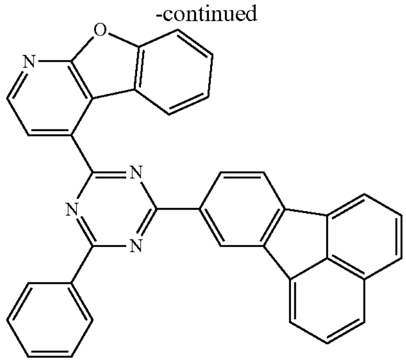
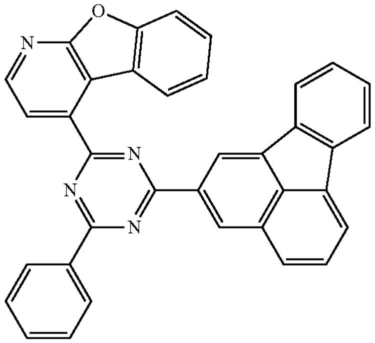
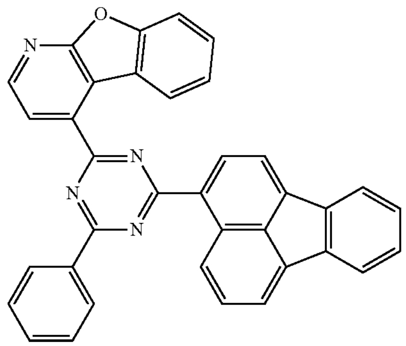
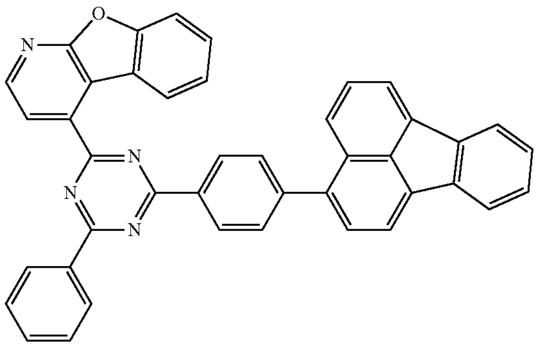
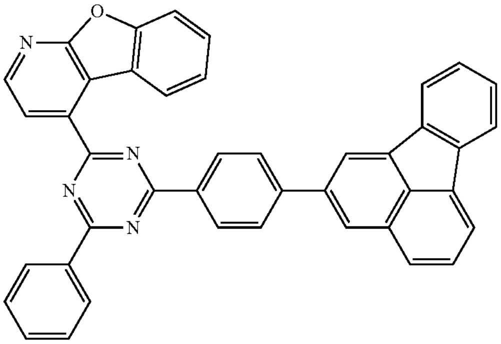

-continued
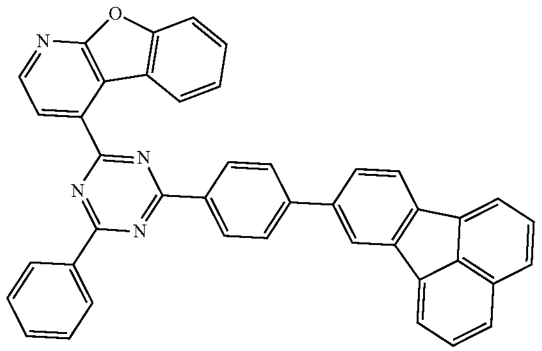
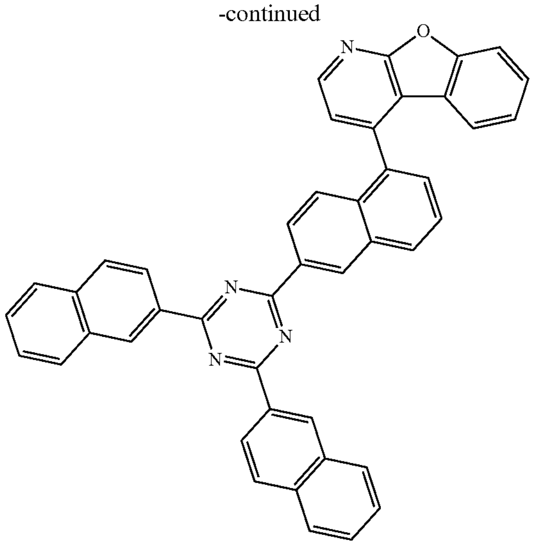
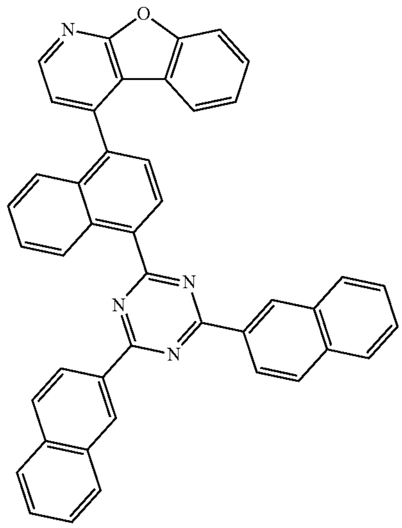
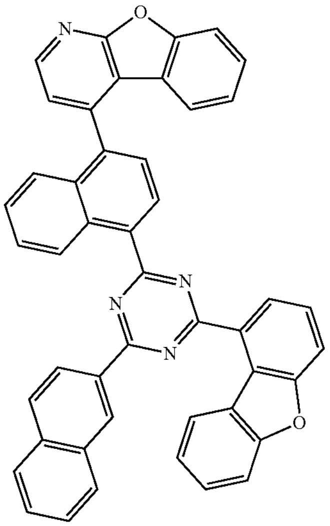
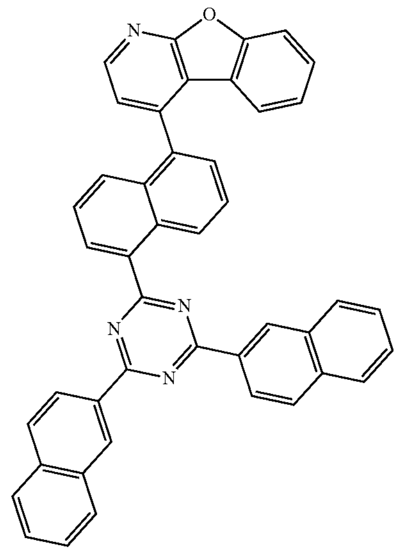
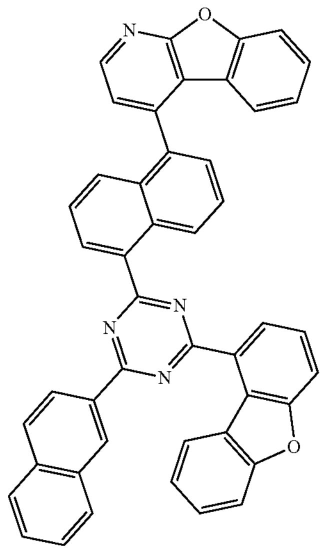
-continued

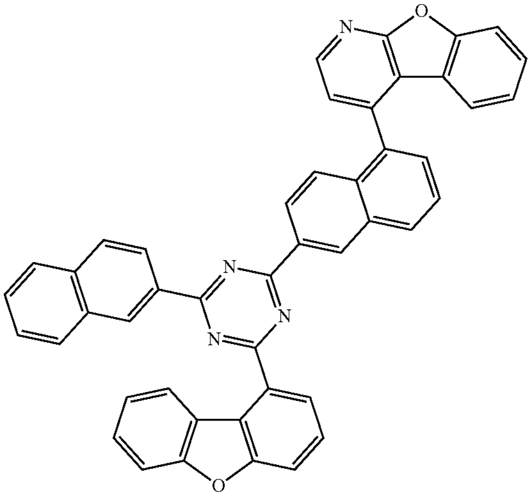
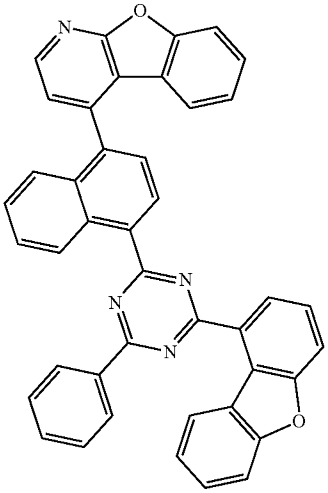
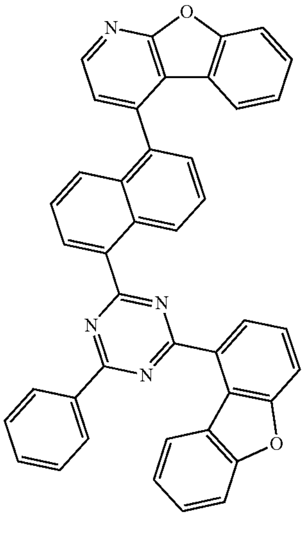
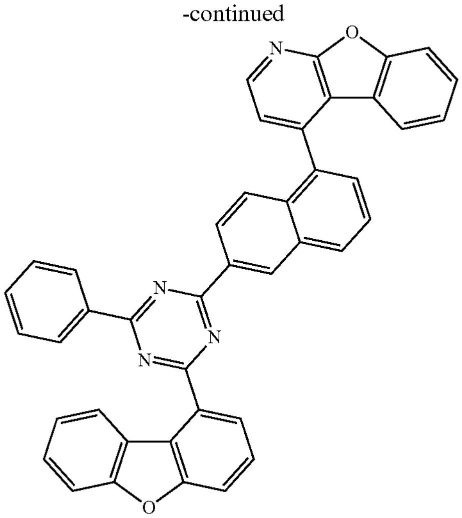
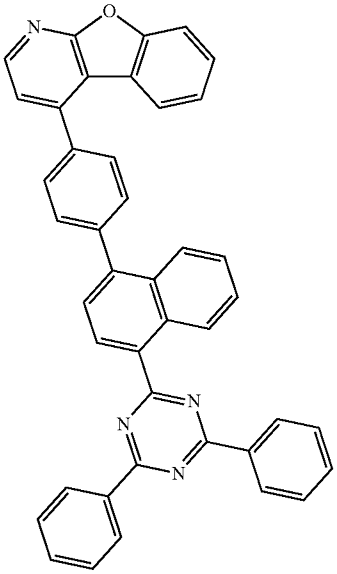
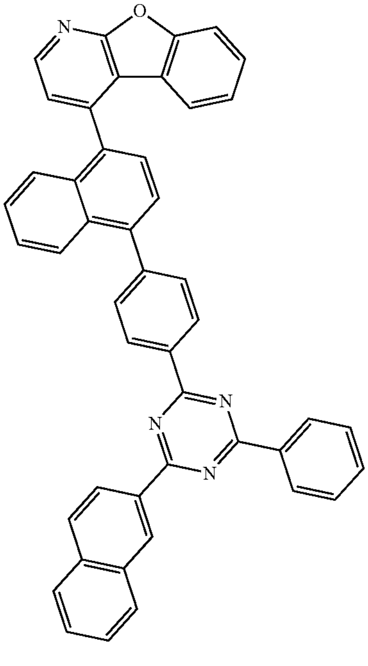

-continued
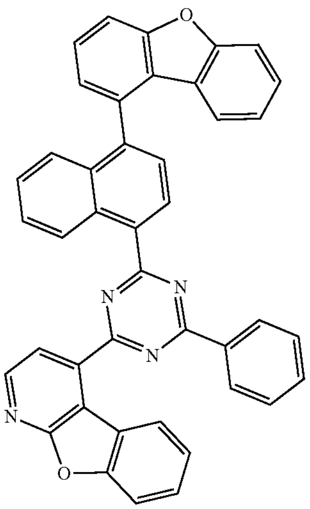
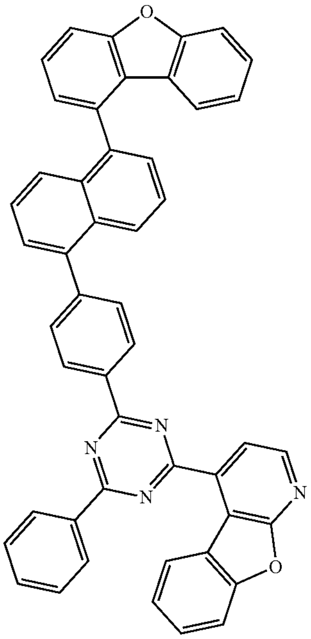
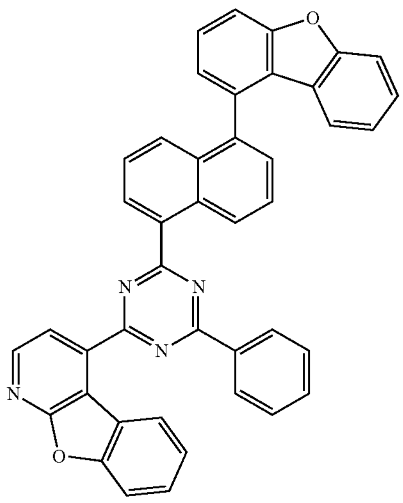
-continued
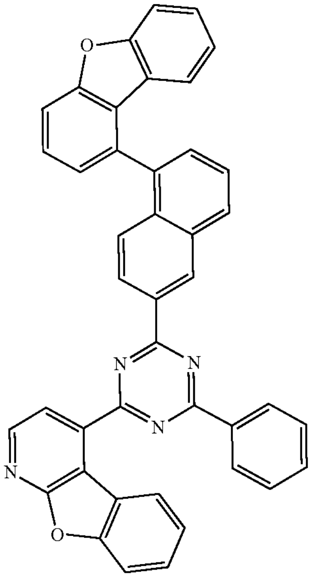
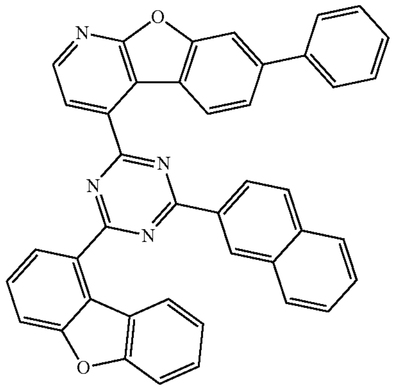
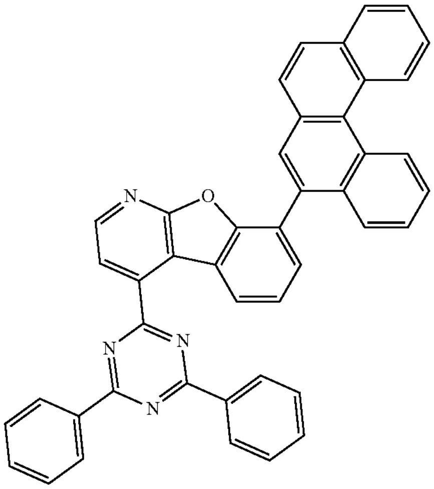

-continued
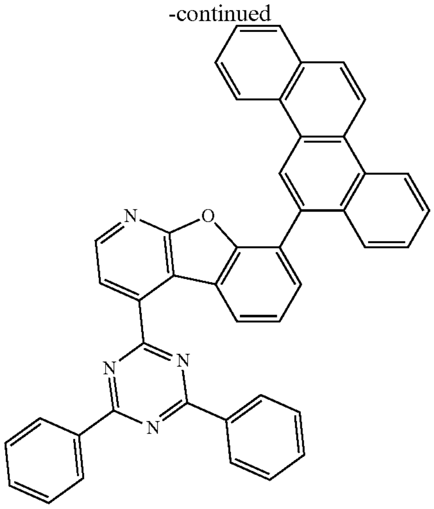
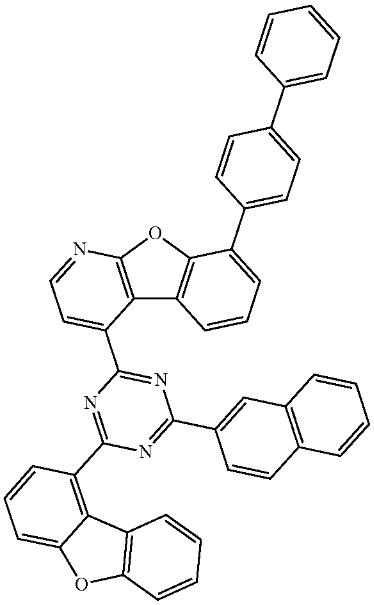
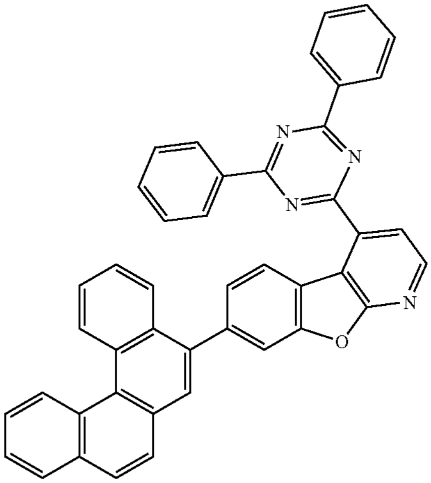
-continued
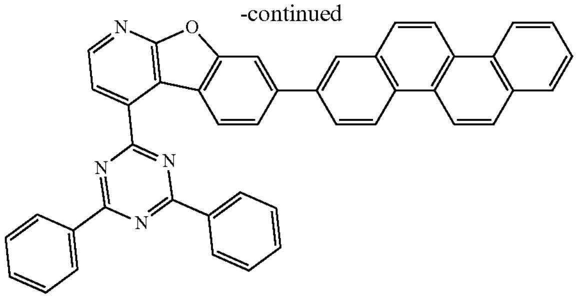
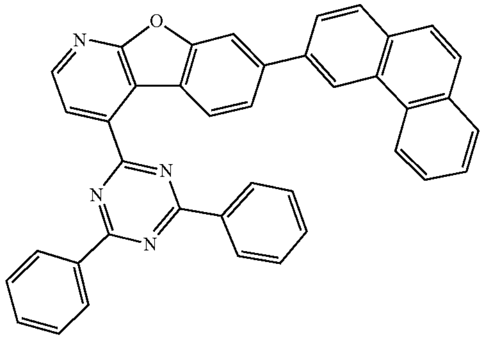
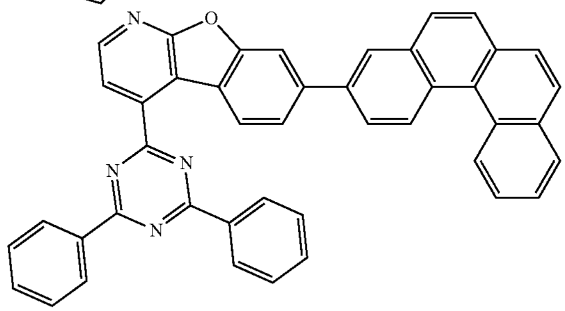
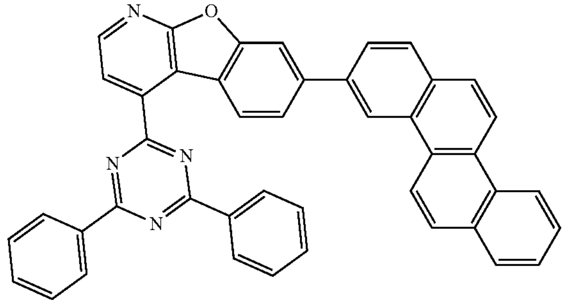
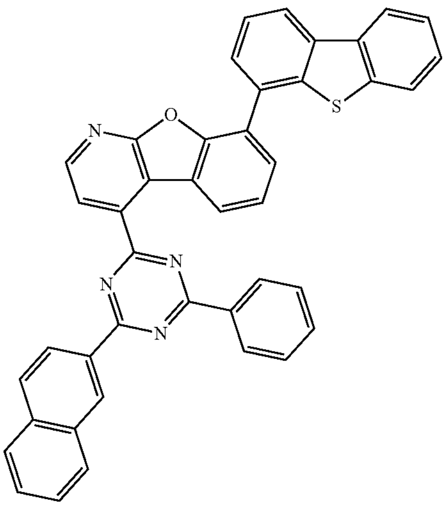

-continued
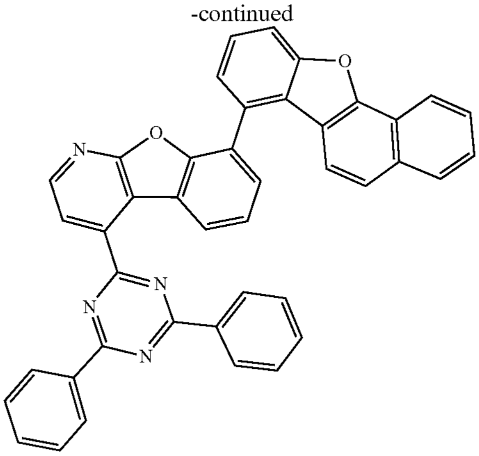
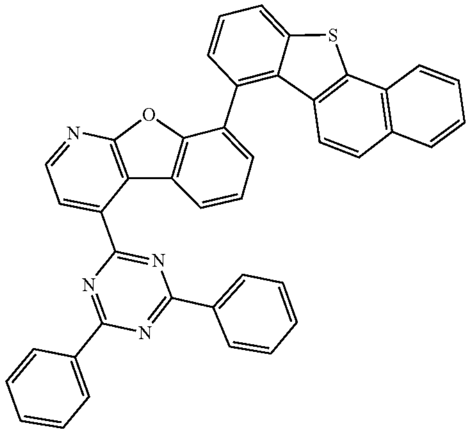
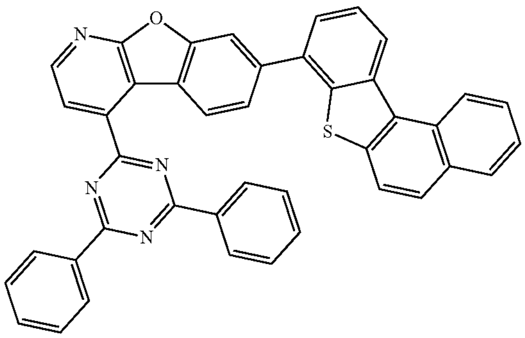
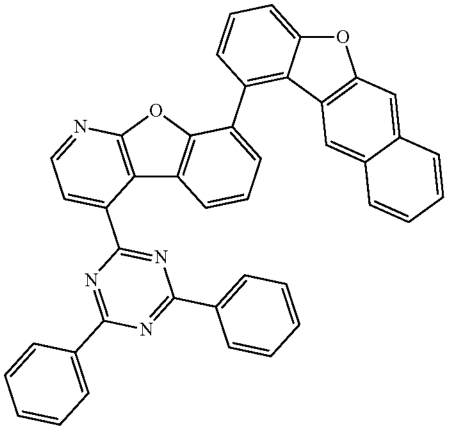
-continued
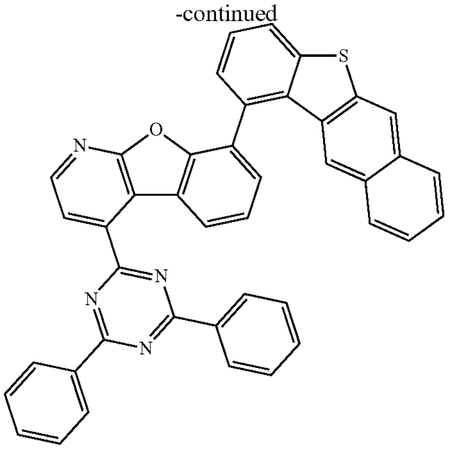
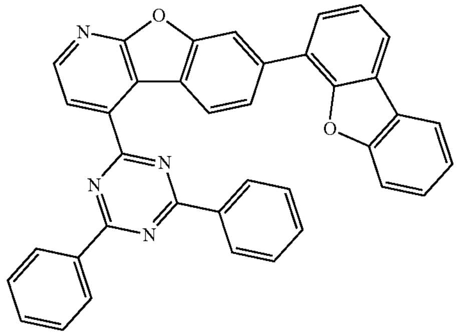
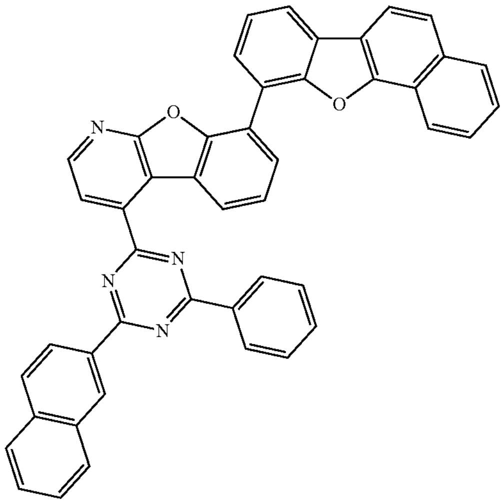
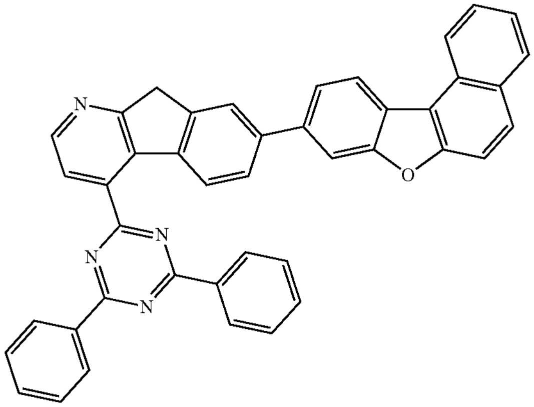

-continued
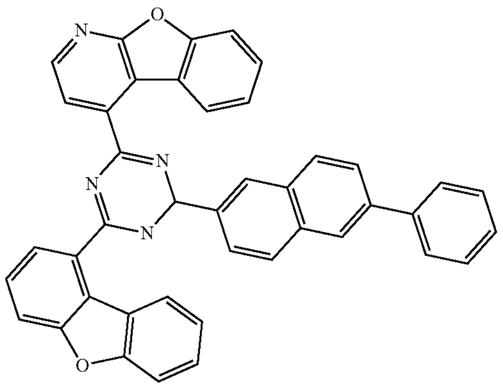
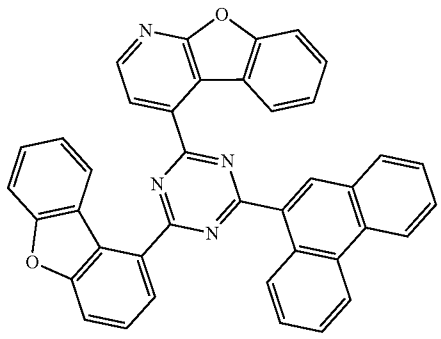
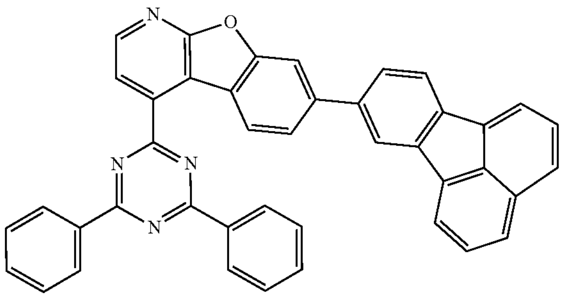
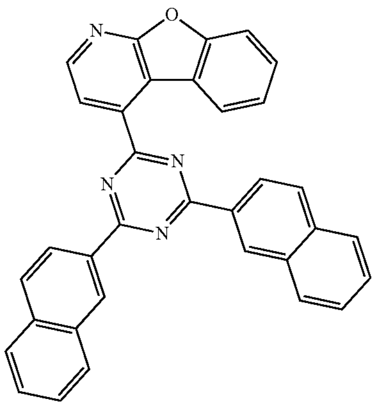
-continued
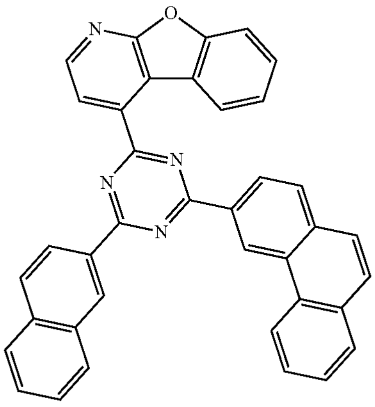
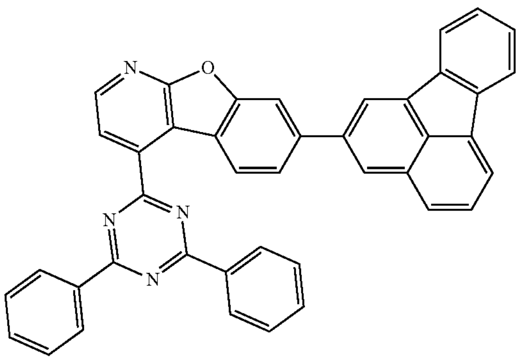
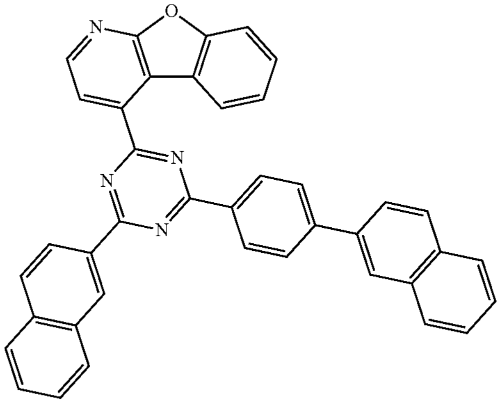
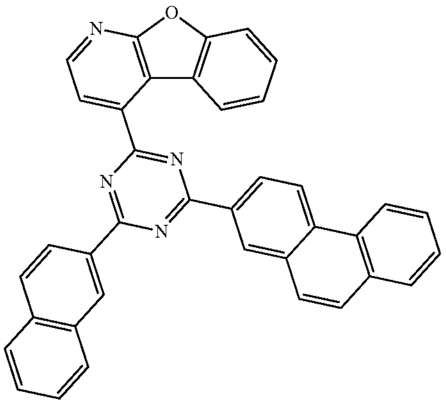

-continued
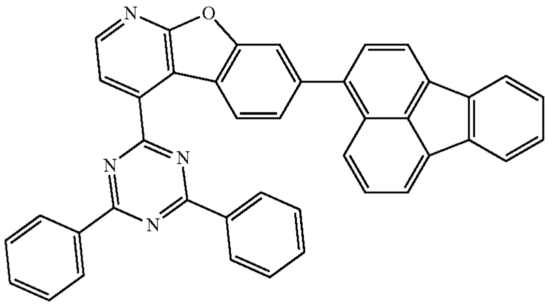
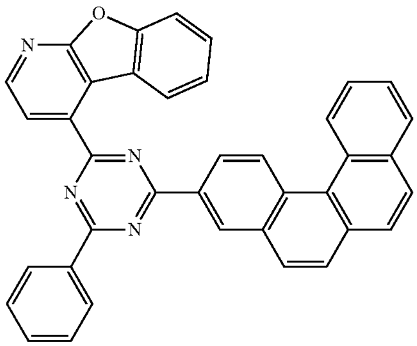
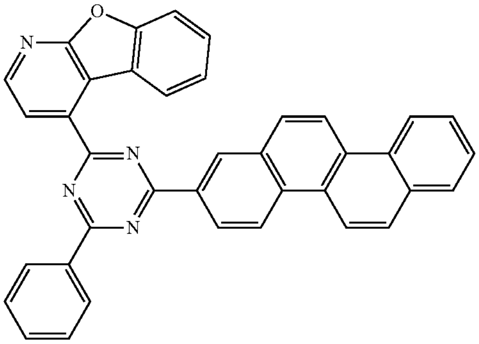
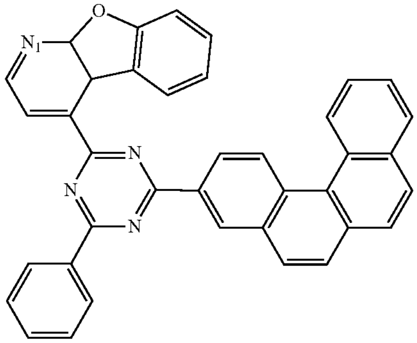
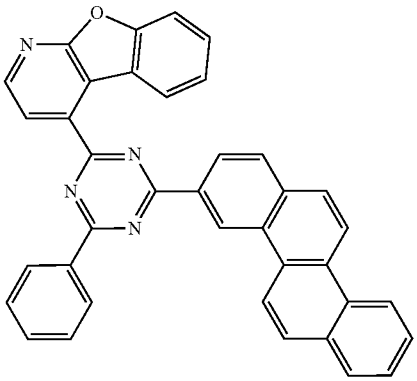
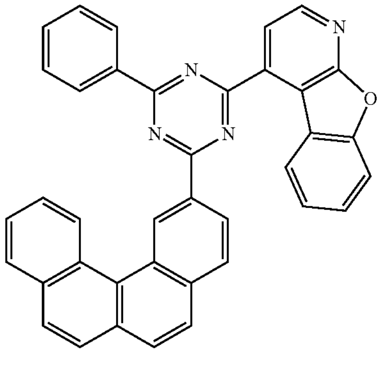
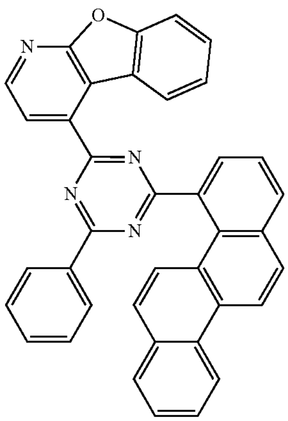
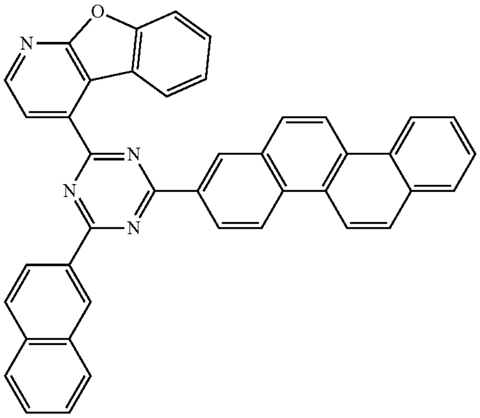

-continued
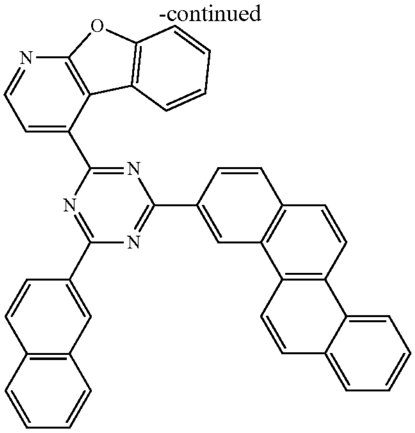
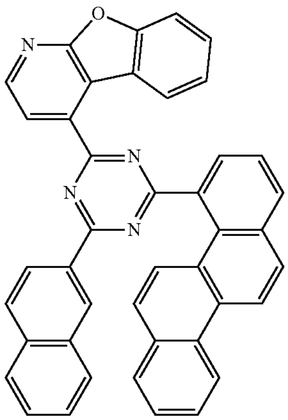
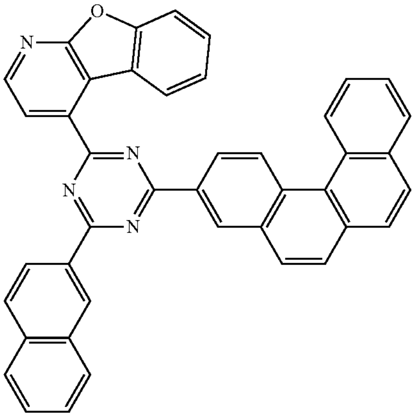
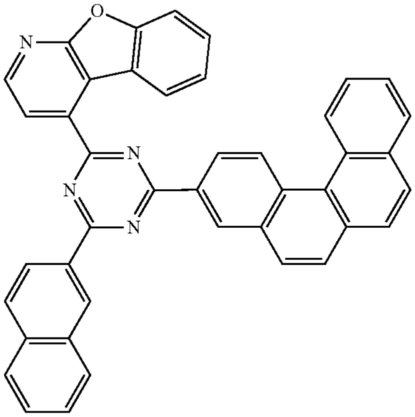
-continued
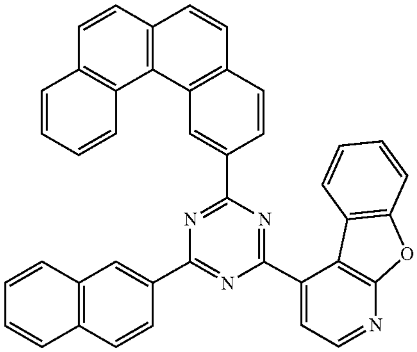
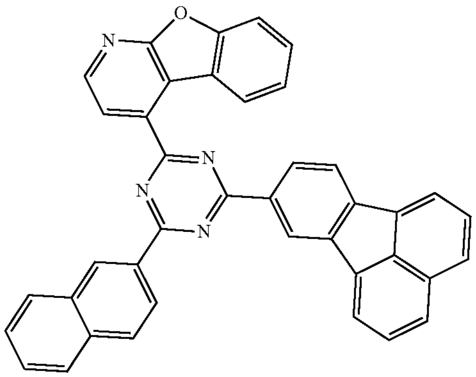
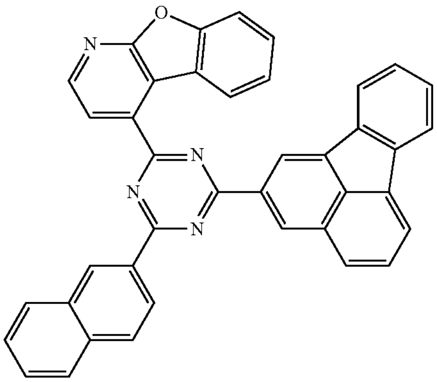
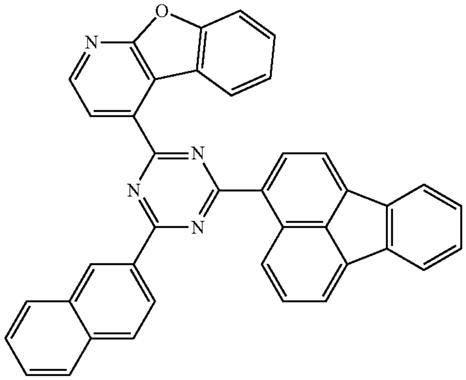

-continued
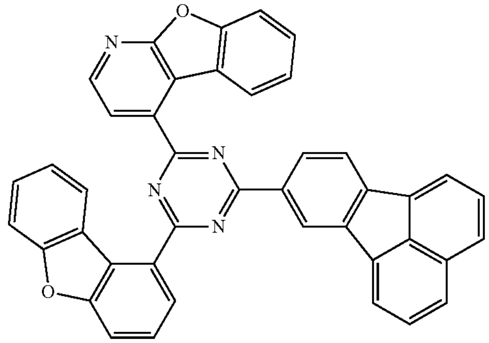
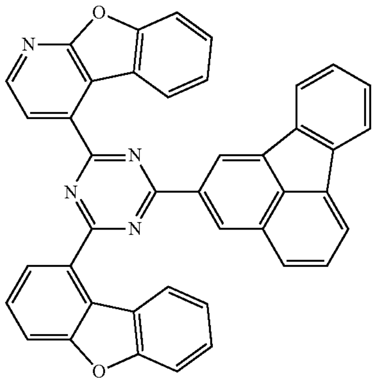
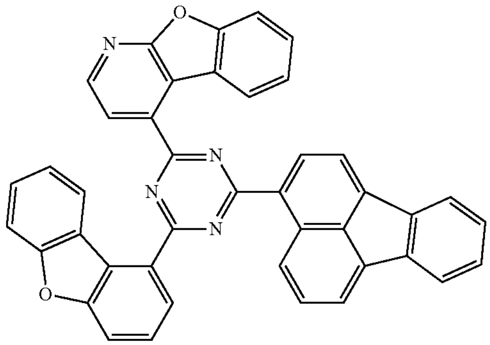
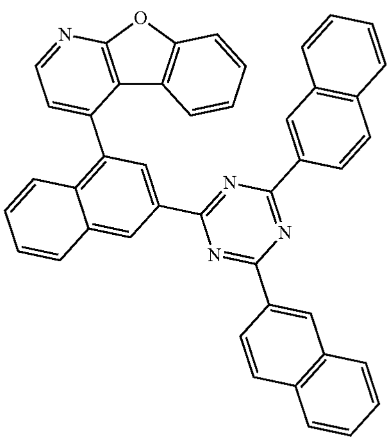
-continued
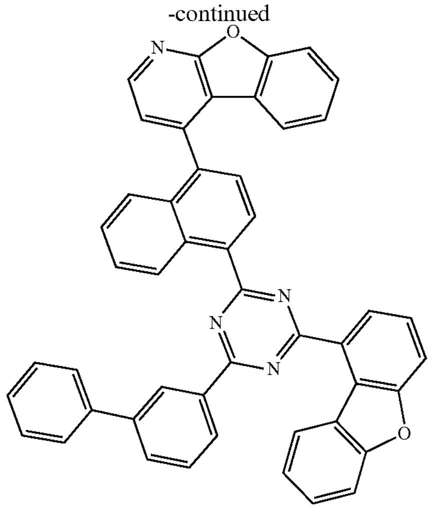
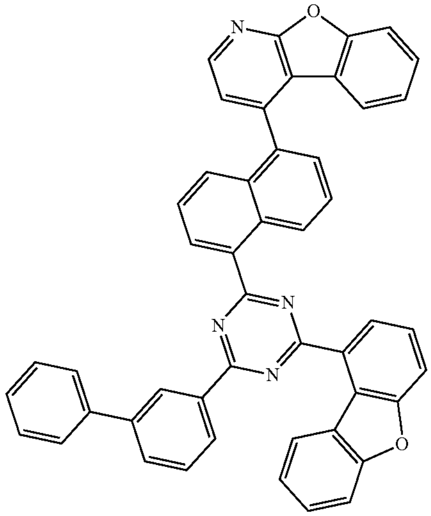
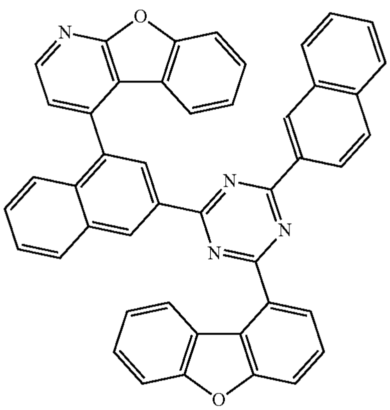

-continued
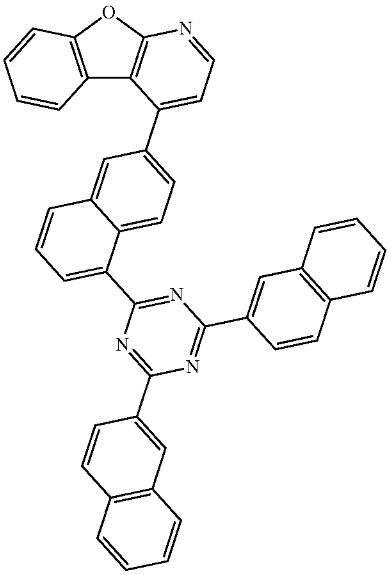
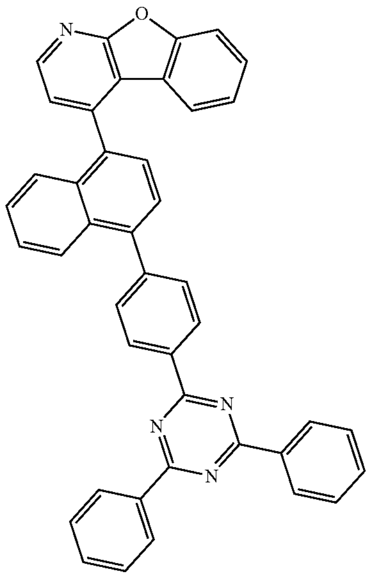
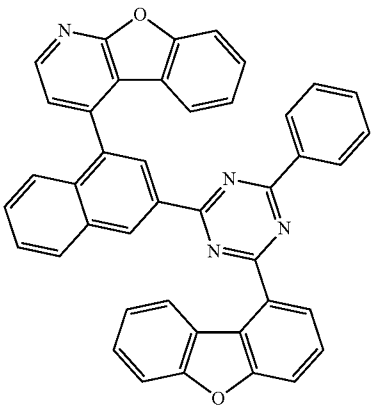
-continued
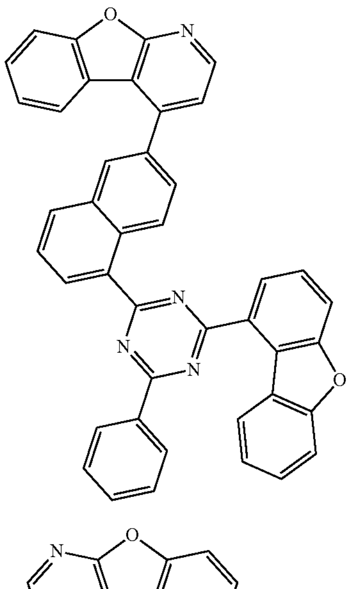
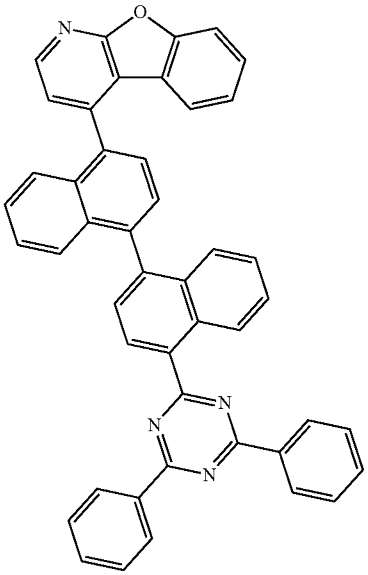
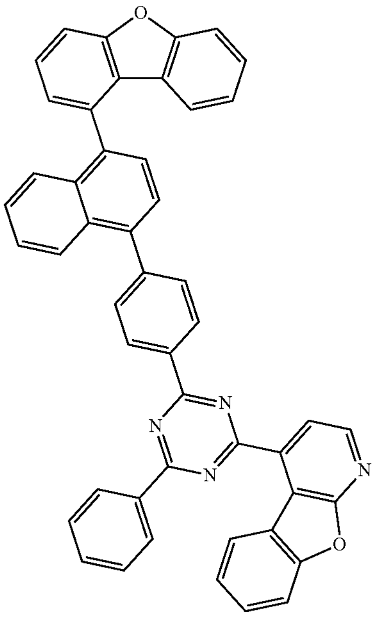

-continued
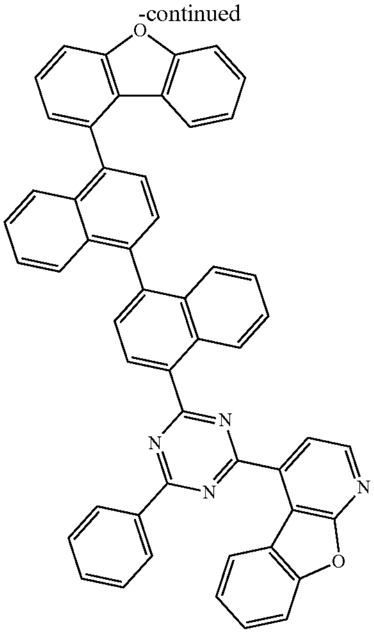
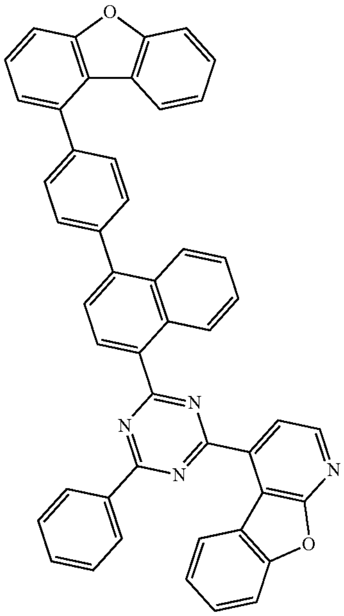
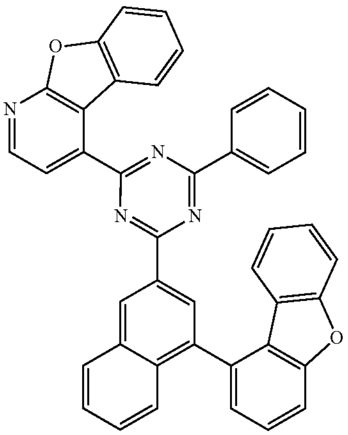
-continued
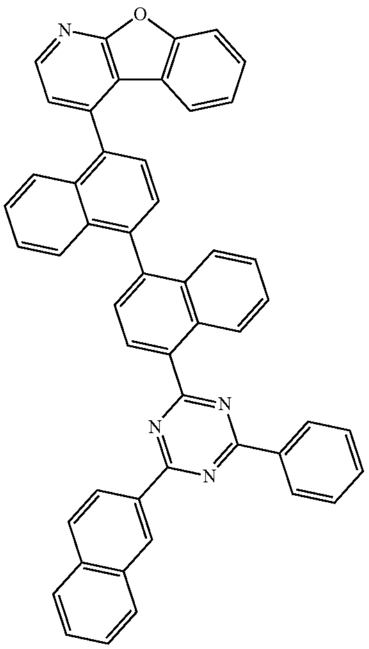
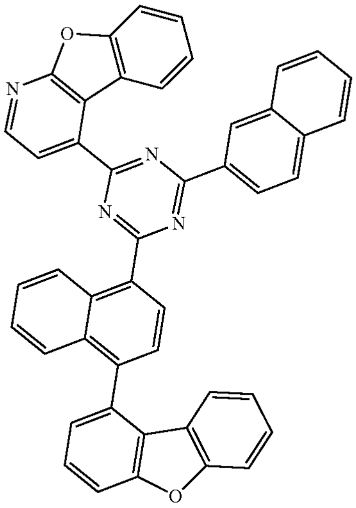
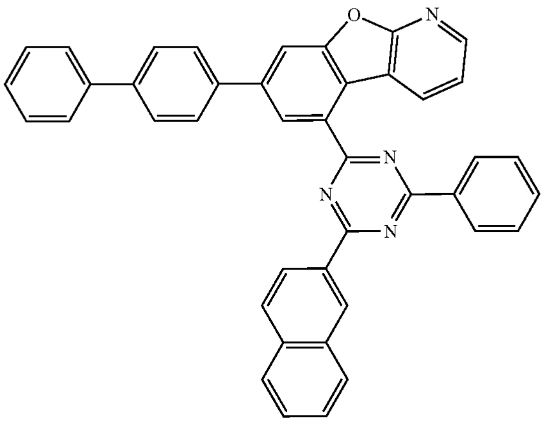

-continued
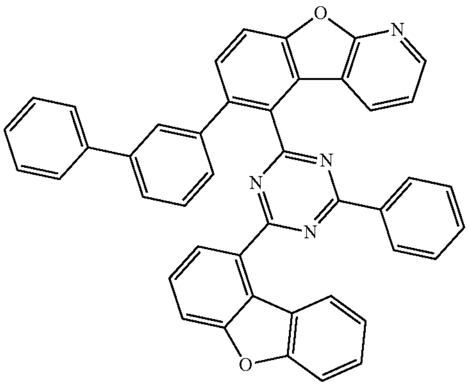
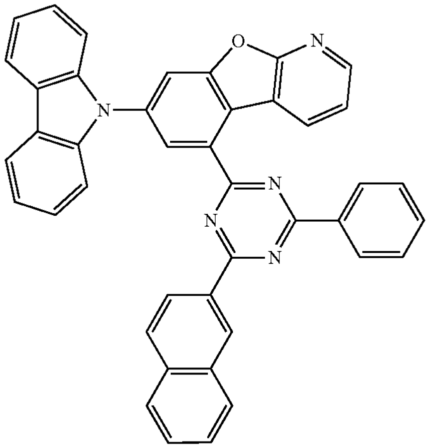
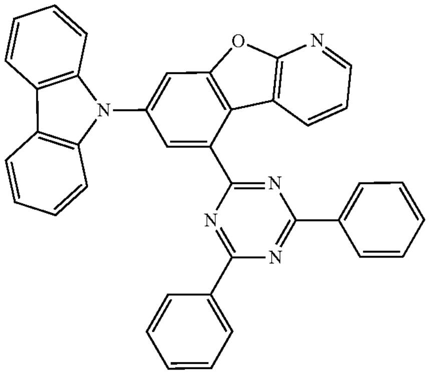
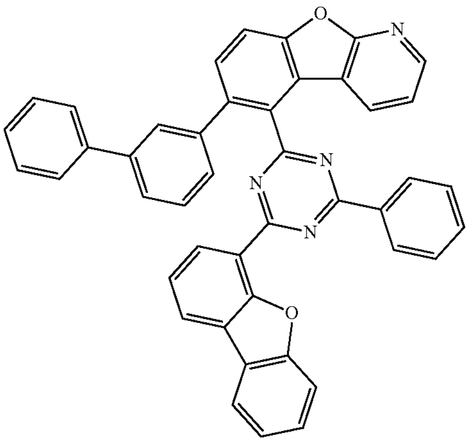
-continued
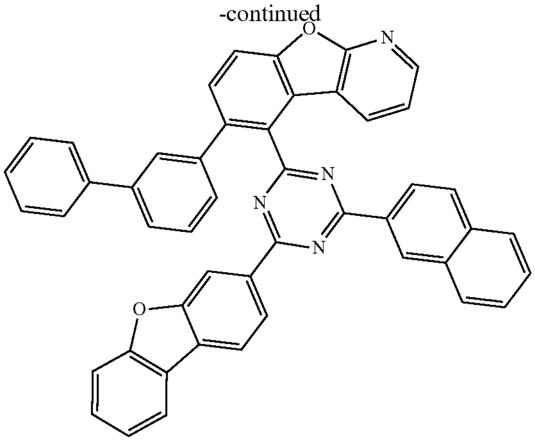
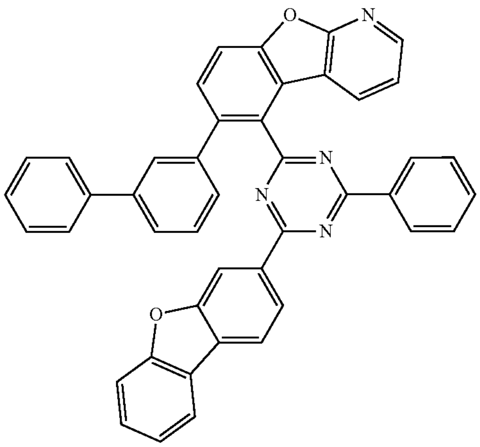
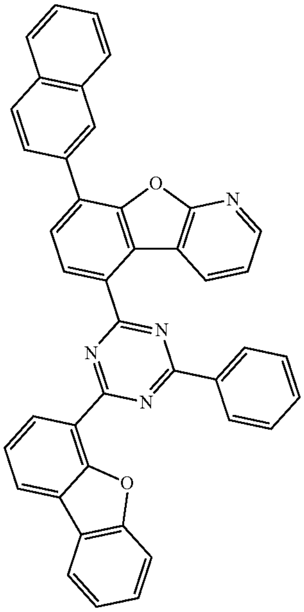

-continued
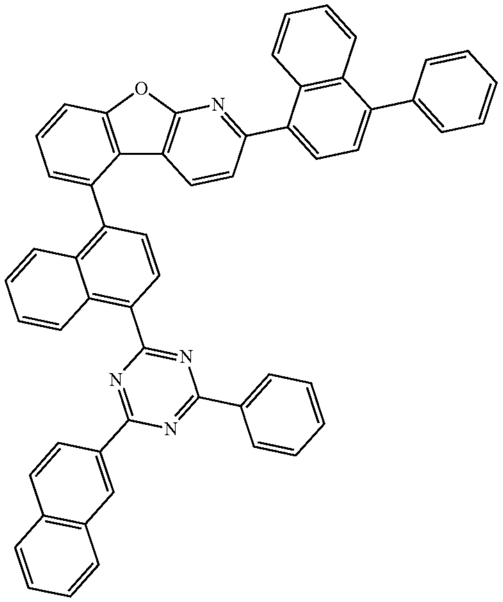
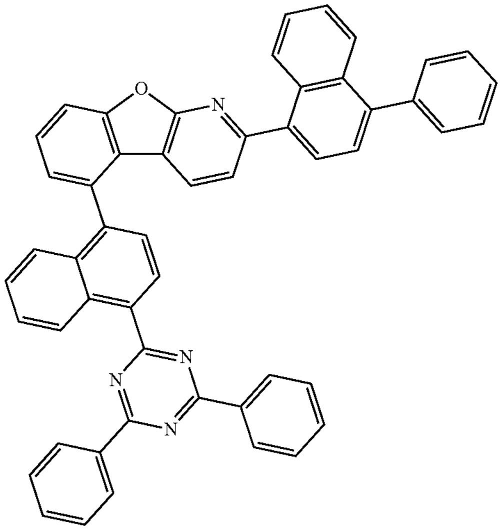
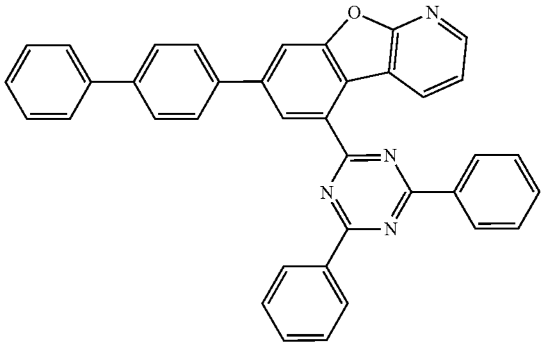
-continued
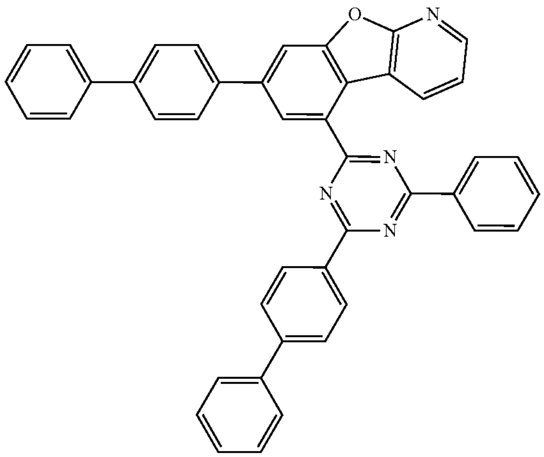
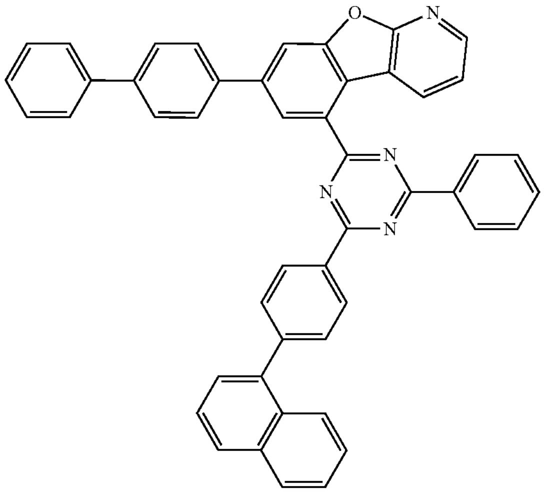
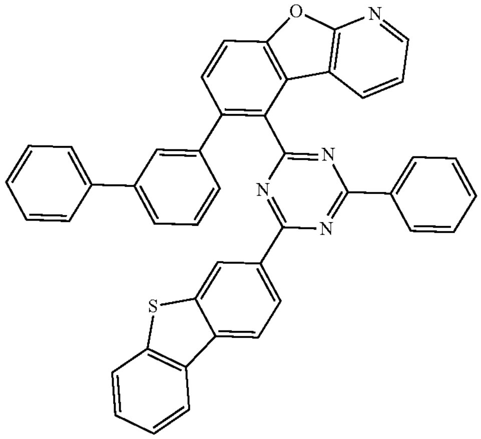

-continued
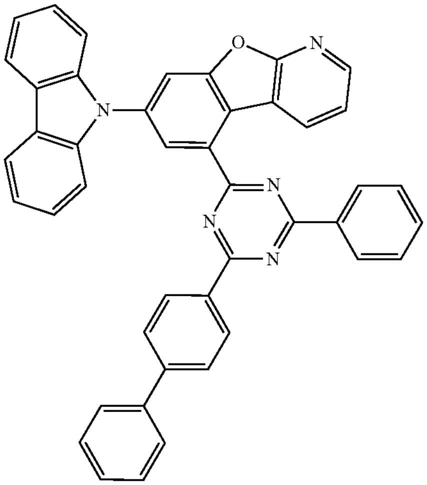
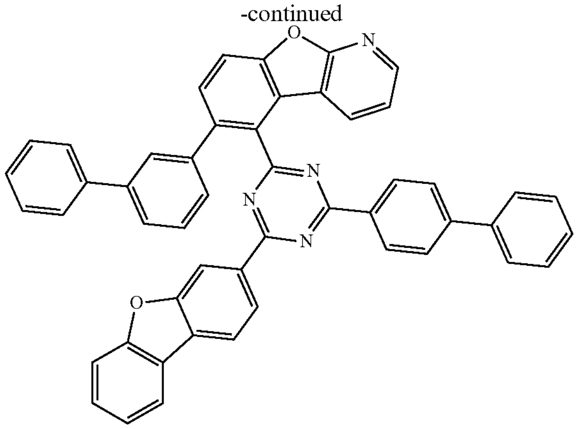
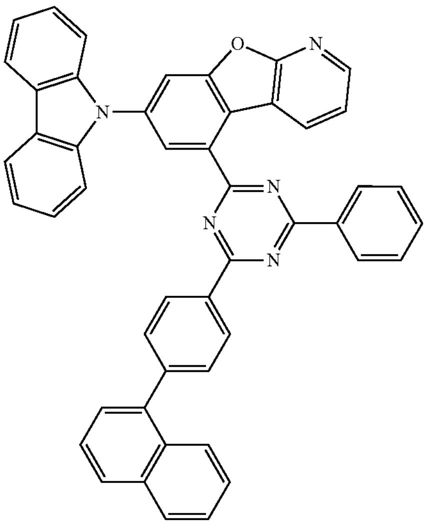
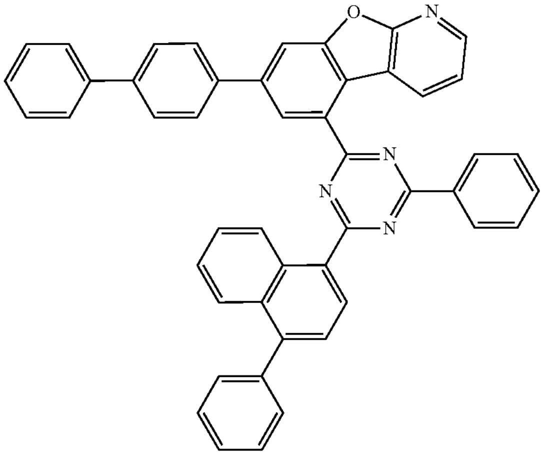
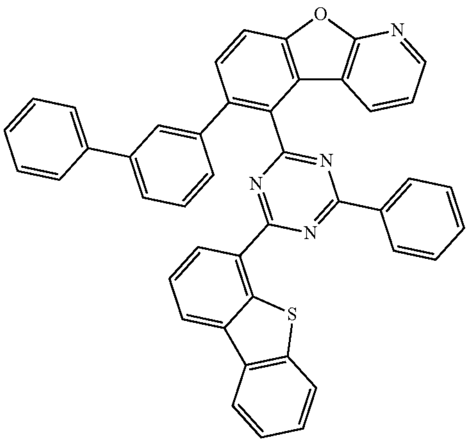
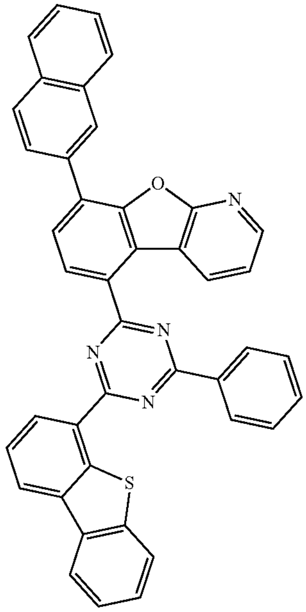

-continued
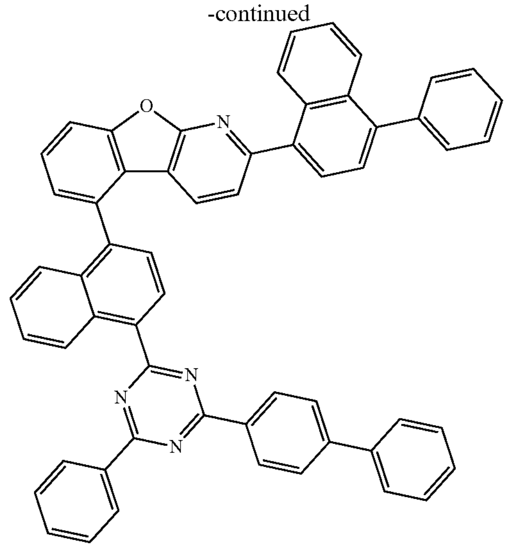
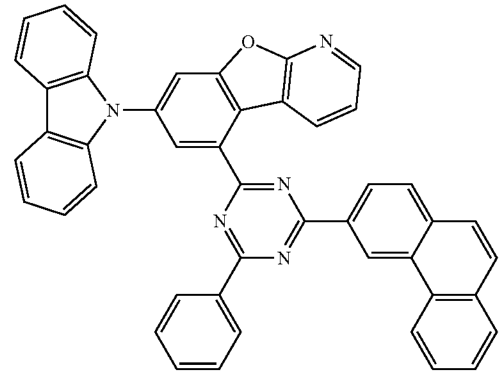
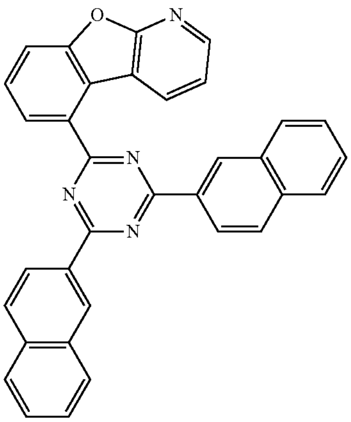
-continued
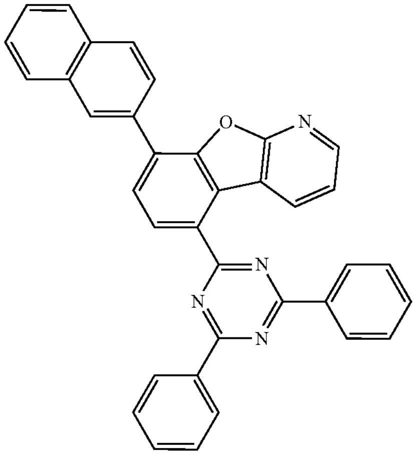
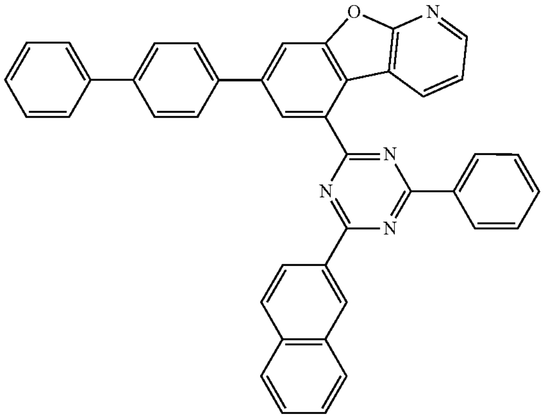
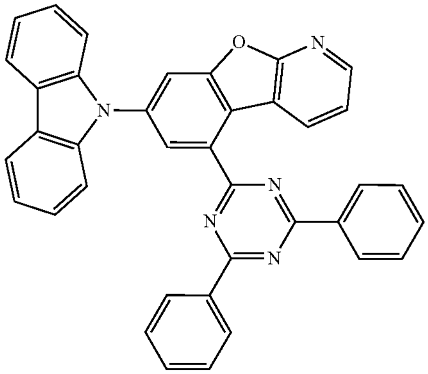
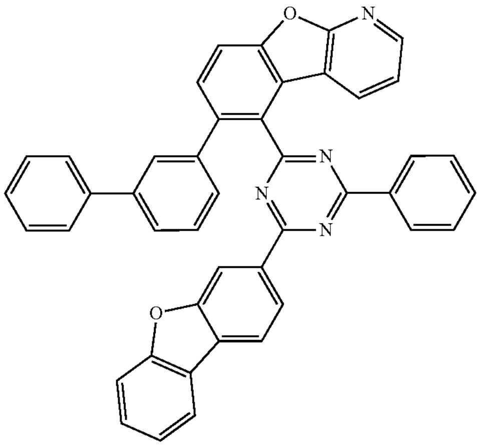

-continued
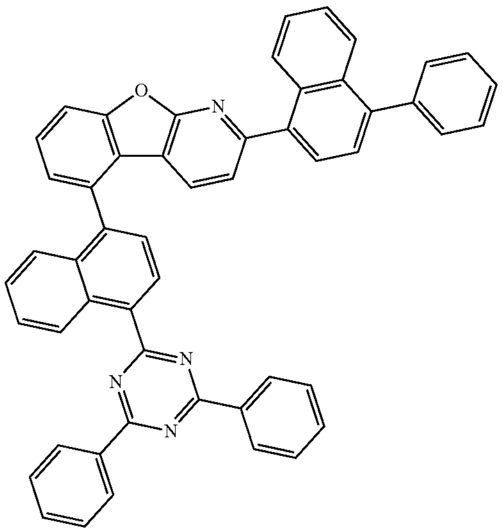
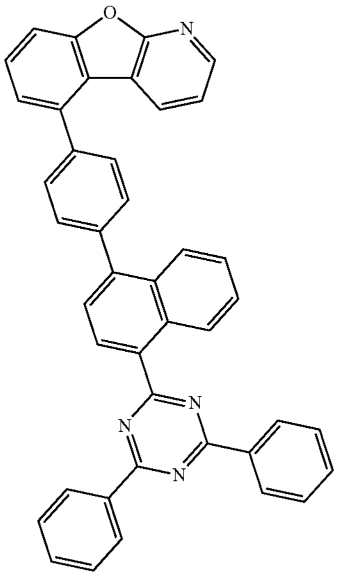
-continued
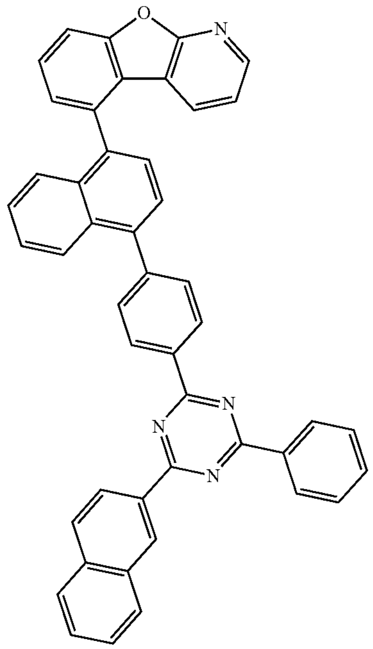
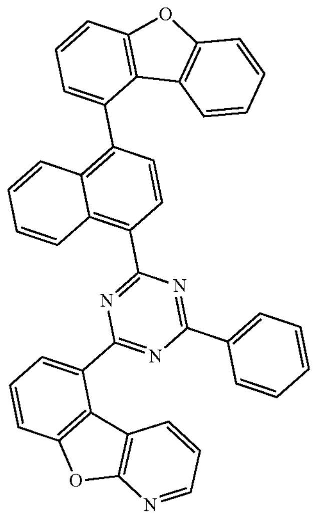

-continued
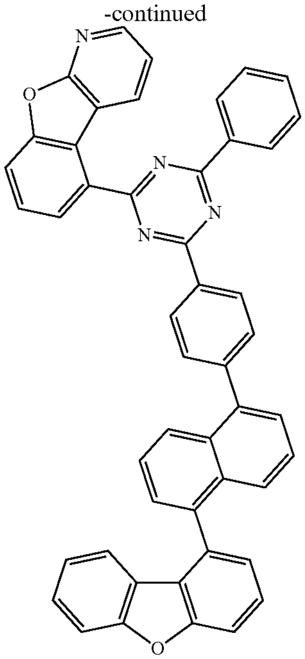
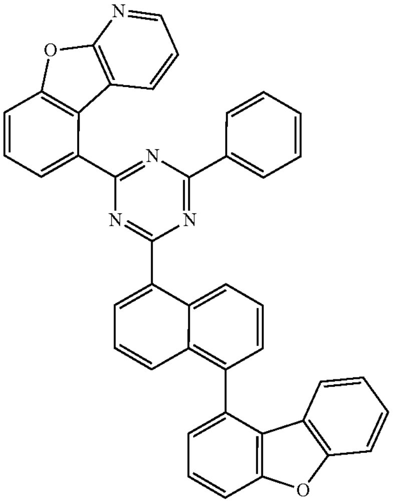
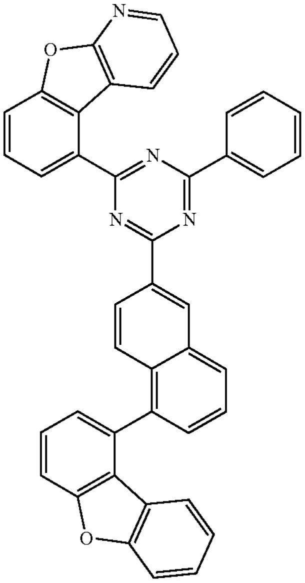
-continued
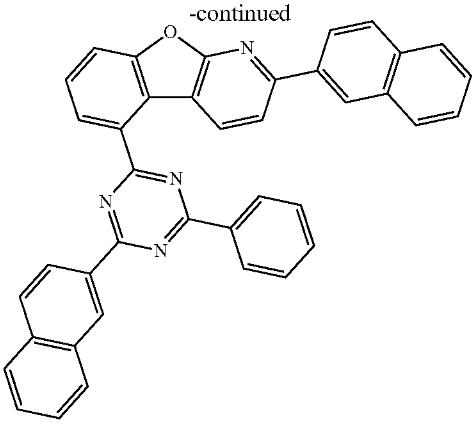
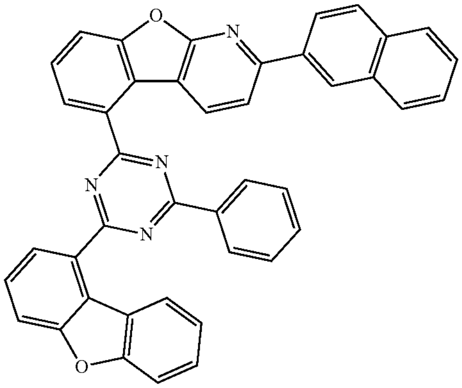
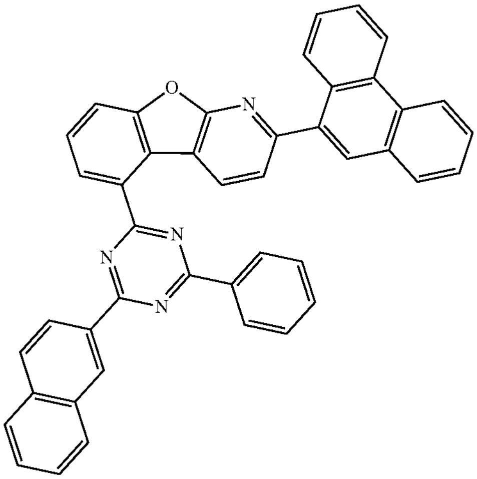

-continued
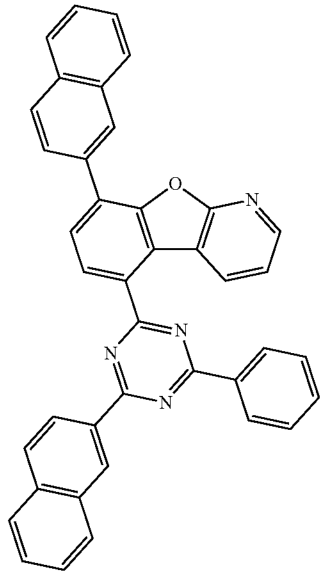
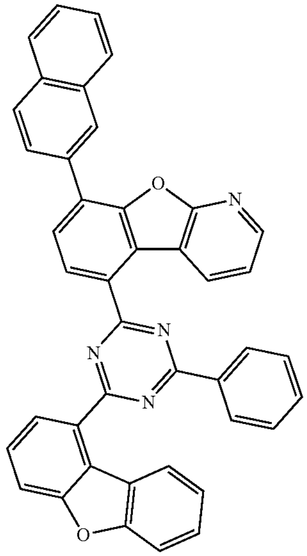
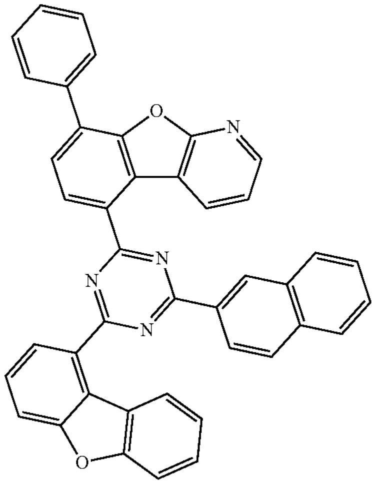
-continued
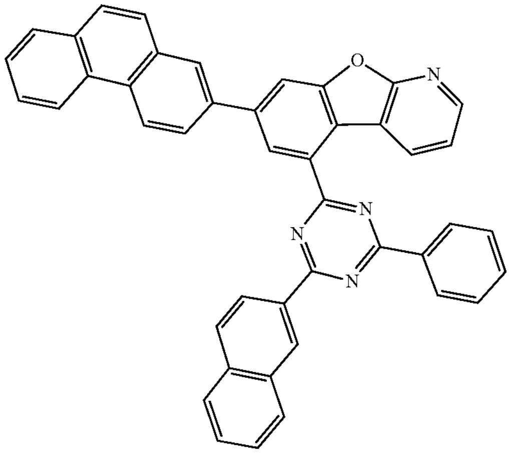
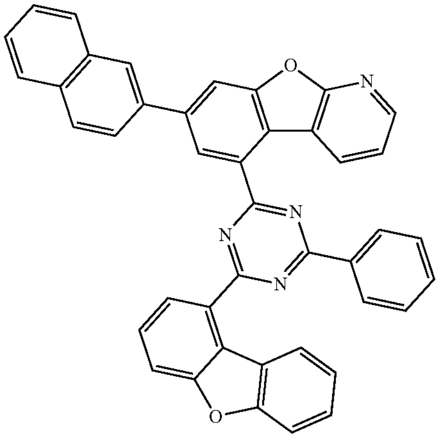
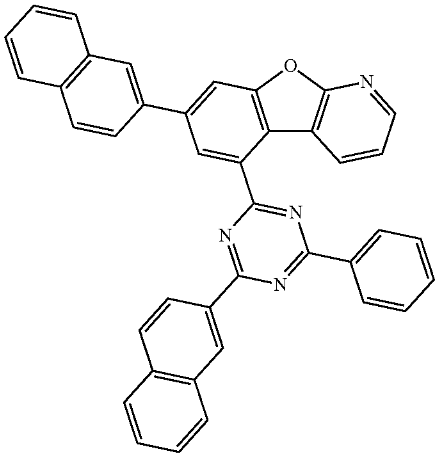

-continued
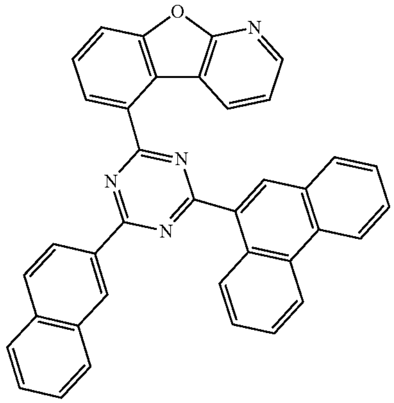
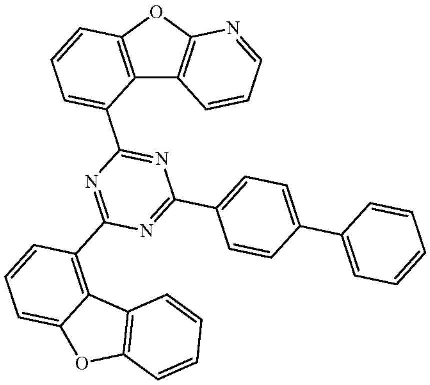
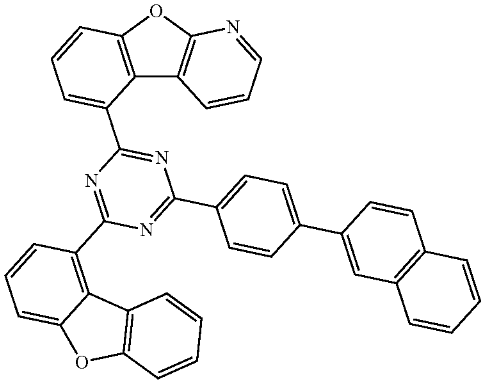
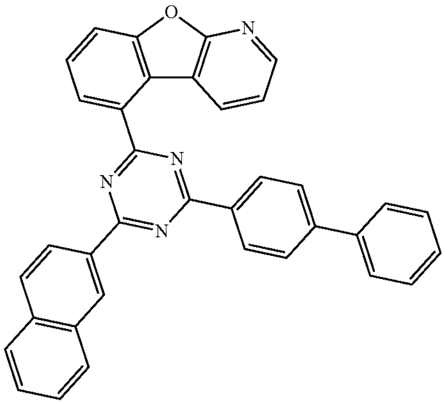
-continued
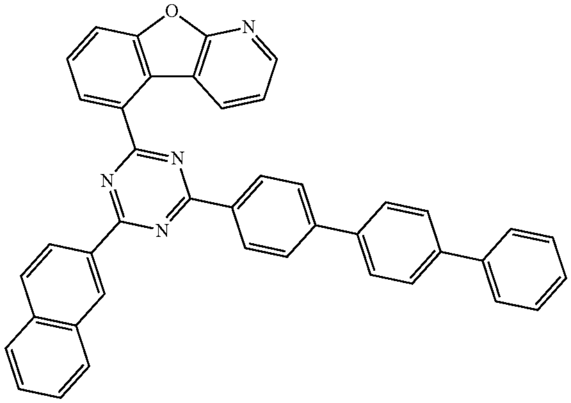
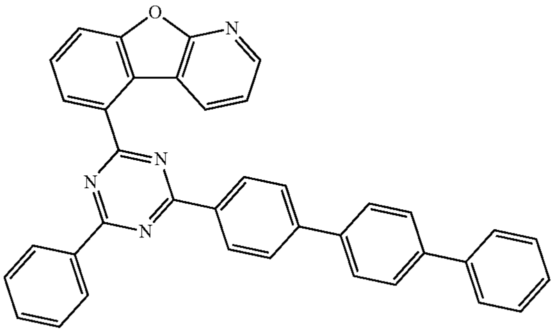
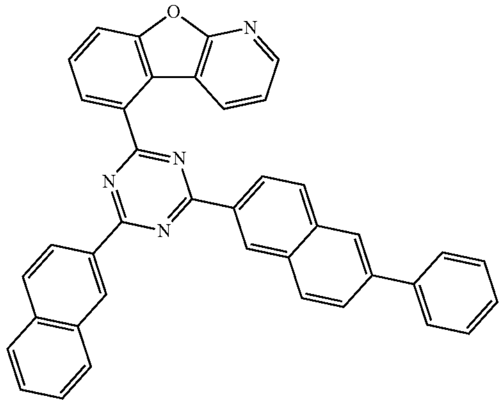
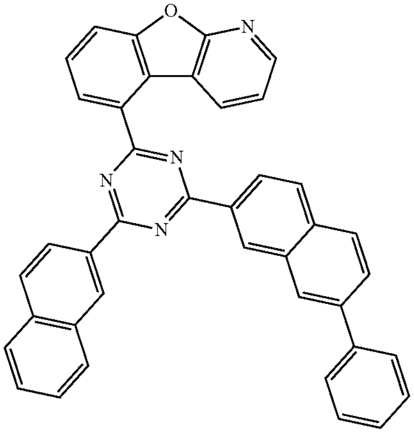

-continued
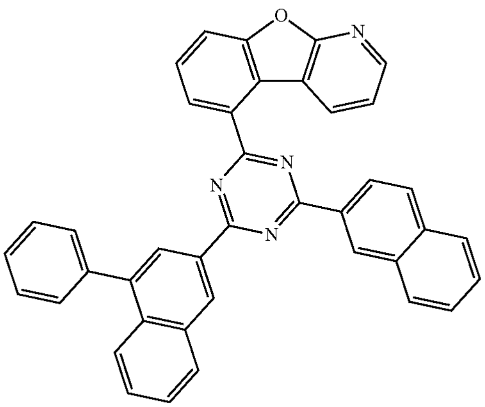
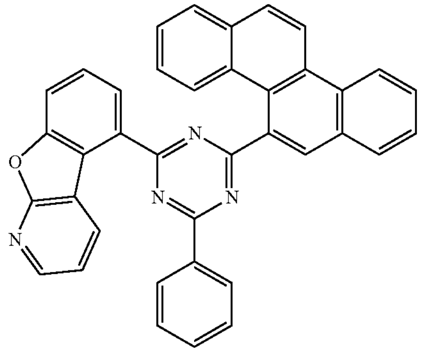
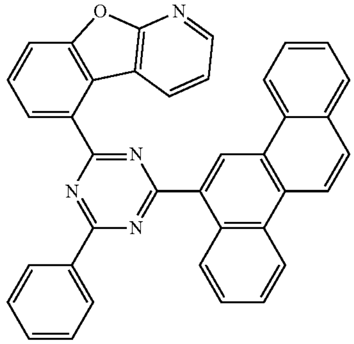
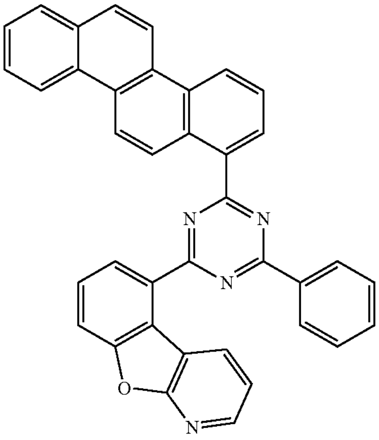
-continued
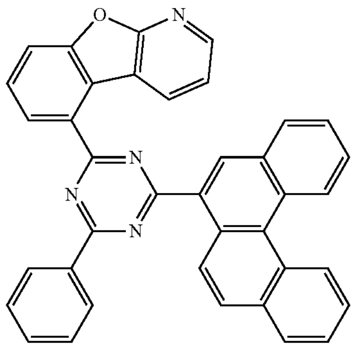
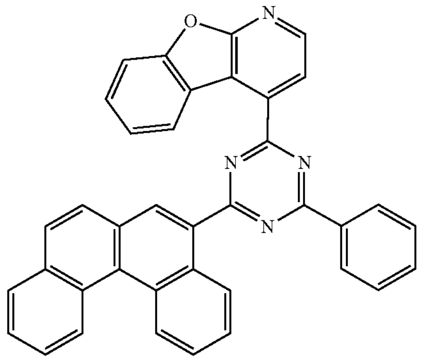
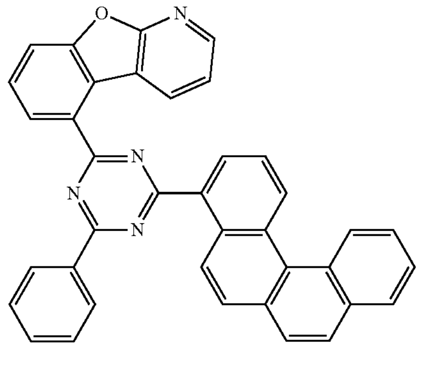
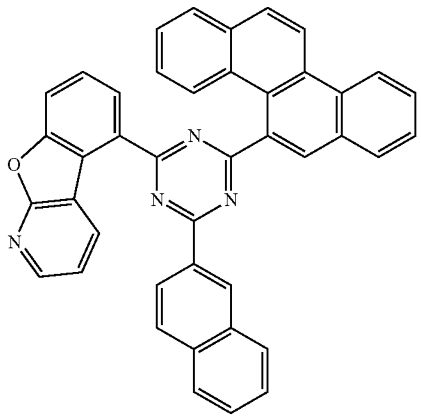

-continued
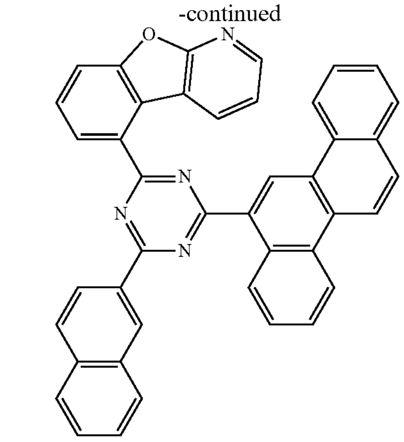
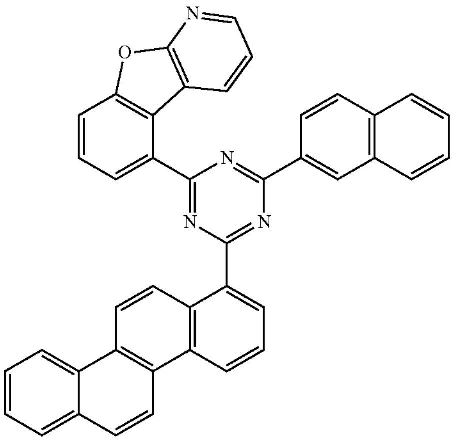
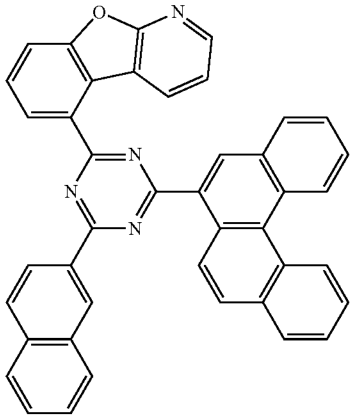
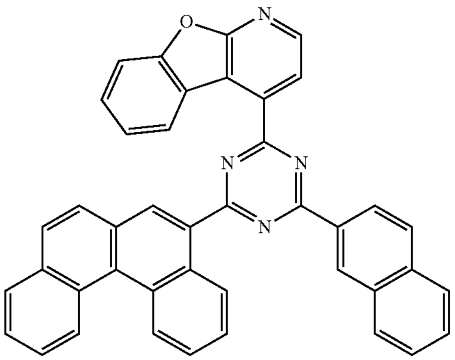
-continued
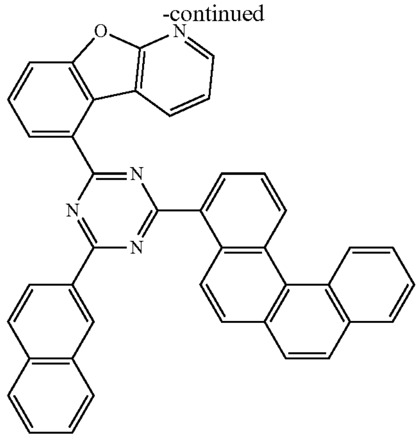
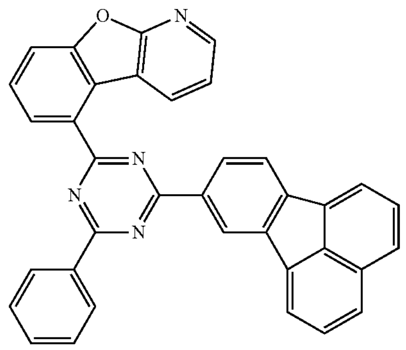
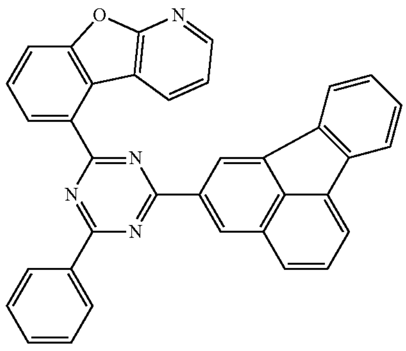
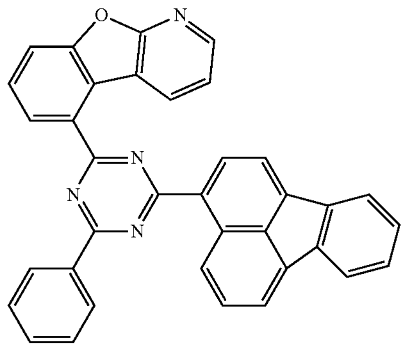

-continued
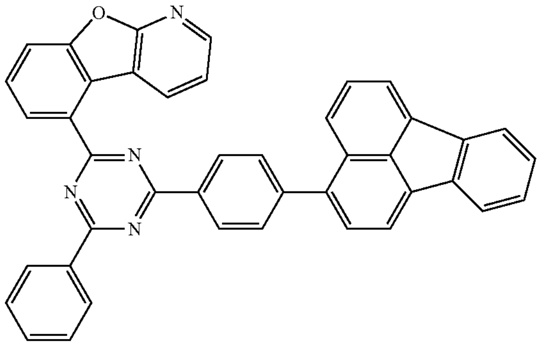
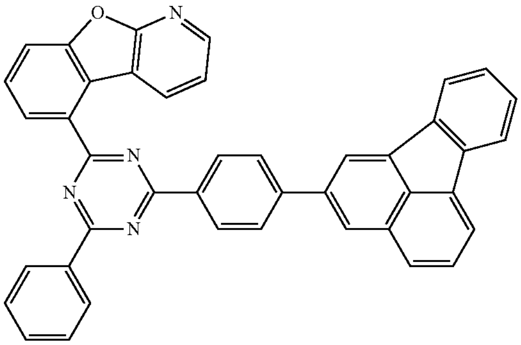
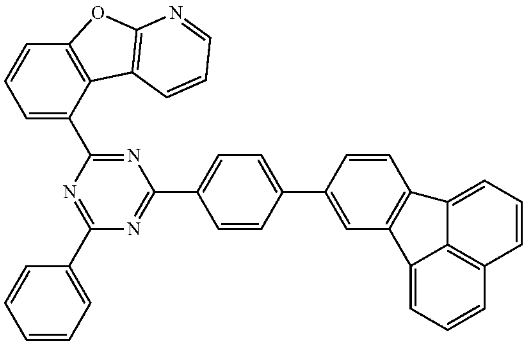
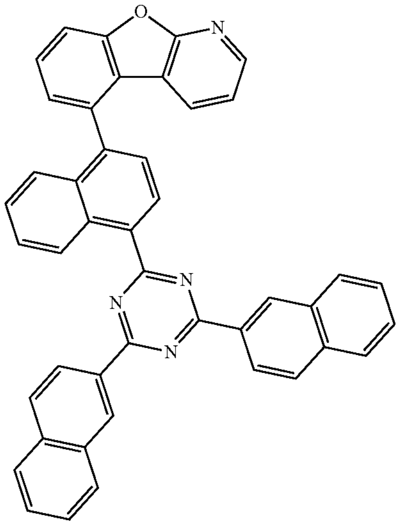
-continued
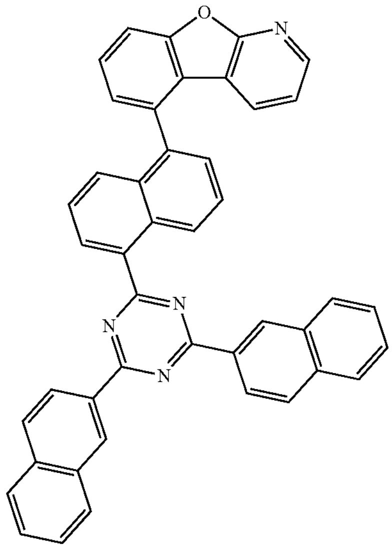
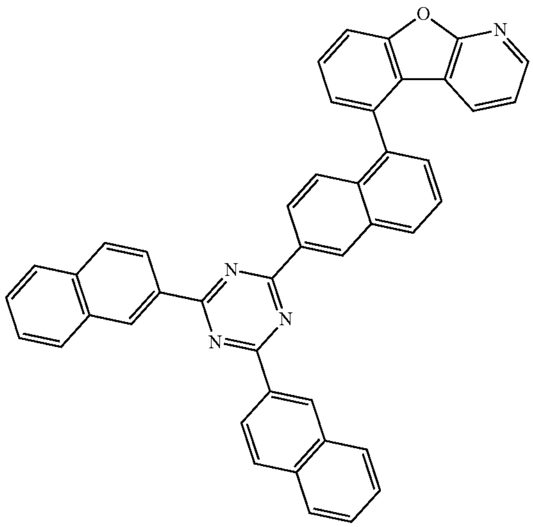
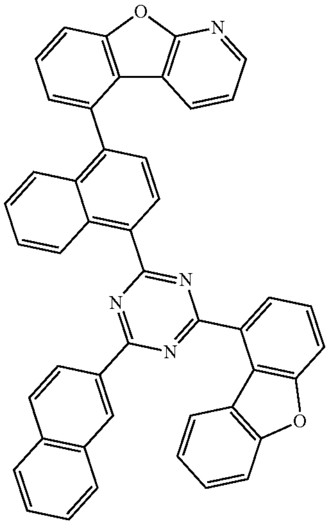

-continued
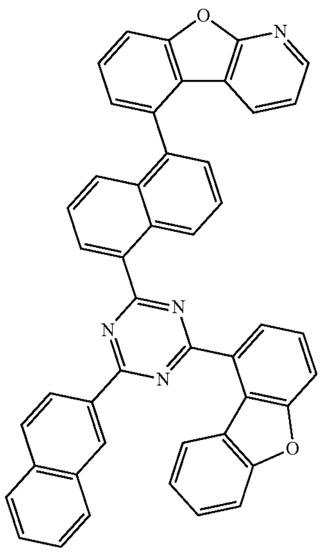
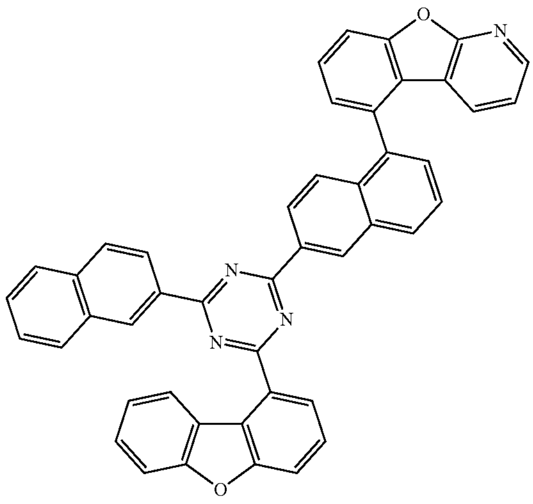
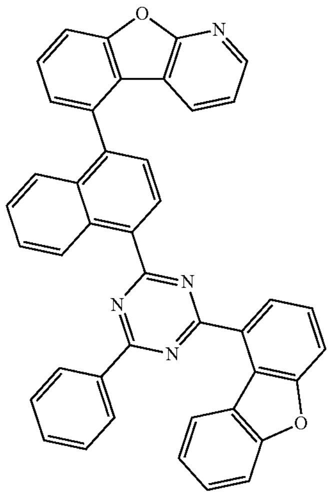
-continued
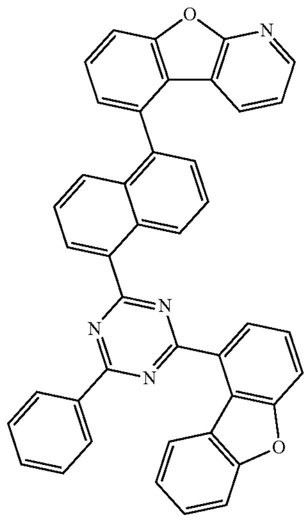
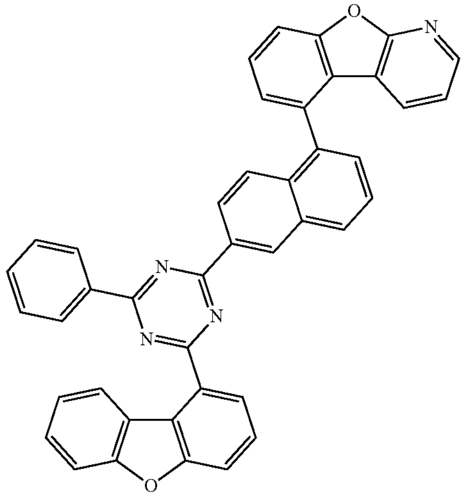
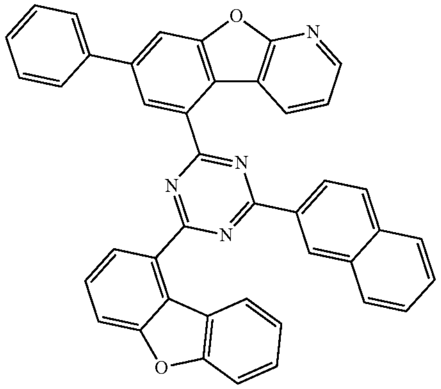
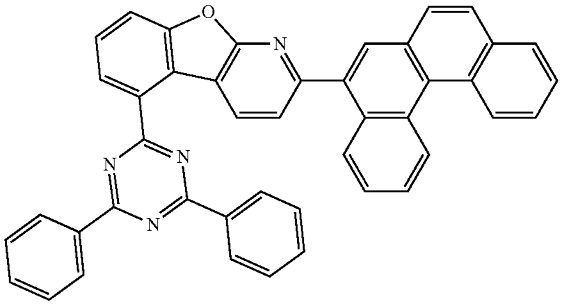

-continued
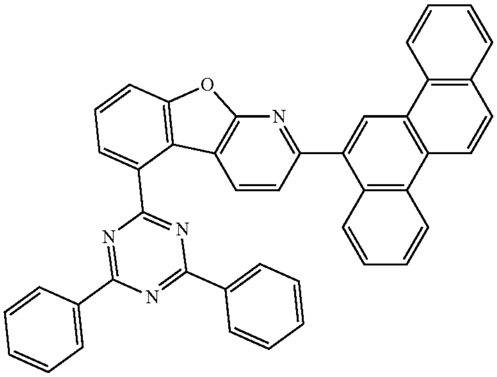
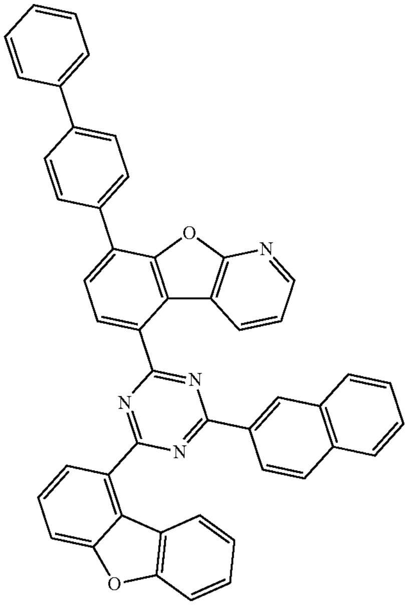
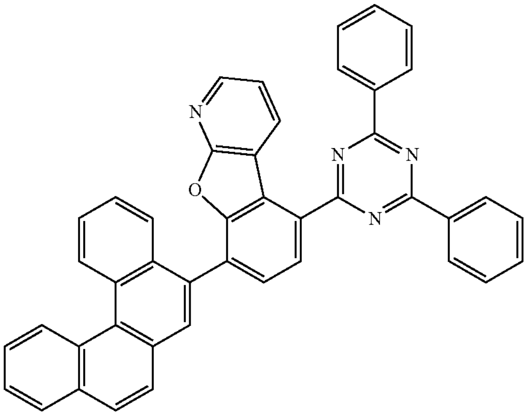
-continued
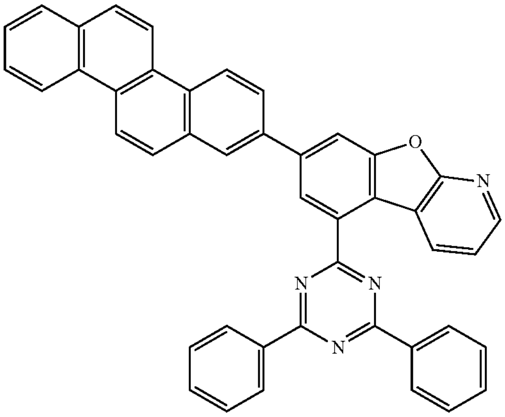
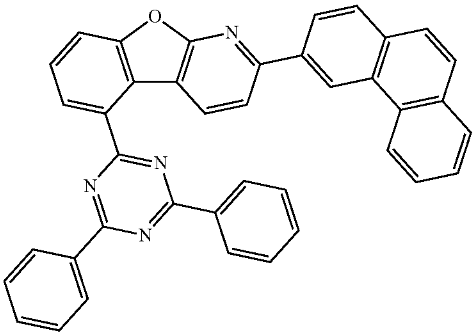
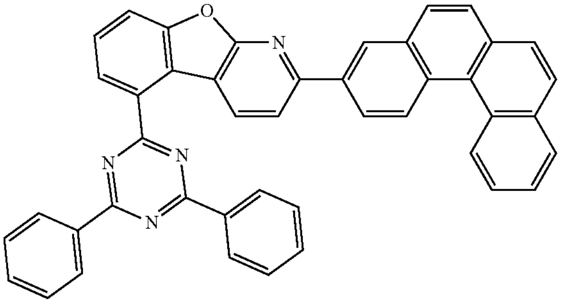
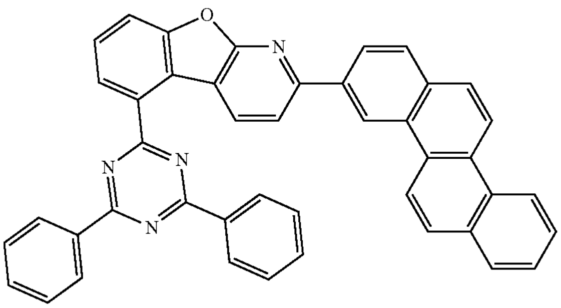

-continued
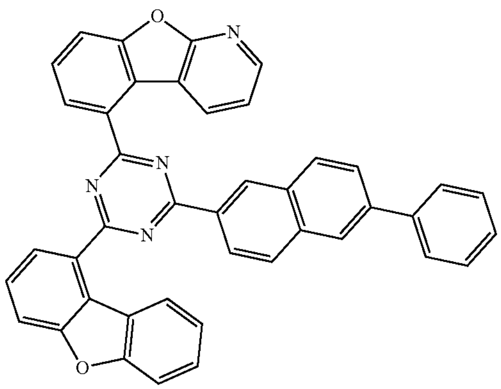
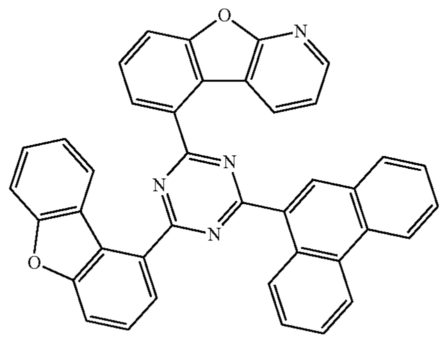
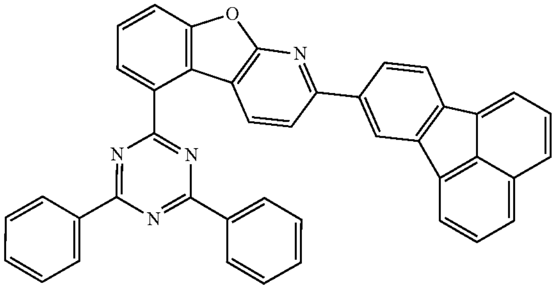
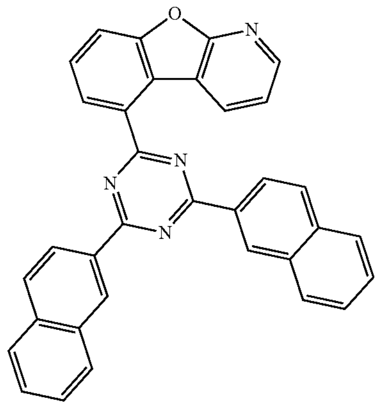
-continued
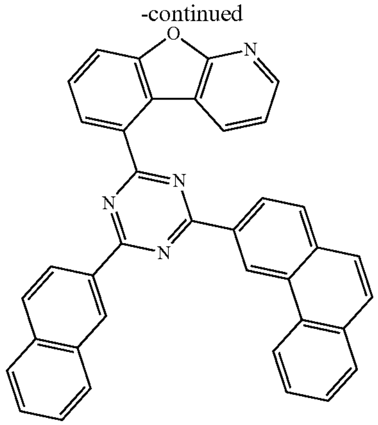
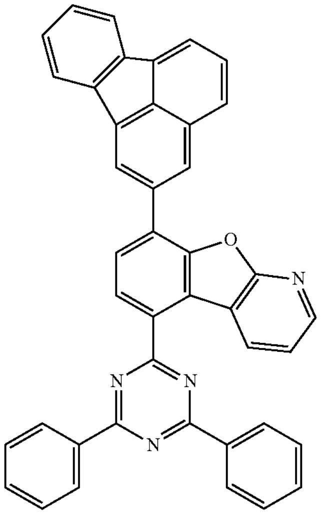
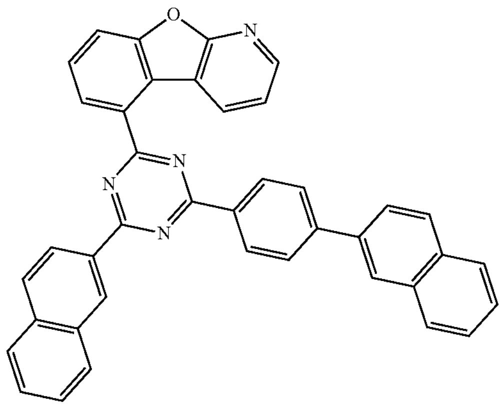
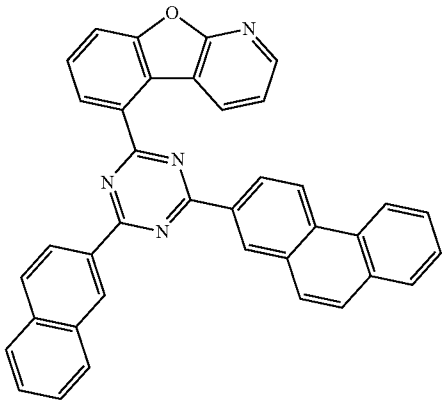

-continued
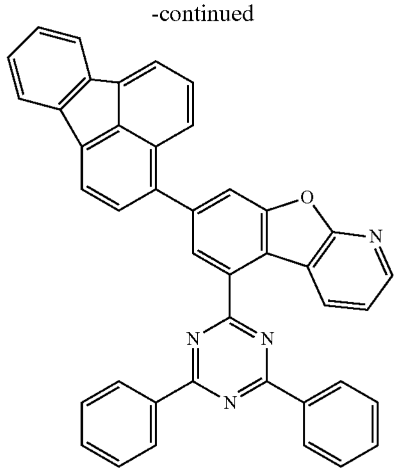
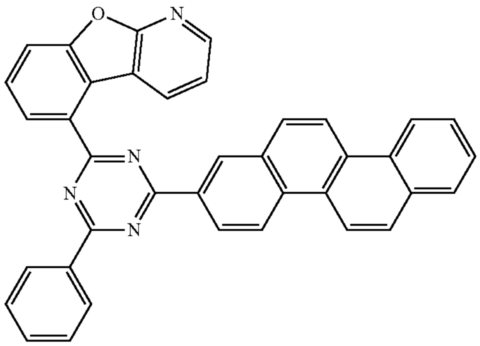
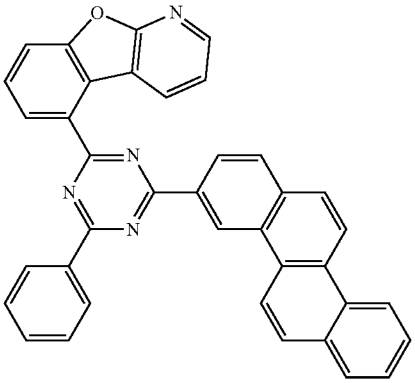
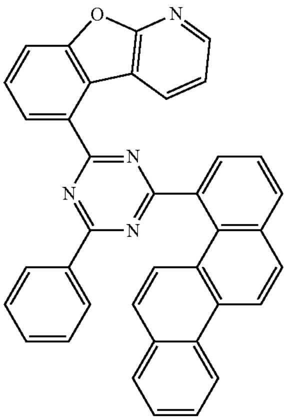
-continued
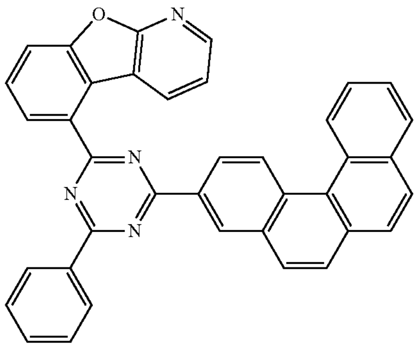
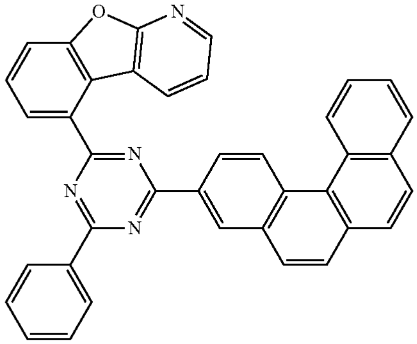
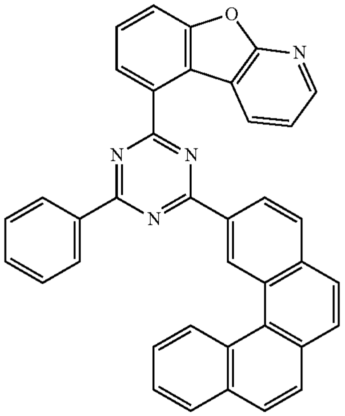
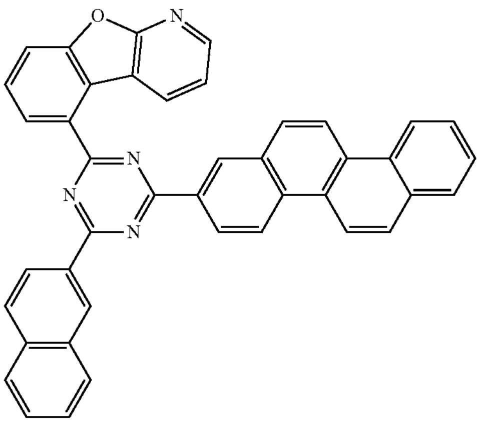

-continued
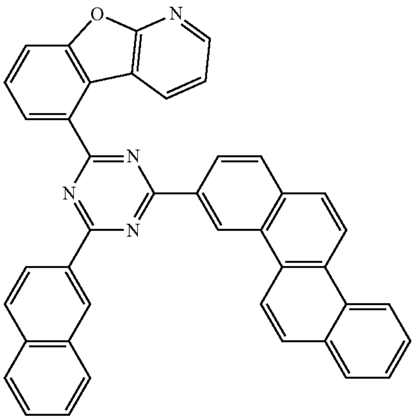
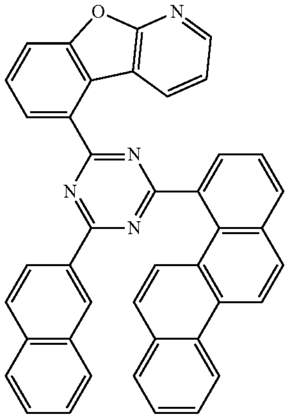
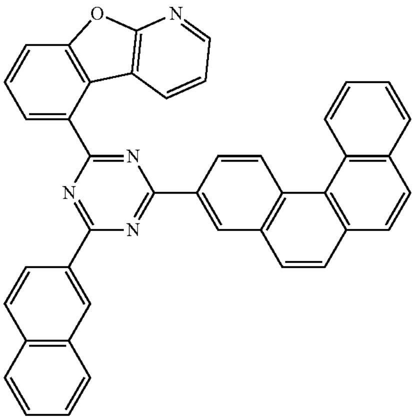
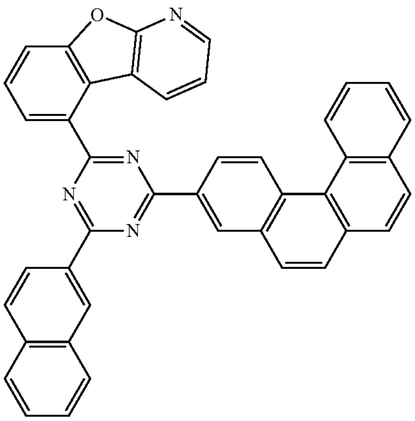
-continued
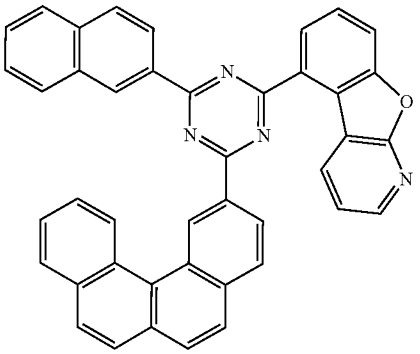
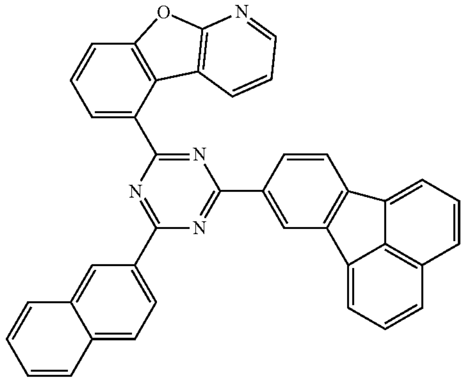
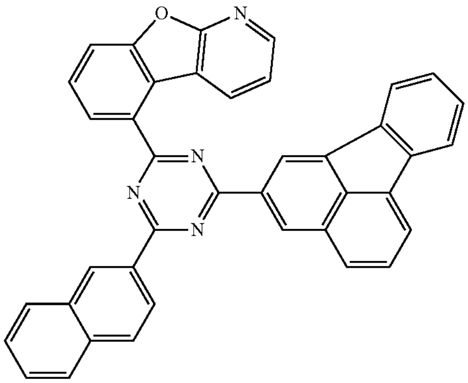
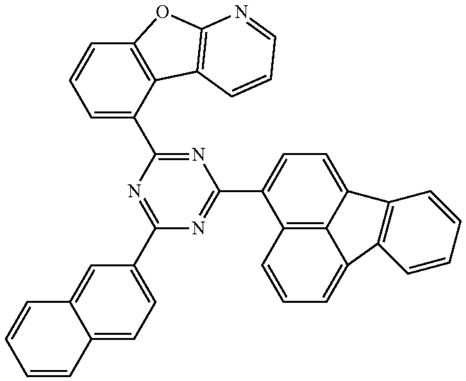

-continued
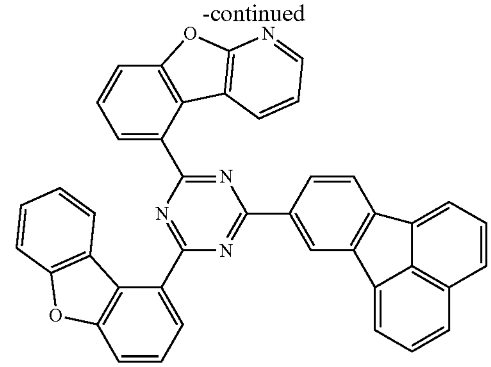
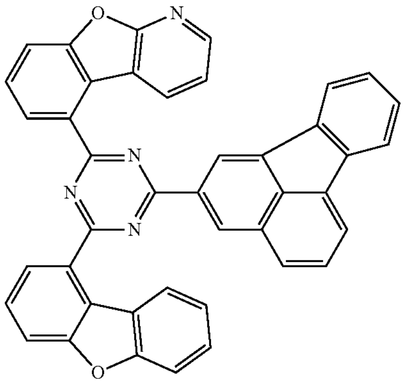
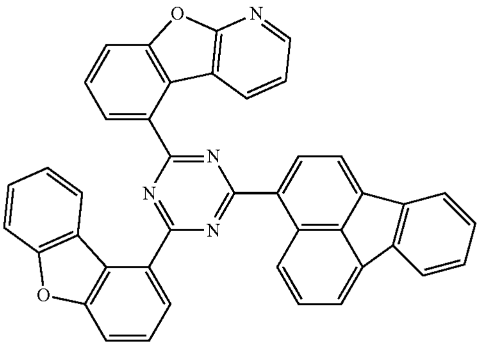
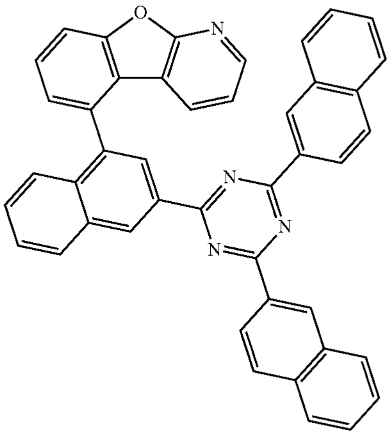
-continued
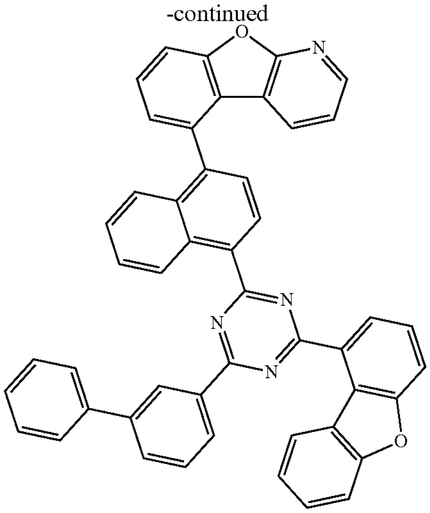
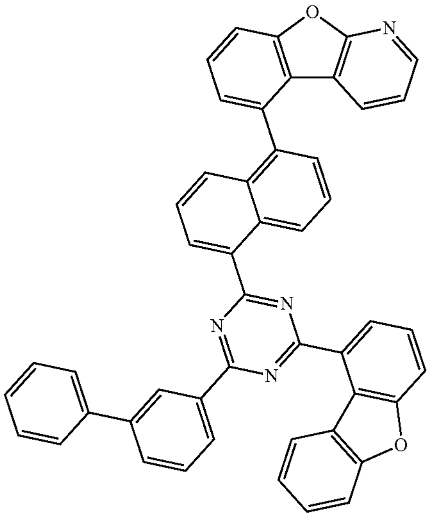
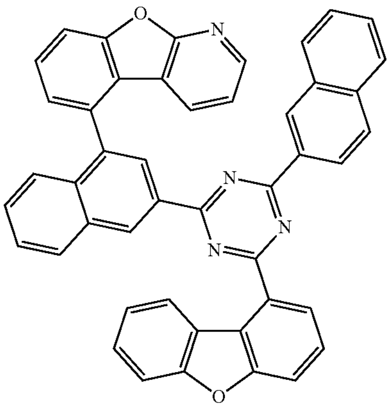

-continued
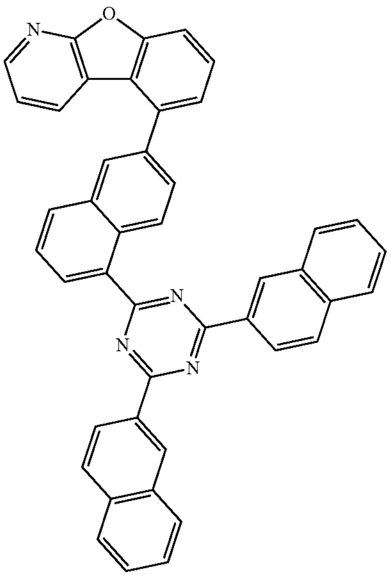
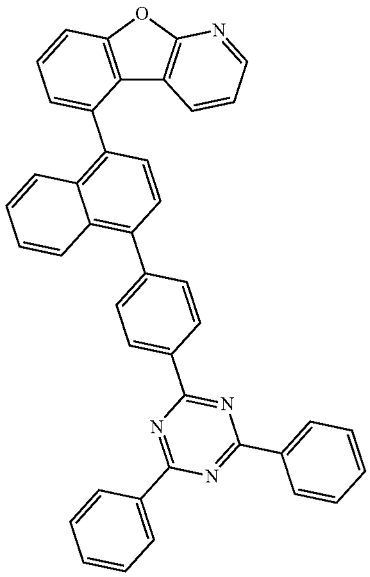
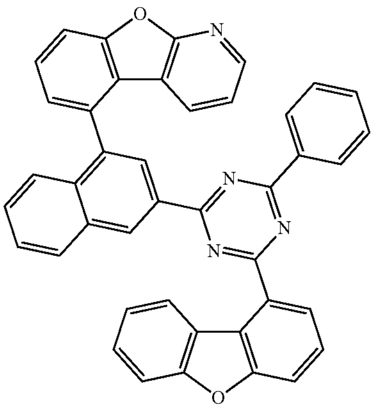
-continued
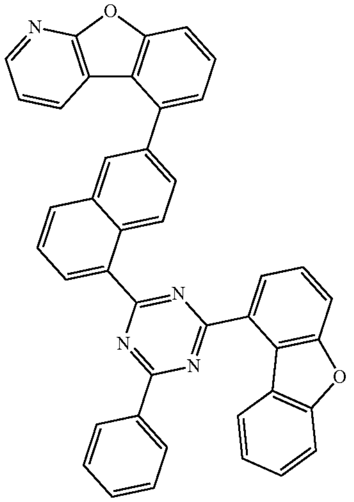
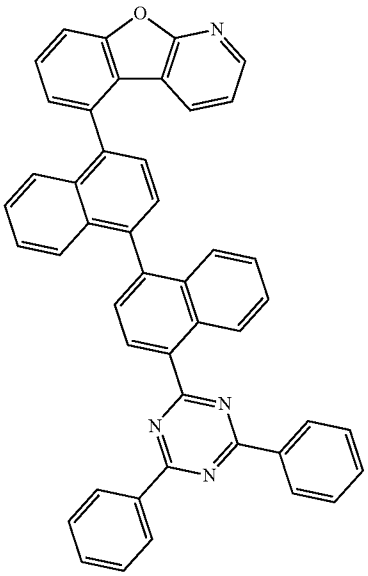
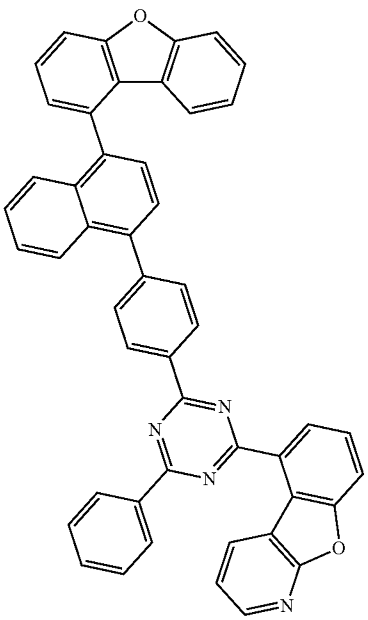

-continued
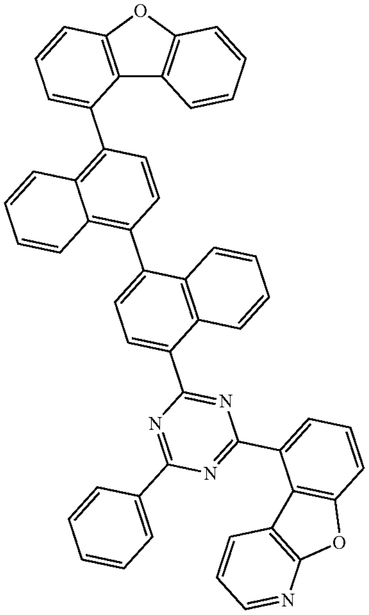
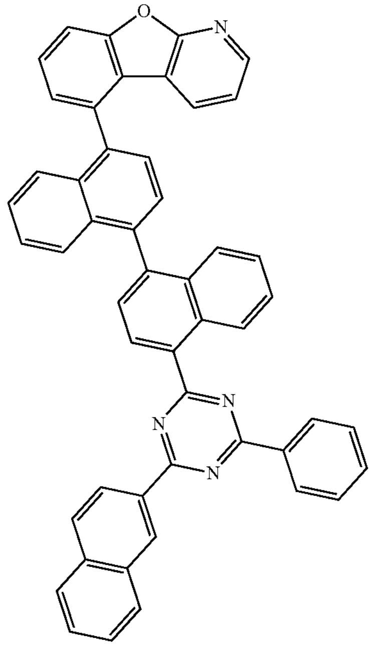
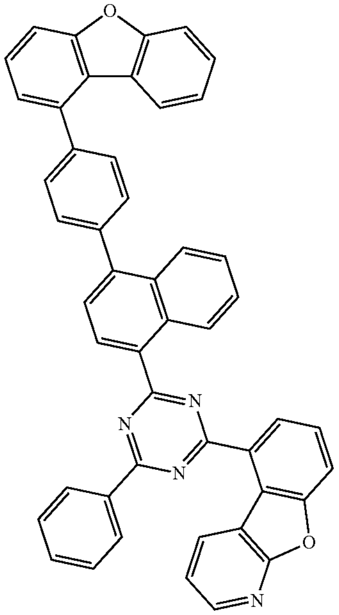
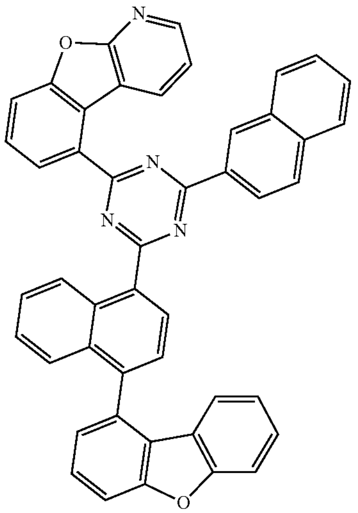
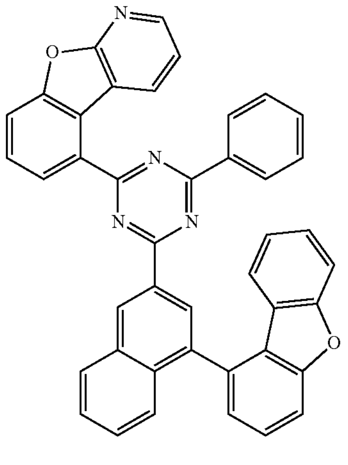
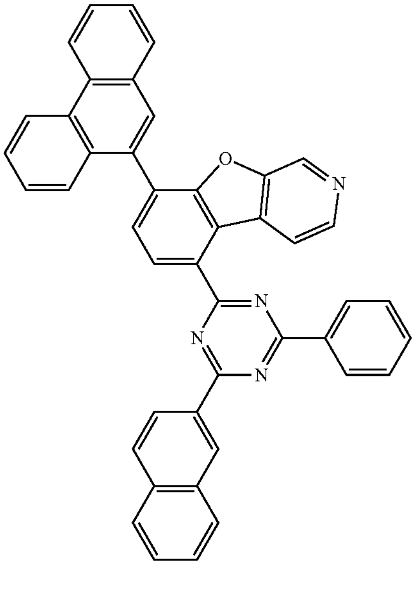

-continued
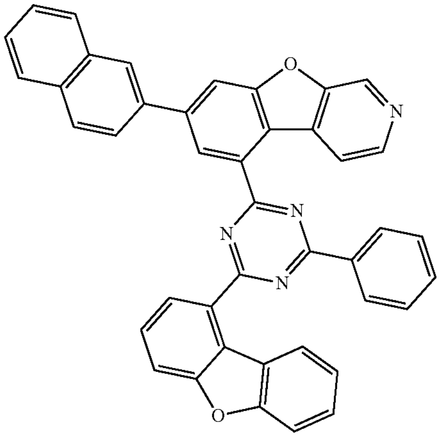
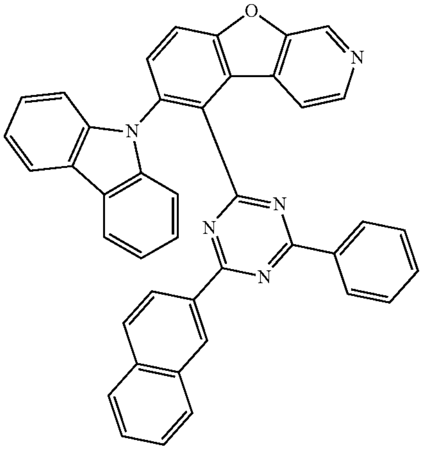
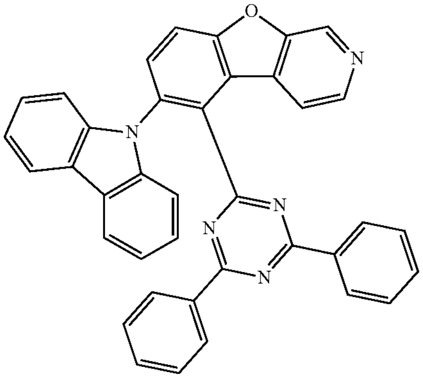
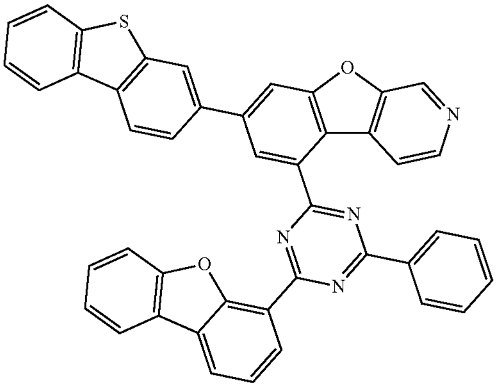
-continued
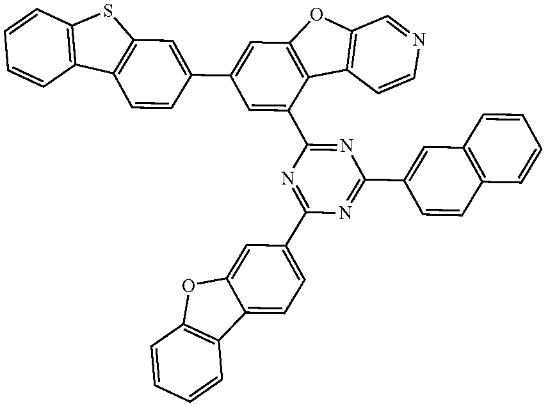
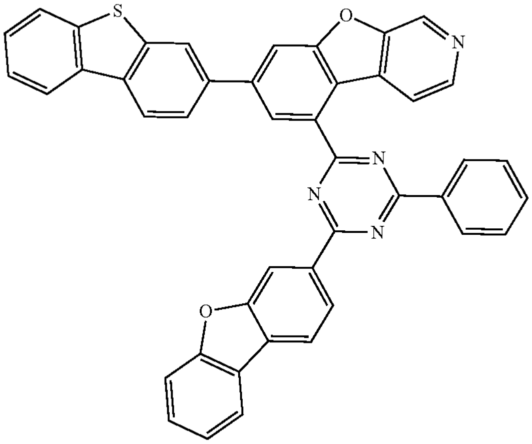
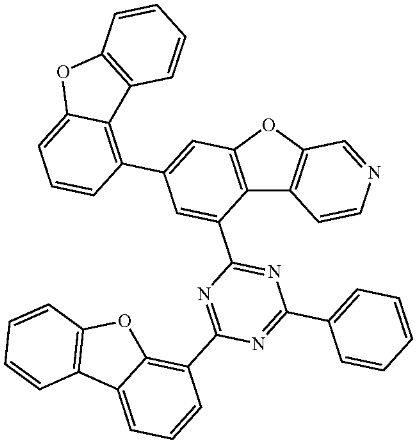

-continued
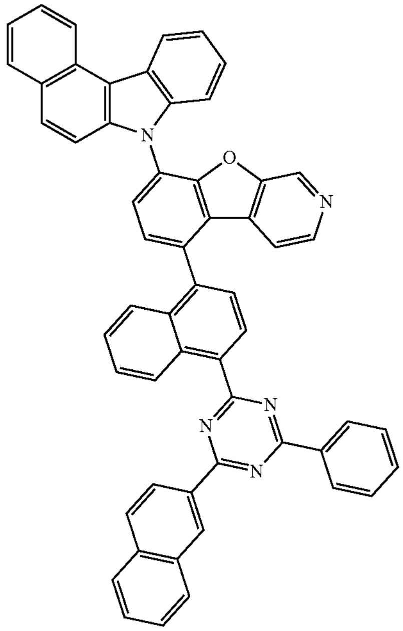
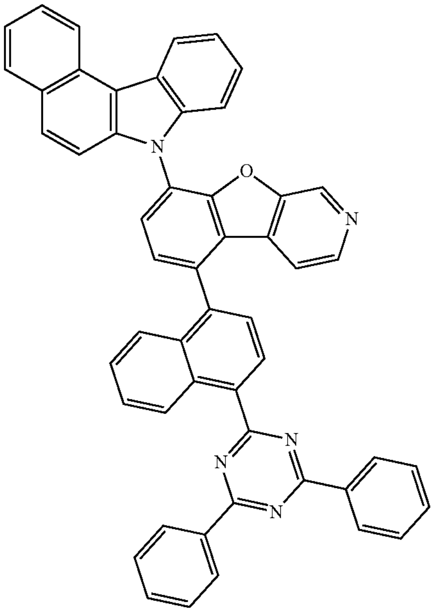
-continued
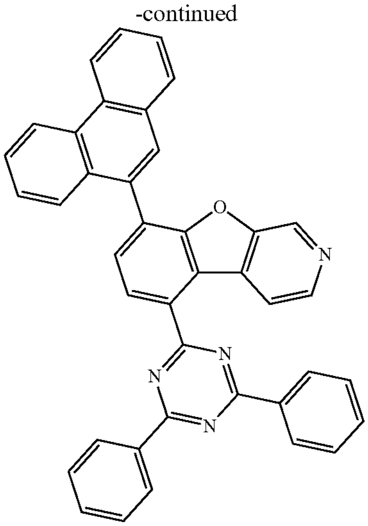
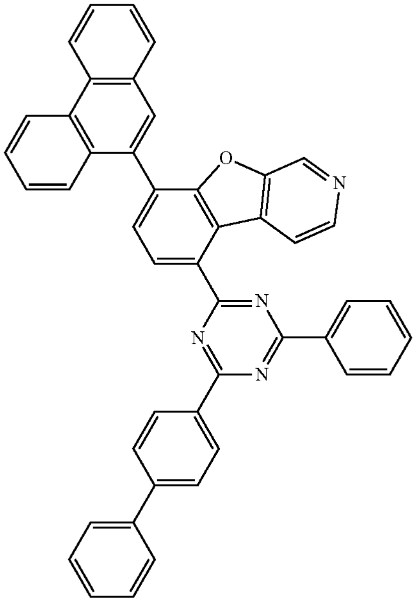

-continued
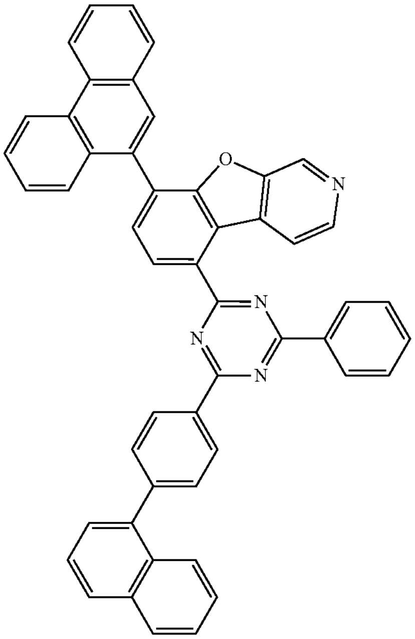
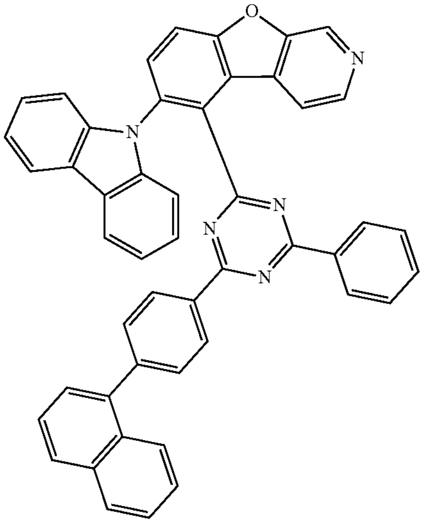
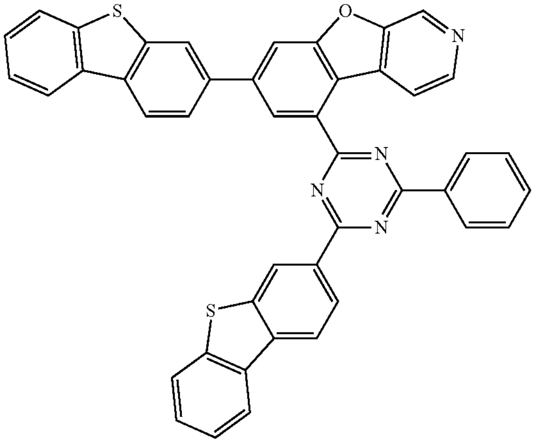
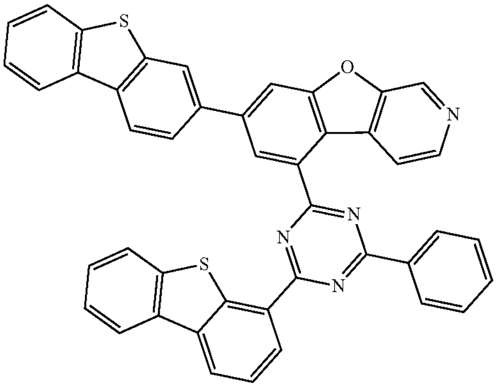
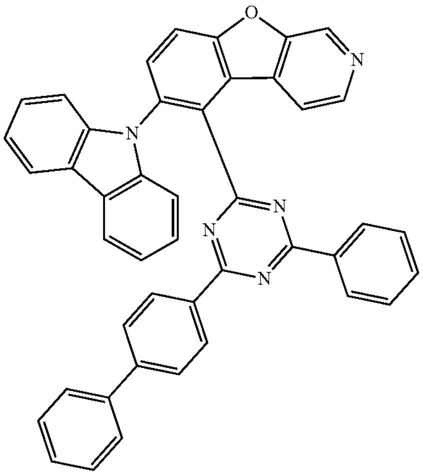
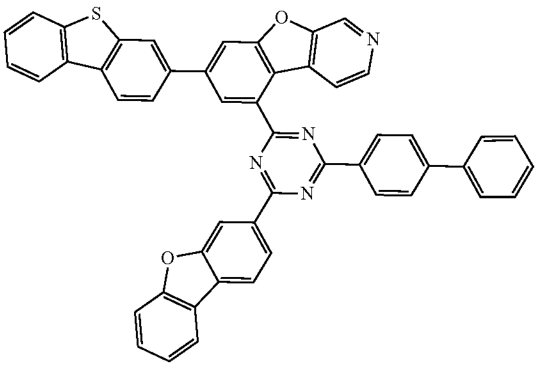
-continued -continued
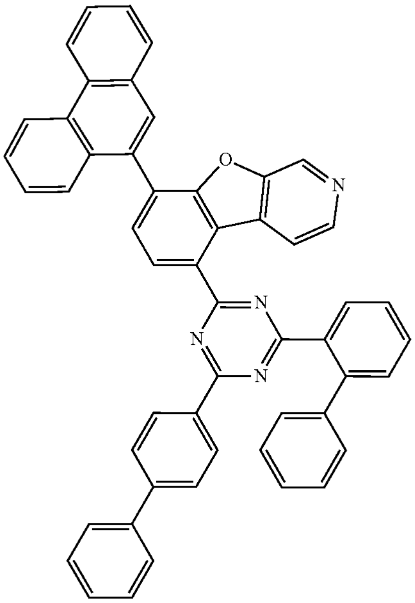
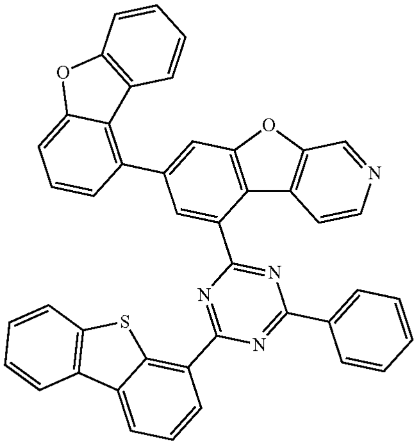
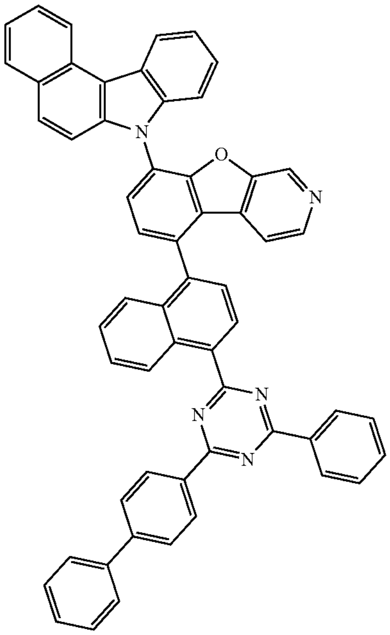
-continued
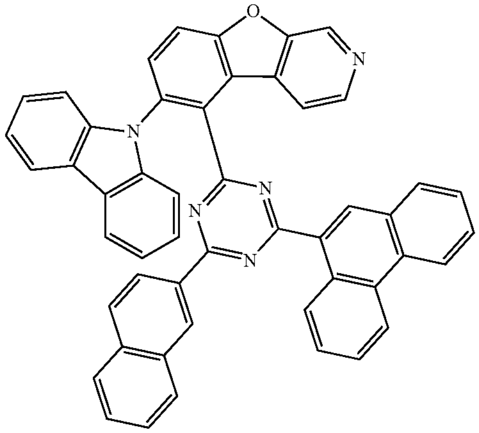
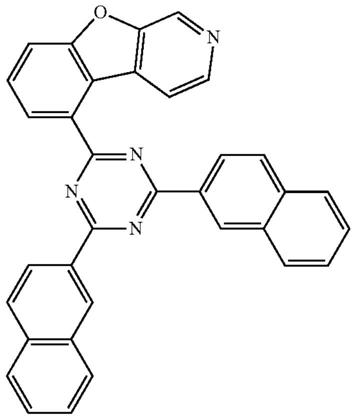
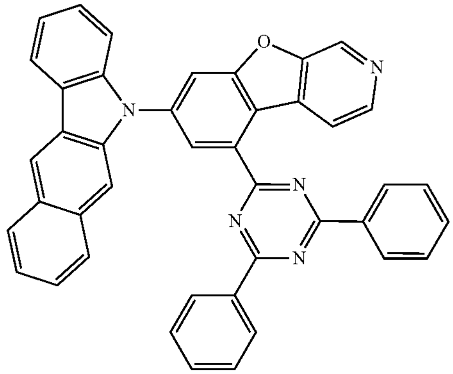

-continued
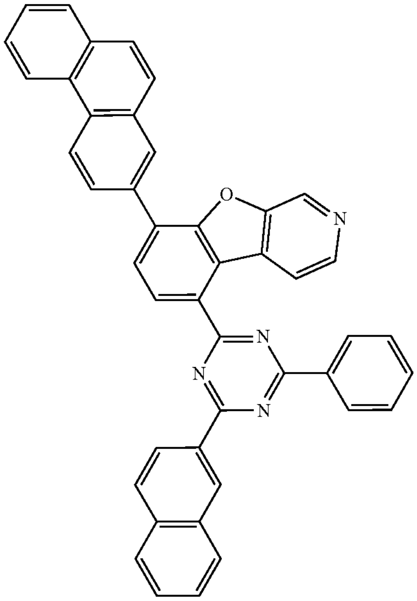
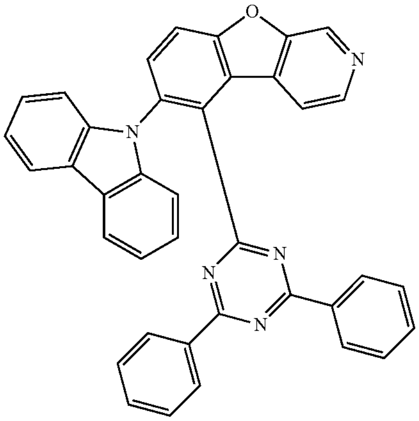
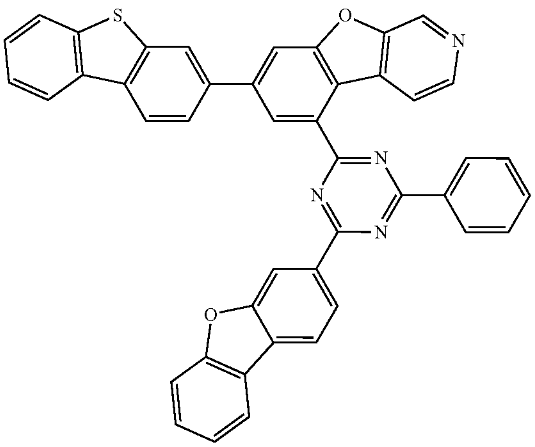
-continued
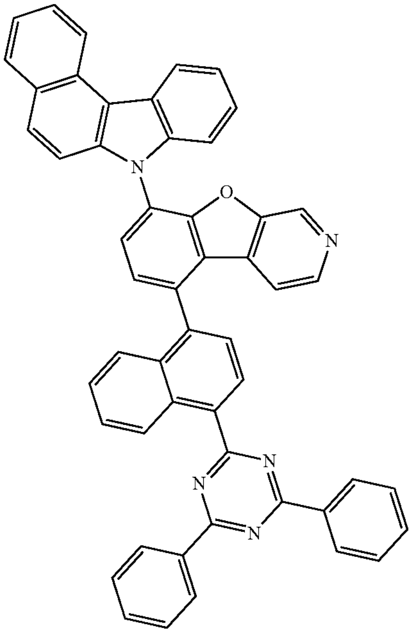
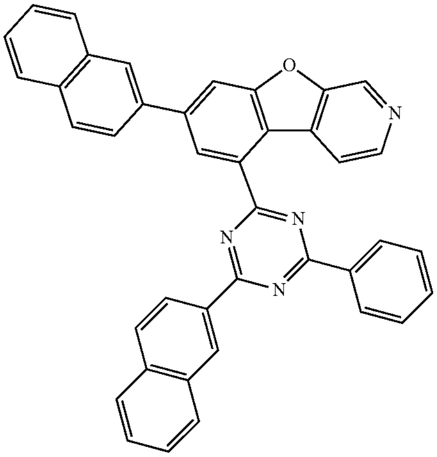
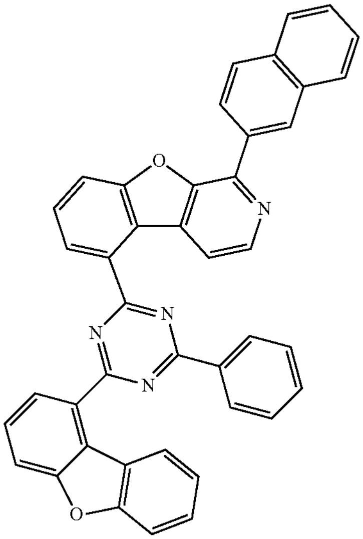

-continued
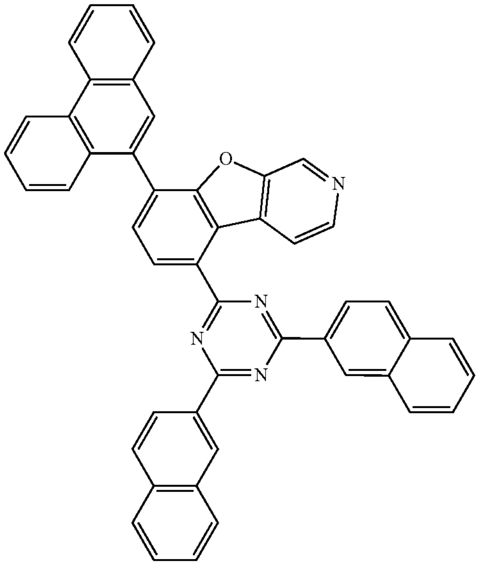
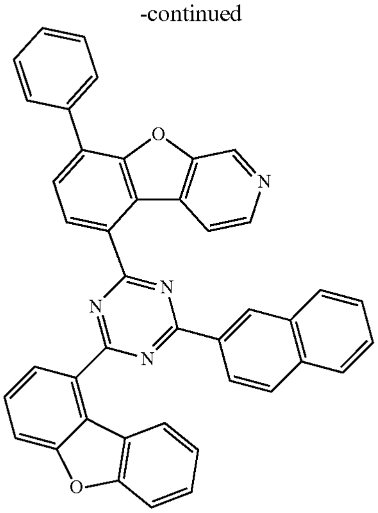
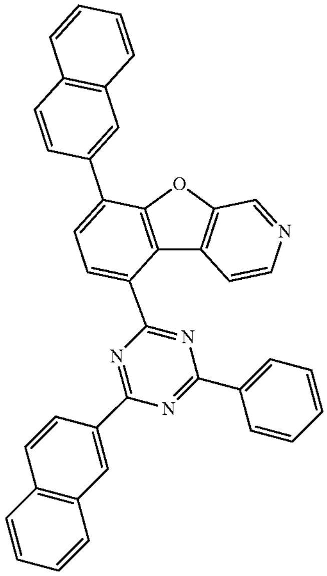
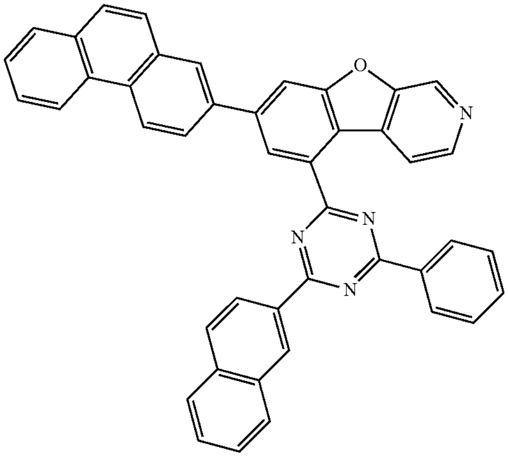
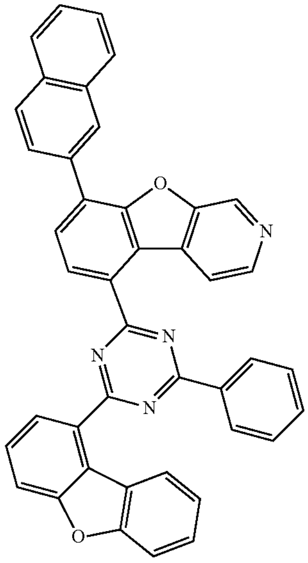
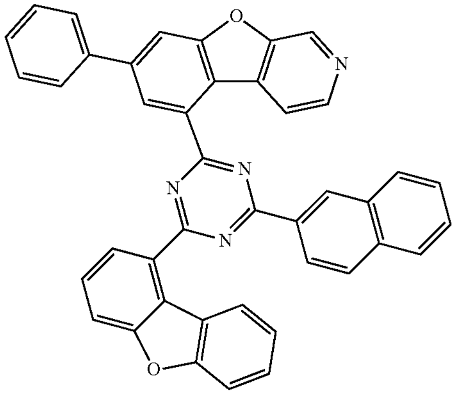
-continued -continued
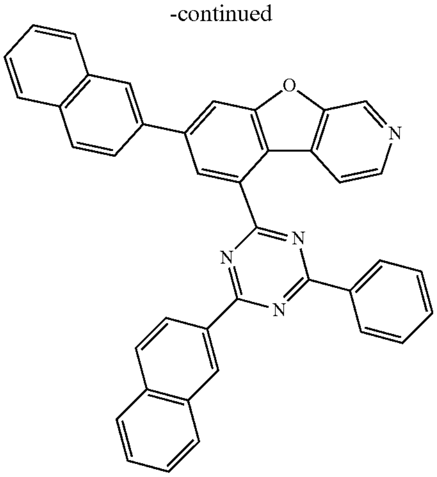
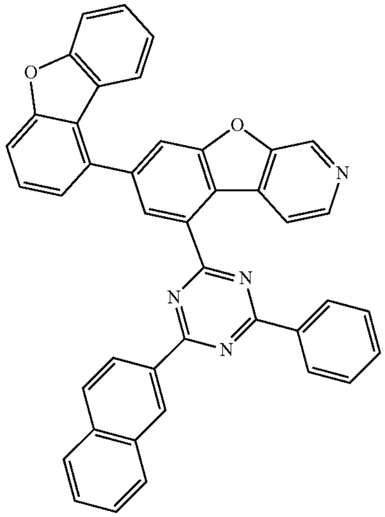
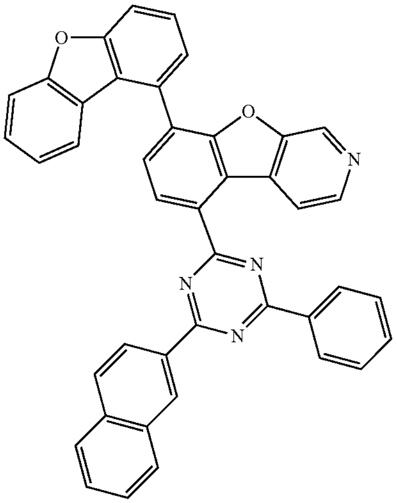
-continued
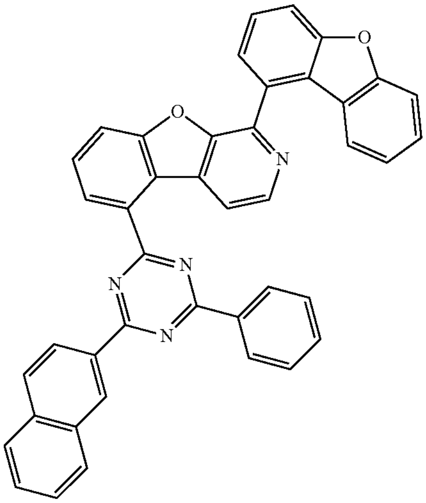
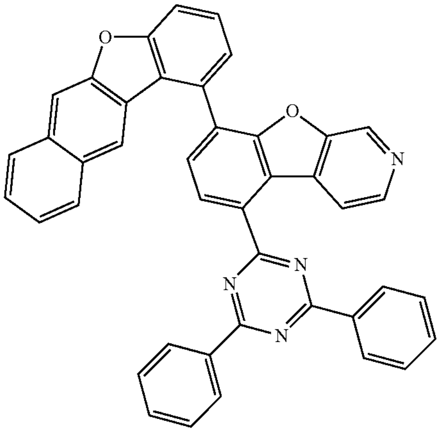
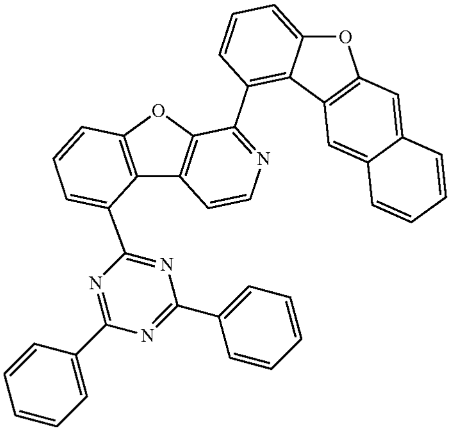

-continued
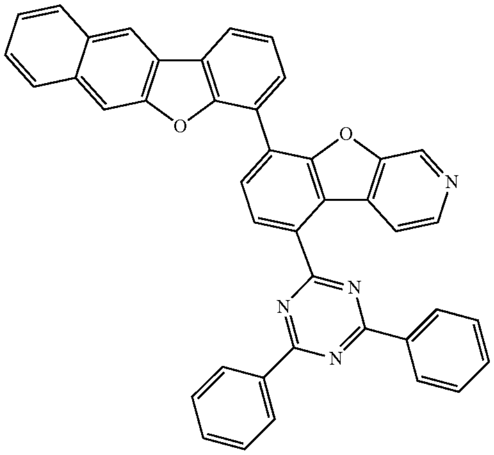
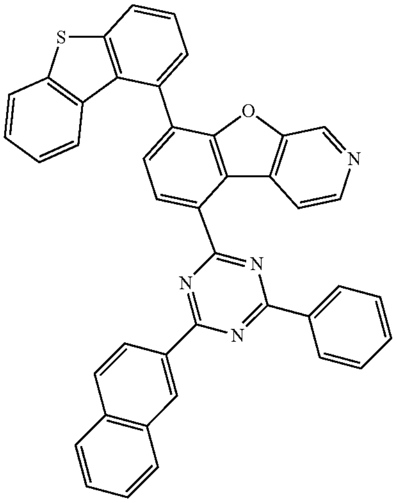
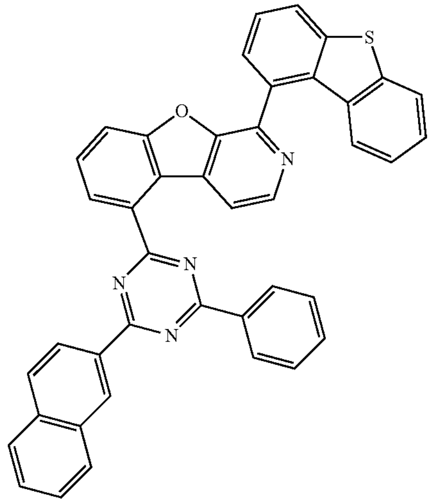
-continued
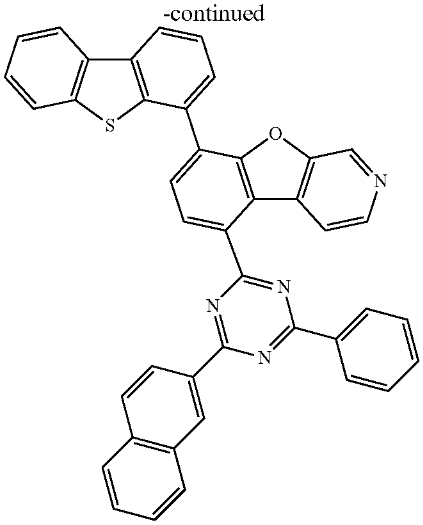
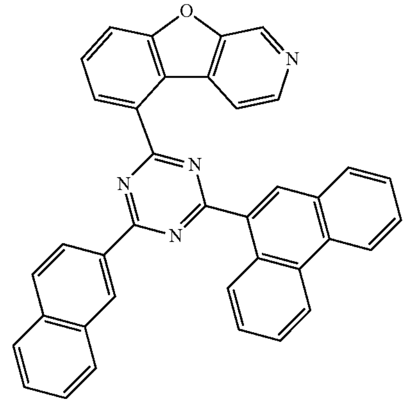
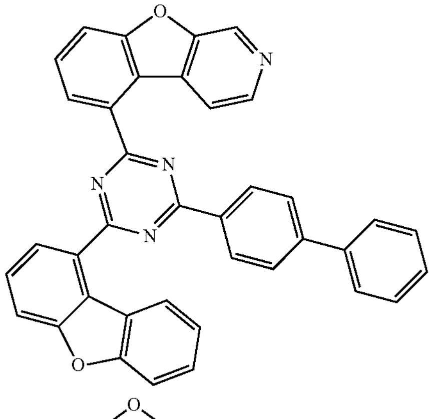
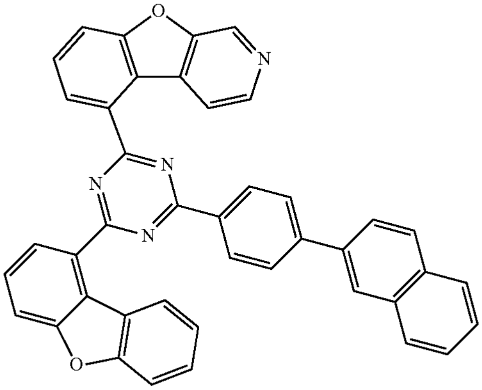

-continued
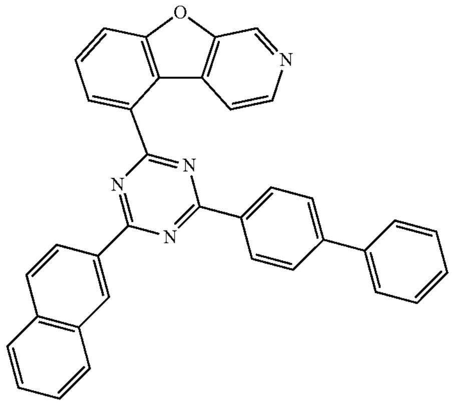
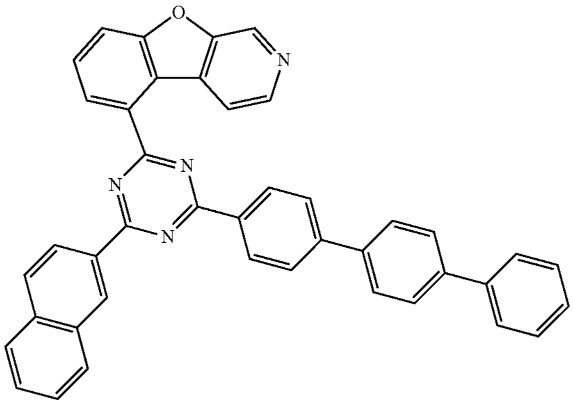
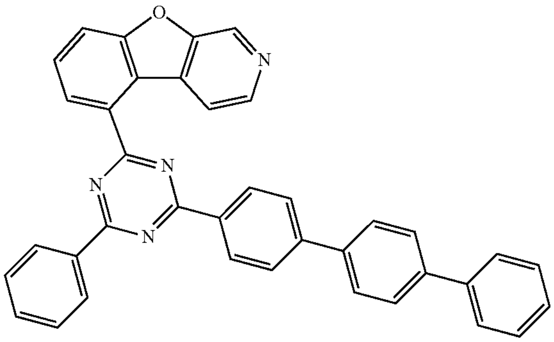
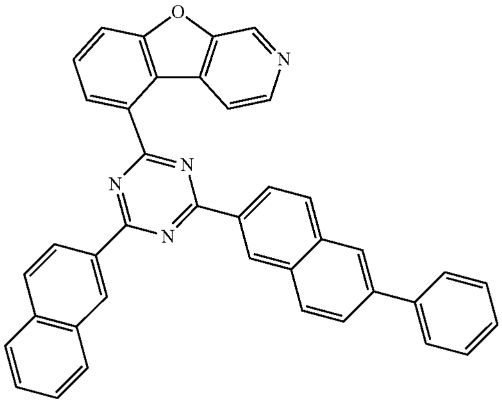
-continued
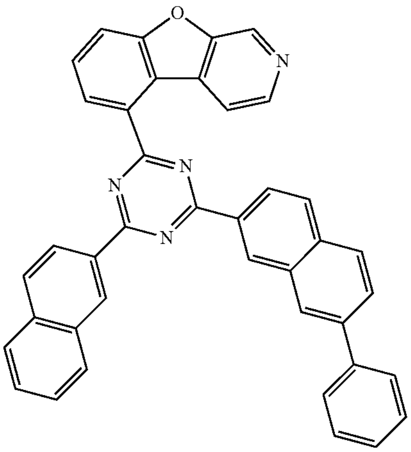
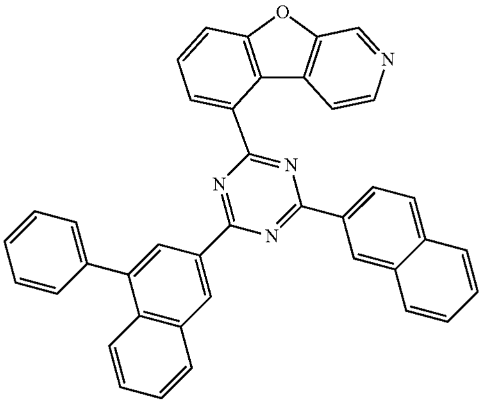
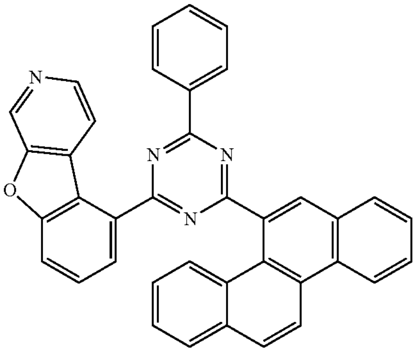
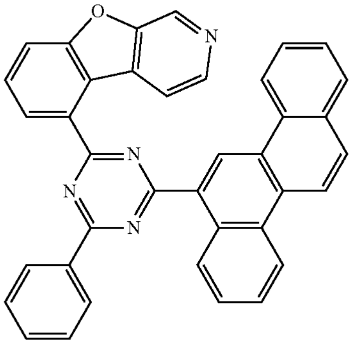

-continued
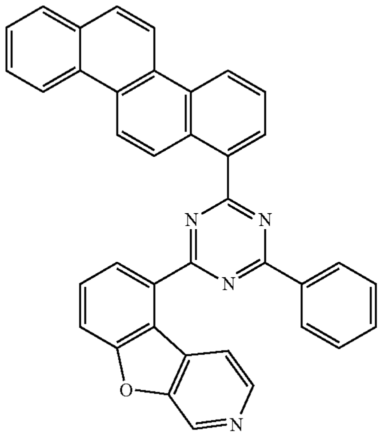
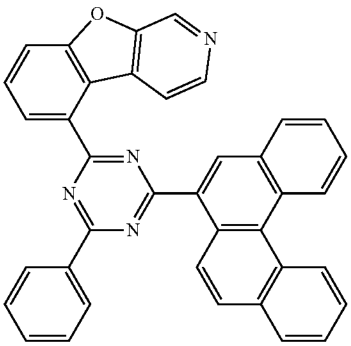
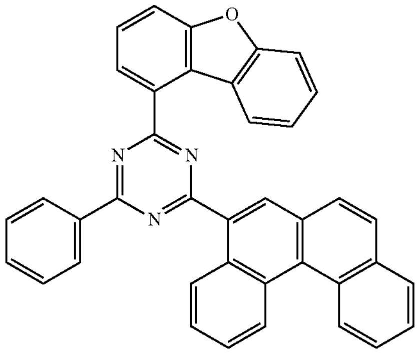
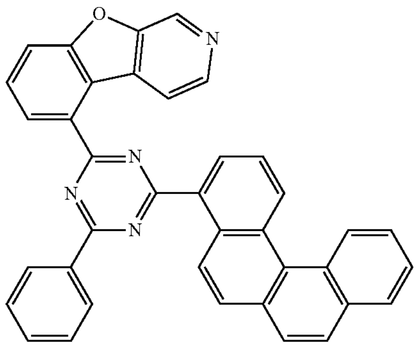
-continued
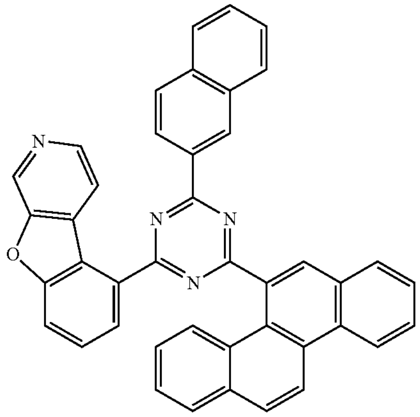
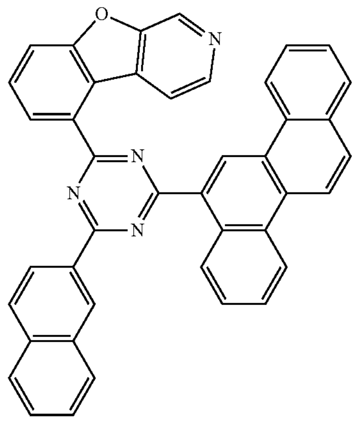
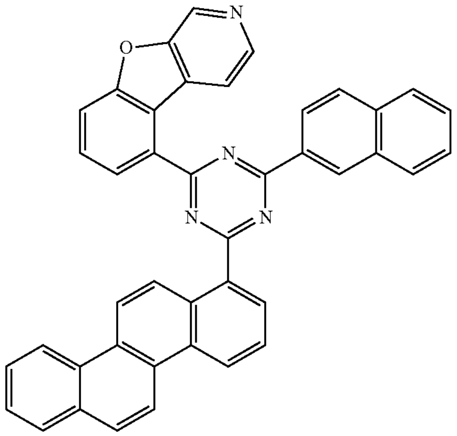
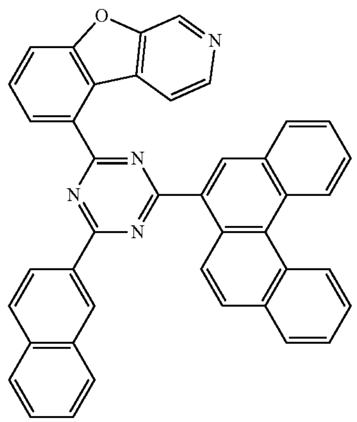

-continued
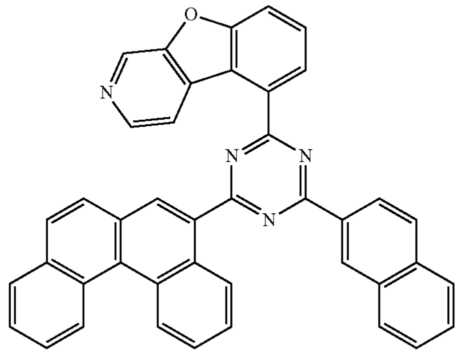
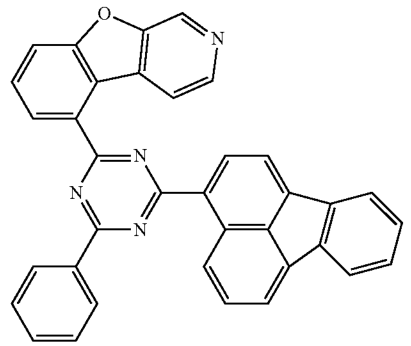
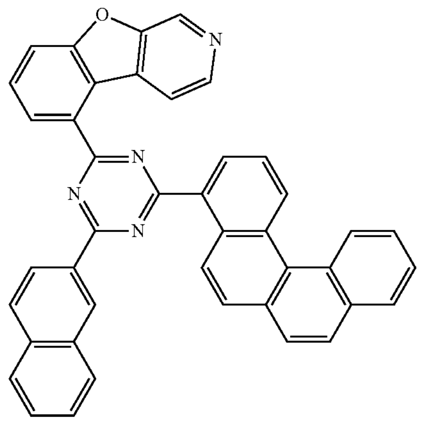
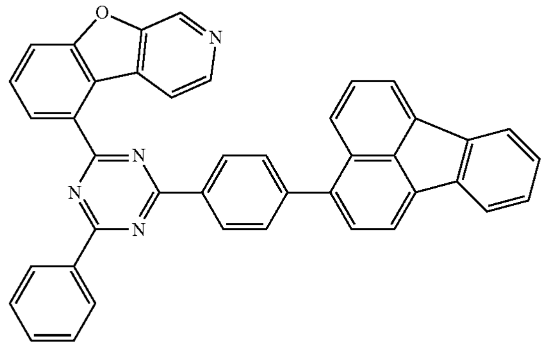
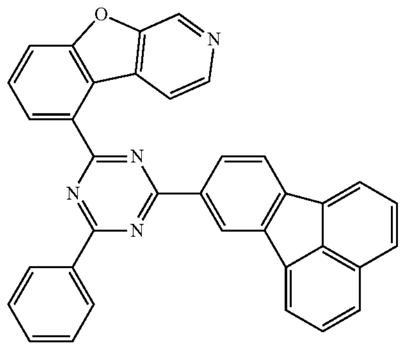
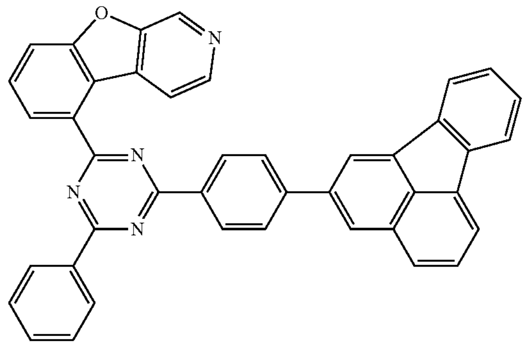
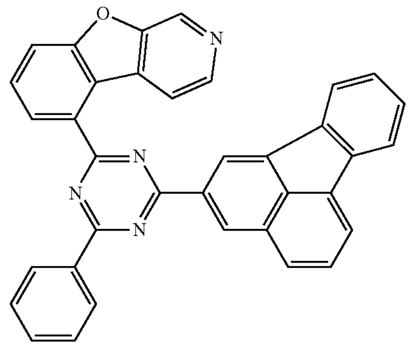
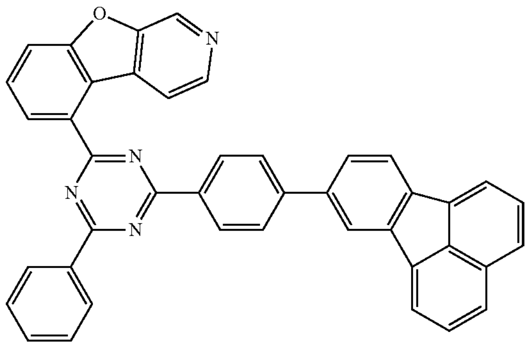
-continued -continued
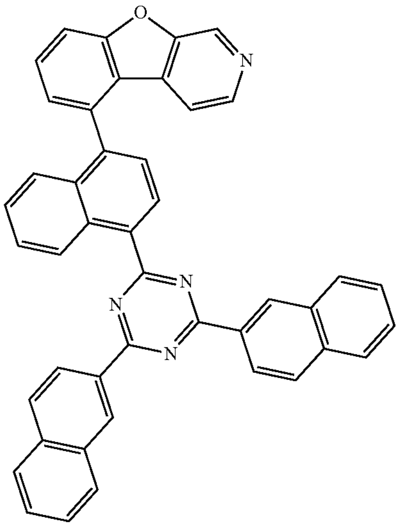
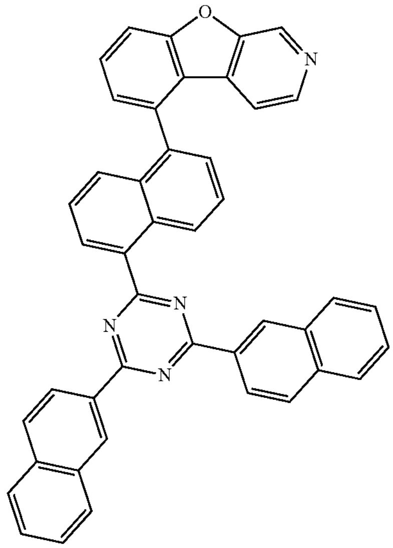
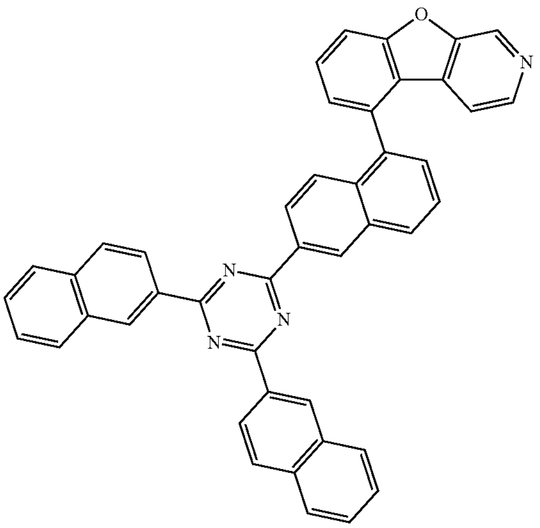
-continued
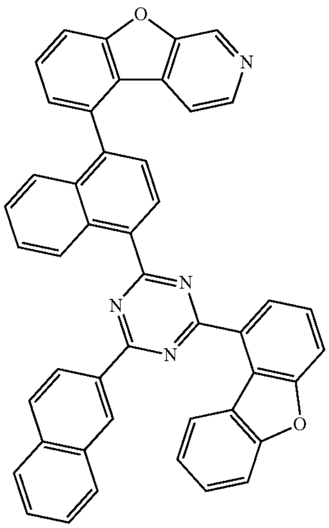
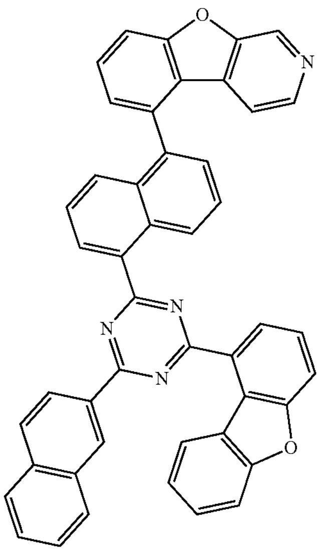
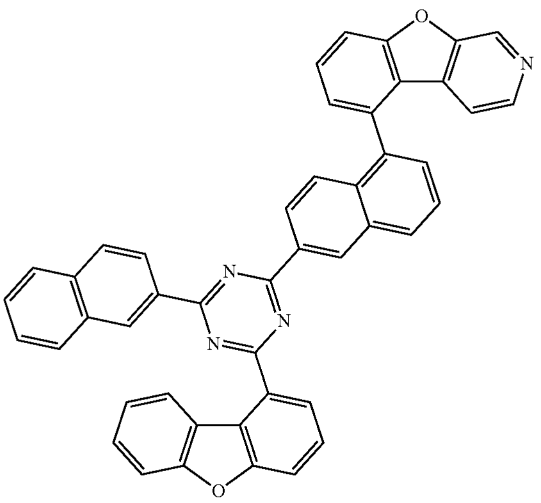

-continued
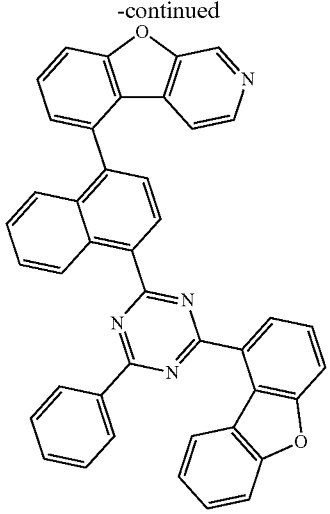
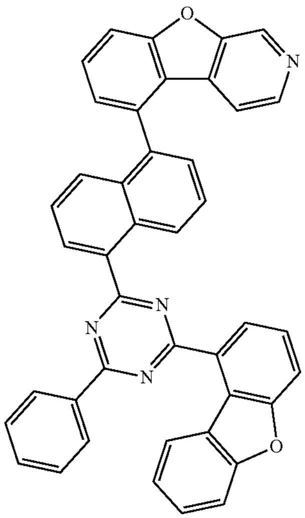
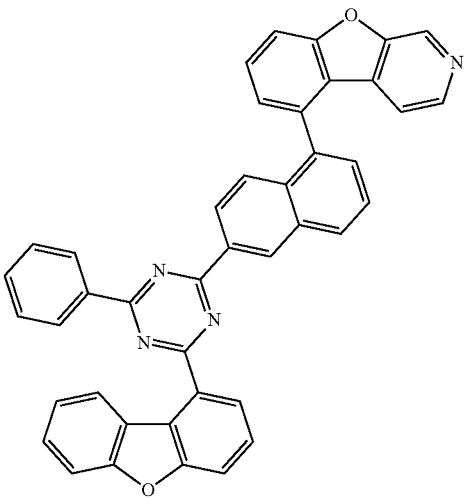
-continued
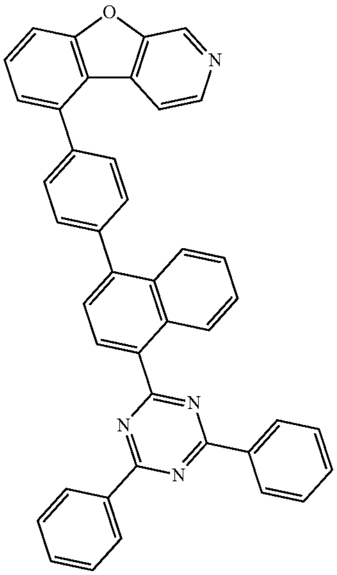
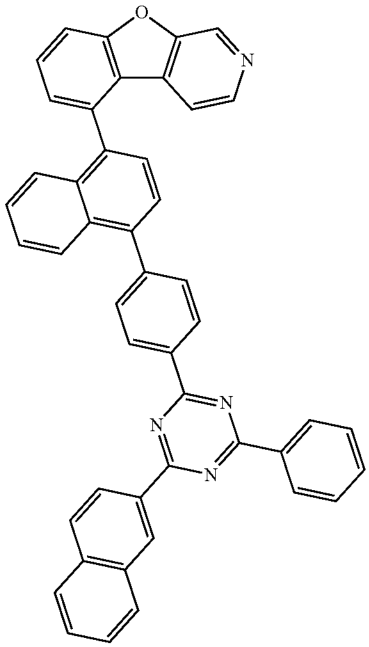

-continued
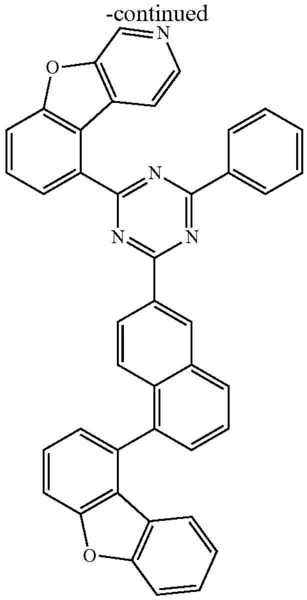
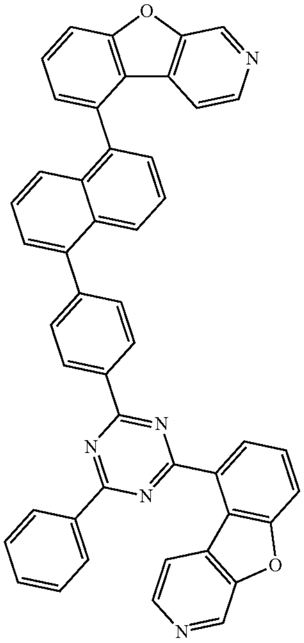
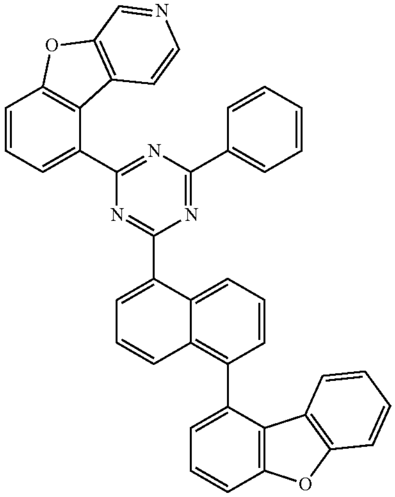
-continued
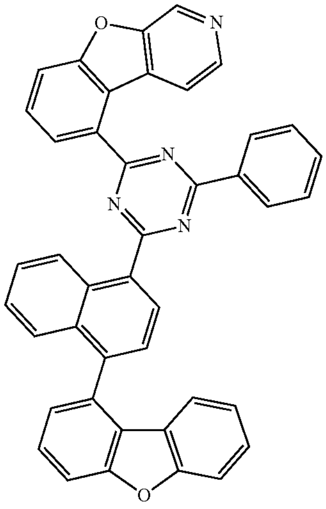
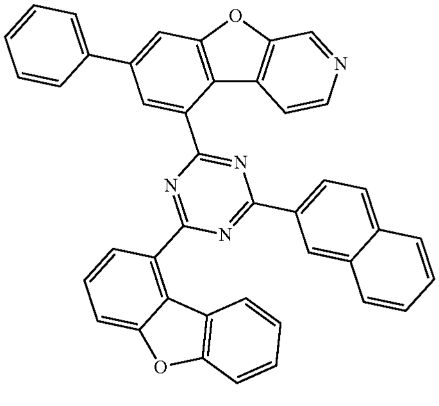
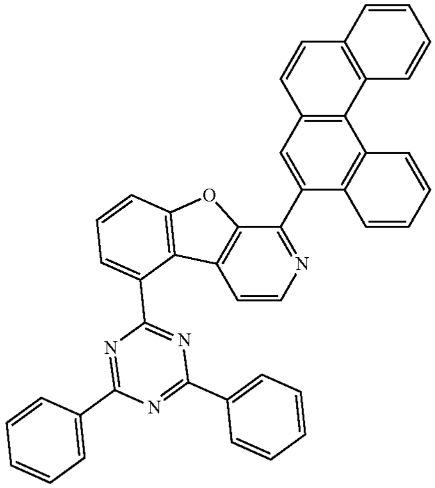

-continued
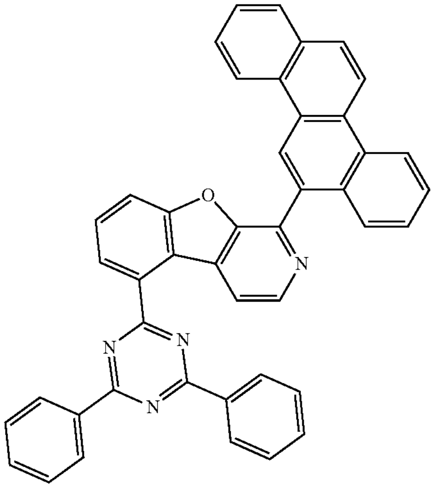
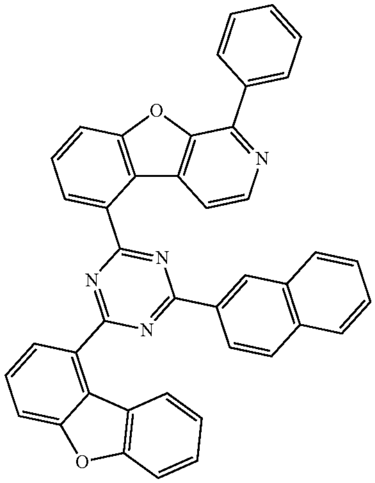
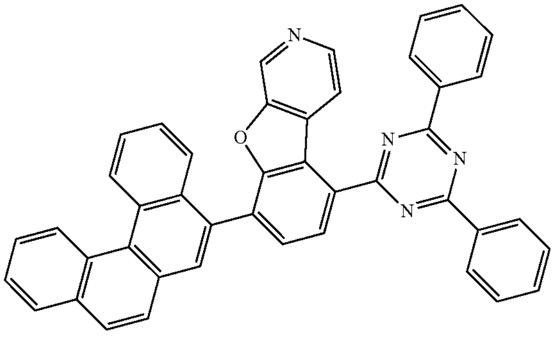
-continued
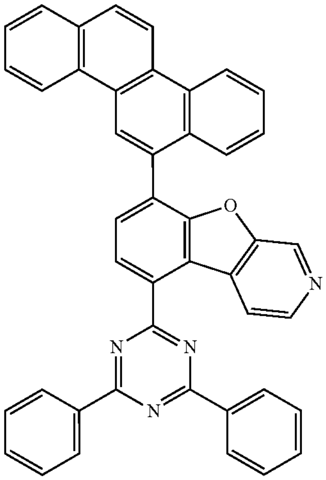
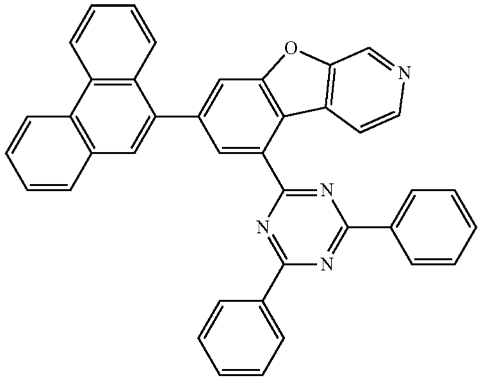
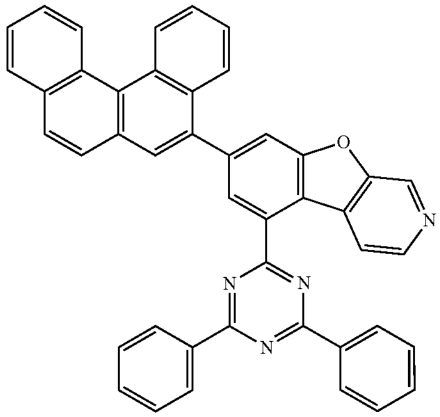
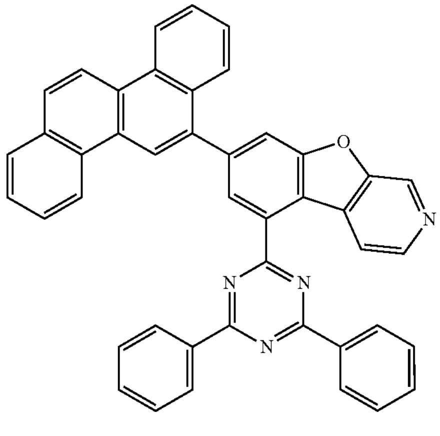

-continued
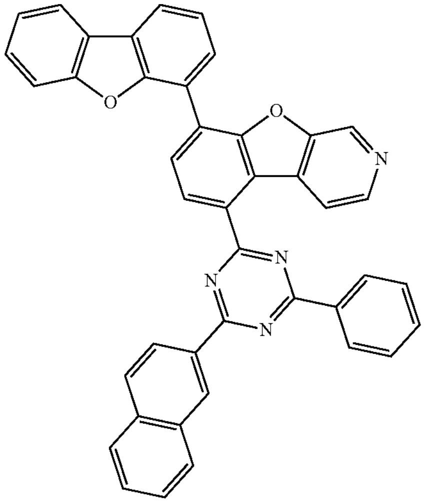
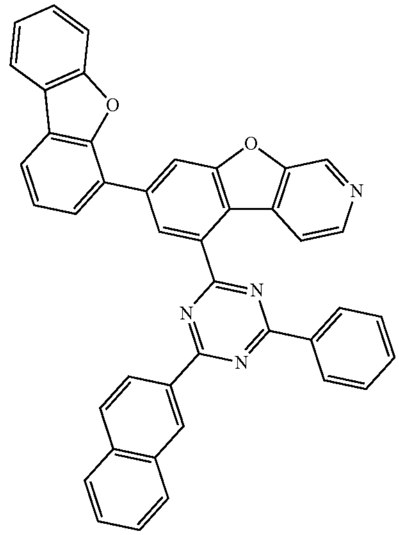
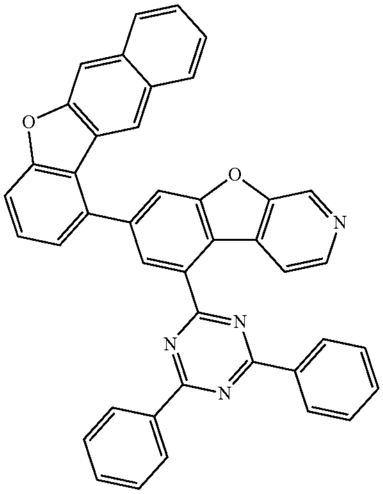
-continued
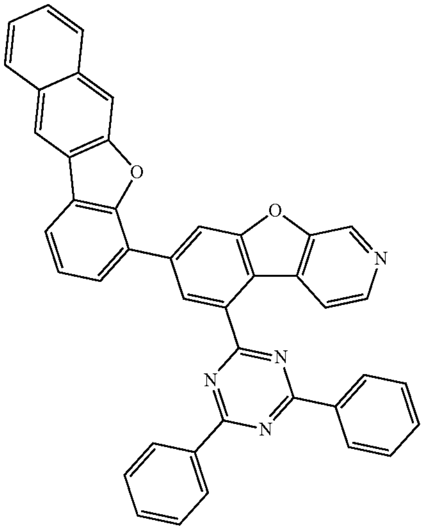
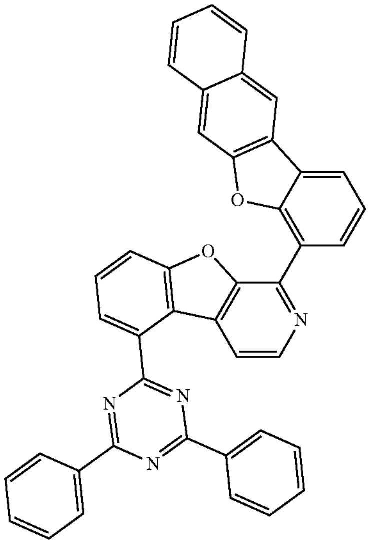
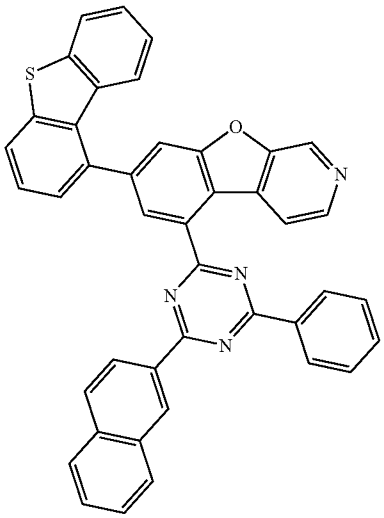

-continued
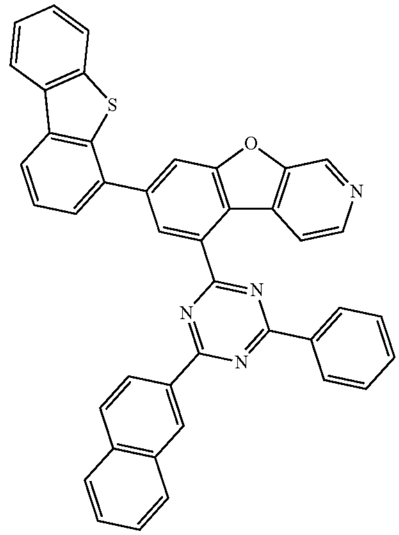
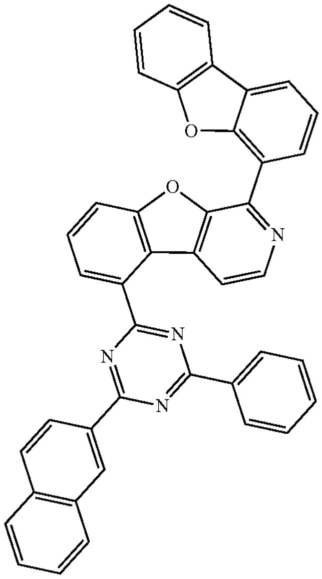
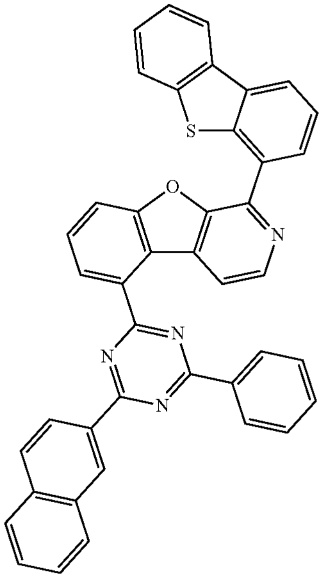
-continued
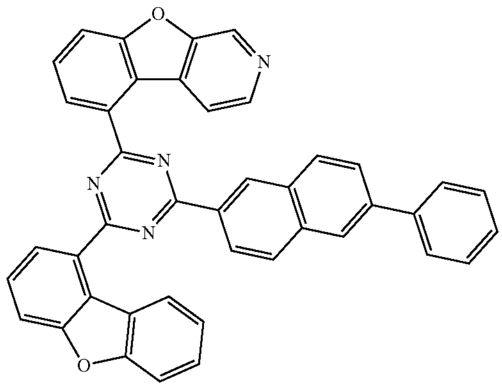
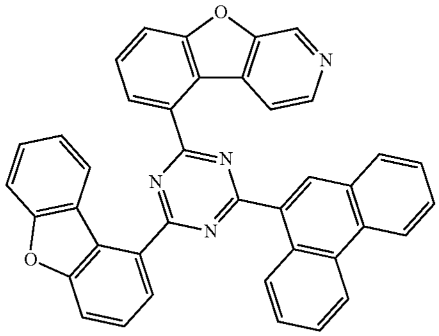
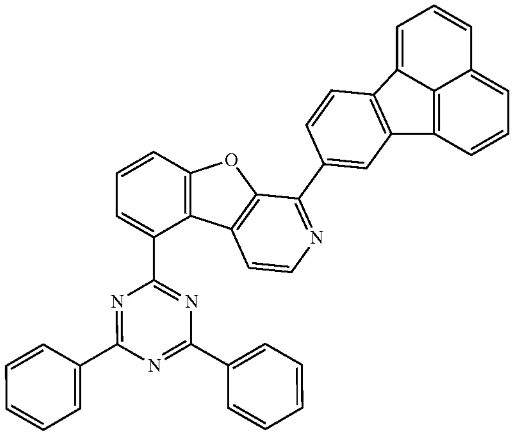
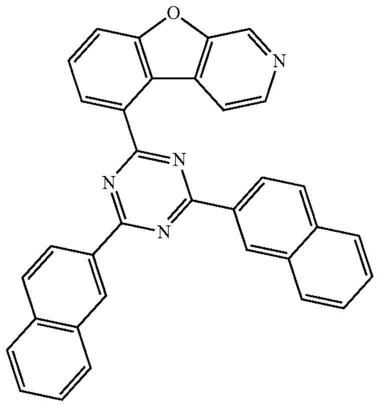

-continued
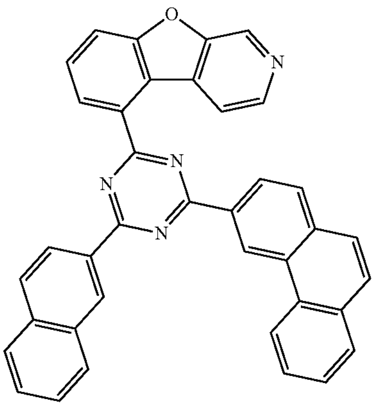
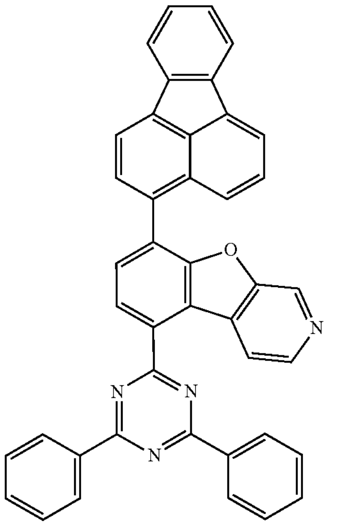
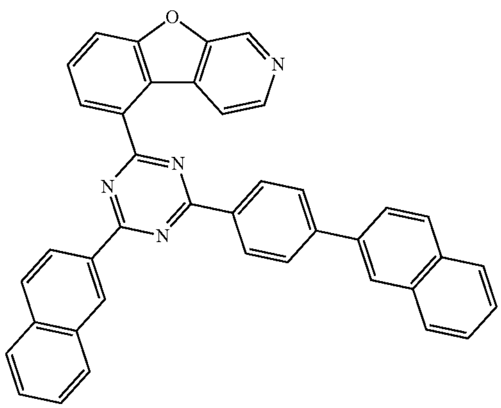
-continued
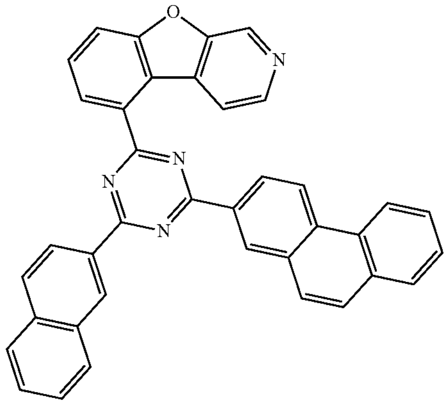
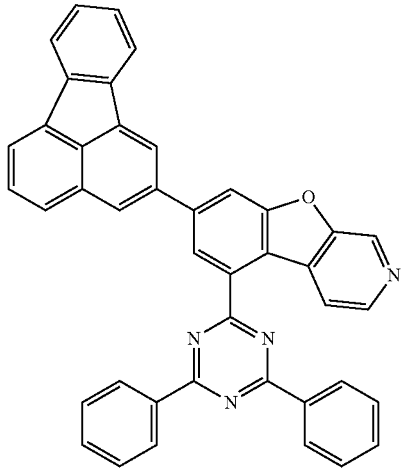
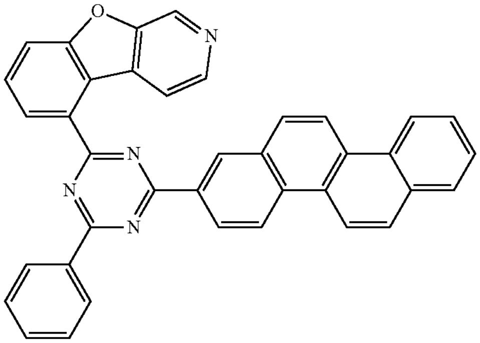
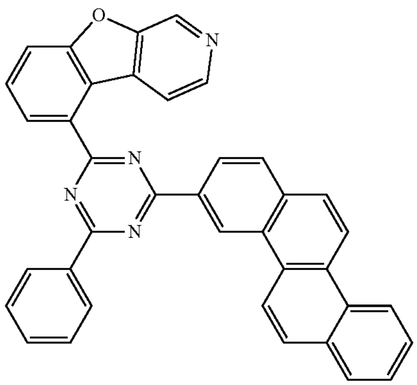

-continued
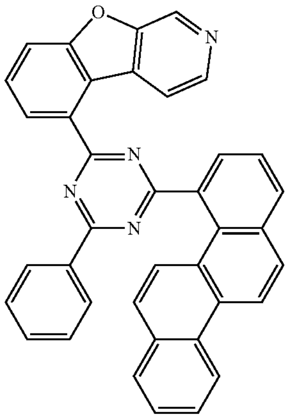
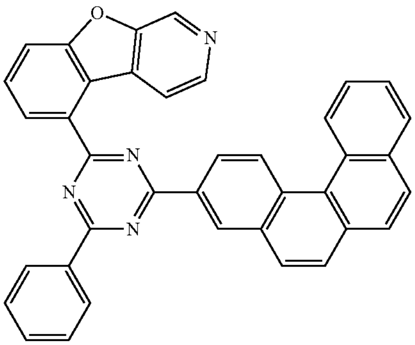
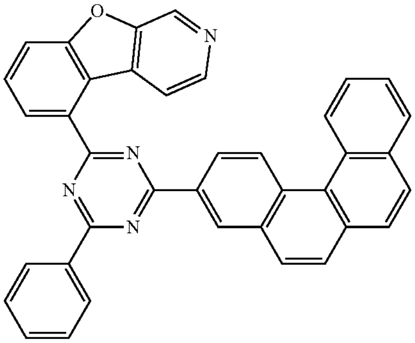
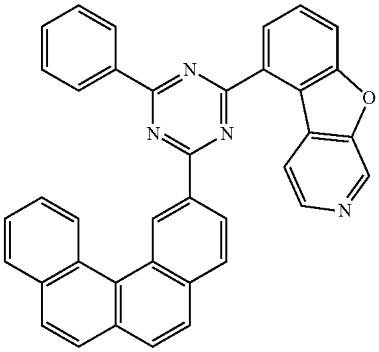
-continued
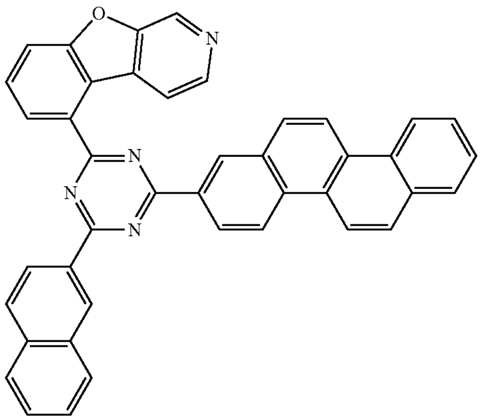
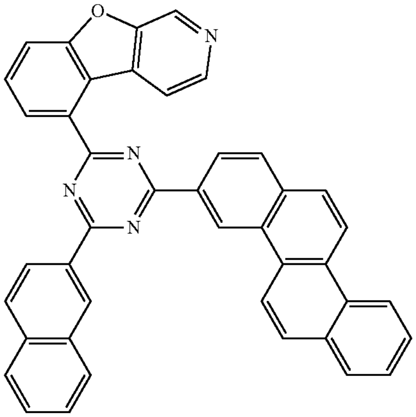
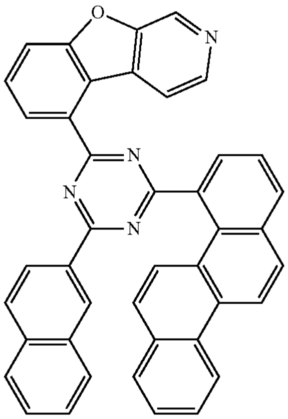
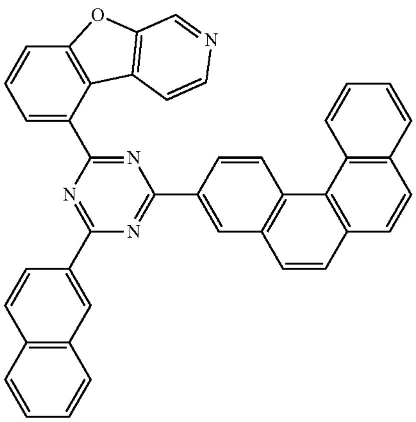

-continued
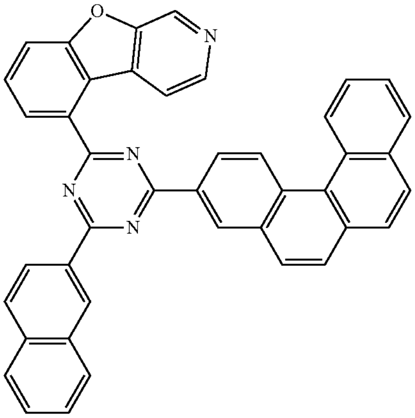
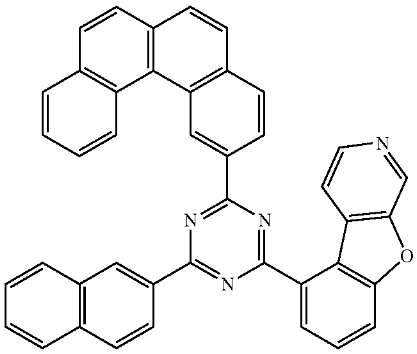
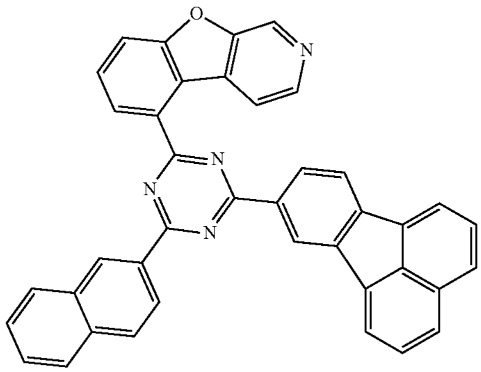
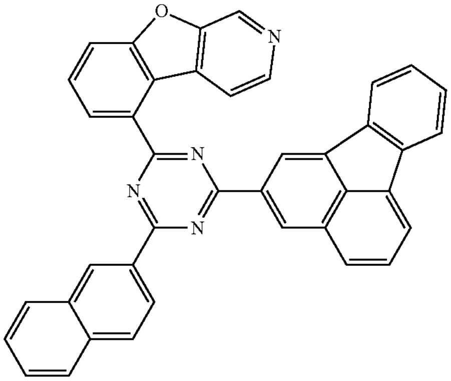
-continued
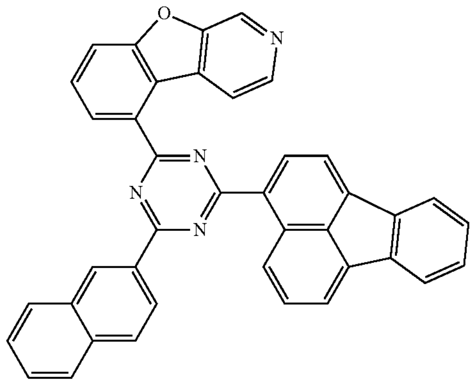
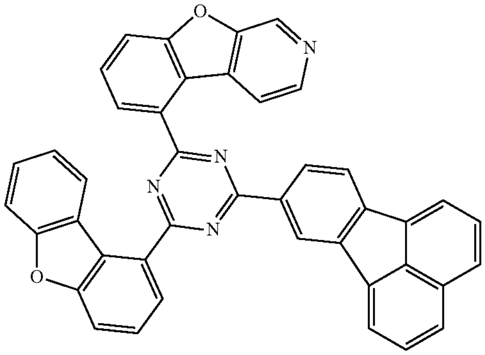
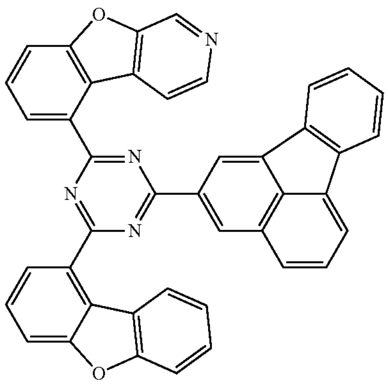
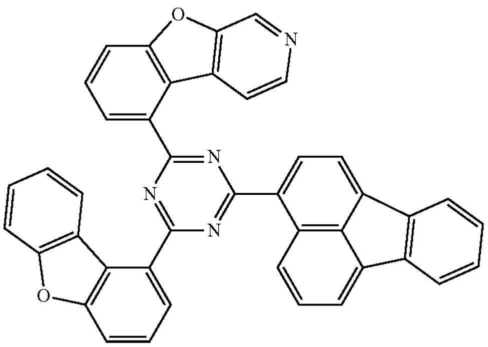

-continued
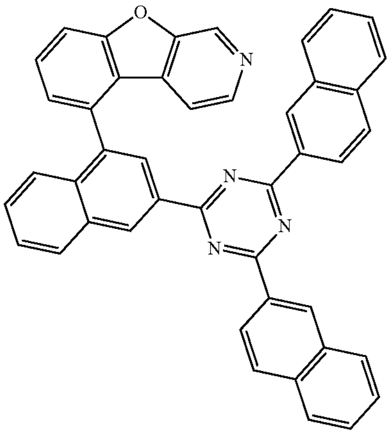
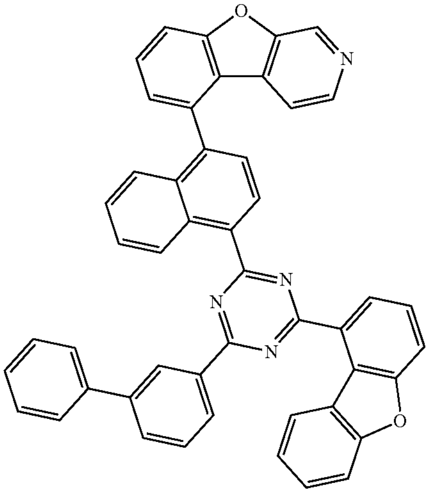
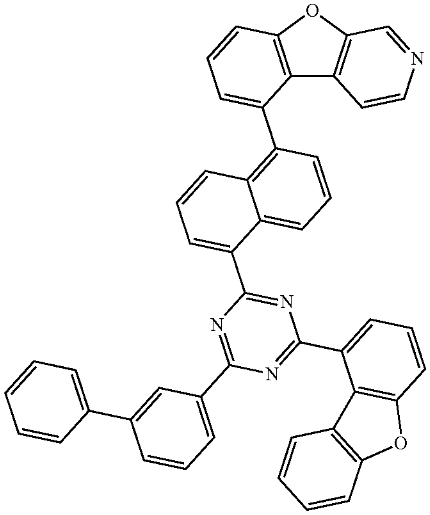
-continued
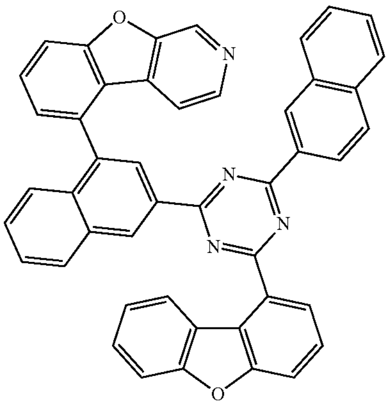
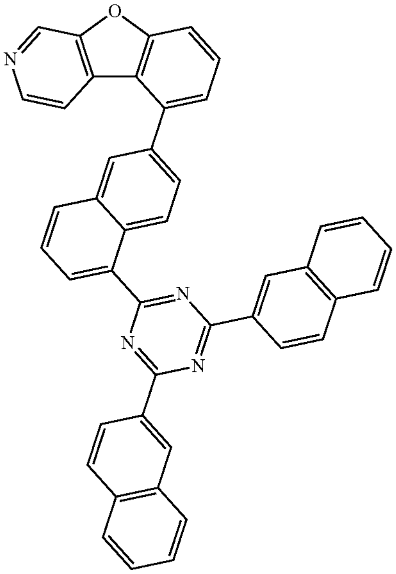
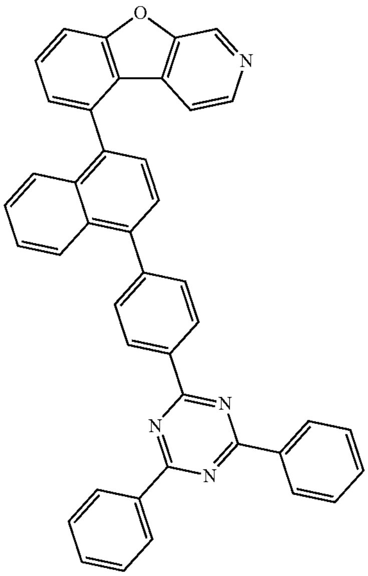

-continued
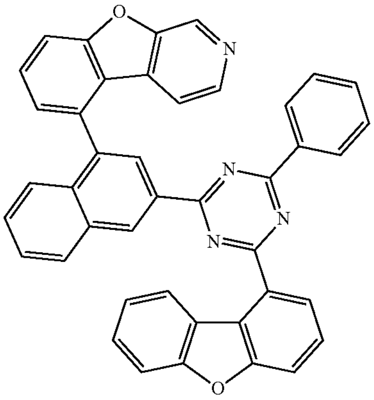
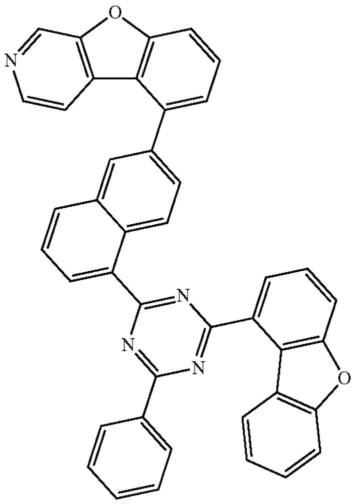
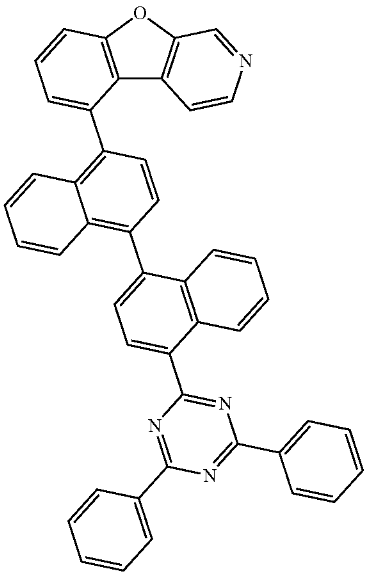
-continued
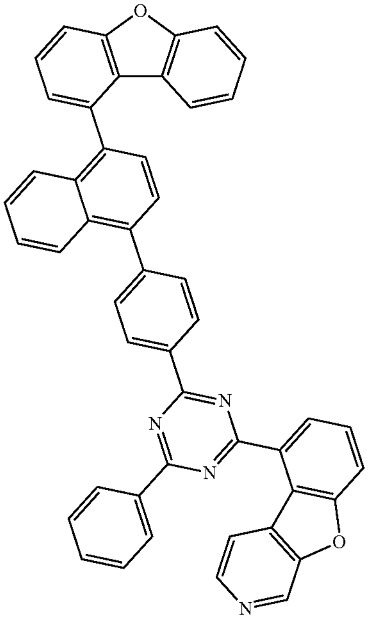
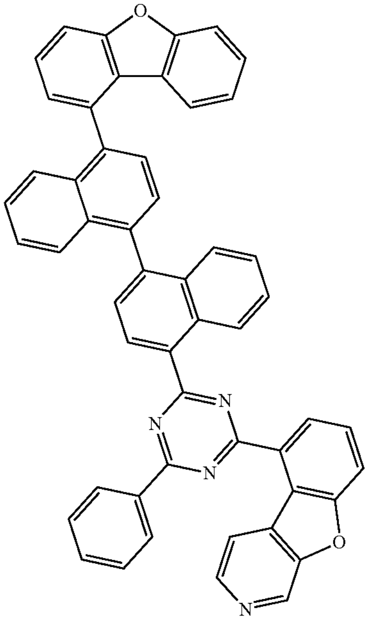

-continued
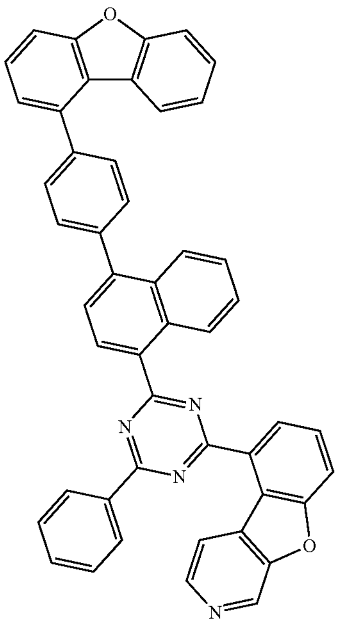
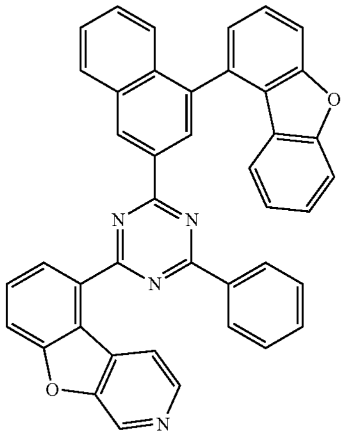
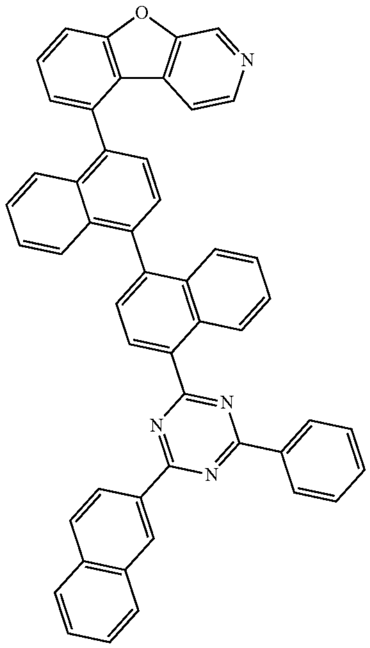
-continued
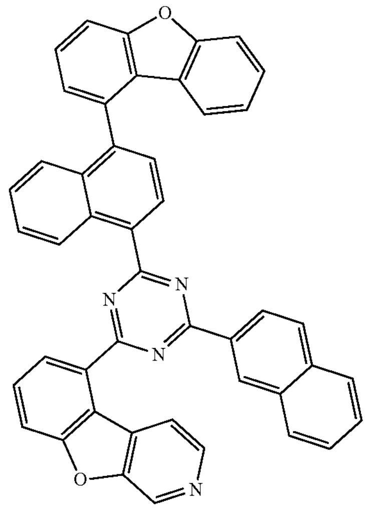
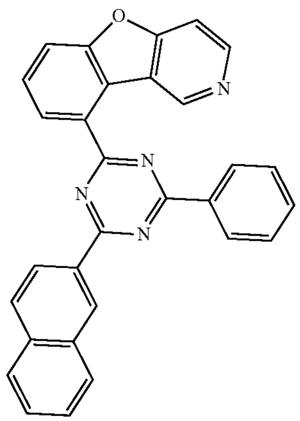
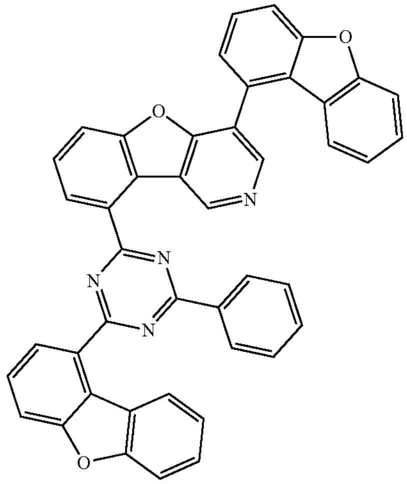

-continued
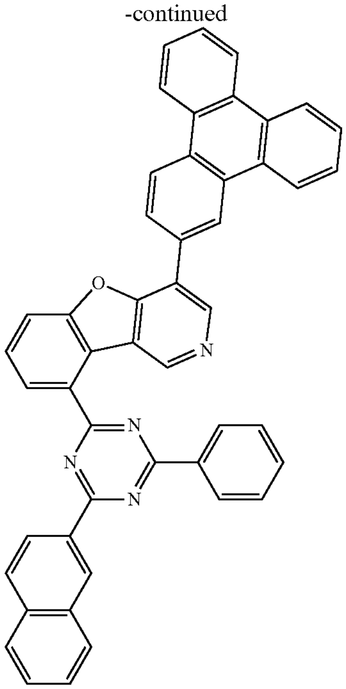
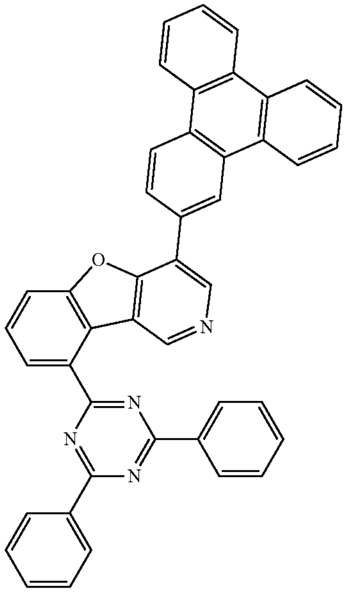
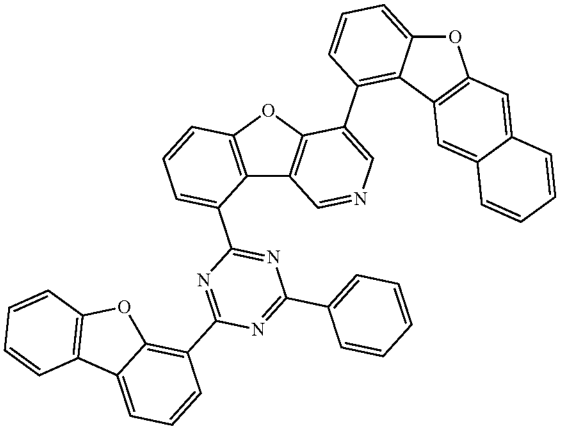
-continued
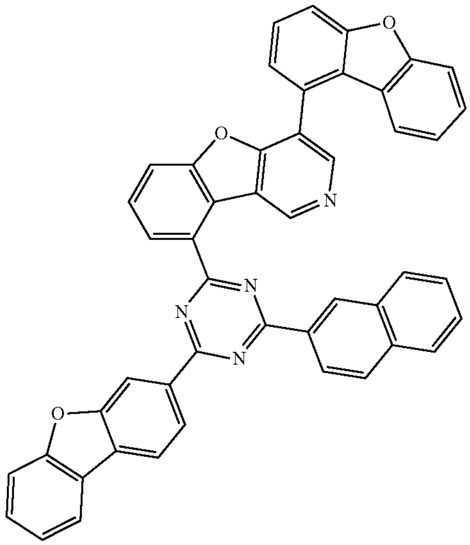
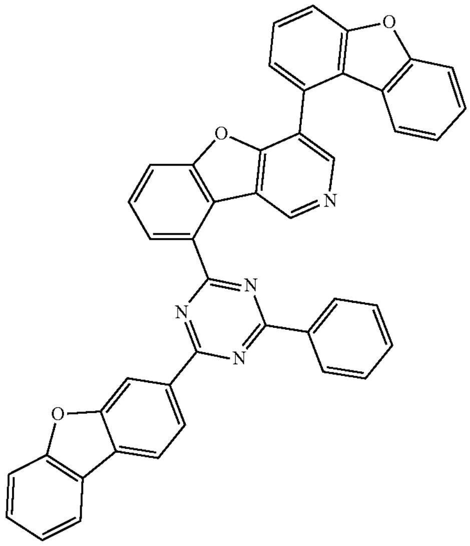
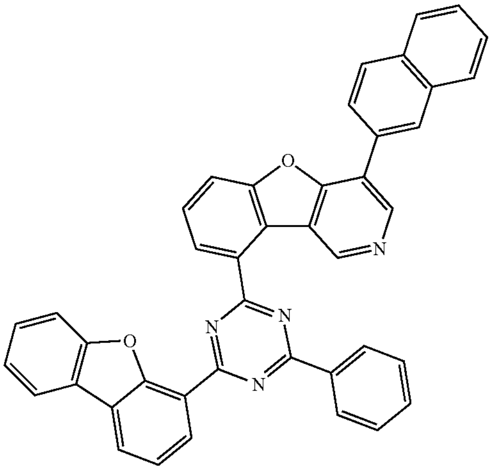

-continued
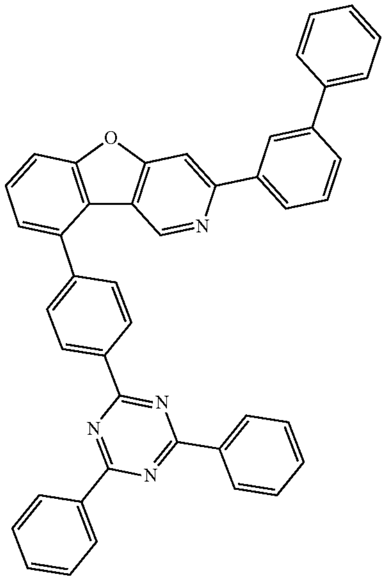
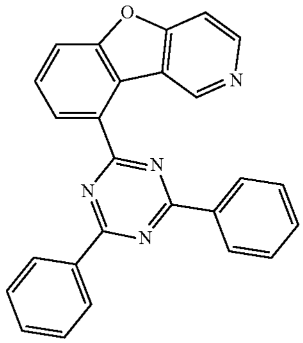
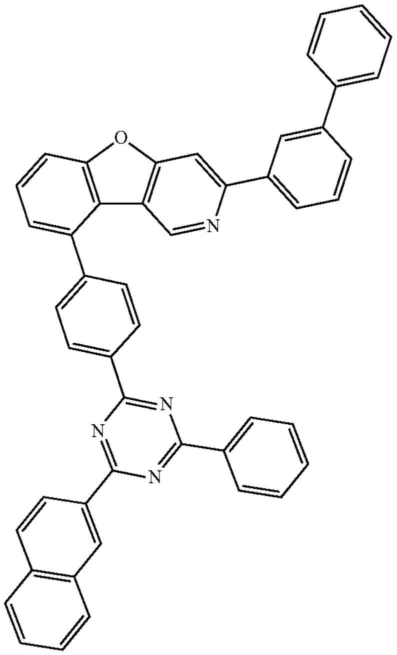
-continued
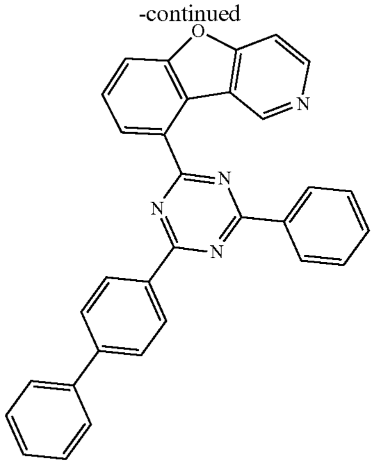
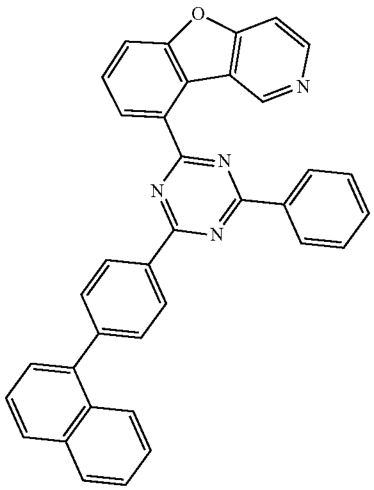
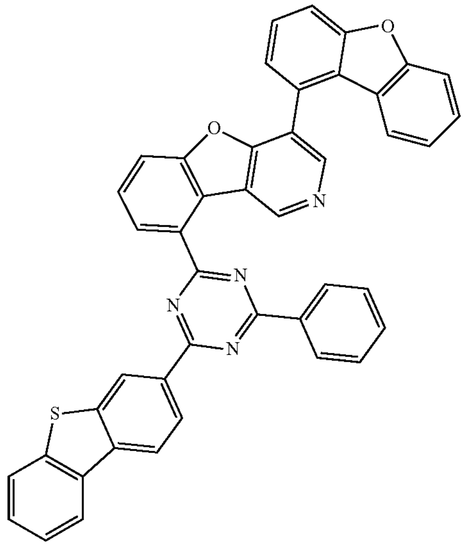

-continued
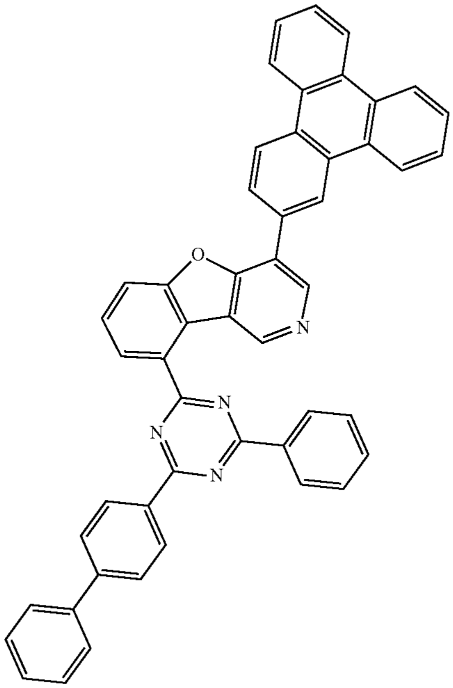
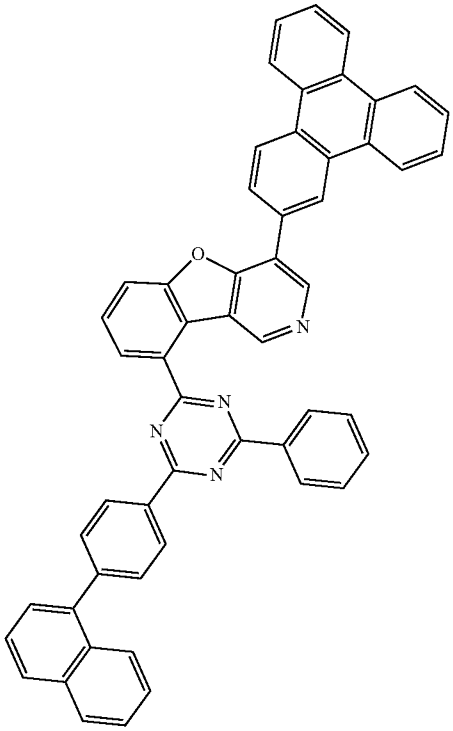
-continued
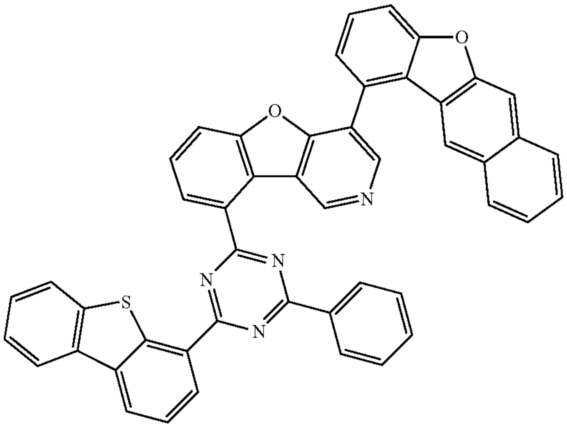
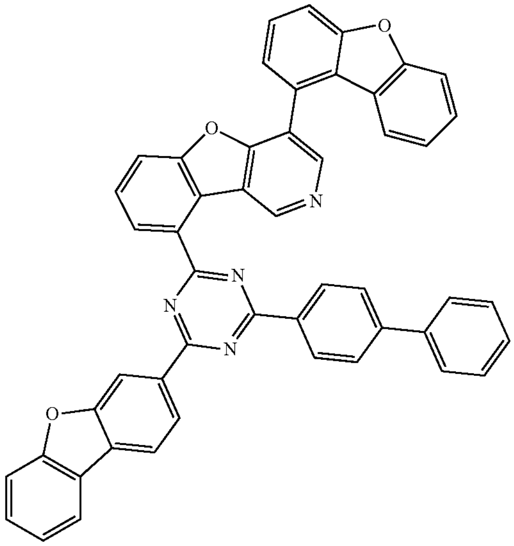
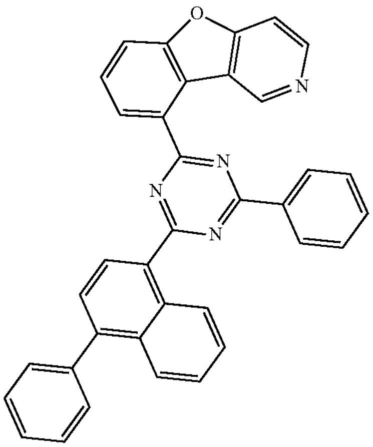

-continued
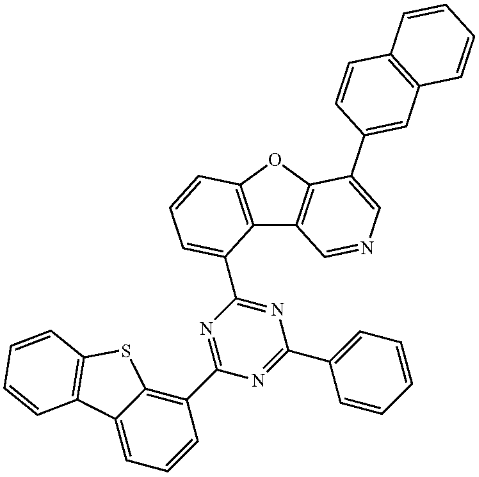
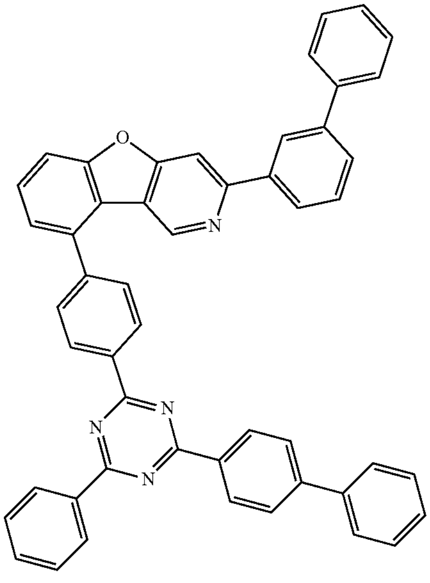
-continued
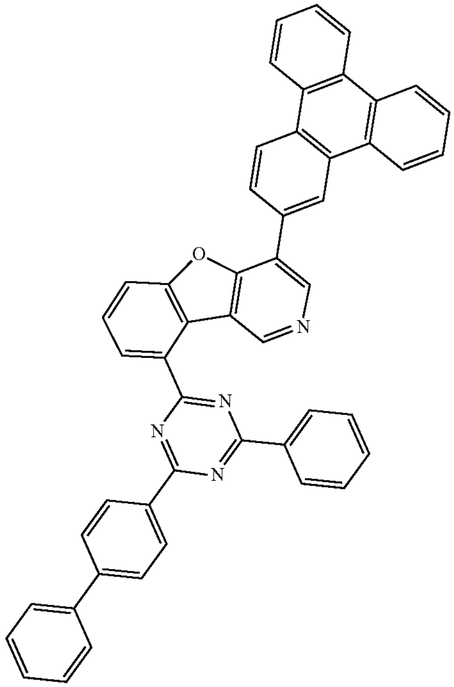
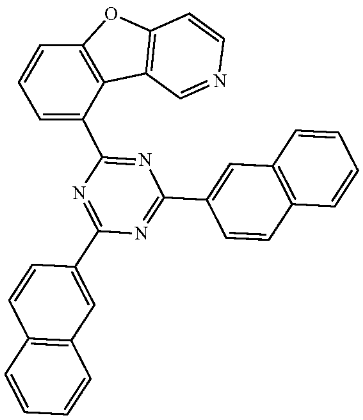
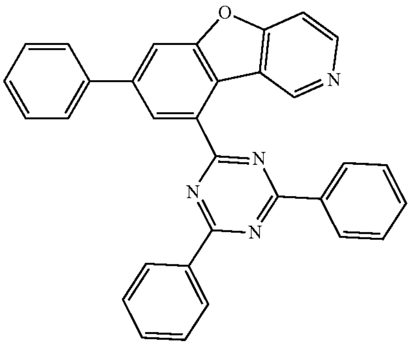

-continued
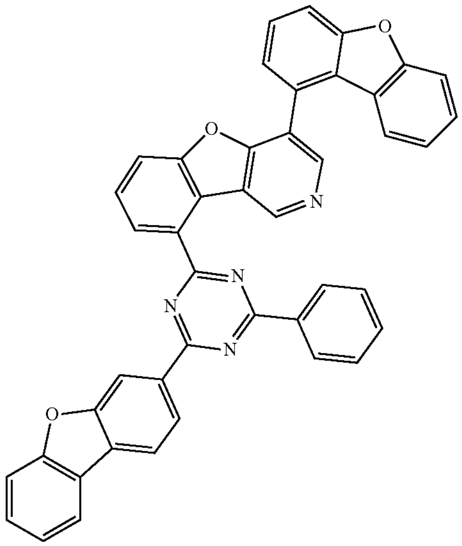
-continued
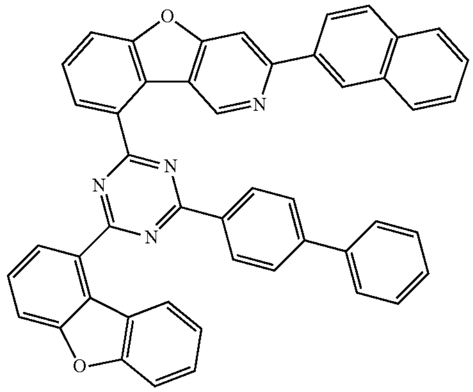
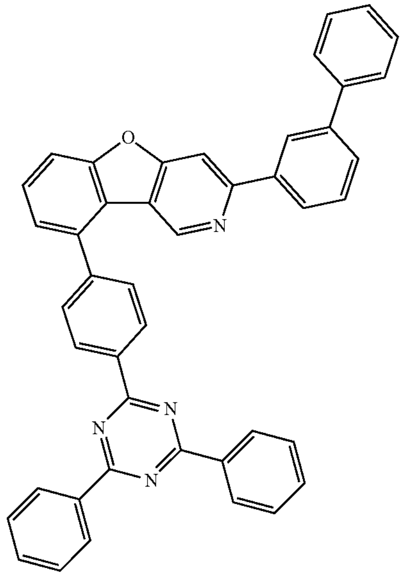
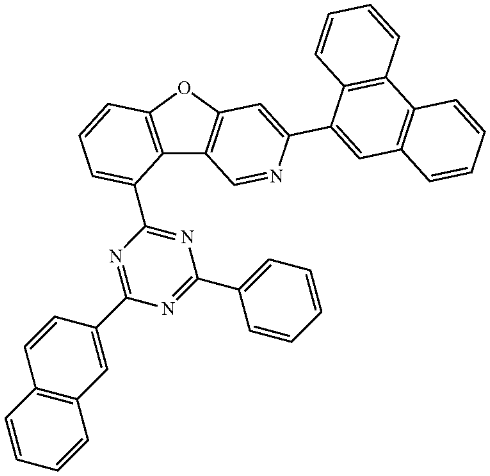
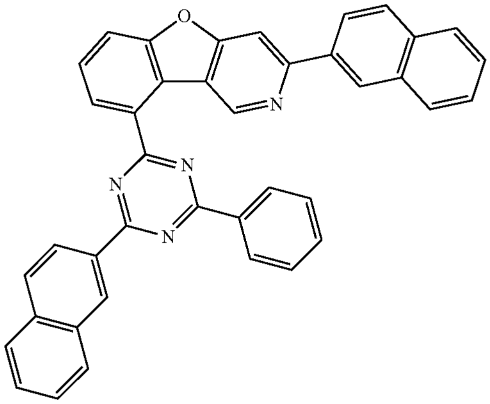
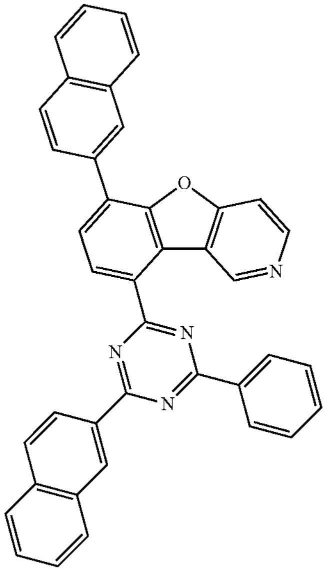

-continued
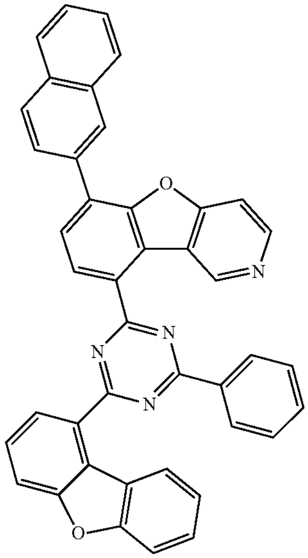
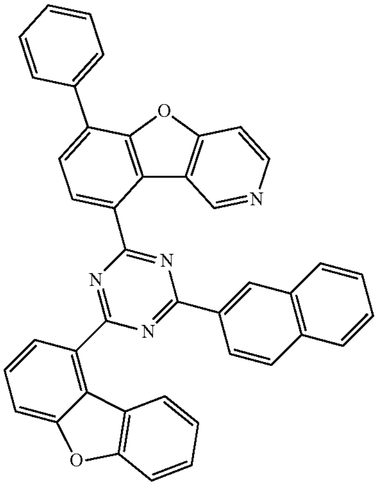
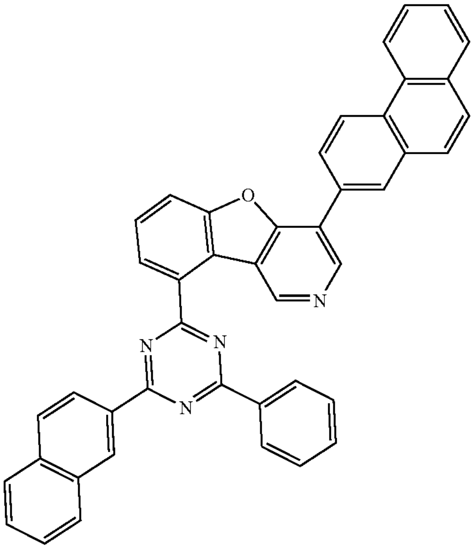
-continued
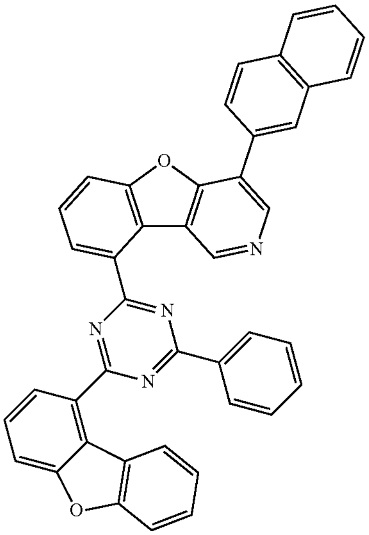
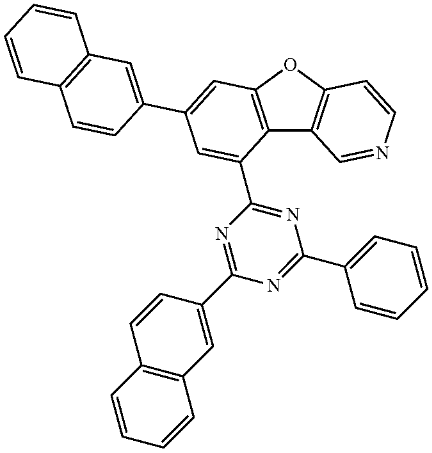
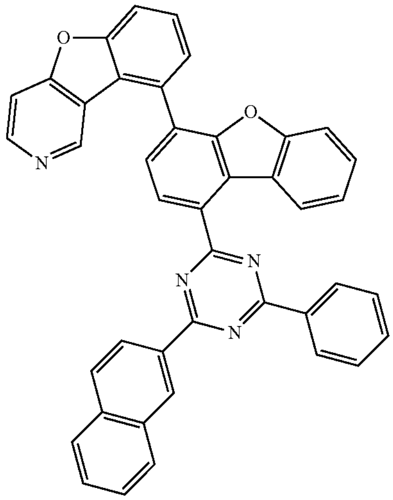

-continued
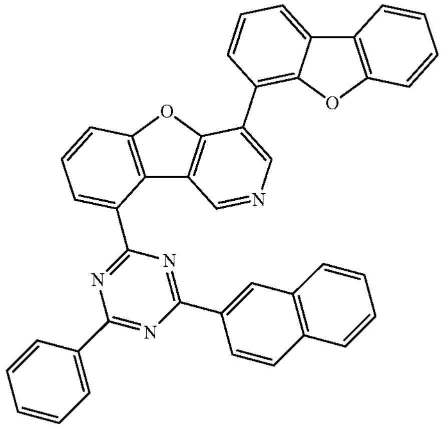
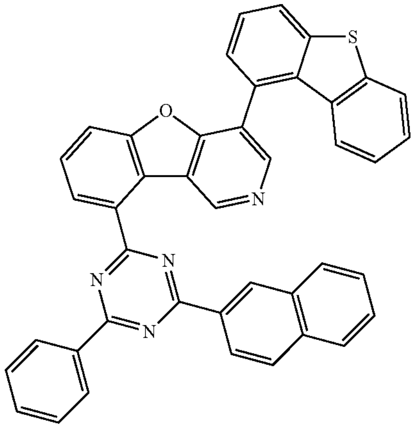
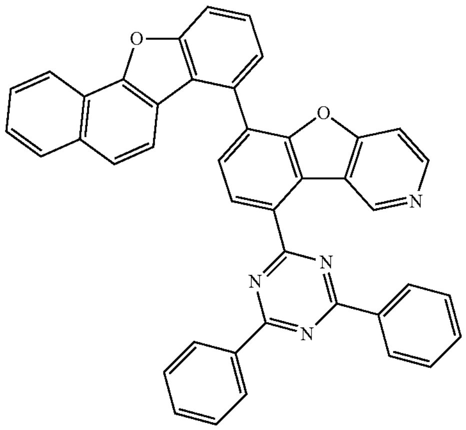
-continued
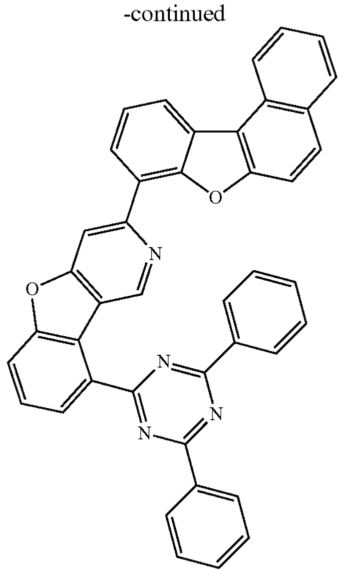
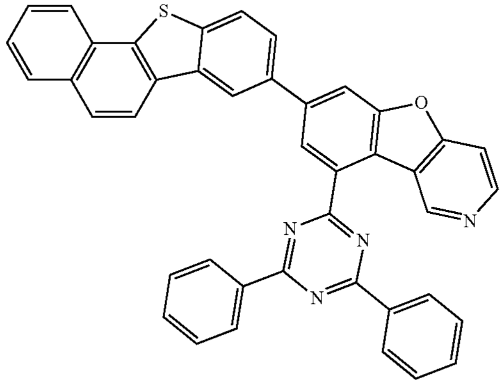
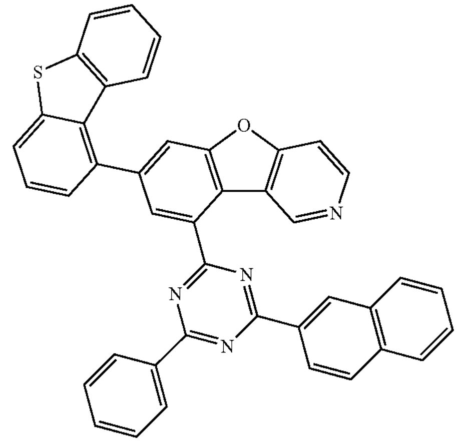
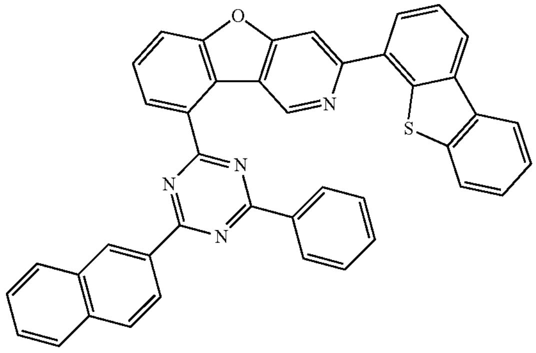

-continued
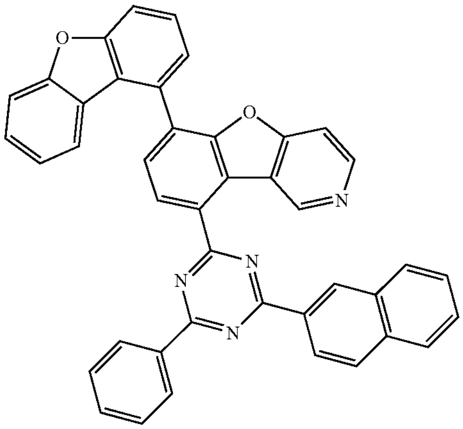
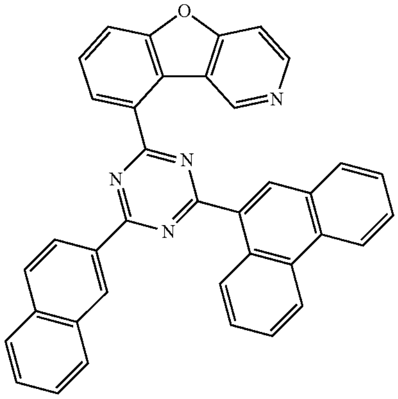
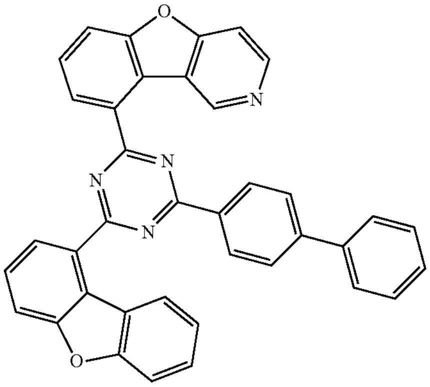
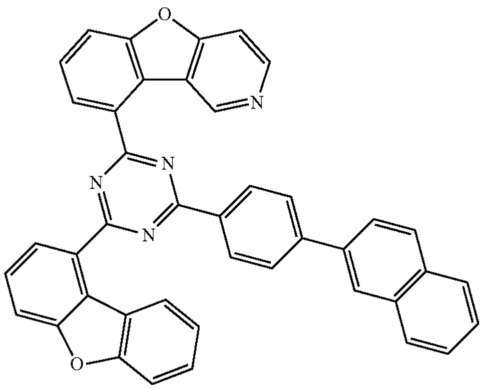
-continued
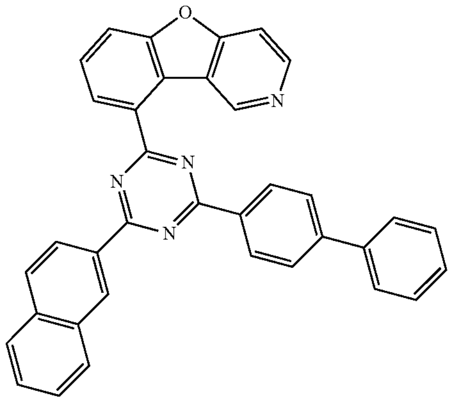
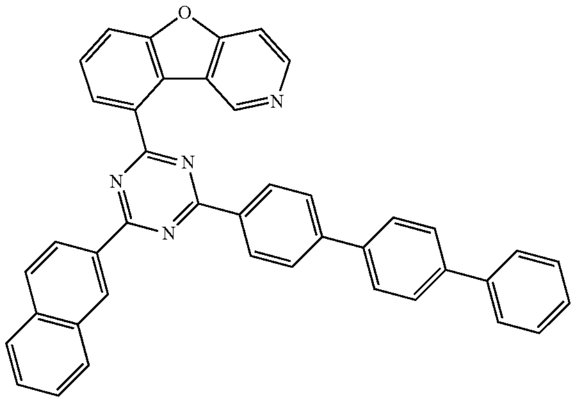
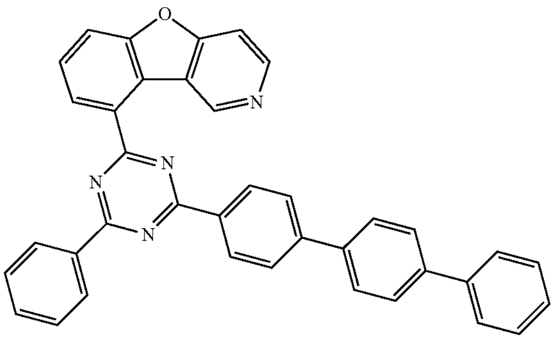
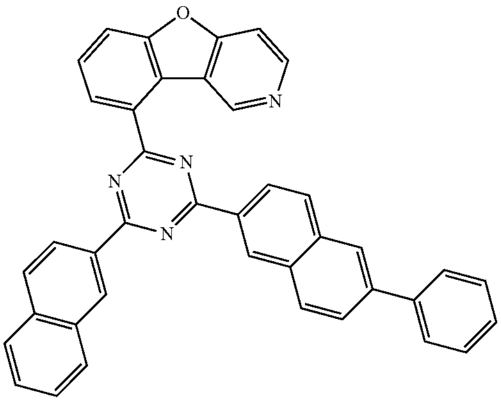

-continued
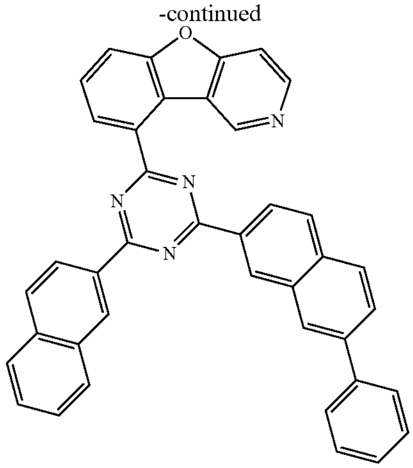
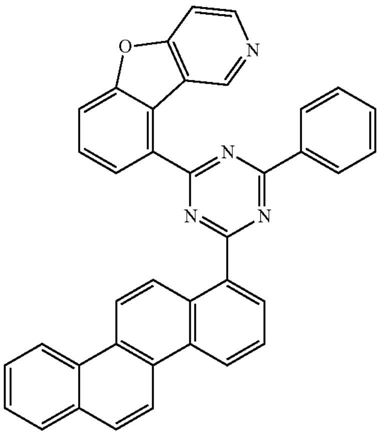
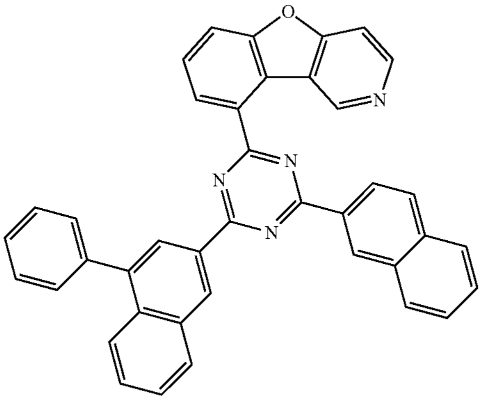
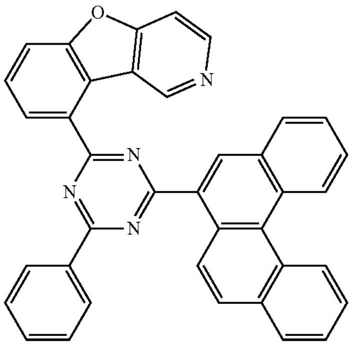
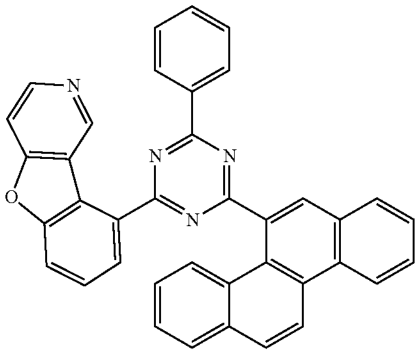
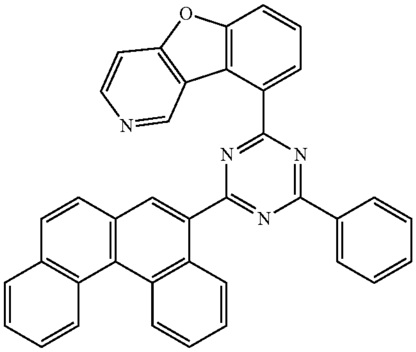
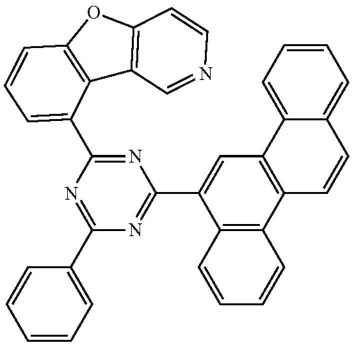
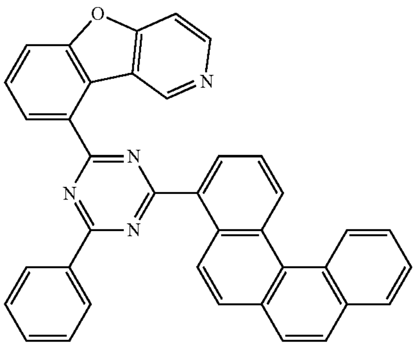

-continued
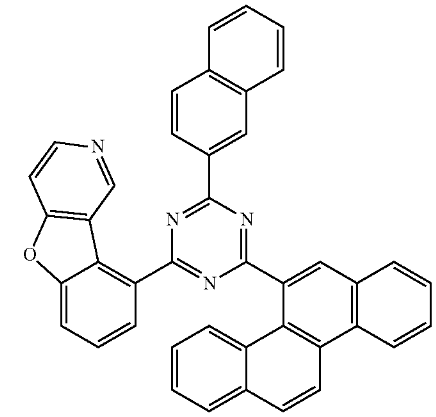
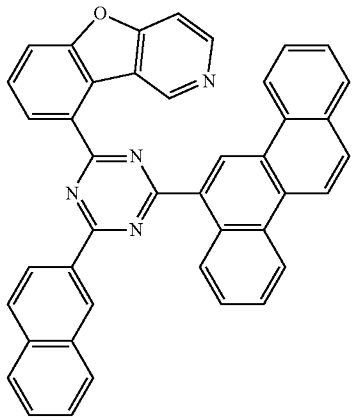
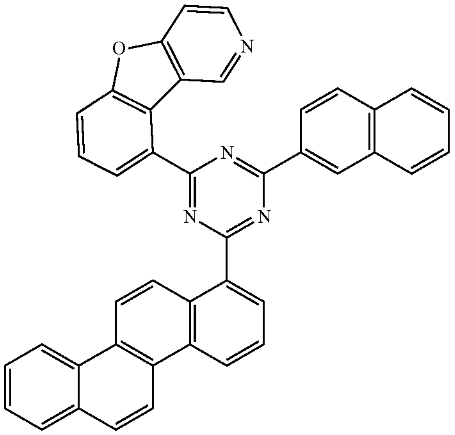
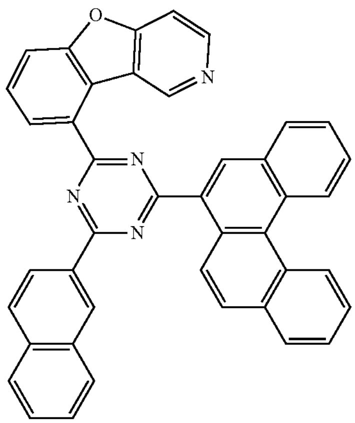
-continued
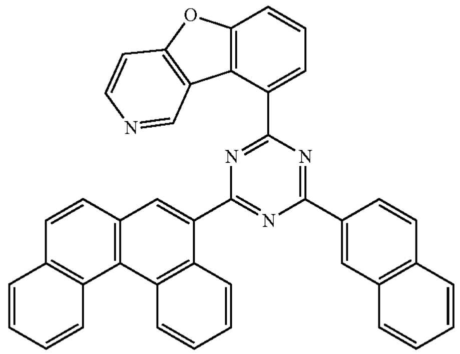
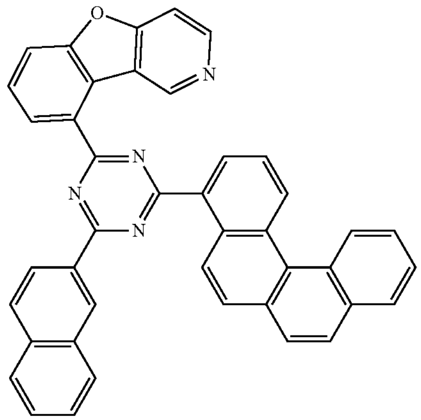
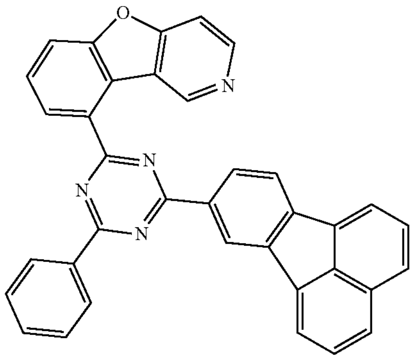
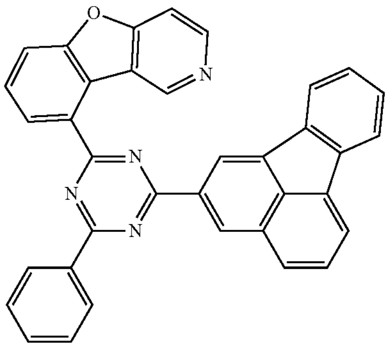

-continued
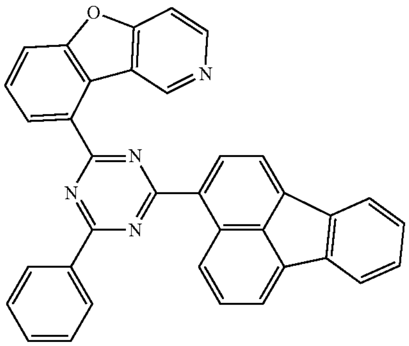
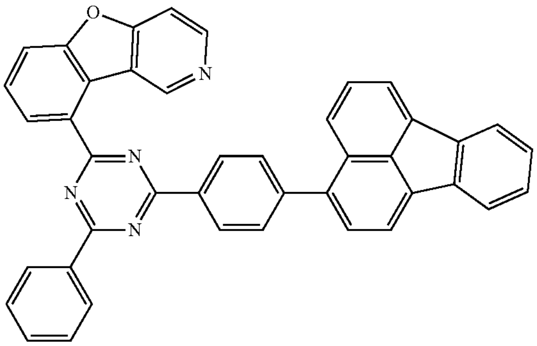
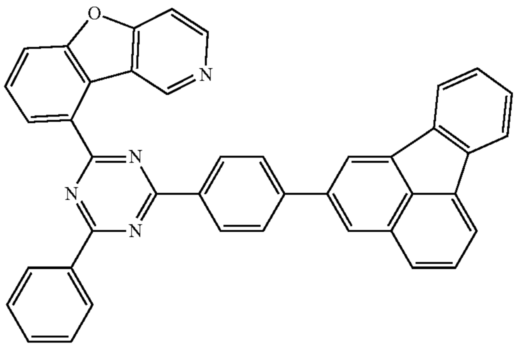
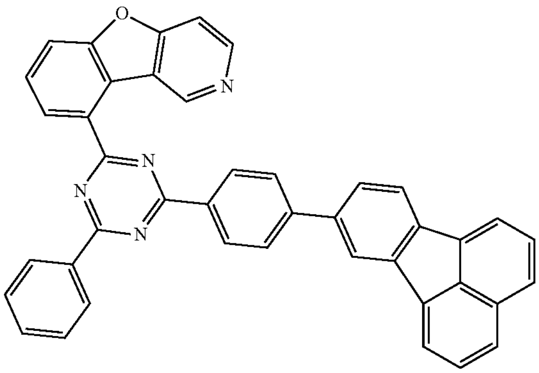
-continued
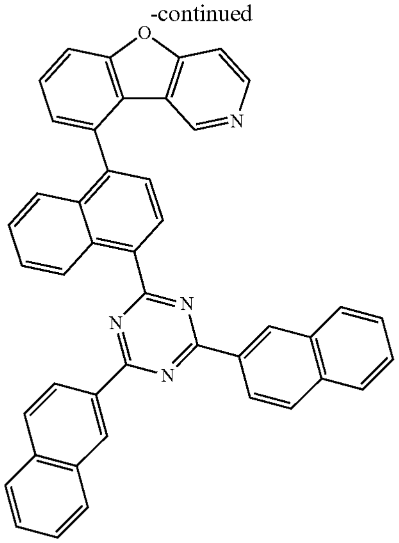
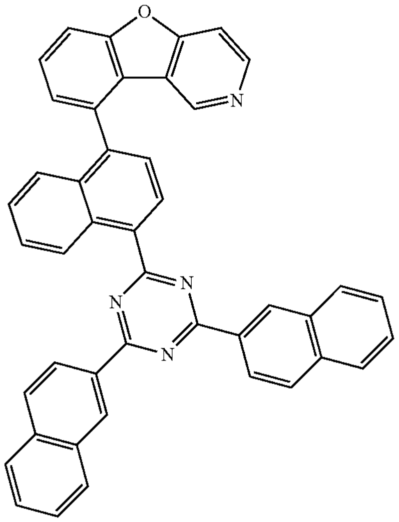
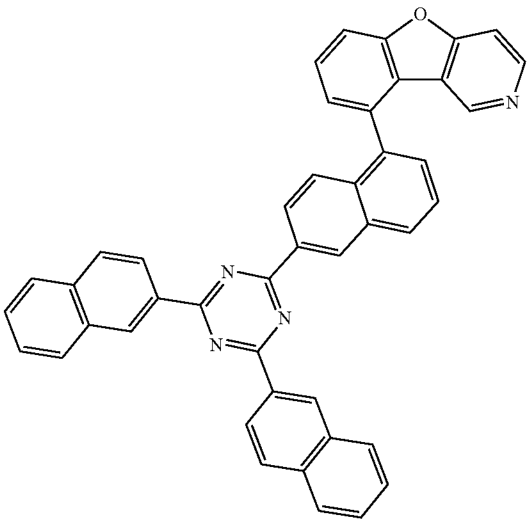

-continued
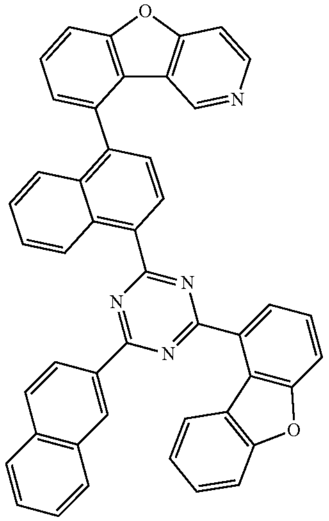
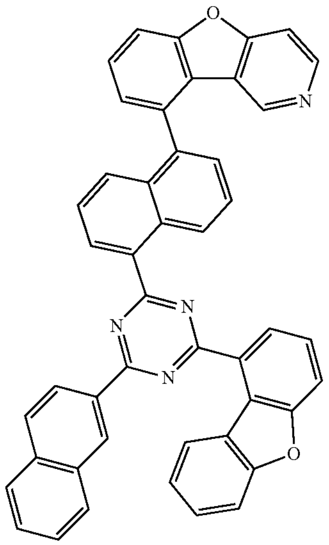
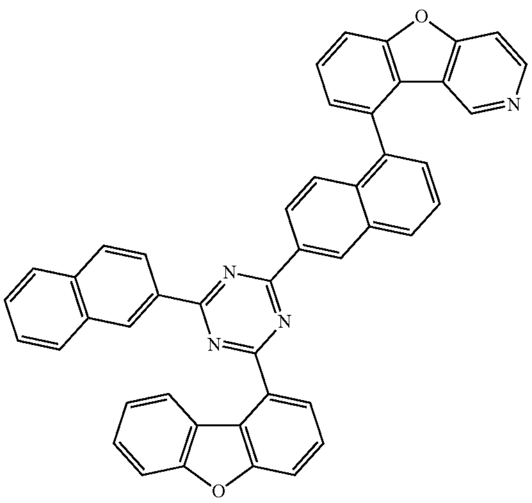
-continued
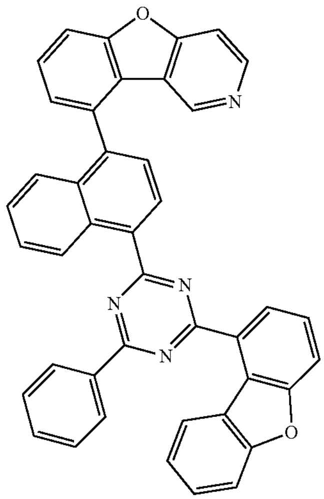
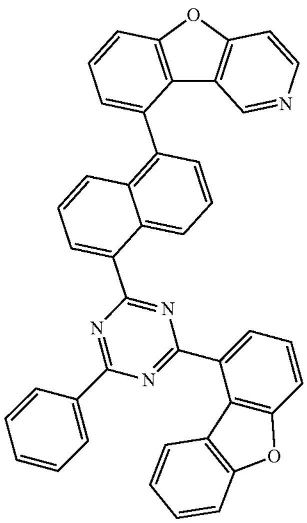
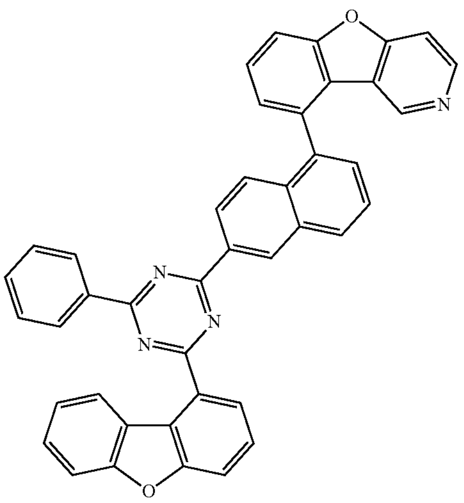

-continued
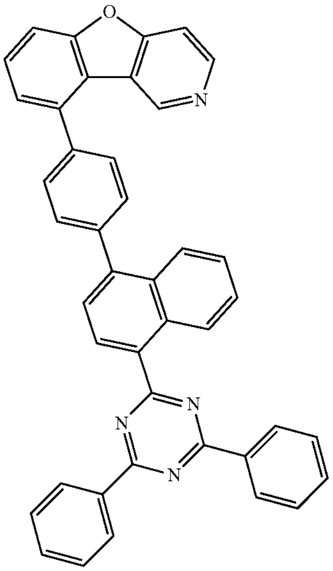
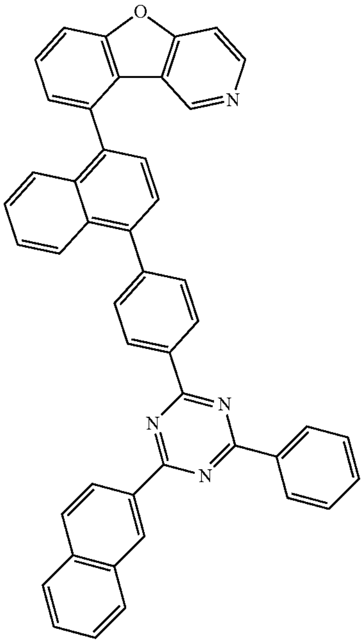
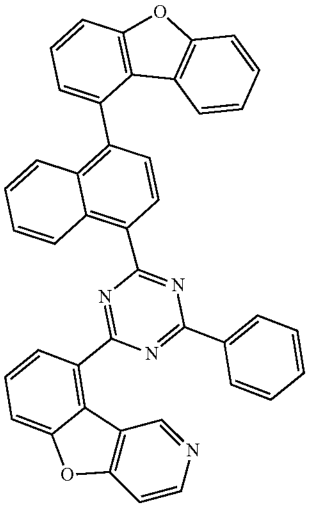
-continued
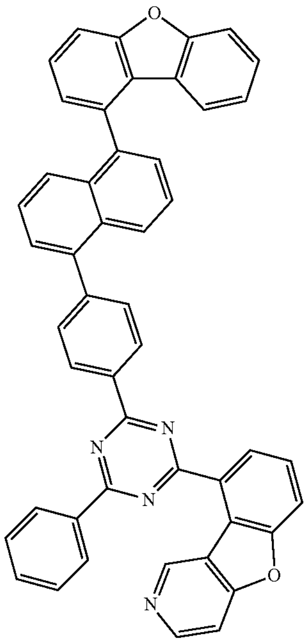
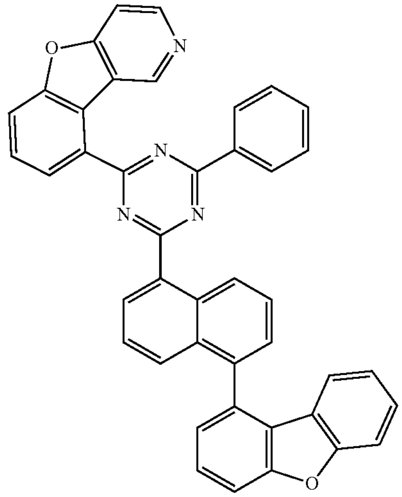
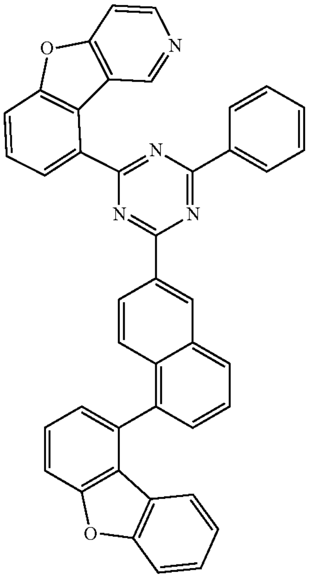

-continued
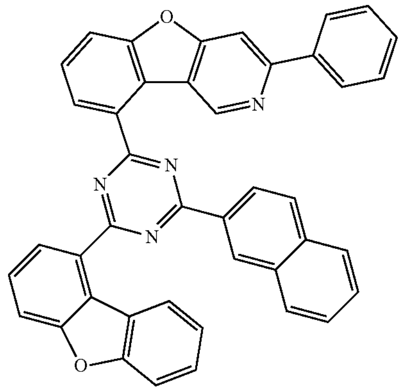
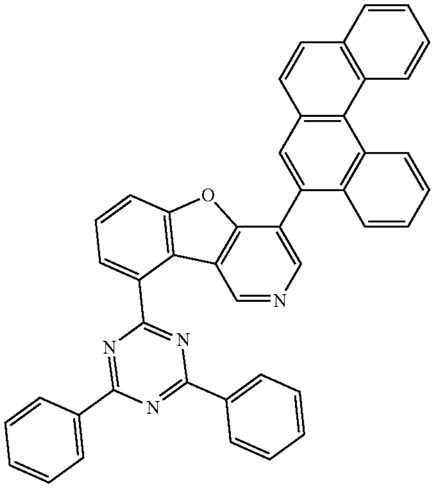
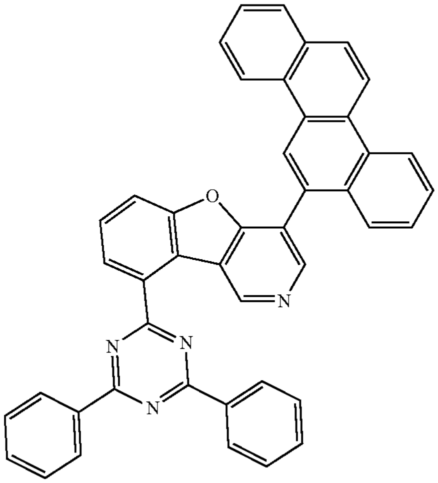
-continued
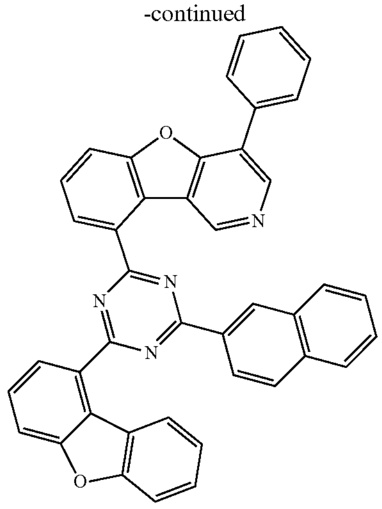
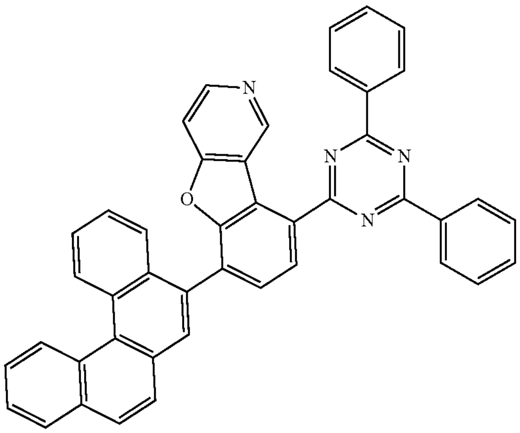
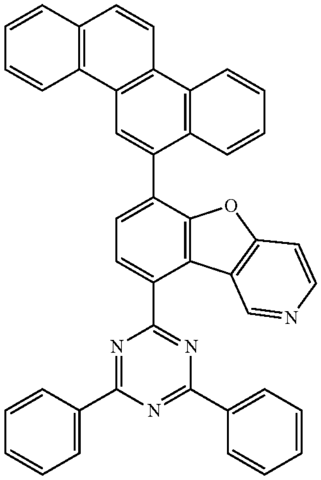

-continued
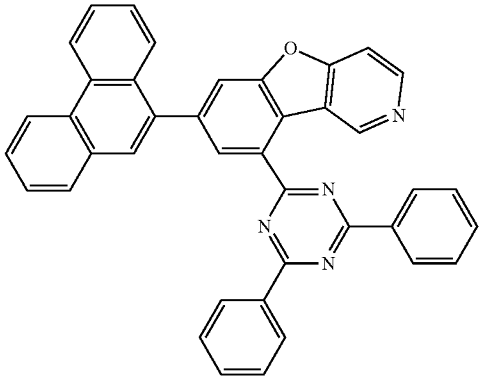
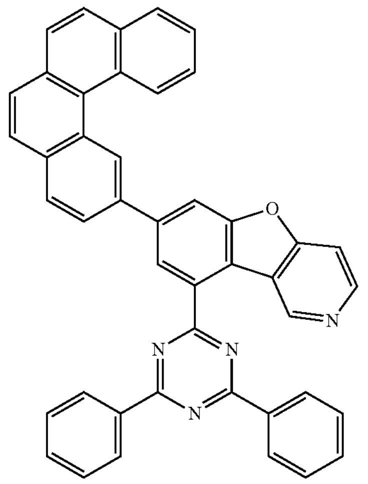
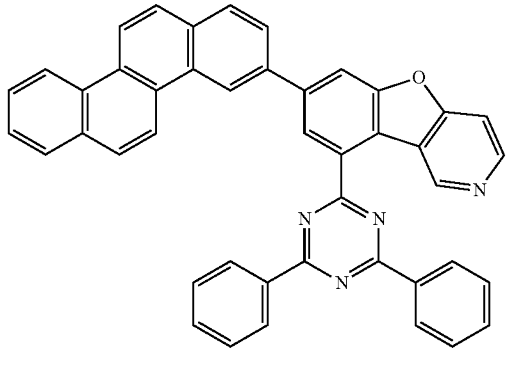
-continued
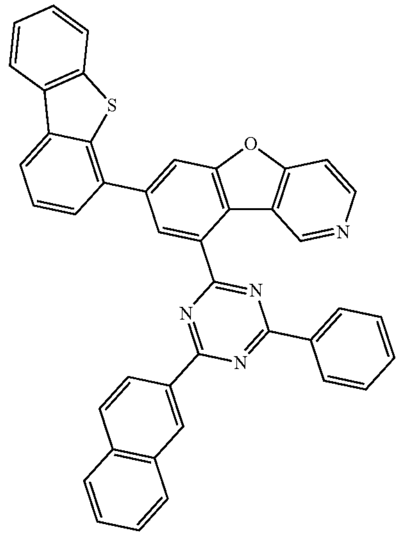
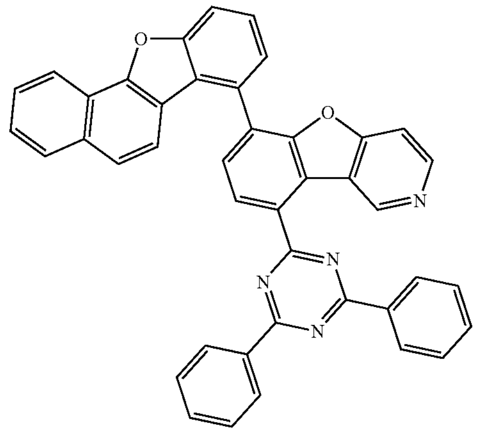
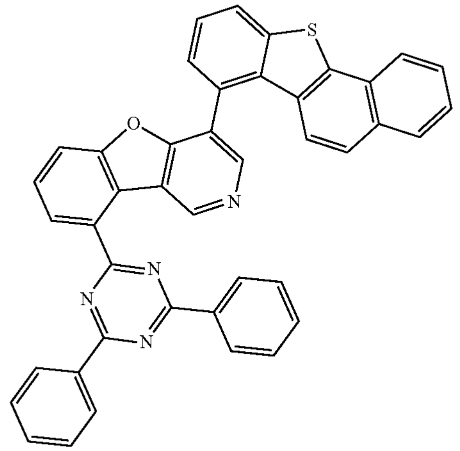

-continued
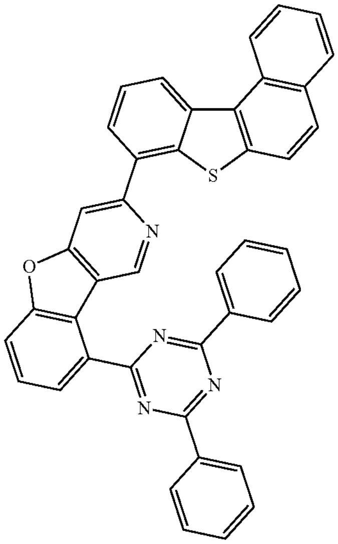
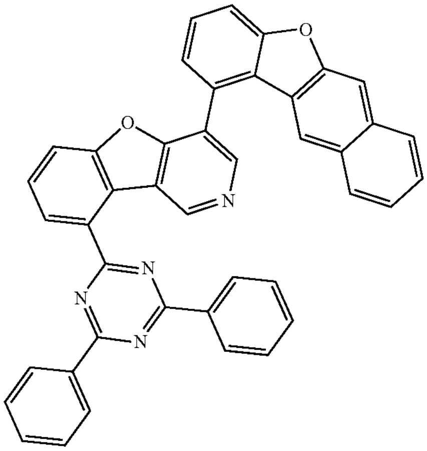
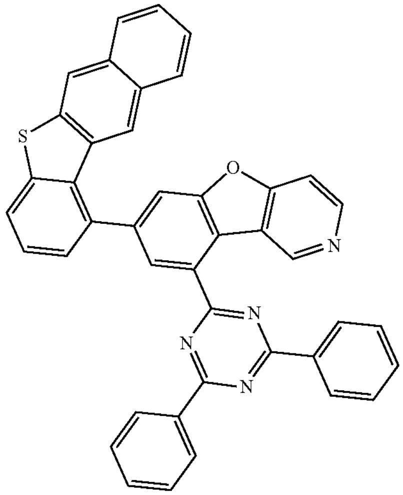
-continued
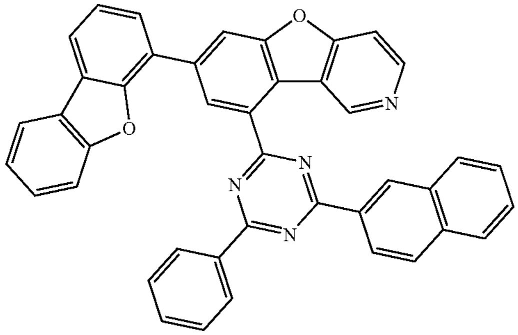
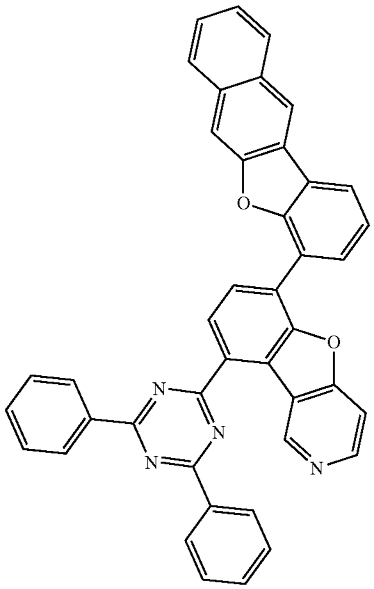
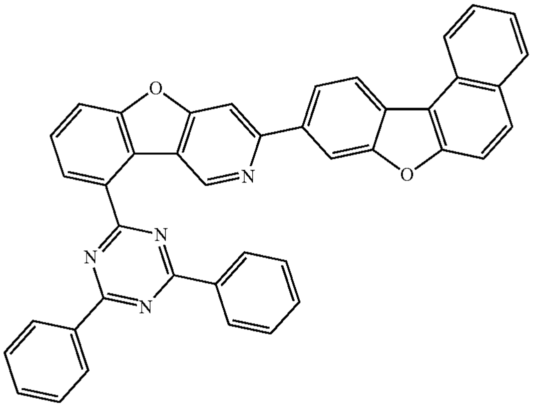
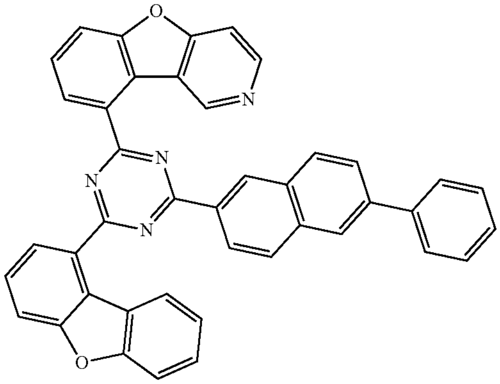

-continued
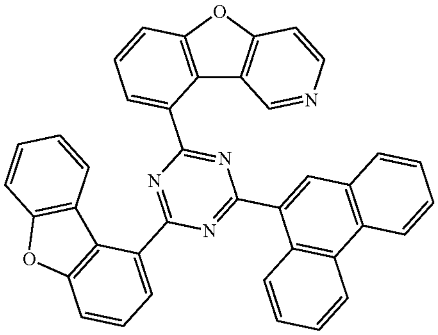
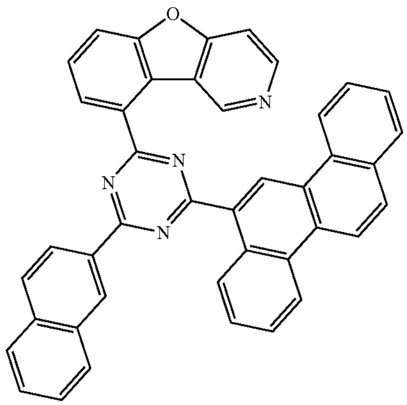
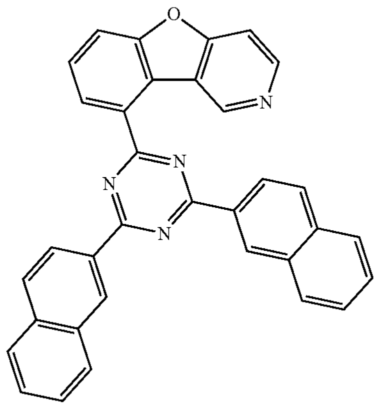
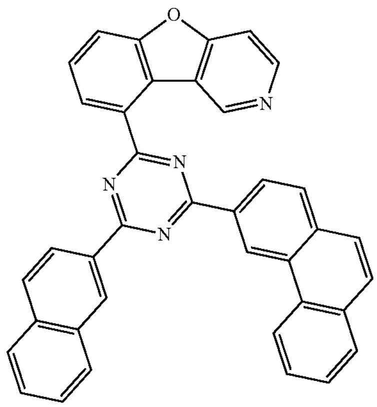
-continued
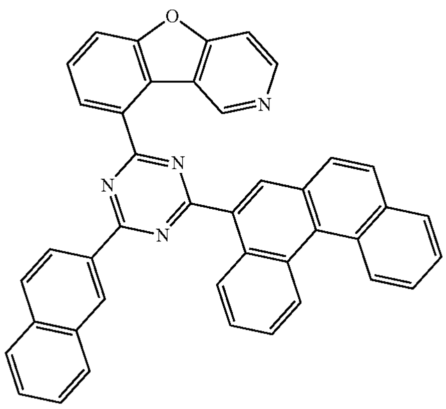
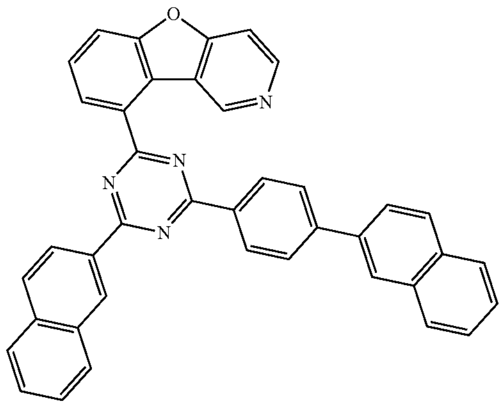
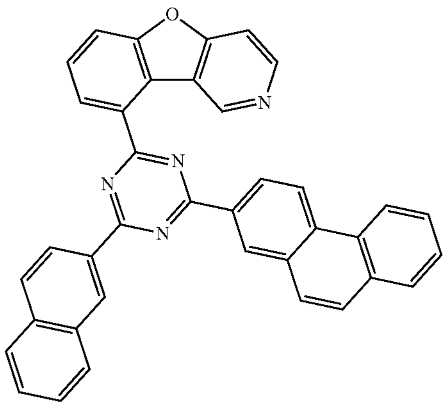
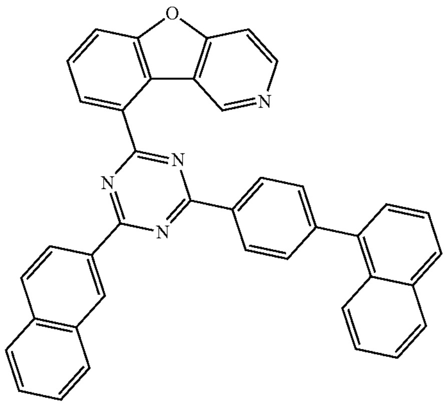

-continued
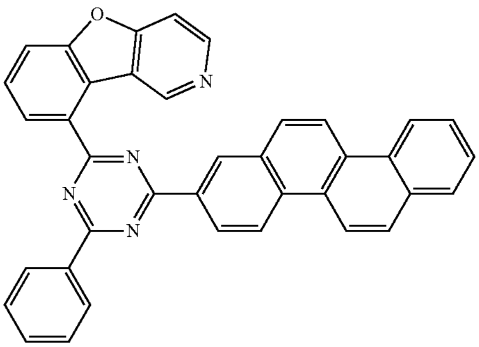
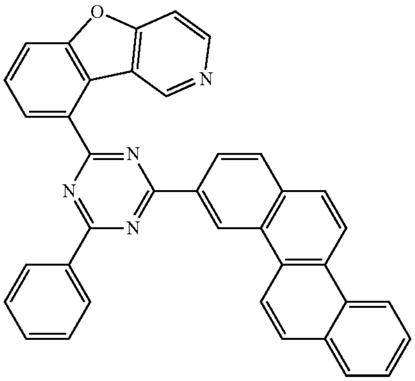
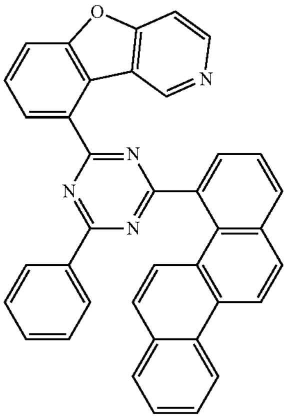
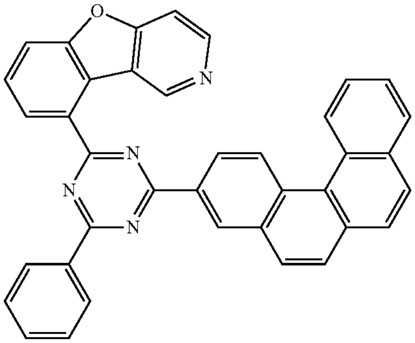
-continued
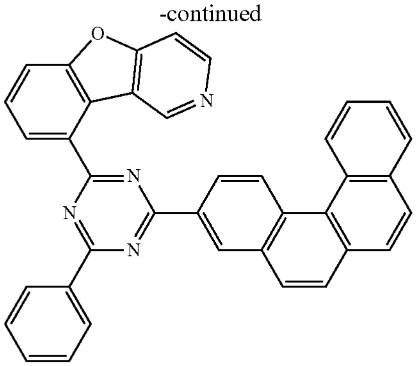
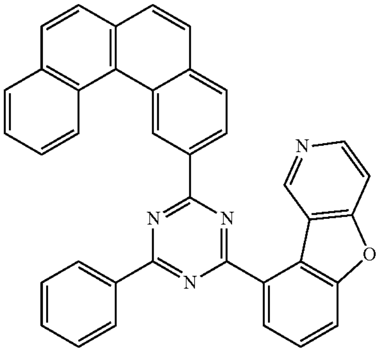
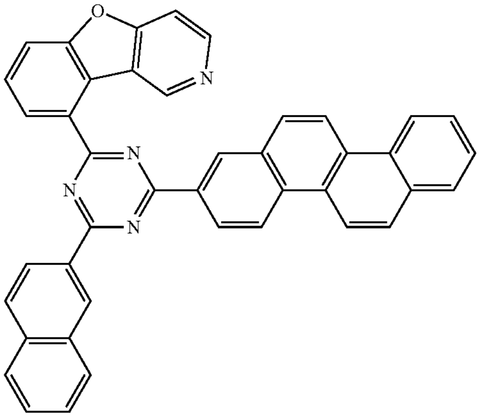
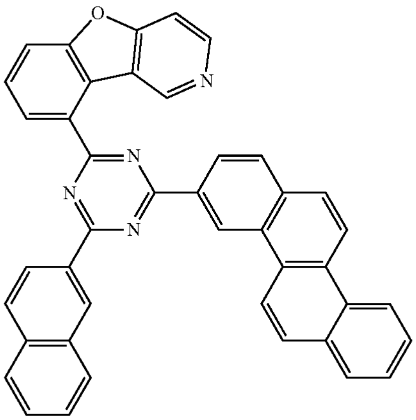

-continued
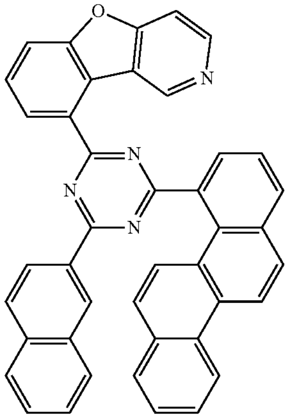
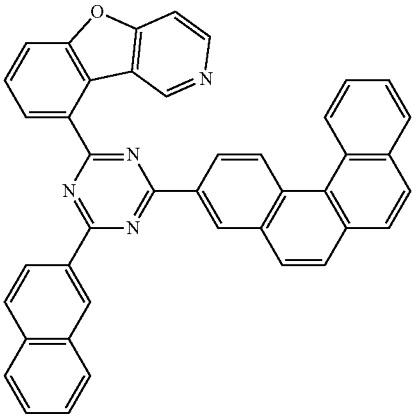
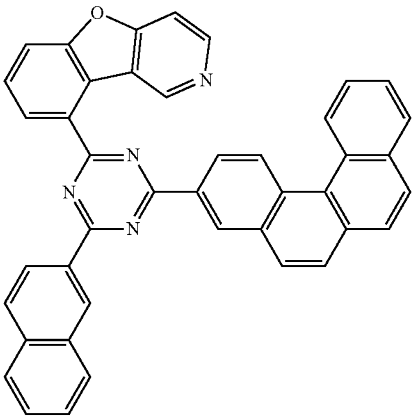
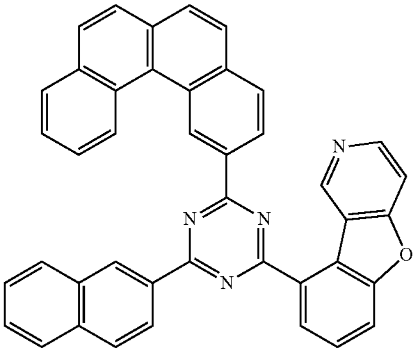
-continued
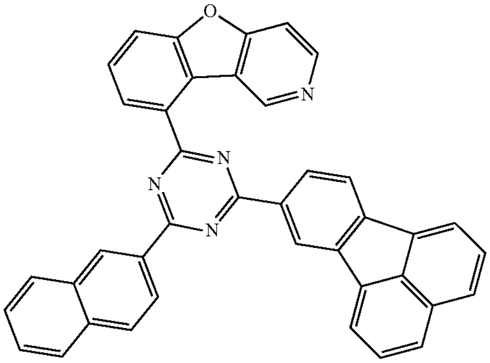
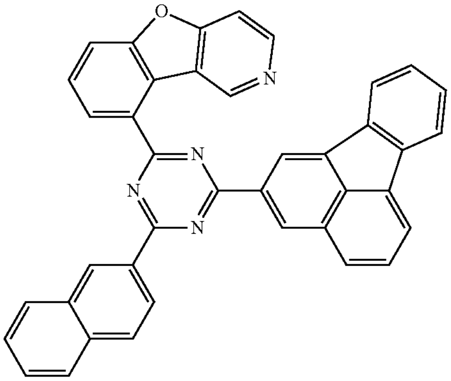
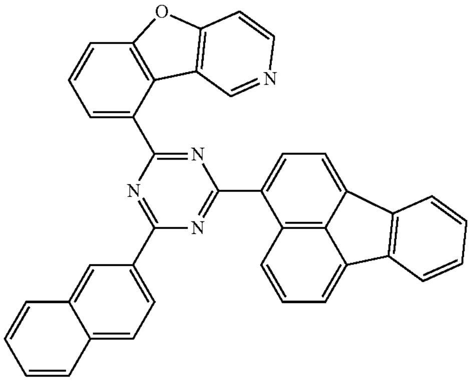
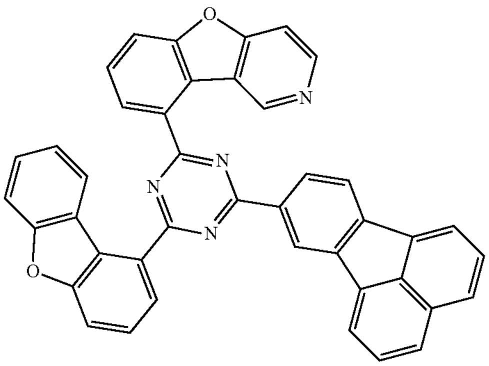

-continued
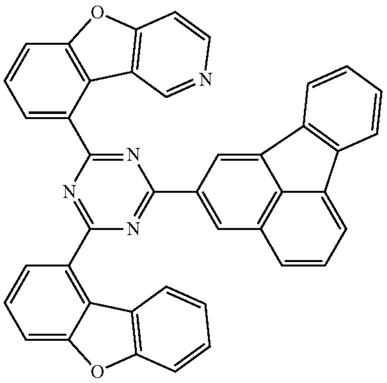
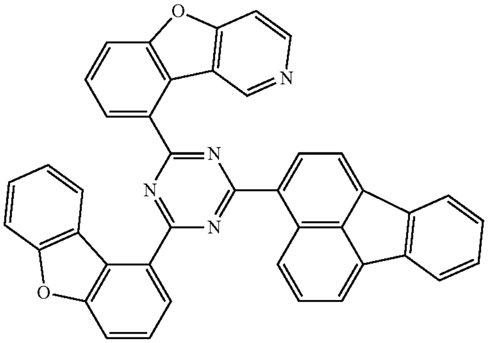
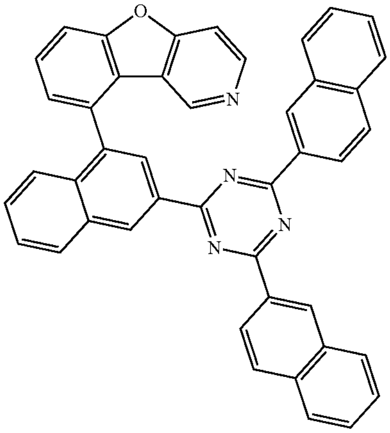
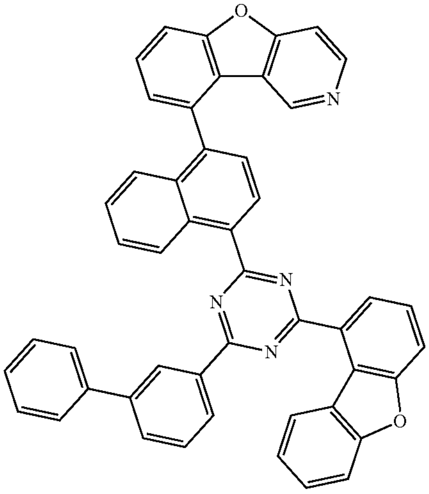
-continued
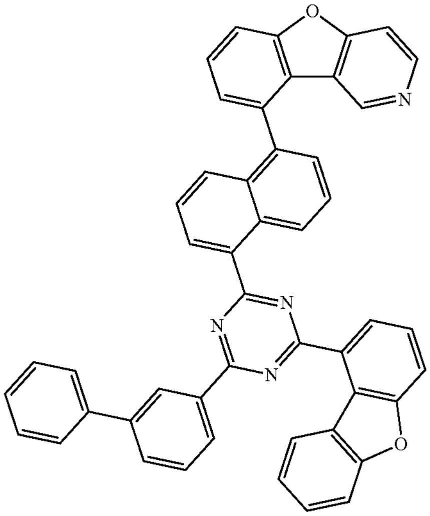
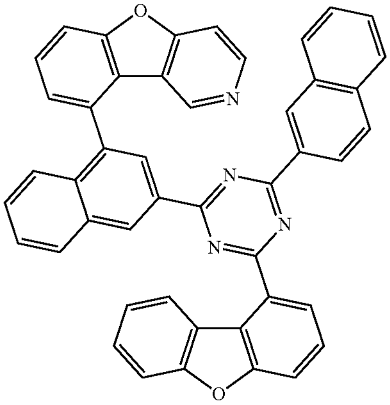
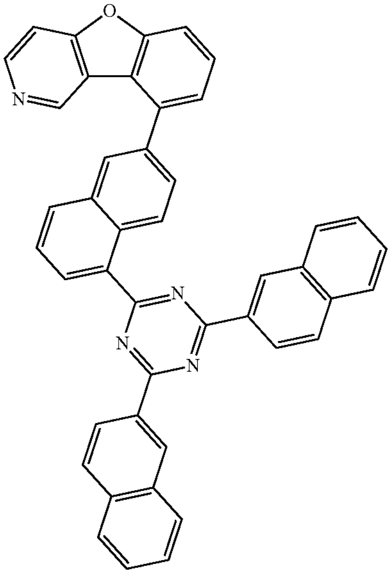

-continued
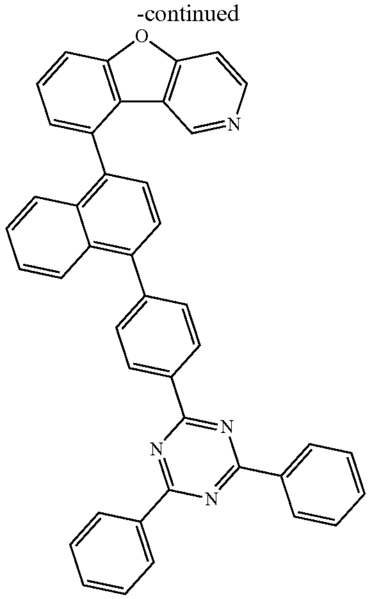
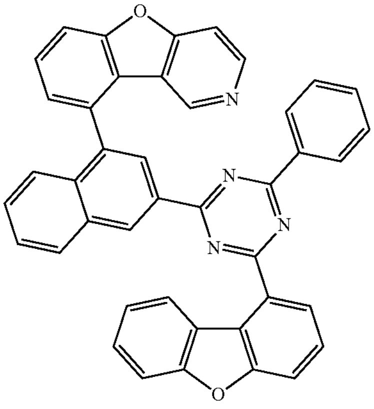
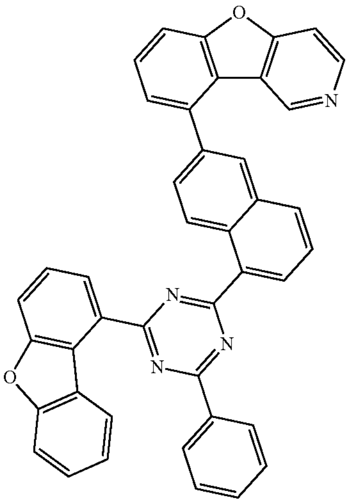
-continued
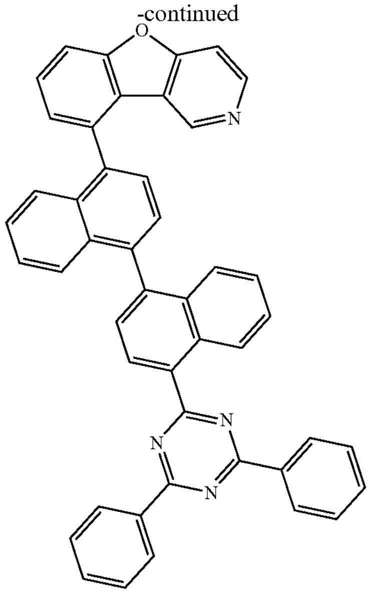
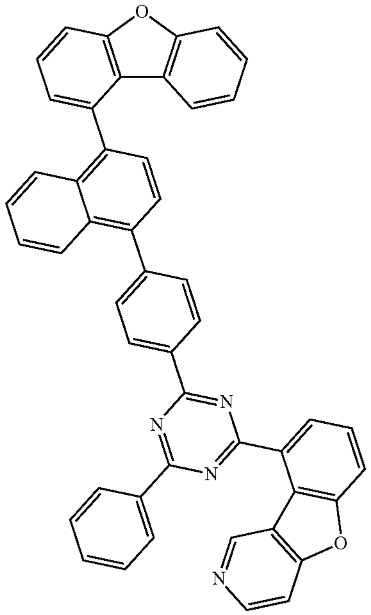

-continued
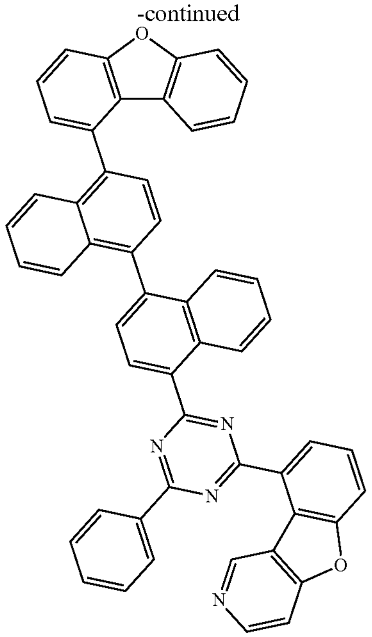
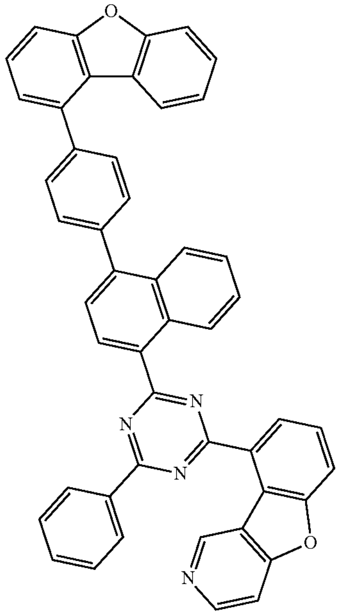
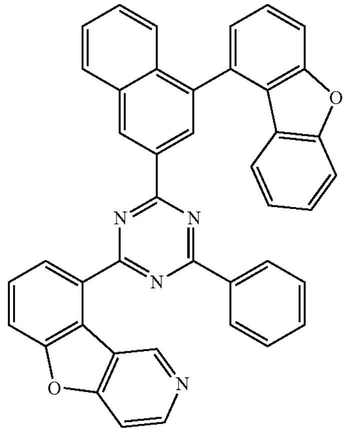
-continued
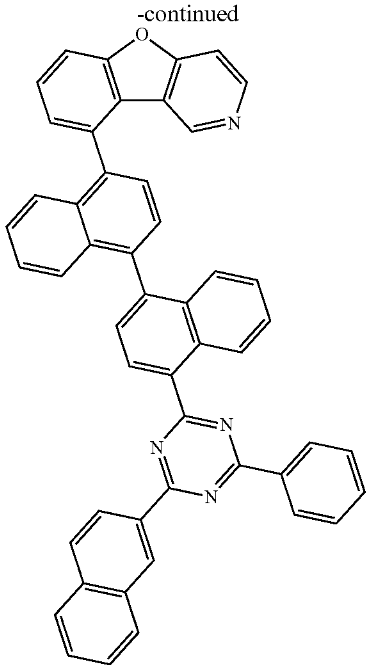
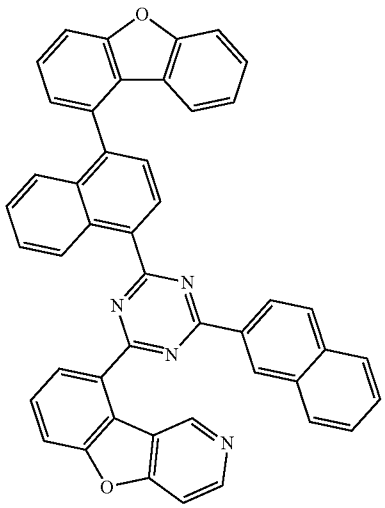

-continued
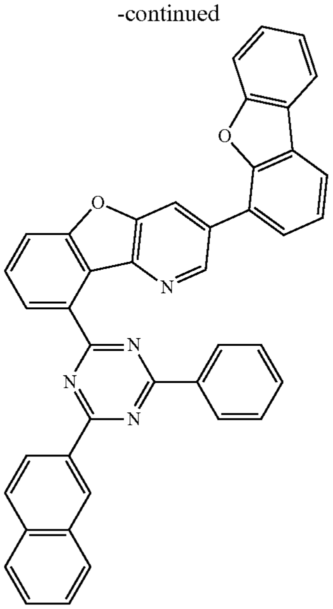
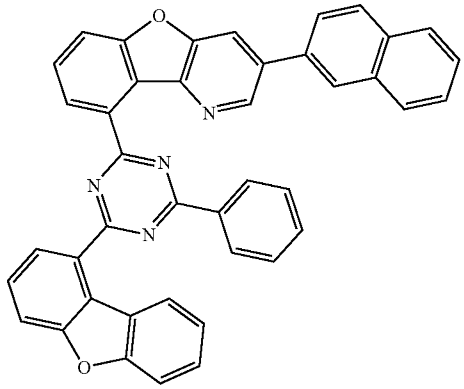
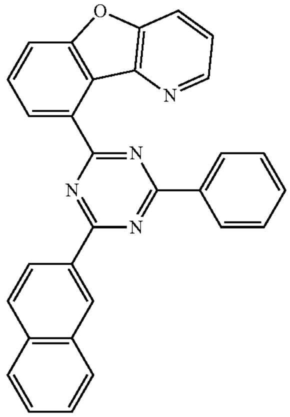
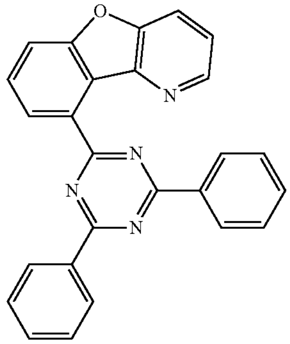
-continued
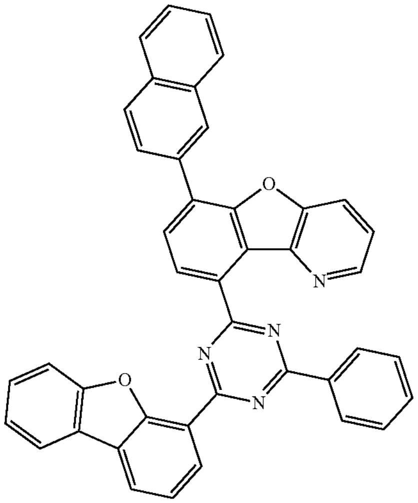
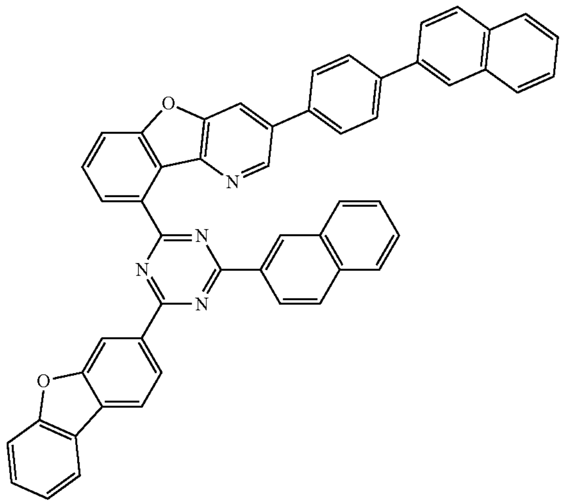
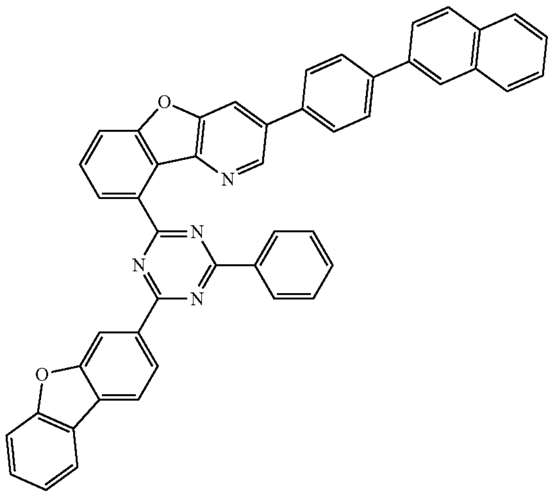

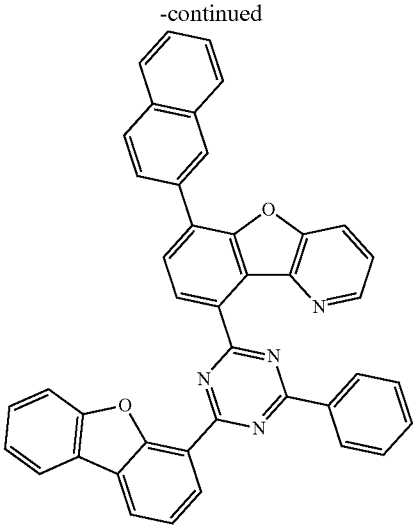
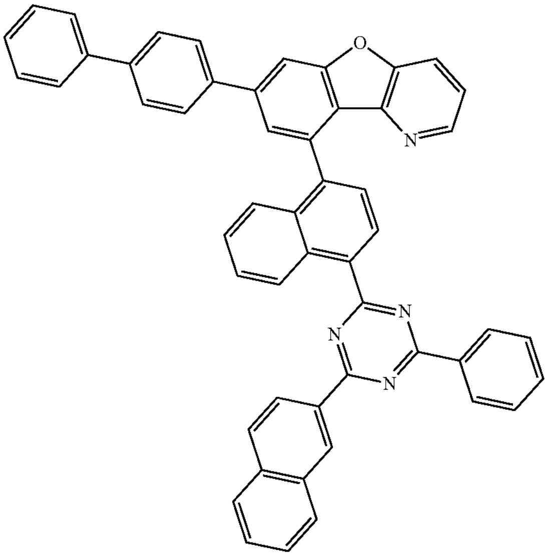
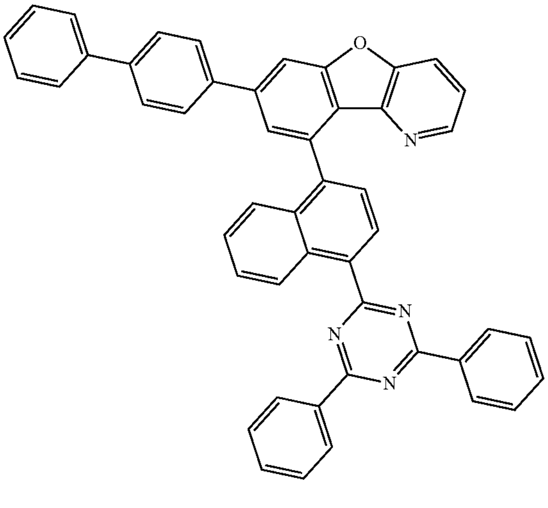
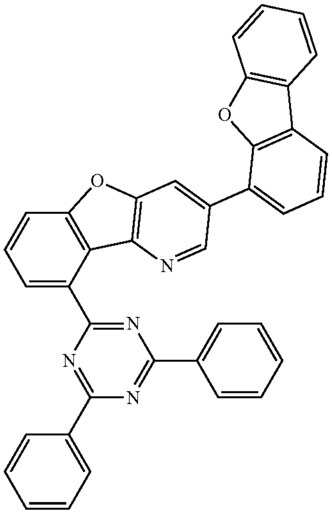
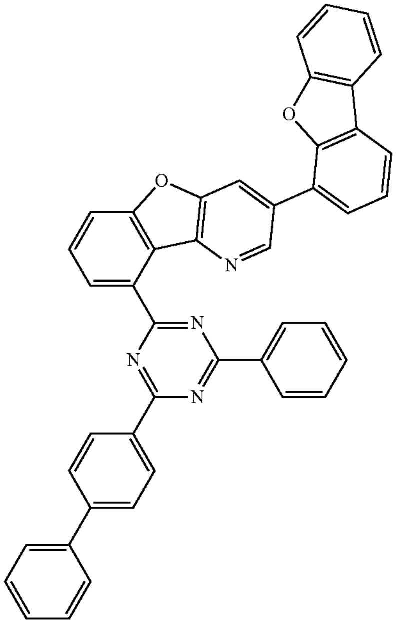

-continued
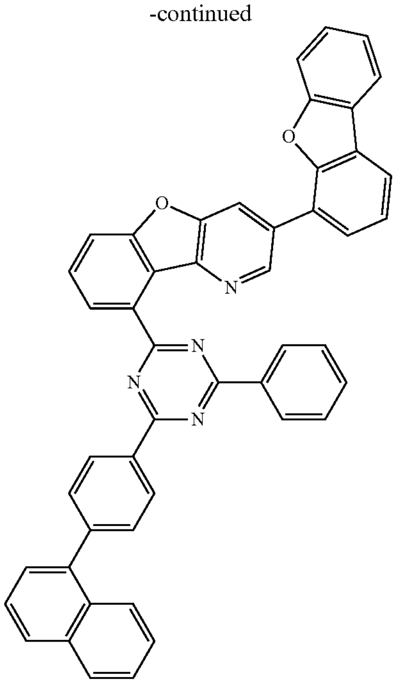
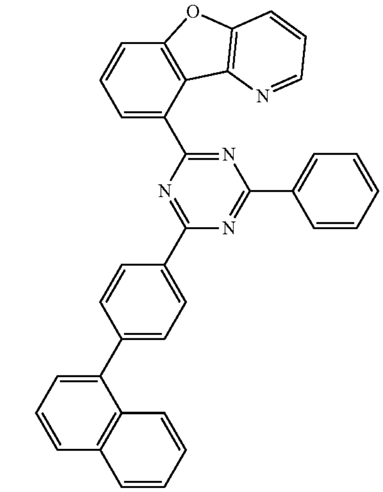
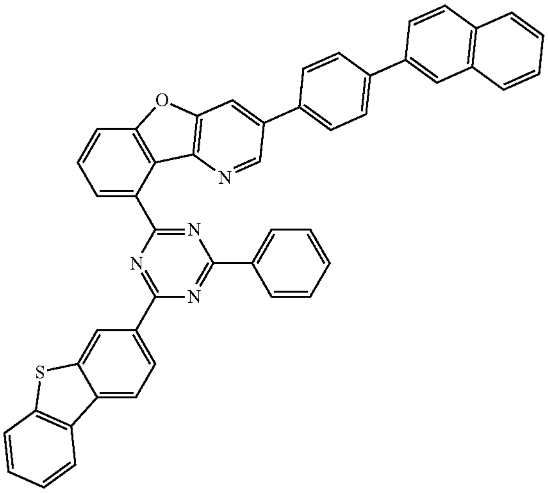
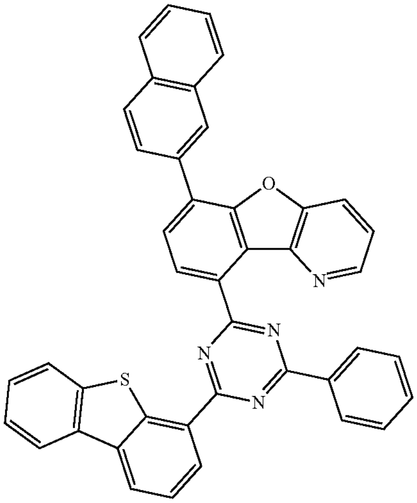
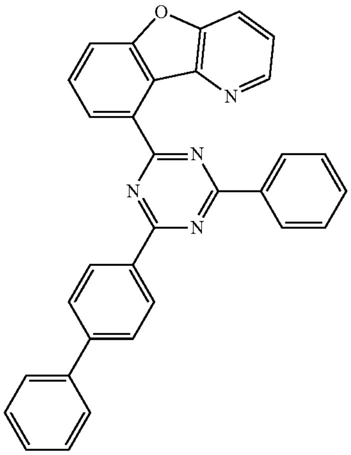
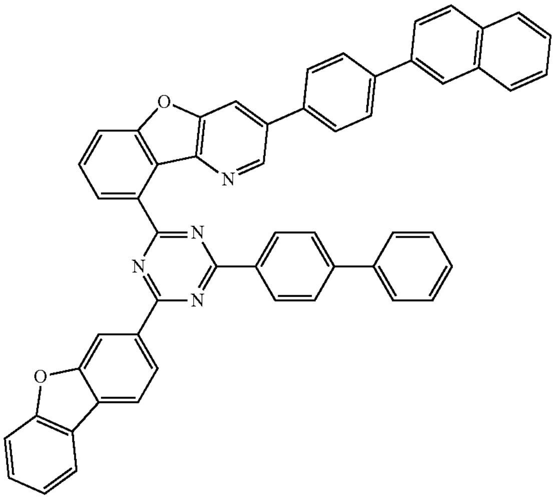
-continued -continued
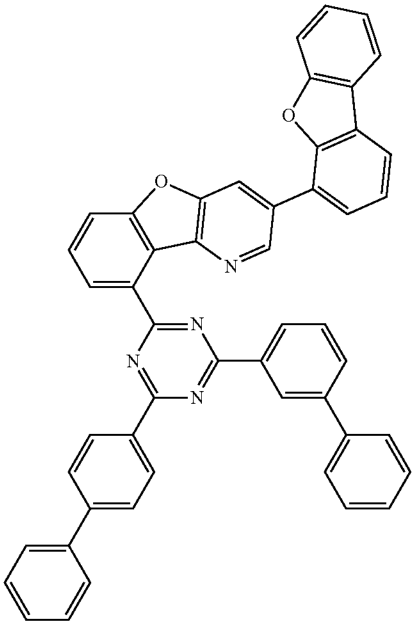
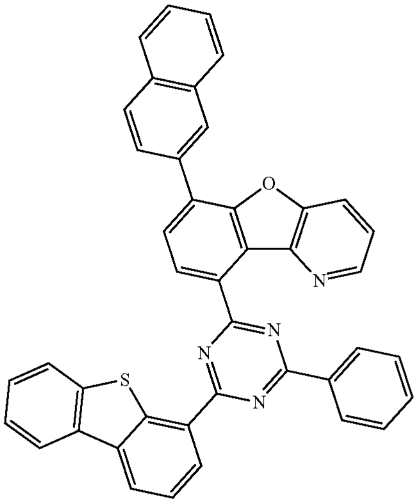
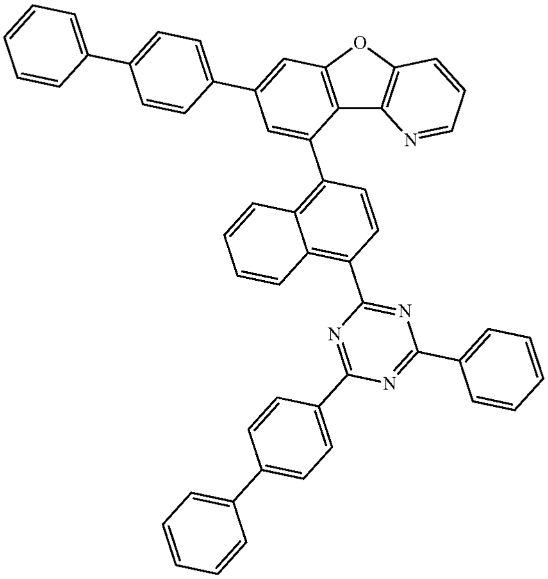
-continued
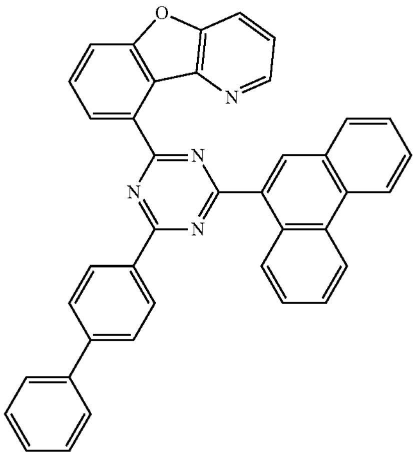
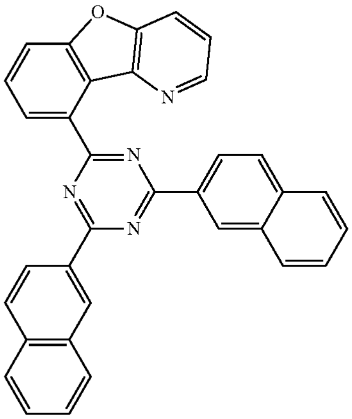
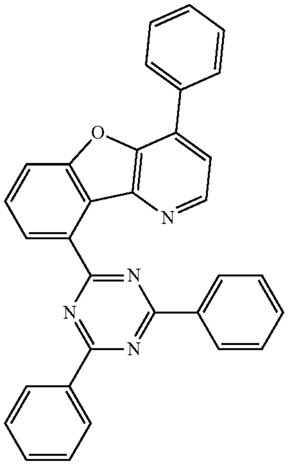

-continued
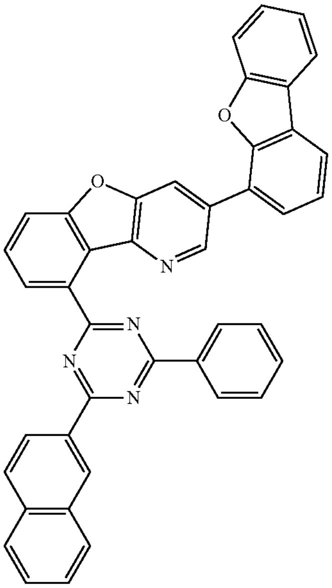
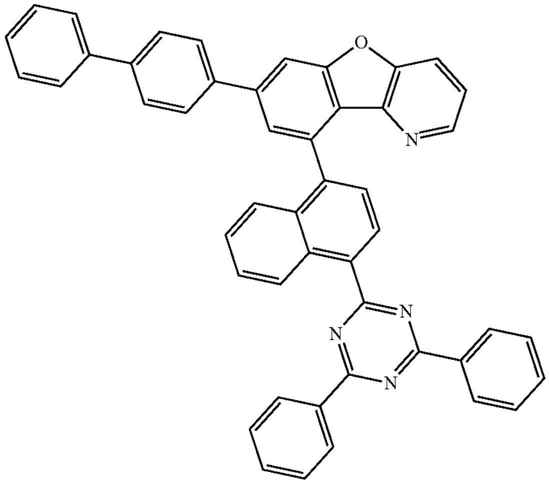
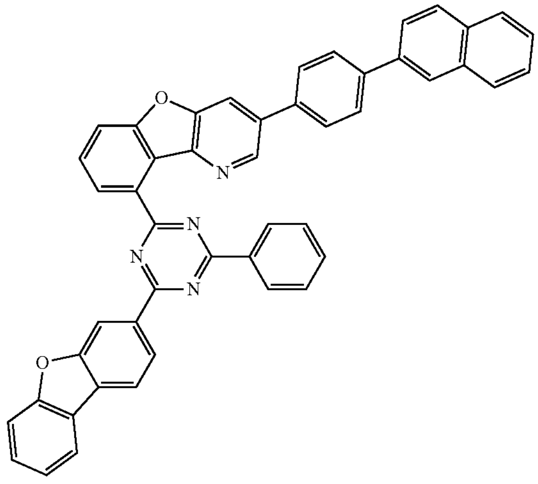
-continued
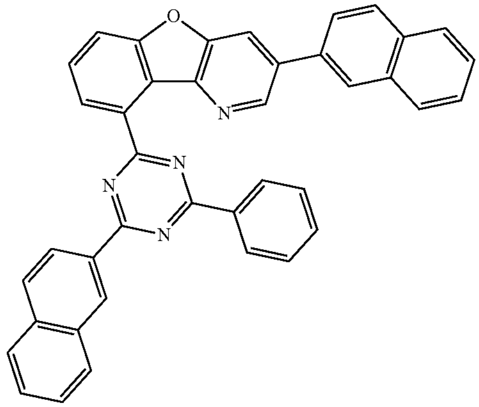
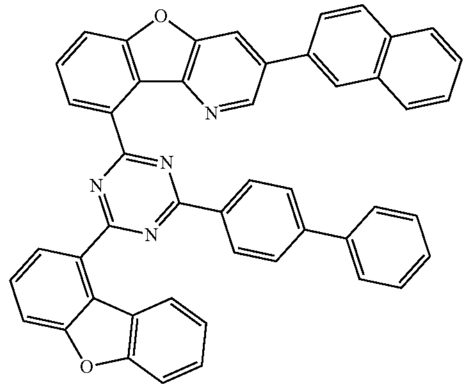
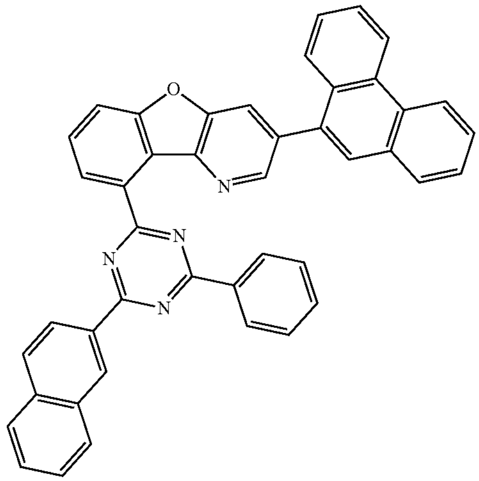

-continued
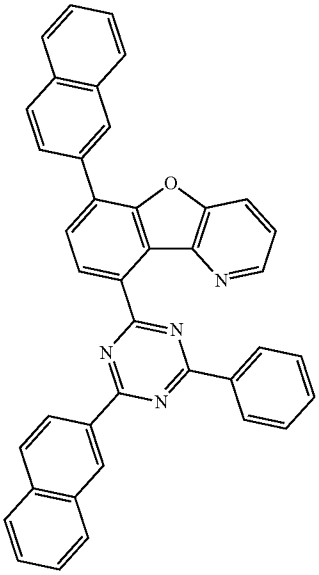
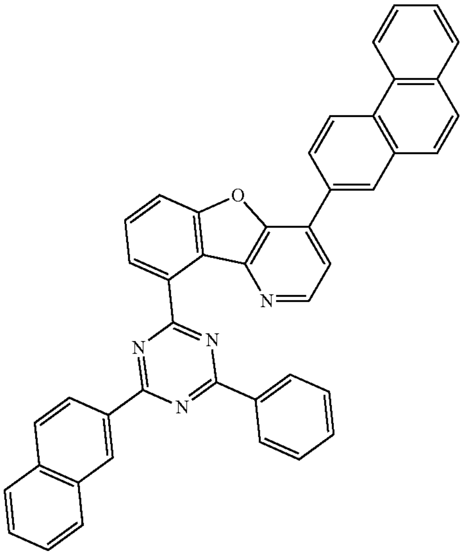
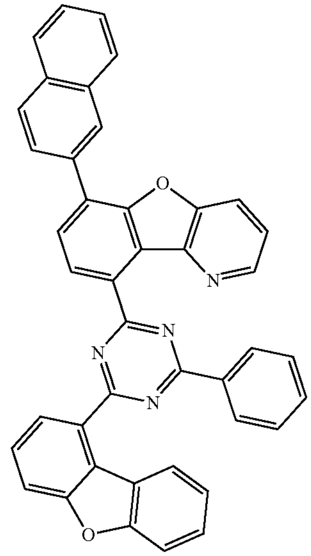
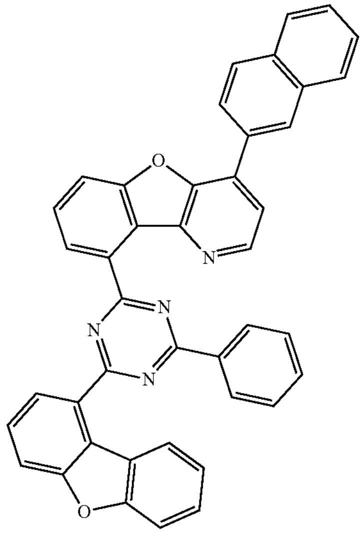
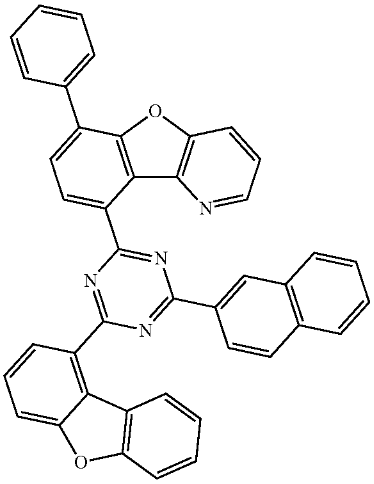
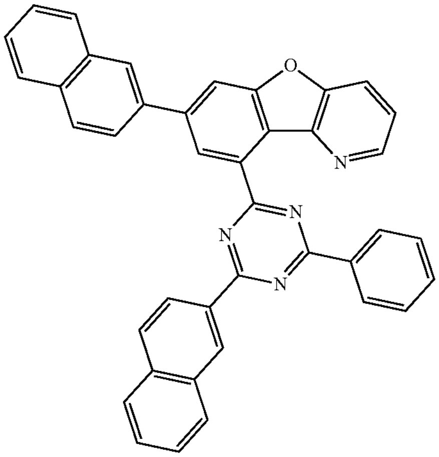
-continued

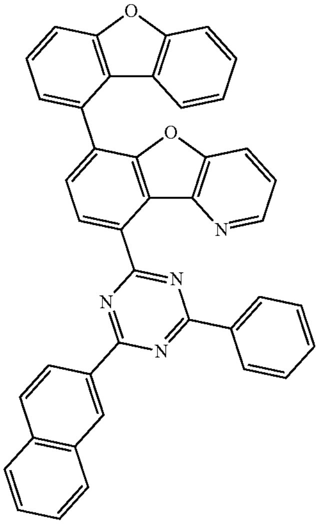
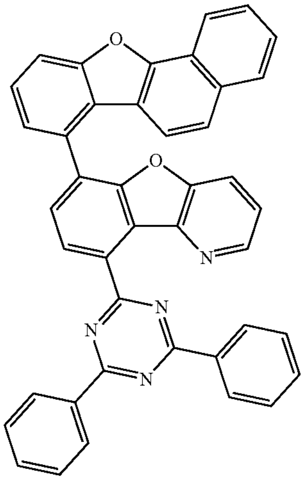
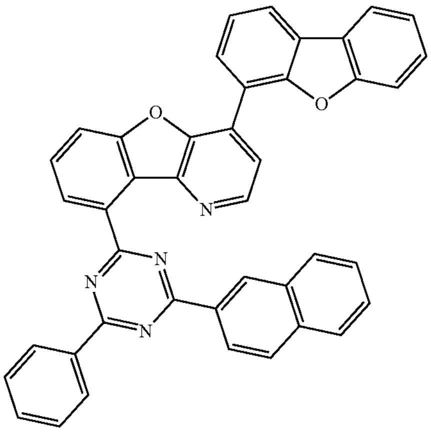
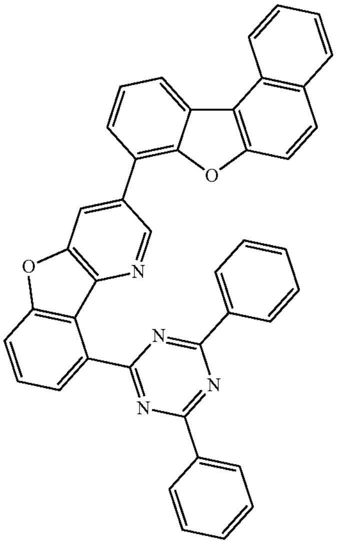
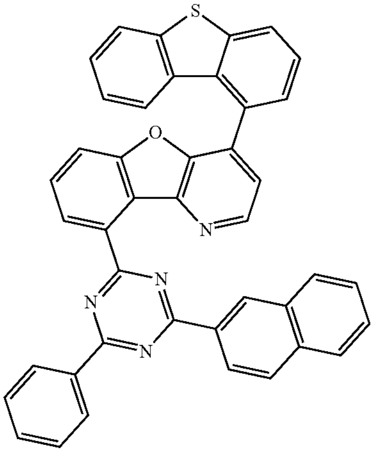
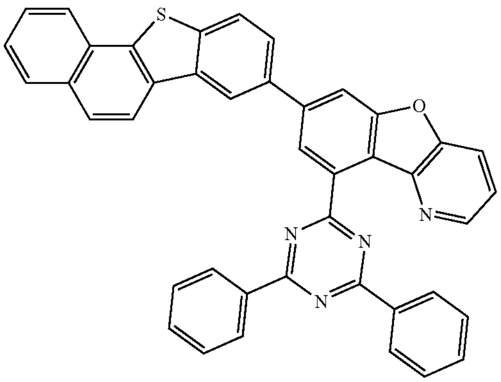

-continued
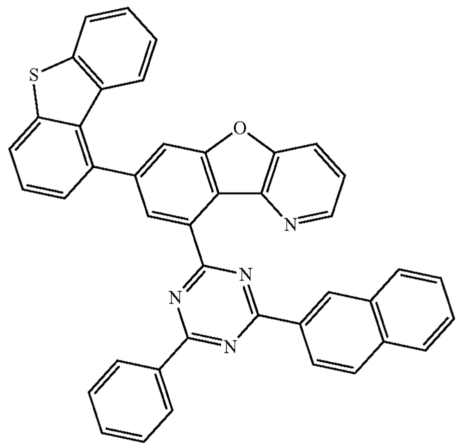
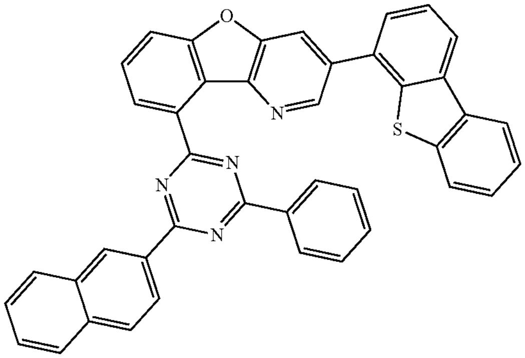
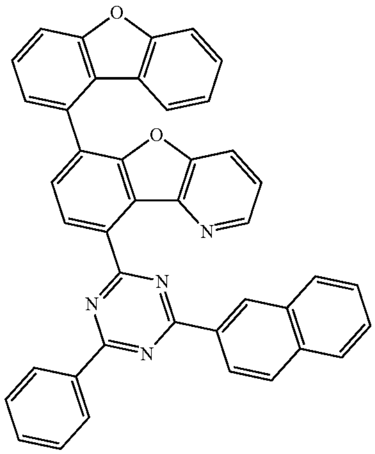
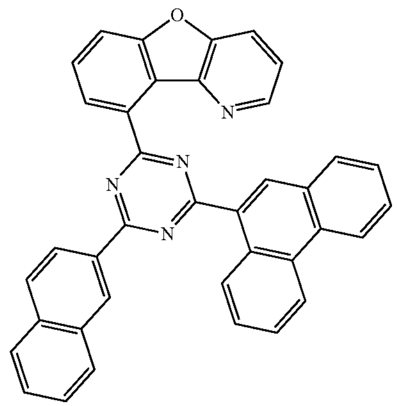
-continued
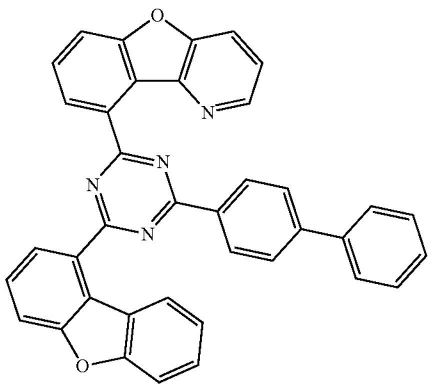
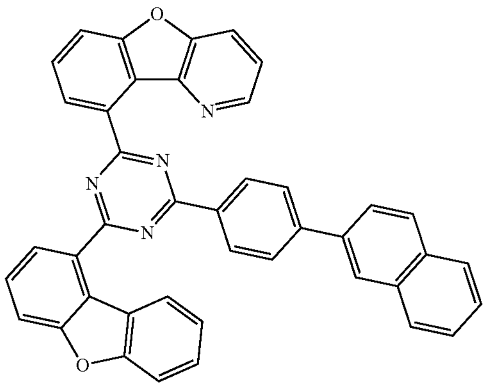
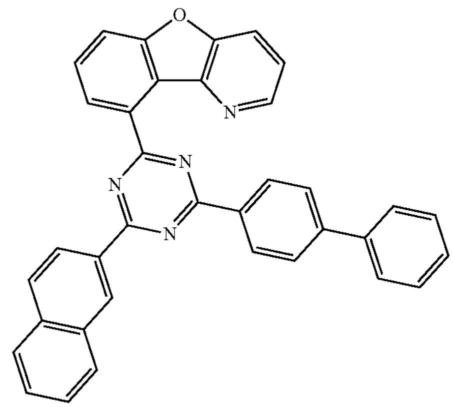
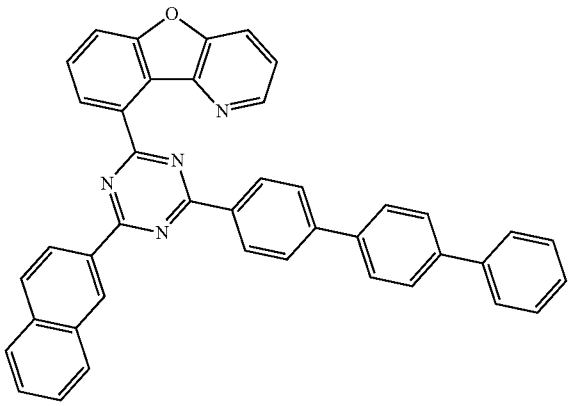

-continued
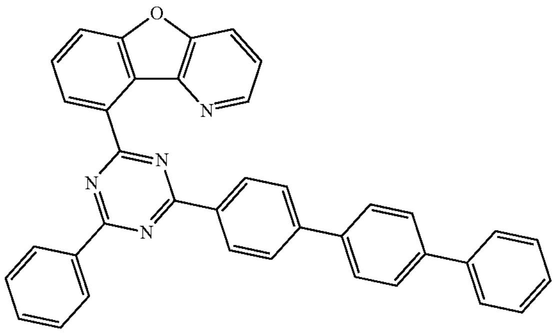
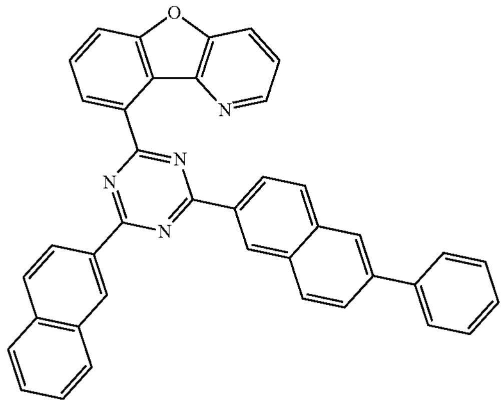
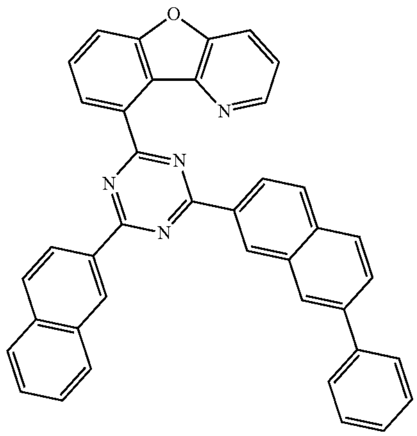
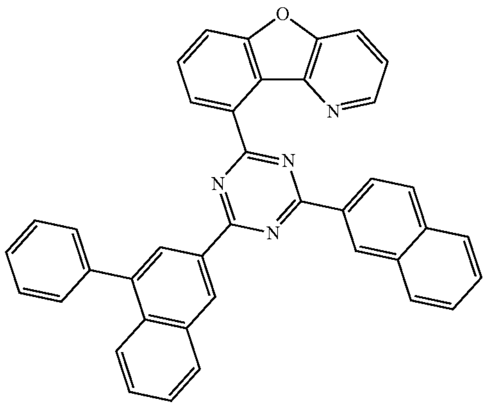
-continued
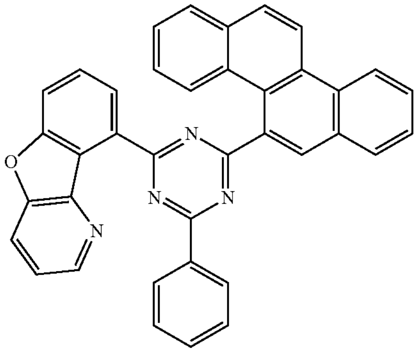
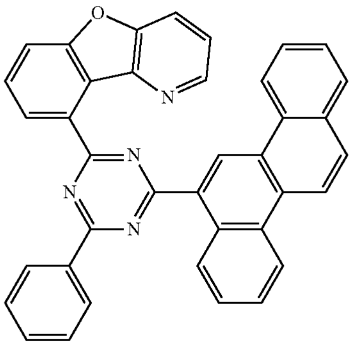
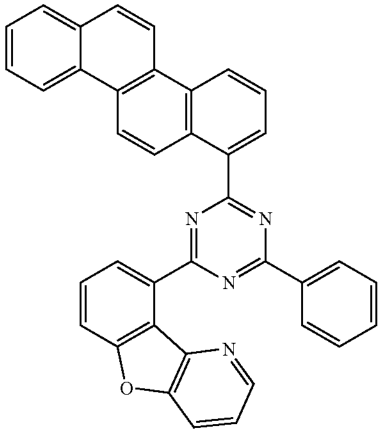
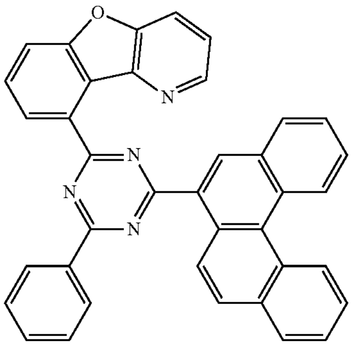

-continued
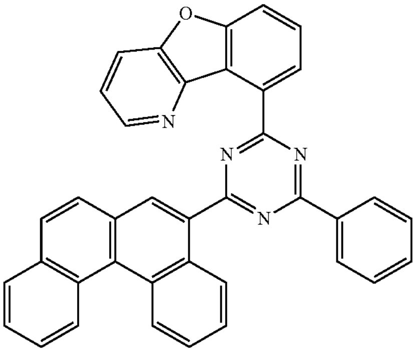
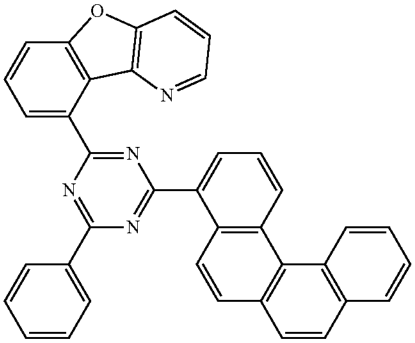
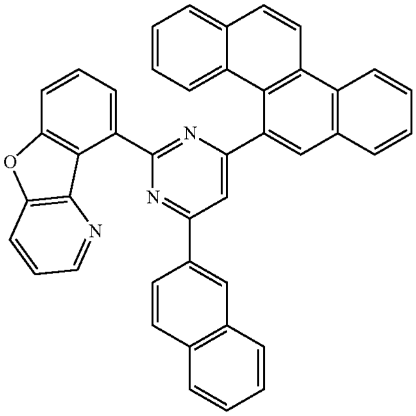
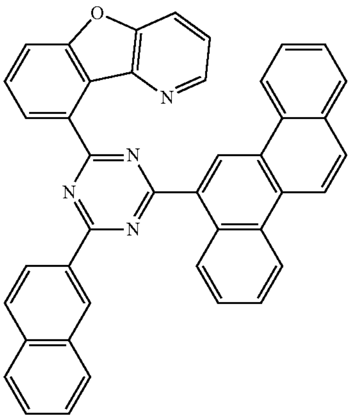
-continued
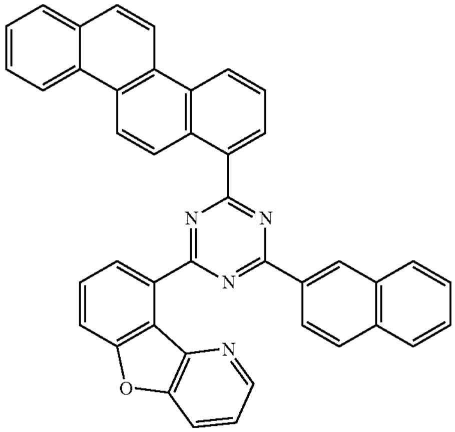
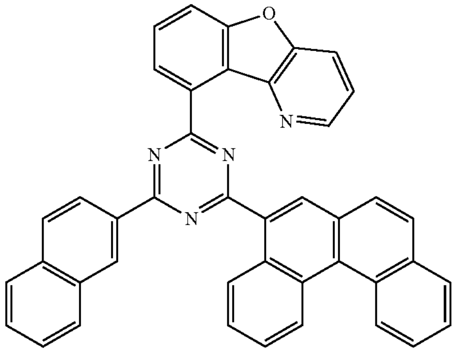
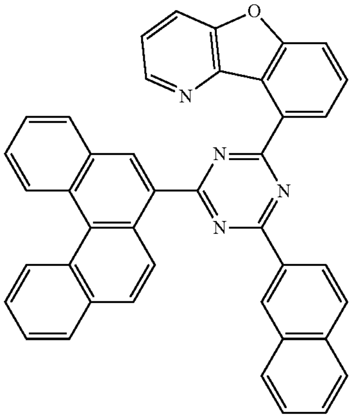
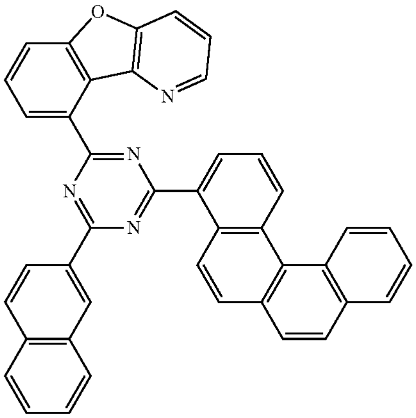

-continued
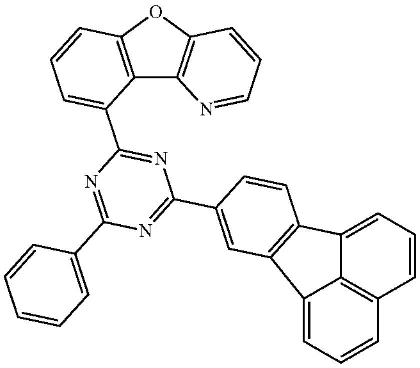
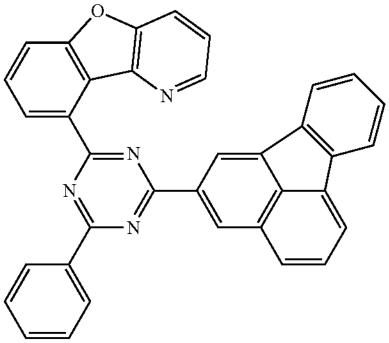
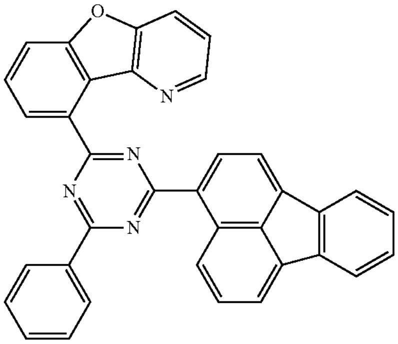
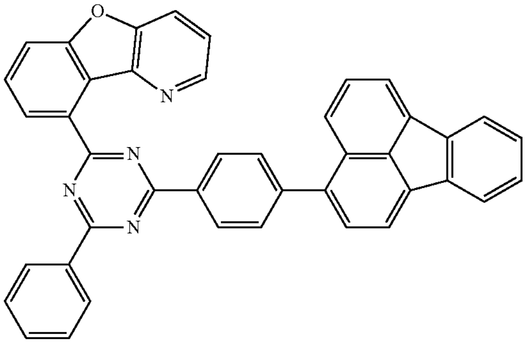
-continued
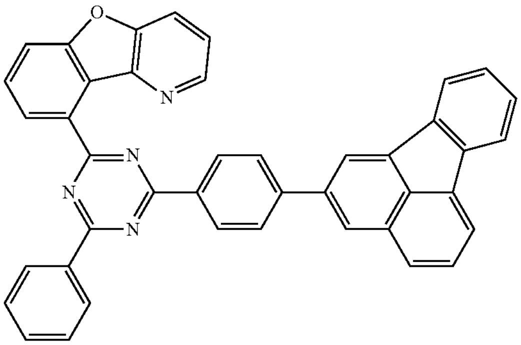
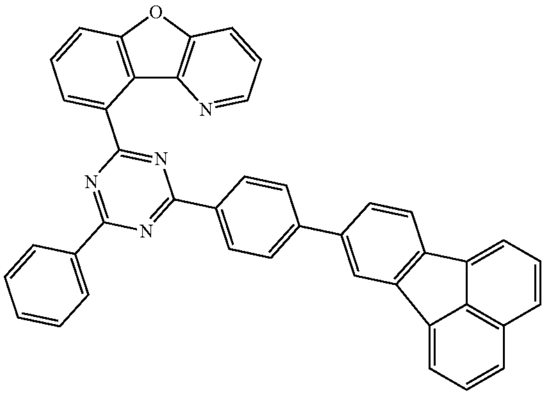
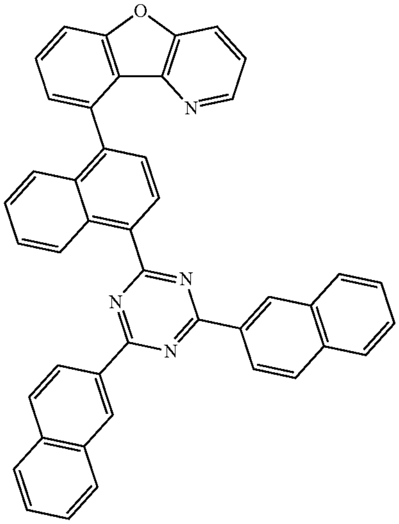

-continued
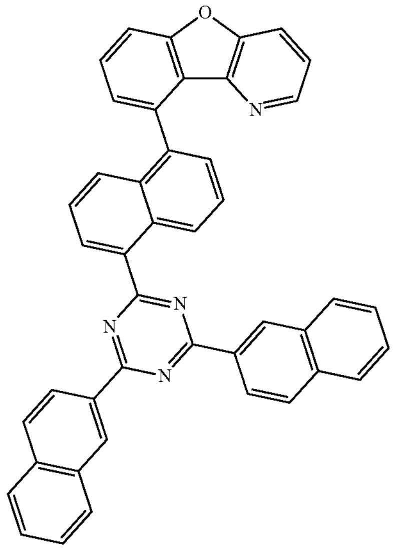
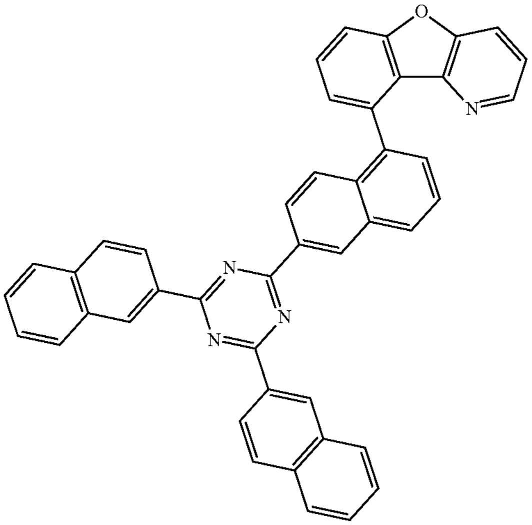
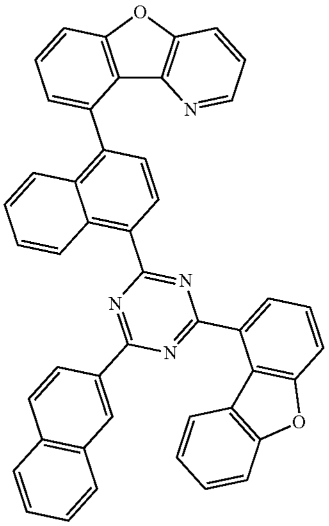
-continued
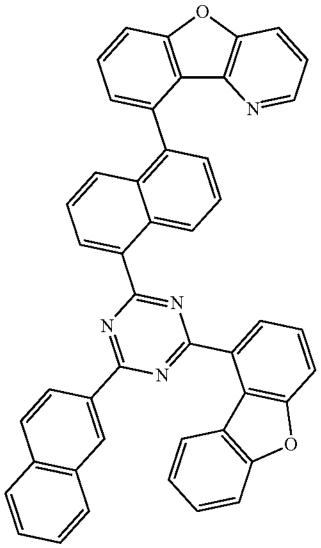
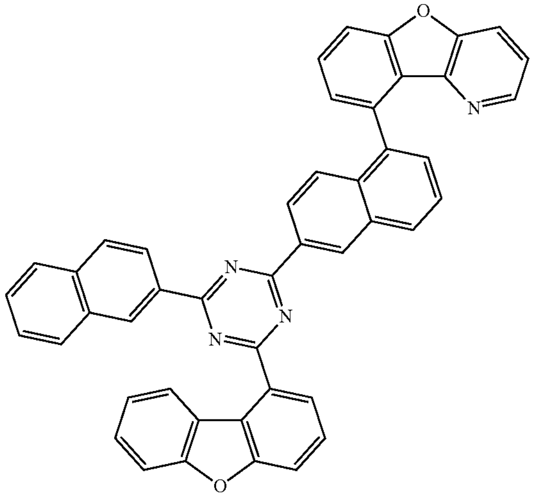
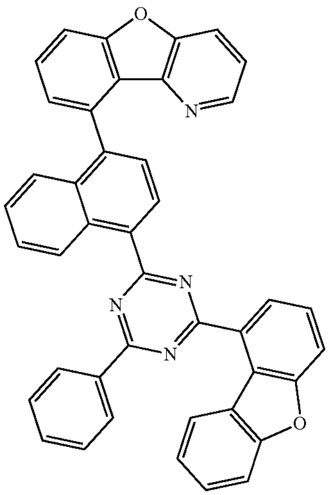

-continued
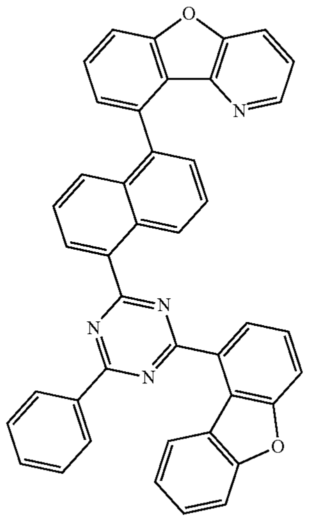
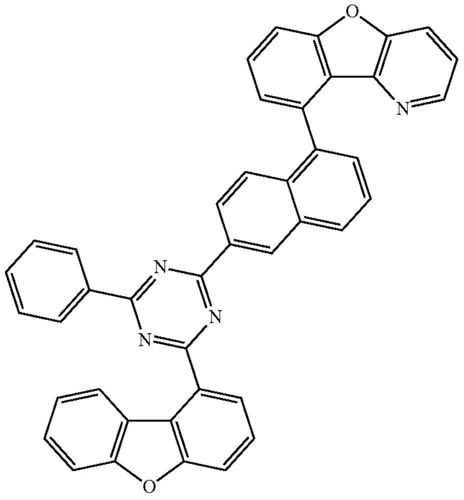
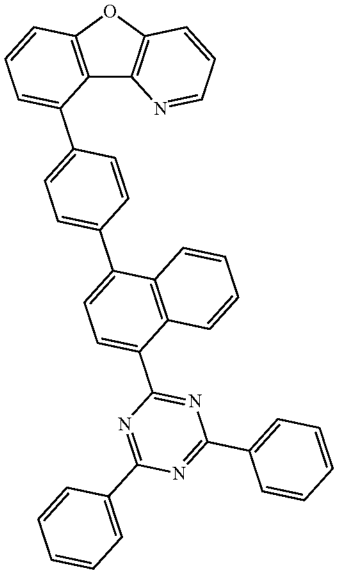
-continued
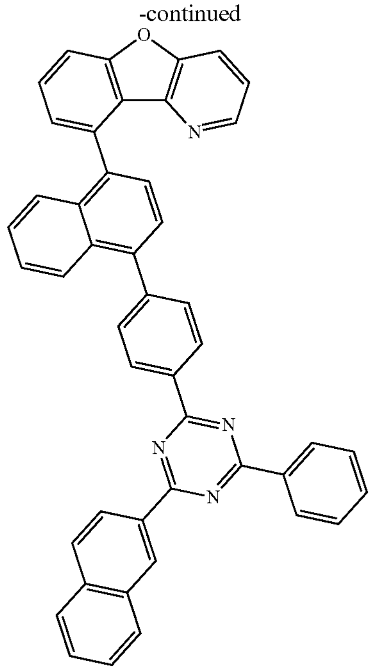
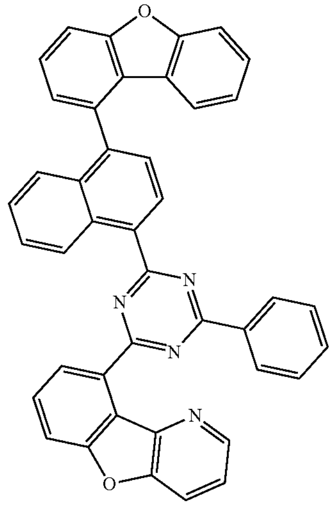

-continued
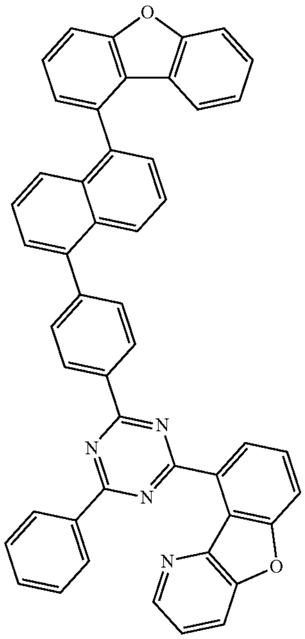
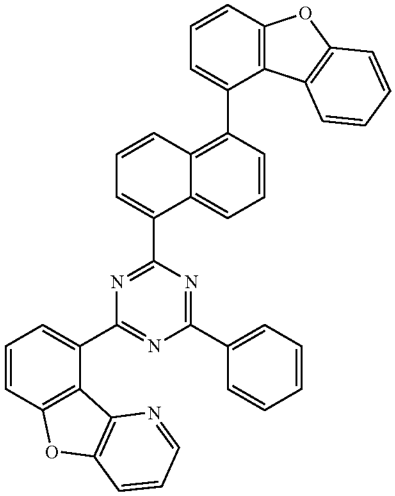
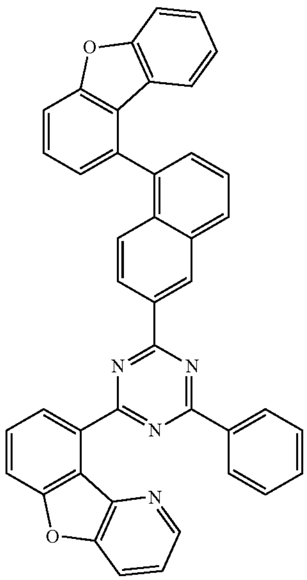
-continued
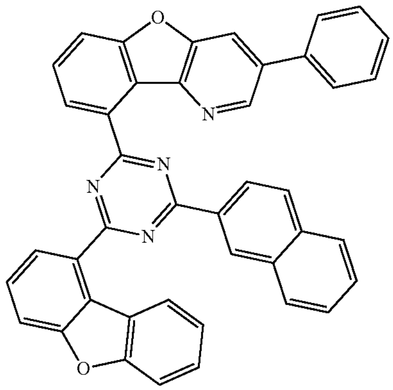
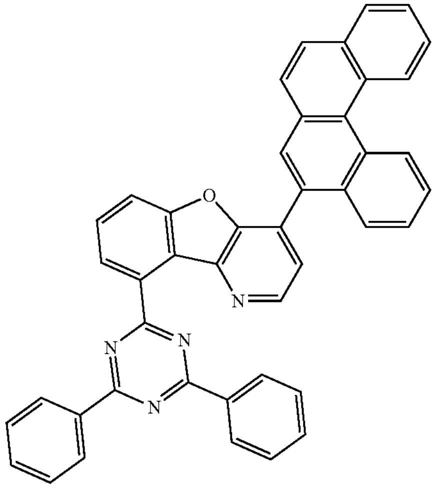
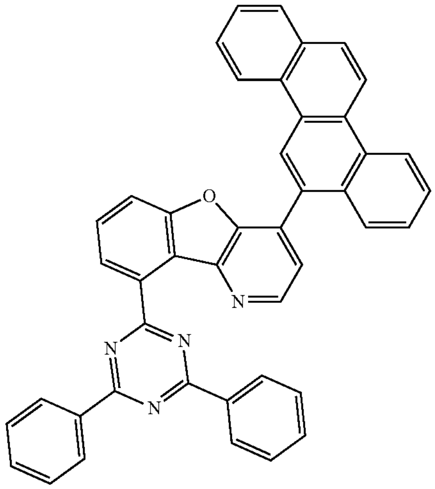

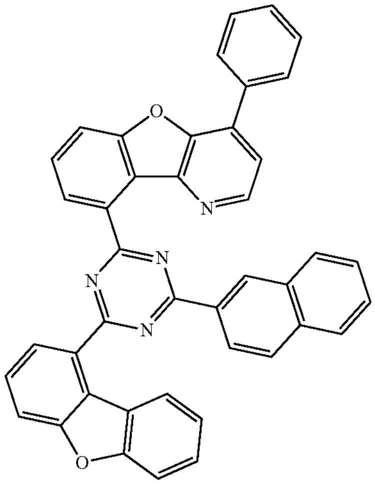
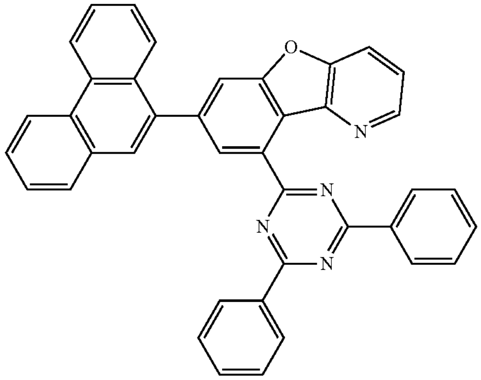
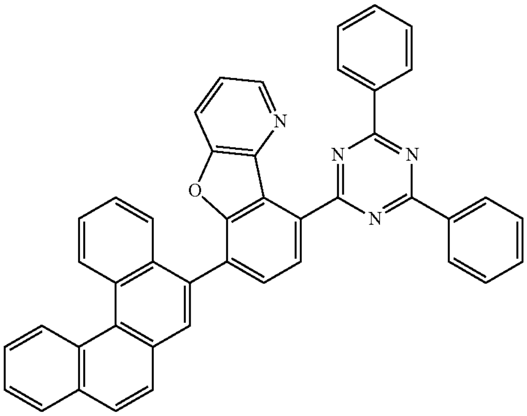
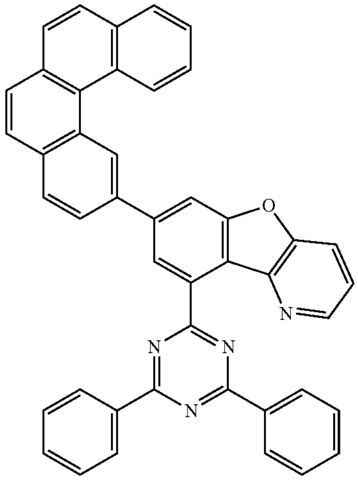
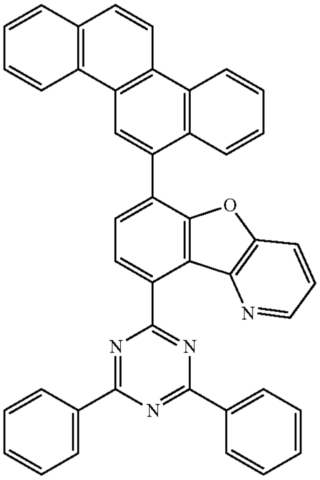
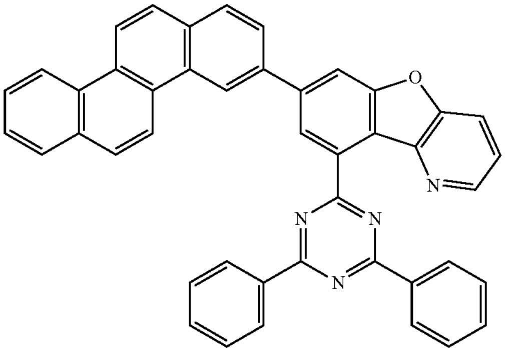

-continued
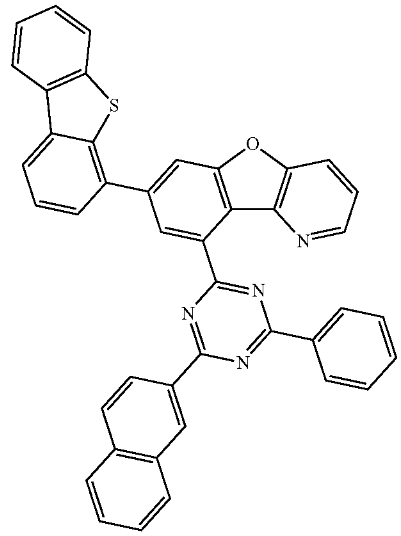
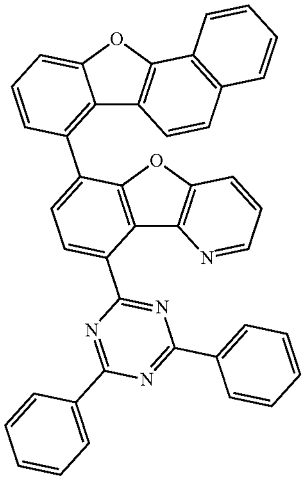
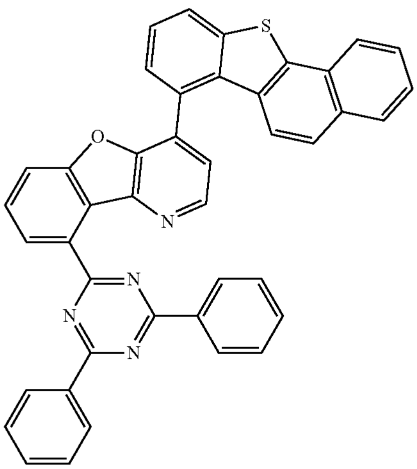
-continued
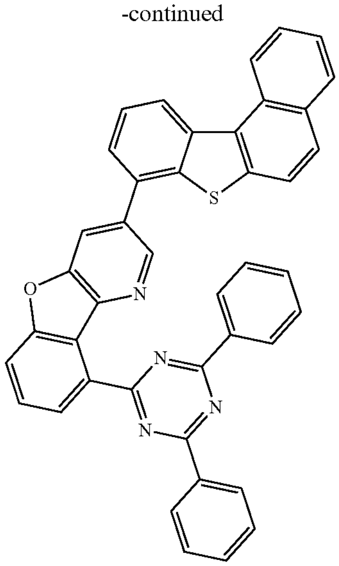
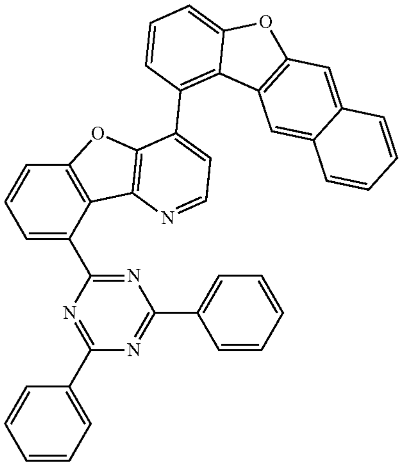
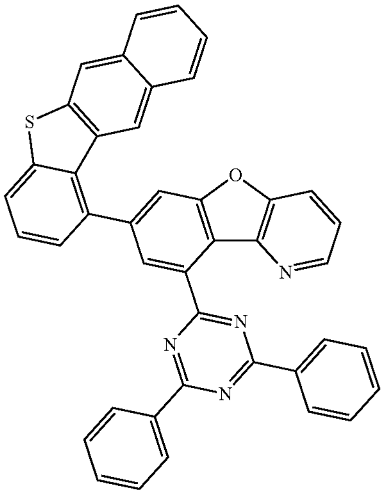

-continued
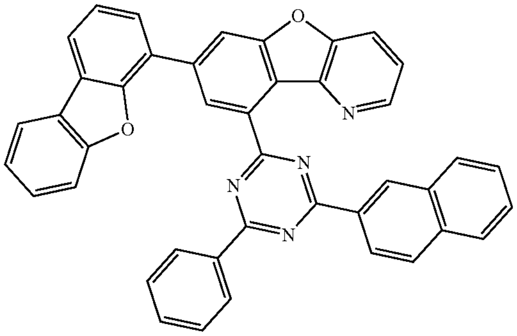
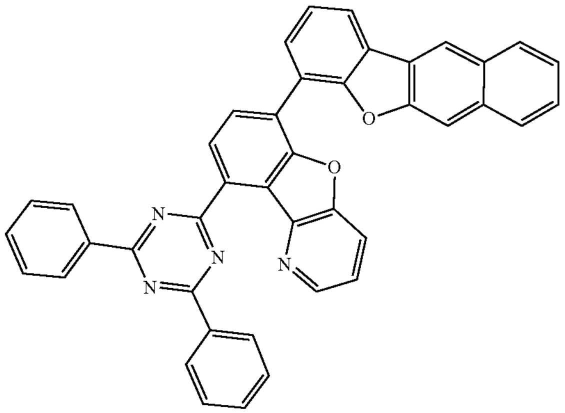
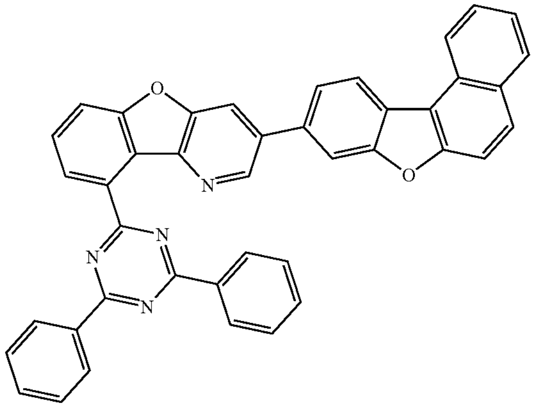
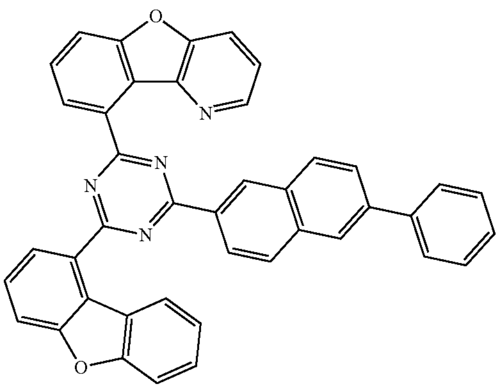
-continued
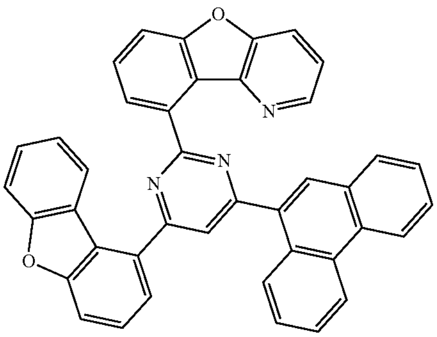
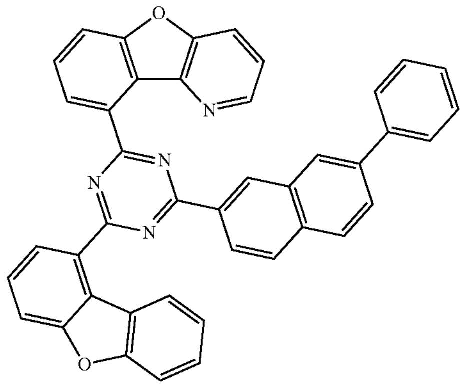
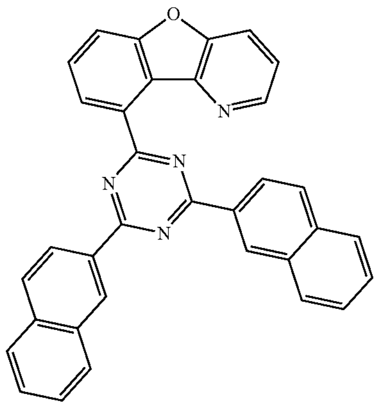
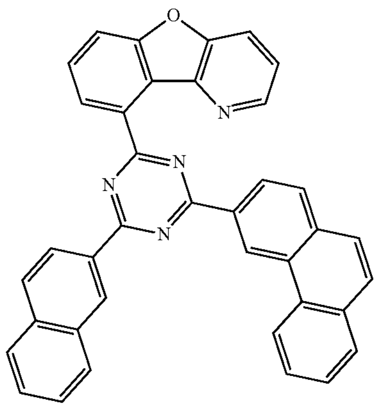

-continued
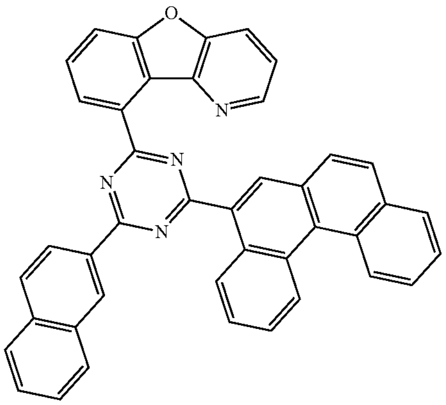
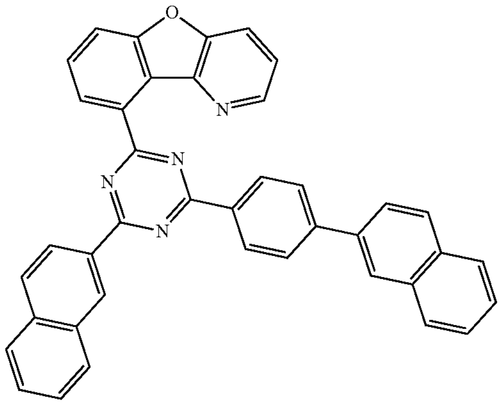
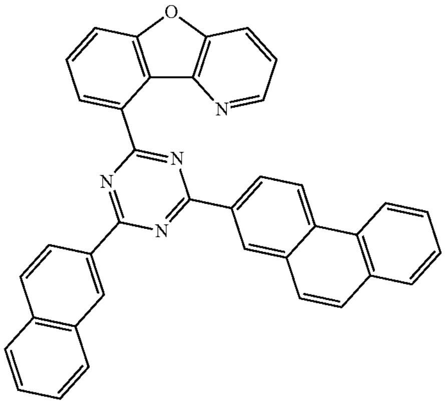
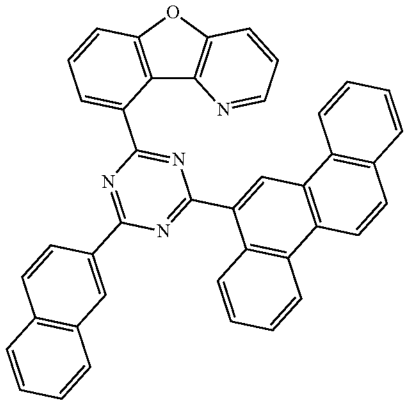
-continued
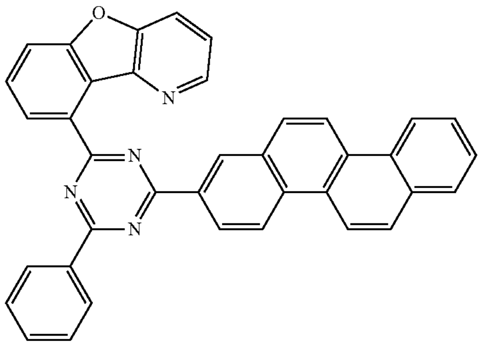
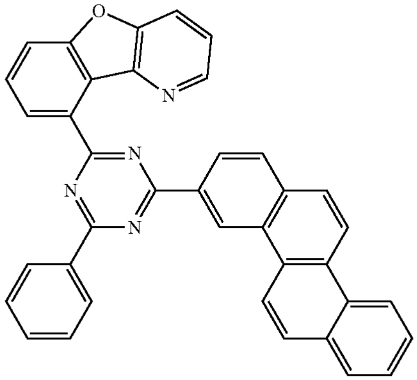
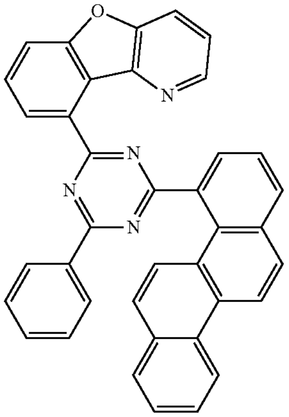
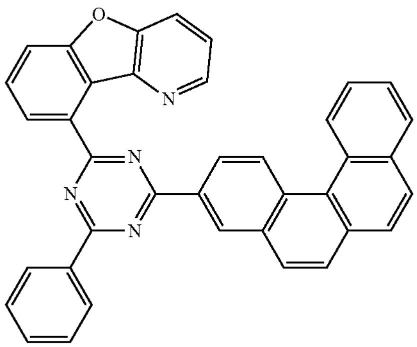

-continued
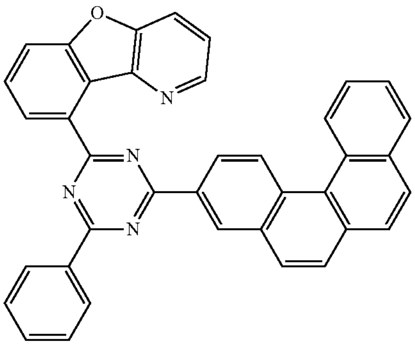
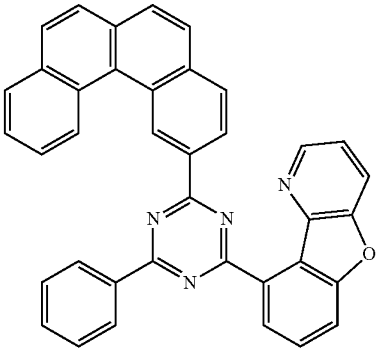
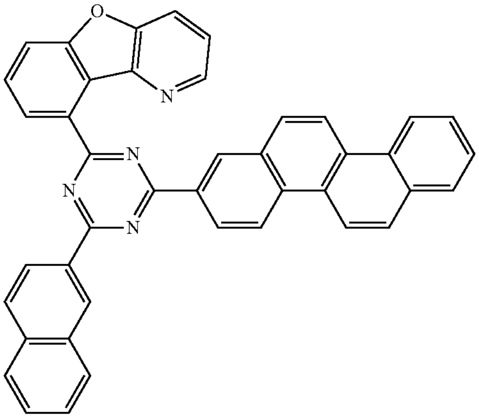
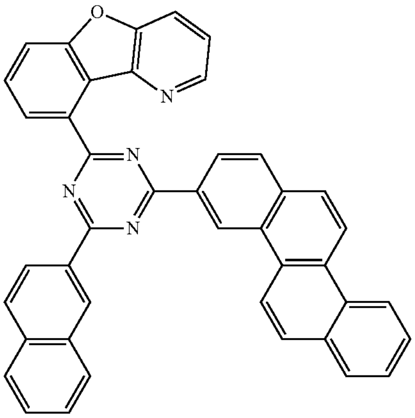
-continued
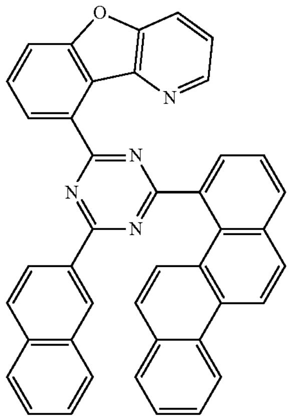
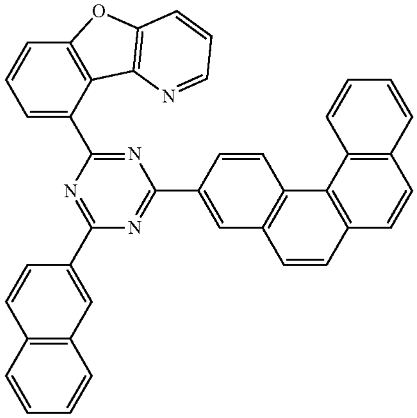
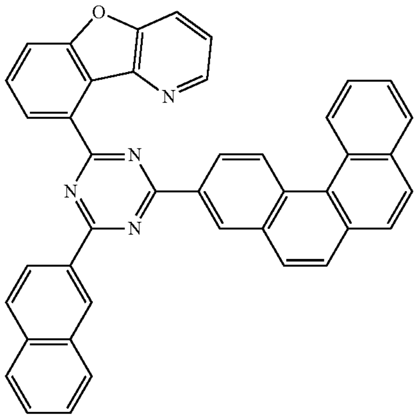
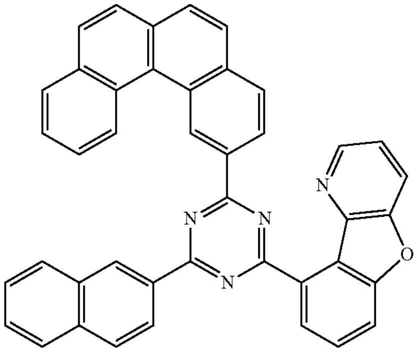

-continued
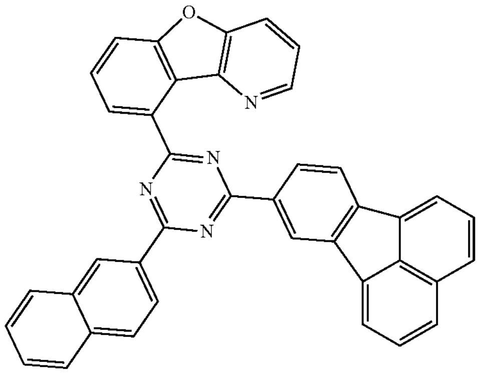
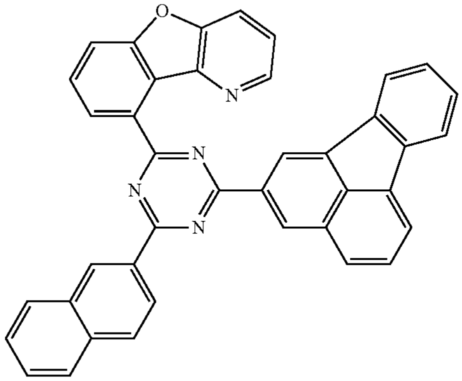
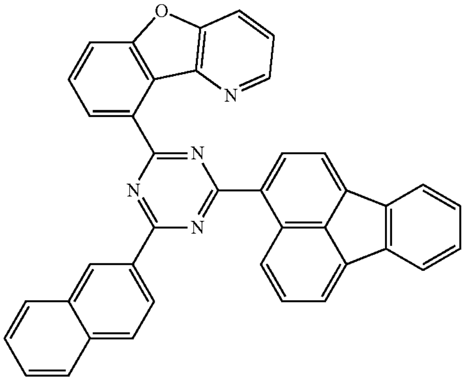
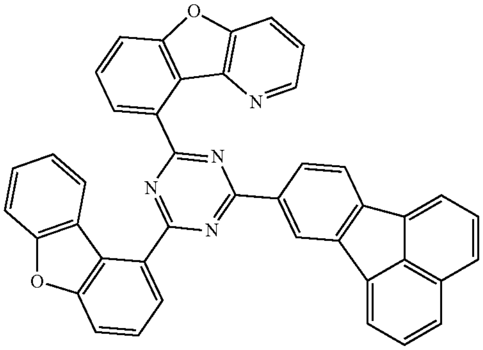
-continued
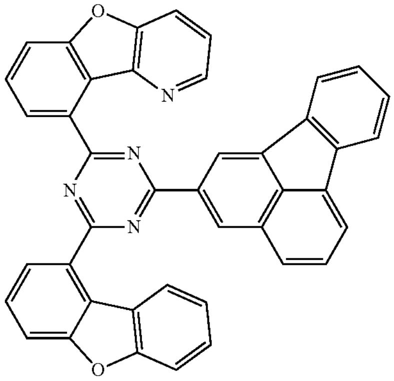
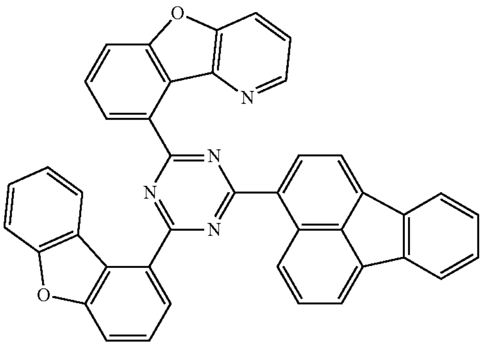
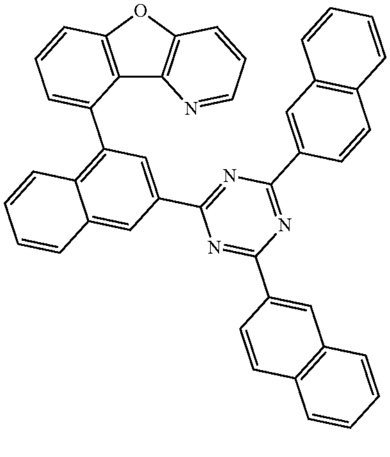
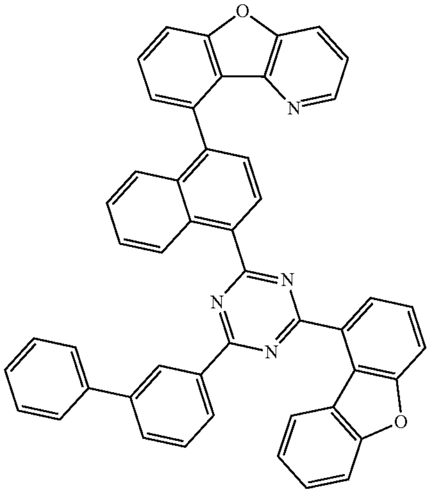

-continued
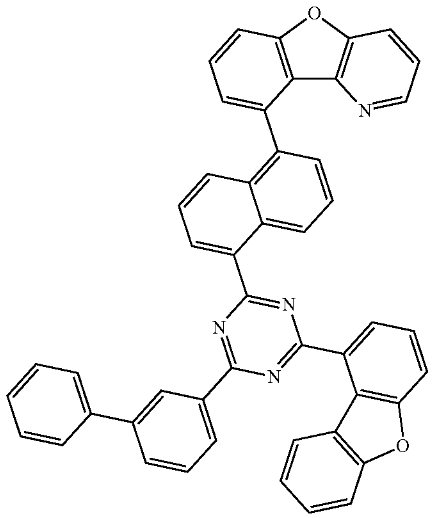
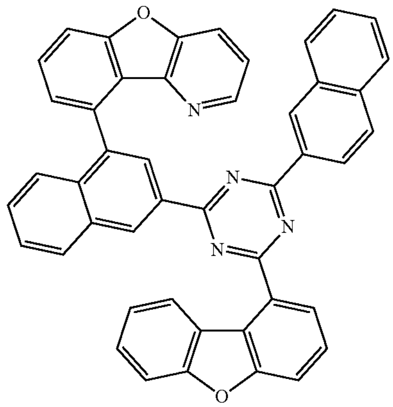
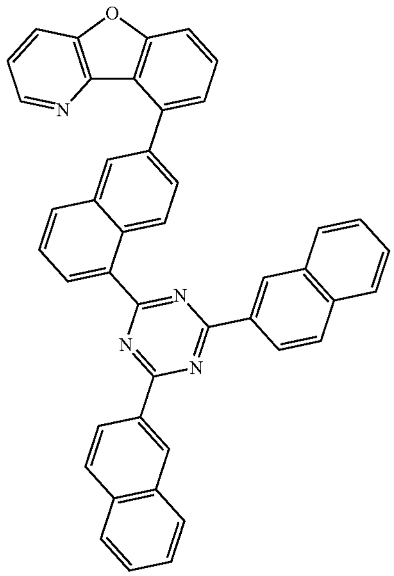
-continued
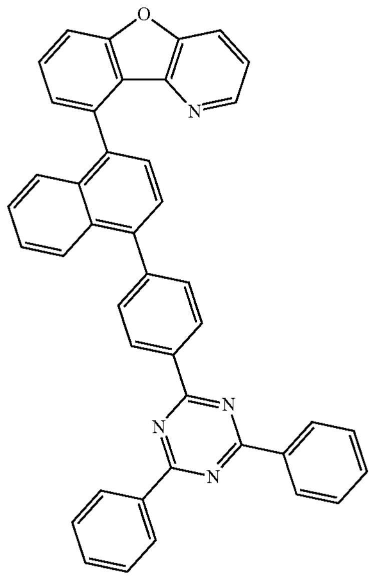
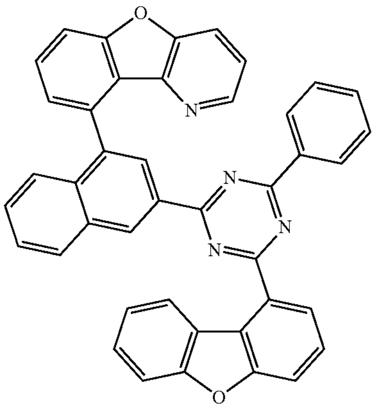
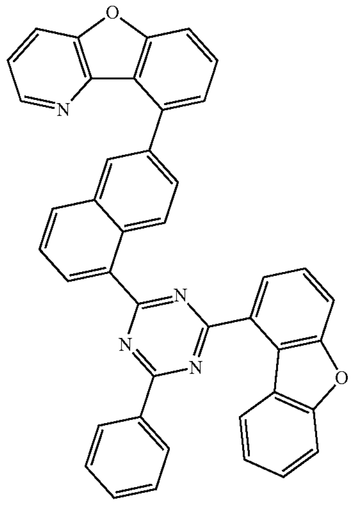

-continued
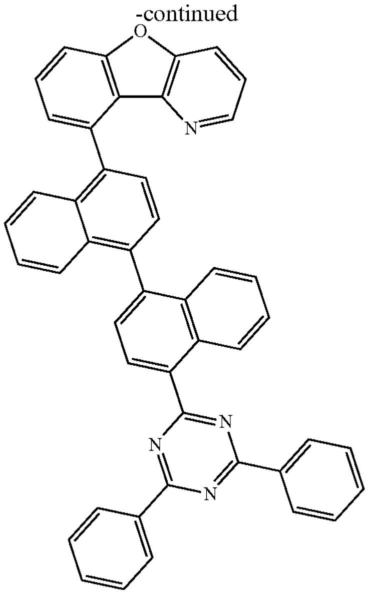
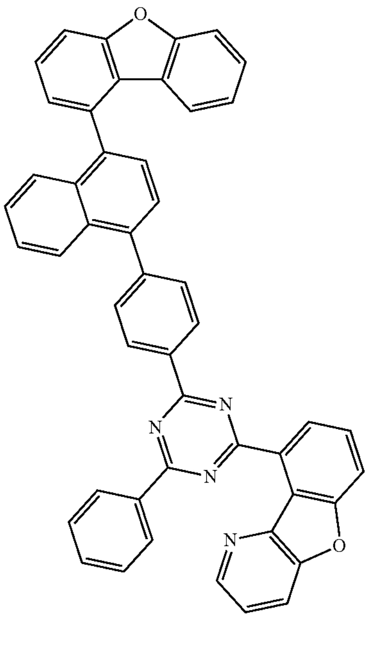
-continued
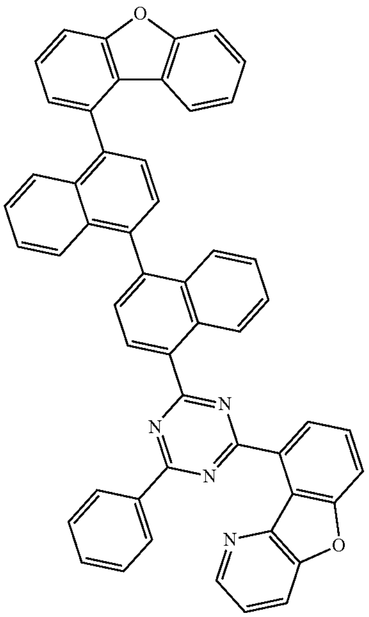
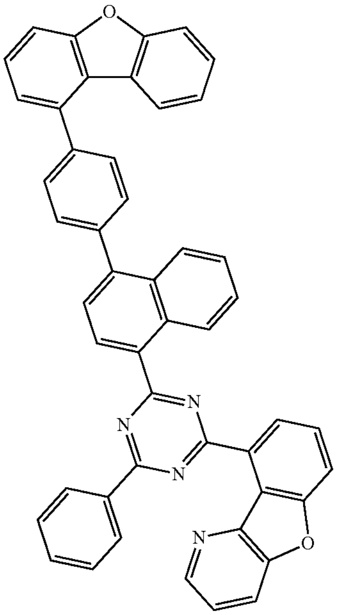
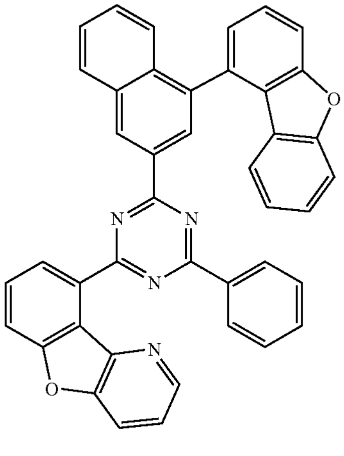

-continued

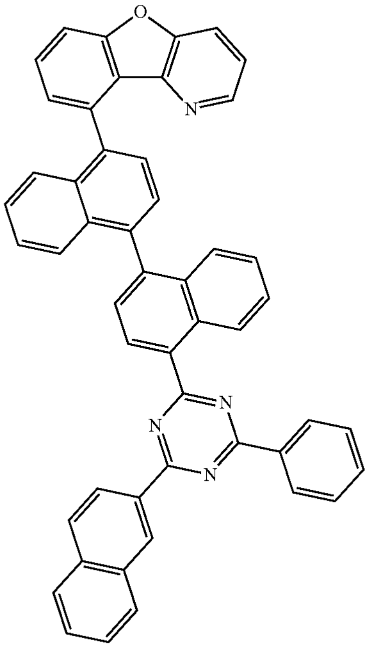

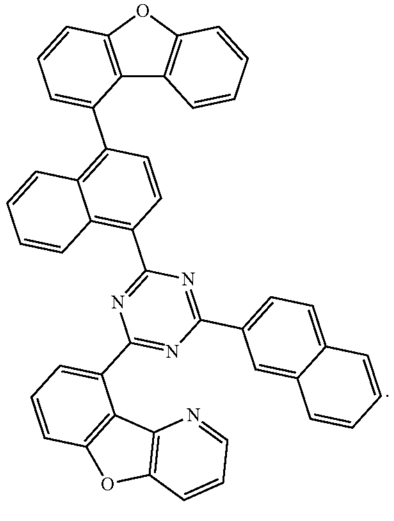

Meanwhile, the compound of Chemical Formula 1 can be prepared, for example, by the preparation method as shown in the following Reaction Scheme 1.

[Reaction Scheme 1]

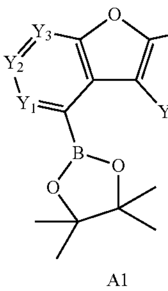

+

A1

-continued

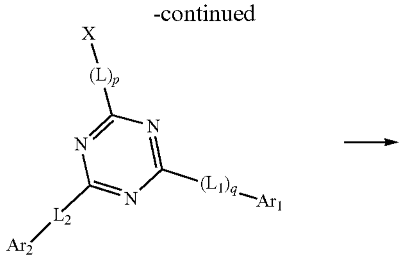

A2

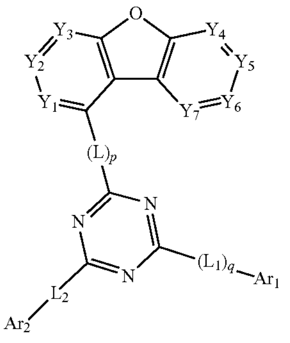

1 wherein in Reaction Scheme 1, X is halogen, preferably bromo, or chloro, and the definitions of other substituents are the same as described above.

Specifically, the compound of Chemical Formula 1 can be prepared by subjecting the starting materials A1 and A2 to a Suzuki coupling reaction. The Suzuki coupling reaction is preferably carried out in the presence of a palladium catalyst and a base, and a reactive group for the Suzuki coupling reaction can be appropriately modified, and the method for preparing the compound of Chemical Formula 1 can be further embodied in Preparation Examples described hereinafter.

(Organic Light Emitting Device)

Further, the present disclosure provides an organic light emitting device comprising a compound of Chemical Formula 1. In one example, the present disclosure provides an organic light emitting device comprising: a first electrode; a second electrode that is provided opposite to the first electrode; and one or more organic material layers that are provided between the first electrode and the second electrode, wherein one or more layers of the organic material layers includes the compound of Chemical Formula 1.

The organic material layer of the organic fight emitting device of the present disclosure can have a single-layer structure, or it can have a multilayered structure in which two or more organic material layers are stacked. For example, the organic light emitting device of the present disclosure can have a structure comprising a hole injection layer, a hole transport layer, a light emitting layer, an electron transport layer, an electron injection layer and the like as the organic material layer. However, the structure of the organic light emitting device is not limited thereto, and it can include a smaller number of organic layers.

In one embodiment, the organic material layer can include a light emitting layer, wherein the organic material layer including the above compound can be a light emitting layer.

In another embodiment, the organic material layer can include a hole injection layer, a hole transport layer, a light emitting layer and an electron injection and transport layer, wherein the organic material layer including the above compound can be a light emitting layer.

In another embodiment, the organic material layer can include a hole injection layer, a hole transport layer, an electron blocking layer, a light emitting layer and an electron injection and transport layer, wherein the organic material layer including the above compound can be a light emitting layer.

In yet another embodiment, the organic material layer can include a hole injection layer, a hole transport layer, an electron blocking layer, a light emitting layer, a hole blocking layer, and an electron injection and transport layer, wherein the organic material layer including the above compound can be a light emitting layer.

Further, the organic light emitting device according to the present disclosure can be a normal type organic light emitting device in which an anode, one or more organic material layers and a cathode are sequentially stacked on a substrate wherein the first electrode is an anode, and the second electrode is a cathode. Further, the organic light emitting device according to the present disclosure can be an inverted type organic light emitting device in which a cathode, one or more organic material layers and an anode are sequentially stacked on a substrate wherein the first electrode is a cathode and the second electrode is an anode. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound of Chemical Formula 1 can be included in the light emitting layer.

FIG. 2 shows an example of an organic light emitting device comprising a substrate 1, an anode 2, a hole injection layer 5, a hole transport layer 6, an electron blocking layer 7, a light emitting layer 3, a hole blocking layer 8, an electron injection and transport layer 9, and a cathode 4.

The organic light emitting device according to the present disclosure can be manufactured by materials and methods known in the art, except that the light emitting layer includes the compound according to the present disclosure, and is manufactured according to the above-mentioned method.

For example, the organic light emitting device according to the present disclosure can be manufactured by sequentially stacking an anode, an organic material layer and a cathode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon.

In addition to such a method, the organic light emitting device can be manufactured by sequentially depositing a cathode material, an organic material layer and an anode material on a substrate (International Publication WO20031012890). However, the manufacturing method is not limited thereto.

In one example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive compounds such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and further is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrilehexaazatriphenylene-based organic material, a quinacridone-based organic material, a perylene-based organic material, anthraquinone, polyaniline and polythiophene-based conductive compound, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive compound, a block copolymer in which a conjugate portion and a non-conjugate portion are present together, and the like, but are not limited thereto.

The electron blocking layer refers to a layer which is formed on the hole transport layer, preferably provided in contact with the light emitting layer, and serves to adjust the hole mobility, prevent excessive movement of electrons, and increase the probability of hole-electron coupling, thereby improving the efficiency of the organic light emitting device. The electron blocking layer includes an electron blocking material, and examples of such electron blocking material can include an arylamine-based organic material or the like, but is not limited thereto.

The light emitting layer can include a host material and a dopant material. The host material can be the compound of Chemical Formula 1. Further, the host material can be a fused aromatic ring derivative, a heterocycle-containing compound or the like in addition to the compound of Chemical Formula 1. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocycle-containing compounds include carbazole derivatives, dibenzofuran derivatives, ladder-type furan compounds, pyrimidine derivatives, and the like, but are not limited thereto.

Further, the dopant material includes an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

More specifically, the dopant material can include compounds having the following structures, but is not limited thereto:

Dp-1

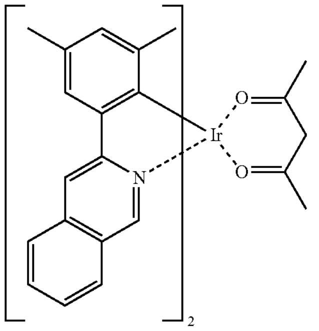

Dp-2

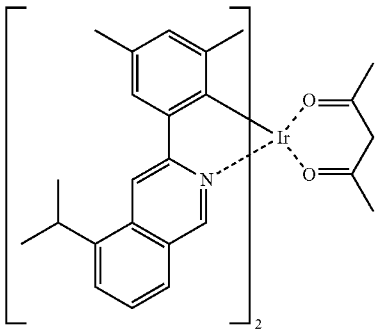

-continued

Dp-3

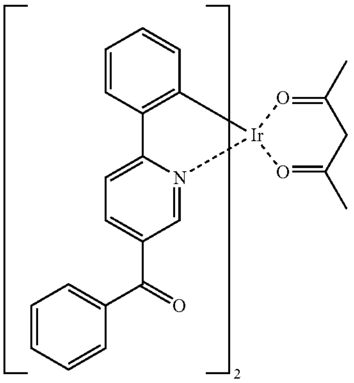

Dp-4

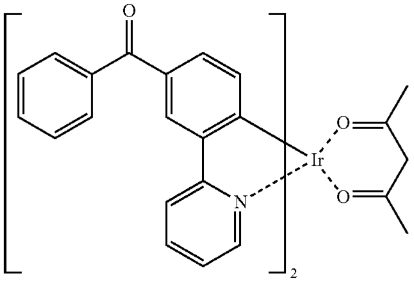

Dp-5

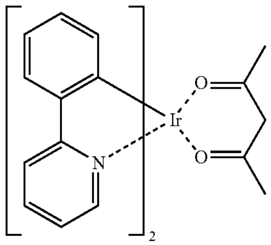

Dp-6

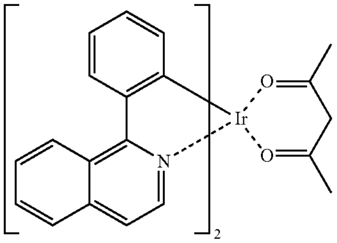

Dp-7

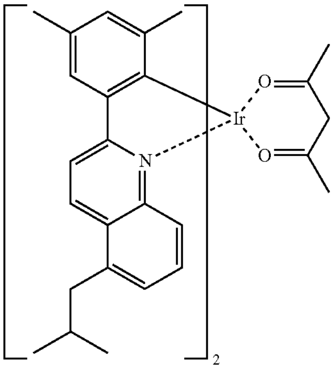

-continued
Dp-8
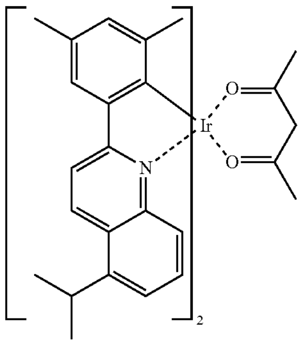
Dp-9
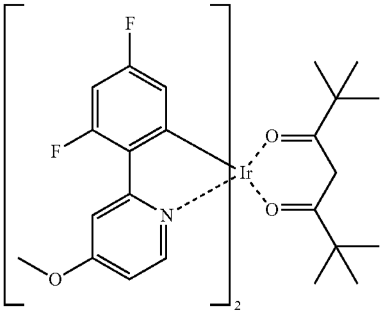
Dp-10
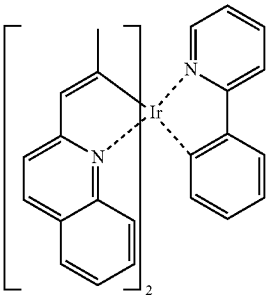
Dp-11
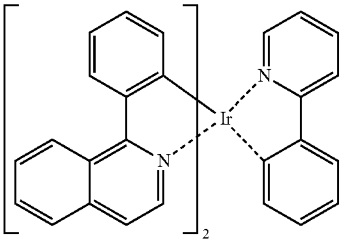
Dp-12
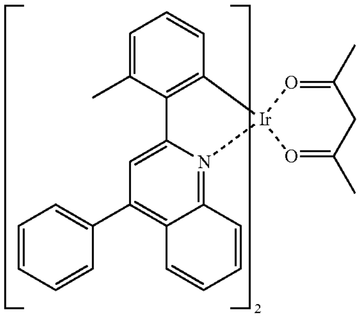
-continued
Dp-13
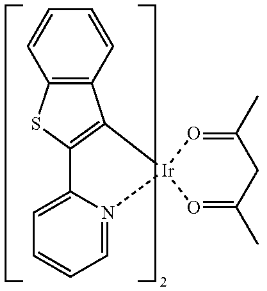
Dp-14
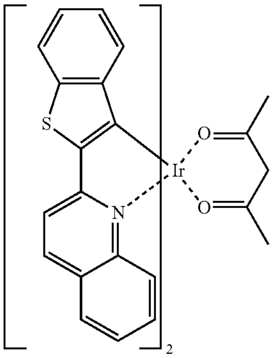
Dp-15
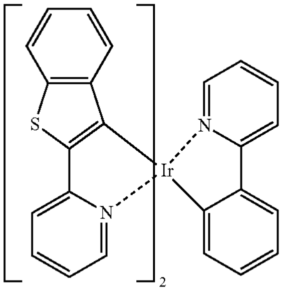
Dp-16
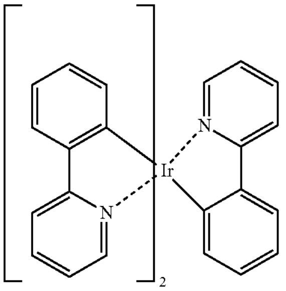
Dp-17
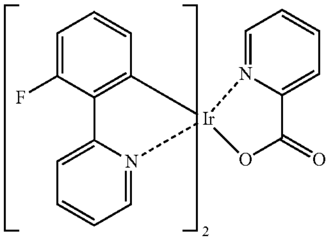

-continued
Dp-18
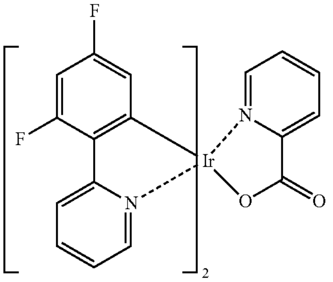
Dp-19
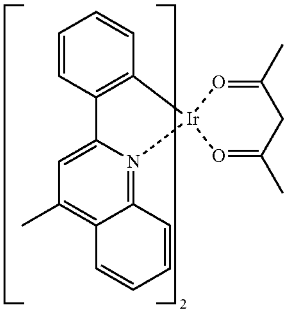
Dp-20
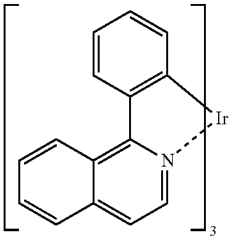
Dp-21
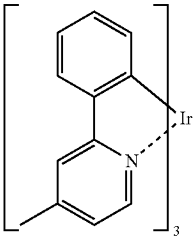
Dp-22
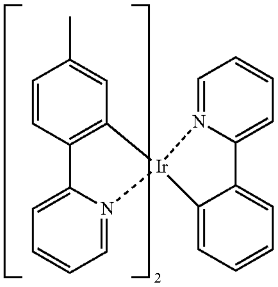
-continued
Dp-23
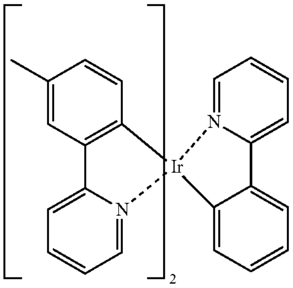
Dp-24
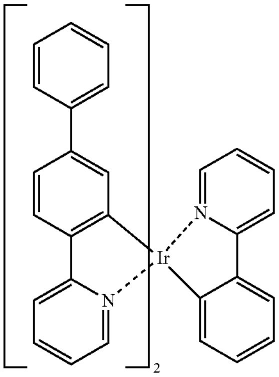
Dp-25
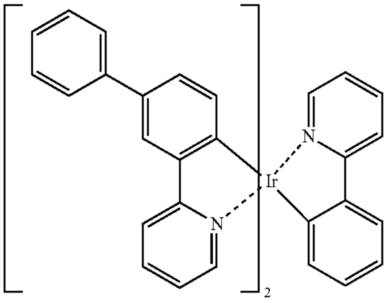
Dp-26
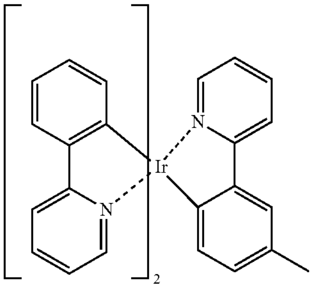
Dp-27
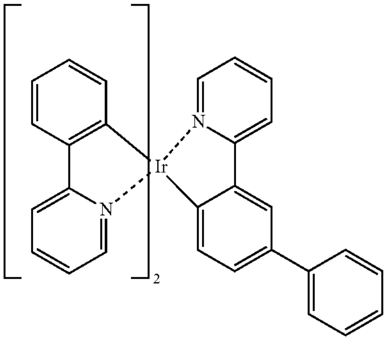

-continued
Dp-28
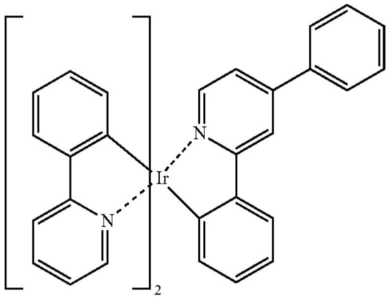
Dp-29
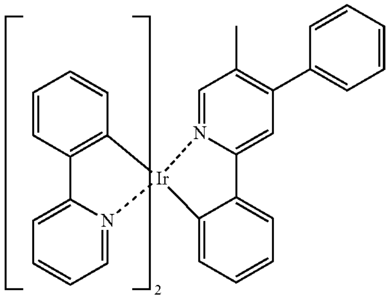
Dp-30
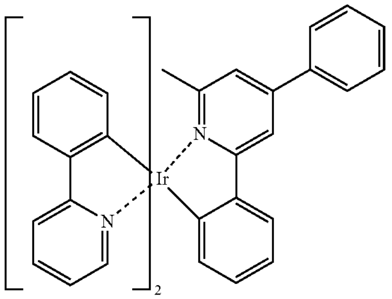
Dp-31
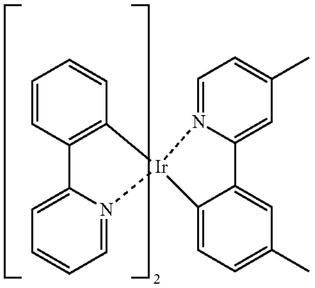
Dp-32
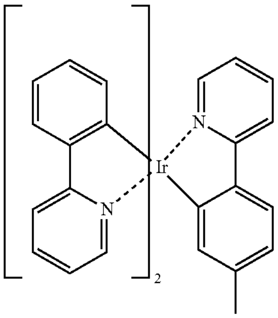
-continued
Dp-33
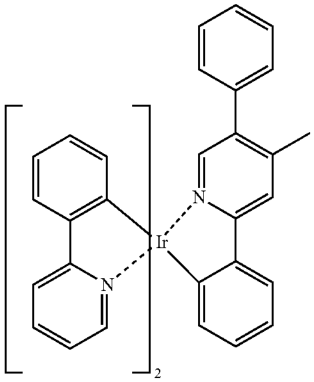
Dp-34
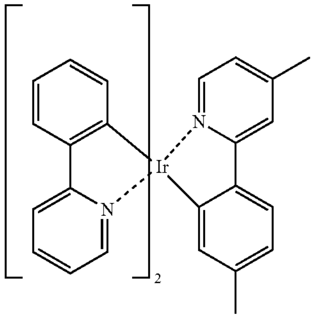
Dp-35
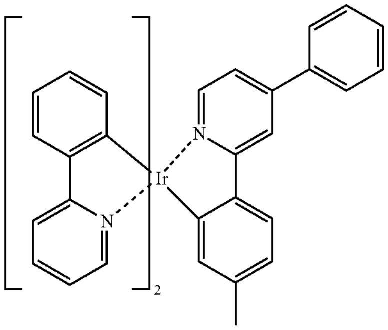
Dp-36
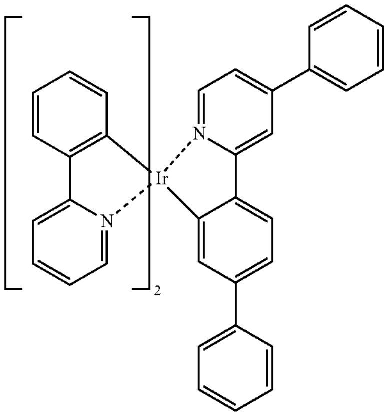

-continued

Dp-37

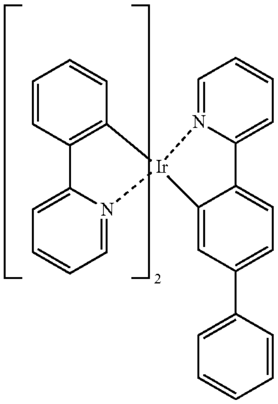

Dp-38

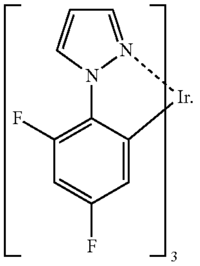

The hole blocking layer refers to a layer which is formed on the light emitting layer, preferably provided in contact with the light emitting layer, and serves to adjust the electron mobility, prevent excessive movement of holes, and increase the probability of hole-electron coupling, thereby improving the efficiency of the organic light emitting device. The hole blocking layer includes a hole blocking material, and examples of such hole blocking material can include a compound having an electron-withdrawing group introduced therein, such as azine derivatives including triazine; triazole derivatives; oxadiazole derivatives; phenanthroline derivatives; phosphine oxide derivatives, but is not limited thereto.

The electron injection and transport layer is a layer for simultaneously performing the roles of an electron transport layer and an electron injection layer that inject electrons from an electrode and transport the received electrons up to the light emitting layer, and is formed on the light emitting layer or the hole blocking layer. The electron injection and transport material is suitably a material which can receive electrons well from a cathode and transfer the electrons to a light emitting layer, and has a large mobility for electrons. Specific examples of the electron injection and transport material include: an Al complex of 8-hydroxyquinoline; a complex including $Alq_3$; an organic radical compound; a hydroxyflavone-metal complex, a triazine derivative, and the like, but are not limited thereto. Alternatively, it can be used together with fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

The electron injection and transport layer can also be formed as a separate layer such as an electron injection layer and an electron transport layer. In such a case, the electron transport layer is formed on the light emitting layer or the hole blocking layer, and the above-mentioned electron injection and transport material can be used as the electron transport material included in the electron transport layer. In addition, the electron injection layer is formed on the electron transport layer, and examples of the electron injection material included in the electron injection layer include LiF, NaCl, CsF, $Li_2O$, BaO, fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure can be a bottom emission device, a top emission device, or a double-sided light emitting device, and in particular, can be a bottom emission device that requires relatively high luminous efficiency.

In addition, the compound of Chemical Formula 1 can be included in an organic solar cell or an organic transistor in addition to an organic light emitting device.

The preparation of the compound of Chemical Formula 1 and the organic light emitting device including the same will be described in detail in the following examples. However, these examples are presented for illustrative purposes only, and are not intended to limit the scope of the present disclosure.

SYNTHESIS EXAMPLE A: SYNTHESIS OF INTERMEDIATE COMPOUND A

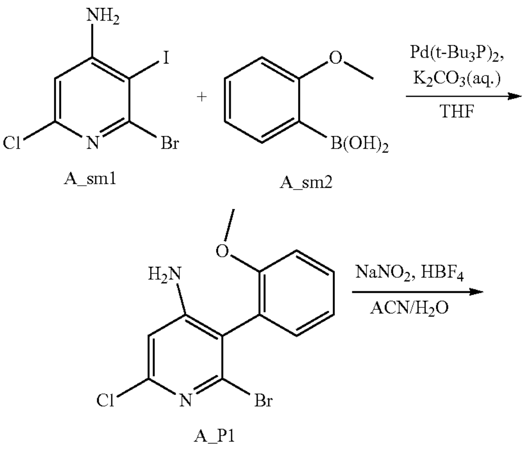

A_sm1
A_sm2
A_P1

-continued

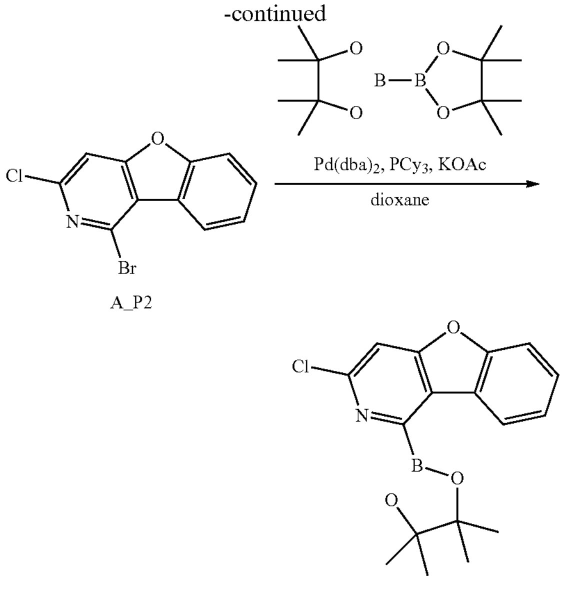

A_P2

A

A_sm1 (15 g, 45 mmol) and A_sm2 (8.2 g, 54 mmol) were added to 300 mL of THF under a nitrogen atmosphere, and the mixture was stirred and refluxed. Then, potassium carbonate (18.7 g, 135 mmol) was dissolved in 56 mL of water, added thereto, sufficiently stirred, and then bis(tri-tert-butylphosphine)palladium(0) (0.2 g, 0.4 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 10.7 g of A_P1. (Yield: 76%, MS: $[M+H]^+$=313).

Next, A_P1 (10 g, 31.9 mmol) and $HBF_4$ (5.6 g, 63.8 mmol) were added to 100 mL of ACN under a nitrogen atmosphere, and the mixture was stirred. Then, $NaNO_2$ (4.4 g, 63.8 mmol) was dissolved in 20 mL of $H_2O$ and slowly added at 0° C. After reacting for 10 hours, the mixture was heated to room temperature, and then diluted by adding 200 mL of water. The solution was completely dissolved in chloroform, washed twice with water, the organic layer was separated, treated with anhydrous magnesium sulfate, filtered, and the filtrate was distilled under reduced pressure. The concentrated compound was purified by silica gel column chromatography to give 5.8 g of A_P2. (Yield: 65%, MS: $[M+H]^+$=282)

Next, A_P2 (15 g, 53.1 mmol) and bis(pinacolato)diboron (14.8 g, 58.4 mmol) were added to 300 mL of 1,4-dioxane under a nitrogen atmosphere, and the mixture was stirred under reflux. Then, potassium acetate (7.8 g, 79.6 mmol) was added thereto, sufficiently stirred, and then bis(dibenzylideneacetone)palladium(0) (0.9 g, 1.6 mmol) and tricyclohexylphosphine(0.9 g, 3.2 mmol) were added. After reacting for 9 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.5 g of Compound A. (Yield: 77%, MS: $[M+H]^+$=330)

SYNTHESIS EXAMPLE B: SYNTHESIS OF INTERMEDIATE COMPOUND B

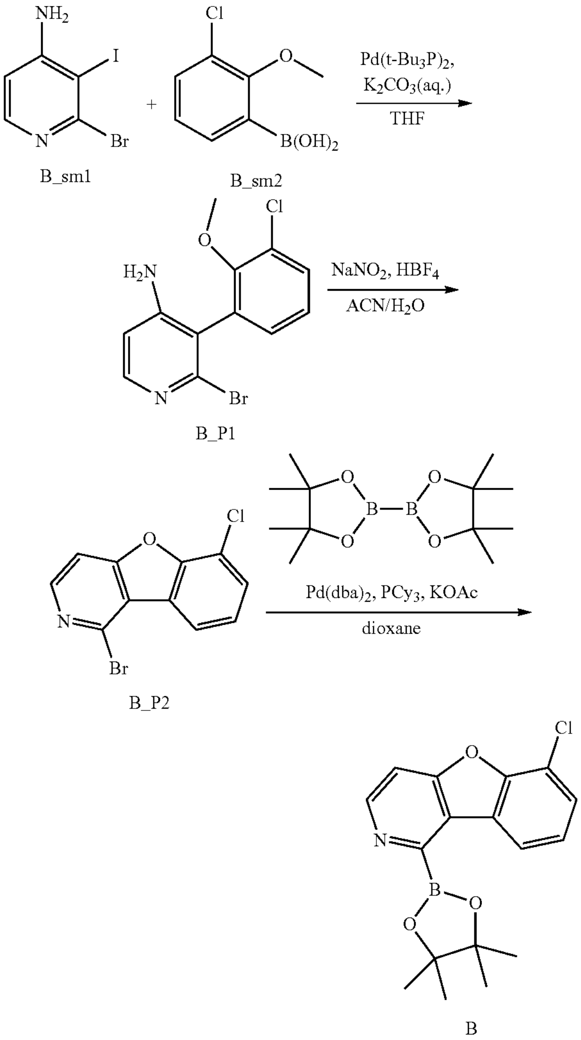

B_sm1 B_sm2

B_P1

B_P2

B

B_sm1 (15 g, 50.2 mmol) and B_sm2 (11.2 g, 60.2 mmol) were added to 300 mL of THF under a nitrogen atmosphere, and the mixture was stirred and refluxed. Then, potassium carbonate (20.8 g, 150.5 mmol) was dissolved in 62 mL of water, added thereto, sufficiently stirred, and then bis(tri-tert-butylphosphine)palladium(0) (0.3 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 12.5 g of B_P1. (Yield: 80%, MS: $[M+H]^+$=313)

Next, B_P1 (10 g, 31.9 mmol) and $HBF_4$ (5.6 g, 63.8 mmol) were added to 100 mL of ACN under a nitrogen atmosphere, and the mixture was stirred. Then, $NaNO_2$ (4.4 g, 63.8 mmol) was dissolved in 20 mL of $H_2O$ and slowly added at 0° C. After reacting for 10 hours, the mixture was heated to room temperature, and then diluted by adding 200 mL of water. The solution was completely dissolved in chloroform, washed twice with water, the organic layer was separated, treated with anhydrous magnesium sulfate, filtered, and the filtrate was distilled under reduced pressure. The concentrated compound was purified by silica gel column chromatography to give 5.6 g of B_P2. (Yield: 62%, MS: $[M+H]^+$=282)

Next, B_P2 (15 g, 53.1 mmol) and bis(pinacolato)diboron (14.8 g, 58.4 mmol) were added to 300 mL of 1,4-dioxane under a nitrogen atmosphere, and the mixture was stirred under reflux. Then, potassium acetate (7.8 g, 79.6 mmol) was added thereto, sufficiently stirred, and then bis(dibenzylideneacetone)palladium(0) (0.9 g, 1.6 mmol) and tricyclohexylphosphine (0.9 g, 3.2 mmol) were added. After reacting for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 12.4 g of Compound B. (Yield: 71%, MS: $[M+H]^+$=330)

SYNTHESIS EXAMPLE C: SYNTHESIS OF INTERMEDIATE COMPOUND C

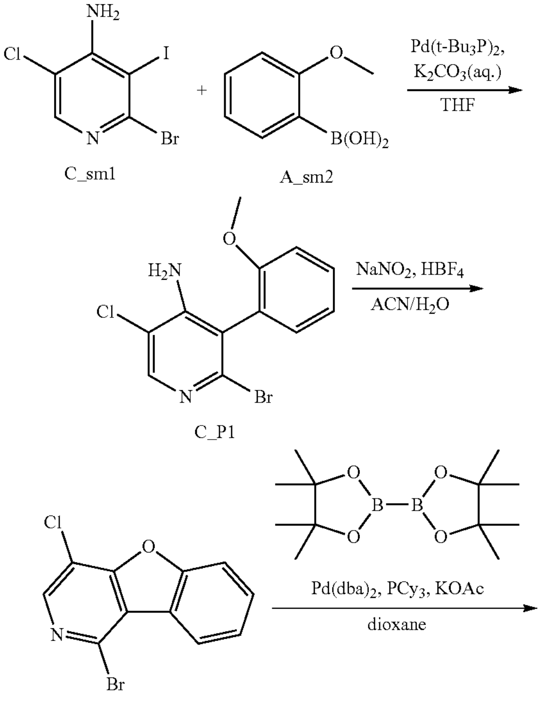

C_sml
A_sm2
C_P1
C_P2

-continued

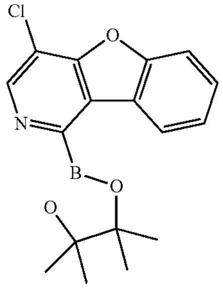

C

Compound C was prepared in the same manner as in Synthesis Example A, except that C-sm1 was used instead of A-sm1 as a starting material in Synthesis Example A. (Yield: 72%, MS: $[M+H]^+$=330)

SYNTHESIS EXAMPLE D: SYNTHESIS OF INTERMEDIATE COMPOUND D

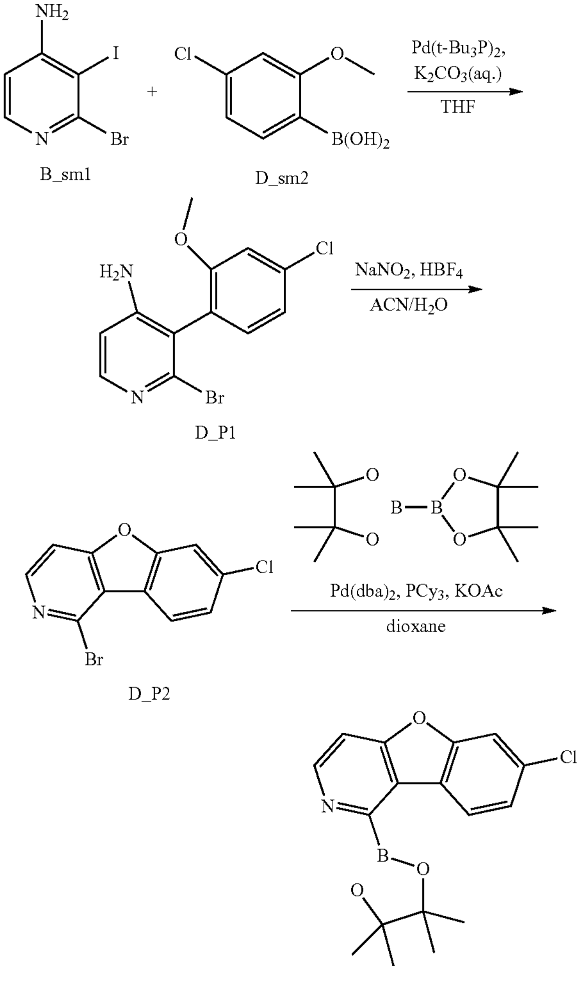

B_sml
D_sm2
D_P1
D_P2

D

Compound D was prepared in the same manner as in Synthesis Example B, except that D-sm2 was used instead of B-sm2 as a starting material in Synthesis Example B. (Yield: 76%, MS: $[M+H]^+$=330)

SYNTHESIS EXAMPLE E: SYNTHESIS OF INTERMEDIATE COMPOUND E

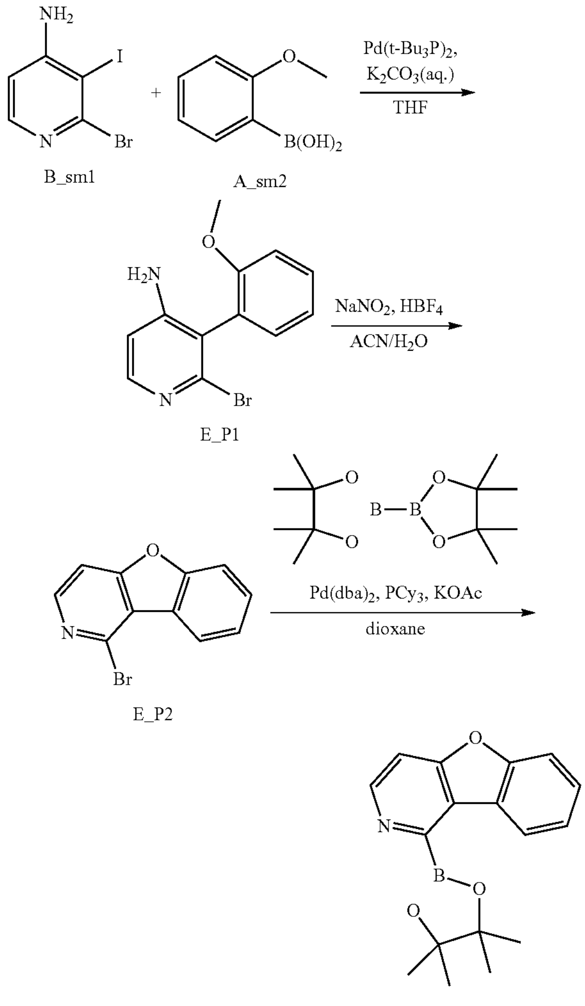

B_sml A_sm2 E_P1 E_P2 E

Compound E was prepared in the same manner as in Synthesis Example B, except that A-sm2 was used instead of B-sm2 as a starting material in Synthesis Example B. (Yield: 73%, MS: $[M+H]^+$=296)

SYNTHESIS EXAMPLE F: SYNTHESIS OF INTERMEDIATE COMPOUND F

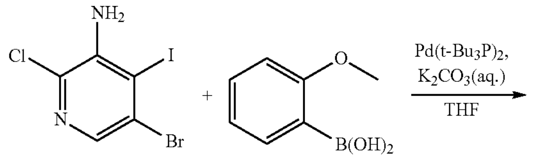

F_sml A_sm2

-continued

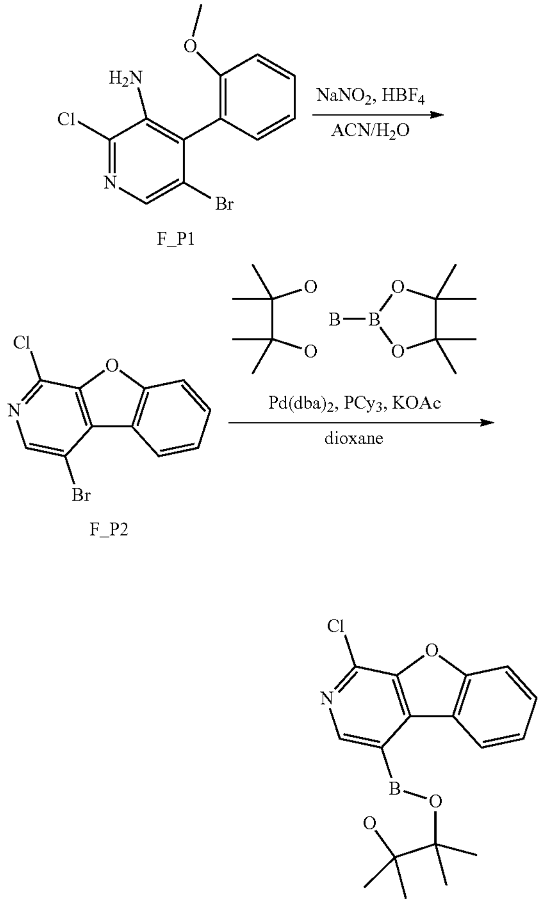

F_P1 F_P2 F

Compound F was prepared in the same manner as in Synthesis Example A, except that F-sm1 was used instead of A-sm1 as a starting material in Synthesis Example A. (Yield: 67%, MS: $[M+H]^+$=330)

SYNTHESIS EXAMPLE G: SYNTHESIS OF INTERMEDIATE COMPOUND G

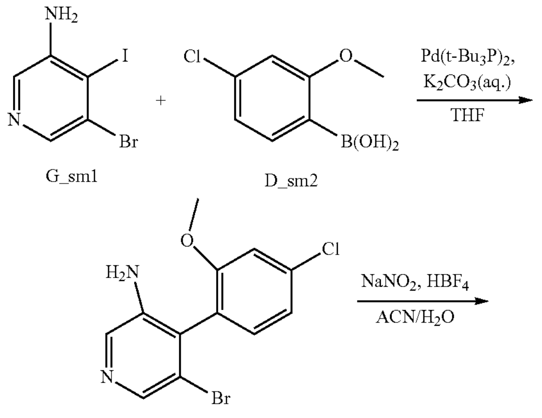

G_sml D_sm2 G_P1

-continued

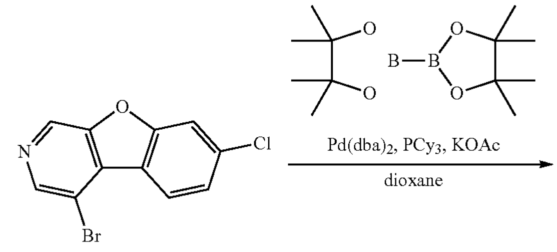

G_P2

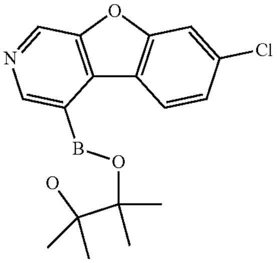

G

Compound G was prepared in the same manner as in Synthesis Example B, except that G-sm1 was used instead of B-sm1, and D-sm2 instead of B-sm2 as a starting material in Synthesis Example B. (Yield: 71%, MS: $[M+H]^+=330$)

SYNTHESIS EXAMPLE H: SYNTHESIS OF INTERMEDIATE COMPOUND H

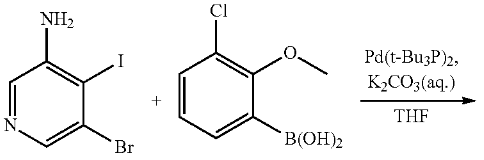

G_sm1 B_sm2

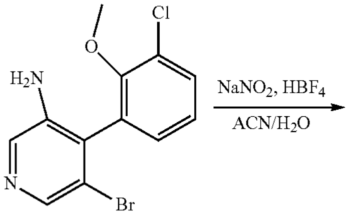

H_P1

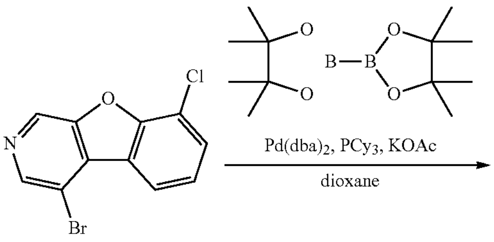

H_P2

-continued

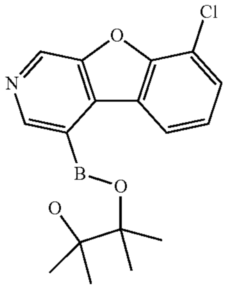

H

Compound H was prepared in the same manner as in Synthesis Example B, except that G-sm1 was used instead of B-sm1 as a starting material in Synthesis Example B. (Yield: 74%, MS: $[M+H]^+=330$)

SYNTHESIS EXAMPLE I: SYNTHESIS OF INTERMEDIATE COMPOUND I

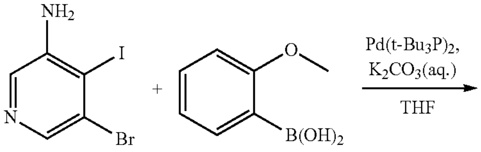

G_sm1 A_sm2

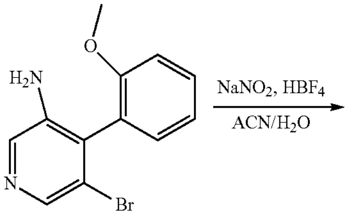

I_P1

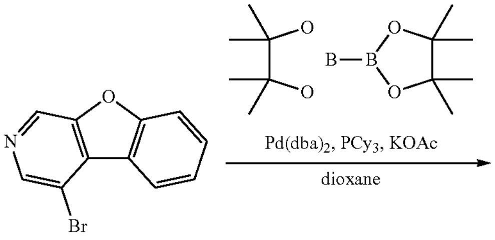

I_P2

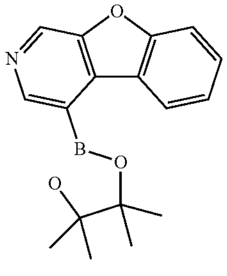

I

Compound I was prepared in the same manner as in Synthesis Example A, except that G-sm1 was used instead of A-sm1 as a starting material in Synthesis Example A. (Yield: 69%, MS: $[M+H]^+$=296)

SYNTHESIS EXAMPLE J: SYNTHESIS OF INTERMEDIATE COMPOUND J

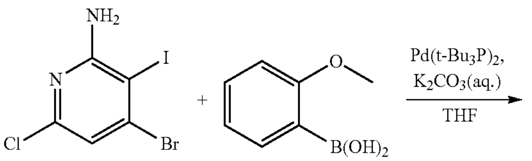

J_sm1 A_sm2

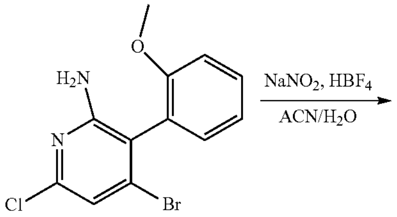

J_P1

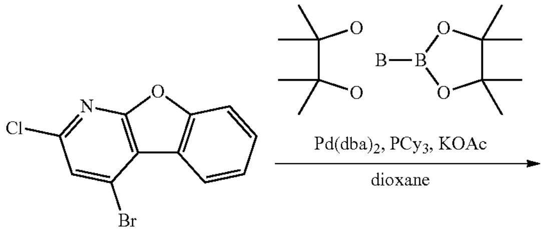

J_P2

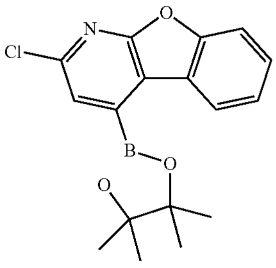

J

Compound J was prepared in the same manner as in Synthesis Example A, except that J-sm1 was used instead of A-sm1 as a starting material in Synthesis Example A. (Yield: 65%, MS: $[M+H]^+$=330)

SYNTHESIS EXAMPLE K: SYNTHESIS OF INTERMEDIATE COMPOUND K

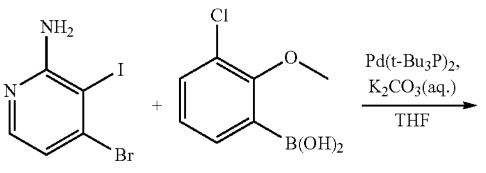

K_sm1 B_sm2

-continued

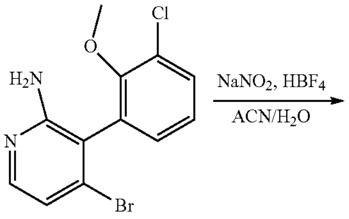

K_P1

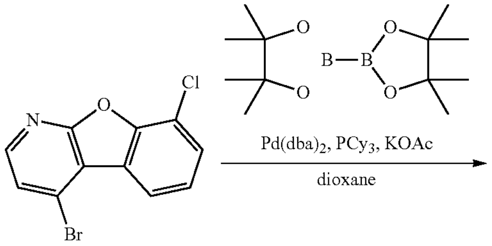

K_P2

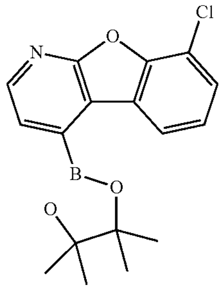

K

Compound K was prepared in the same manner as in Synthesis Example B, except that K-sm1 was used instead of B-sm1 as a starting material in Synthesis Example B. (Yield: 74%, MS: $[M+H]^+$=330)

SYNTHESIS EXAMPLE L: SYNTHESIS OF INTERMEDIATE COMPOUND L

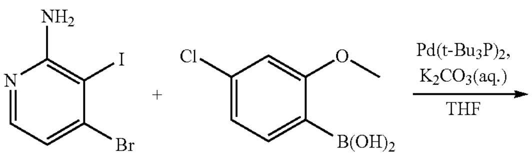

K_sm1 D_sm2

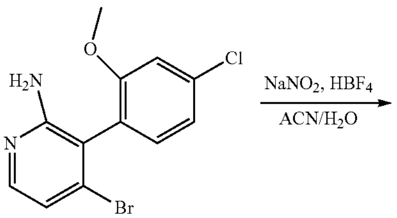

L_P1

-continued

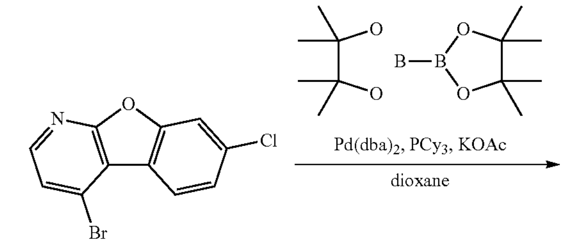

L_P2

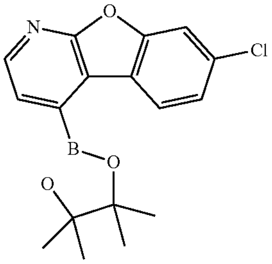

L

Compound L was prepared in the same manner as in Synthesis Example B, except that K-sm1 was used instead of B-sm1, and D-sm2 instead of B-sm2 as a starting material in Synthesis Example B. (Yield: 72%, MS: $[M+H]^+$=330)

SYNTHESIS EXAMPLE M: SYNTHESIS OF INTERMEDIATE COMPOUND M

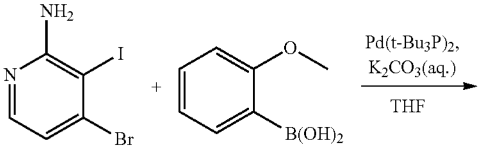

K_sm1 A_sm2

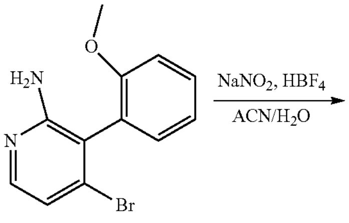

M_P1

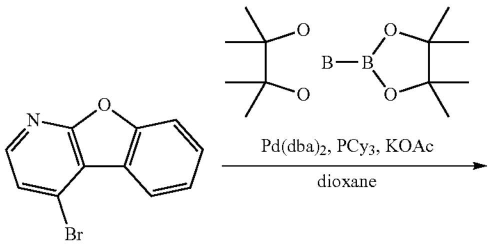

M_P2

-continued

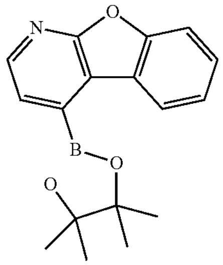

M

Compound M was prepared in the same manner as in Synthesis Example A, except that K-sm1 was used instead of A-sm1 as a starting material in Synthesis Example A. (Yield: 67%, MS: $[M+H]^+$=296)

SYNTHESIS EXAMPLE N: SYNTHESIS OF INTERMEDIATE COMPOUND N

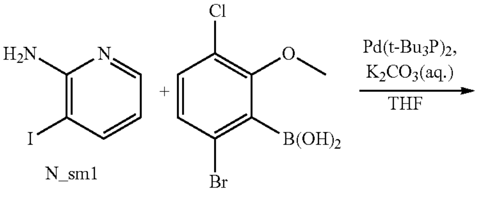

N_sm1 N_sm2

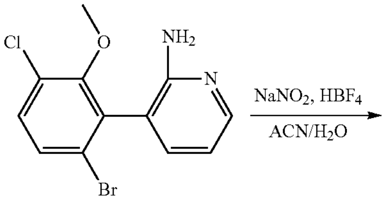

N_P1

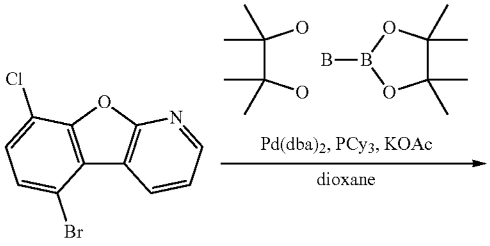

N_P2

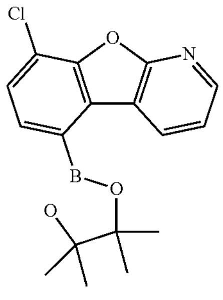

N

N_sm1 (15 g, 68.2 mmol) and N_sm2 (21.7 g, 81.8 mmol) were added to 300 mL of THF under a nitrogen atmosphere, and the mixture was stirred and refluxed. Then, potassium carbonate (28.3 g, 204.5 mmol) was dissolved in 85 mL of water, added thereto, sufficiently stirred, and then bis(tri-tert-butylphosphine)palladium(0) (0.3 g, 0.7 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.6 g of N_P1. (Yield: 64%, MS: $[M+H]^+=313$)

Next, N_P1 (10 g, 31.9 mmol) and $HBF_4$ (5.6 g, 63.8 mmol) were added to 100 mL of ACN under a nitrogen atmosphere, and the mixture was stirred. Then, $NaNO_2$ (4.4 g, 63.8 mmol) was dissolved in 20 mL of $H_2O$ and slowly added at 0° C. After reacting for 10 hours, the mixture was heated to room temperature, and then diluted by adding 200 mL of water. The solution was completely dissolved in chloroform, washed twice with water, the organic layer was separated, treated with anhydrous magnesium sulfate, filtered, and the filtrate was distilled under reduced pressure. The concentrated compound was purified by silica gel column chromatography to give 7.2 g of N_P2. (Yield: 80%, MS: $[M+H]^+=282$)

Next, N_P2 (15 g, 53.1 mmol) and bis(pinacolato)diboron (14.8 g, 58.4 mmol) were added to 300 mL of 1,4-dioxane under a nitrogen atmosphere, and the mixture was stirred under reflux. Then, potassium acetate (7.8 g, 79.6 mmol) was added thereto, sufficiently stirred, and then bis(dibenzylideneacetone)palladium(0) (0.9 g, 1.6 mmol) and tricyclohexylphosphine (0.9 g, 3.2 mmol) were added. After reacting for 9 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 12.1 g of Compound N. (Yield: 69%, MS: $[M+H]^+=330$)

SYNTHESIS EXAMPLE O: SYNTHESIS OF INTERMEDIATE COMPOUND O

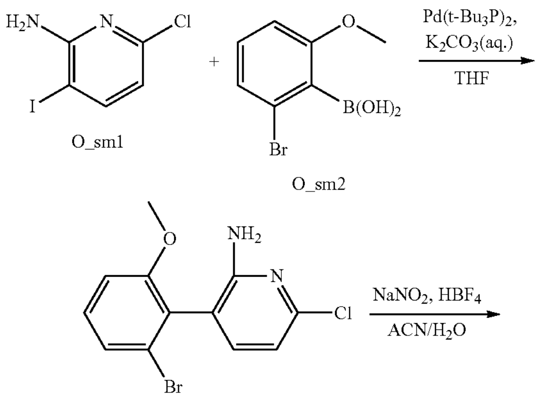

O_sm1 O_sm2 O_P1

-continued

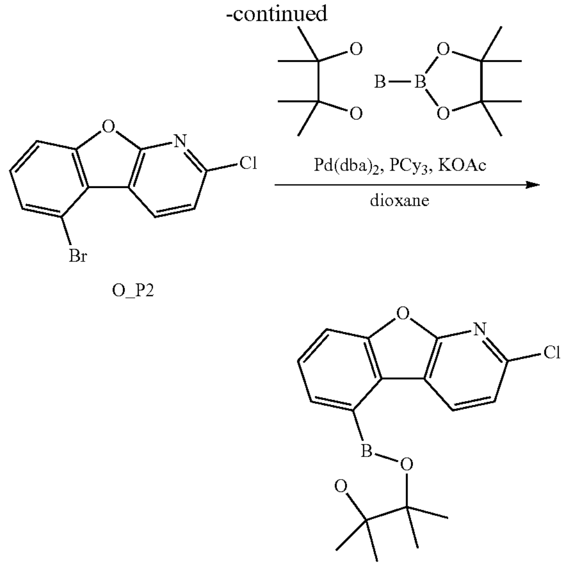

O_P2

O

O_sm1 (15 g, 58.9 mmol) and O_sm2 (16.3 g, 70.7 mmol) were added to 300 mL of THF under a nitrogen atmosphere, and the mixture was stirred and refluxed. Then, potassium carbonate (24.4 g, 176.8 mmol) was dissolved in 73 mL of water, added thereto, sufficiently stirred, and then bis(tri-tert-butylphosphine)palladium(0) (0.3 g, 0.6 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 11 g of O_P1. (Yield: 60%, MS: $[M+H]^+=313$)

Next, O_P1 (10 g, 31.9 mmol) and $HBF_4$ (5.6 g, 63.8 mmol) were added to 100 mL of ACN under a nitrogen atmosphere, and the mixture was stirred. Then, $NaNO_2$ (4.4 g, 63.8 mmol) was dissolved in 20 mL of $H_2O$ and slowly added at 0° C. After reacting for 10 hours, the mixture was heated to room temperature, and then diluted by adding 200 mL of water. The solution was completely dissolved in chloroform, washed twice with water, the organic layer was separated, treated with anhydrous magnesium sulfate, filtered, and the filtrate was distilled under reduced pressure. The concentrated compound was purified by silica gel column chromatography to give 5.9 g of O_P2. (Yield: 66%, MS: $[M+H]^+=282$)

Next, O_P2 (15 g, 53.1 mmol) and bis(pinacolato)diboron (14.8 g, 58.4 mmol) were added to 300 mL of 1,4-dioxane under a nitrogen atmosphere, and the mixture was stirred under reflux. Then, potassium acetate (7.8 g, 79.6 mmol) was added thereto, sufficiently stirred, and then bis(dibenzylideneacetone)palladium(0) (0.9 g, 1.6 mmol) and tricyclohexylphosphine (0.9 g, 3.2 mmol) were added, After reacting for 9 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 11.5 g of Compound O. (Yield: 66%, MS: $[M+H]^+=330$)

SYNTHESIS EXAMPLE P: SYNTHESIS OF INTERMEDIATE COMPOUND P

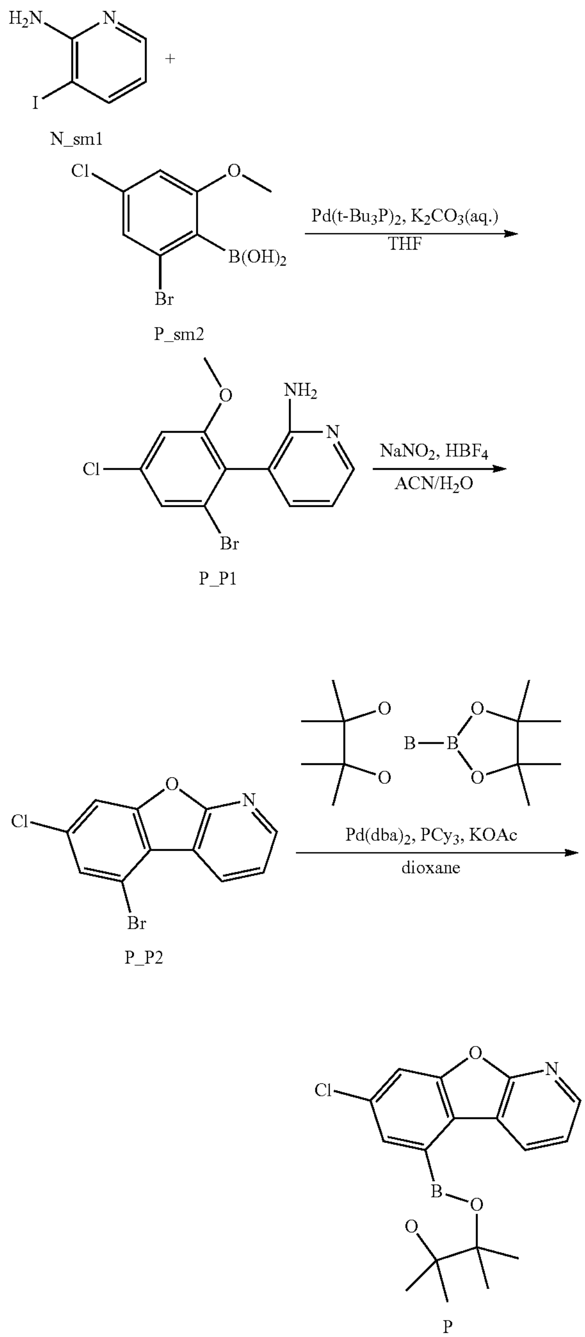

N_sm1, P_sm2, P_P1, P_P2, P

Compound P was prepared in the same manner as in Synthesis Example N, except that P-sm2 was used instead of N-sm2 as a starting material in Synthesis Example N. (Yield: 68%, MS: $[M+H]^+=330$)

SYNTHESIS EXAMPLE Q: SYNTHESIS OF INTERMEDIATE COMPOUND Q

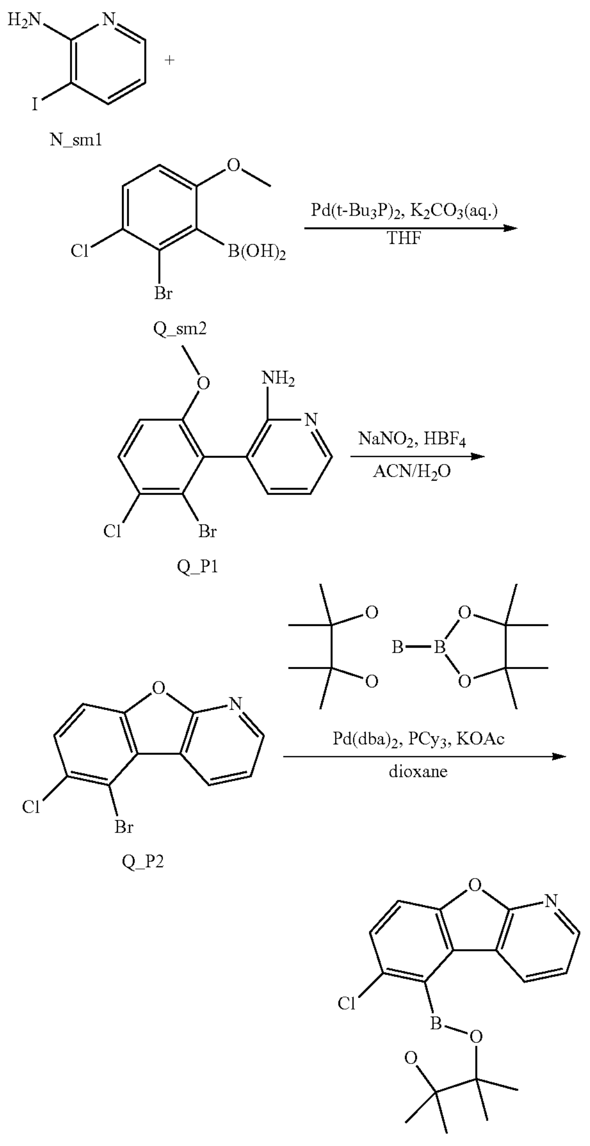

N_sm1, Q_sm2, Q_P1, Q_P2, Q

Compound Q was prepared in the same manner as in Synthesis Example N, except that Q-sm2 was used instead of N-sm2 as a starting material in Synthesis Example N. (Yield: 63%, MS: $[M+H]^+=330$)

SYNTHESIS EXAMPLE R: SYNTHESIS OF INTERMEDIATE COMPOUND R

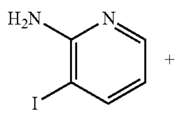

N_sm1

-continued

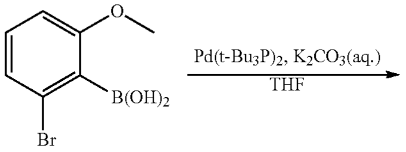

R_sm2

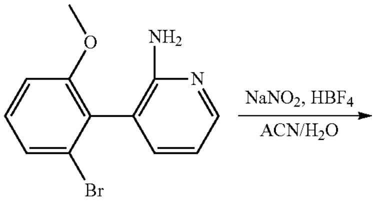

R_P1

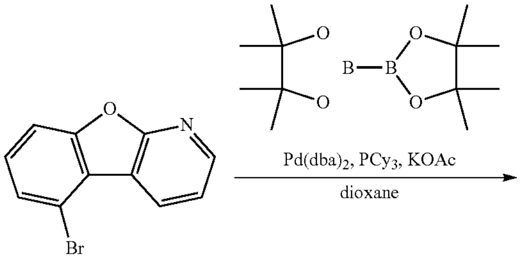

R_P2

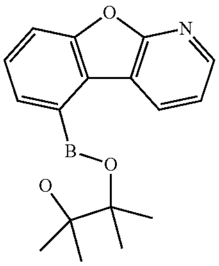

R

Compound R was prepared in the same manner as in Synthesis Example N, except that R-sm2 was used instead of N-sm2 as a starting material in Synthesis Example N. (Yield: 70%, MS: $[M+H]^+$=296)

SYNTHESIS EXAMPLE S: SYNTHESIS OF INTERMEDIATE COMPOUND S

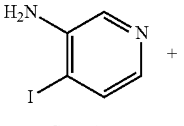

S_sm1

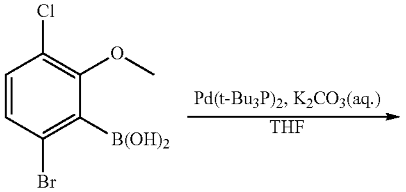

N_sm2

-continued

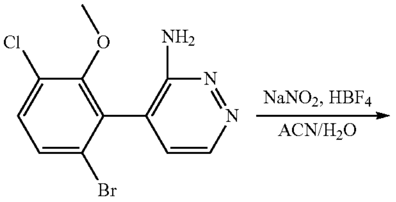

S_P1

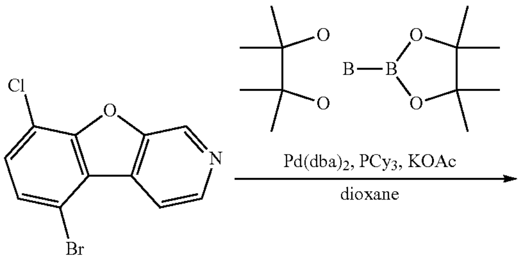

S_P2

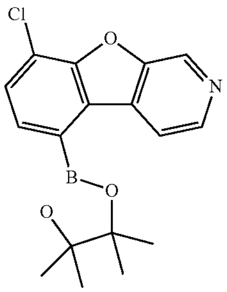

S

Compound S was prepared in the same manner as in Synthesis Example N, except that S-sm1 was used instead of N-sm1 as a starting material in Synthesis Example N. (Yield: 73%, MS: $[M+H]^+$=330)

SYNTHESIS EXAMPLE T: SYNTHESIS OF INTERMEDIATE COMPOUND T

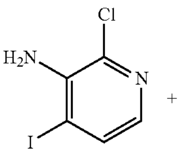

T_sm1

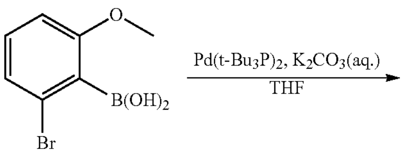

O_sm2

-continued

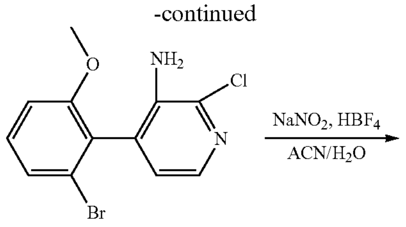

T_P1

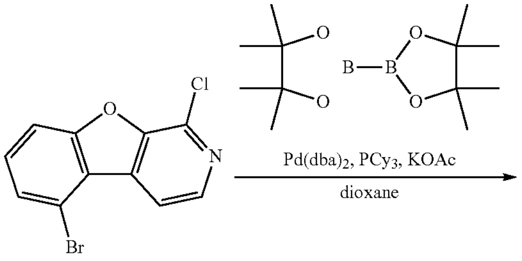

T_P2

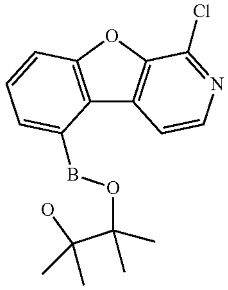

T

Compound T was prepared in the same manner as in Synthesis Example O, except that T-sm1 was used instead of O-sm1 as a starting material in Synthesis Example O. (Yield: 72%, MS: $[M+H]^+$=330)

SYNTHESIS EXAMPLE U: SYNTHESIS OF INTERMEDIATE COMPOUND U

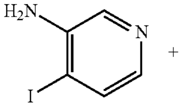

S_sm1

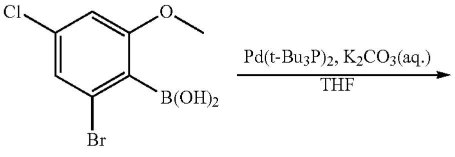

U_sm2

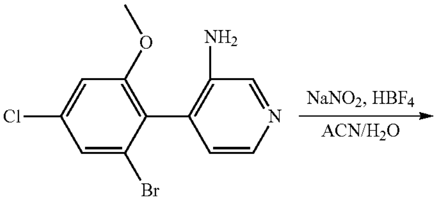

U_P1

-continued

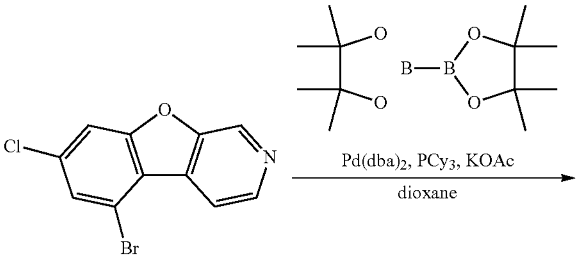

U_P2

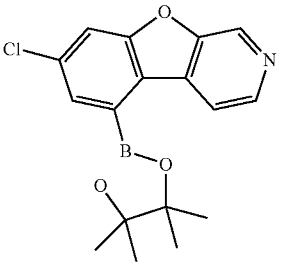

U

Compound U was prepared in the same manner as in Synthesis Example N, except that S-sm1 was used instead of N-sm1, and U-sm2 instead of N-sm2 as a starting material in Synthesis Example N. (Yield: 67%, MS: $[M+H]^+$=330)

SYNTHESIS EXAMPLE V: SYNTHESIS OF INTERMEDIATE COMPOUND V

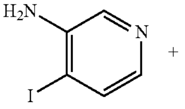

S_sm1

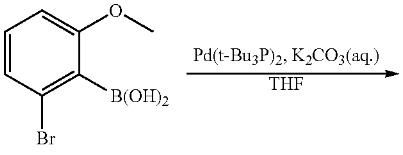

R_sm2

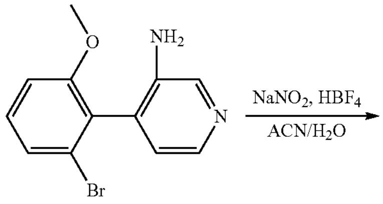

V_P1

-continued

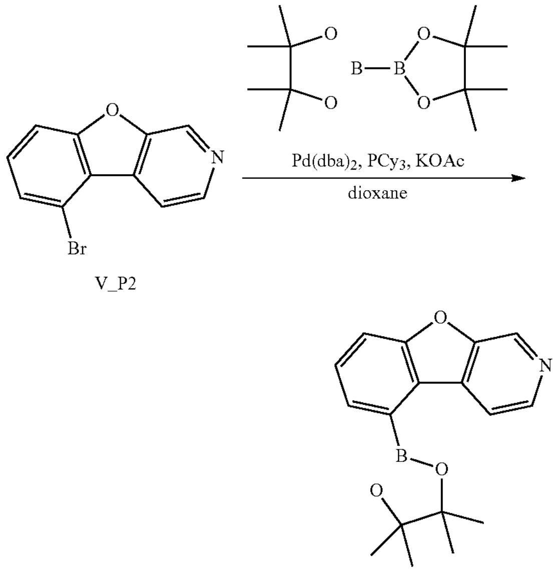

V_P2

V

Compound V was prepared in the same manner as in Synthesis Example N, except that S-sm1 was used instead of N-sm1, and R-sm2 instead of N-sm2 as a starting material in Synthesis Example N. (Yield: 63%, MS: $[M+H]^+=296$).

SYNTHESIS EXAMPLE W: SYNTHESIS OF INTERMEDIATE COMPOUND W

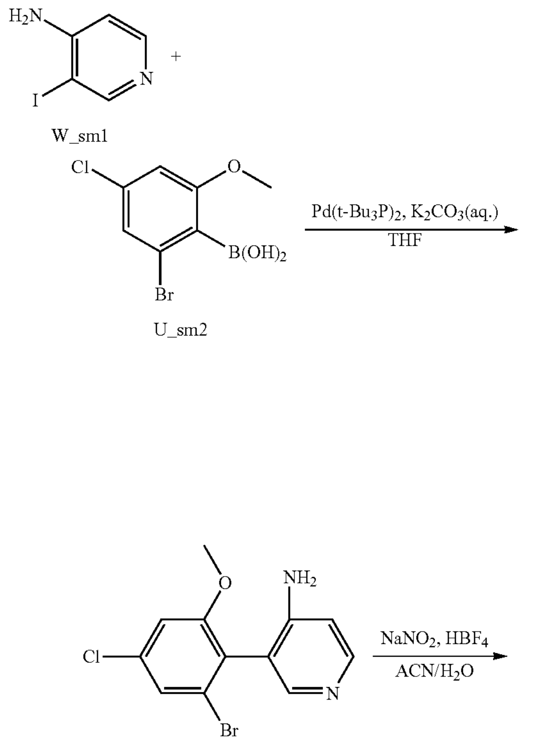

W_sm1

U_sm2

W_P1

-continued

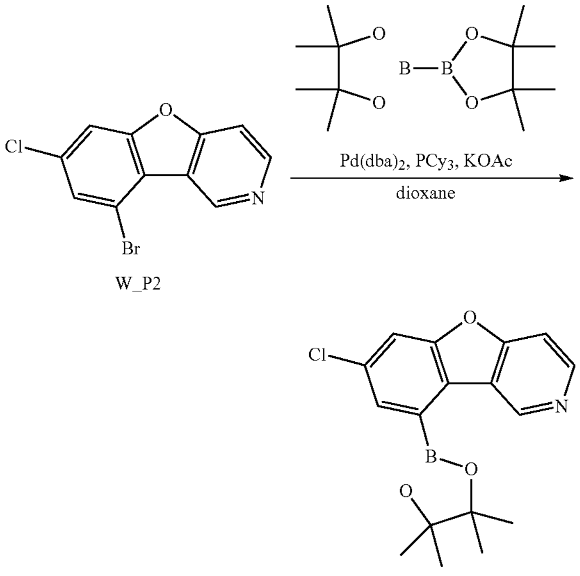

W_P2

W

Compound W was prepared in the same manner as in Synthesis Example N, except that W-sm1 was used instead of N-sm1, and U-sm2 instead of N-sm2 as a starting material in Synthesis Example N. (Yield: 68%, MS: $[M+H]^+=330$)

SYNTHESIS EXAMPLE X: SYNTHESIS OF INTERMEDIATE COMPOUND X

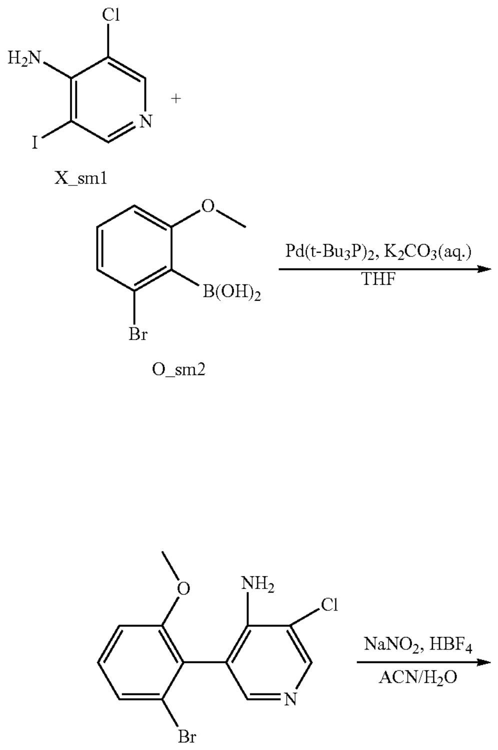

X_sm1

O_sm2

X_P1

-continued

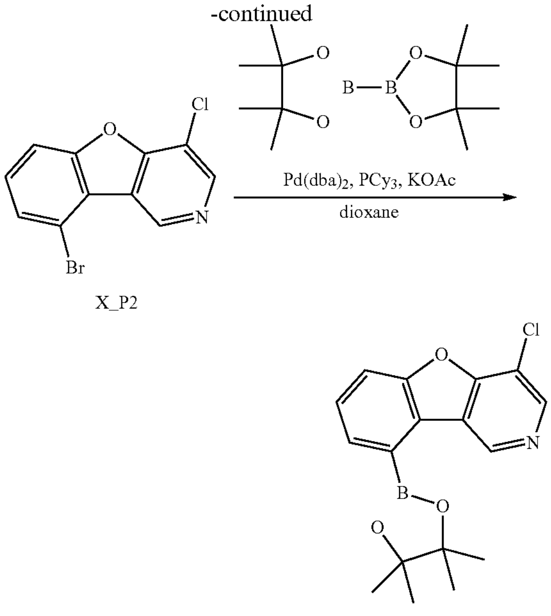

X_P2

X

Compound X was prepared in the same manner as in Synthesis Example O, except that X-sm1 was used instead of O-sm1 as a starting material in Synthesis Example O. (Yield: 72%, MS: $[M+H]^+$=330)

SYNTHESIS EXAMPLE Y: SYNTHESIS OF INTERMEDIATE COMPOUND Y

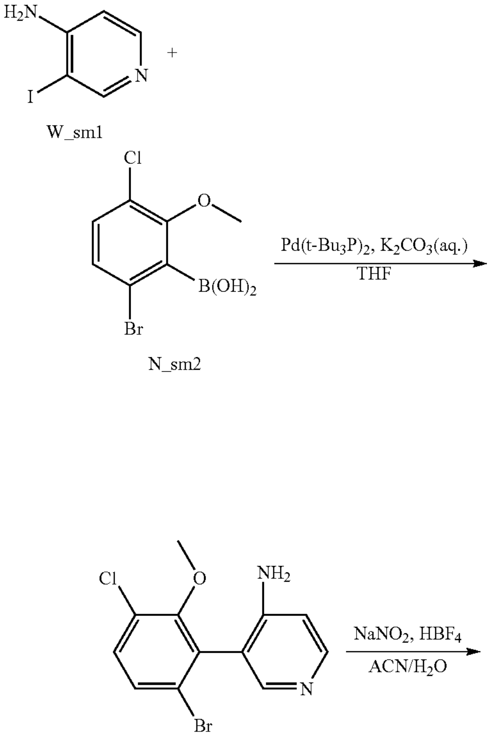

W_sm1

N_sm2

Y_P1

-continued

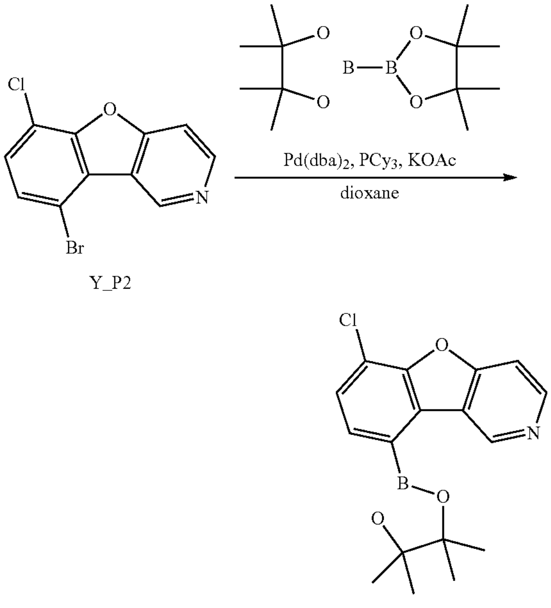

Y_P2

Y

Compound Y was prepared in the same manner as in Synthesis Example N, except that W-sm1 was used instead of N-sm1 as a starting material in Synthesis Example N. (Yield: 74%, MS: $[M+H]^+$=330)

SYNTHESIS EXAMPLE Z: SYNTHESIS OF INTERMEDIATE COMPOUND Z

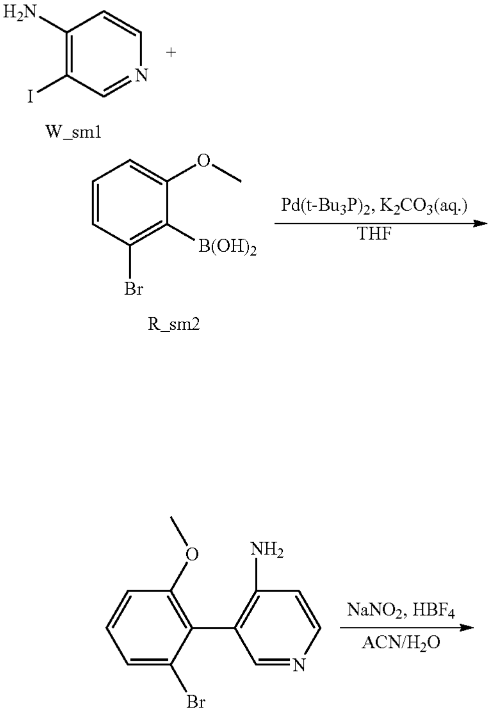

W_sm1

R_sm2

Z_P1

-continued

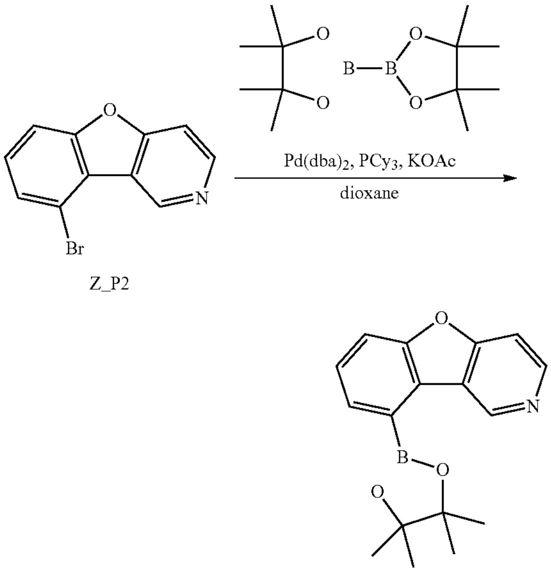

Z_P2

Z

Compound Z was prepared in the same manner as in Synthesis Example N, except that W-sm1 was used instead of N-sm1, and R-sm2 instead of N-sm2 as a starting material in Synthesis Example N. (Yield: 68%, MS: $[M+H]^+=296$)

SYNTHESIS EXAMPLE AA: SYNTHESIS OF INTERMEDIATE COMPOUND AA

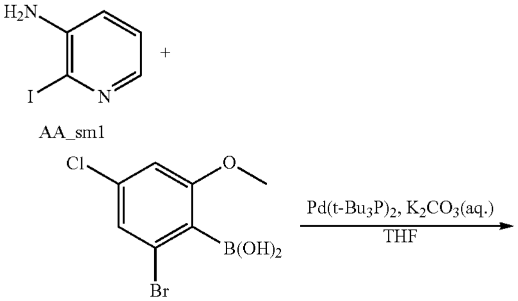

AA_sm1

U_sm2

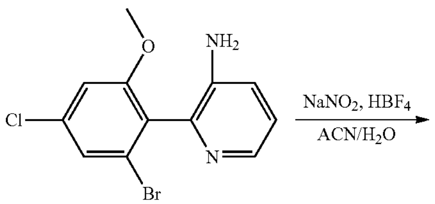

AA_P1

-continued

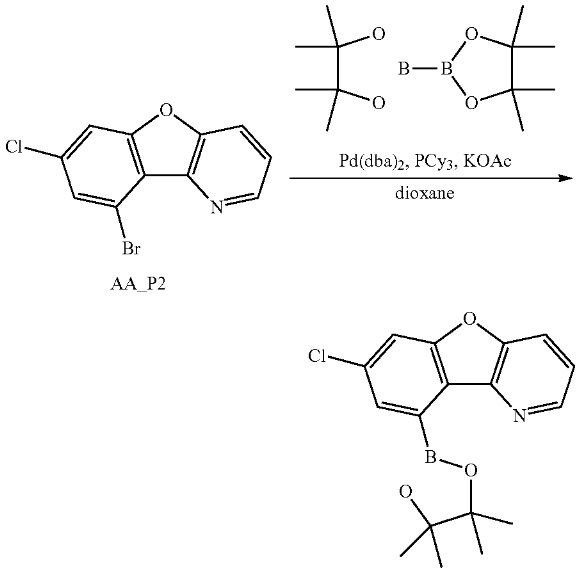

AA_P2

AA

Compound AA was prepared in the same manner as in Synthesis Example N, except that AA-sm1 was used instead of N-sm1, and U-sm2 instead of N-sm2 as a starting material in Synthesis Example N. (Yield: 63%, MS: $[M+H]^+=330$)

SYNTHESIS EXAMPLE AB: SYNTHESIS OF INTERMEDIATE COMPOUND AB

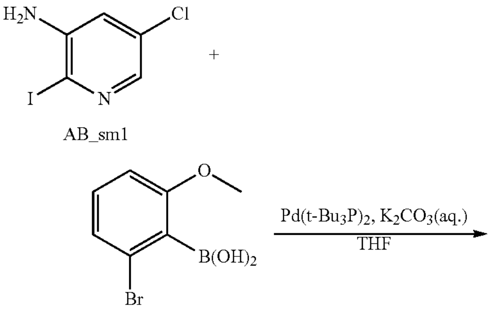

AB_sm1

O_sm2

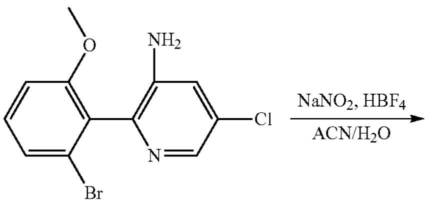

AB_P1

-continued

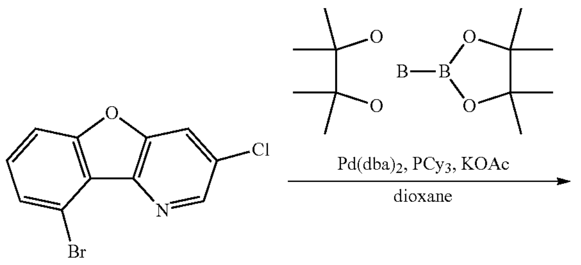

AB_P2

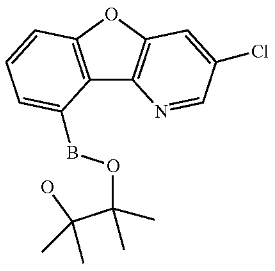

AB

Compound AB was prepared in the same manner as in Synthesis Example O, except that AB-sm1 was used instead of O-sm1 as a starting material in Synthesis Example O. (Yield: 71%, MS: $[M+H]^+=330$)

SYNTHESIS EXAMPLE AC: SYNTHESIS OF INTERMEDIATE COMPOUND AC

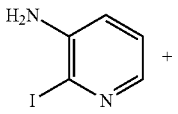

AA_sm1

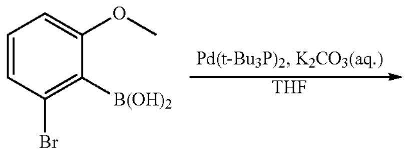

R_sm2

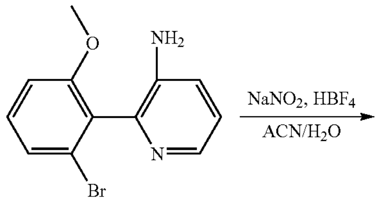

AC_P1

-continued

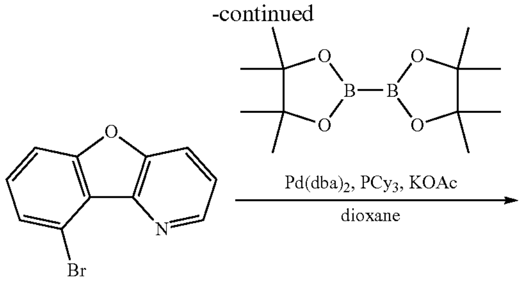

AC_P2

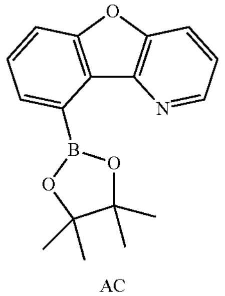

AC

Compound AC was prepared in the same manner as in Synthesis Example N, except that AA-sm1 was used instead of N-sm1, and R-sm2 instead of N-sm2 as a starting material in Synthesis Example N. (Yield: 65%, MS: $[M+H]^+=296$)

SYNTHESIS EXAMPLE 1: PREPARATION OF COMPOUND 1

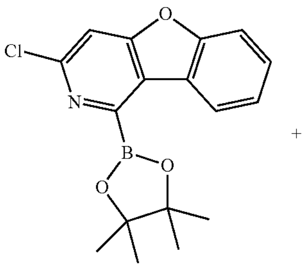

A

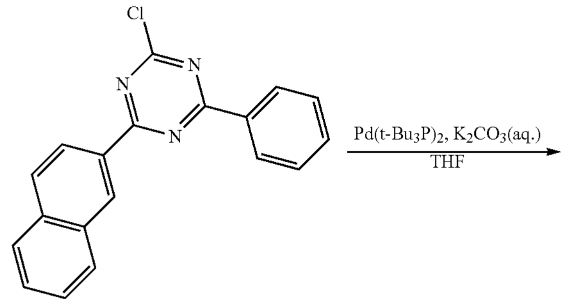

Trz1

-continued

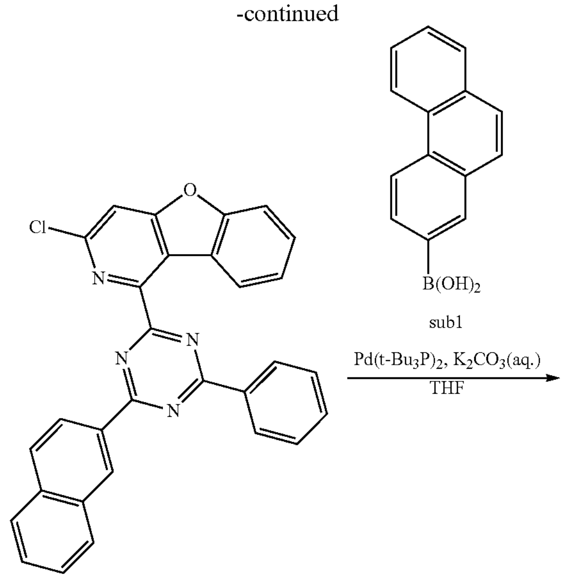

sub1 subA-1

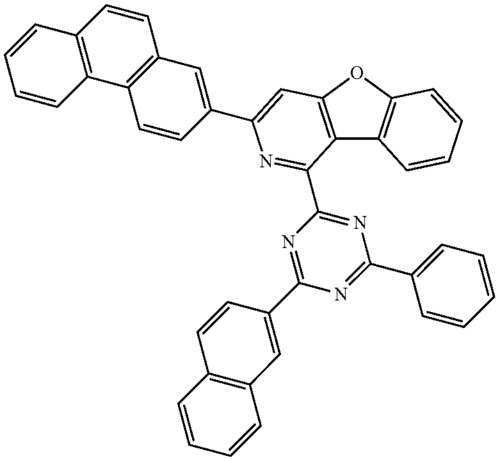

1

Compound A (15 g, 45.5 mmol) and Trz1 (15.2 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.9 g of subA-1. (Yield: 63%, MS: $[M+H]^+=485$)

Next, subA-1 (15 g, 30.9 mmol) and sub1 (7.2 g, 32.5 mmol) were added to 300 mL of THF under a nitrogen atmosphere, and the mixture was stirred and refluxed. Then, potassium carbonate (12.8 g, 92.8 mmol) was dissolved in 38 L of water, added thereto, sufficiently stirred, and then bis(tri-tert-butylphosphine)palladium(0) (0.2 g, 0.3 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 11.6 g of Compound 1. (Yield: 60%, MS: $[M+H]^+=627$)

SYNTHESIS EXAMPLE 2: PREPARATION OF COMPOUND 2

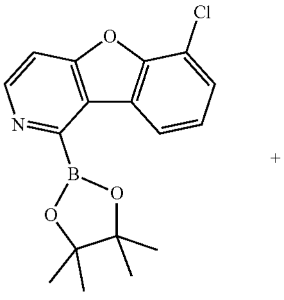

B

+

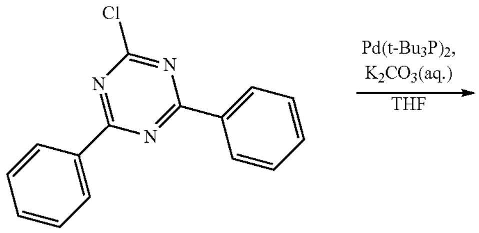

Trz2

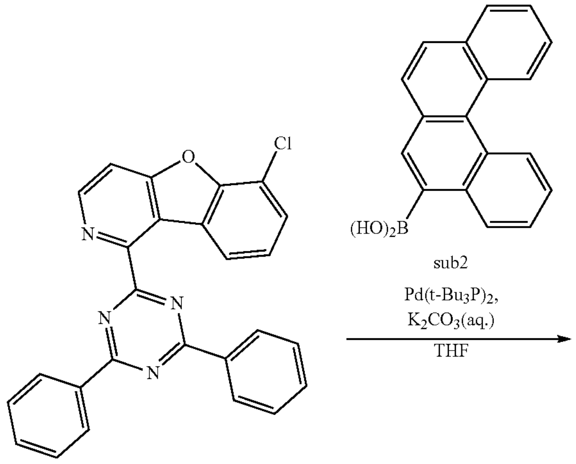

sub2 subB-1

-continued

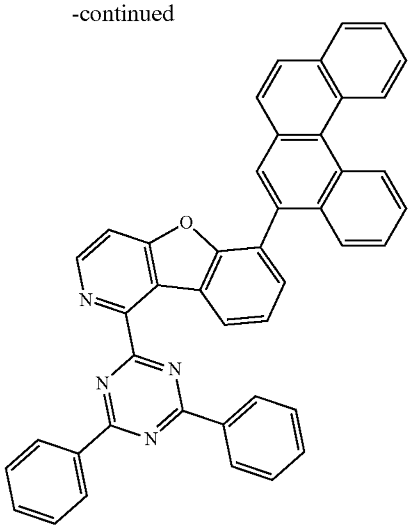

2

Compound B (15 g, 45.5 mmol) and Trz2 (12.8 g, 47.8 mmol) were added to 300 mL of THF under a nitrogen atmosphere, and the mixture was stirred and refluxed. Then, potassium carbonate (18.9 g, 136.5 mmol) was dissolved in 57 L of water, added thereto, sufficiently stirred, and then bis(tri-tert-butylphosphine)palladium(0) (0.2 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.6 g of subB-1. (Yield: 69%, MS: $[M+H]^+$=435)

Next, subB-1 (15 g, 34.5 mmol) and sub2 (9.9 g, 36.2 mmol) were added to 300 mL of THF under a nitrogen atmosphere, and the mixture was stirred and refluxed. Then, potassium carbonate (14.3 g, 103.5 mmol) was dissolved in 43 of water, added thereto, sufficiently stirred, and then bis(tri-tert-butylphosphine)palladium(0) (0.2 g, 0.3 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 14.5 g of Compound 2. (Yield: 67%, MS: $[M+H]^+$=627)

SYNTHESIS EXAMPLE 3: PREPARATION OF COMPOUND 3

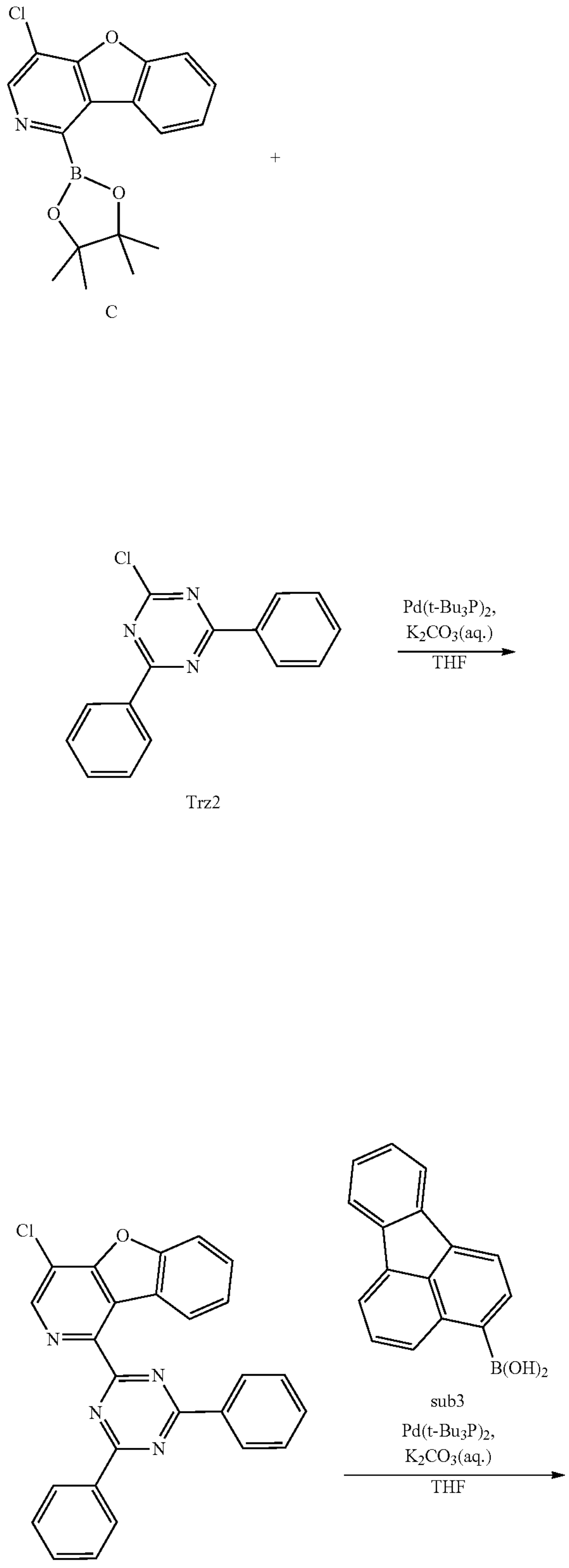

C

Trz2 subC-1 sub3

-continued

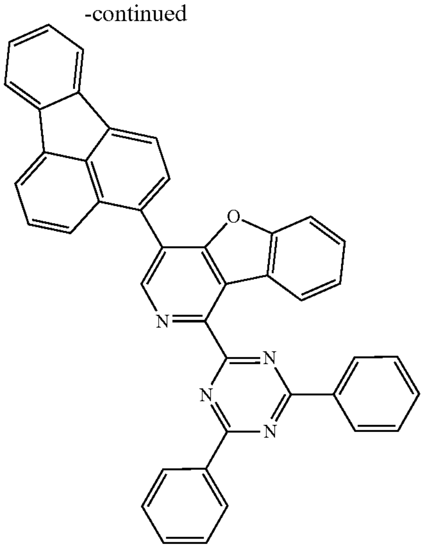

3

Compound C (15 g, 45.5 mmol) and Trz2 (12.8 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 12.6 g of subC-1. (Yield: 64%, MS: $[M+H]^+$=435)

Next, subC-1 (15 g, 34.5 mmol) and sub3 (8.9 g, 36.2 mmol) were added to 300 mL of THF under a nitrogen atmosphere, and the mixture was stirred and refluxed. Then, potassium carbonate (14.3 g, 103.5 mmol) was dissolved in 43 mL of water, added thereto, sufficiently stirred, and then bis(tri-tert-butylphosphine)palladium(0) (0.2 g, 0.3 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 14.1 g of Compound 3. (Yield: 68%, MS: $[M+H]^+$=601)

SYNTHESIS EXAMPLE 4: PREPARATION OF COMPOUND 4

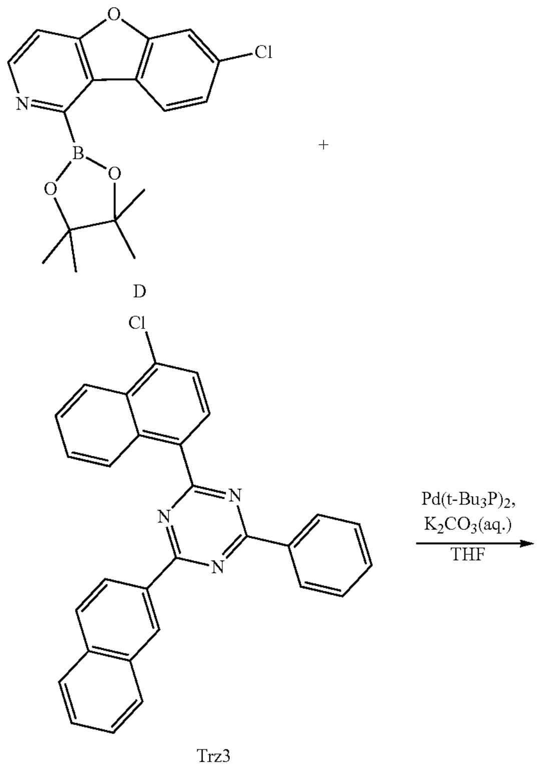

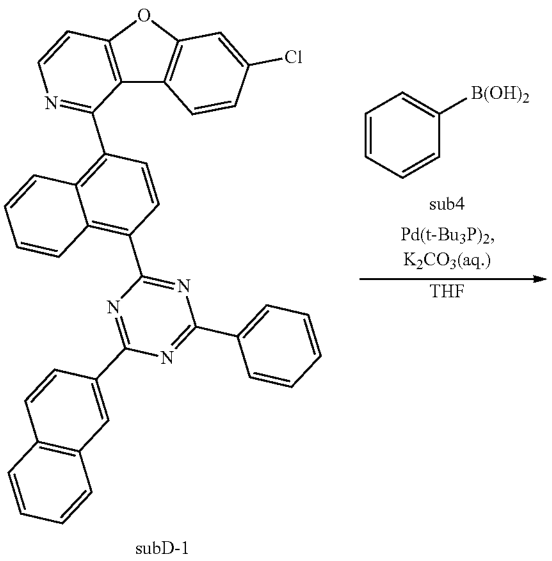

-continued

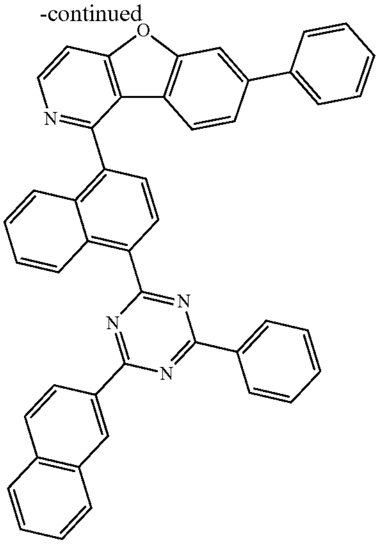

4

Compound D (15 g, 45.5 mmol) and Trz3 (21.2 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 21.1 g of subD-1. (Yield: 76%, MS: $[M+H]^+=611$)

Next, subD-1 (15 g, 24.5 mmol) and sub4 (3.1 g, 25.8 mmol) were added to 300 mL of THF under a nitrogen atmosphere, and the mixture was stirred and refluxed. Then, potassium carbonate (10.2 g, 73.6 mmol) was dissolved in 31 mL of water, added thereto, sufficiently stirred, and then bis(tri-tert-butylphosphine)palladium(0) (0.1 g, 0.2 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 12.8 g of Compound 4. (Yield: 80%, MS: $[M+H]^+=653$)

SYNTHESIS EXAMPLE 5: PREPARATION OF COMPOUND 5

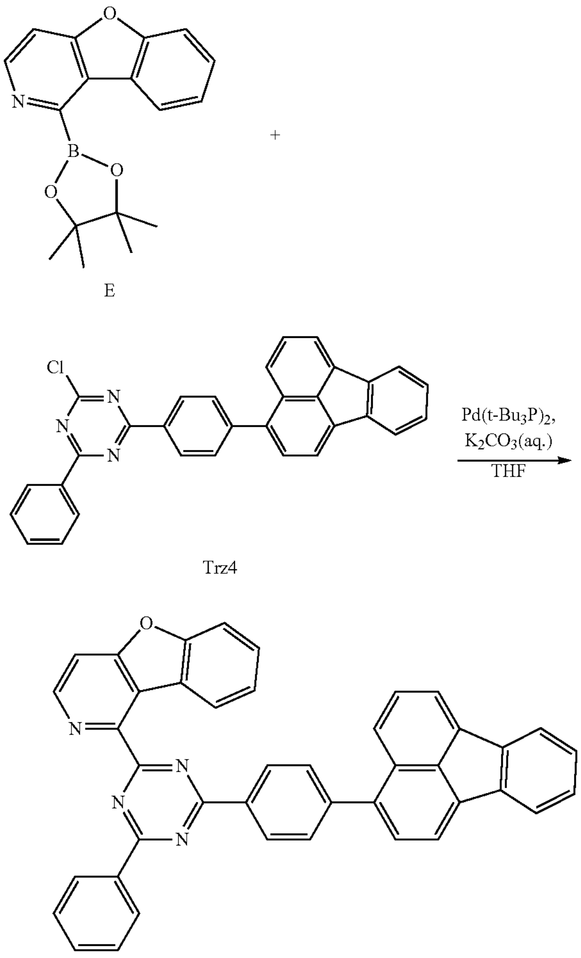

5

Compound E (15 g, 50.8 mmol) and Trz4 (25 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 20.4 g of Compound 5. (Yield: 67%, MS: $[M+H]^+=601$)

SYNTHESIS EXAMPLE 6: PREPARATION OF COMPOUND 6

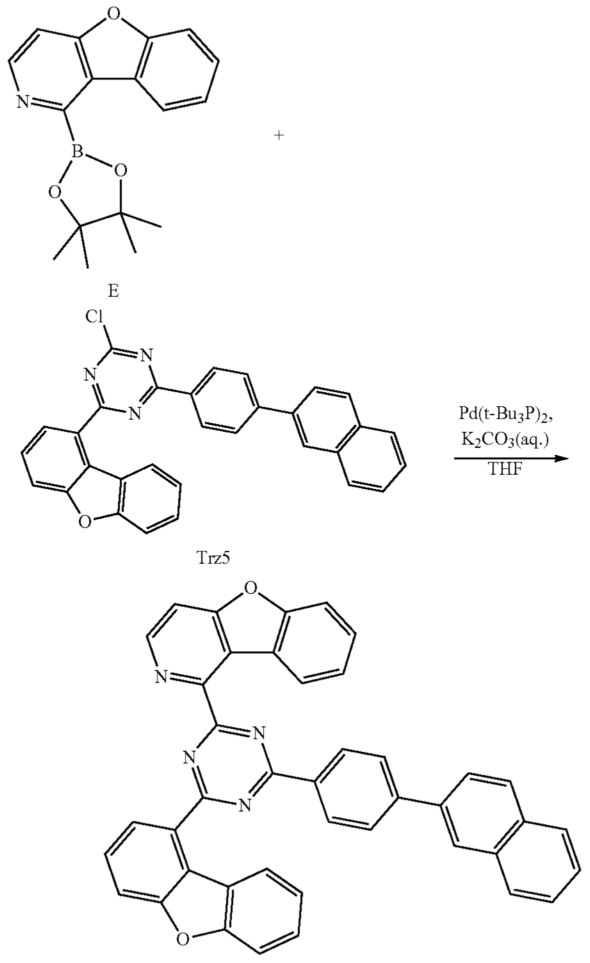

E

Trz5

6

Compound E (15 g, 50.8 mmol) and Trz5 (25.8 g, 53.4 mmol) were added to 300 mL of THF under a nitrogen atmosphere, and the mixture was stirred and refluxed. Then, potassium carbonate (21.1 g, 152.5 mmol) was dissolved in 63 L of water, added thereto, sufficiently stirred, and then bis(tri-tert-butylphosphine)palladium(0) (0.3 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 20.4 g of Compound 6. (Yield: 65%, MS: $[M+H]^+$=617)

SYNTHESIS EXAMPLE 7: PREPARATION OF COMPOUND 7

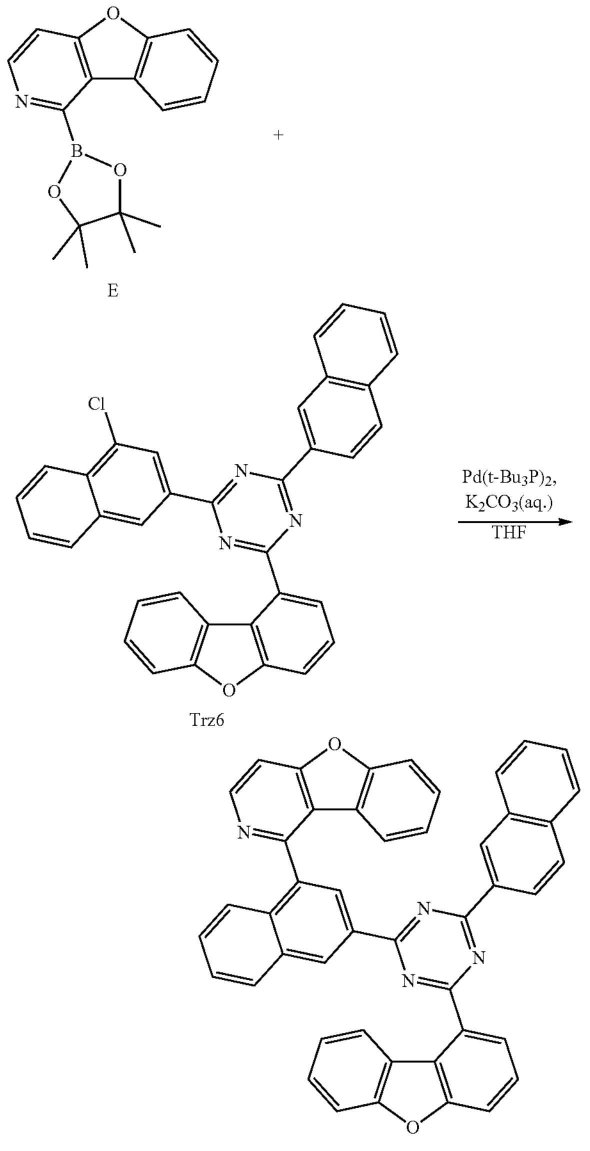

E

Trz6

7

Compound E (15 g, 50.8 mmol) and Trz6 (28.5 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 20.7 g of Compound 7. (Yield: 61%, MS: $[M+H]^+$=667)

SYNTHESIS EXAMPLE 8: PREPARATION OF COMPOUND 8

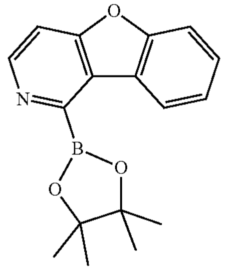

E

+

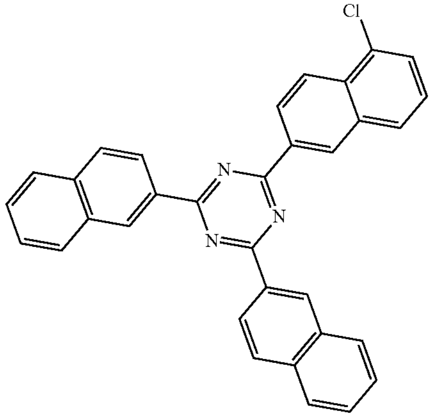

Trz7

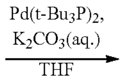

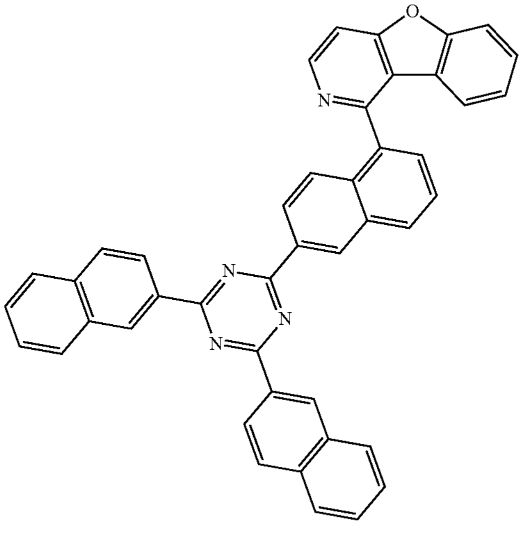

8

Compound E (15 g, 50.8 mmol) and Trz7 (26.4 g, 53.4 mmol) were added to 300 mL of THF under a nitrogen atmosphere, and the mixture was stirred and refluxed. Then, potassium carbonate (21.1 g, 152.5 mmol) was dissolved in 63 L of water, added thereto, sufficiently stirred, and then bis(tri-tert-butylphosphine)palladium(0) (0.3 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 24.2 g of Compound 8. (Yield: 76%, MS: $[M+H]^+$=627)

SYNTHESIS EXAMPLE 9: PREPARATION OF COMPOUND 9

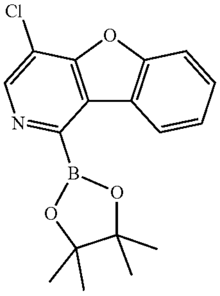

F

+

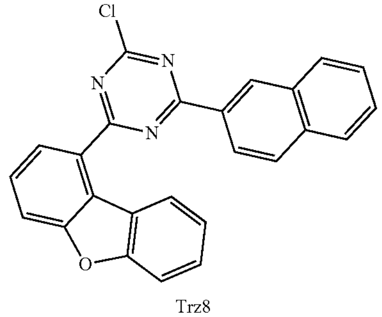

Trz8

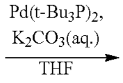

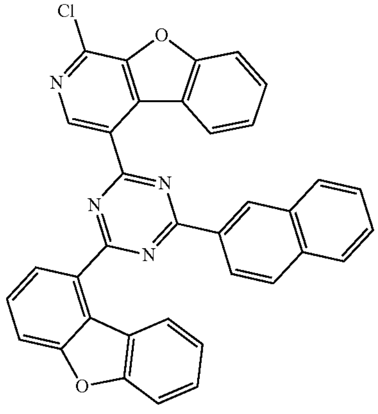

subF-1

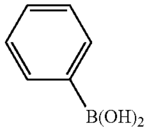

sub4

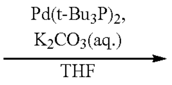

-continued

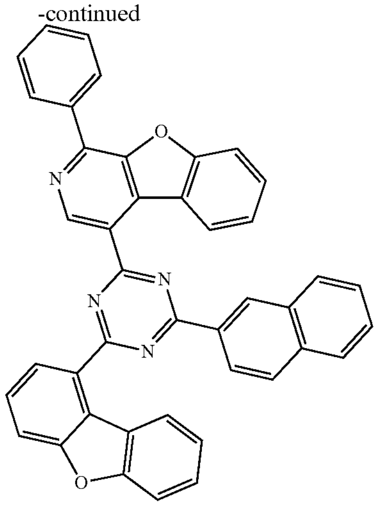

9

Compound F(15 g, 45.5 mmol) and Trz8 (19.5 g, 47.8 mmol) were added to 300 mL of THF under a nitrogen atmosphere, and the mixture was stirred and refluxed. Then, potassium carbonate (18.9 g, 136.5 mmol) was dissolved in 57 L of water, added thereto, sufficiently stirred, and then bis(tri-tert-butylphosphine)palladium(0) (0.2 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 17 g of subF-1. (Yield: 65%, MS: $[M+H]^+=575$)

Next, subF-1 (15 g, 26.1 mmol) and sub4 (3.3 g, 27.4 mmol) were added to 300 mL of THF under a nitrogen atmosphere, and the mixture was stirred and refluxed. Then, potassium carbonate (10.8 g, 78.3 mmol) was dissolved in 32 mL of water, added thereto, sufficiently stirred, and then bis(tri-tert-butylphosphine)palladium(0) (0.1 g, 0.3 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 12.9 g of Compound 9. (Yield: 80%, MS: $[M+H]^+=617$)

SYNTHESIS EXAMPLE 10: PREPARATION OF COMPOUND 10

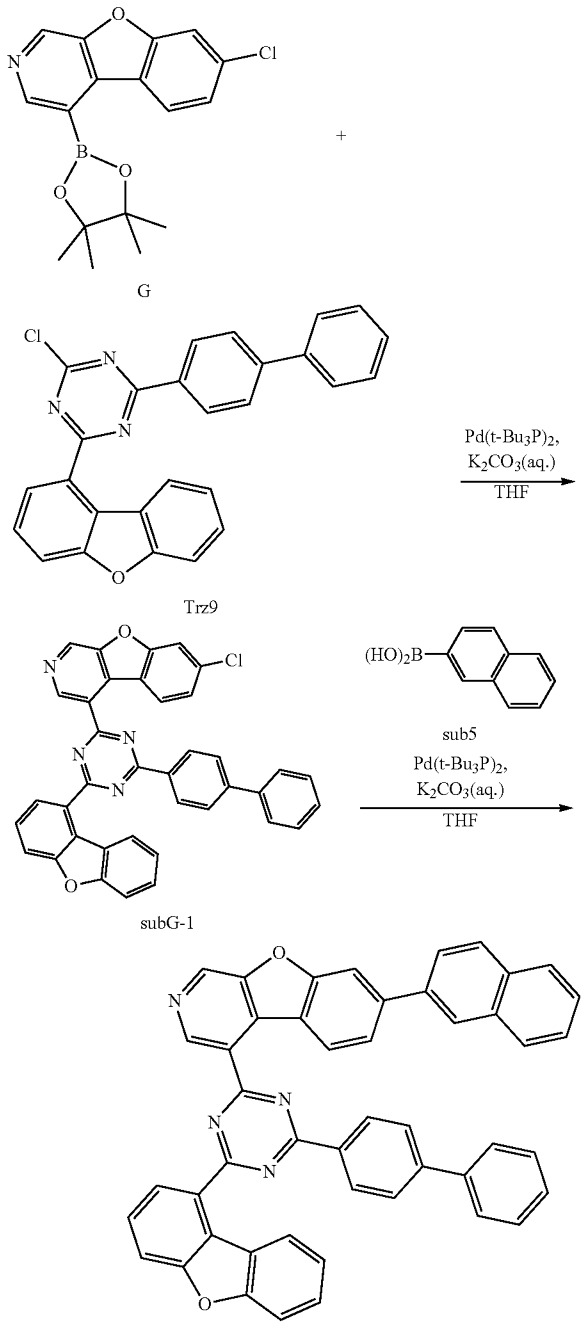

10

Compound G (15 g, 45.5 mmol) and Trz9 (20.7 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 21.9 g of subG-1. (Yield: 80%, MS: $[M+H]^+$=601)

Next, subG-1 (15 g, 25 mmol) and sub5 (4.5 g, 26.2 mmol) were added to 300 mL of THF under a nitrogen atmosphere, and the mixture was stirred and refluxed. Then, potassium carbonate (10.3 g, 74.9 mmol) was dissolved in 31 mL of water, added thereto, sufficiently stirred, and then bis(tri-tert-butylphosphine)palladium(0) (0.1 g, 0.2 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13 g of Compound 10. (Yield: 75%, MS: $[M+H]^+$=693)

SYNTHESIS EXAMPLE 11: PREPARATION OF COMPOUND 11

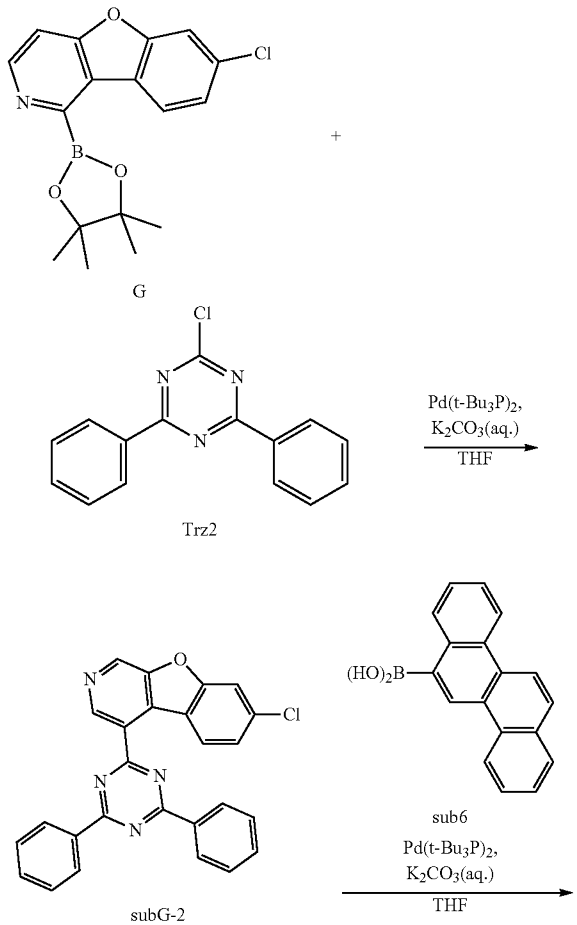

G

Trz2 subG-2 sub6

-continued

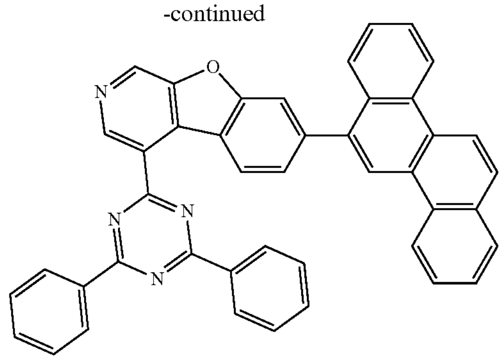

11

Compound G (15 g, 45.5 mmol) and Trz2 (12.8 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.8 g of subG-2. (Yield: 70%, MS: $[M+H]^+$=435)

Next, subG-2 (15 g, 34.5 mmol) and sub6 (17.5 g, 36.2 mmol) were added to 300 mL of THF under a nitrogen atmosphere, and the mixture was stirred and refluxed. Then, potassium carbonate (14.3 g, 103.5 mmol) was dissolved in 43 mL of water, added thereto, sufficiently stirred, and then bis(tri-tert-butylphosphine)palladium(0) (0.2 g, 0.3 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 14 g of Compound 11. (Yield: 65%, MS: $[M+H]^+$=627)

SYNTHESIS EXAMPLE 12: PREPARATION OF COMPOUND 12

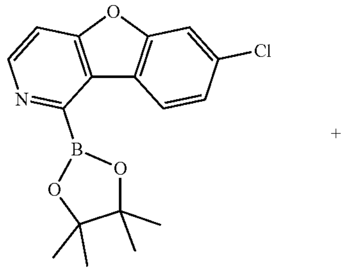

G

-continued

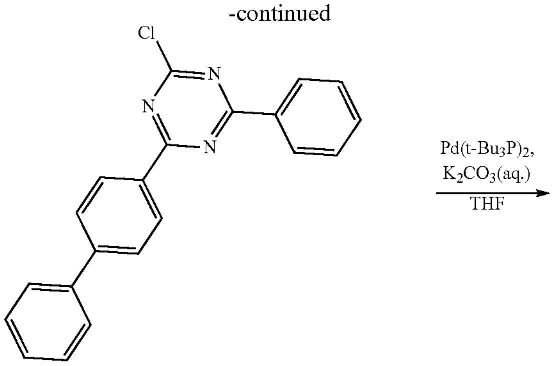

Trz10

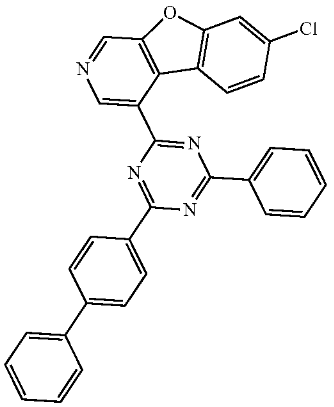

subG-3

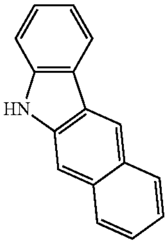

sub7

Pd(t-Bu3P)2,
NaOtBu
Xylene

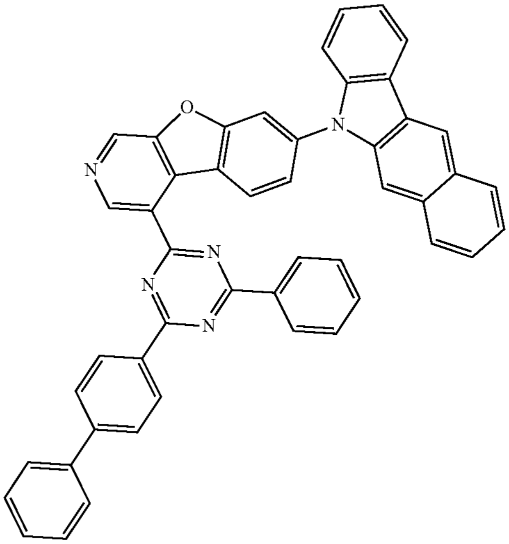

12

Compound G (15 g, 45.5 mmol) and Trz10 (16.4 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 14.2 g of subG-3. (Yield: 61%, MS: $[M+H]^+=511$)

Next, subG-3 (10 g, 19.6 mmol), sub7 (4.3 g, 20 mmol) and sodium tert-butoxide (2.4 g, 25.4 mmol) were added to 200 mL of xylene under a nitrogen atmosphere, and the mixture was stirred and refluxed. Then, bis(tri-tert-butylphosphine)palladium(0) (0.1 g, 0.2 mmol) was added thereto. When the reaction was completed after 5 hours, the reaction mixture was cooled to room temperature, and the solvent was removed under reduced pressure. Then, the compound was again completely dissolved in chloroform, washed twice with water, and then the organic layer was separated, treated with anhydrous magnesium sulfate and then filtered, and the filtrate was distilled under reduced pressure. The concentrated compound was purified by silica gel column chromatography to give 9.5 g of Compound 12. (Yield: 70%, MS: $[M+H]^+=692$)

SYNTHESIS EXAMPLE 13: PREPARATION OF COMPOUND 13

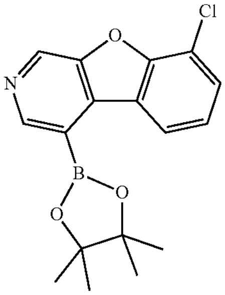

H

+

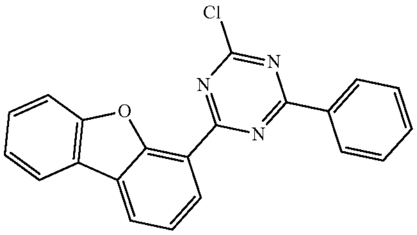

Trz11

Pd(t-Bu3P)2,
K2CO3(aq.)
THF

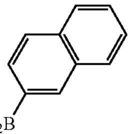

sub5

Pd(t-Bu3P)2,
K2CO3(aq.)
THF

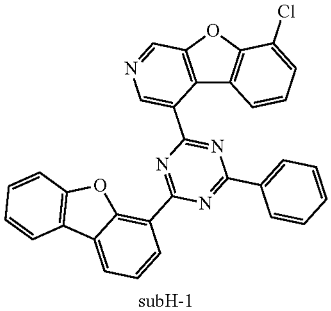

subH-1

-continued

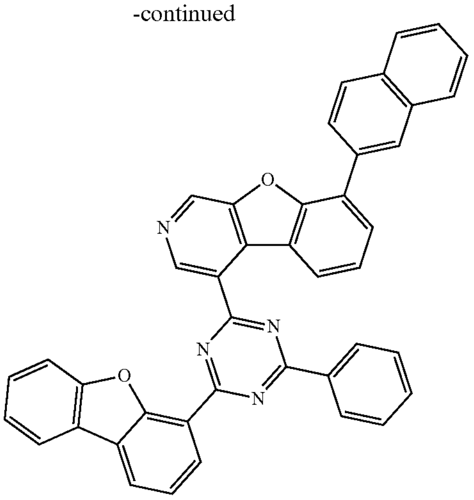

13

Compound H (15 g, 45.5 mmol) and Trz11 (17.1 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 16.2 g of subH-1. (Yield: 68%, MS: $[M+H]^+=525$)

Next, subH-1 (15 g, 28.6 mmol) and sub5 (5.2 g, 30 mmol) were added to 300 mL of THF under a nitrogen atmosphere, and the mixture was stirred and refluxed. Then, potassium carbonate (11.8 g, 85.7 mmol) was dissolved in 36 mL of water, added thereto, sufficiently stirred, and then bis(tri-tert-butylphosphine)palladium(0) (0.1 g, 0.3 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 10.9 g of Compound 13. (Yield: 62%, MS: $[M+H]^+=617$)

SYNTHESIS EXAMPLE 14: PREPARATION OF COMPOUND 14

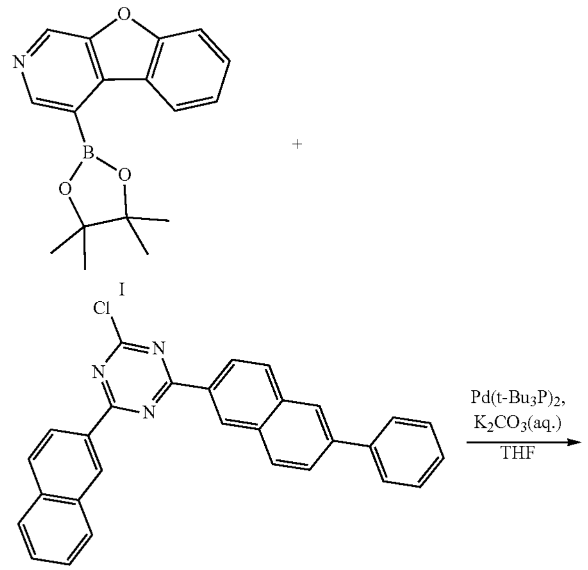

Trz12

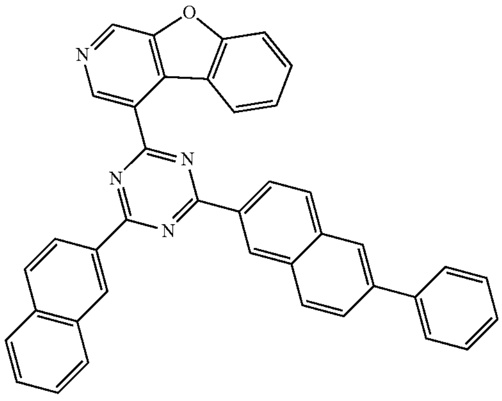

14

Compound 1 (15 g, 50.8 mmol) and Trz12 (23.7 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 17.6 g of Compound 14. (Yield: 60%, MS: $[M+H]^+=577$)

SYNTHESIS EXAMPLE 15: PREPARATION OF COMPOUND 15

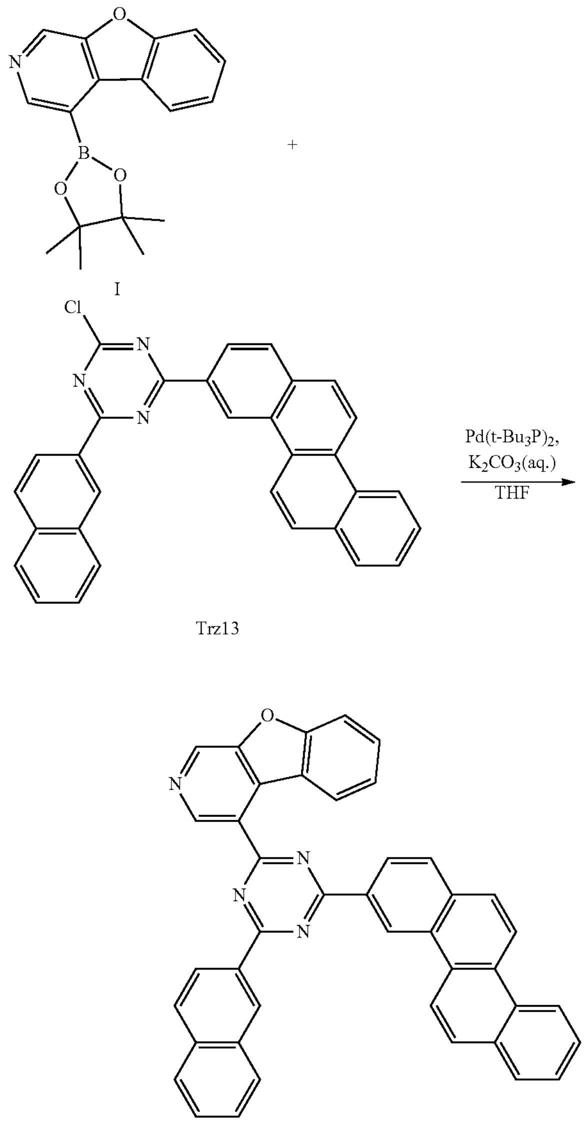

I

Trz13

15

Compound I (15 g, 50.8 mmol) and Trz13 (25 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 21.7 g of Compound 15. (Yield: 71%, MS: $[M+H]^+$=601)

SYNTHESIS EXAMPLE 16: PREPARATION OF COMPOUND 16

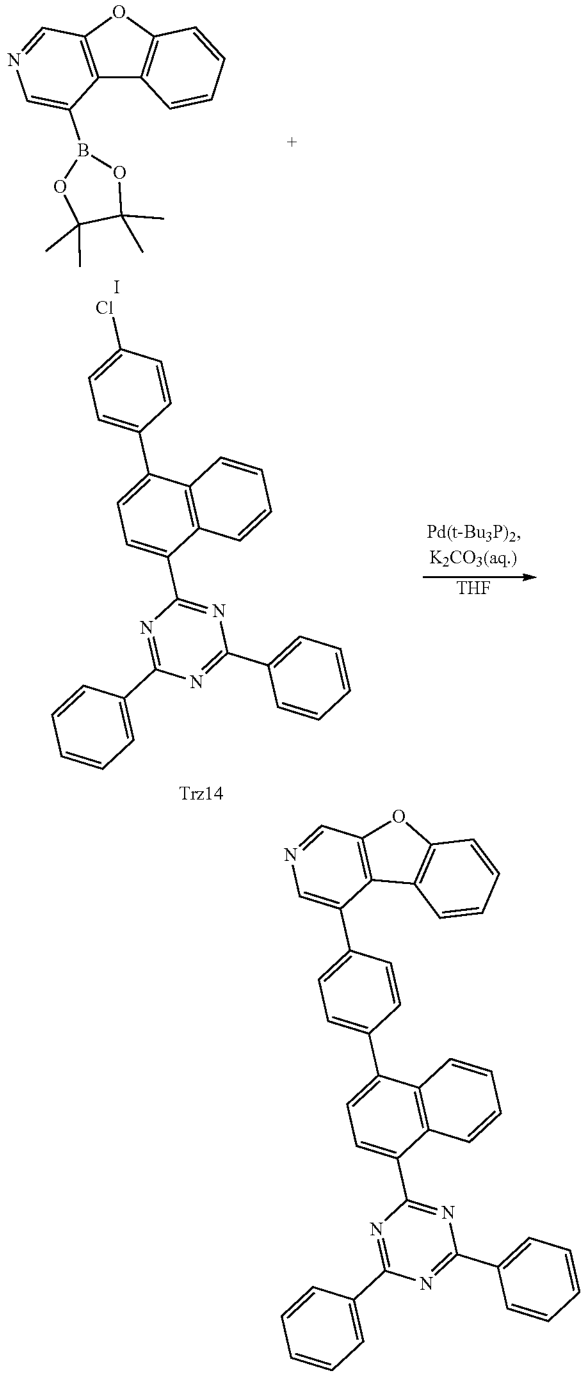

I

Trz14

16

Compound I (15 g, 50.8 mmol) and Trz14 (25.1 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 21.4 g of Compound 16. (Yield: 70%, MS: $[M+H]^+=603$)

SYNTHESIS EXAMPLE 17: PREPARATION OF COMPOUND 17

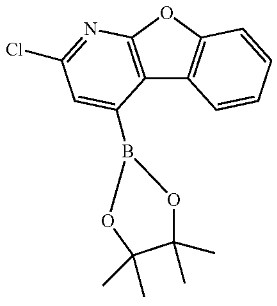

J

+

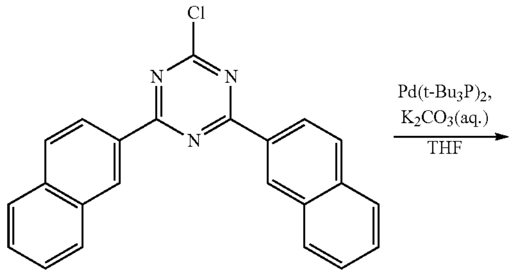

Trz15

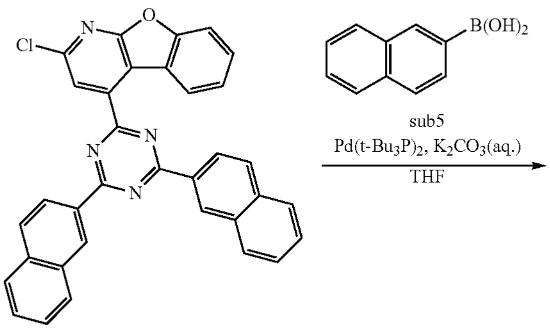

subJ-1

-continued

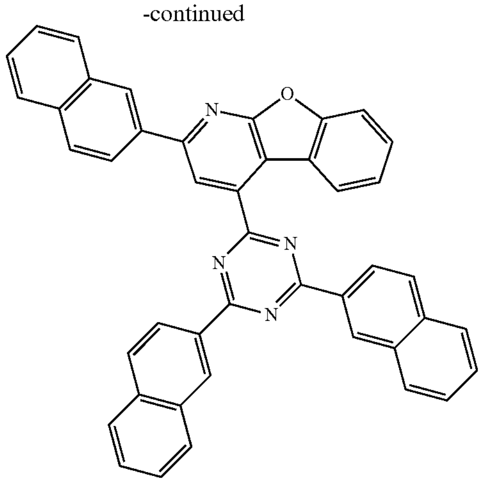

17

Compound J (15 g, 45.5 mmol) and Trz15 (17.6 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 15.6 g of subJ-1. (Yield: 64%, MS: $[M+H]^+=535$)

Next, subJ-1 (15 g, 28 mmol) and sub5 (5.1 g, 29.4 mmol) were added to 300 mL of THF under a nitrogen atmosphere, and the mixture was stirred and refluxed. Then, potassium carbonate (11.6 g, 84.1 mmol) was dissolved in 35 mL of water, added thereto, sufficiently stirred, and then bis(tri-tert-butylphosphine)palladium(0) (0.1 g, 0.3 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.7 g of Compound 17. (Yield: 78%, MS: $[M+H]^+=627$)

SYNTHESIS EXAMPLE 18: PREPARATION OF COMPOUND 18

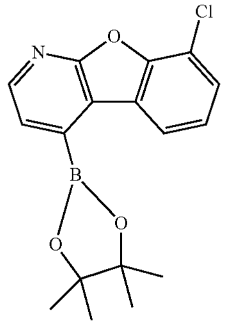

K

+

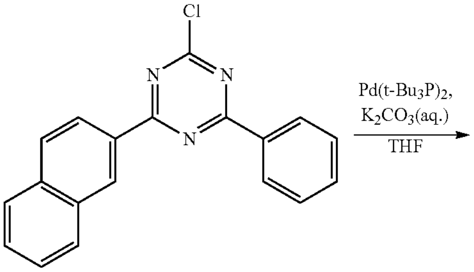

Trz1

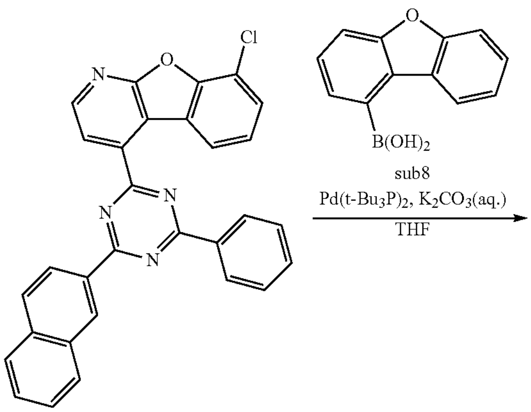

subK-1

-continued

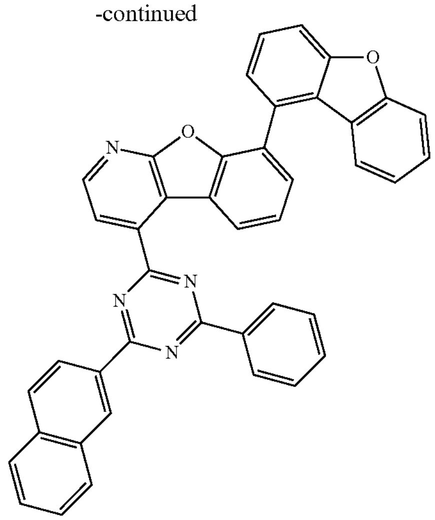

18

Compound K (15 g, 45.5 mmol) and Trz1 (15.2 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.9 g of subK-1. (Yield: 63%, MS: $[M+H]^+$=485)

Next, subK-1 (15 g, 30.9 mmol) and sub8 (6.9 g, 32.5 mmol) were added to 300 mL of THF under a nitrogen atmosphere, and the mixture was stirred and refluxed. Then, potassium carbonate (12.8 g, 92.8 mmol) was dissolved in 38 of water, added thereto, sufficiently stirred, and then bis(tri-tert-butylphosphine)palladium(0) (0.2 g, 0.3 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 12.4 g of Compound 18. (Yield: 65%, MS: $[M+H]^+$=617)

SYNTHESIS EXAMPLE 19: PREPARATION OF COMPOUND 19

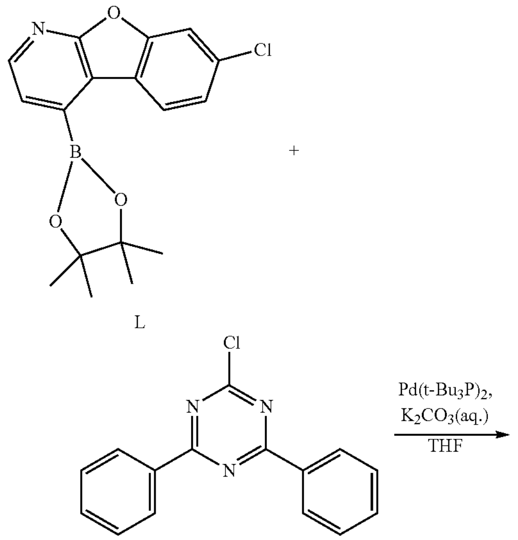

L

Trz2

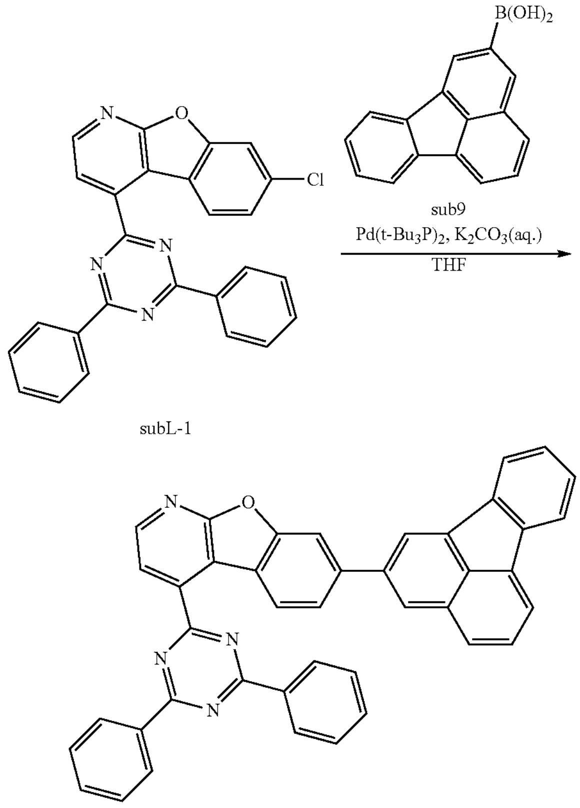

sub9 subL-1

19

Compound L (15 g, 45.5 mmol) and Trz2 (12.8 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.6 g of subL-1. (Yield: 69%, MS: $[M+H]^+$=435)

Next, subL-1 (15 g, 34.5 mmol) and sub9 (8.9 g, 36.2 mmol) were added to 300 mL of THF under a nitrogen atmosphere, and the mixture was stirred and refluxed. Then, potassium carbonate (14.3 g, 103.5 mmol) was dissolved in 43 of water, added thereto, sufficiently stirred, and then bis(tri-tert-butylphosphine)palladium(0) (0.2 g, 0.3 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.2 g of Compound 19. (Yield: 64%, MS: $[M+H]^+$=601)

SYNTHESIS EXAMPLE 20: PREPARATION OF COMPOUND 20

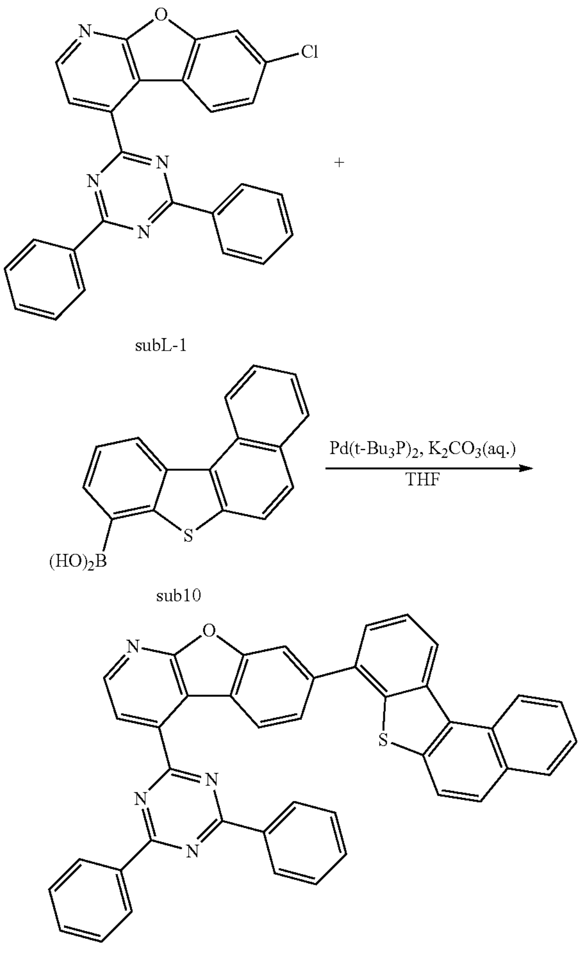

subL-1 sub10

20 subL-1 (15 g, 34.5 mmol) and sub10 (10.1 g, 36.2 mmol) were added to 300 mL of THF under a nitrogen atmosphere, and the mixture was stirred and refluxed. Then, potassium carbonate (14.3 g, 103.5 mmol) was dissolved in 43 mL of water, added thereto, sufficiently stirred, and then bis(tri-tert-butylphosphine)palladium(0) (0.2 g, 0.3 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 14.4 g of Compound 20. (Yield: 66%, MS: $[M+H]^+=633$)

SYNTHESIS EXAMPLE 21: PREPARATION OF COMPOUND 21

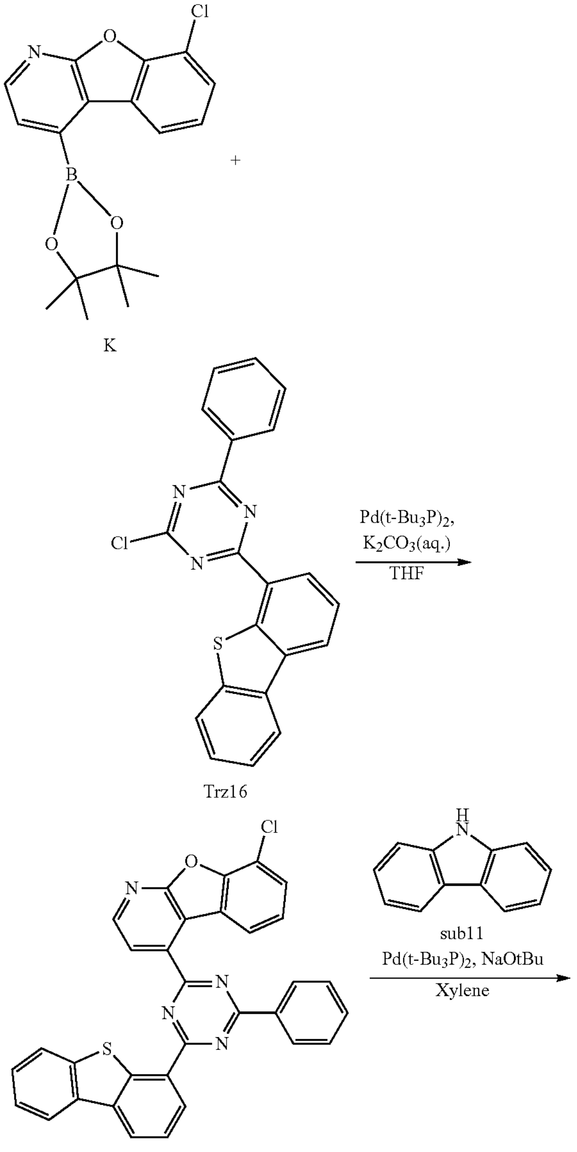

K

Trz16 sub11 subK-2

-continued

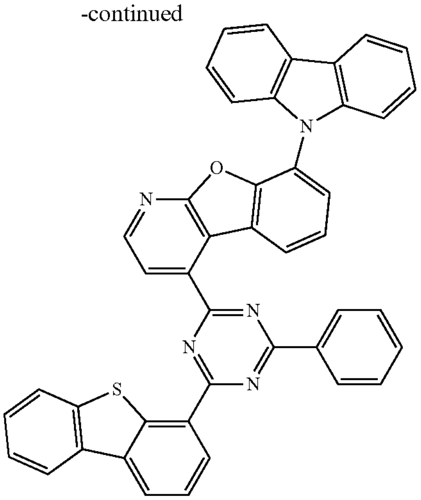

21

Compound K (15 g, 45.5 mmol) and Trz16 (17.9 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 16.7 g of subK-2. (Yield: 68%, MS: $[M+H]^+=541$)

Next, subK-2 (10 g, 18.5 mmol), sub11 (3.2 g, 18.9 mmol) and sodium tert-butoxide (2.3 g, 24 mmol) were added to 200 mL of xylene under a nitrogen atmosphere, and the mixture was stirred and refluxed. Then, bis(tri-tert-butylphosphine)palladium(0) (0.1 g, 0.2 mmol) was added thereto. When the reaction was completed after 5 hours, the reaction mixture was cooled to room temperature, and the solvent was removed under reduced pressure. Then, the compound was again completely dissolved in chloroform, washed twice with water, and then the organic layer was separated, treated with anhydrous magnesium sulfate and then filtered, and the filtrate was distilled under reduced pressure. The concentrated compound was purified by silica gel column chromatography to give 7.8 g of Compound 21. (Yield: 63%, MS: $[M+H]^+=672$)

SYNTHESIS EXAMPLE 22: PREPARATION OF COMPOUND 22

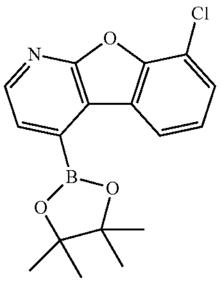

+

K

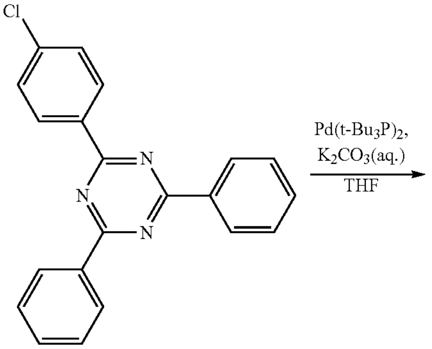

Trz17

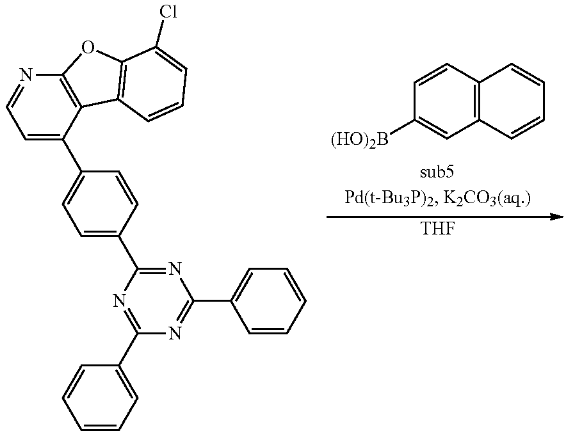

subK-3

-continued

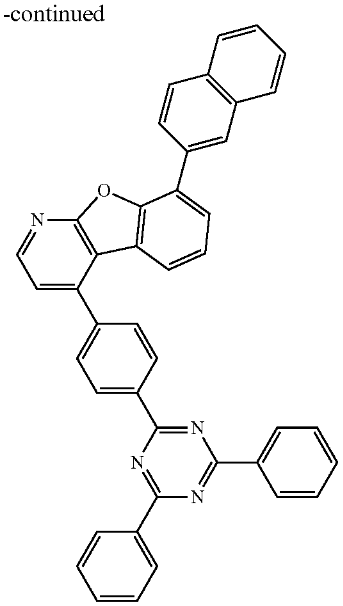

22

Compound K (15 g, 45.5 mmol) and Trz17 (16.4 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 15.3 g of subK-3. (Yield: 66%, MS: $[M+H]^+=511$)

Next, subK-3 (15 g, 29.4 mmol) and sub5 (5.3 g, 30.8 mmol) were added to 300 mL of THF under a nitrogen atmosphere, and the mixture was stirred and refluxed. Then, potassium carbonate (12.2 g, 88.1 mmol) was dissolved in 37 mL of water, added thereto, sufficiently stirred, and then bis(tri-tert-butylphosphine)palladium(0) (0.2 g, 0.3 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.8 g of Compound 22. (Yield: 78%, MS: $[M+H]^+=603$)

SYNTHESIS EXAMPLE 23: PREPARATION OF COMPOUND 23

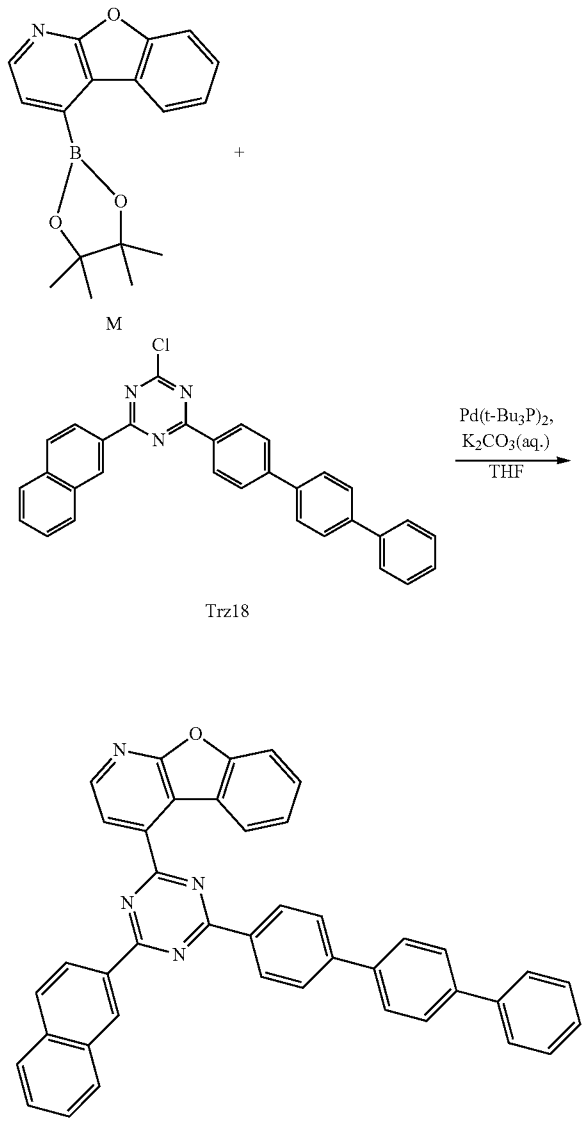

M

Trz18

23

Compound M (15 g, 50.8 mmol) and Trz18 (25.1 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 19.9 g of Compound 23. (Yield: 65%, MS: $[M+H]^+=603$)

SYNTHESIS EXAMPLE 24: PREPARATION OF COMPOUND 24

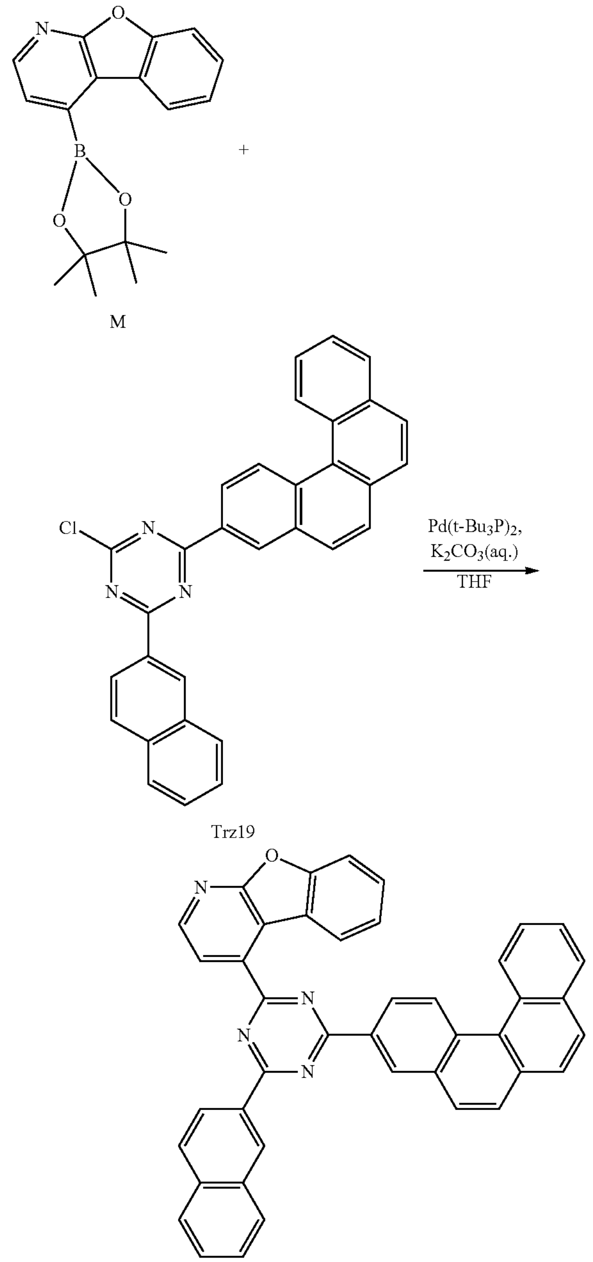

M

Trz19

24

Compound M (15 g, 50.8 mmol) and Trz19 (25 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 20.4 g of Compound 24. (Yield: 67%, MS: $[M+H]^+=601$)

SYNTHESIS EXAMPLE 25: PREPARATION OF COMPOUND 25

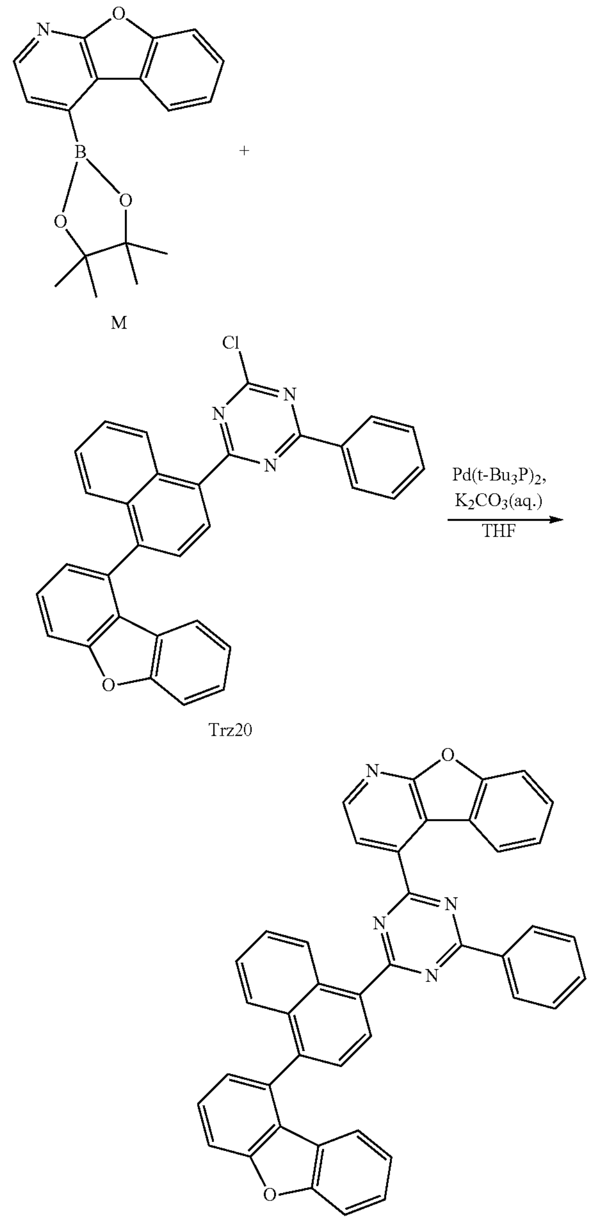

M

Trz20

25

Compound M (15 g, 50.8 mmol) and Trz20 (25.8 g, 53.4 mmol) were added to 300 mL of THF under a nitrogen atmosphere, and the mixture was stirred and refluxed. Then, potassium carbonate (21.1 g, 152.5 mmol) was dissolved in 63 L of water, added thereto, sufficiently stirred, and then bis(tri-tert-butylphosphine)palladium(0) (0.3 g, 0.5 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 19.7 g of Compound 25. (Yield: 63%, MS: $[M+H]^+=617$)

SYNTHESIS EXAMPLE 26: PREPARATION OF COMPOUND 26

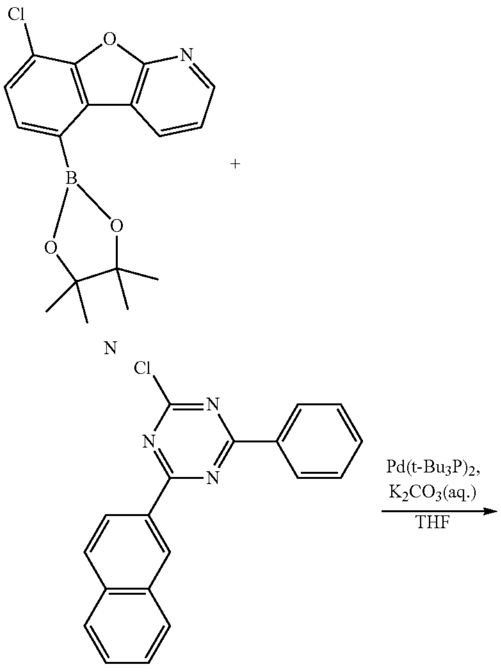

N

Trz1

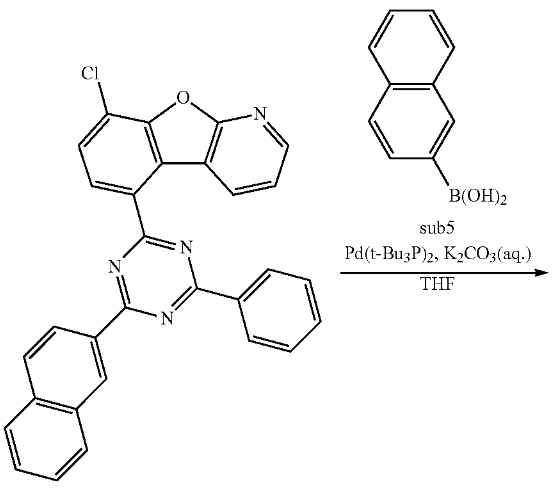

subN-1

-continued

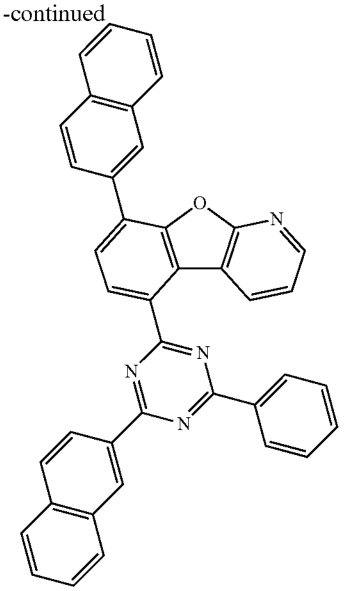

26

Compound N (15 g, 45.5 mmol) and Trz1 (15.2 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 15.9 g of subN-1. (Yield: 72%, MS: $[M+H]^+$=485)

Next, subN-1 (15 g, 30.9 mmol) and sub5 (5.6 g, 32.5 mmol) were added to 300 mL of THF under a nitrogen atmosphere, and the mixture was stirred and refluxed. Then, potassium carbonate (12.8 g, 92.8 mmol) was dissolved in 38 of water, added thereto, sufficiently stirred, and then bis(tri-tert-butylphosphine)palladium(0) (0.2 g, 0.3 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 12.7 g of Compound 26. (Yield: 71%, MS: $[M+H]^+$=577)

SYNTHESIS EXAMPLE 27: PREPARATION OF COMPOUND 27

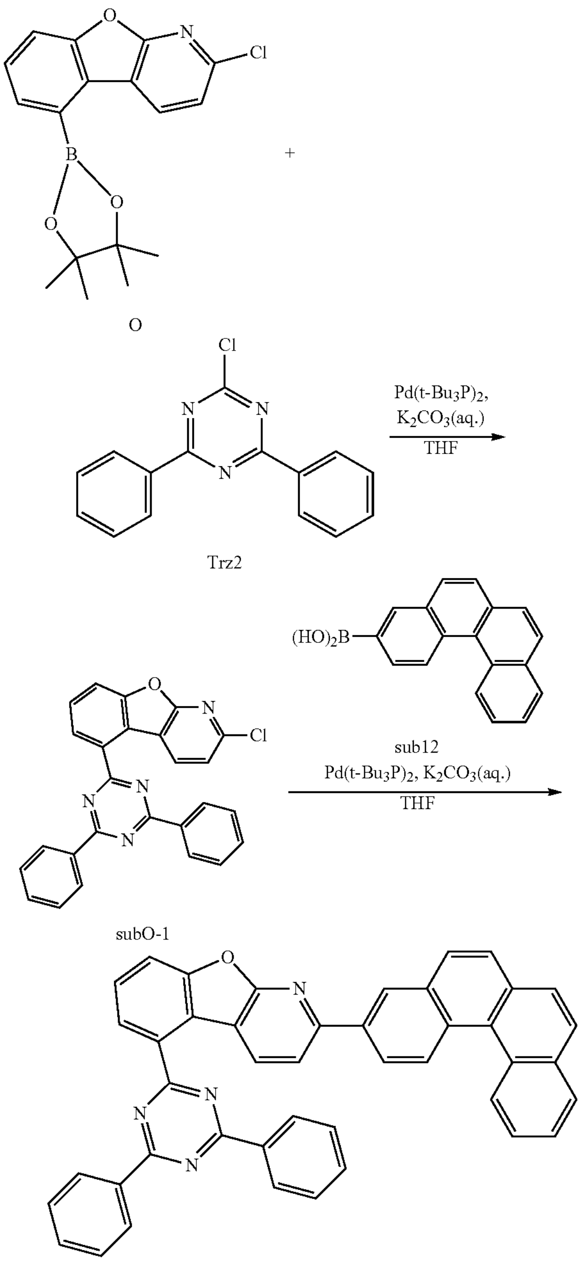

27

Compound O (15 g, 45.5 mmol) and Trz2 (12.8 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 15 g of subO-1. (Yield: 76%, MS: $[M+H]^+$=435)

Next, subO-1 (15 g, 34.5 mmol) and sub12 (9.9 g, 36.2 mmol) were added to 300 mL of THF under a nitrogen atmosphere, and the mixture was stirred and refluxed. Then, potassium carbonate (14.3 g, 103.5 mmol) was dissolved in 43 mL of water, added thereto, sufficiently stirred, and then bis(tri-tert-butylphosphine)palladium(0) (0.2 g, 0.3 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 15.8 g of Compound 27. (Yield: 73%, MS: $[M+H]^+$=627)

SYNTHESIS EXAMPLE 28: PREPARATION OF COMPOUND 28

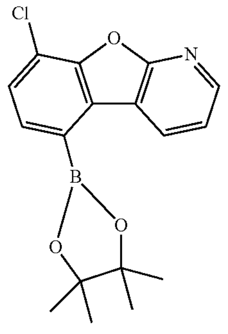

N

+

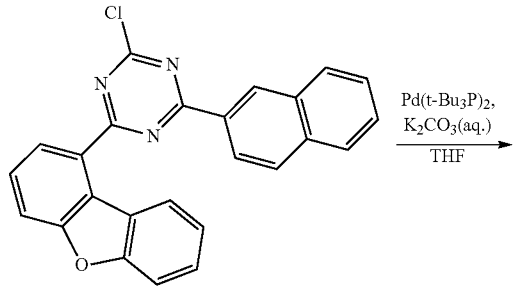

Trz8

-continued

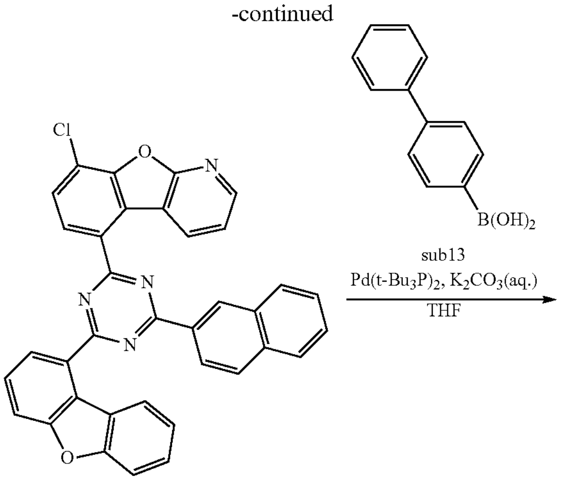

subN-2

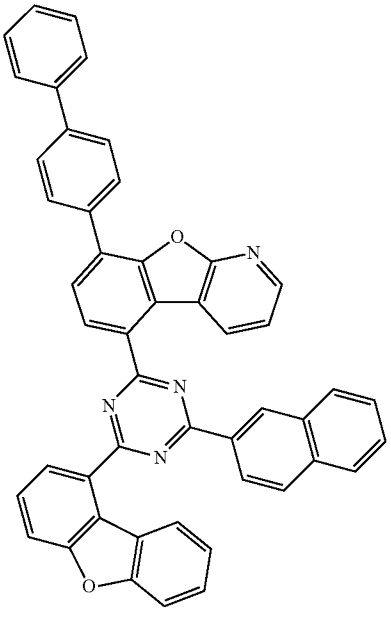

28

Compound N (15 g, 45.5 mmol) and Trz8 (12.8 g, 47.8 mmol) were added to 300 mL of THF under a nitrogen atmosphere, and the mixture was stirred and refluxed. Then, potassium carbonate (18.9 g, 136.5 mmol) was dissolved in 57 of water, added thereto, sufficiently stirred, and then bis(tri-tert-butylphosphine)palladium(0) (0.2 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 20.4 g of subN-2. (Yield: 78%, MS: $[M+H]^+$=575)

Next, subN-2 (15 g, 26.1 mmol) and sub13 (5.4 g, 27.4 mmol) were added to 300 mL of THF under nitrogen atmosphere, and the mixture was stirred and refluxed. Then, potassium carbonate (10.8 g, 78.3 mmol) was dissolved in 32 of water, added thereto, sufficiently stirred, and then bis(tri-tert-butylphosphine)palladium(0) (0.1 g, 0.3 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 10.8 g of Compound 28. (Yield: 60%, MS: $[M+H]^+$=693)

SYNTHESIS EXAMPLE 29: PREPARATION OF COMPOUND 29

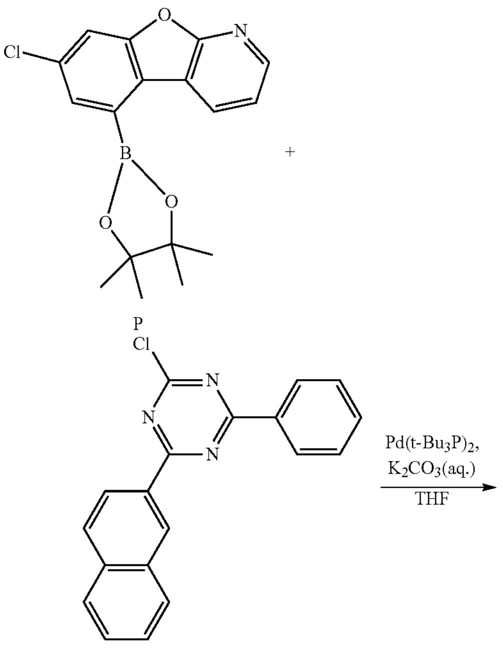

Trzl

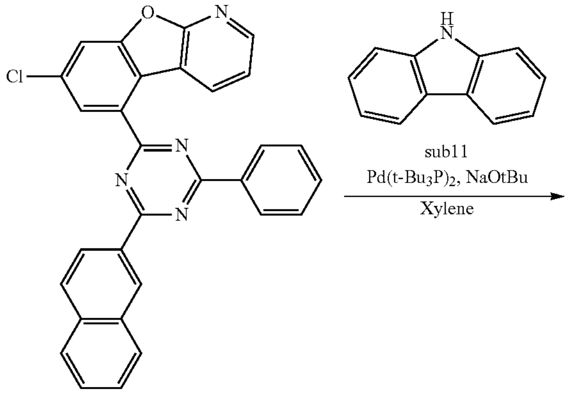

subP-1

-continued

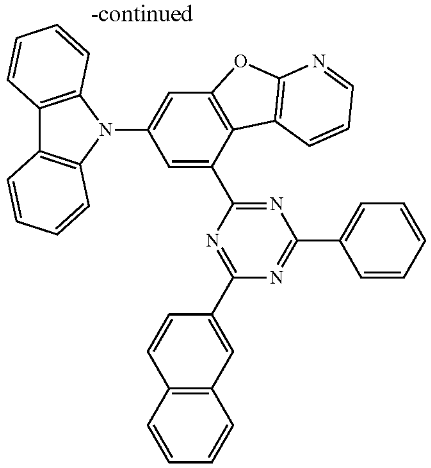

29

Compound P (15 g, 45.5 mmol) and Trz1 (15.2 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.7 g of subP-1. (Yield: 62%, MS: $[M+H]^+$=485)

Next, subP-1 (10 g, 20.6 mmol), sub11 (3.5 g, 21 mmol) and sodium tert-butoxide (2.6 g, 26.8 mmol) were added to 200 mL of xylene under a nitrogen atmosphere, and the mixture was stirred and refluxed. Then, bis(tri-tert-butylphosphine)palladium(0) (0.1 g, 0.2 mmol) was added thereto. When the reaction was completed after 5 hours, the reaction mixture was cooled to room temperature, and the solvent was removed under reduced pressure. Then, the compound was again completely dissolved in chloroform, washed twice with water, and then the organic layer was separated, treated with anhydrous magnesium sulfate and then filtered, and the filtrate was distilled under reduced pressure. The concentrated compound was purified by silica gel column chromatography to give 6.5 g of Compound 29. (Yield: 51%, MS: $[M+H]^+$=616)

SYNTHESIS EXAMPLE 30: PREPARATION OF COMPOUND 30

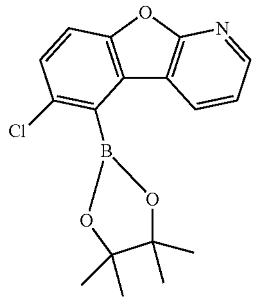

Q

+

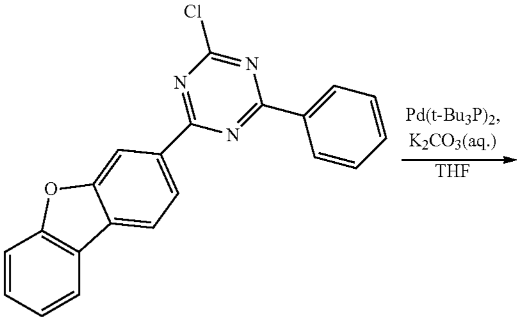

Trz21

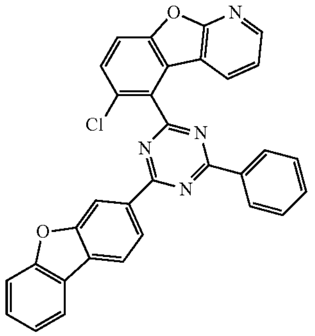

subQ-1

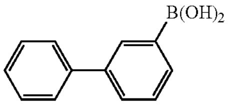

sub14

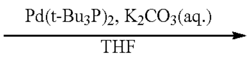

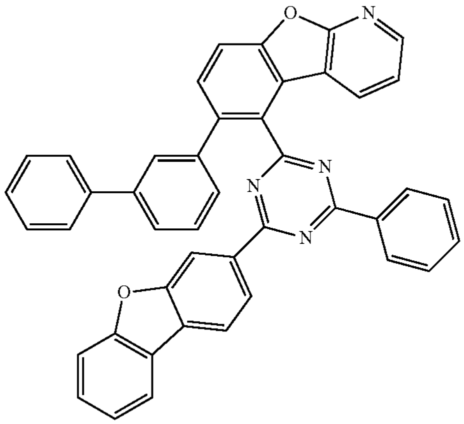

30

Compound Q (15 g, 45.5 mmol) and Trz21 (17.1 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 16.5 g of subQ-1. (Yield: 69%, MS: $[M+H]^+=525$)

Next, subQ-1 (15 g, 28.6 mmol) and sub14 (5.9 g, 30 mmol) were added to 300 mL of THF under a nitrogen atmosphere, and the mixture was stirred and refluxed. Then, potassium carbonate (11.8 g, 85.7 mmol) was dissolved in 36 mL of water, added thereto, sufficiently stirred, and then bis(tri-tert-butylphosphine)palladium(0) (0.1 g, 0.3 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 14.7 g of Compound 30. (Yield: 80%, MS: $[M+H]^+=643$)

SYNTHESIS EXAMPLE 31: PREPARATION OF COMPOUND 31

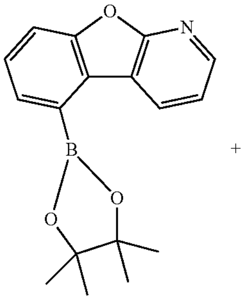

R

+

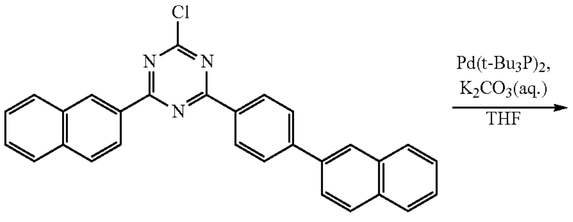

Trz22

-continued

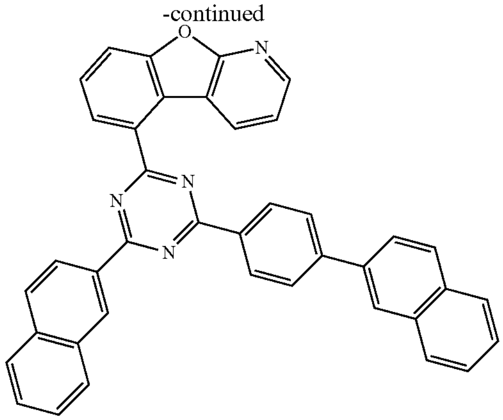

31

Compound R (15 g, 50.8 mmol) and Trz22 (23.7 g, 53.4 mmol) were added to 300 mL of THF under a nitrogen atmosphere, and the mixture was stirred and refluxed. Then, potassium carbonate (21.1 g, 152.5 mmol) was dissolved in 63 of water, added thereto, sufficiently stirred, and then bis(tri-tert-butylphosphine)palladium(0) (0.3 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 18.7 g of Compound 31. (Yield: 64%, MS: $[M+H]^+$=577)

SYNTHESIS EXAMPLE 32: PREPARATION OF COMPOUND 32

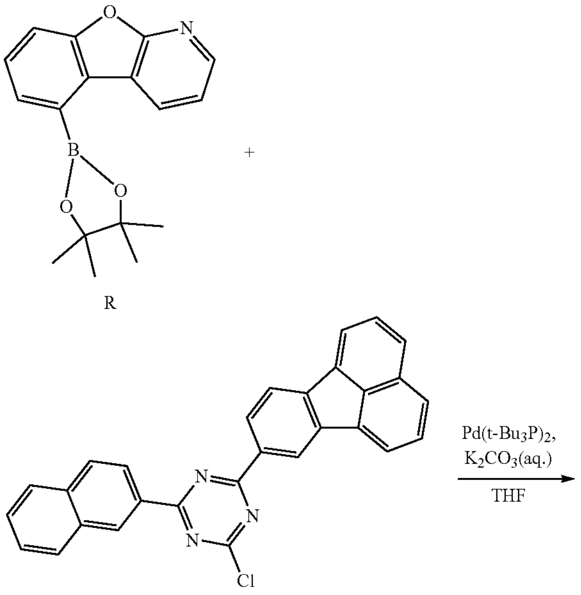

R

Trz23

-continued

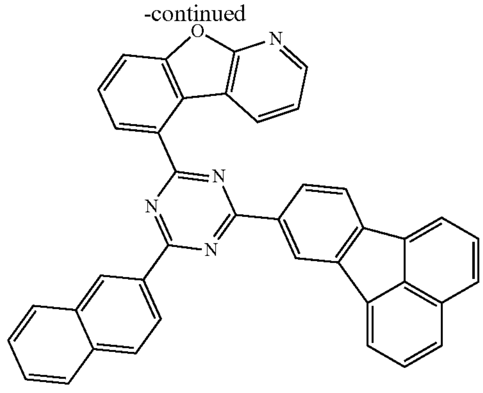

32

Compound R (15 g, 50.8 mmol) and Trz23 (23.6 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 23.1 g of Compound 32. (Yield: 79%, MS: $[M+H]^+$=575)

SYNTHESIS EXAMPLE 33: PREPARATION OF COMPOUND 33

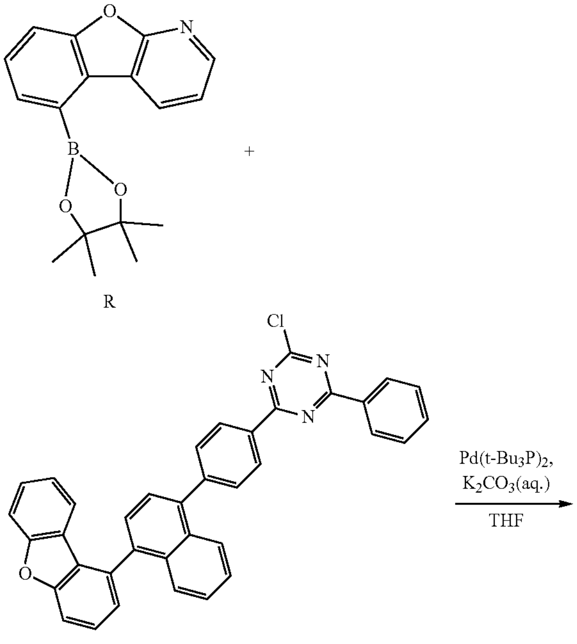

R

Trz24

-continued

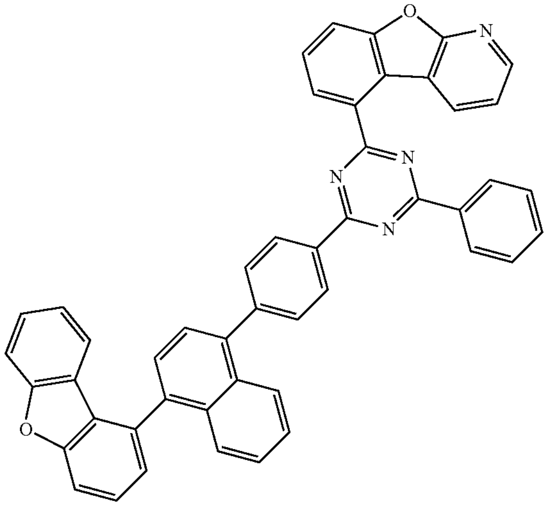

33

Compound R (15 g, 50.8 mmol) and Trz24 (29.9 g, 53.4 mmol) were added to 300 mL of THF under a nitrogen atmosphere, and the mixture was stirred and refluxed. Then, potassium carbonate (21.1 g, 152.5 mmol) was dissolved in 63 of water, added thereto, sufficiently stirred, and then bis(tri-tert-butylphosphine)palladium(0) (0.3 g, 0.5 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 26 g of Compound 33. (Yield: 74%, MS: $[M+H]^+$=693)

SYNTHESIS EXAMPLE 34: PREPARATION OF COMPOUND 34

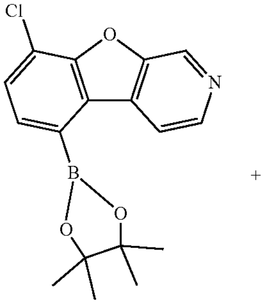

S

-continued

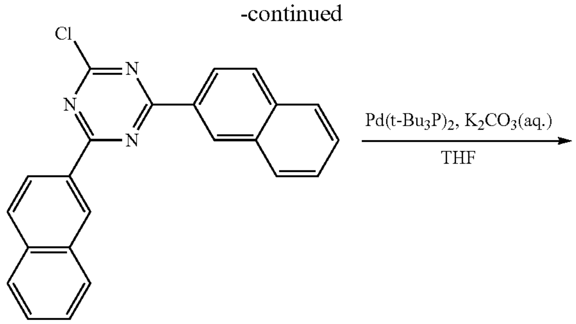

Trz15

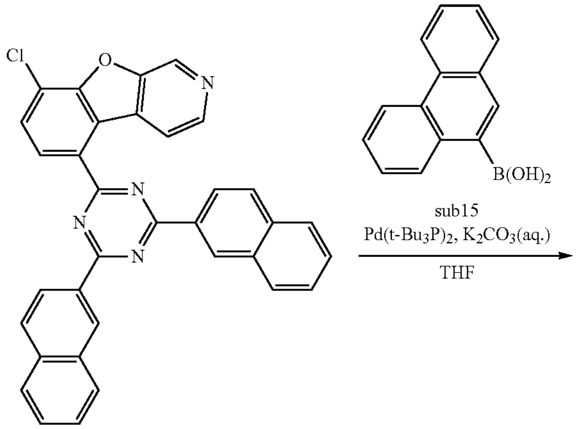

sub15 subS-1

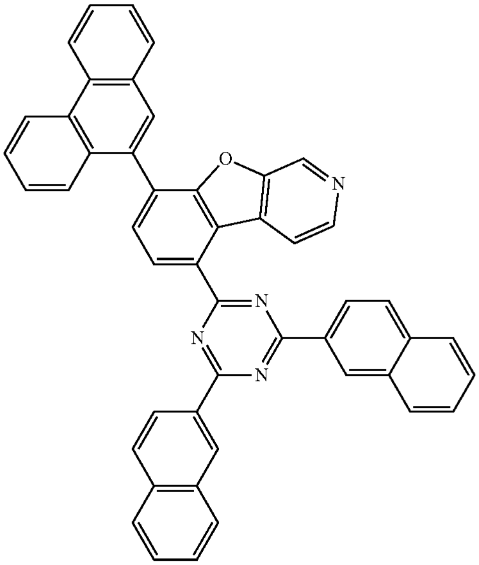

34

Compound S (15 g, 45.5 mmol) and Trz15 (17.6 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 19 g of subS-1. (Yield: 78%, MS: $[M+H]^+$=535)

Next, subS-1 (15 g, 28 mmol) and sub15 (6.5 g, 29.4 mmol) were added to 300 mL of THF under a nitrogen atmosphere, and the mixture was stirred and refluxed. Then, potassium carbonate (11.6 g, 84.1 mmol) was dissolved in 35 mL of water, added thereto, sufficiently stirred, and then bis(tri-tert-butylphosphine)palladium(0) (0.1 g, 0.3 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.3 g of Compound 34. (Yield: 70%, MS: $[M+H]^+$=677)

SYNTHESIS EXAMPLE 35: PREPARATION OF COMPOUND 35

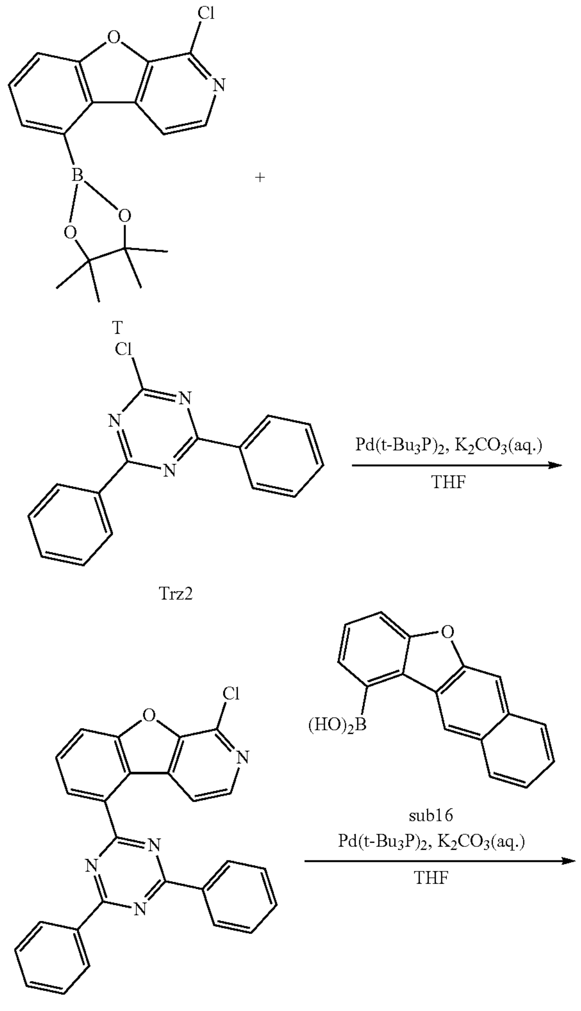

T

Trz2 sub16 subT-1

-continued

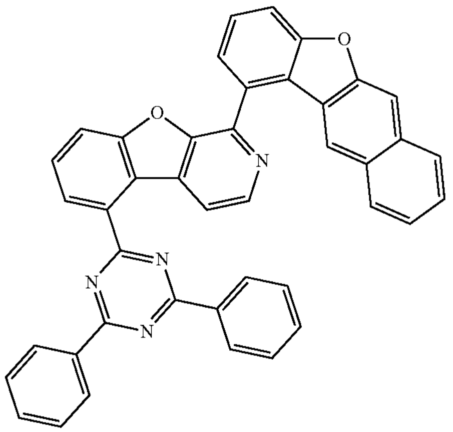

35

Compound T (15 g, 45.5 mmol) and Trz2 (12.8 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 14.4 g of subT-1. (Yield: 73%, MS: $[M+H]^+$=435)

Next, subT-1 (15 g, 34.5 mmol) and sub16 (9.5 g, 36.2 mmol) were added to 300 mL of THF under a nitrogen atmosphere, and the mixture was stirred and refluxed. Then, potassium carbonate (14.3 g, 103.5 mmol) was dissolved in 43 n L of water, added thereto, sufficiently stirred, and then bis(tri-tert-butylphosphine)palladium(0) (0.2 g, 0.3 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 17 g of Compound 35. (Yield: 80%, MS: $[M+H]^+$=617)

SYNTHESIS EXAMPLE 36: PREPARATION OF COMPOUND 36

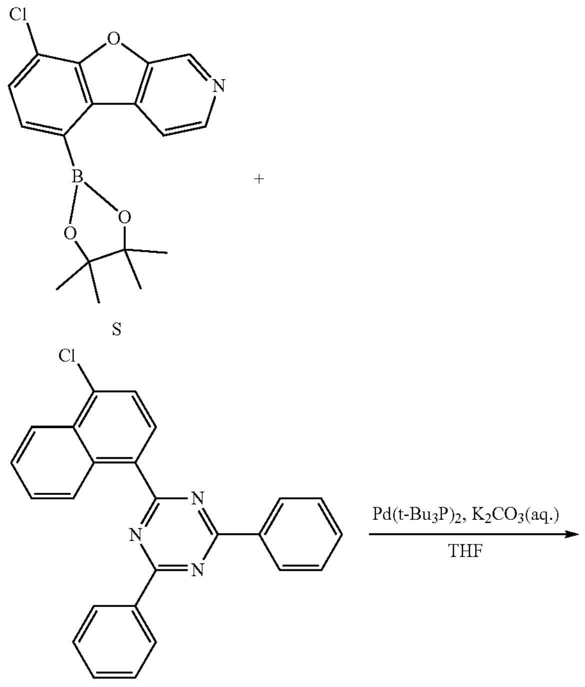

S

Trz25

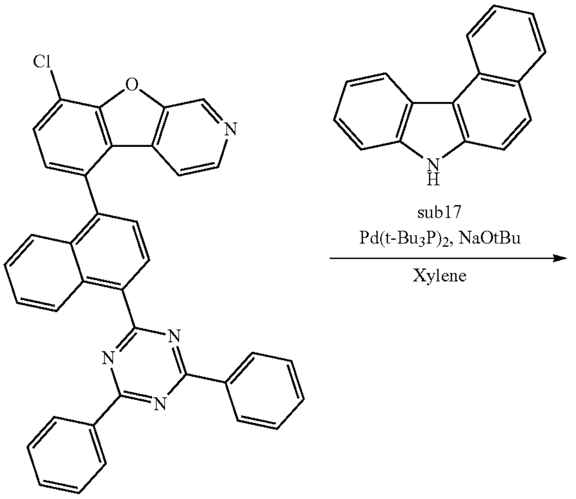

sub17 subS-2

-continued

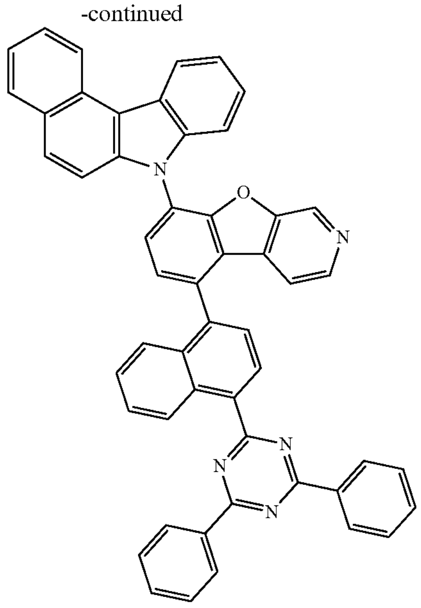

36

Compound S (15 g, 45.5 mmol) and Trz25 (18.8 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 19.6 g of subS-2. (Yield: 77%, MS: $[M+H]^+$=561)

Next, subS-2 (10 g, 17.8 mmol), sub17 (4 g, 18.2 mmol), and sodium tert-butoxide (2.2 g, 23.2 mmol) were added to 200 mL of xylene under a nitrogen atmosphere, and the mixture was stirred and refluxed. Then, bis(tri-tert-butylphosphine)palladium(0) (0.1 g, 0.2 mmol) was added thereto. When the reaction was completed after 5 hours, the reaction mixture was cooled to room temperature, and the solvent was removed under reduced pressure. Then, the compound was again completely dissolved in chloroform, washed twice with water, and then the organic layer was separated, treated with anhydrous magnesium sulfate and then filtered, and the filtrate was distilled under reduced pressure. The concentrated compound was purified by silica gel column chromatography to give 7.3 g of Compound 36. (Yield: 55%, MS: $[M+H]^+$=742)

SYNTHESIS EXAMPLE 37: PREPARATION OF COMPOUND 37

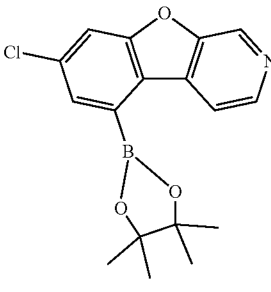

+

U

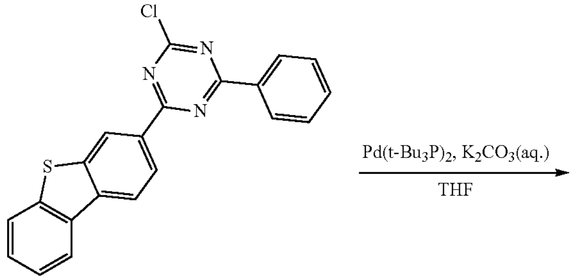

Trz26

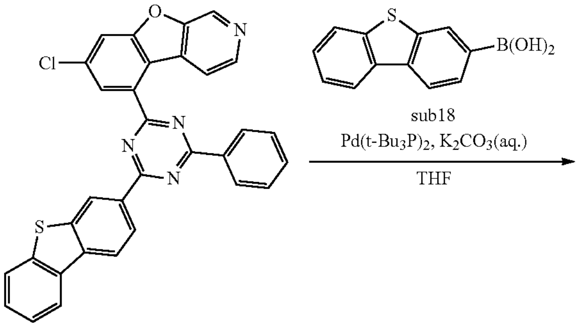

subU-1

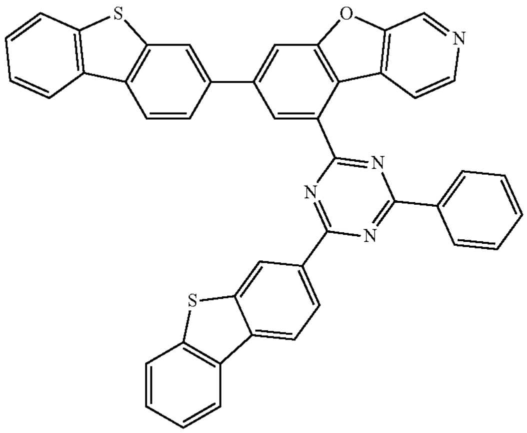

37

Compound U (15 g, 45.5 mmol) and Trz26 (17.9 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 18.7 g of subU-1. (Yield: 76%, MS: $[M+H]^+$=541)

Next, subU-1 (15 g, 27.7 mmol) and sub18 (6.6 g, 29.1 mmol) were added to 300 mL of THF under a nitrogen atmosphere, and the mixture was stirred and refluxed. Then, potassium carbonate (11.5 g, 83.2 mmol) was dissolved in 34 L of water, added thereto, sufficiently stirred, and then bis(tri-tert-butylphosphine)palladium(0) (0.1 g, 0.3 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.5 g of Compound 37. (Yield: 71%, MS: $[M+H]^+$=689)

SYNTHESIS EXAMPLE 38: PREPARATION OF COMPOUND 38

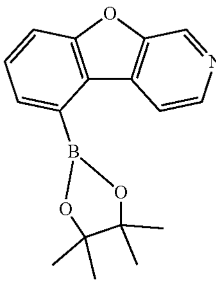

+

V

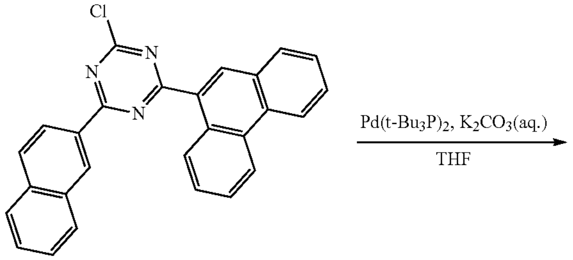

Trz27

-continued

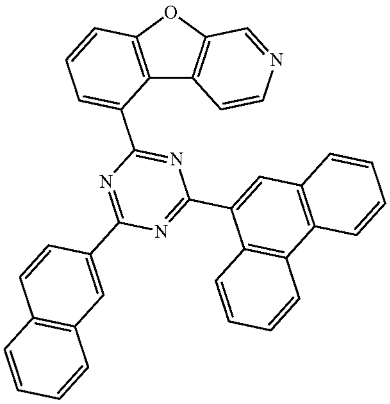

38

-continued

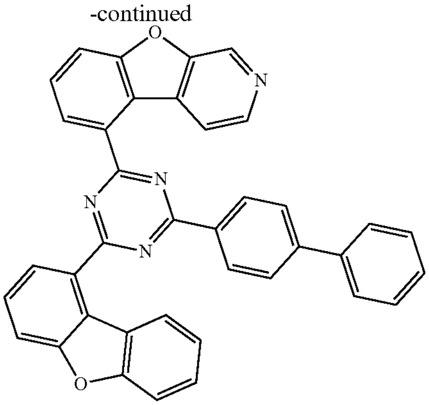

39

Compound V (15 g, 50.8 mmol) and Trz27 (22.3 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 16.8 g of Compound 38. (Yield: 60%, MS: $[M+H]^+$=551)

SYNTHESIS EXAMPLE 39: PREPARATION OF COMPOUND 39

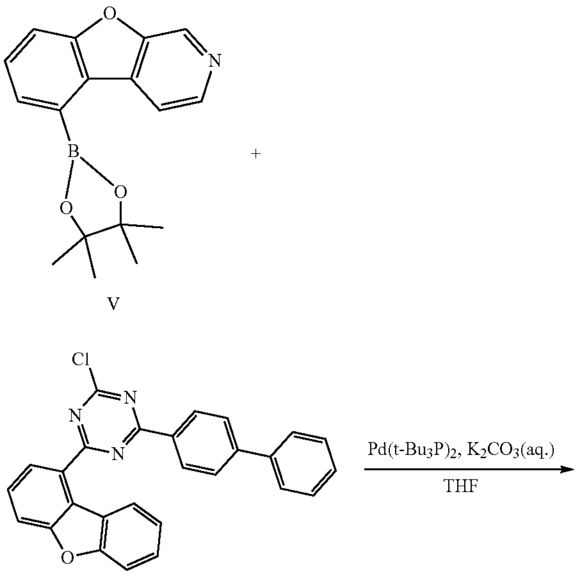

V

Trz28

Compound V (15 g, 50.8 mmol) and Trz28 (23.2 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 20.1 g of Compound 39. (Yield: 70%, MS: $[M+H]^+$=567)

SYNTHESIS EXAMPLE 40: PREPARATION OF COMPOUND 40

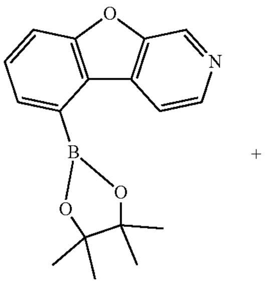

V

-continued

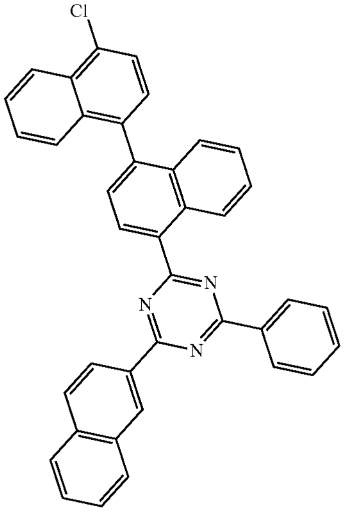

Trz29

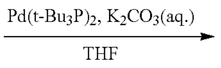

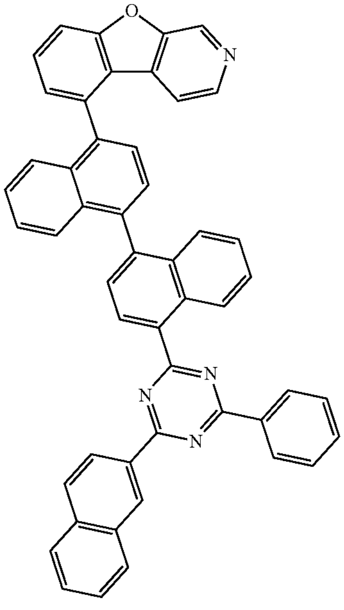

40

Next, Compound V (15 g, 50.8 mmol) and Trz29 (30.4 g, 53.4 mmol) were added to 300 mL of THF under a nitrogen atmosphere, and the mixture was stirred and refluxed. Then, potassium carbonate (21.1 g, 152.5 mmol) was dissolved in 63 of water, added thereto, sufficiently stirred, and then bis(tri-tert-butylphosphine)palladium(0) (0.3 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 24.6 g of Compound 40. (Yield: 69%, MS: $[M+H]^+=703$)

SYNTHESIS EXAMPLE 41: PREPARATION OF COMPOUND 41

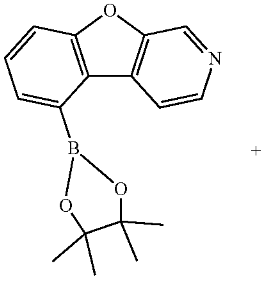

V

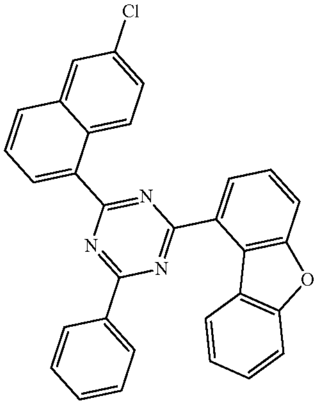

Trz30

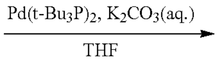

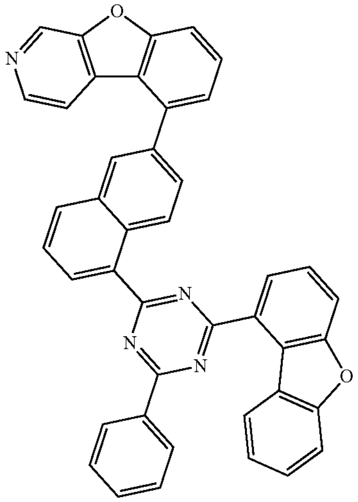

41

Compound V (15 g, 50.8 mmol) and Trz30 (25.8 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 23.8 g of Compound 41. (Yield: 76%, MS: $[M+H]^+=617$)

SYNTHESIS EXAMPLE 42: PREPARATION OF COMPOUND 42

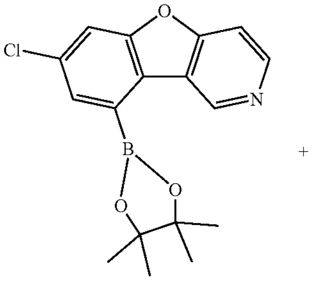

W

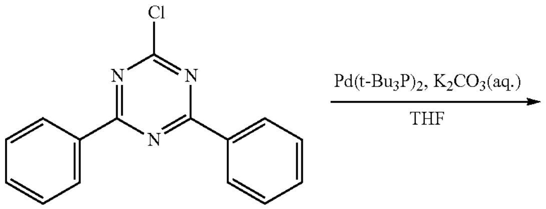

Trz2

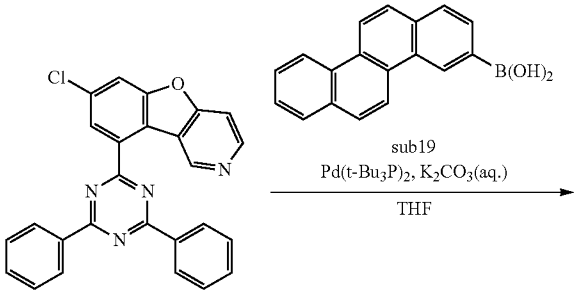

subW-1

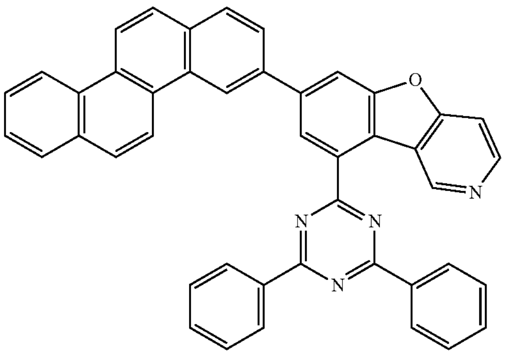

42

Compound W (15 g, 45.5 mmol) and Trz2 (12.8 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13 g of subW-1. (Yield: 66%, MS: $[M+H]^+=435$)

Next, subW-1 (15 g, 34.5 mmol) and sub19 (9.9 g, 36.2 mmol) were added to 300 mL of THF under a nitrogen atmosphere, and the mixture was stirred and refluxed. Then, potassium carbonate (14.3 g, 103.5 mmol) was dissolved in 43 L of water, added thereto, sufficiently stirred, and then bis(tri-tert-butylphosphine)palladium(0) (0.2 g, 0.3 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 16.4 g of Compound 42. (Yield: 76%, MS: $[M+H]^+=627$)

SYNTHESIS EXAMPLE 43: PREPARATION OF COMPOUND 43

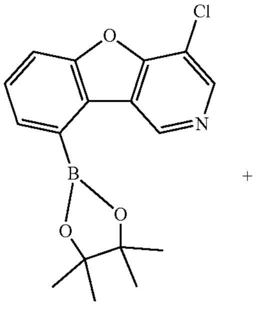

X

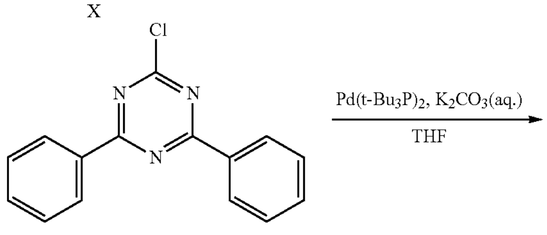

Trz2

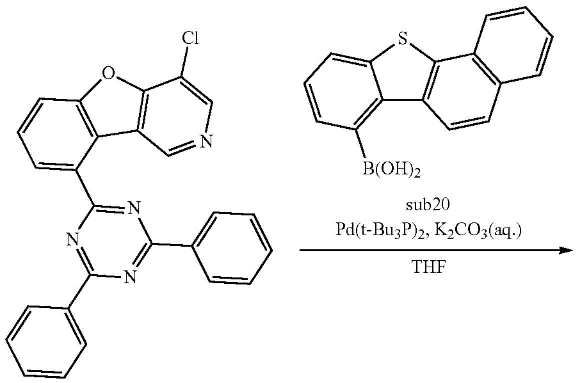

subX-1

-continued

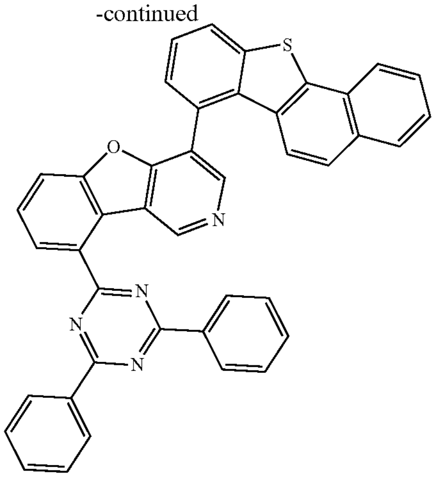

43

Compound X (15 g, 45.5 mmol) and Trz2 (12.8 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 14 g of subX-1. (Yield: 71%, MS: $[M+H]^+$=435)

Next, subX-1 (15 g, 34.5 mmol) and sub20 (10.1 g, 36.2 mmol) were added to 300 mL of THF under a nitrogen atmosphere, and the mixture was stirred and refluxed. Then, potassium carbonate (14.3 g, 103.5 mmol) was dissolved in 43 mL of water, added thereto, sufficiently stirred, and then bis(tri-tert-butylphosphine)palladium(0) (0.2 g, 0.3 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 14 g of Compound 43. (Yield: 64%, MS: $[M+H]^+$=633)

SYNTHESIS EXAMPLE 44: PREPARATION OF COMPOUND 44

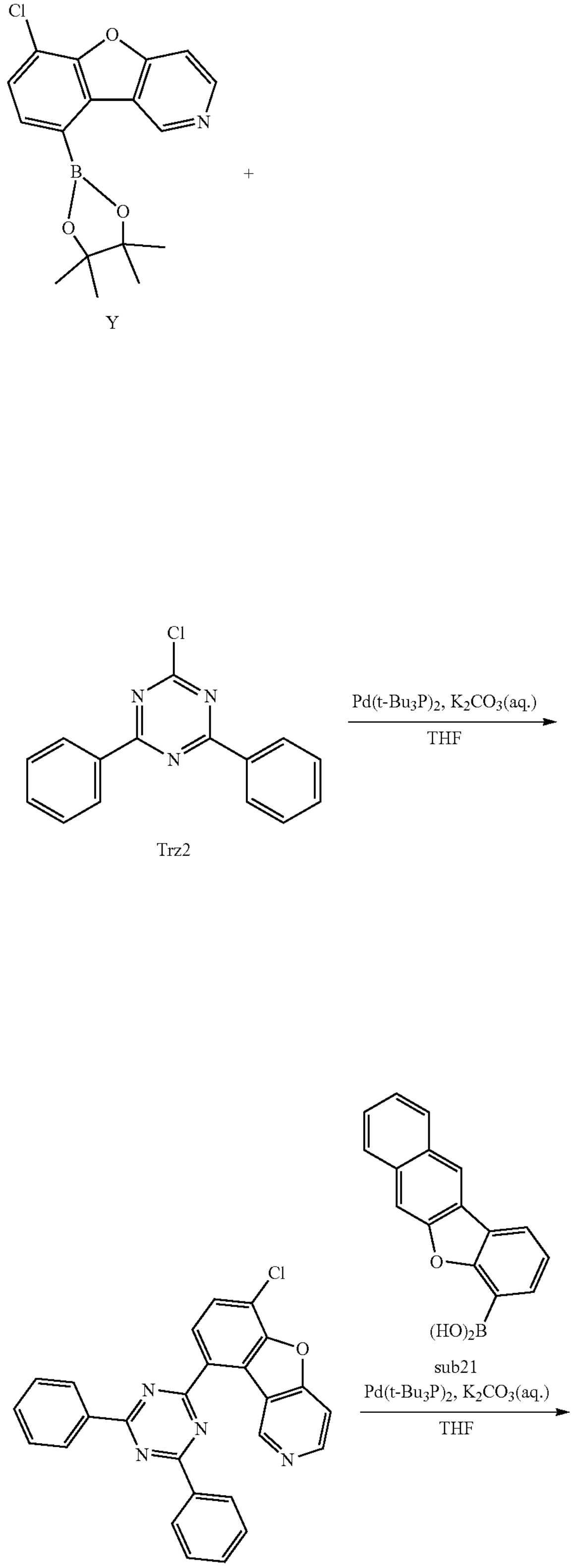

Y

Trz2 sub21 subY-1

-continued

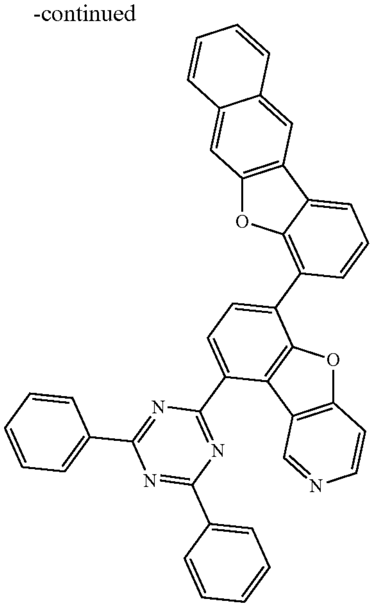

44

Compound Y (15 g, 45.5 mmol) and Trz2 (12.6 g, 47.8 mmol) were added to 300 mL of THF under a nitrogen atmosphere, and the mixture was stirred and refluxed. Then, potassium carbonate (18.9 g, 136.5 mmol) was dissolved in 57 of water, added thereto, sufficiently stirred, and then bis(tri-tert-butylphosphine)palladium(0) (0.2 g, 0.5 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 15.8 g of subY-1. (Yield: 80%, MS: $[M+H]^+$=435)

Next, subY-1 (15 g, 34.5 mmol) and sub21 (9.5 g, 36.2 mmol) were added to 300 mL of THF under a nitrogen atmosphere, and the mixture was stirred and refluxed. Then, potassium carbonate (14.3 g, 103.5 mmol) was dissolved in 43 L of water, added thereto, sufficiently stirred, and then bis(tri-tert-butylphosphine)palladium(0) (0.2 g, 0.3 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 14.9 g of Compound 44. (Yield: 70%, MS: $[M+H]^+$=617)

SYNTHESIS EXAMPLE 45: PREPARATION OF COMPOUND 45

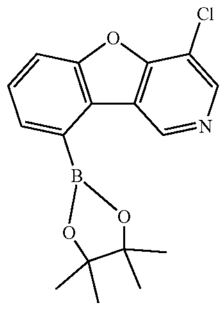

X

+

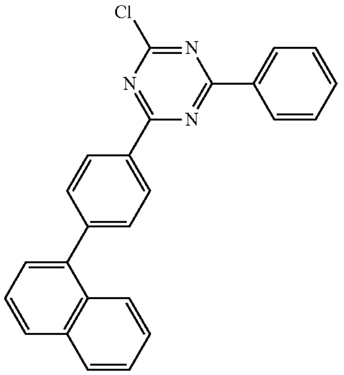

Trz31

$Pd(t\text{-}Bu_3P)_2$, $K_2CO_3$(aq.)

THF

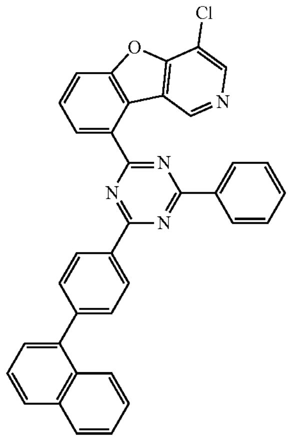

subX-2

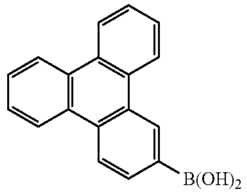

sub22

$Pd(t\text{-}Bu_3P)_2$, $K_2CO_3$(aq.)

THF

-continued

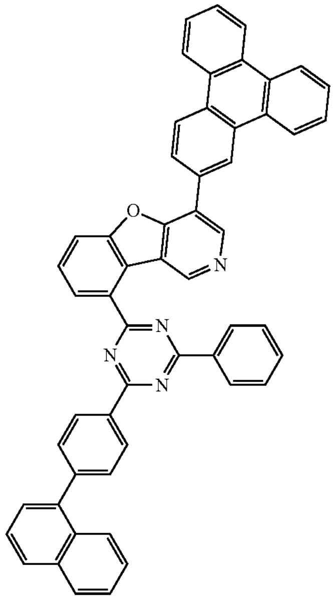

45

Compound X (15 g, 45.5 mmol) and Trz31 (18.8 g, 47.8 mmol) were added to 300 mL of THF under a nitrogen atmosphere, and the mixture was stirred and refluxed. Then, potassium carbonate (18.9 g, 136.5 mmol) was dissolved in 57 of water, added thereto, sufficiently stirred, and then bis(tri-tert-butylphosphine)palladium(0) (0.2 g, 0.5 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 18.1 g of subX-2. (Yield: 71%, MS: $[M+H]^+=561$)

Next, subX-2 (15 g, 26.7 mmol) and sub22 (7.6 g, 28.1 mmol) were added to 300 mL of THF under a nitrogen atmosphere, and the mixture was stirred and refluxed. Then, potassium carbonate (11.1 g, 80.2 mmol) was dissolved in 33 mL of water, added thereto, sufficiently stirred, and then bis(tri-tert-butylphosphine)palladium(0) (0.1 g, 0.3 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 15.7 g of Compound 45. (Yield: 78%, MS: $[M+H]^+=753$)

SYNTHESIS EXAMPLE 46: PREPARATION OF COMPOUND 46

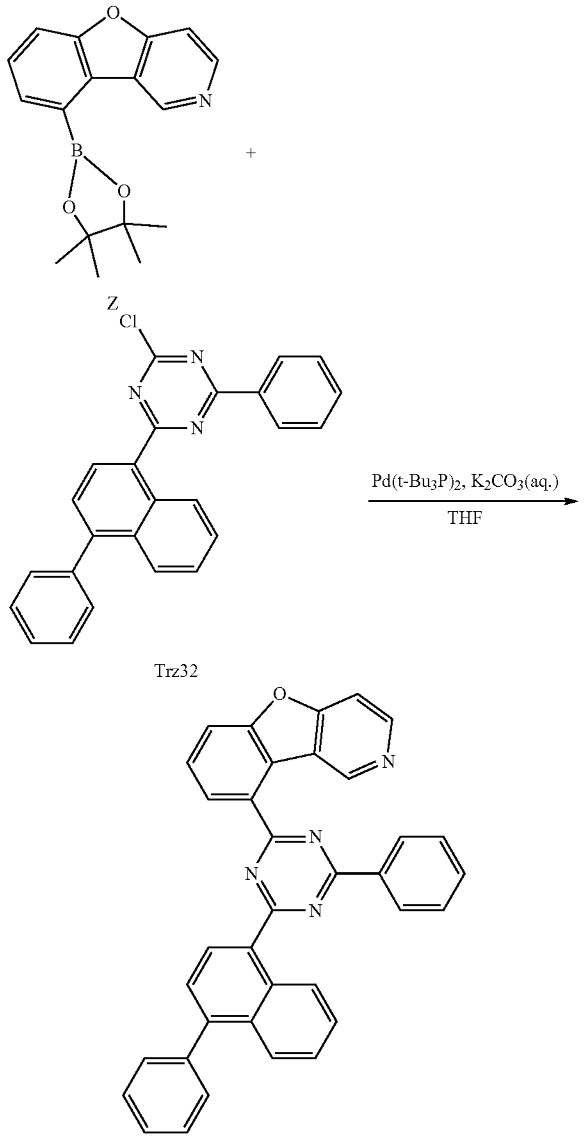

Z

Trz32

46

Compound Z (15 g, 50.8 mmol) and Trz32 (21 g, 53.4 mmol) were added to 300 mL of THF under a nitrogen atmosphere, and the mixture was stirred and refluxed. Then, potassium carbonate (21.1 g, 152.5 mmol) was dissolved in 63 of water, added thereto, sufficiently stirred, and then bis(tri-tert-butylphosphine)palladium(0) (0.3 g, 0.5 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 16.6 g of Compound 46. (Yield: 62%, MS: $[M+H]^+=527$)

SYNTHESIS EXAMPLE 47: PREPARATION OF COMPOUND 47

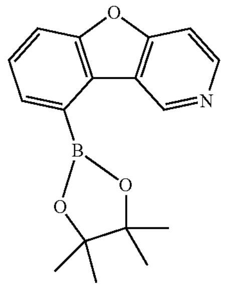

+

Z

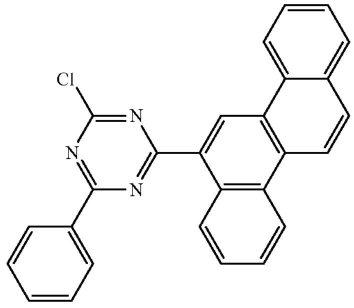

Trz33

Pd(t-Bu$_3$P)$_2$,
$K_2CO_3$(aq.)
THF

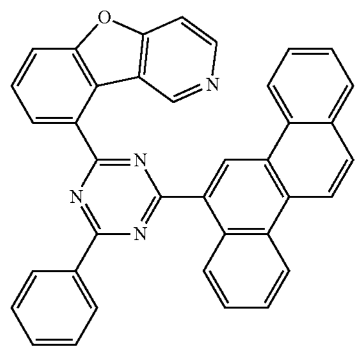

47

Compound Z (15 g, 50.8 mmol) and Trz33 (22.3 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 19.3 g of Compound 47. (Yield: 69%, MS: $[M+H]^+$=551)

SYNTHESIS EXAMPLE 48: PREPARATION OF COMPOUND 48

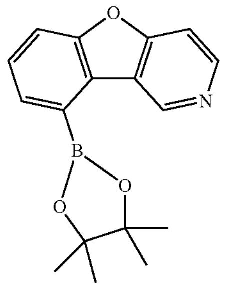

+

Z

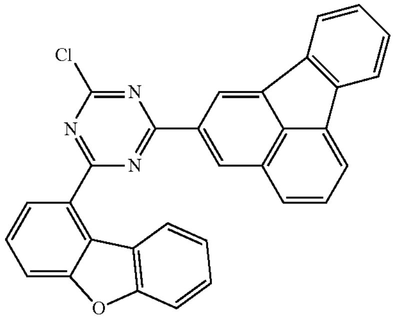

Trz34

Pd(t-Bu$_3$P)$_2$,
$K_2CO_3$(aq.)
THF

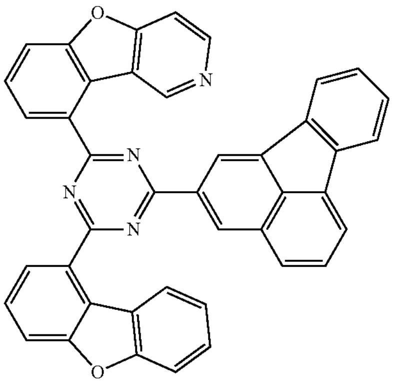

48

Compound Z (15 g, 50.8 mmol) and Trz34 (25.7 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 23.1 g of Compound 48. (Yield: 74%, MS: $[M+H]^+$=615)

SYNTHESIS EXAMPLE 49: PREPARATION OF COMPOUND 49

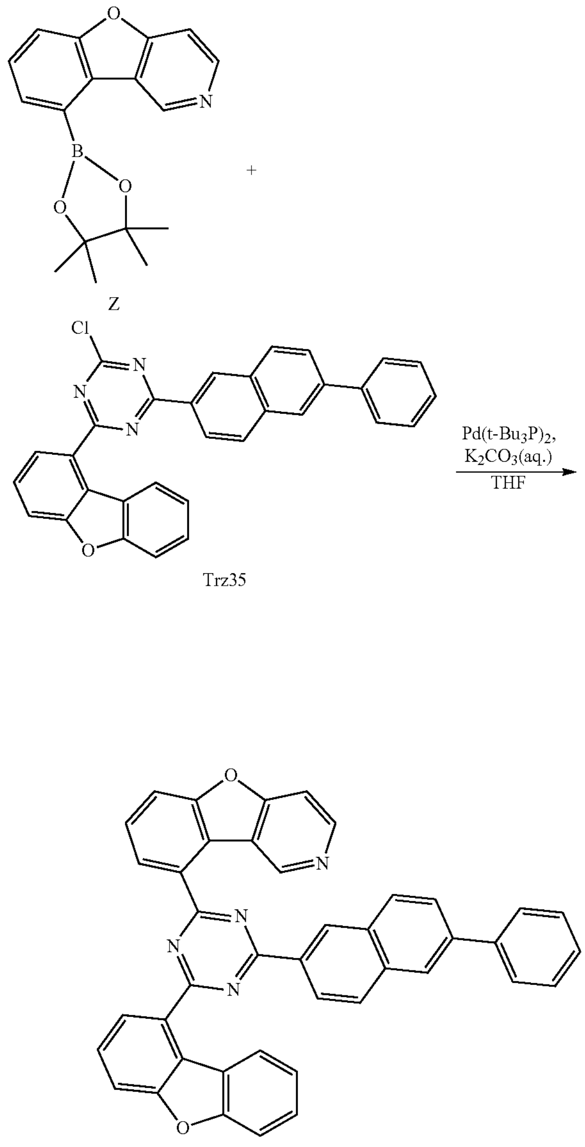

Z

Trz35

49

Compound Z (15 g, 50.8 mmol) and Trz35 (25.8 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 22.9 g of Compound 49. (Yield: 73%, MS: $[M+H]^+$=617)

SYNTHESIS EXAMPLE 50: PREPARATION OF COMPOUND 50

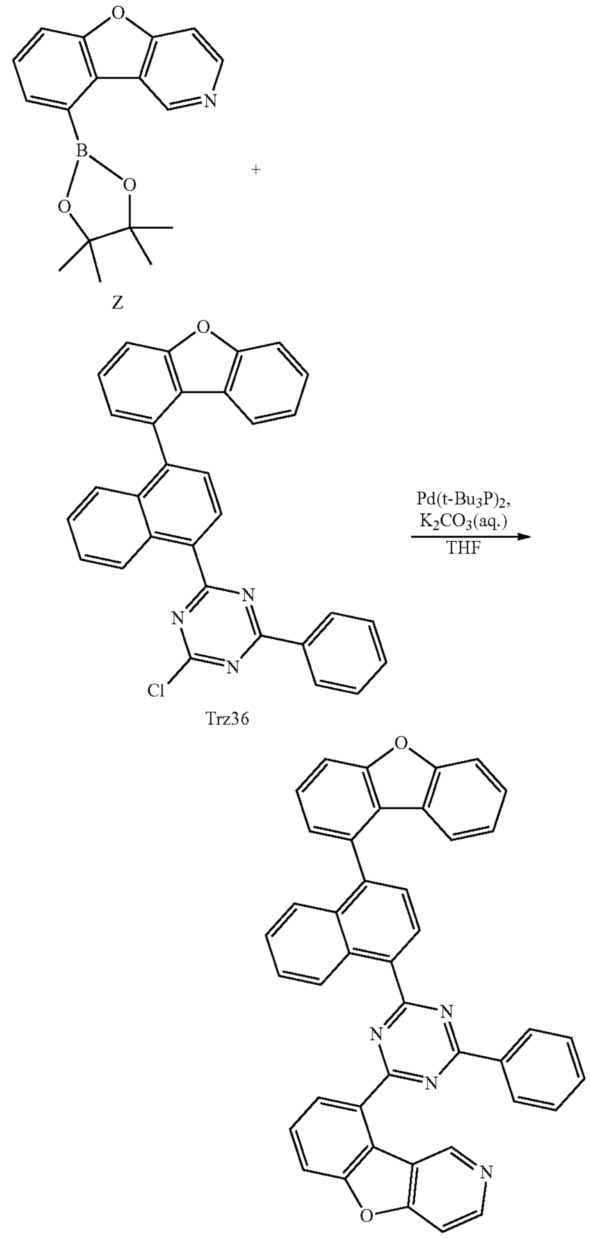

Z

Trz36

50

Compound Z (15 g, 50.8 mmol) and Trz36 (25.8 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 19.4 g of Compound 50. (Yield: 62%, MS: $[M+H]^+$=617)

SYNTHESIS EXAMPLE 51: PREPARATION OF COMPOUND 51

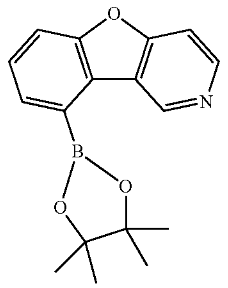

Z

+

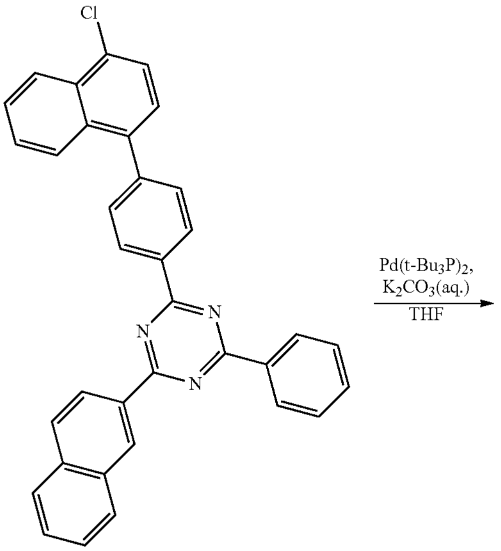

Trz37

-continued

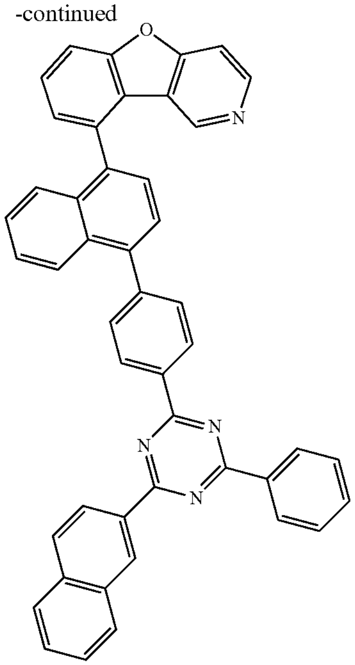

51

Compound Z (15 g, 50.8 mmol) and Trz37 (27.8 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 19.9 g of Compound 51. (Yield: 60%, MS: $[M+H]^+$=653)

SYNTHESIS EXAMPLE 52: PREPARATION OF COMPOUND 52

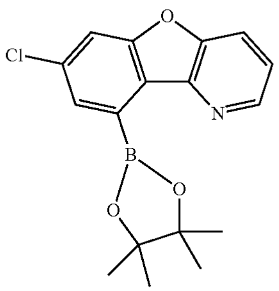

AA

+

-continued

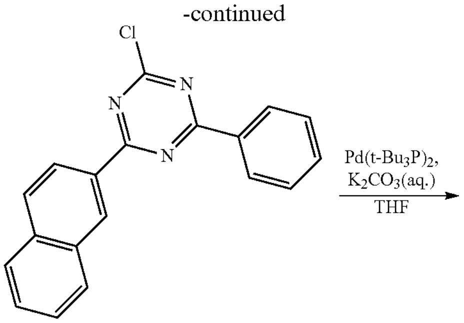

Trzl

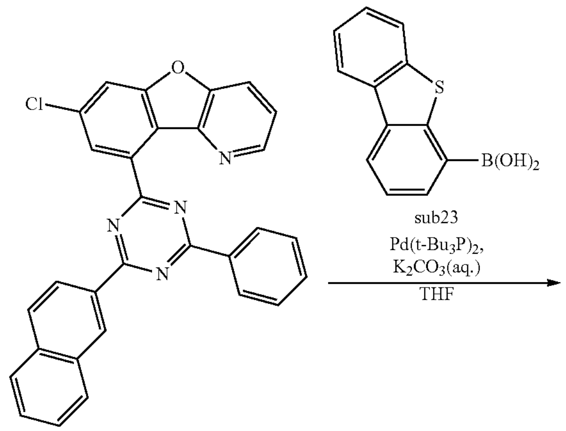

subAA-1

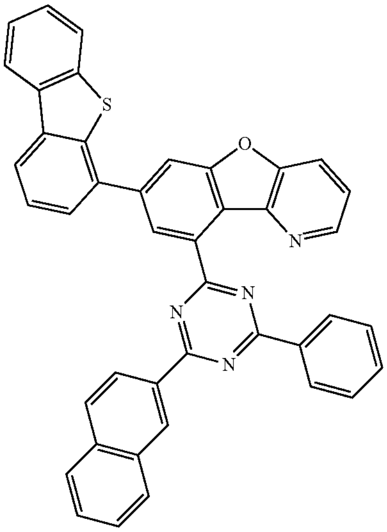

52

Compound AA (15 g, 45.5 mmol) and Trz1 (15.2 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 17.2 g of subAA-1. (Yield: 78%, MS: $[M+H]^+=485$)

Next, subAA-1 (15 g, 30.9 mmol) and sub23 (7.4 g, 32.5 mmol) were added to 300 mL of THF under a nitrogen atmosphere, and the mixture was stirred and refluxed. Then, potassium carbonate (12.8 g, 92.8 mmol) was dissolved in 38 of water, added thereto, sufficiently stirred, and then bis(tri-tert-butylphosphine)palladium(0) (0.2 g, 0.3 mmol) was added. After reacting for 12 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.9 g of Compound 52. (Yield: 71%, MS: $[M+H]^+=633$)

SYNTHESIS EXAMPLE 53: PREPARATION OF COMPOUND 53

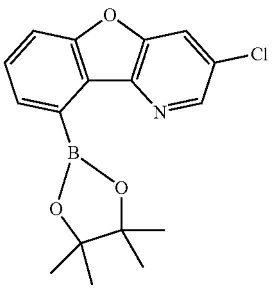

AB

+

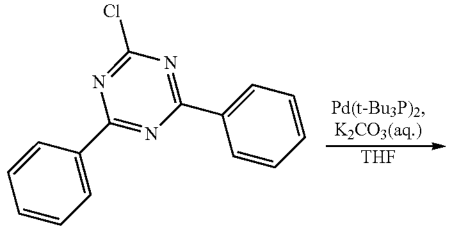

Trz2

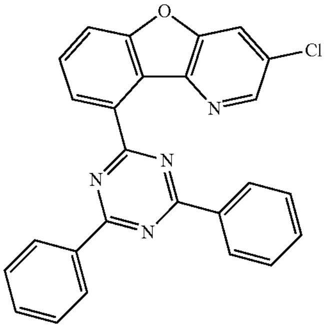

subAB-1

-continued

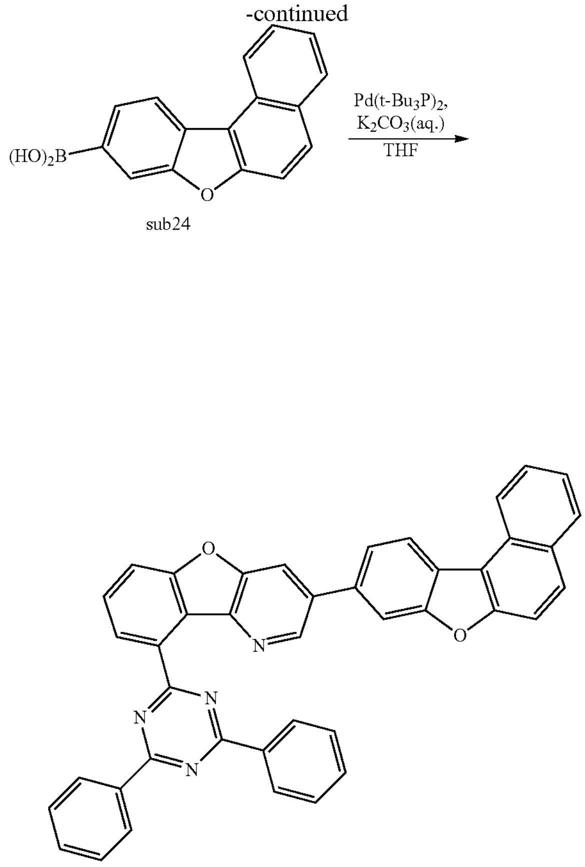

sub24

53

Compound AB (15 g, 45.5 mmol) and Trz2 (12.8 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 14 g of subAB-1. (Yield: 71%, MS: $[M+H]^+$=435)

Next, subAB-1 (10 g, 23 mmol), sub24 (6.3 g, 24.1 mmol) and sodium tert-butoxide (2.9 g, 29.9 mmol) were added to 200 mL of xylene under a nitrogen atmosphere, and the mixture was stirred and refluxed. Then, bis(tri-tert-butylphosphine)palladium(0) (0.1 g, 0.2 mmol) was added thereto. When the reaction was completed after 5 hours, the reaction mixture was cooled to room temperature, and the solvent was removed under reduced pressure. Then, the compound was again completely dissolved in chloroform, washed twice with water, and then the organic layer was separated, treated with anhydrous magnesium sulfate and then filtered, and the filtrate was distilled under reduced pressure. The concentrated compound was purified by silica gel column chromatography to give 8.6 g of Compound 53. (Yield: 61%, MS: $[M+H]^+$=617)

SYNTHESIS EXAMPLE 54: PREPARATION OF COMPOUND 54

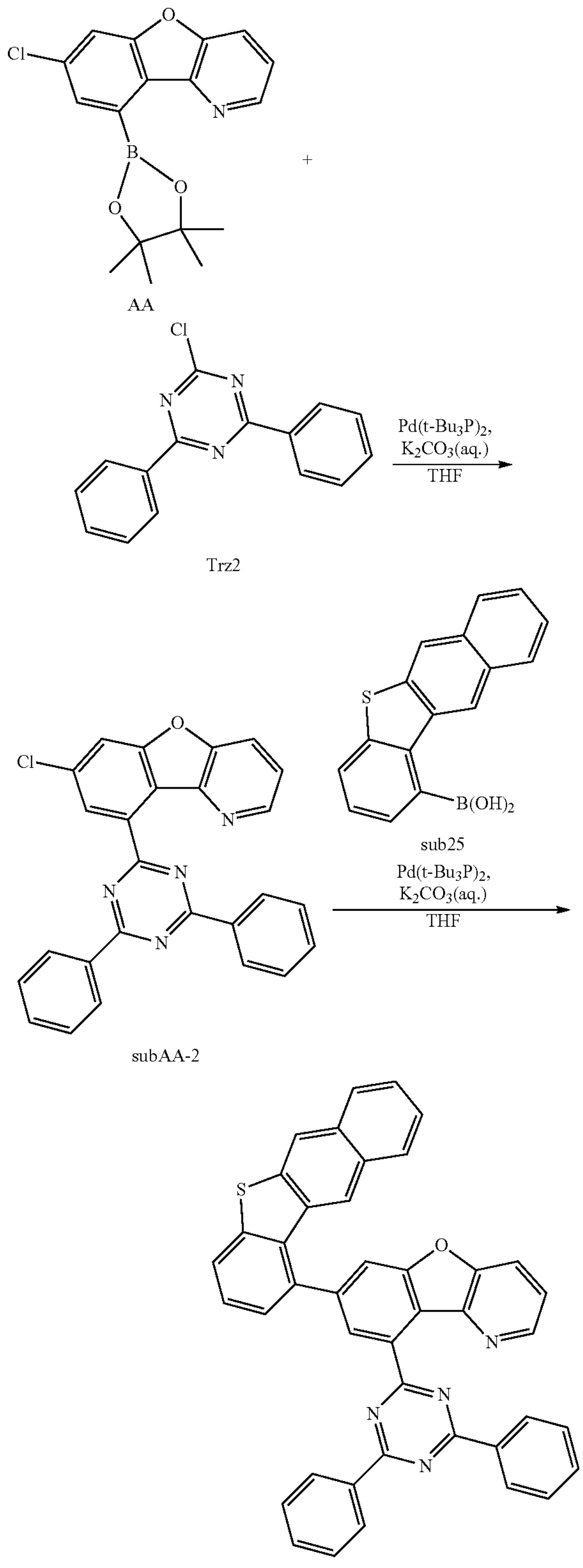

AA

Trz2 sub25 subAA-2

54

Compound AA (15 g, 45.5 mmol) and Trz2 (12.8 g, 47.8 mmol) were added to 300 mL of THF under a nitrogen atmosphere, and the mixture was stirred and refluxed. Then, potassium carbonate (18.9 g, 136.5 mmol) was dissolved in 57 of water, added thereto, sufficiently stirred, and then bis(tri-tert-butylphosphine)palladium(0) (0.2 g, 0.5 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 12.6 g of subAA-2 (Yield: 64%, MS: $[M+H]^+=435$)

Next, subAA-2 (15 g, 34.5 mmol) and sub25 (10.1 g, 36.2 mmol) were added to 300 mL of THF under a nitrogen atmosphere, and the mixture was stirred and refluxed. Then, potassium carbonate (14.3 g, 103.5 mmol) was dissolved in 43 of water, added thereto, sufficiently stirred, and then bis(tri-tert-butylphosphine)palladium(0) (0.2 g, 0.3 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.3 g of Compound 54. (Yield: 61%, MS: $[M+H]^+=633$)

SYNTHESIS EXAMPLE 55: PREPARATION OF COMPOUND 55

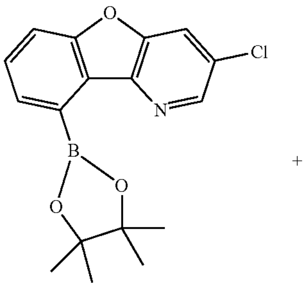

AB

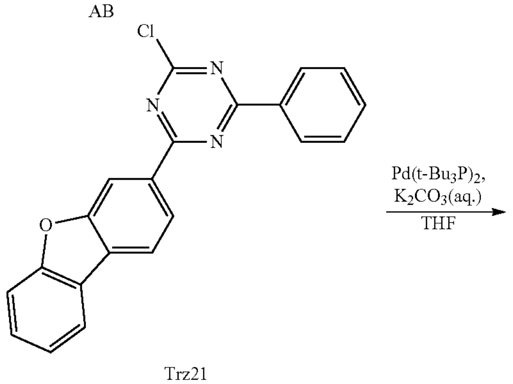

Trz21

-continued

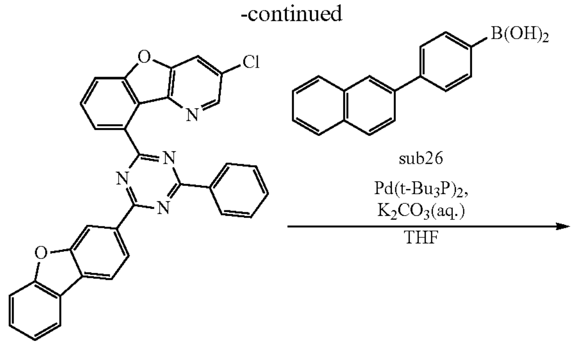

subAB-2

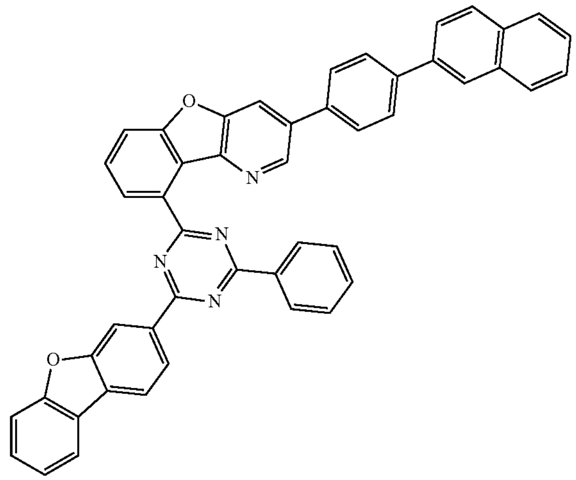

55

Compound AB (15 g, 45.5 mmol) and Trz21 (17.1 g, 47.8 mmol) were added to 300 mL of THF under a nitrogen atmosphere, and the mixture was stirred and refluxed. Then, potassium carbonate (18.9 g, 136.5 mmol) was dissolved in 57 of water, added thereto, sufficiently stirred, and then bis(tri-tert-butylphosphine)palladium(0) (0.2 g, 0.5 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 15.5 g of subAB-2 (Yield: 65%, MS: $[M+H]^+=525$)

Next, subAB-2 (15 g, 28.6 mmol) and sub26 (7.4 g, 30 mmol) were added to 300 mL of THF under a nitrogen atmosphere, and the mixture was stirred and refluxed. Then, potassium carbonate (11.8 g, 85.7 mmol) was dissolved in 36 mL of water, added thereto, sufficiently stirred, and then bis(tri-tert-butylphosphine)palladium(0) (0.1 g, 0.3 mmol) was added. After reacting for 8 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 12.5 g of Compound 55. (Yield: 63%, MS: $[M+H]^+$=693)

SYNTHESIS EXAMPLE 56: PREPARATION OF COMPOUND 56

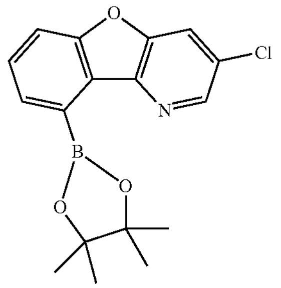

AB

+

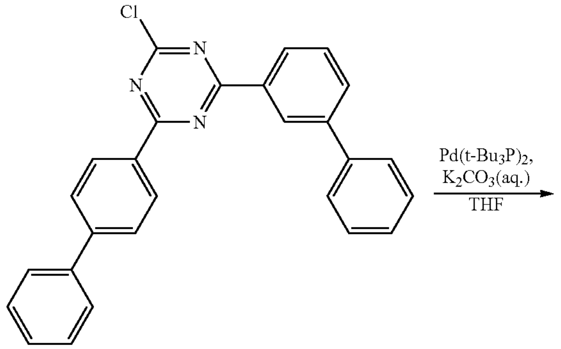

Trz38

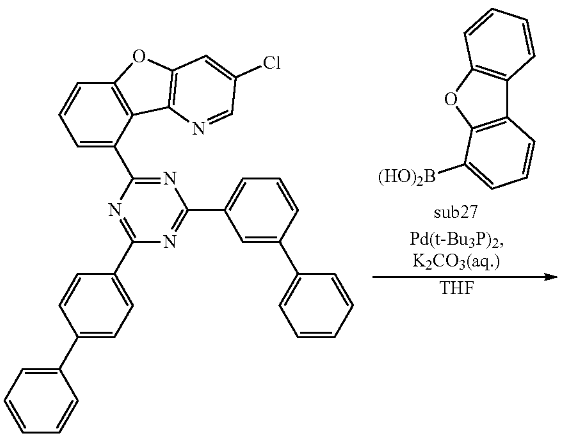

subAB-3

-continued

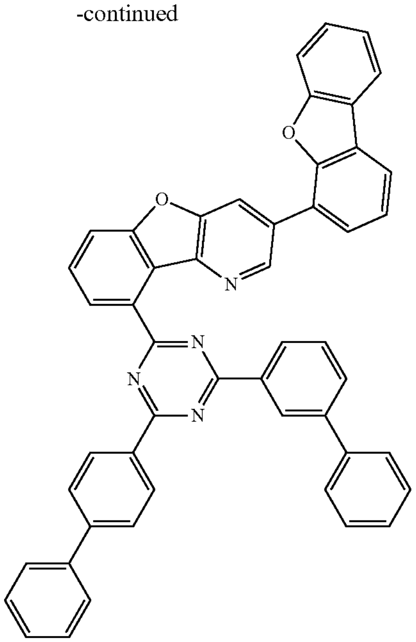

56

Compound AB (15 g, 45.5 mmol) and Trz38 (20.1 g, 47.8 mmol) were added to 300 mL of THF under a nitrogen atmosphere, and the mixture was stirred and refluxed. Then, potassium carbonate (18.9 g, 136.5 mmol) was dissolved in 57 mL of water, added thereto, sufficiently stirred, and then bis(tri-tert-butylphosphine)palladium(0) (0.2 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 18.4 g of subAB-3 (Yield: 69%, MS: $[M+H]^+$=587)

Next, subAB-3 (15 g, 25.6 mmol) and sub27 (5.7 g, 26.8 mmol) were added to 300 mL of THF under a nitrogen atmosphere, and the mixture was stirred and refluxed. Then, potassium carbonate (10.6 g, 76.7 mmol) was dissolved in 32 of water, added thereto, sufficiently stirred, and then bis(tri-tert-butylphosphine)palladium(0) (0.1 g, 0.3 mmol) was added. After reacting for 11 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 13.4 g of Compound 56. (Yield: 73%, MS: $[M+H]^+$=719)

SYNTHESIS EXAMPLE 57: PREPARATION OF COMPOUND 57

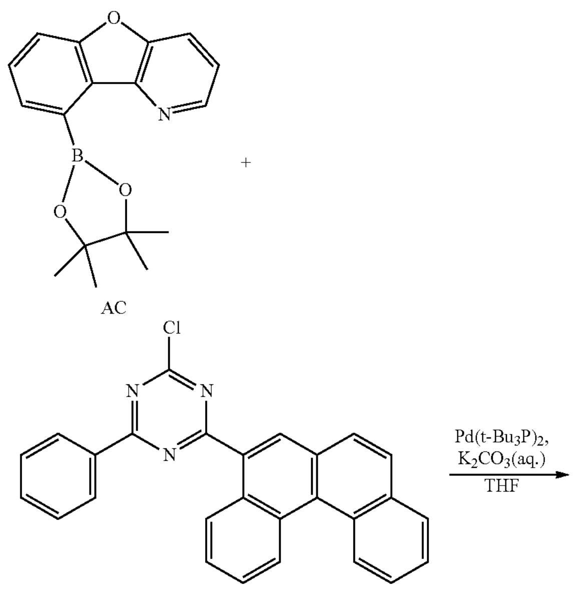

AC

Trz39

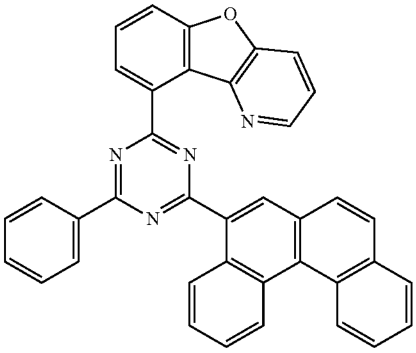

57

Compound AC (15 g, 50.8 mmol) and Trz39 (22.3 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 22.1 g of Compound 57. (Yield: 79%, MS: $[M+H]^+=551$)

SYNTHESIS EXAMPLE 58: PREPARATION OF COMPOUND 58

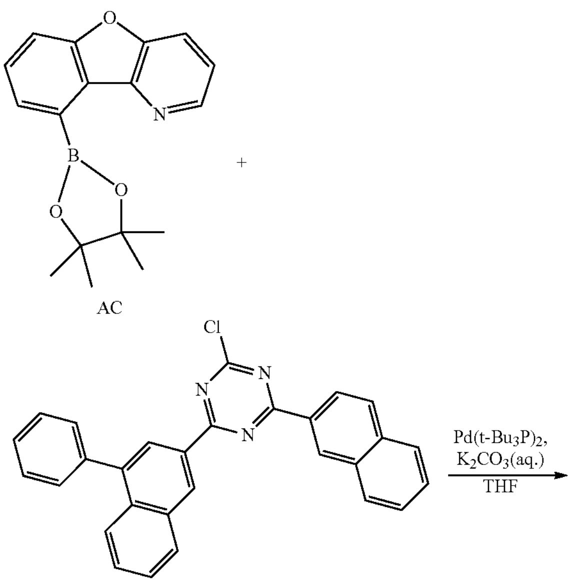

AC

Trz40

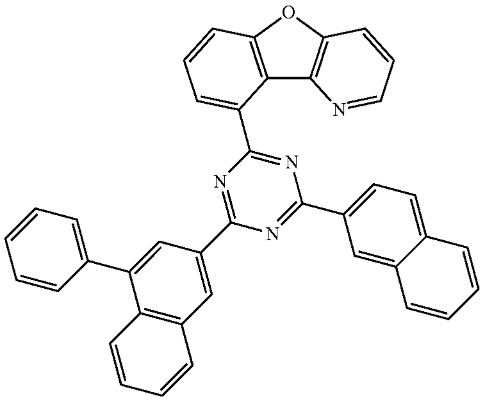

58

Compound AC (15 g, 50.8 mmol) and Trz40 (23.7 g, 53.4 mmol) were added to 300 mL of THF under a nitrogen atmosphere, and the mixture was stirred and refluxed. Then, potassium carbonate (21.1 g, 152.5 mmol) was dissolved in 63 of water, added thereto, sufficiently stirred, and then bis(tri-tert-butylphosphine)palladium(0) (0.3 g, 0.5 mmol) was added. After reacting for 10 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 19.3 g of Compound 58. (Yield: 66%, MS: $[M+H]^+=577$)

SYNTHESIS EXAMPLE 59: PREPARATION OF COMPOUND 59

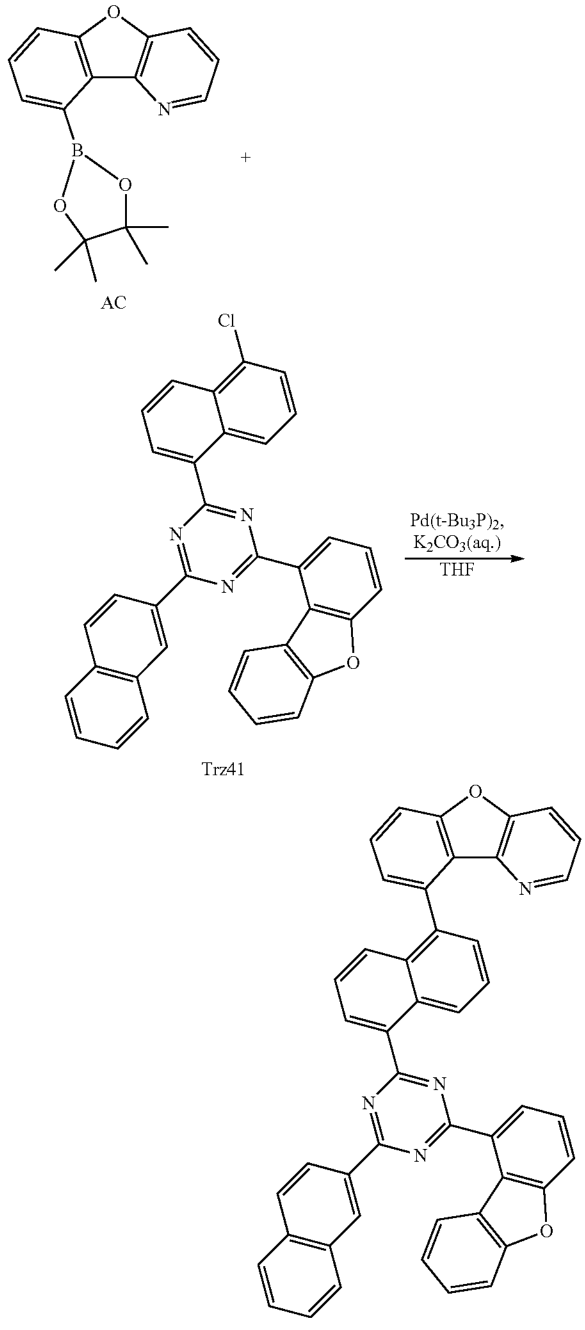

AC

Trz41

59

Compound AC (15 g, 50.8 mmol) and Trz41 (28.5 g, 53.4 mmol) were added to 300 mL of THF under a nitrogen atmosphere, and the mixture was stirred and refluxed. Then, potassium carbonate (21.1 g, 152.5 mmol) was dissolved in 63 mL of water, added thereto, sufficiently stirred, and then bis(tri-tert-butylphosphine)palladium(0) (0.3 g, 0.5 mmol) was added. After reacting for 9 hours, the reaction mixture was cooled to room temperature, the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 24.7 g of Compound 59. (Yield: 73%, MS: $[M+H]^+$=667)

EXAMPLE 1

A glass substrate on which a thin film of ITO (indium tin oxide) was coated in a thickness of 1,000 A was put into distilled water containing a detergent dissolved therein and ultrasonically washed. In this case, the detergent used was a product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, the following Compound HI-1 was formed to a thickness of 1150 Å as a hole injection layer, but the following Compound A-1 was p-doped at a concentration of 1.5 wt. %. The following Compound HT-1 was vacuum deposited on the hole injection layer to form a hole transport layer with a film thickness of 800 Å. Then, the following Compound EB-1 was vacuum deposited to a film thickness of 150 Å on the hole transport layer to form an electron blocking layer.

Then, the Compound 1 prepared in Synthesis Example 1, and the following Compound Dp-7 were vacuum deposited in a weight ratio of 98:2 on the electron blocking layer to form a red light emitting layer with a thickness of 400 Å.

The following Compound HB-1 was vacuum deposited to a film thickness of 30 Å on the light emitting layer to form a hole blocking layer. Then, the following Compound ET-1 and the following Compound LiQ were vacuum deposited in a weight ratio of 2:1 on the hole blocking layer to form an electron injection and transport layer with a film thickness of 300 Å. Lithium fluoride (LiF) and aluminum were sequentially deposited to have a thickness of 12 Å and 1,000 Å, respectively, on the electron injection and transport layer, thereby forming a cathode.

HI-1

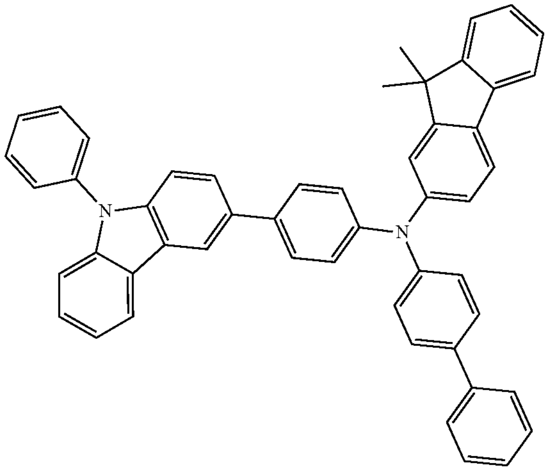

-continued

A-1

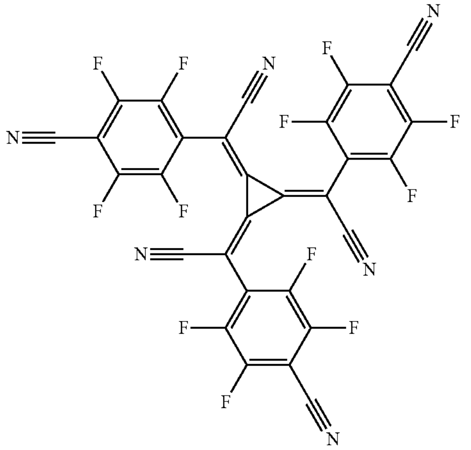

HT-1

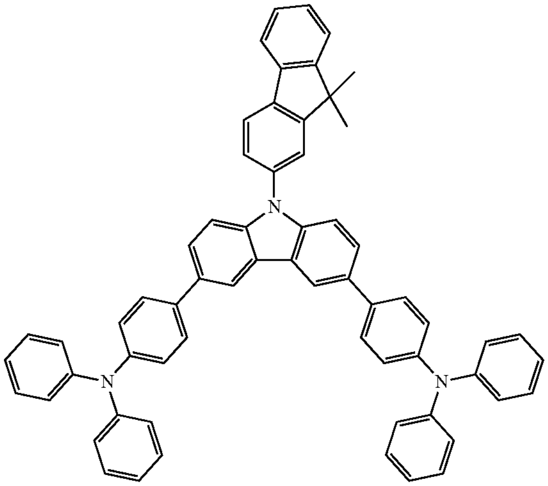

EB-1

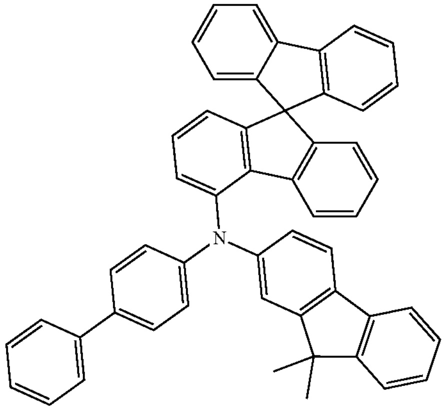

-continued

Dp-7

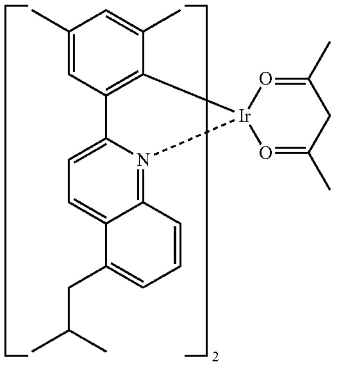

HB-1

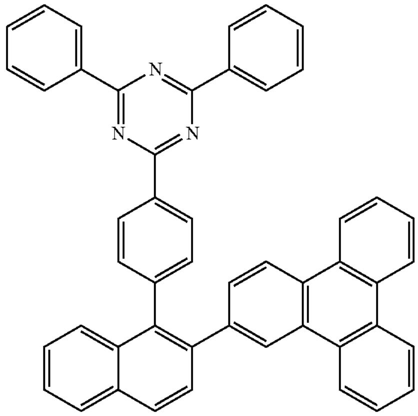

ET-1

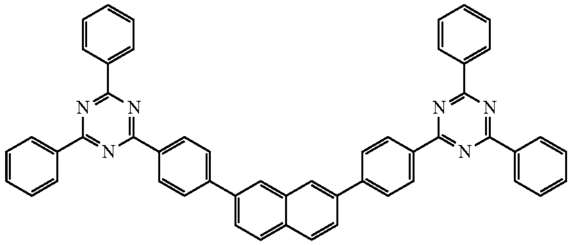

LiQ

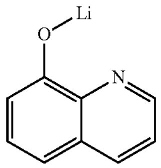

In the above-mentioned processes, the deposition rates of the organic materials were maintained at 0.4 to 0.7 Å/sec, the deposition rates of lithium fluoride and the aluminum of the cathode were maintained at 0.3 Å/sec and 2 Å/sec, respectively, and the degree of vacuum during the deposition was maintained at $2\times10^{-7}$ to $5\times10^{-6}$ torr, thereby manufacturing an organic light emitting device.

EXAMPLES 2 to 59

The organic light emitting devices were manufactured in the same manner as in Example 1, except that the compounds shown in Table 1 below were used instead of Compound 1 in the organic light emitting device of Example 1.

COMPARATIVE EXAMPLES 1 to 8
The organic light emitting devices were manufactured in the same manner as in Example 1, except that the compounds shown in Table 1 below were used instead of Compound 1 in the organic light emitting device of Example 1.
C-1
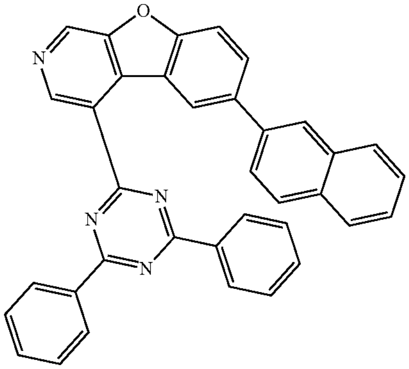
C-2
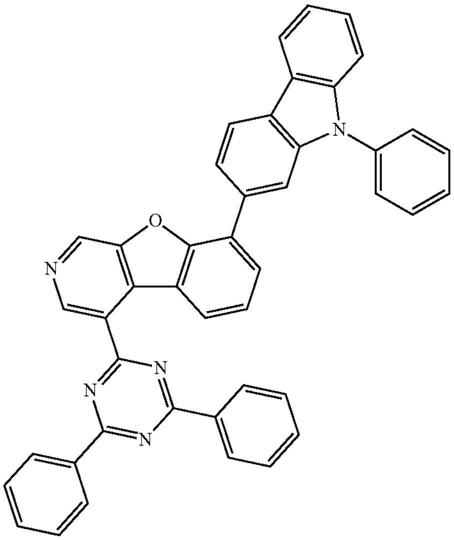
-continued
C-3
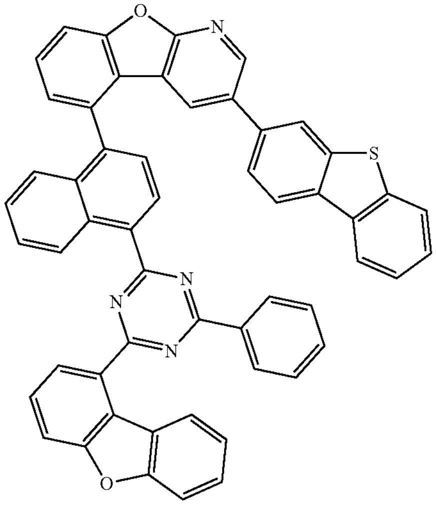
C-4
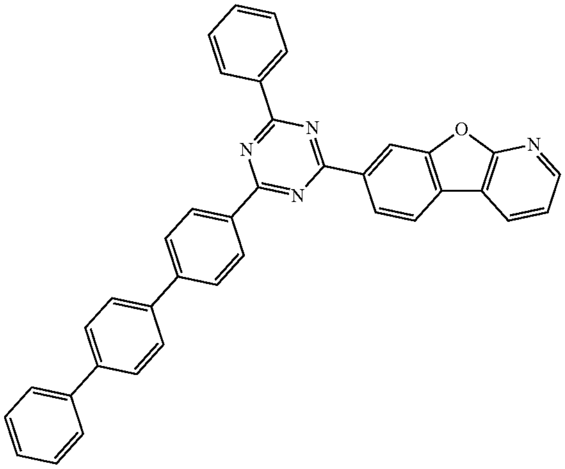
C-5
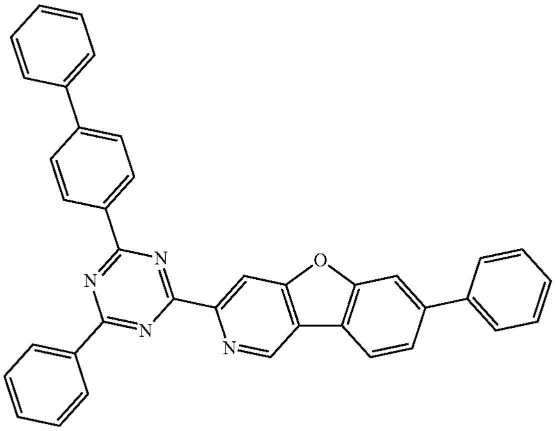

-continued

C-6

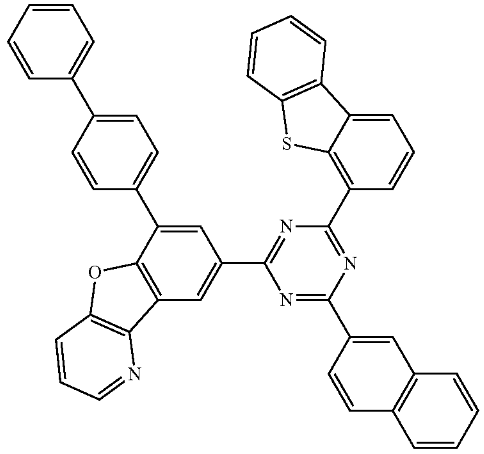

C-7

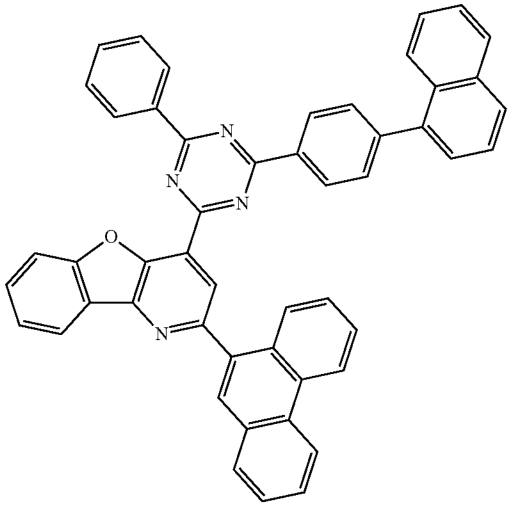

-continued

C-8

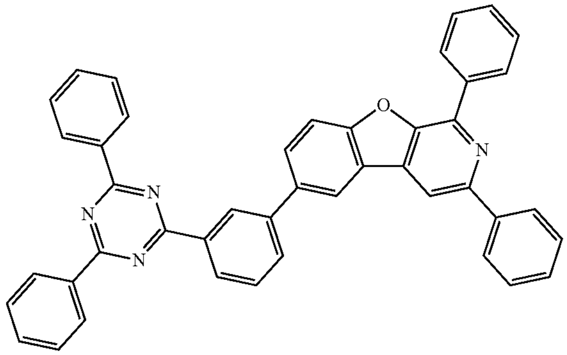

EXPERIMENTAL EXAMPLE

The driving voltage and efficiency were measured by applying a current (15 mA/$cm^2$) to the organic light emitting devices manufactured in the Examples 1 to 59 and Comparative Examples 1 to 8, and the results are shown in Table 1 below. T95 means the time required for the luminance to be reduced to 95% of the initial luminance (6000 nit).

TABLE 1

| Category | Material | Driving voltage (V) | Efficiency (cd/A) | Lifetime T95 (hr) | Luminescent color |
|---|---|---|---|---|---|
| Example 1 | Compound 1 | 3.93 | 18.1 | 124 | Red |
| Example 2 | Compound 2 | 3.90 | 18.5 | 117 | Red |
| Example 3 | Compound 3 | 3.92 | 18.6 | 120 | Red |
| Example 4 | Compound 4 | 3.98 | 19.0 | 123 | Red |
| Example 5 | Compound 5 | 3.87 | 18.8 | 112 | Red |
| Example 6 | Compound 6 | 3.83 | 19.1 | 131 | Red |
| Example 7 | Compound 7 | 3.95 | 19.2 | 126 | Red |
| Example 8 | Compound 8 | 3.91 | 18.8 | 117 | Red |
| Example 9 | Compound 9 | 3.84 | 18.9 | 125 | Red |
| Example 10 | Compound 10 | 3.80 | 20.2 | 147 | Red |
| Example 11 | Compound 11 | 3.78 | 19.7 | 138 | Red |
| Example 12 | Compound 12 | 3.61 | 23.2 | 235 | Red |
| Example 13 | Compound 13 | 3.87 | 19.8 | 123 | Red |
| Example 14 | Compound 14 | 3.71 | 20.1 | 141 | Red |
| Example 15 | Compound 15 | 3.68 | 20.4 | 118 | Red |
| Example 16 | Compound 16 | 3.89 | 18.3 | 165 | Red |
| Example 17 | Compound 17 | 4.01 | 17.1 | 138 | Red |
| Example 18 | Compound 18 | 3.91 | 17.6 | 151 | Red |
| Example 19 | Compound 19 | 3.87 | 19.1 | 178 | Red |
| Example 20 | Compound 20 | 3.95 | 18.3 | 122 | Red |
| Example 21 | Compound 21 | 3.83 | 19.5 | 209 | Red |
| Example 22 | Compound 22 | 4.12 | 17.2 | 128 | Red |
| Example 23 | Compound 23 | 3.95 | 20.2 | 171 | Red |
| Example 24 | Compound 24 | 3.92 | 20.6 | 184 | Red |
| Example 25 | Compound 25 | 3.68 | 21.2 | 198 | Red |
| Example 26 | Compound 26 | 3.88 | 17.8 | 155 | Red |

TABLE 1-continued

| Category | Material | Driving voltage (V) | Efficiency (cd/A) | Lifetime T95 (hr) | Luminescent color |
|---|---|---|---|---|---|
| Example 27 | Compound 27 | 3.81 | 17.4 | 178 | Red |
| Example 28 | Compound 28 | 3.85 | 18.0 | 185 | Red |
| Example 29 | Compound 29 | 3.75 | 21.5 | 201 | Red |
| Example 30 | Compound 30 | 3.97 | 17.1 | 142 | Red |
| Example 31 | Compound 31 | 3.90 | 18.2 | 160 | Red |
| Example 32 | Compound 32 | 3.81 | 19.0 | 173 | Red |
| Example 33 | Compound 33 | 3.88 | 18.0 | 147 | Red |
| Example 34 | Compound 34 | 3.83 | 18.3 | 172 | Red |
| Example 35 | Compound 35 | 3.76 | 19.2 | 188 | Red |
| Example 36 | Compound 36 | 3.80 | 18.8 | 195 | Red |
| Example 37 | Compound 37 | 3.98 | 17.3 | 138 | Red |
| Example 38 | Compound 38 | 3.84 | 18.8 | 165 | Red |
| Example 39 | Compound 39 | 3.71 | 19.1 | 188 | Red |
| Example 40 | Compound 40 | 3.85 | 17.9 | 132 | Red |
| Example 41 | Compound 41 | 3.80 | 18.6 | 157 | Red |
| Example 42 | Compound 42 | 3.84 | 19.1 | 153 | Red |
| Example 43 | Compound 43 | 3.87 | 18.8 | 136 | Red |
| Example 44 | Compound 44 | 3.71 | 19.0 | 172 | Red |
| Example 45 | Compound 45 | 3.90 | 17.7 | 121 | Red |
| Example 46 | Compound 46 | 3.83 | 18.0 | 130 | Red |
| Example 47 | Compound 47 | 3.62 | 19.3 | 188 | Red |
| Example 48 | Compound 48 | 3.66 | 19.8 | 203 | Red |
| Example 49 | Compound 49 | 3.70 | 20.2 | 190 | Red |
| Example 50 | Compound 50 | 3.74 | 19.1 | 172 | Red |
| Example 51 | Compound 51 | 3.73 | 18.6 | 160 | Red |
| Example 52 | Compound 52 | 3.94 | 17.1 | 134 | Red |
| Example 53 | Compound 53 | 3.89 | 18.0 | 175 | Red |
| Example 54 | Compound 54 | 3.87 | 18.7 | 161 | Red |
| Example 55 | Compound 55 | 3.83 | 17.3 | 133 | Red |
| Example 56 | Compound 56 | 3.79 | 17.6 | 116 | Red |
| Example 57 | Compound 57 | 3.67 | 19.8 | 197 | Red |
| Example 58 | Compound 58 | 3.64 | 19.2 | 183 | Red |
| Example 59 | Compound 59 | 3.78 | 18.0 | 157 | Red |
| Comparative Example 1 | C-1 | 4.27 | 16.0 | 97 | Red |
| Comparative Example 2 | C-2 | 4.33 | 16.3 | 101 | Red |
| Comparative Example 3 | C-3 | 4.41 | 15.1 | 86 | Red |
| Comparative Example 4 | C-4 | 4.26 | 13.4 | 67 | Red |
| Comparative Example 5 | C-5 | 4.31 | 14.0 | 61 | Red |
| Comparative Example 6 | C-6 | 4.48 | 13.2 | 38 | Red |
| Comparative Example 7 | C-7 | 4.29 | 16.5 | 98 | Red |
| Comparative Example 8 | C-8 | 4.40 | 14.2 | 55 | Red |

As shown in Table 1, it was confirmed that the organic light emitting devices of the Examples using the compound of Chemical Formula 1 as a host material of the light emitting layer exhibited excellent luminous efficiency and remarkably improved lifetime characteristics, as compared with the organic light emitting devices of Comparative Examples using the compounds not included in Chemical Formula 1.

Specifically, considering that the device according to the Examples exhibited a remarkably lowered driving voltage and improved efficiency characteristics, as compared with Comparative Examples in which Comparative Example Compounds C-1 to C-8 were employed as the host material of the light emitting layer, it can be seen that energy transfer from the compound of Chemical Formula 1, which is the host material, to the red dopant was effectively performed. In addition, considering that the organic light emitting devices of the Examples were improved in lifetime characteristics as well as the efficiency, it is judged that the compound of Chemical Formula 1 also has high stability to electrons and holes. Therefore, when the material of Chemical Formula 1 is used as the host material of the organic light emitting device, it can be confirmed that the driving voltage, luminous efficiency and lifetime characteristics of the organic light emitting device can be improved. In general, considering that the luminous efficiency and lifetime characteristics of an organic light emitting devices have a trade-off relationship with each other, this can be considered that the organic light emitting devices of the Examples exhibit remarkably improved device characteristics as compared with the devices of Comparative Examples.

DESCRIPTION OF SYMBOLS

1: substrate
2: anode
3: light emitting layer
4: cathode
5: hole injection layer
6: hole transport layer
7: electron blocking layer
8: hole blocking layer
9: electron injection and transport layer

The invention claimed is:

1. A compound of Chemical Formula 1:

[Chemical Formula 1]

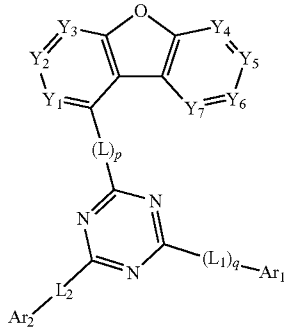

wherein, in Chemical Formula 1:

one of $Y_1$ to $Y_5$ is N, and the rest are each independently C—H, or C-D, and $Y_6$ and $Y_7$ are each independently C—H or C-D; or one of $Y_1$ to $Y_5$ is N, one of the rest is C-L'-R, and the rest are each independently C—H or C-D, and $Y_6$ and $Y_7$ are each independently C—H or C-D; or $Y_1$ to $Y_5$ are each independently C—H, or C-D, one of $Y_6$ and $Y_7$ is N and the other are C—H or C-D; or one of $Y_1$ to $Y_5$ is C-L'-R, and the rest are each independently C—H, or C-D, and one of $Y_6$ and $Y_7$ is N, and the other is C—H or C-D;

L' is a single bond or a substituted or unsubstituted $C_{6-60}$ arylene;

R is a substituted or unsubstituted $C_{6-60}$ aryl or a substituted or unsubstituted $C_{2-60}$ heteroaryl containing any one or more heteroatoms selected from the group consisting of N, O and S, provided that R is not 9-phenylcarbazolyl;

L is a single bond or a $C_{6-20}$ arylene that is unsubstituted or substituted with deuterium;

$L_1$ and $L_2$ are each independently a single bond or a substituted or unsubstituted $C_{6-60}$ arylene;

$Ar_1$ and $Ar_2$ are each independently a substituted or unsubstituted $C_{6-60}$ aryl or a substituted or unsubstituted $C_{2-60}$ heteroaryl containing any one or more heteroatoms selected from the group consisting of N, O and S; and p and q are each independently an integer of 0 to 2.

2. The compound of claim 1, wherein:

L' is a single bond, phenylene that is unsubstituted or substituted with deuterium, or naphthylene that is unsubstituted or substituted with deuterium.

3. The compound of claim 1, wherein:

R is any one structure selected from the group consisting of the following:

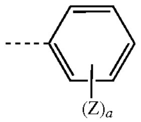

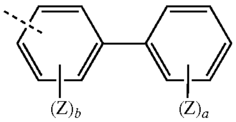

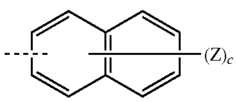

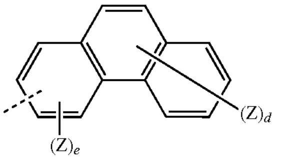

-continued

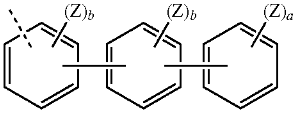

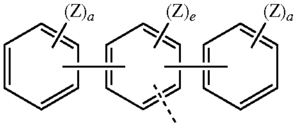

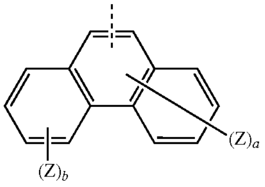

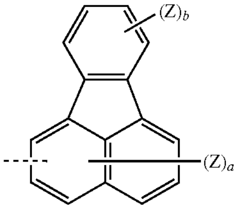

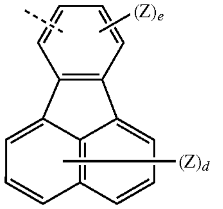

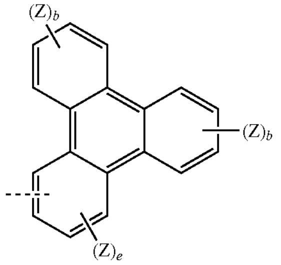

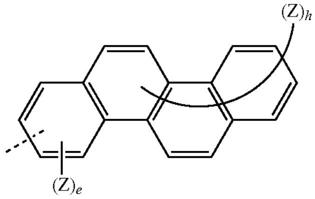

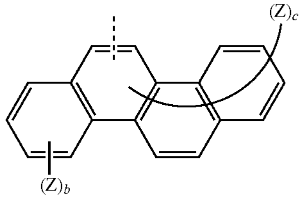

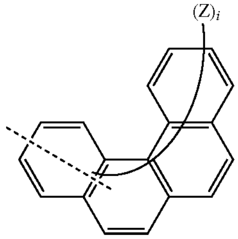

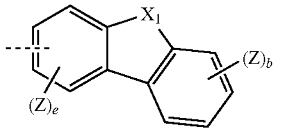

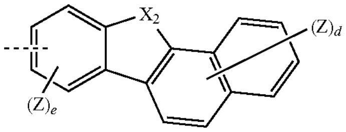

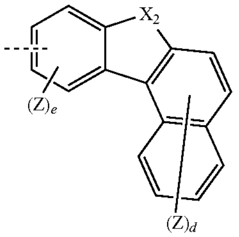

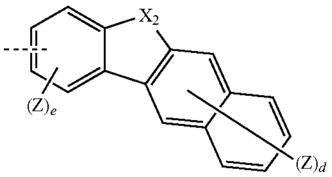

-continued

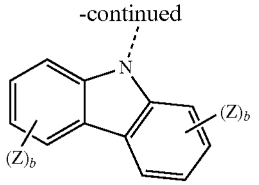

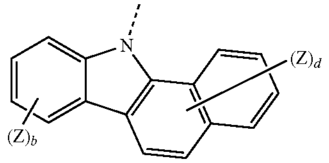

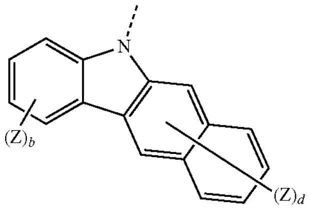

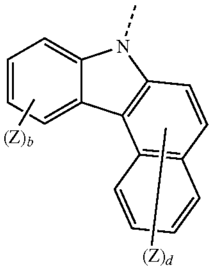

wherein:

$X_1$ is O or S;

$X_2$ is O, S, or N(phenyl);

each Z is independently deuterium (D), a $C_{1-10}$ alkyl, or a $C_{6-20}$ aryl;

each a is independently an integer of 0 to 5;

each b is independently an integer of 0 to 4;

each c is independently an integer of 0 to 7;

each d is independently an integer of 0 to 6;

each e is independently an integer of 0 to 3;

h is an integer of 0 to 8; and i is an integer of 0 to 11.

4. The compound of claim 1, wherein:

L is a single bond, or any one structure selected from the group consisting of the following:

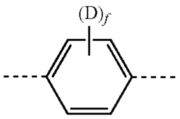

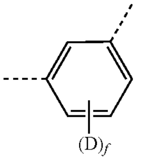

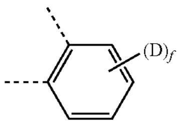

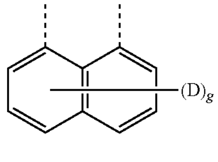

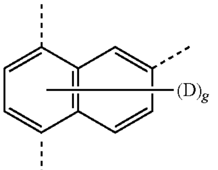

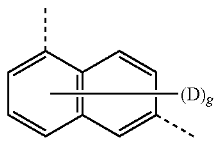

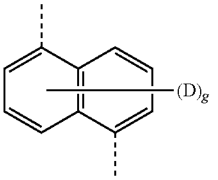

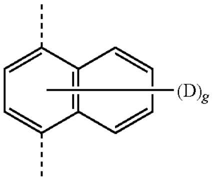

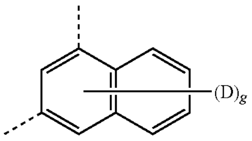

-continued

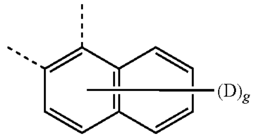

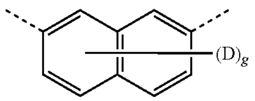

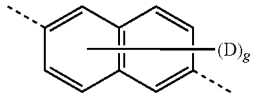

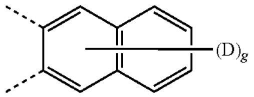

wherein:

D means deuterium;

each f is independently an integer of 0 to 4; and each g is independently an integer of 0 to 6.

5. The compound of claim 1, wherein:

$L_1$ and $L_2$ are each independently a single bond; phenylene that is unsubstituted or substituted with deuterium; biphenyldiyl that is unsubstituted or substituted with deuterium;

or naphthylene that is unsubstituted or substituted with deuterium.

6. The compound of claim 1, wherein:

$Ar_1$ and $Ar_2$ are each independently phenyl, biphenylyl, terphenylyl, naphthyl, phenanthryl, chrysenyl, benzo[c]phenanthrenyl, fluoranthenyl, dibenzofuranyl, dibenzothiophenyl, benzonaphthofuranyl, benzonaphthothiophenyl, carbazolyl, or benzocarbazolyl, where $Ar_1$ and $Ar_2$ are unsubstituted or substituted with one or more substituents selected from the group consisting of deuterium, a $C_{1-10}$ alkyl and a $C_{6-20}$ aryl.

7. The compound of claim 1, wherein:

one of $Ar_1$ and $Ar_2$ is phenyl, biphenylyl, or naphthyl.

8. The compound of claim 1, wherein:

the compound is any one of the following Chemical Formulas 1-1 to 1-7:

1-1

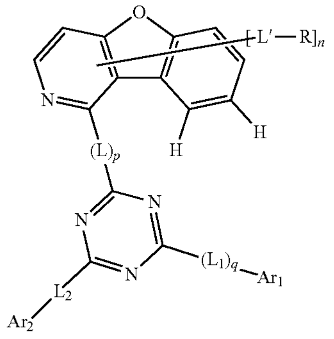

1-2

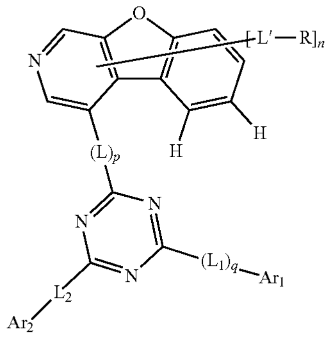

-continued
1-3
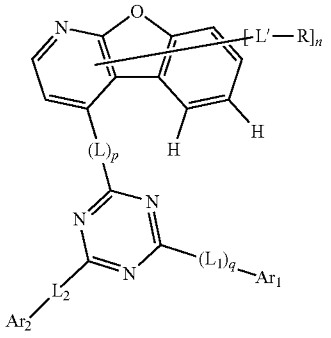
1-4
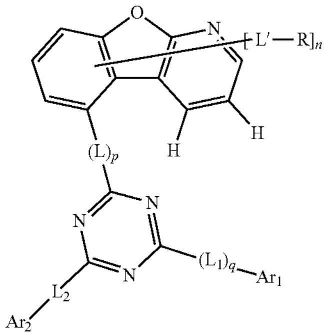
1-5
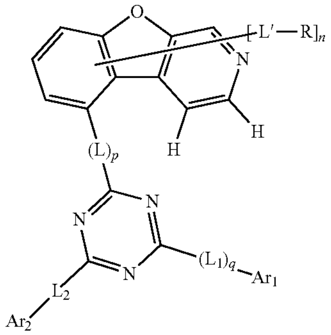
1-6
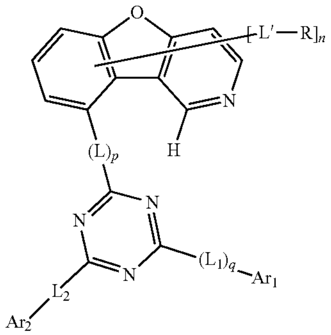
-continued
1-7
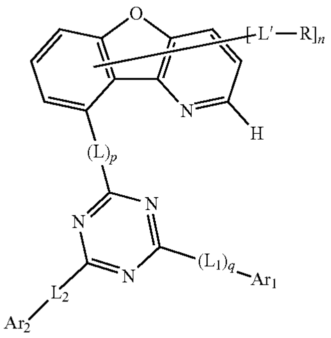
wherein, in Chemical Formulas 1-1 to 1-7:
n is 0 or 1; and
L, L', R, $L_1$, $L_2$, p, q, $Ar_1$ and $Ar_2$ are as defined in claim 1.
9. The compound of claim 1, wherein:
the compound is any one selected from the group consisting of the following compounds:
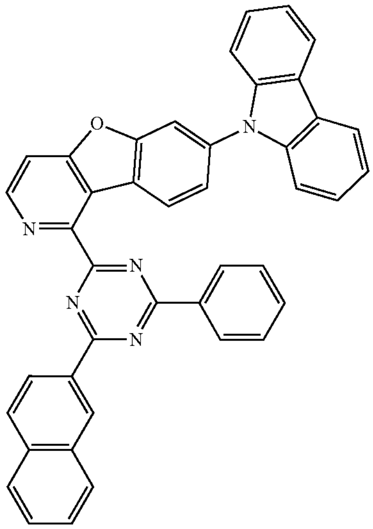
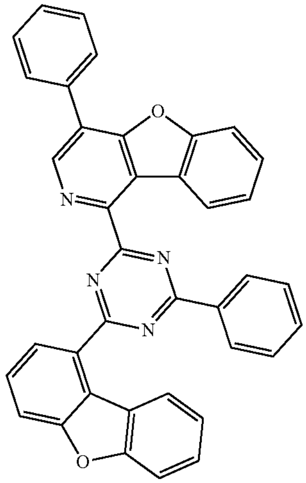

-continued
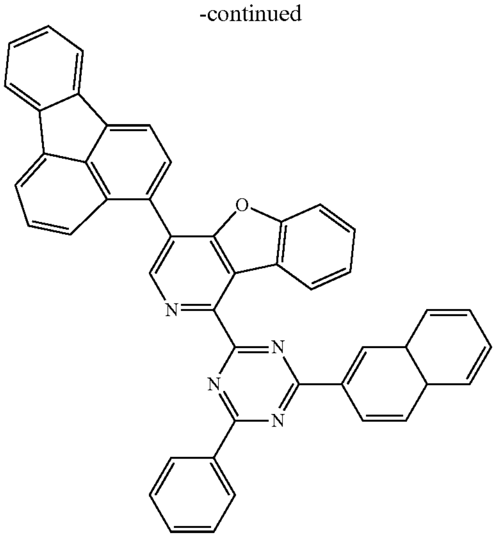
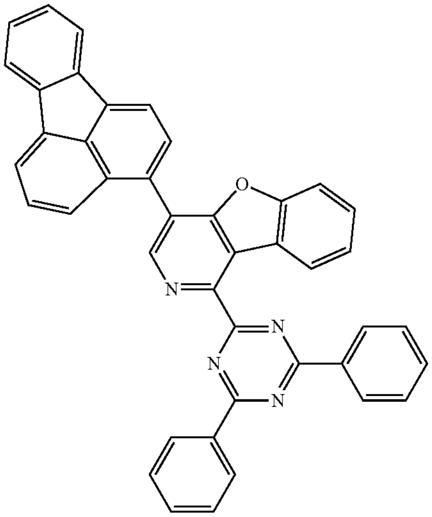
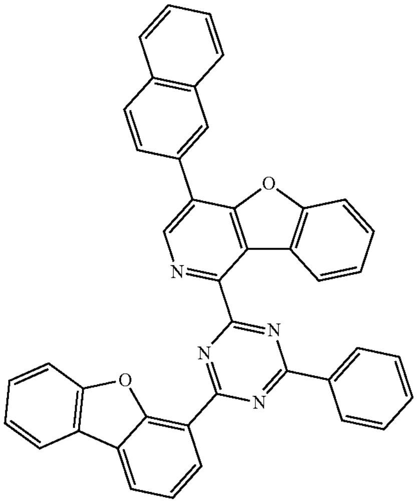
-continued
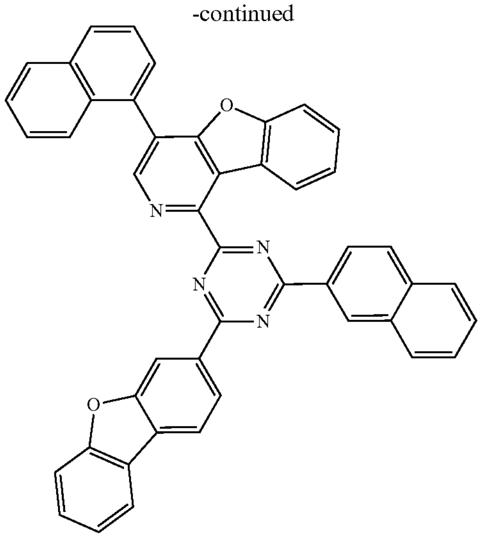
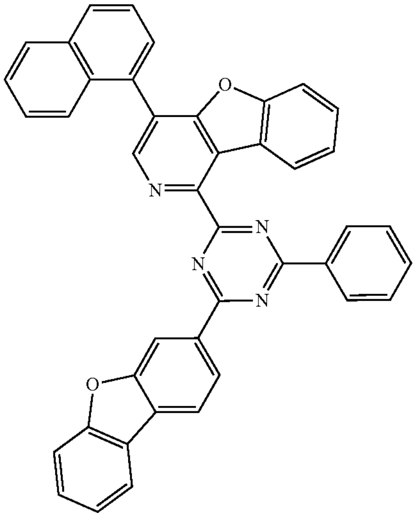
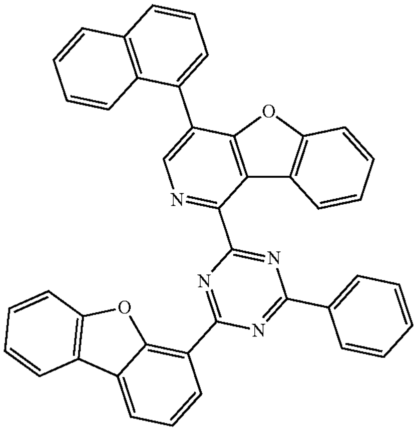

-continued
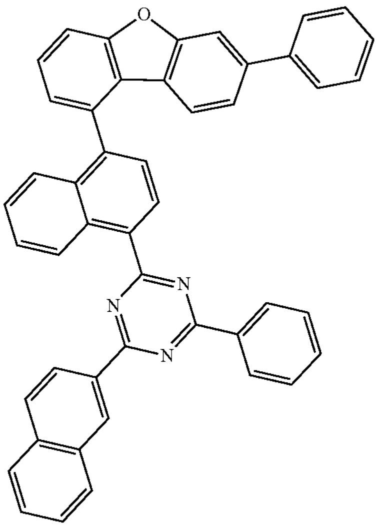
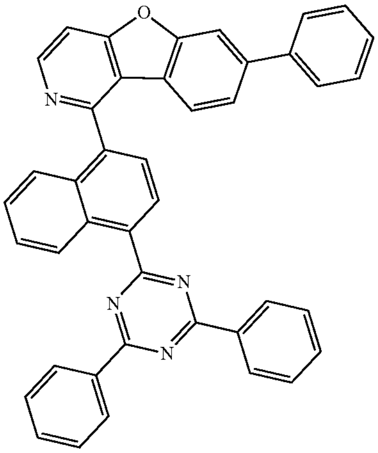
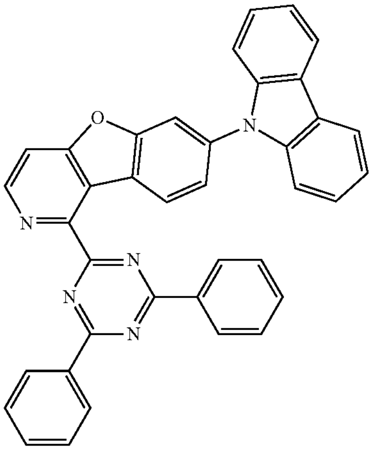
-continued
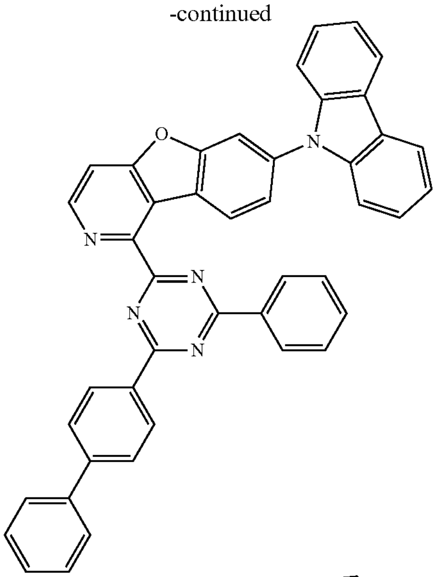
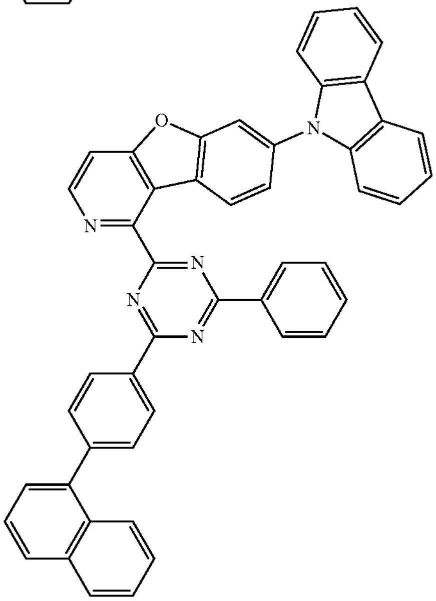
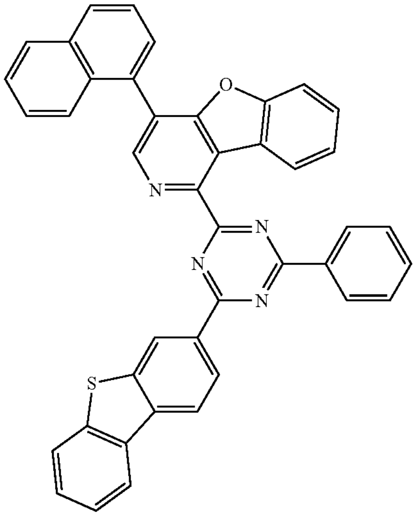

-continued
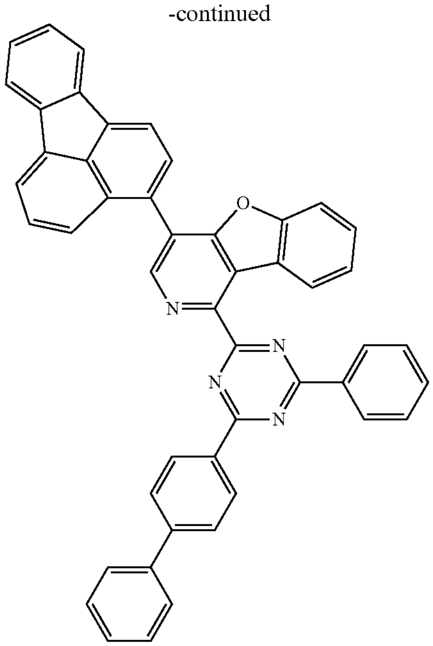
-continued
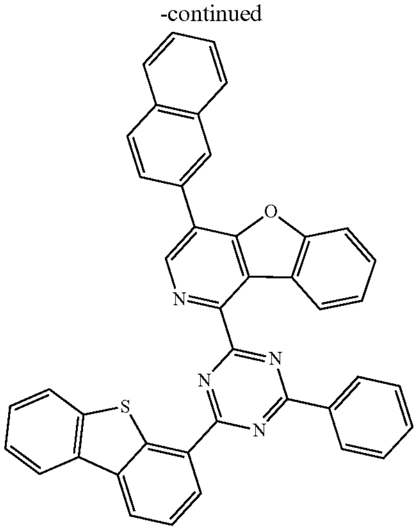
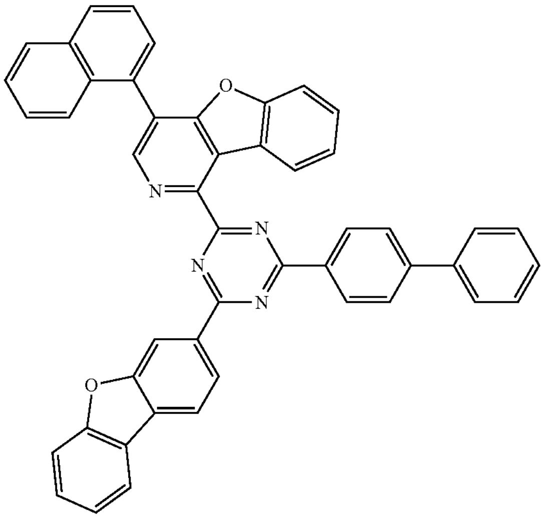
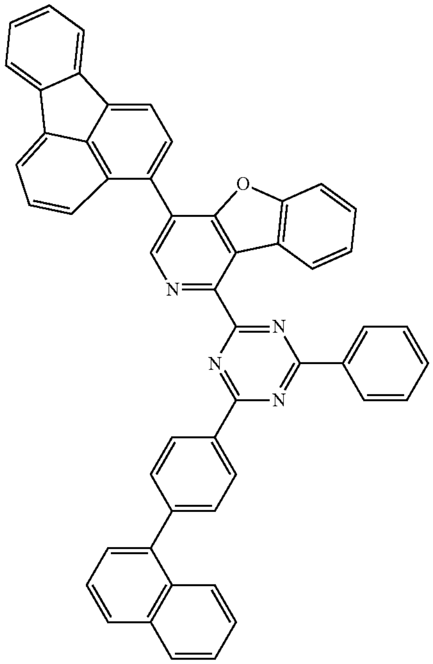
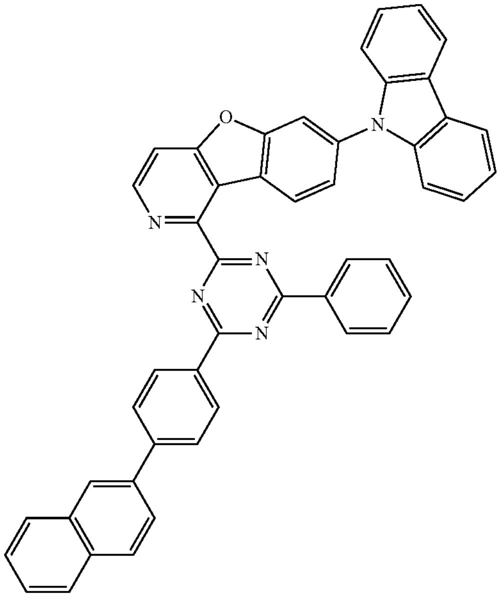

-continued
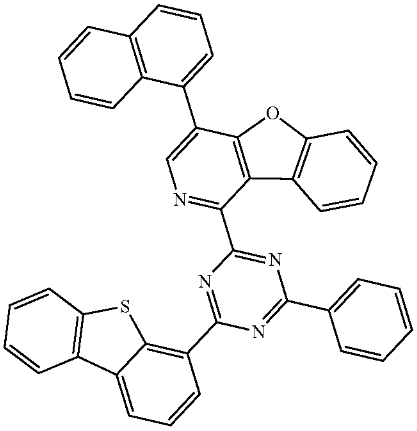
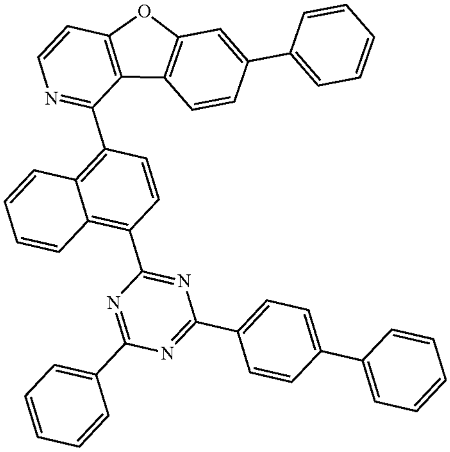
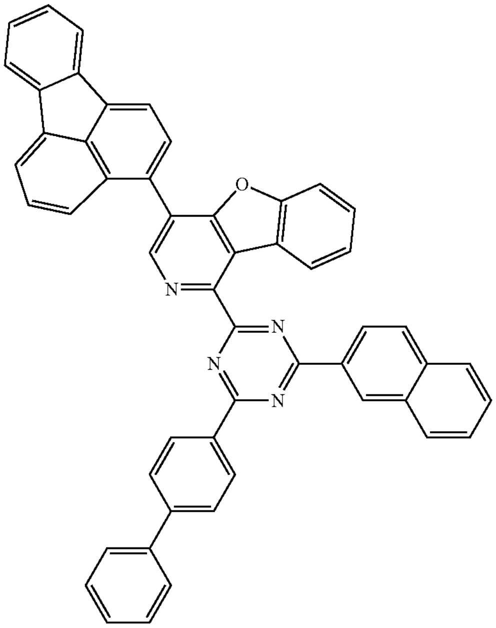
-continued
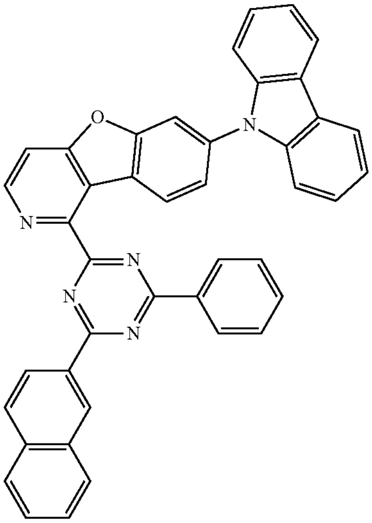
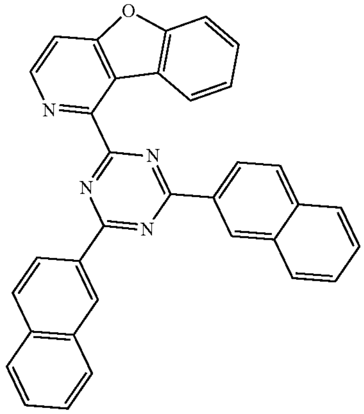
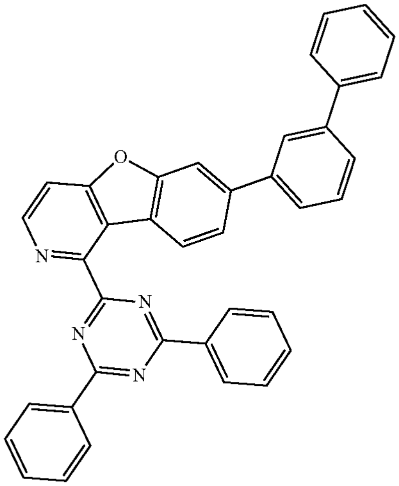

-continued
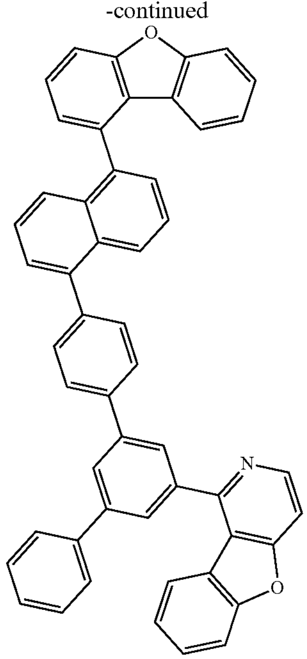
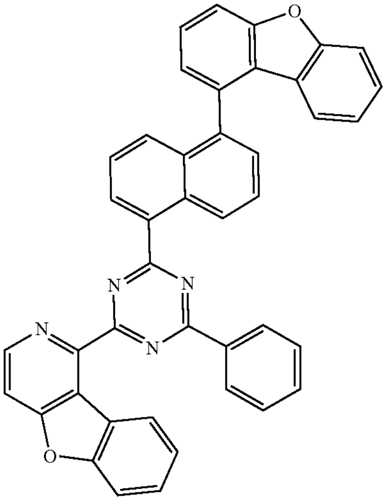
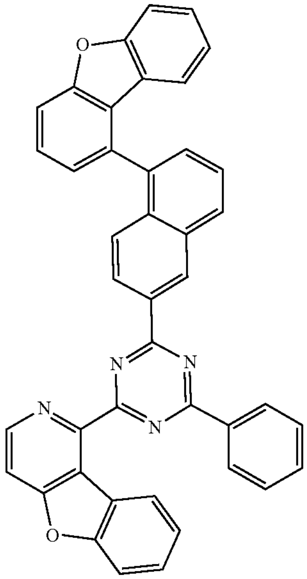
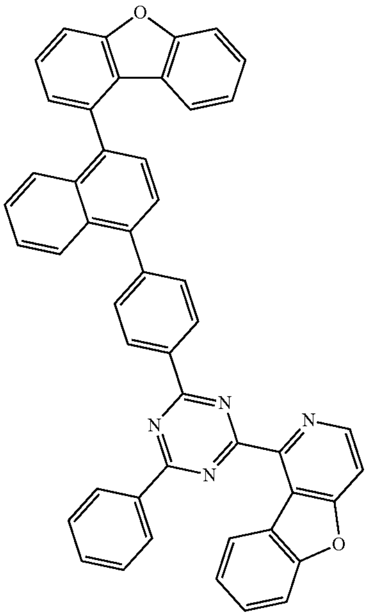
-continued
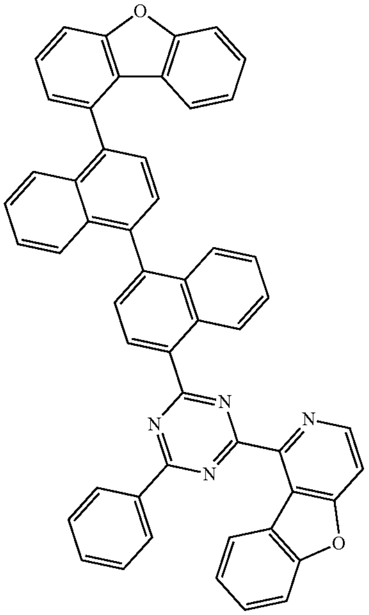

-continued
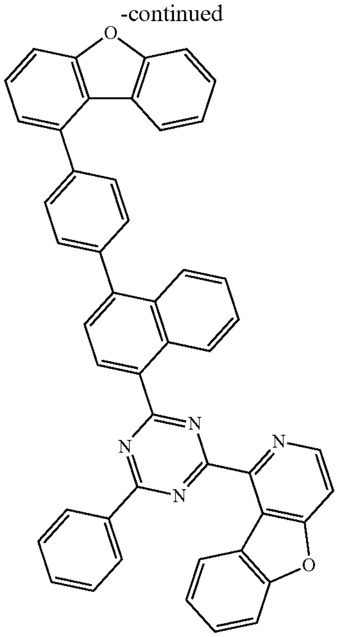
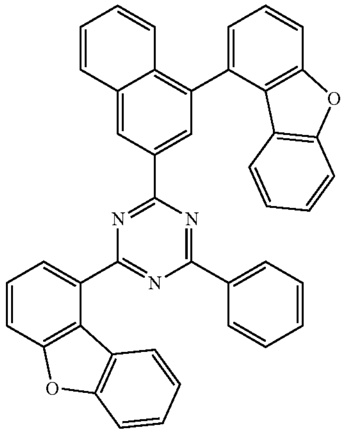
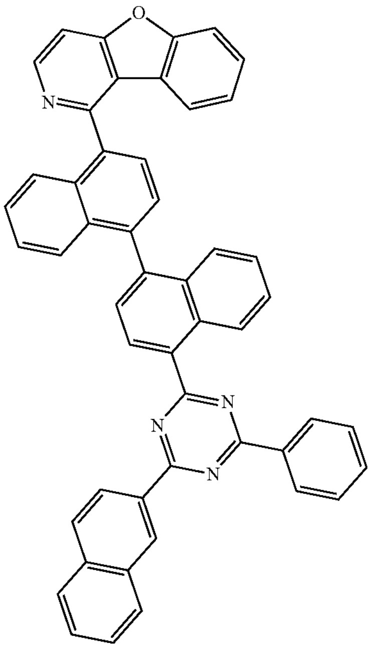
-continued
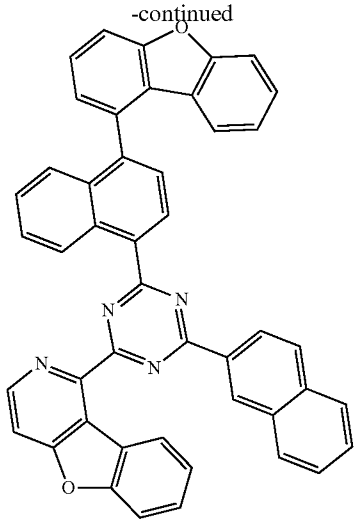
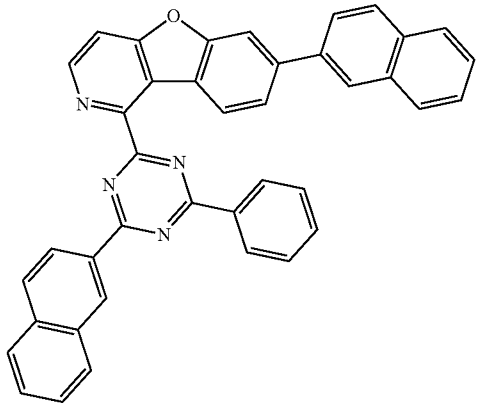
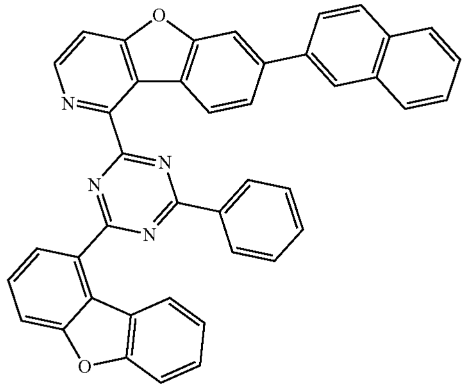

-continued
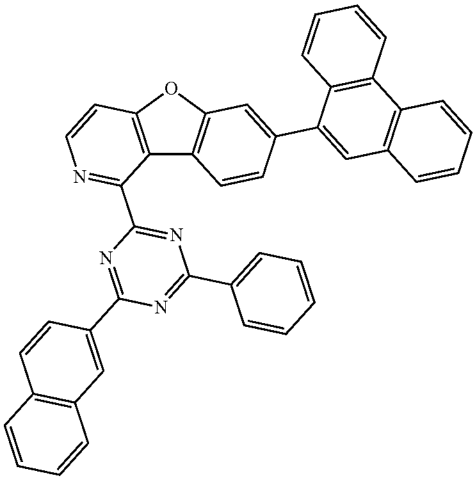
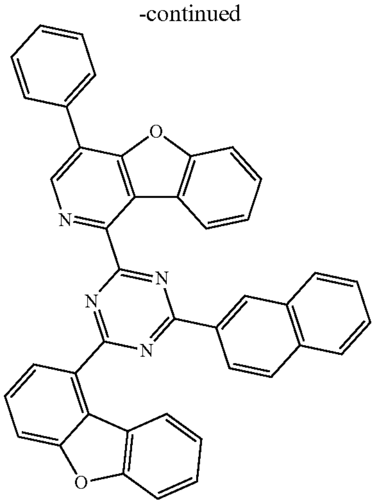
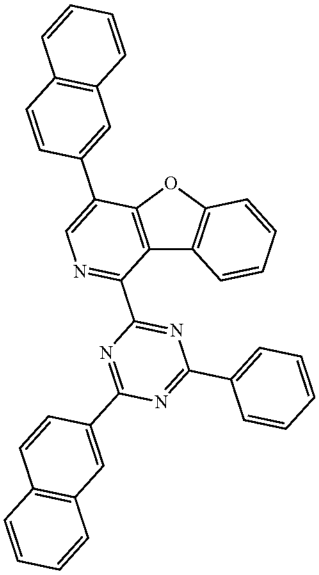
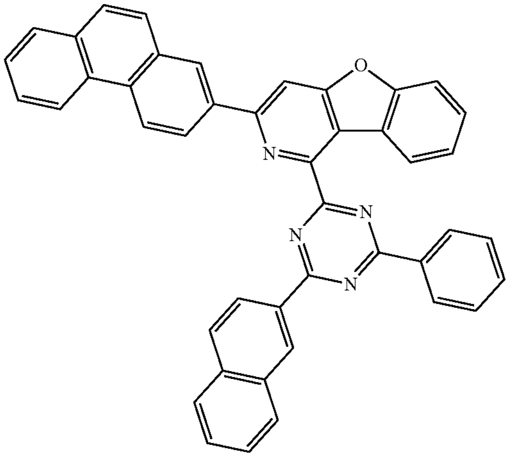
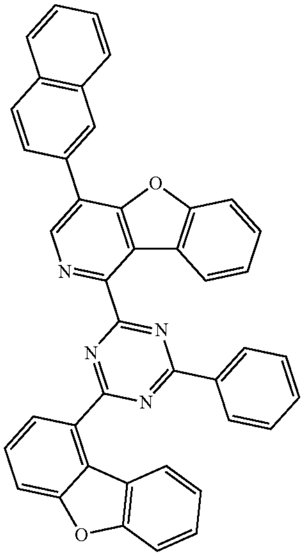
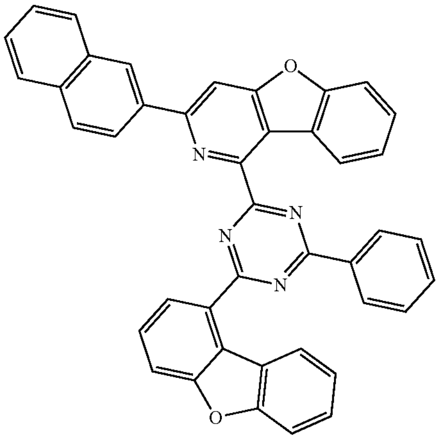

-continued
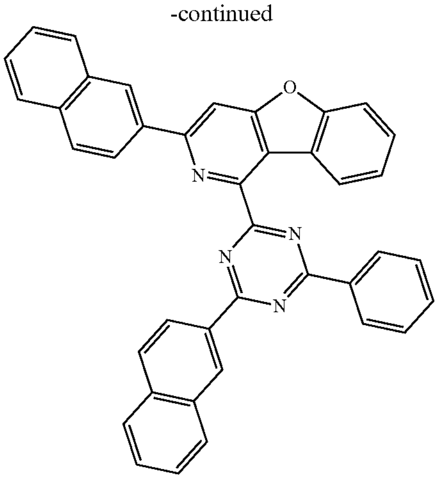
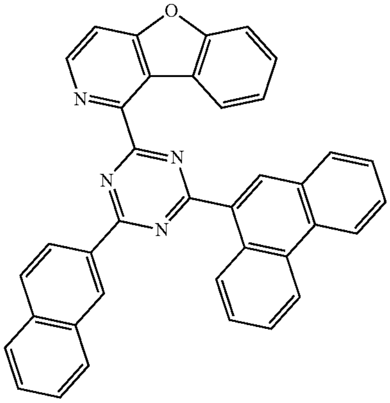
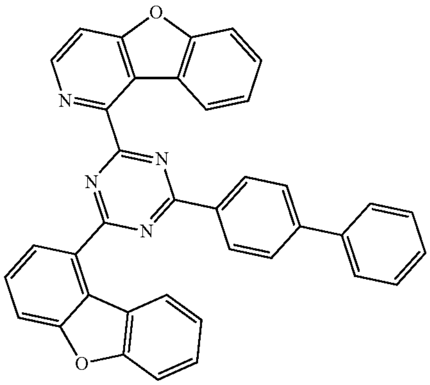
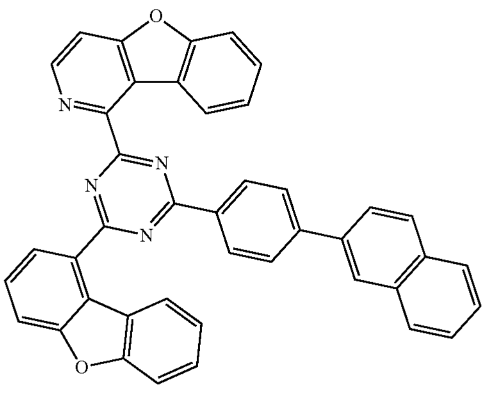
-continued
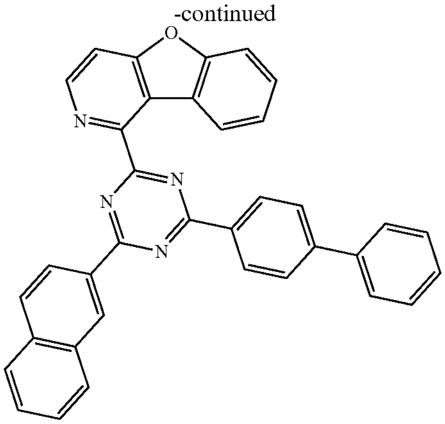
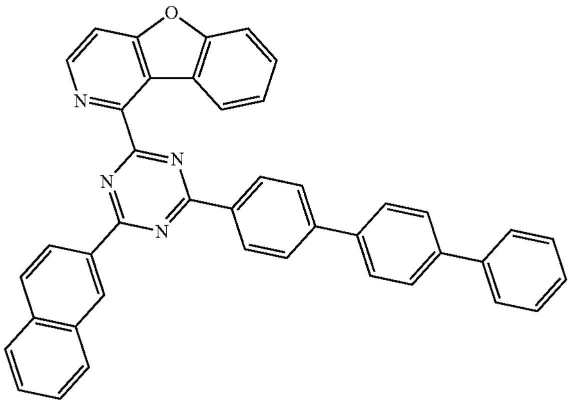
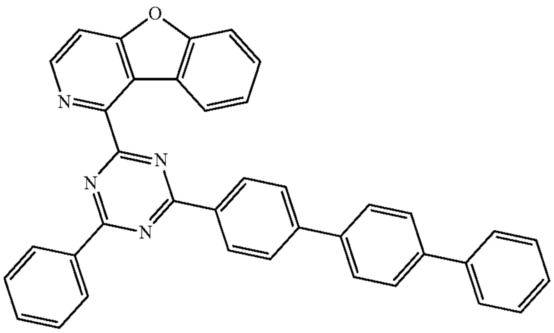
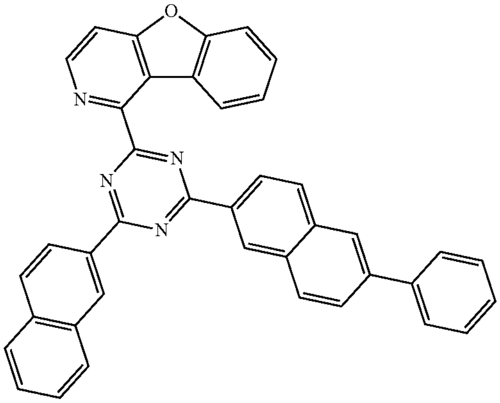

-continued
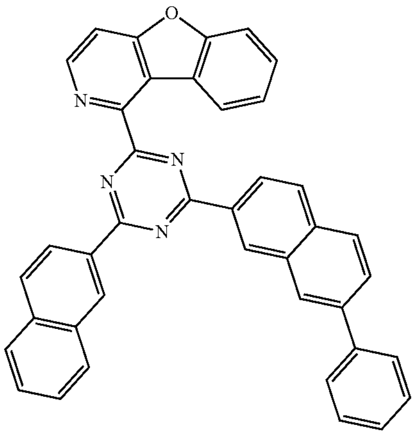
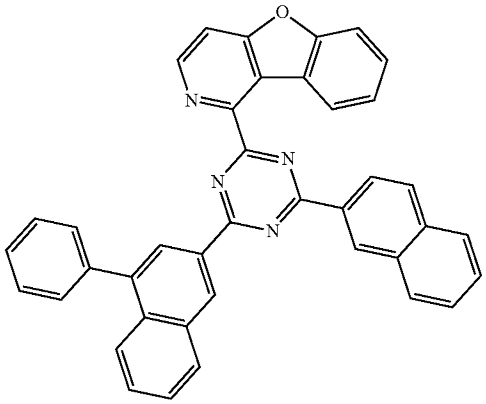
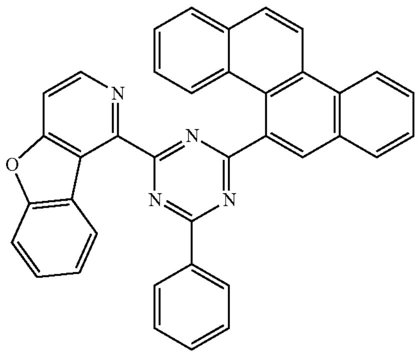
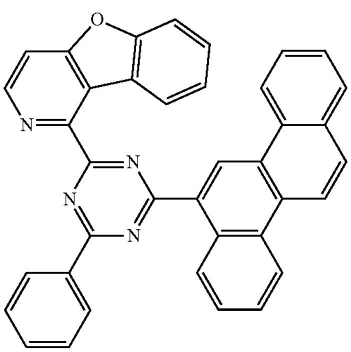
-continued
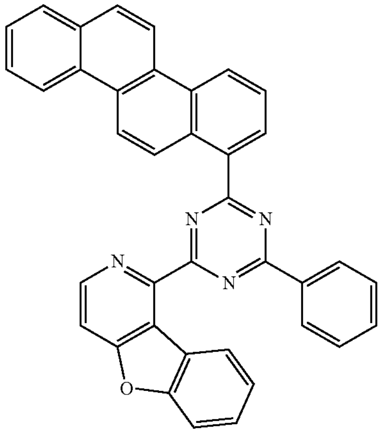
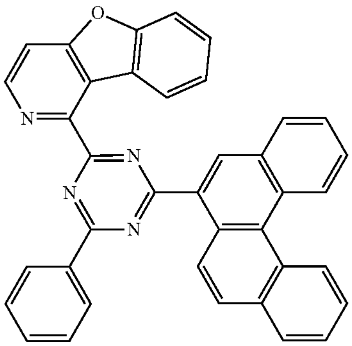
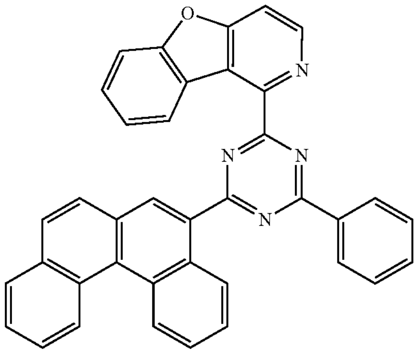
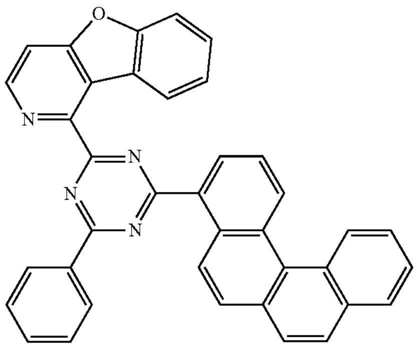

-continued
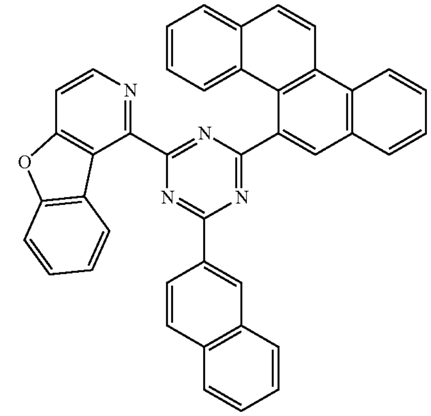
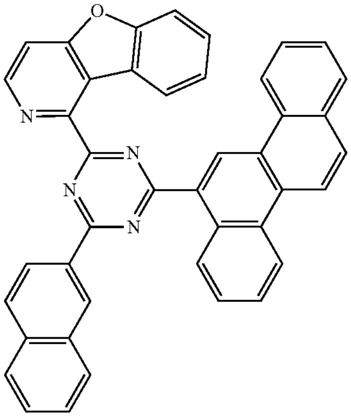
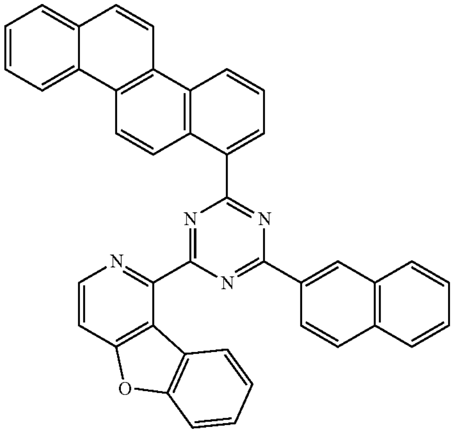
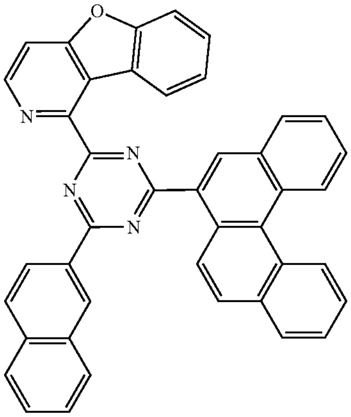
-continued
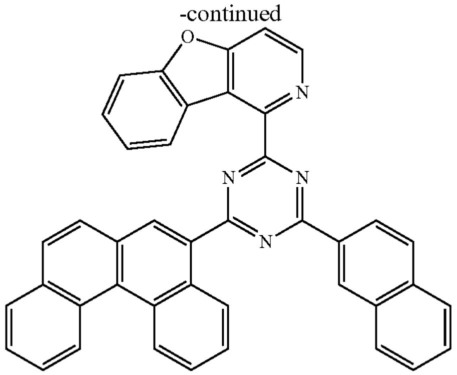
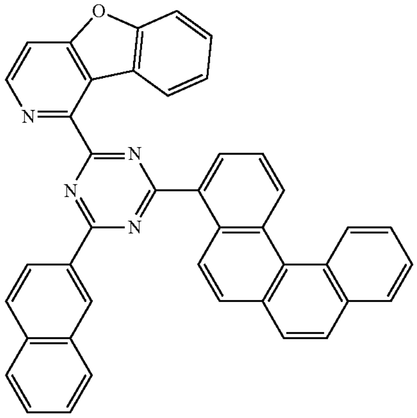
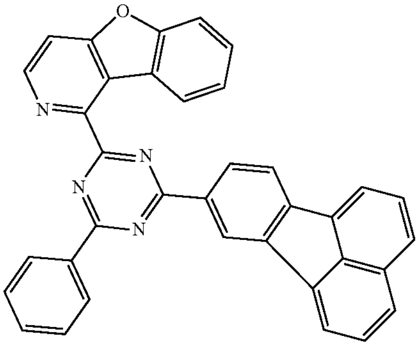
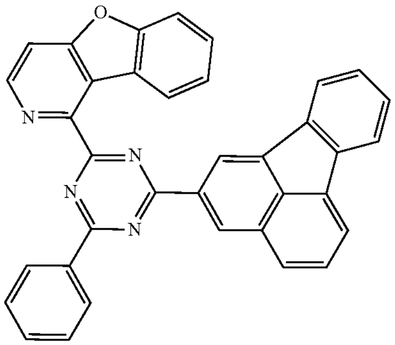

-continued
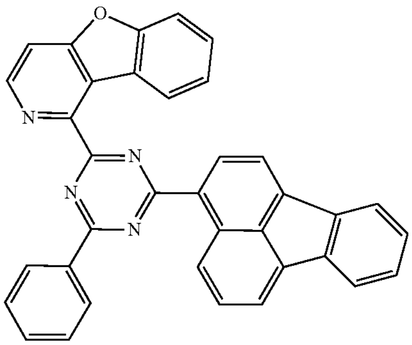
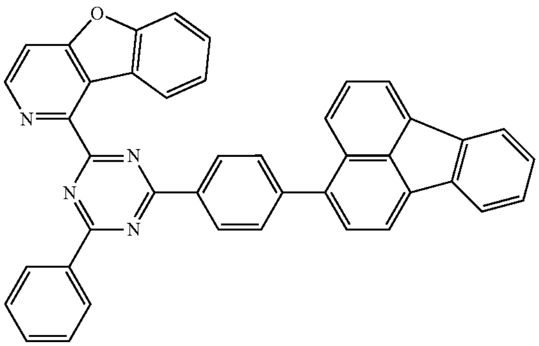
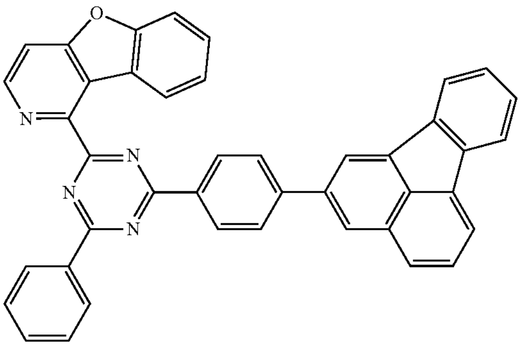
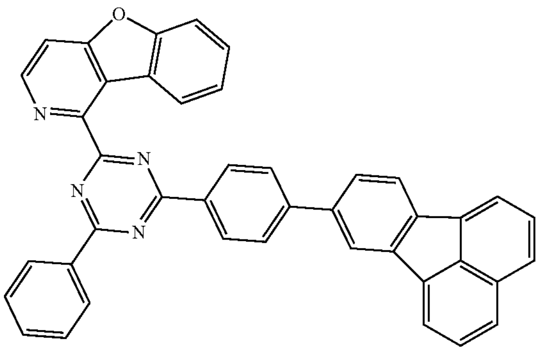
-continued
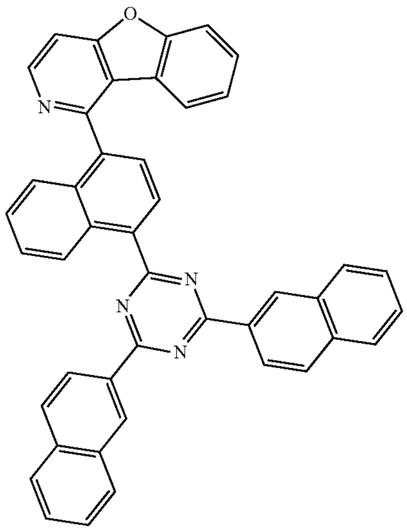
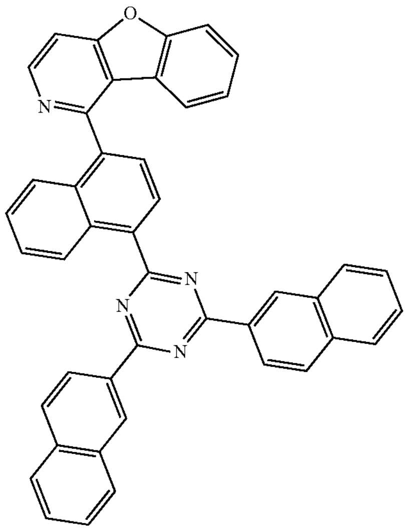
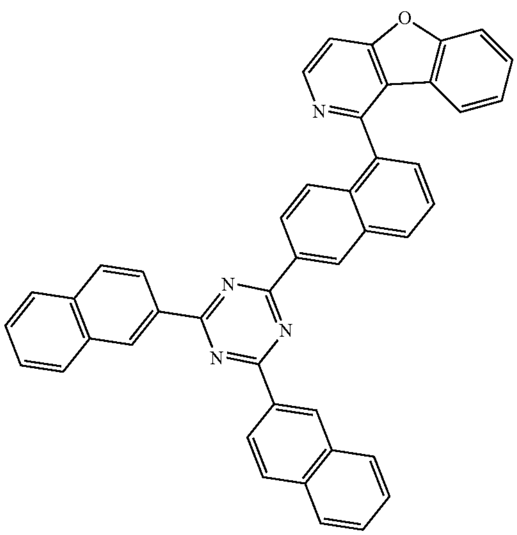

-continued
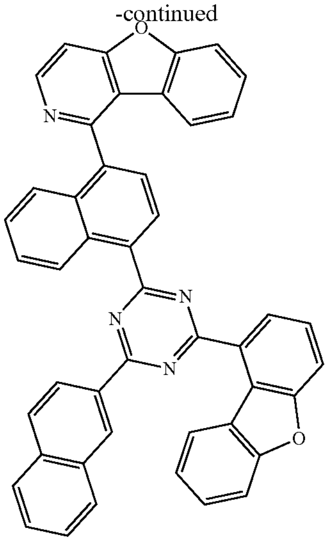
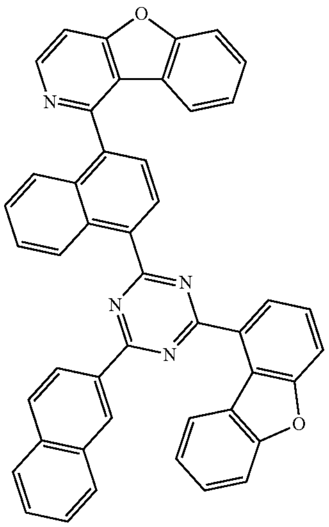
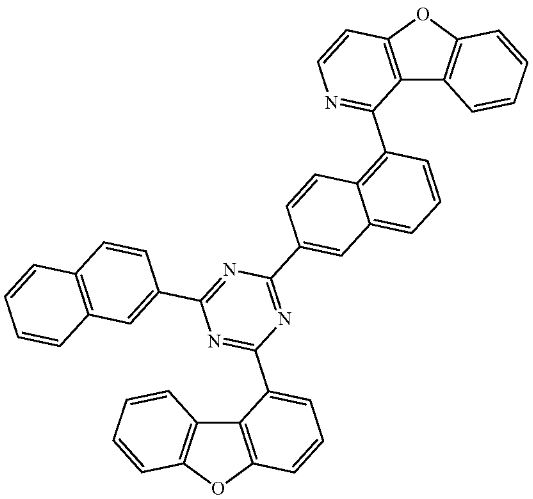
-continued
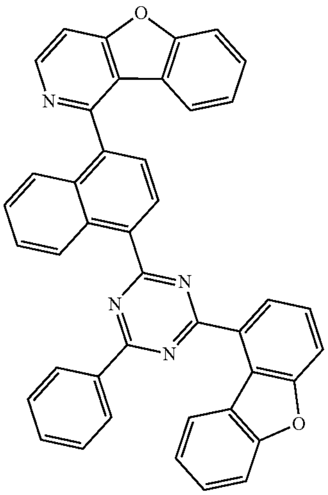
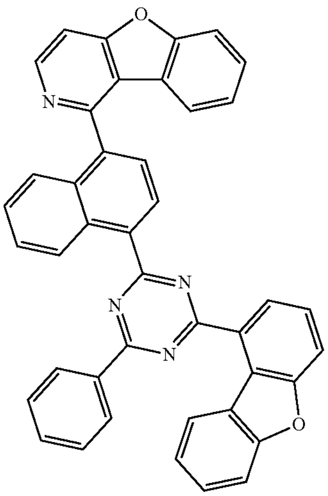
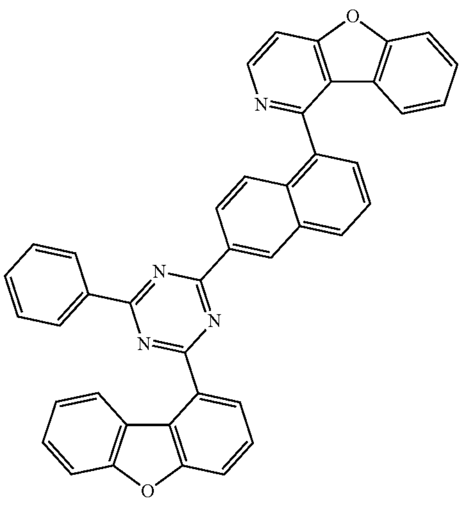

-continued
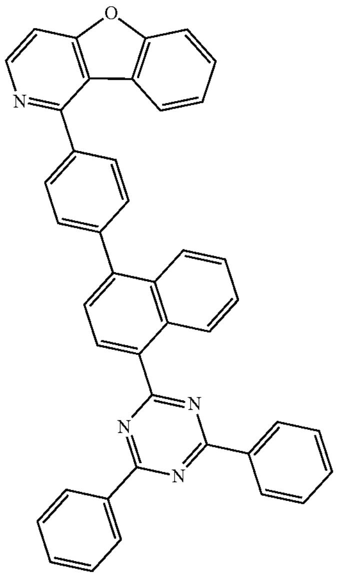
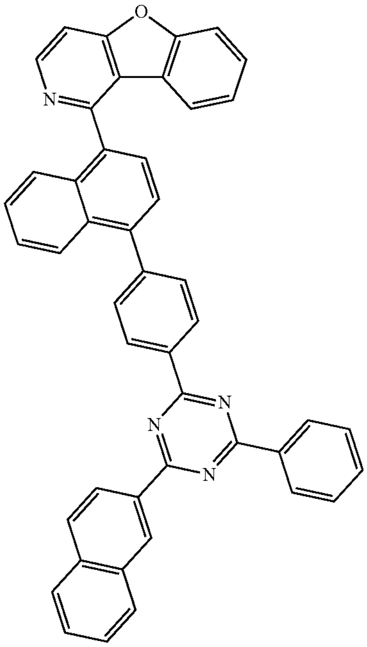
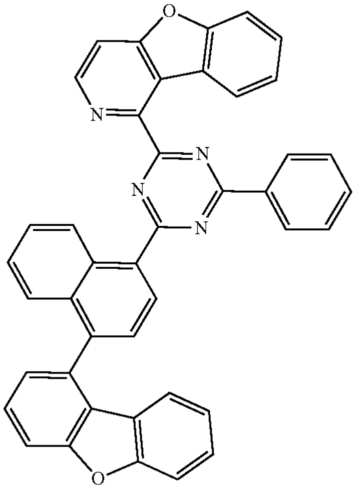
-continued
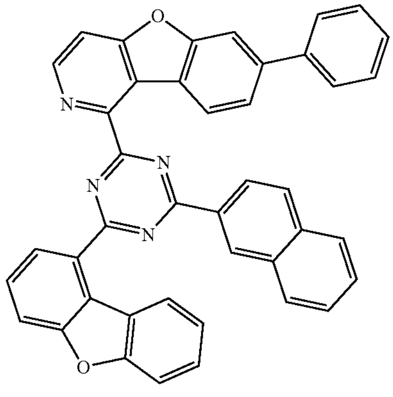
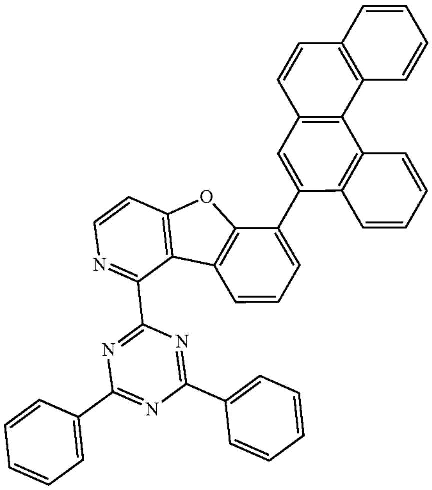
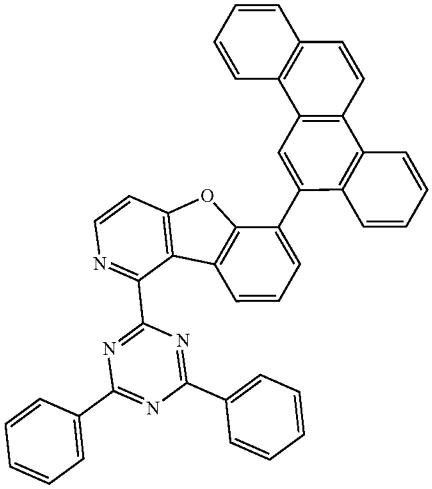

-continued
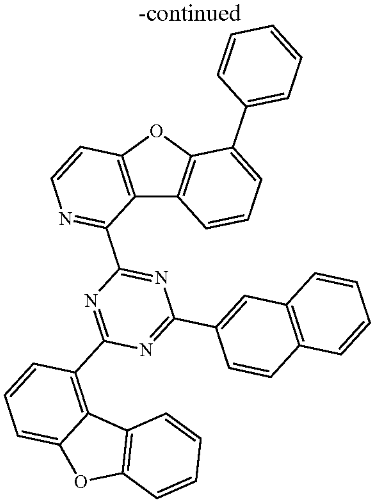
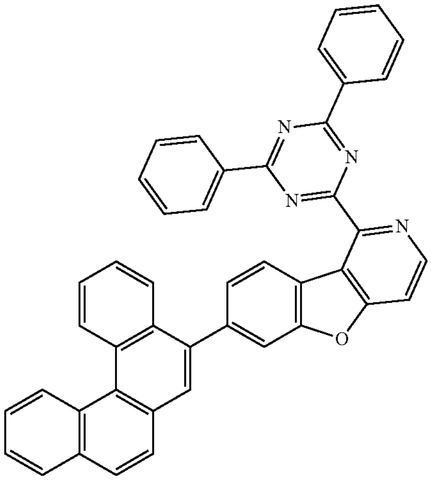
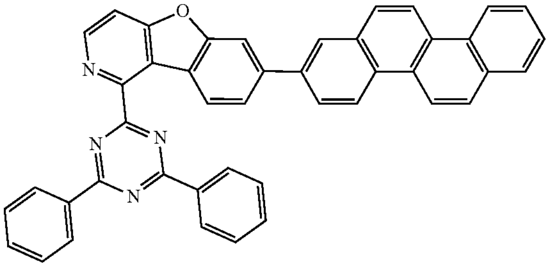
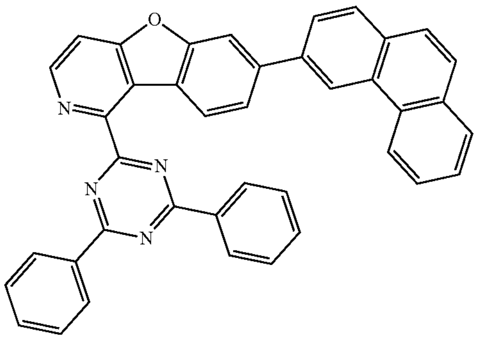
-continued
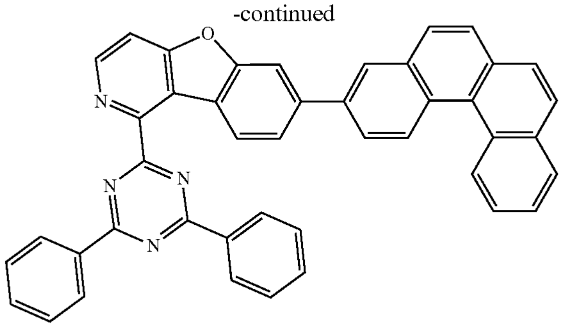
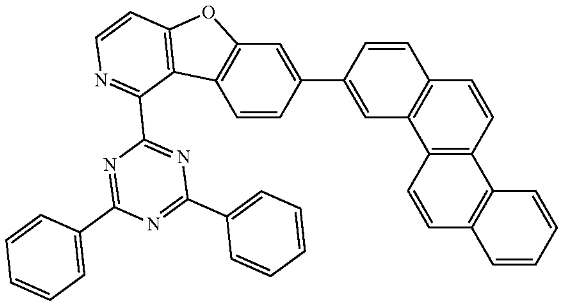
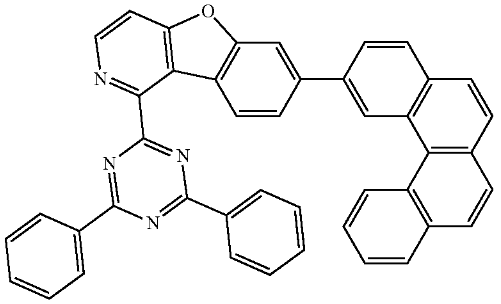
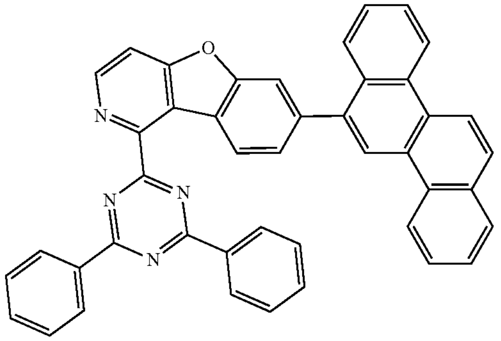
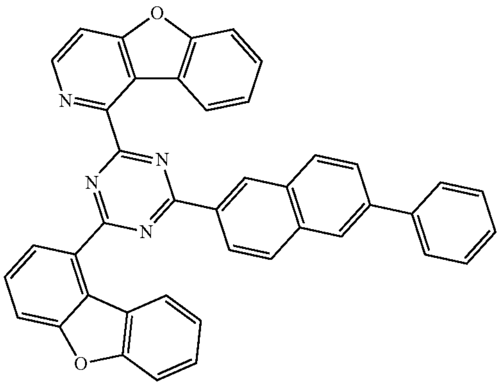

-continued
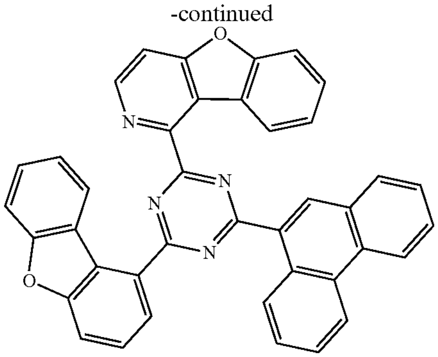
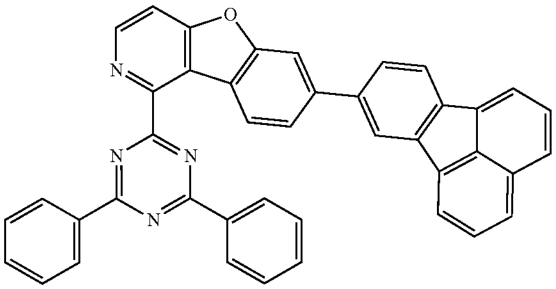
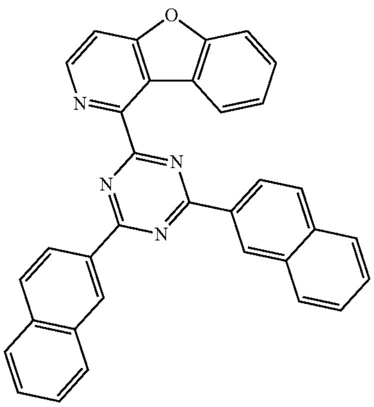
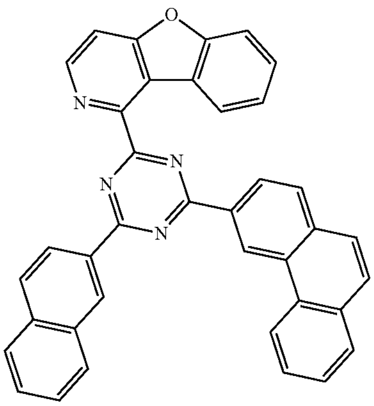
-continued
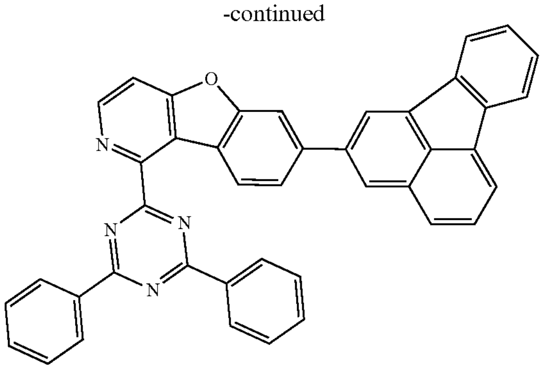
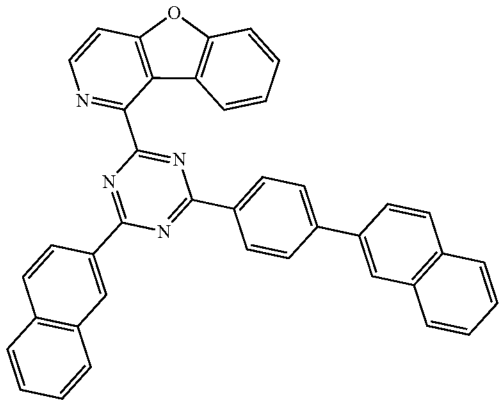
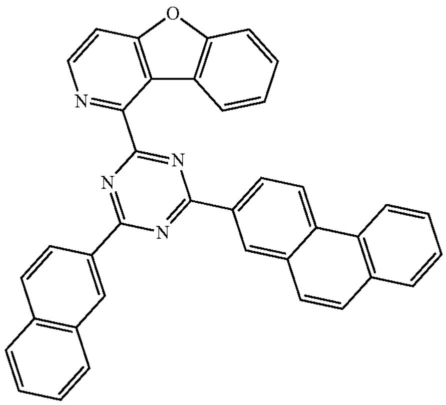
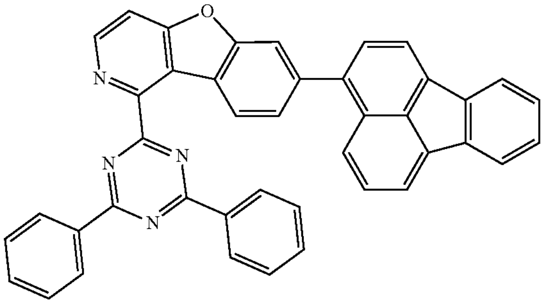

-continued
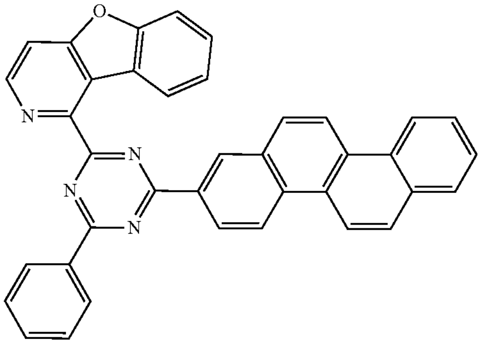
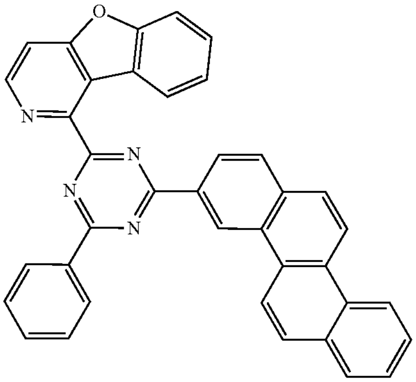
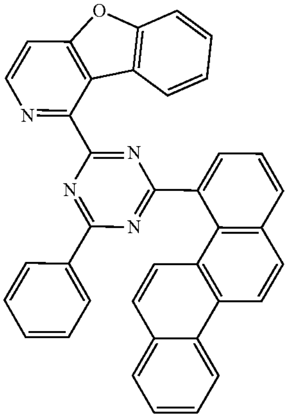
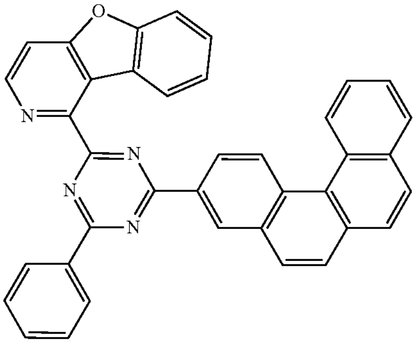
-continued
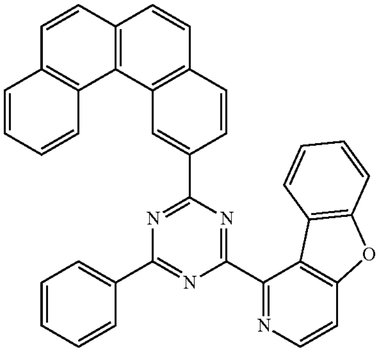
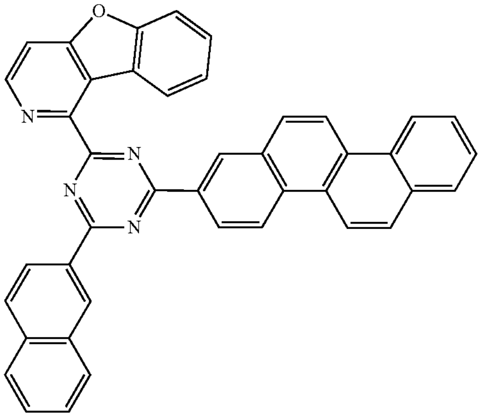
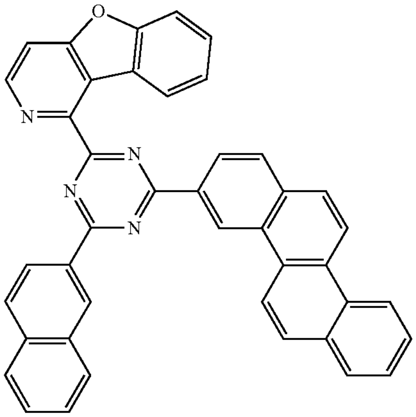
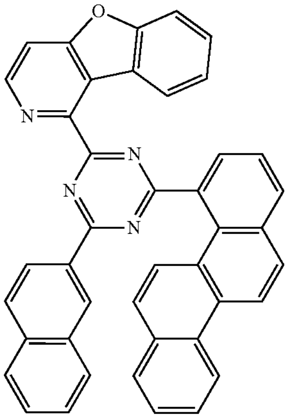

-continued
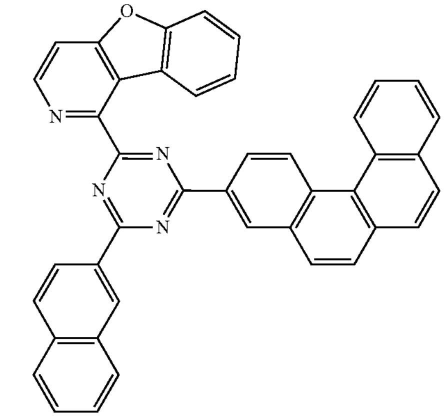
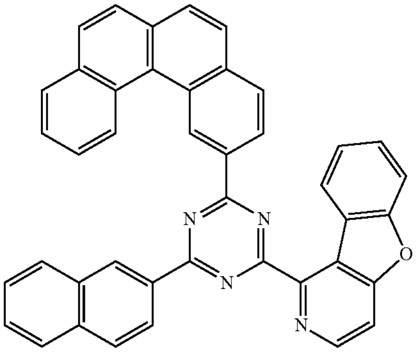
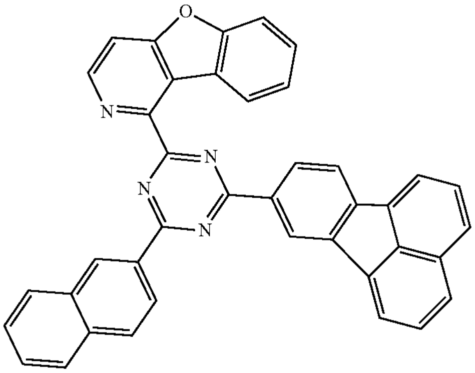
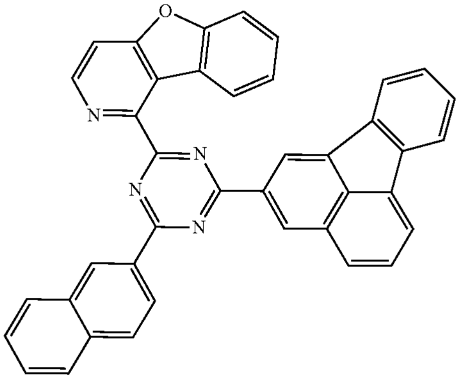
-continued
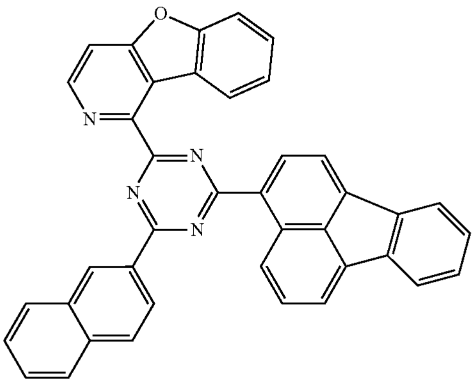
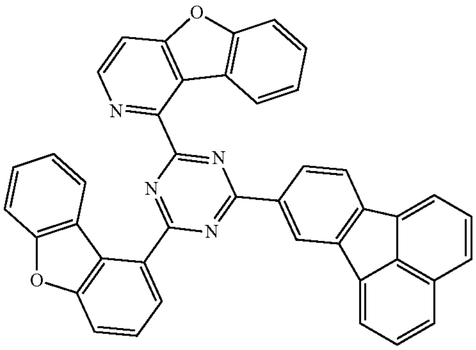
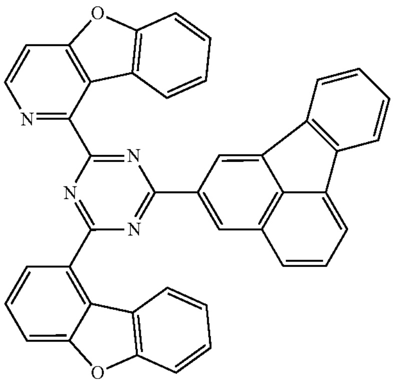
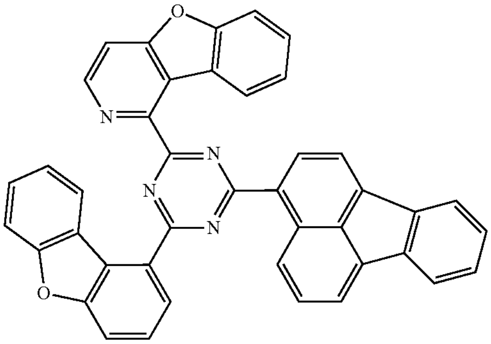

-continued
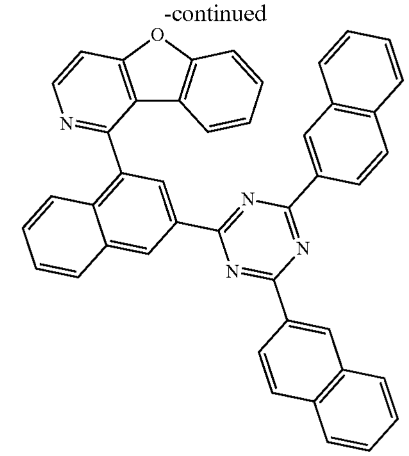
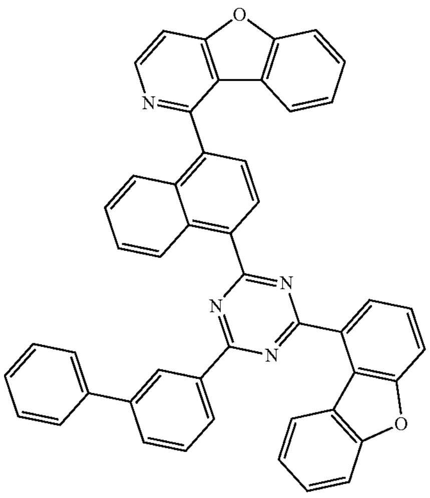
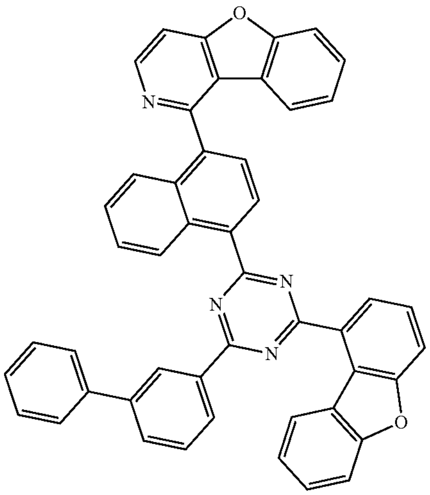
-continued
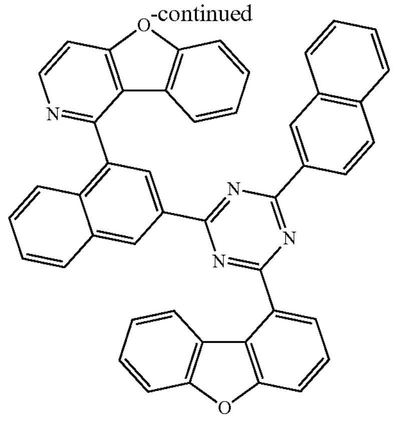
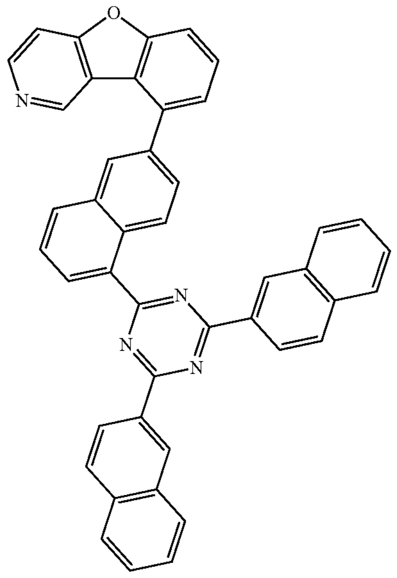
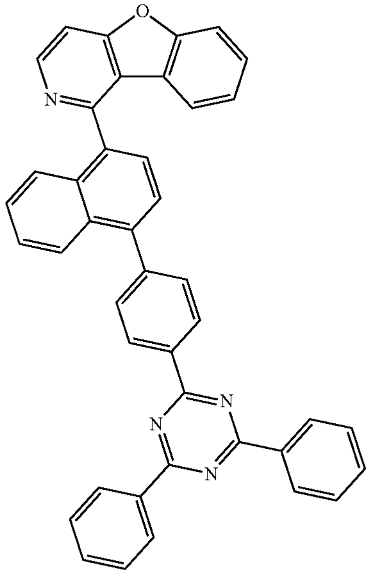

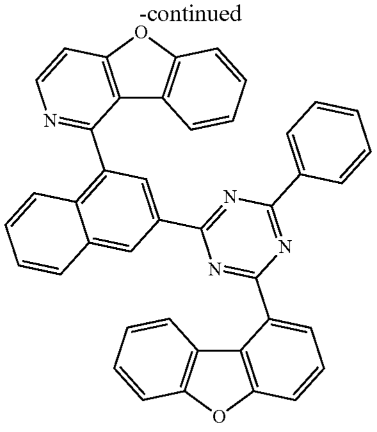
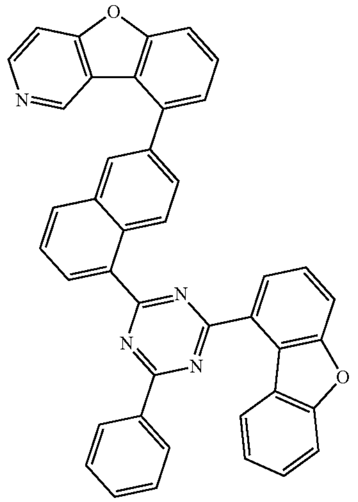
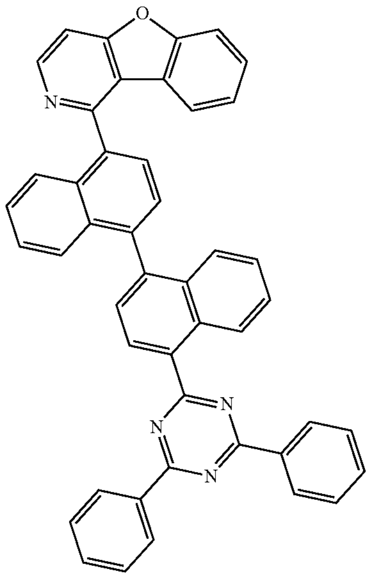
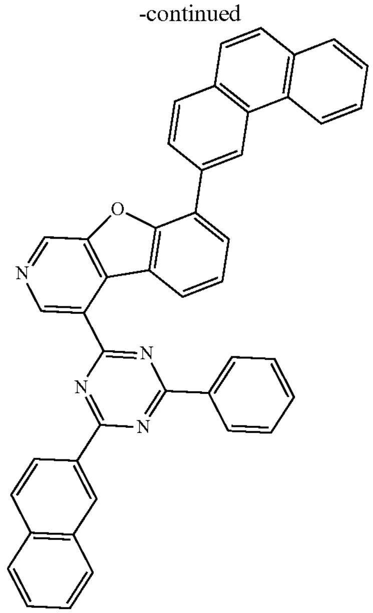
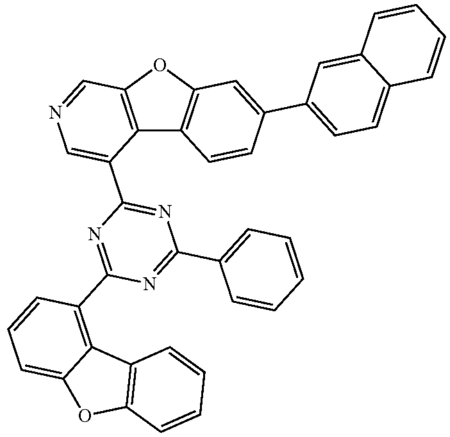
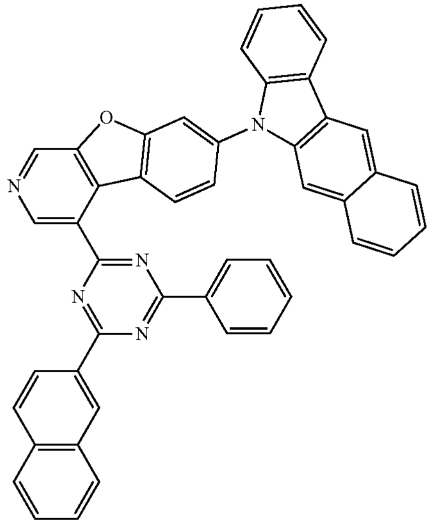

-continued
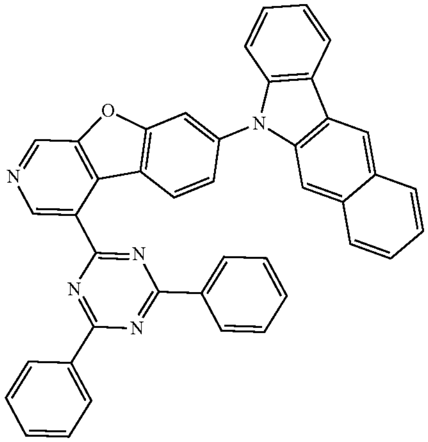
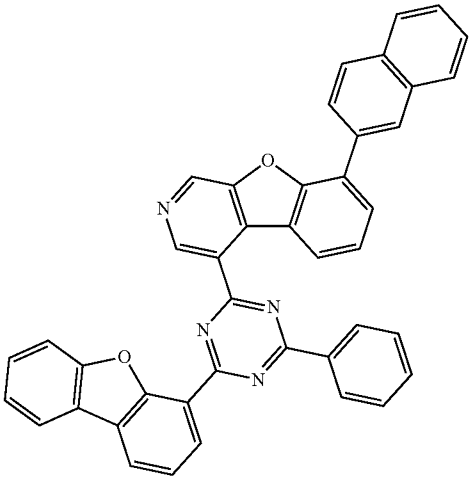
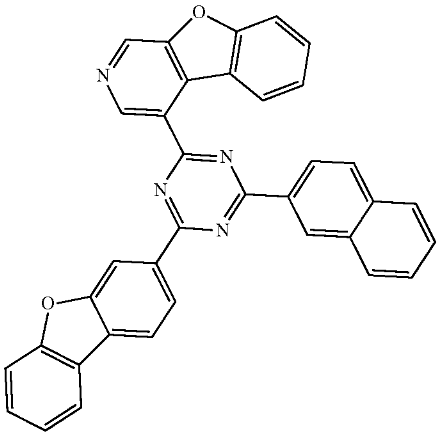
-continued
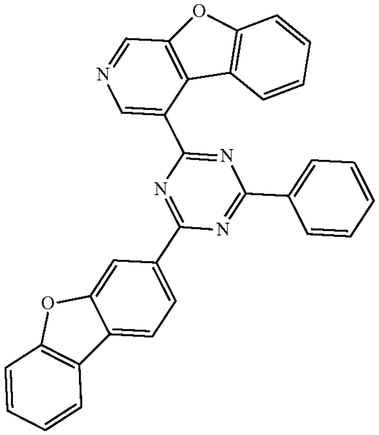
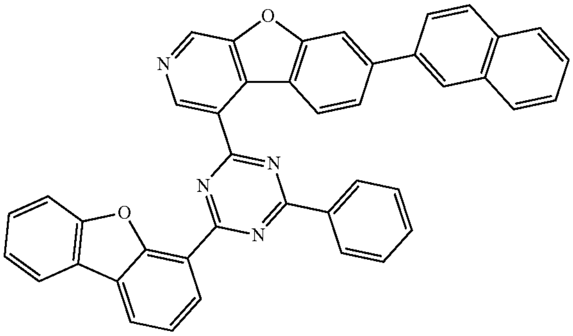
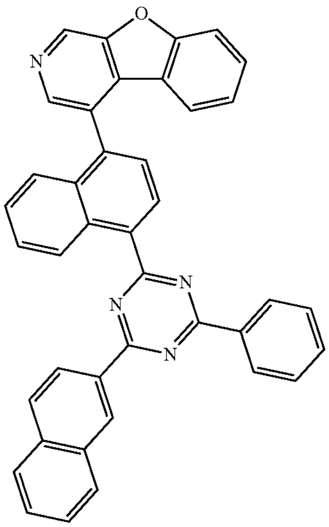

-continued
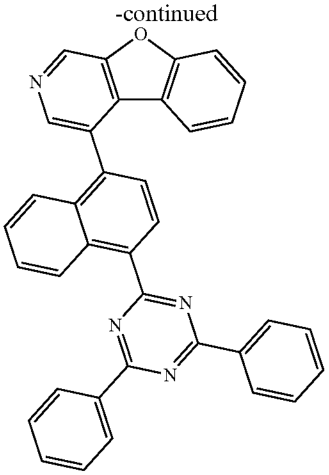
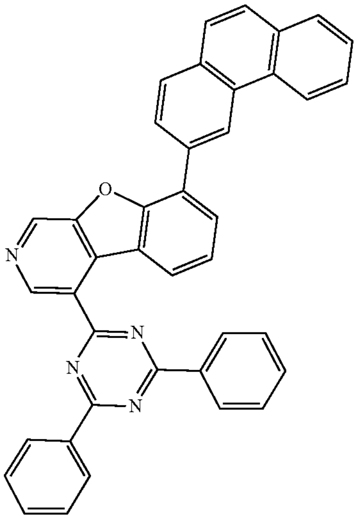
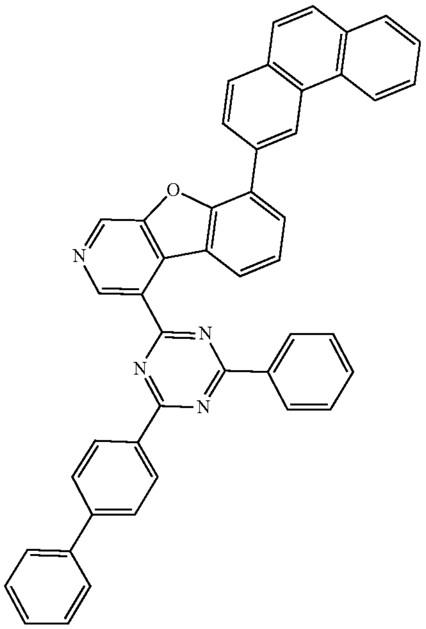
-continued
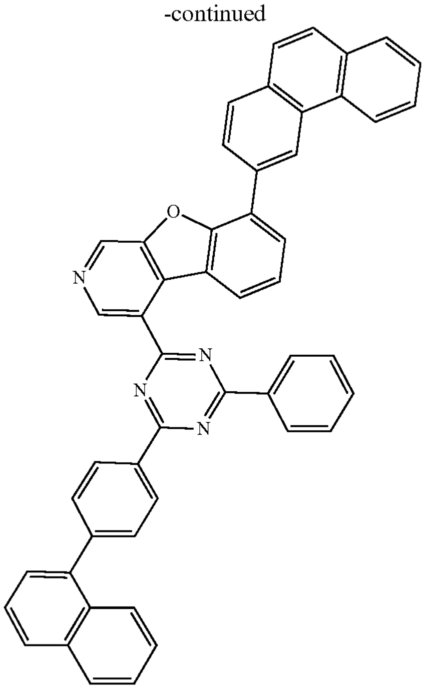
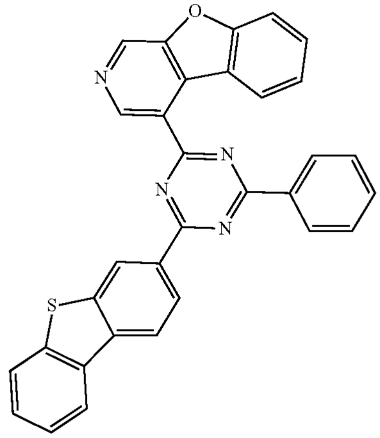
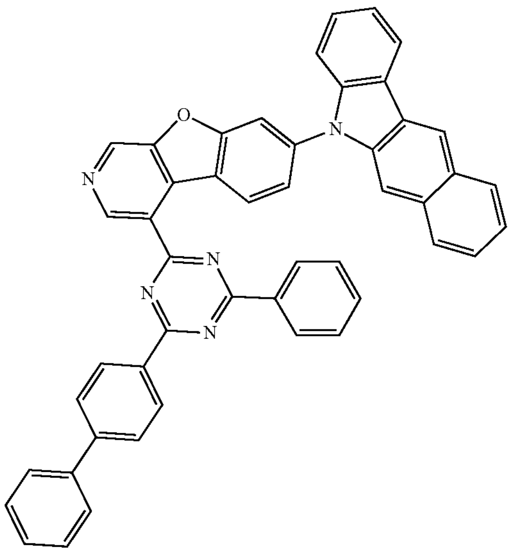

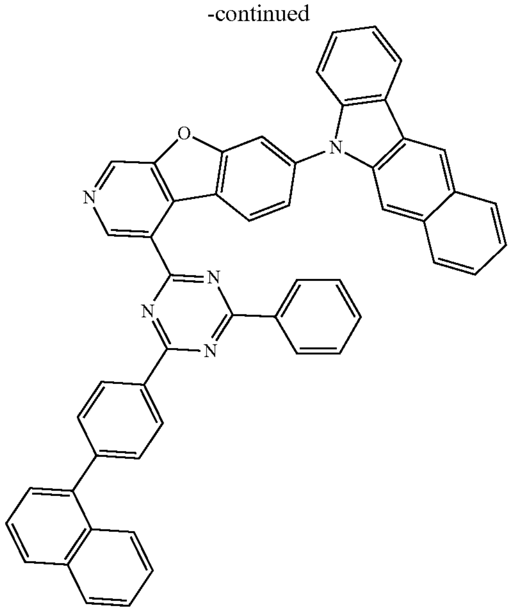
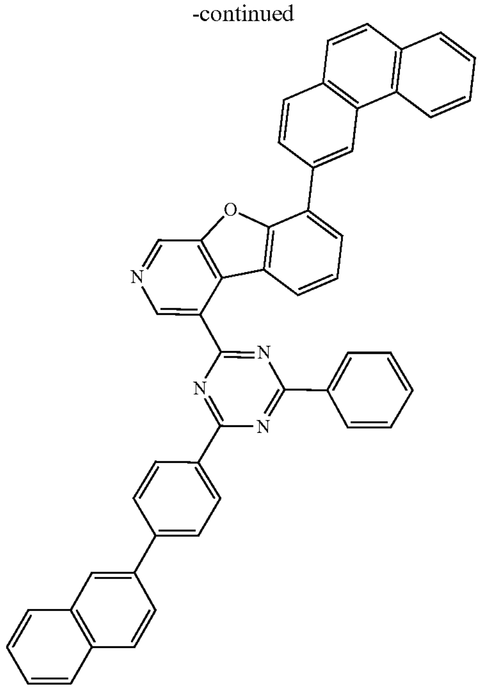
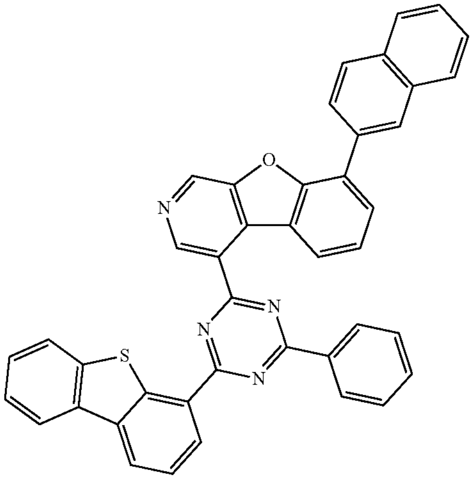
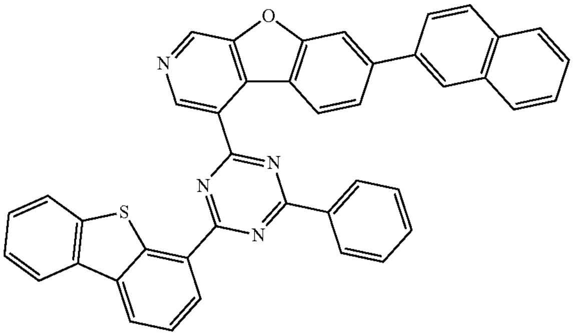
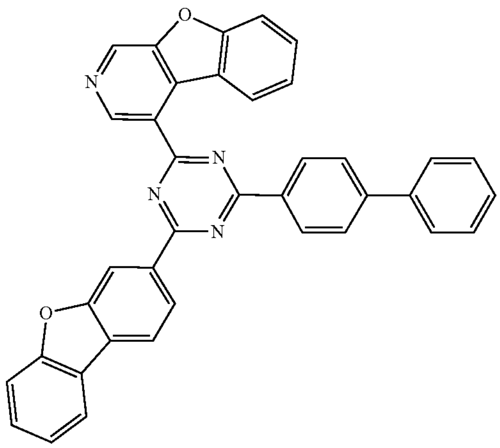
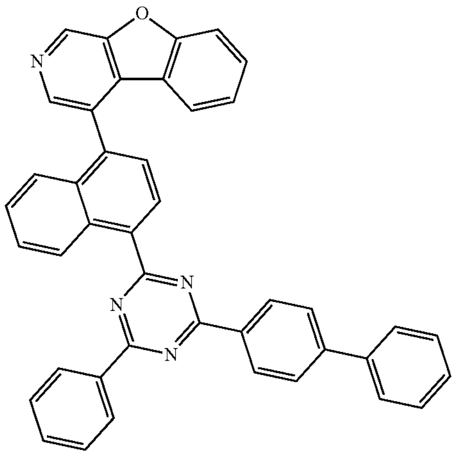

-continued
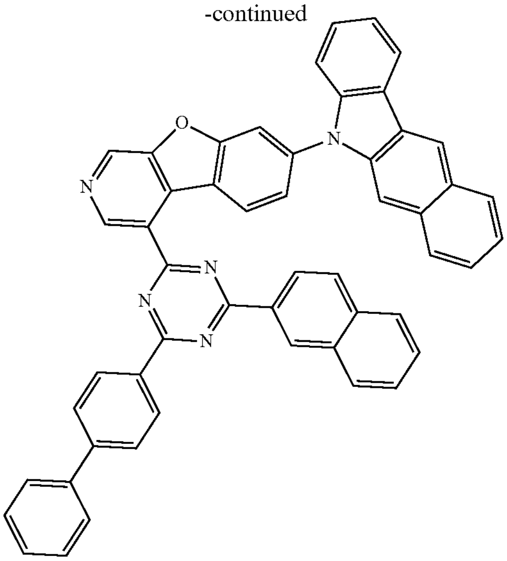
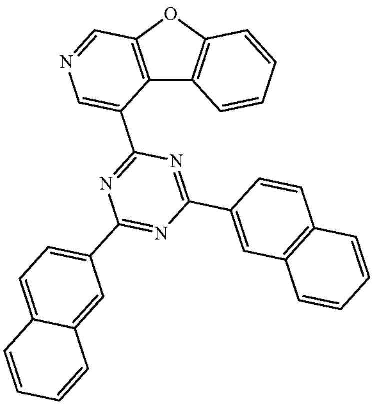
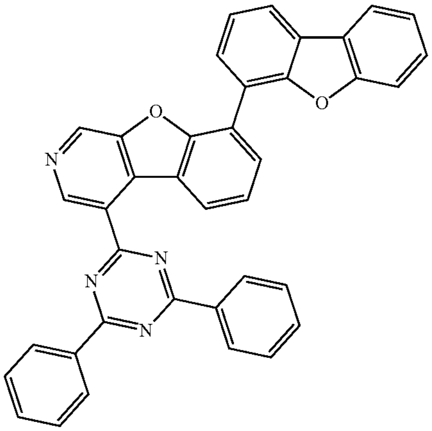
-continued
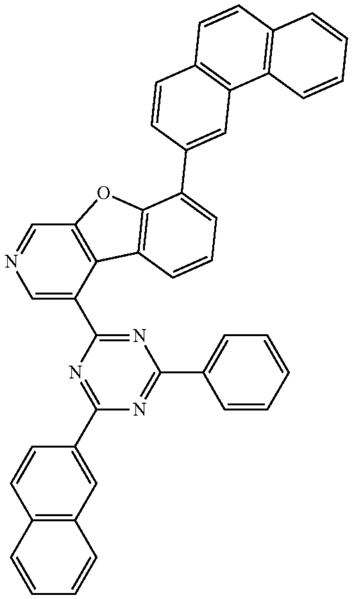
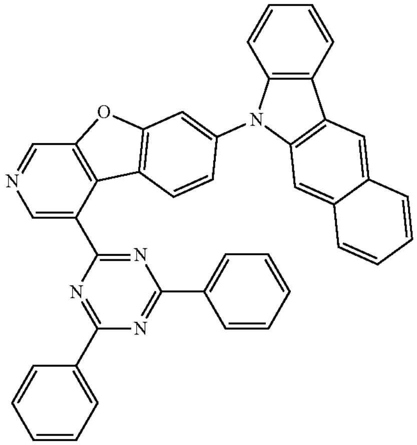
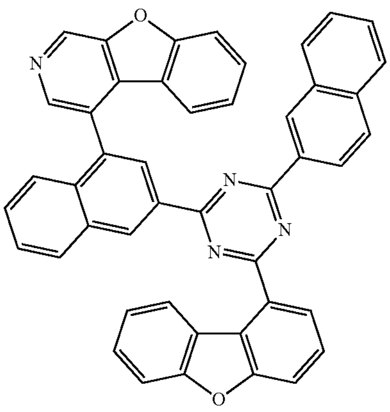

-continued
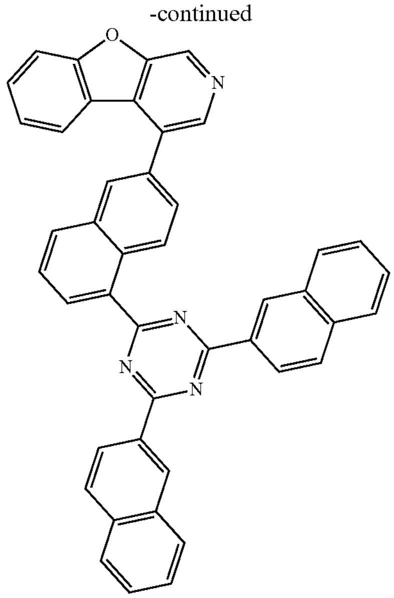
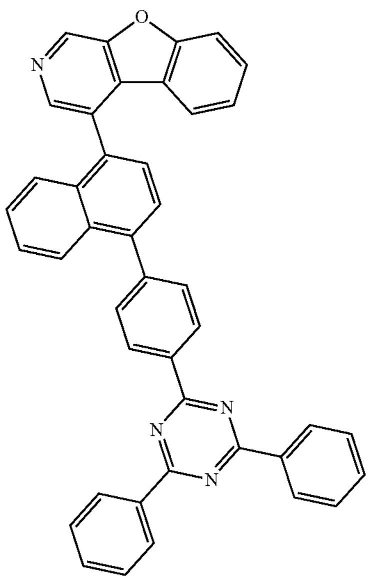
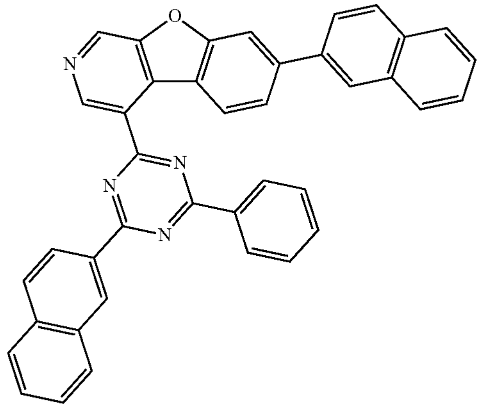
-continued
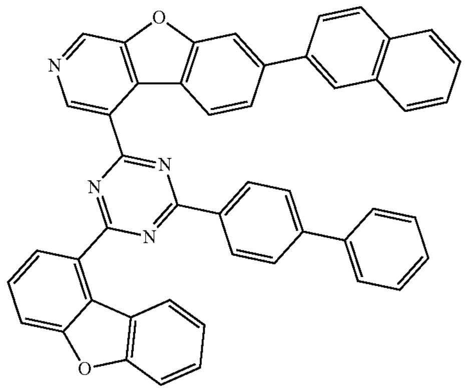
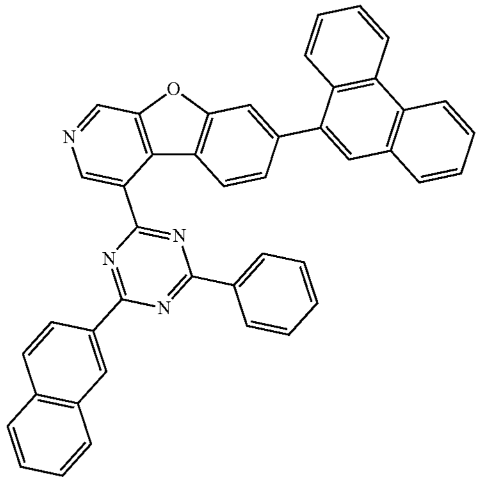
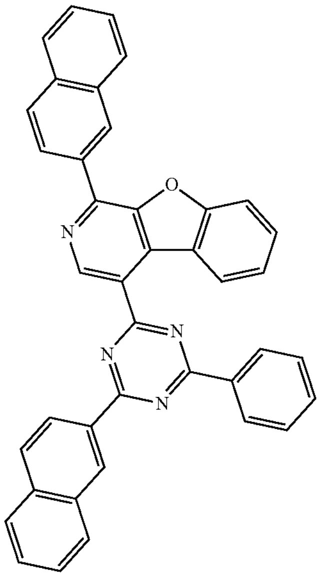

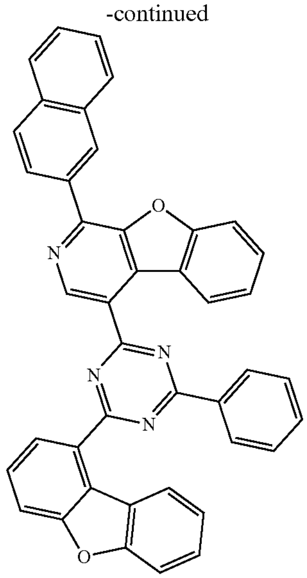
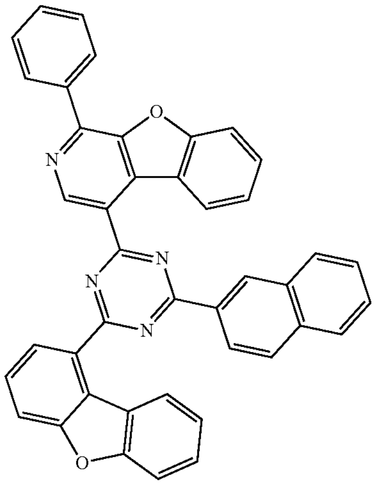
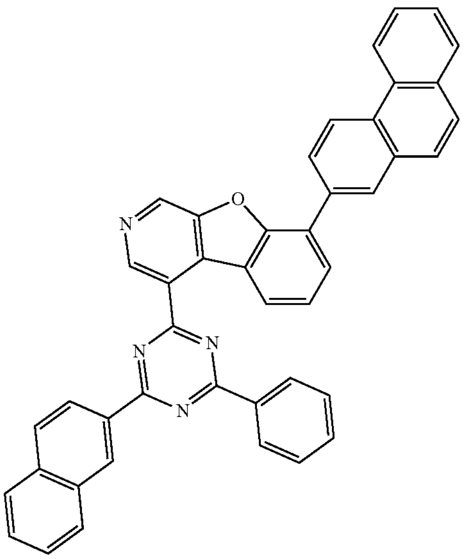
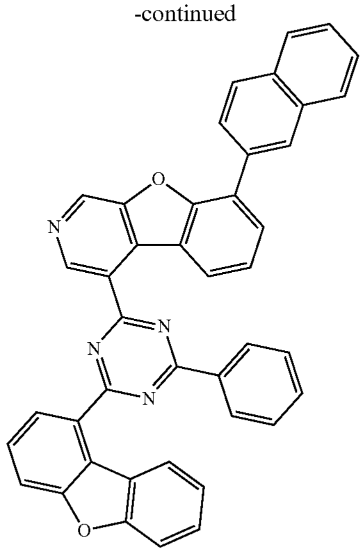
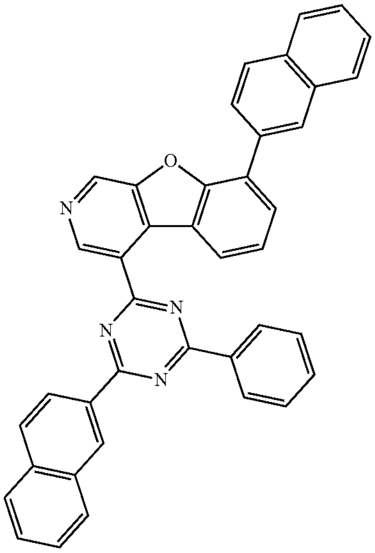
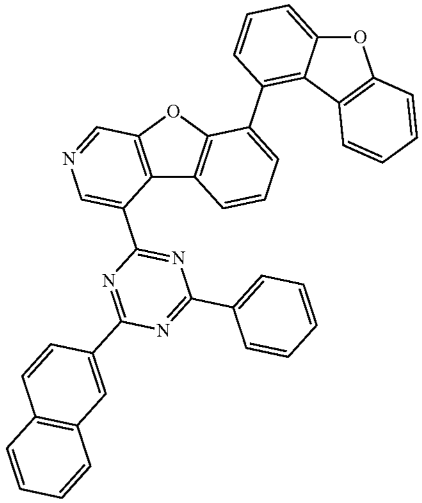

-continued
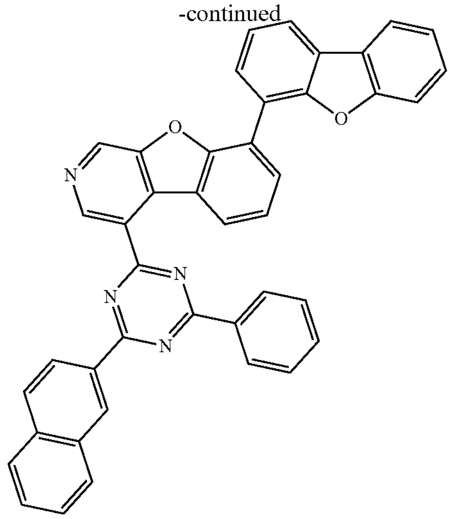
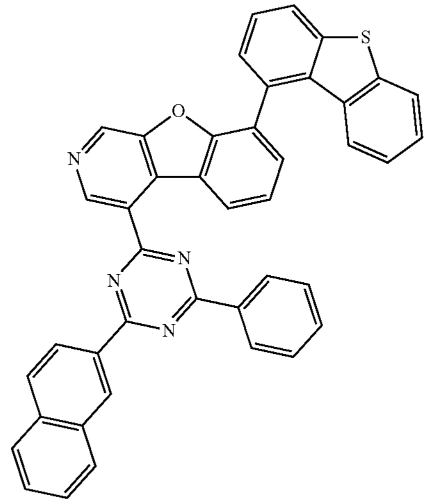
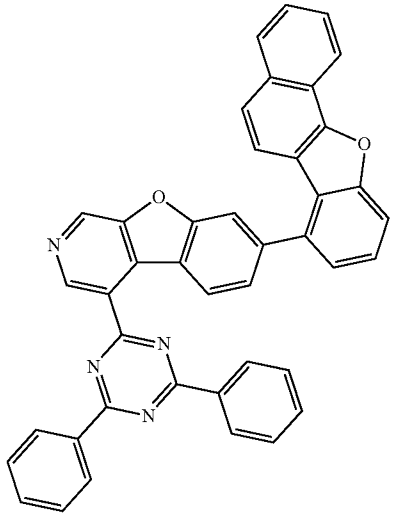
-continued
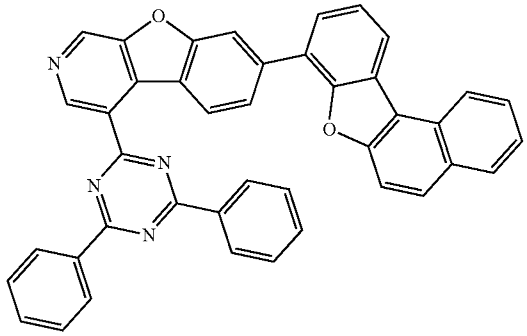
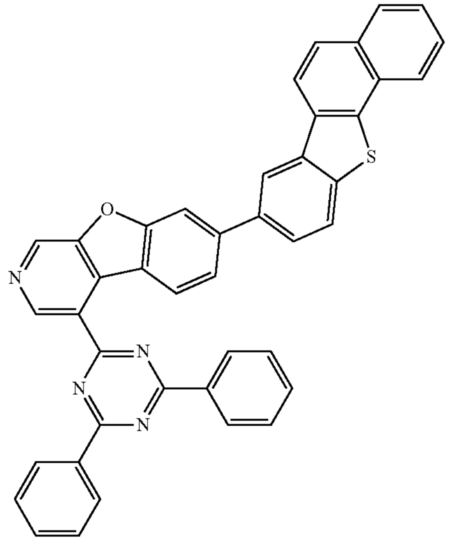
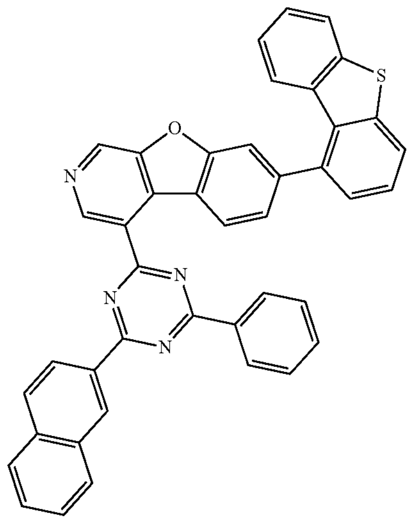

-continued
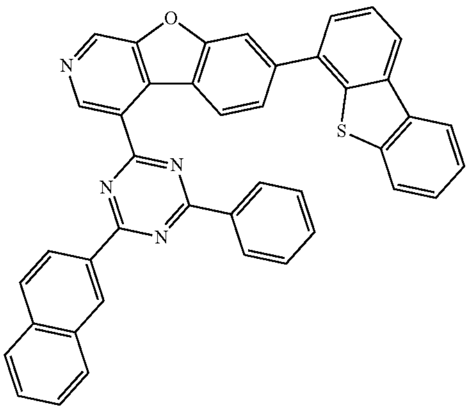
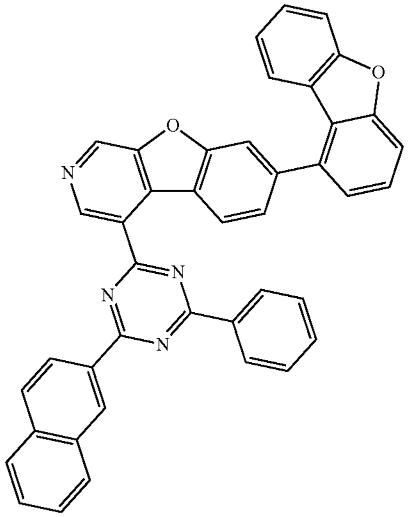
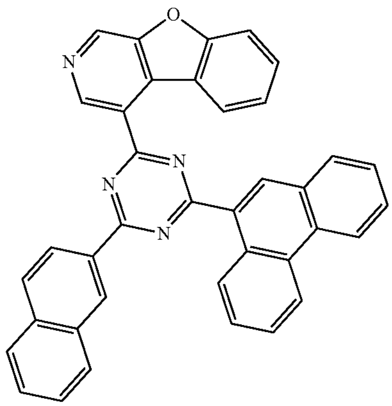
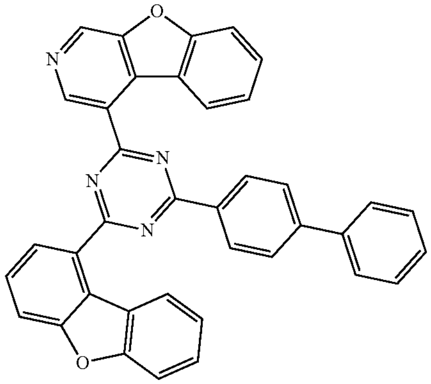
-continued
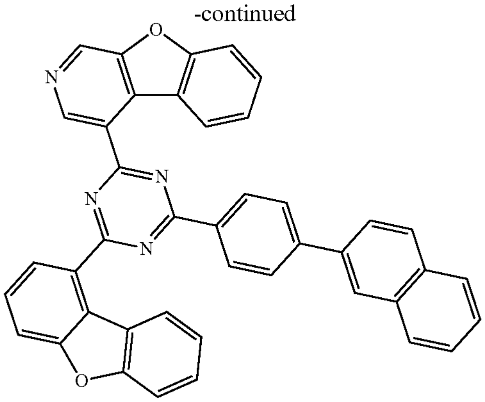
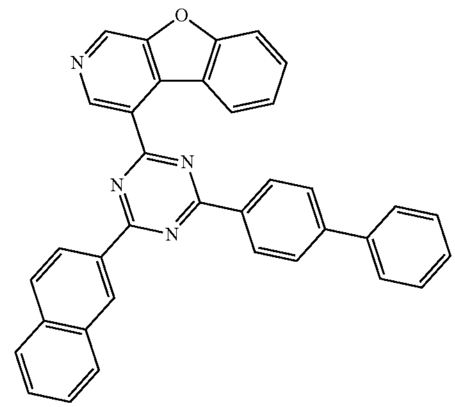
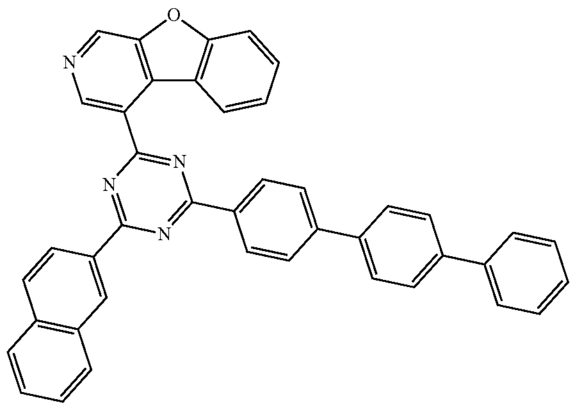
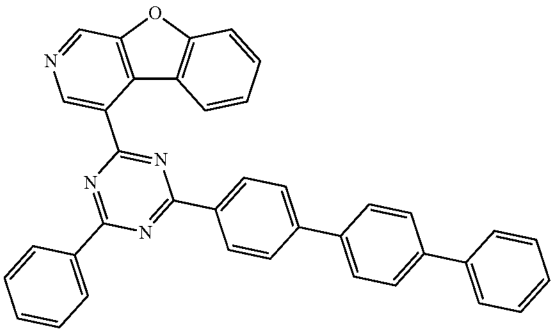

-continued
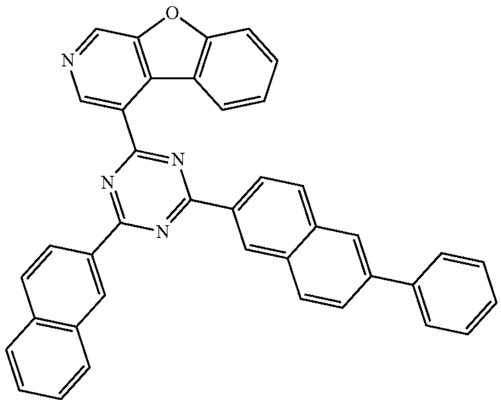
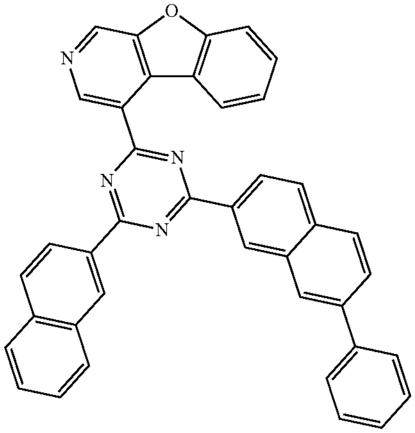
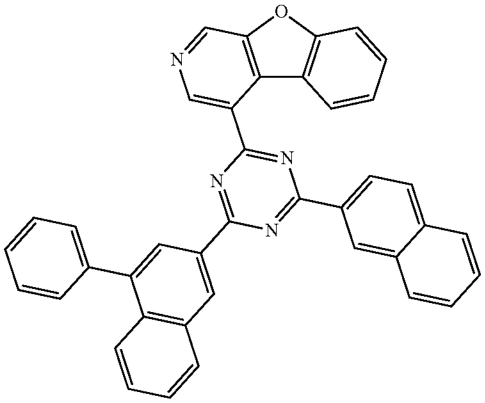
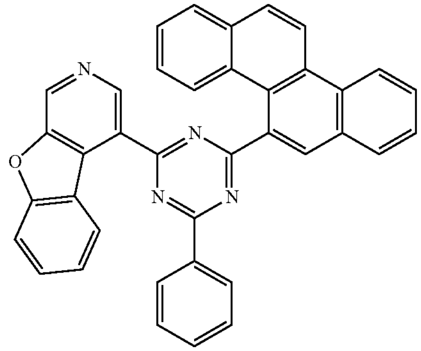
-continued
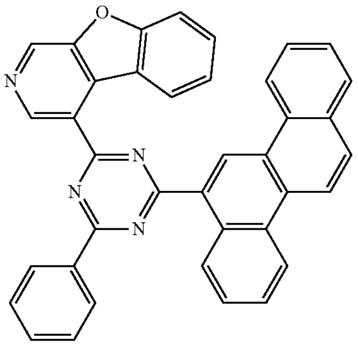
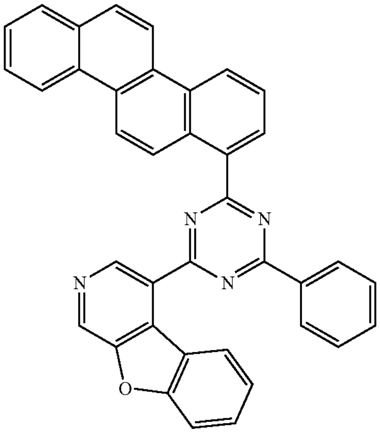
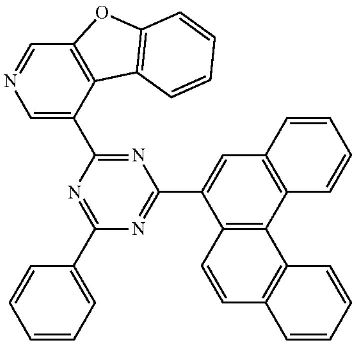
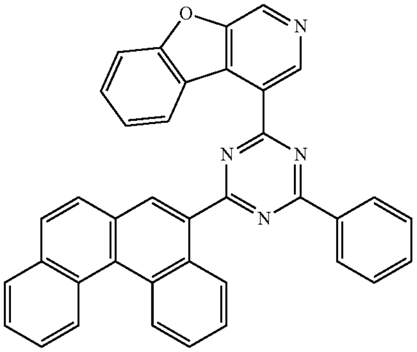

-continued
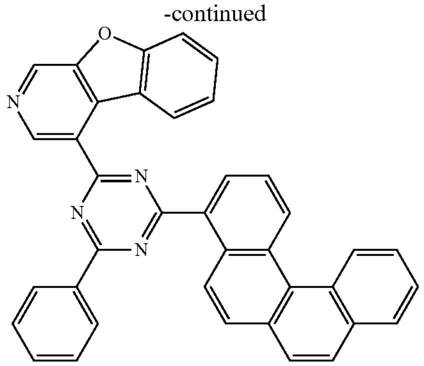
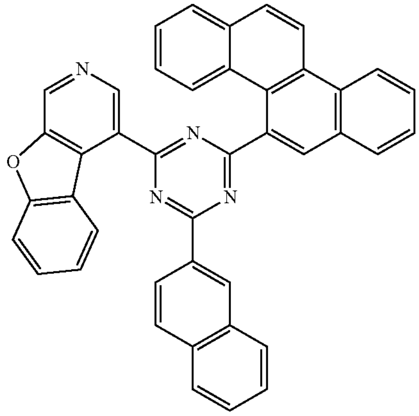
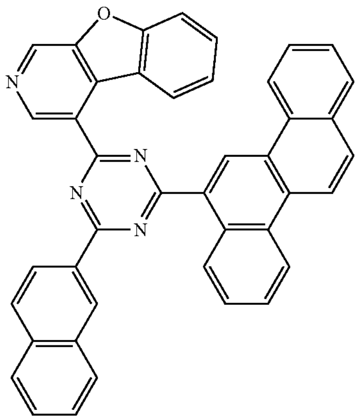
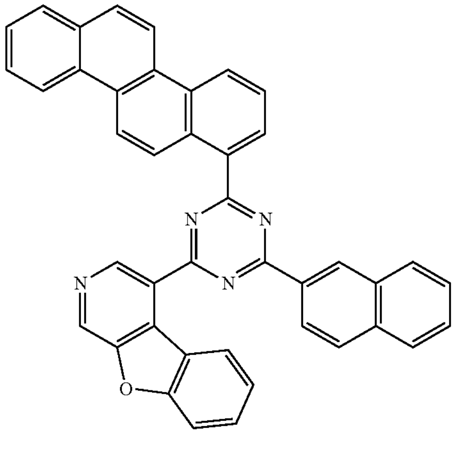
-continued
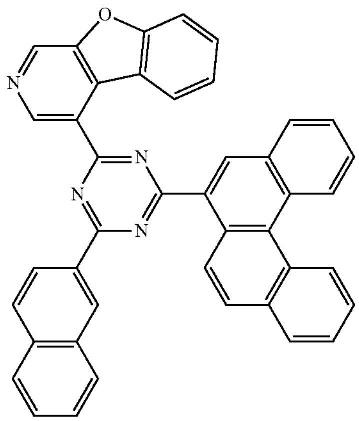
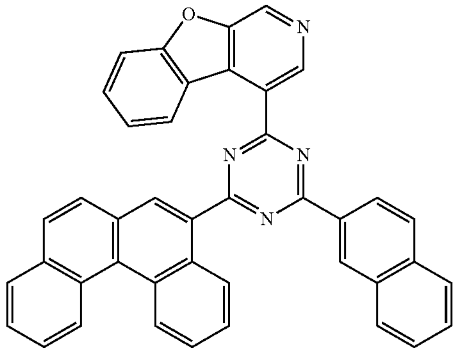
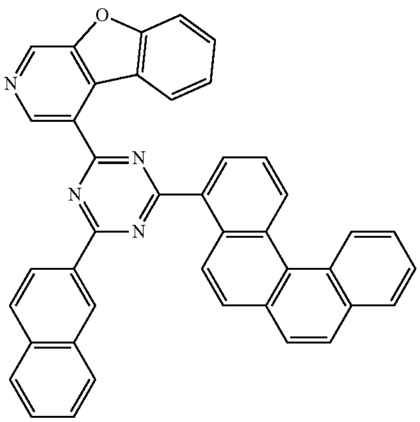
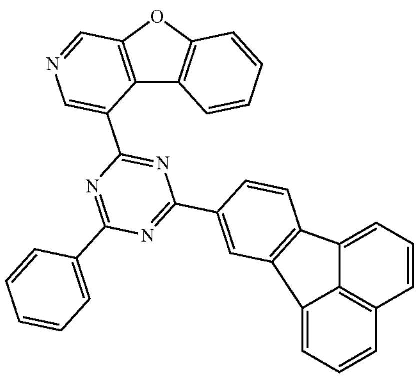

-continued
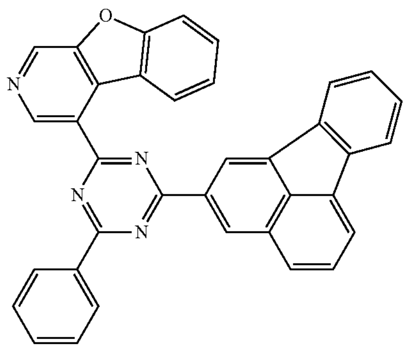
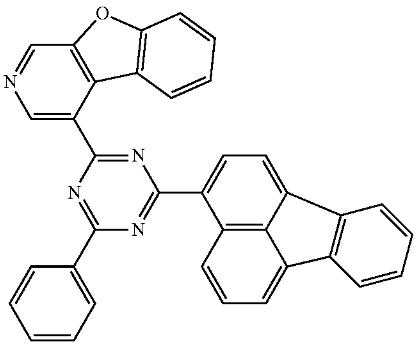
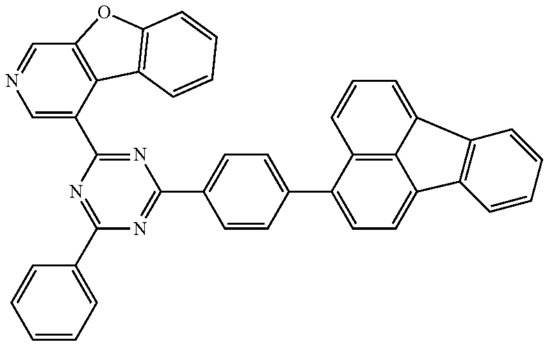
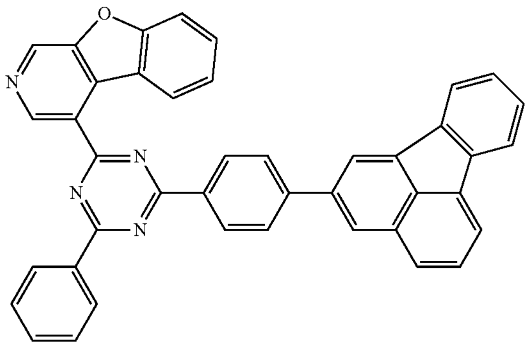
-continued
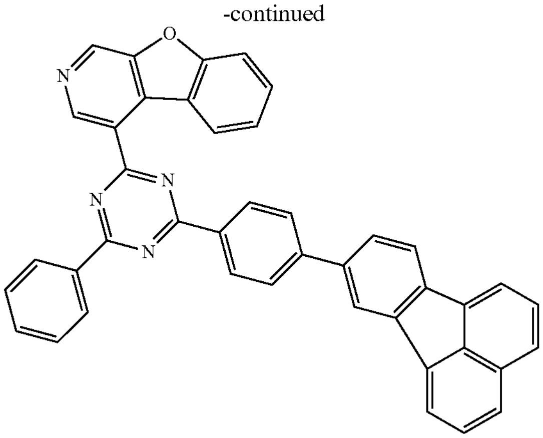
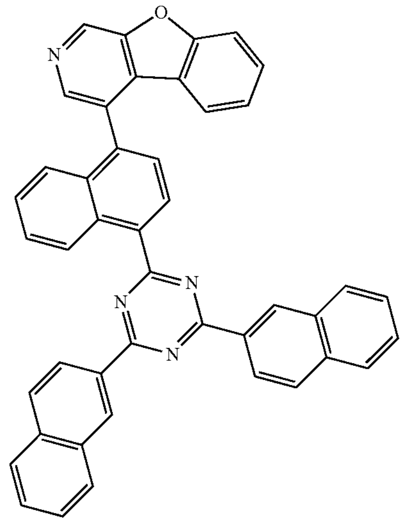
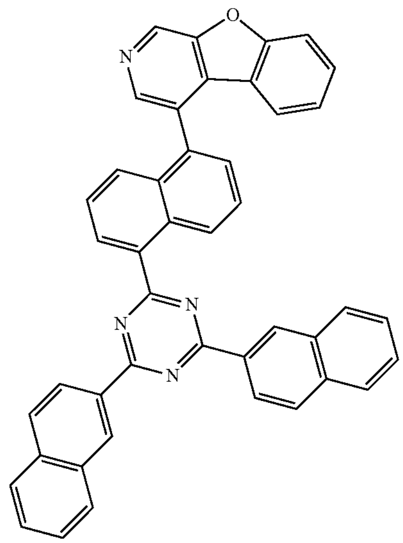

-continued
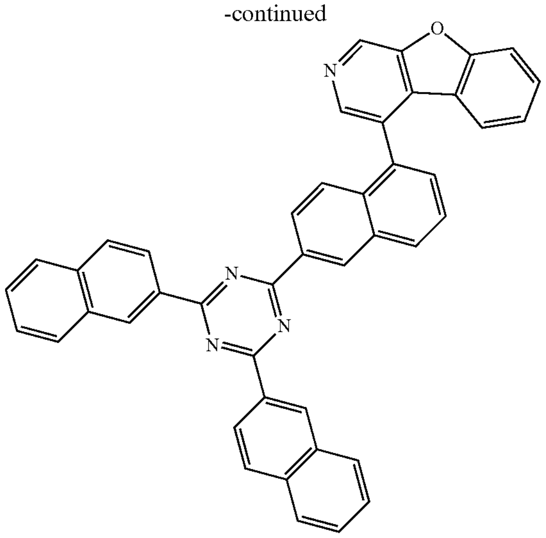
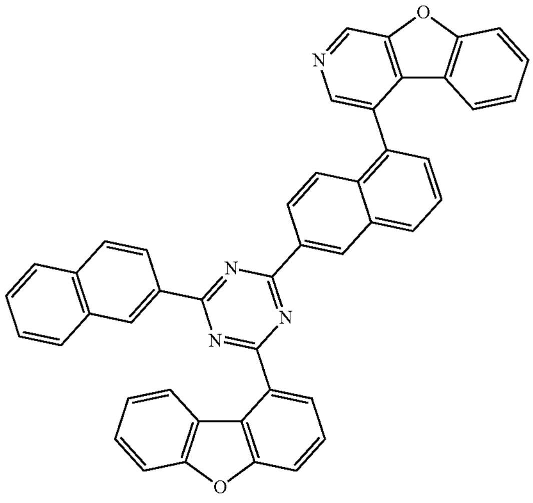
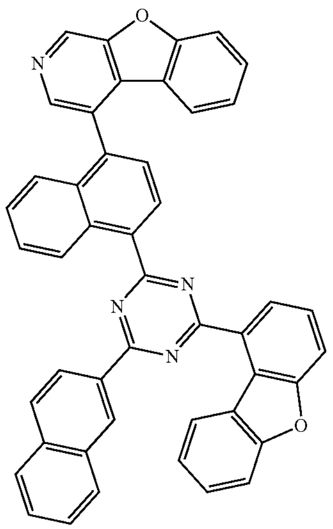
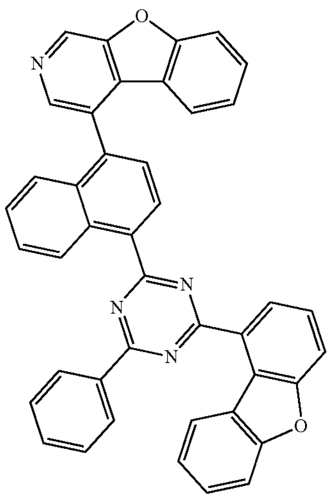
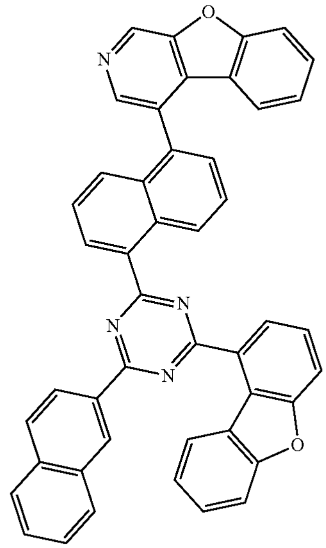
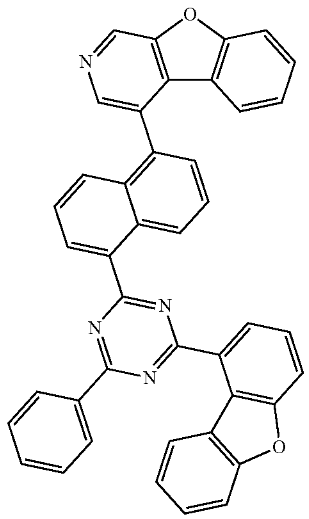
-continued -continued
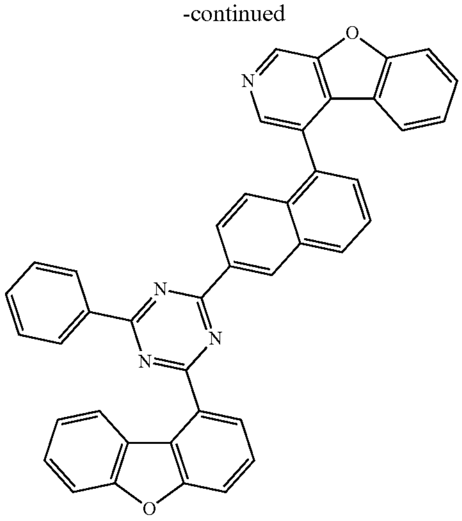
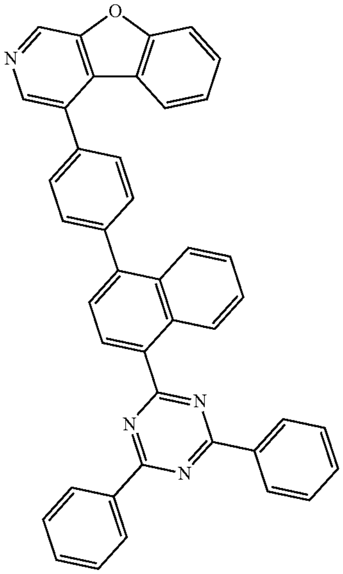
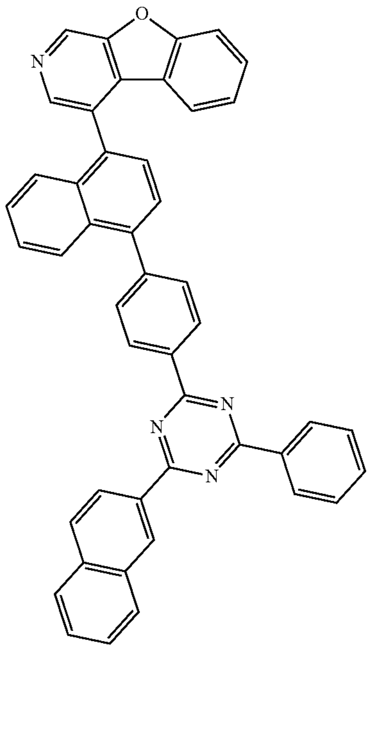
-continued
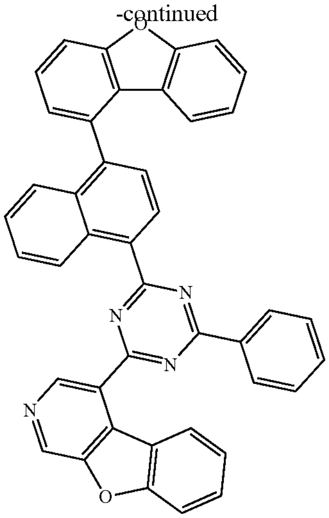
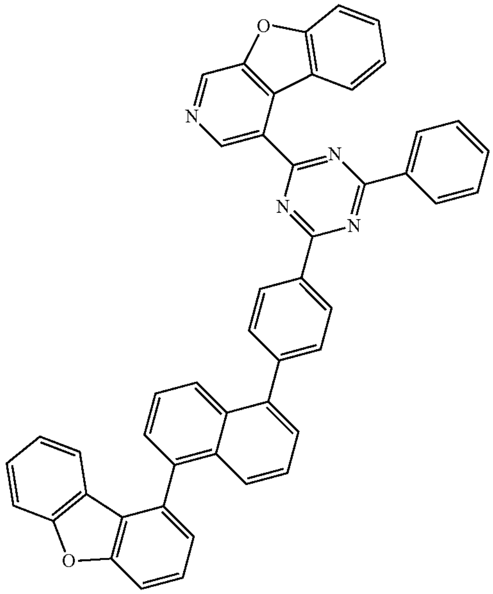
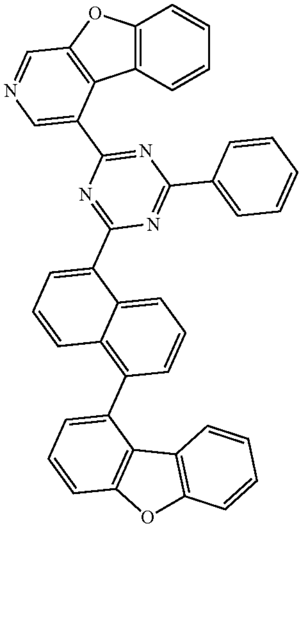

-continued
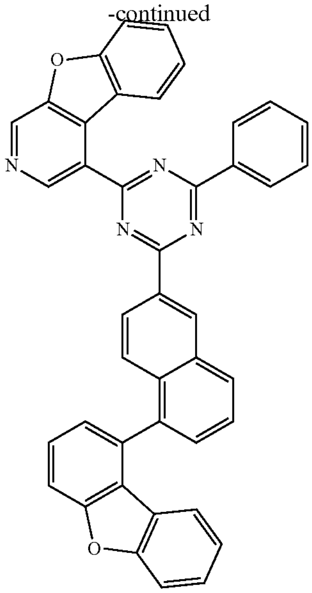
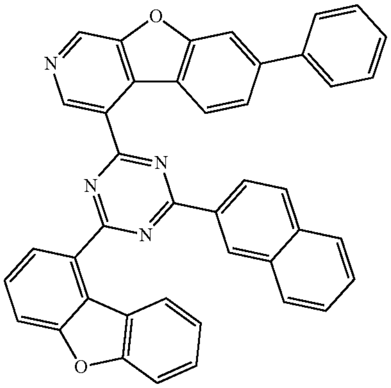
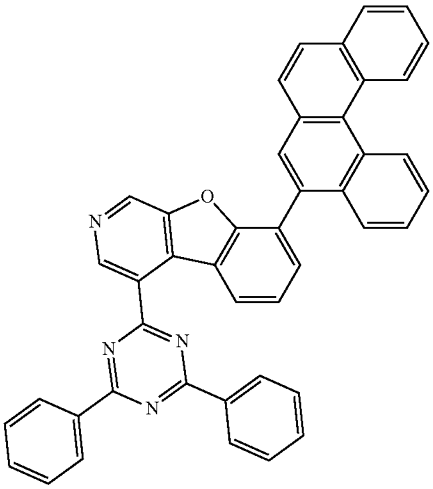
-continued
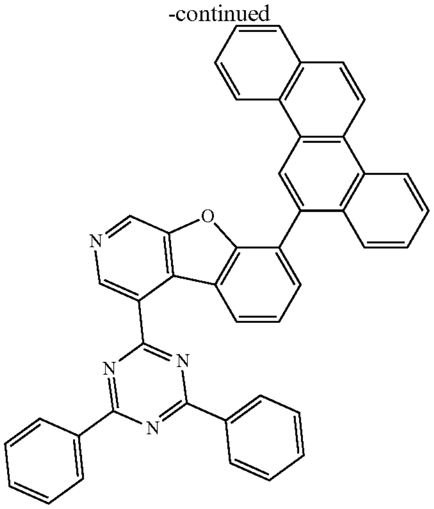
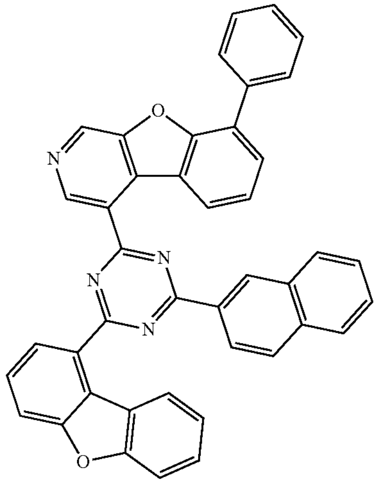
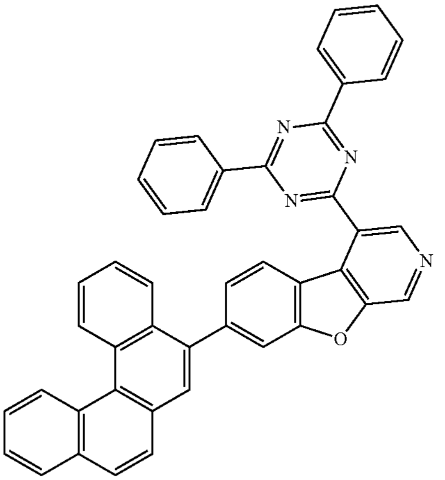
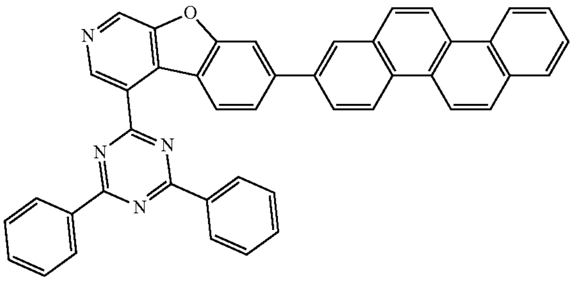

-continued
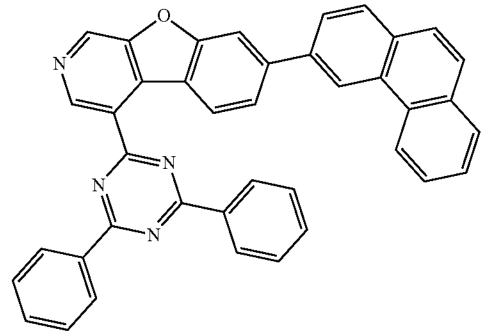
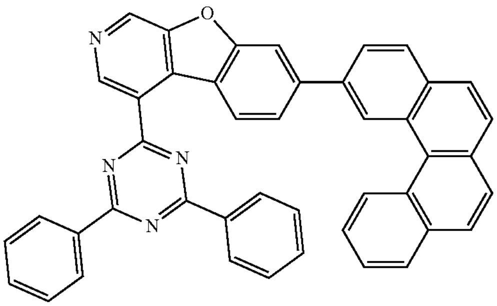
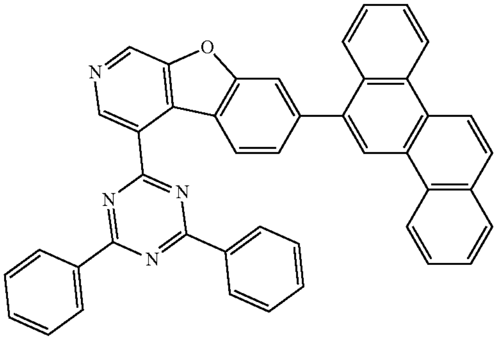
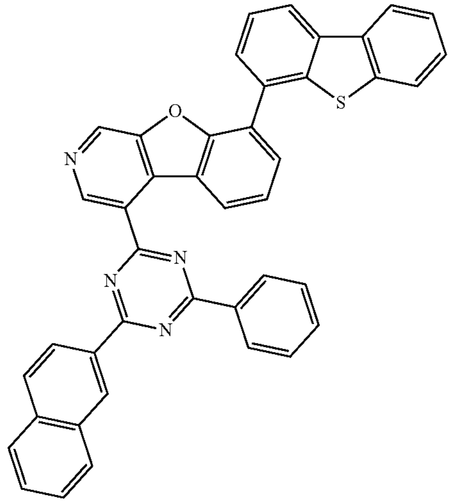
-continued
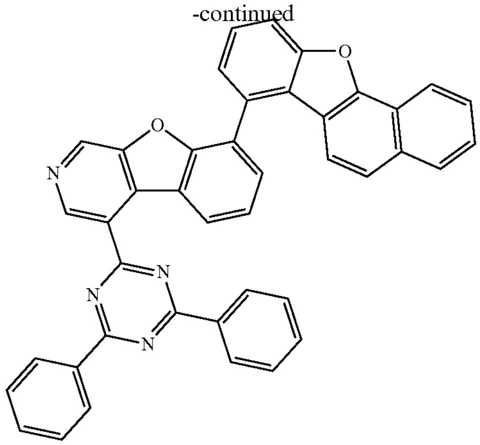
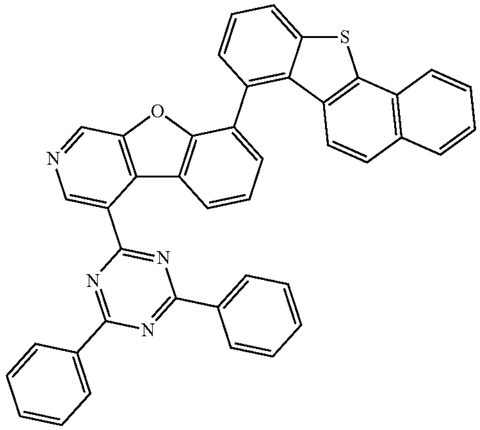
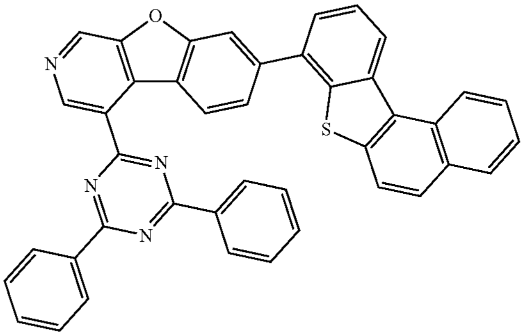
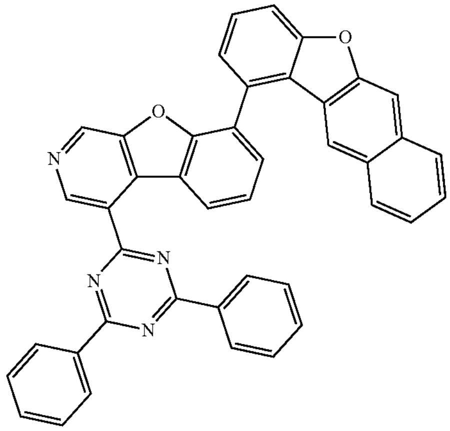

-continued
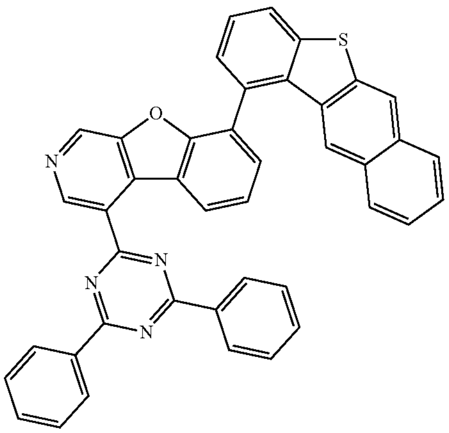
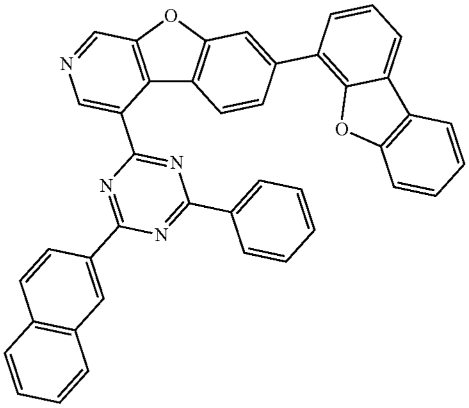
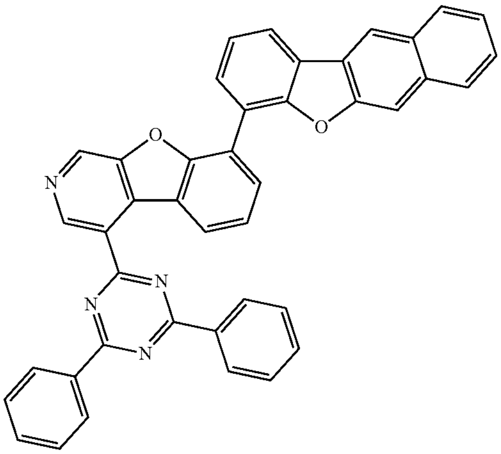
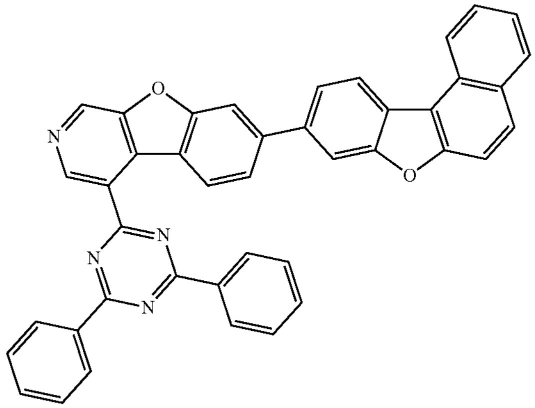
-continued
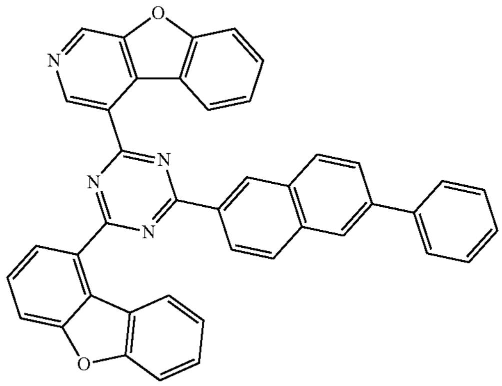
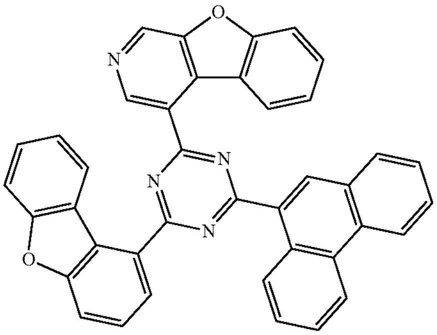
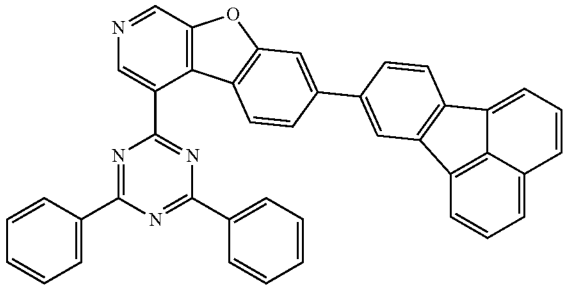
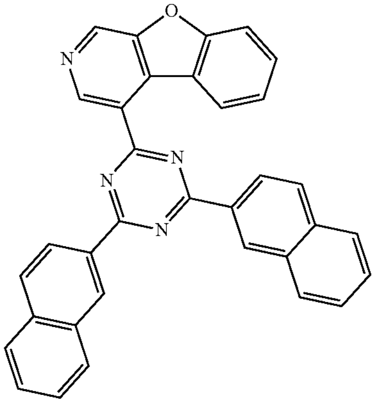

-continued
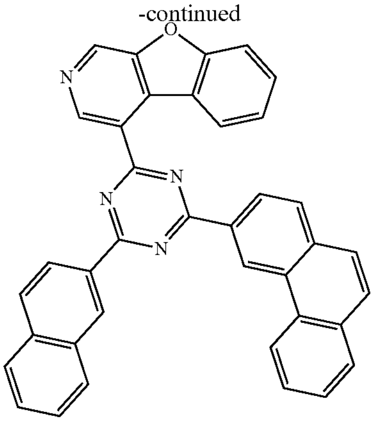
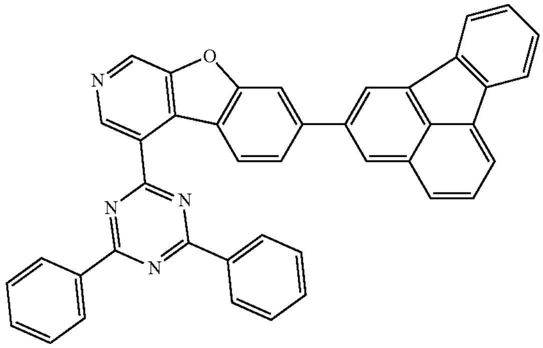
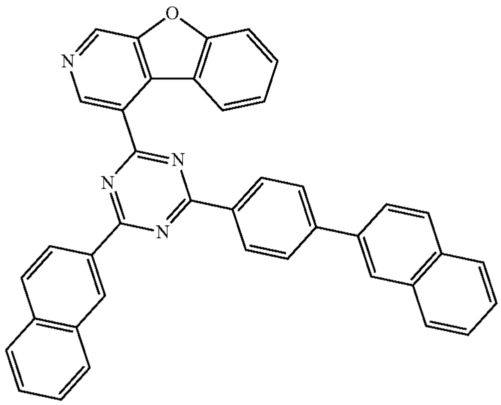
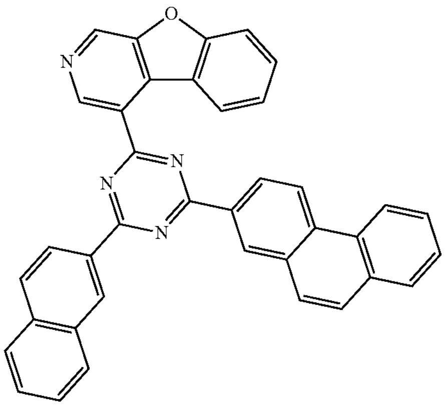
-continued
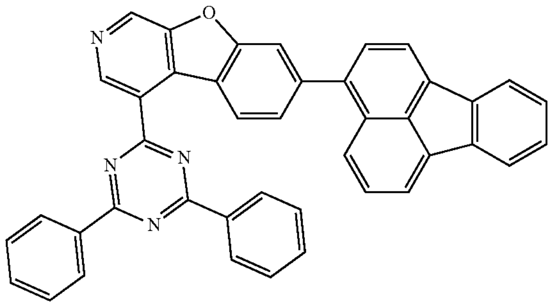
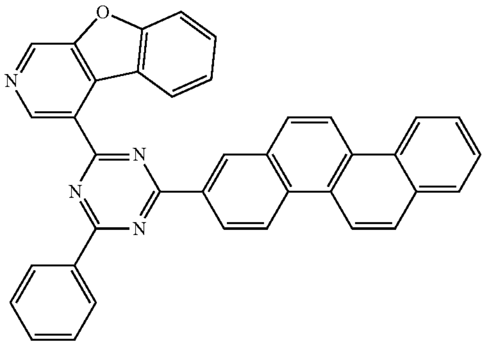
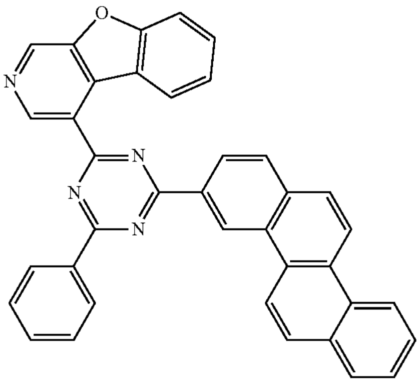
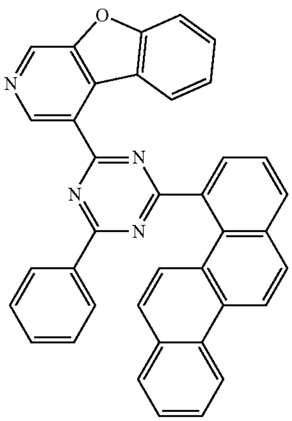

-continued
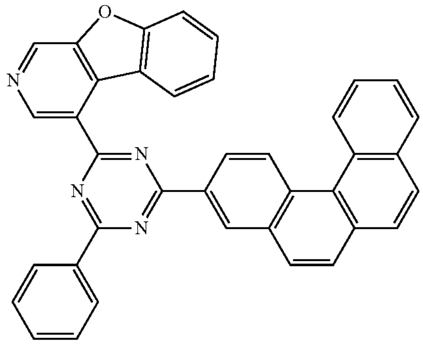
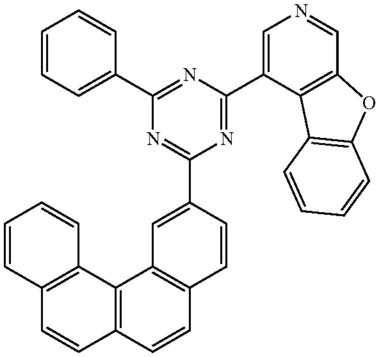
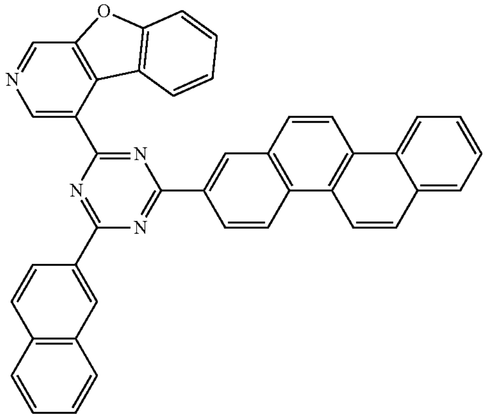
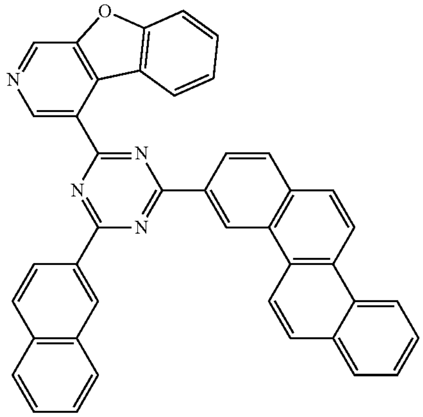
-continued
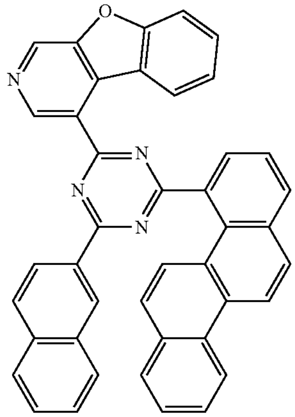
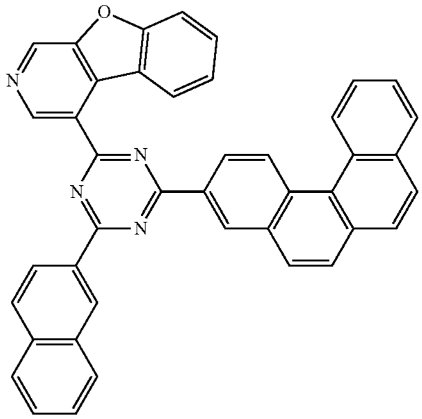
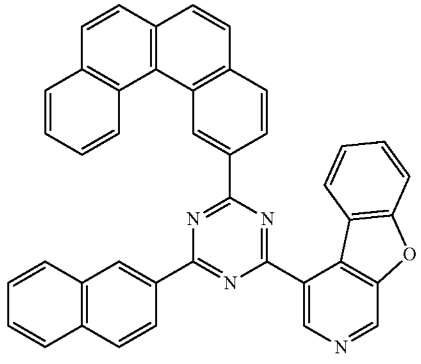
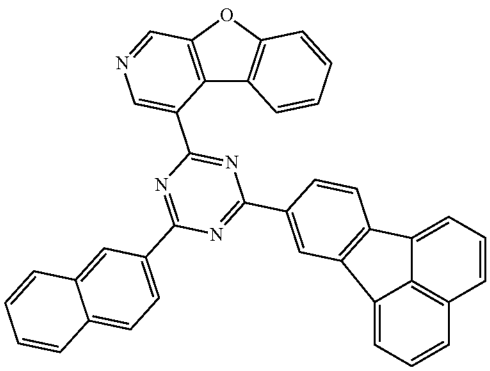

-continued
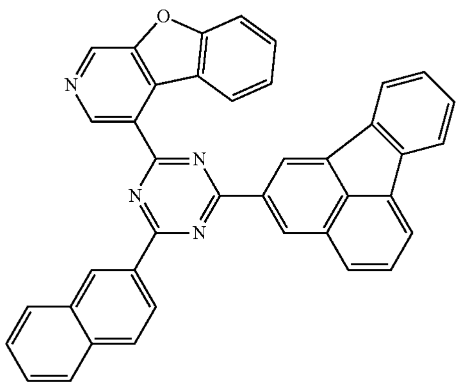
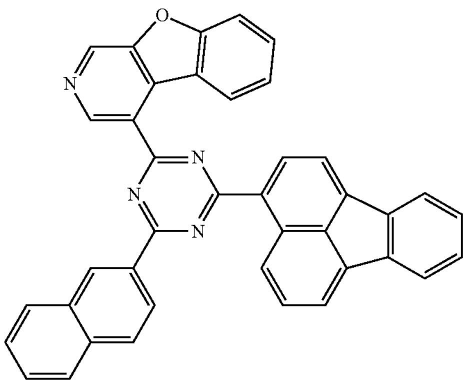
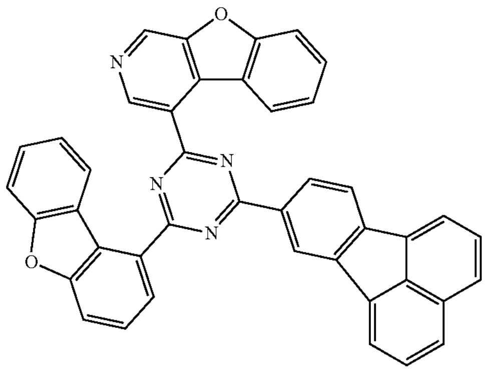
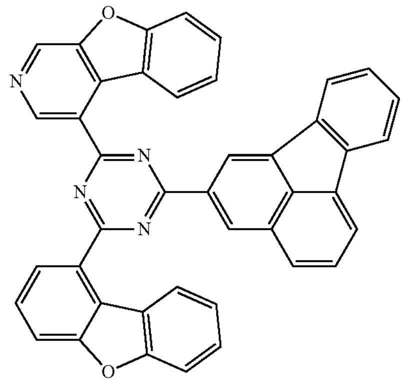
-continued
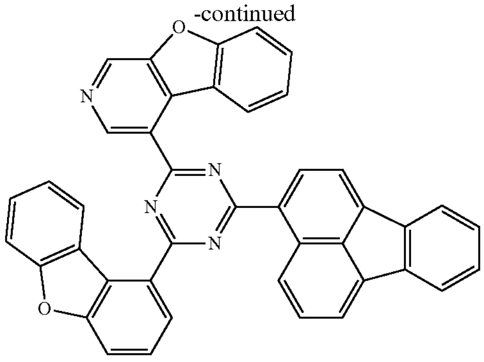
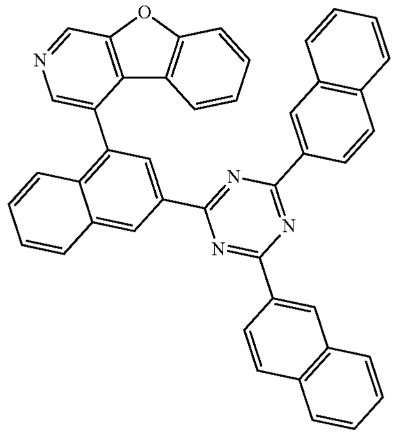
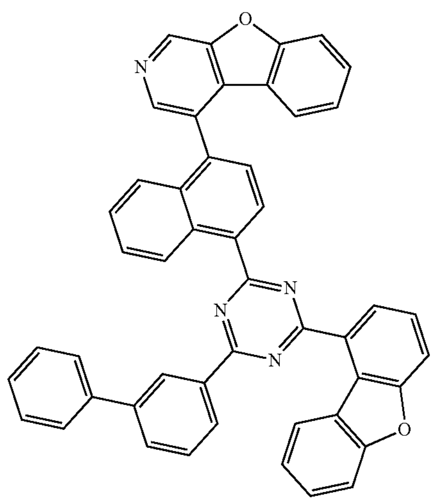

-continued
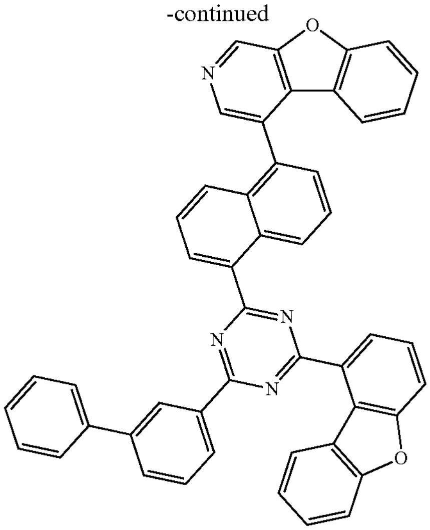
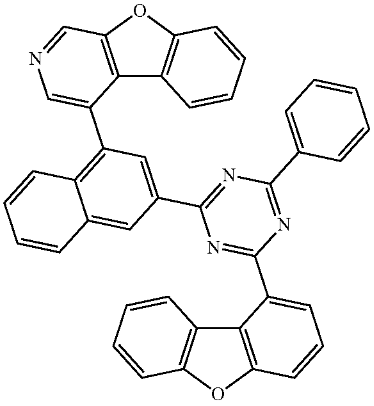
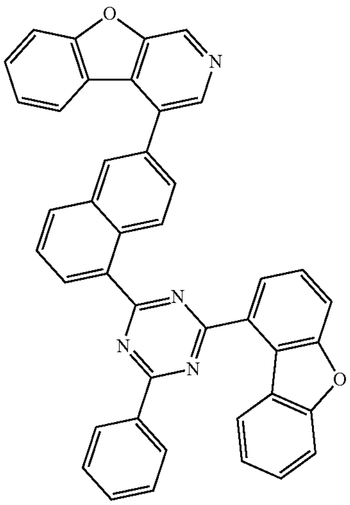
-continued
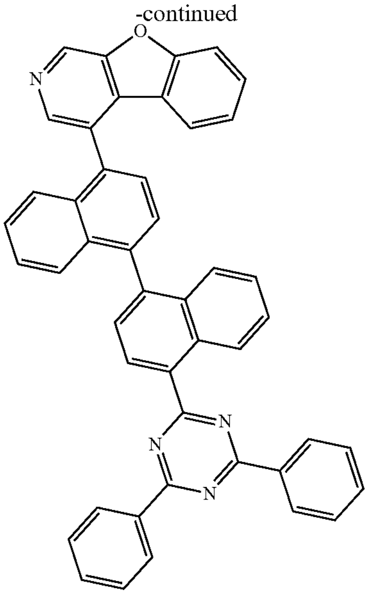
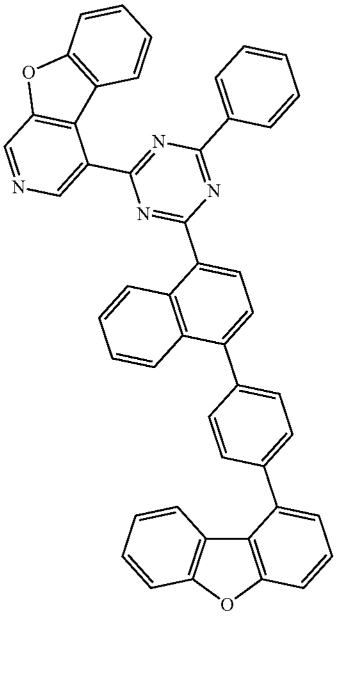

-continued
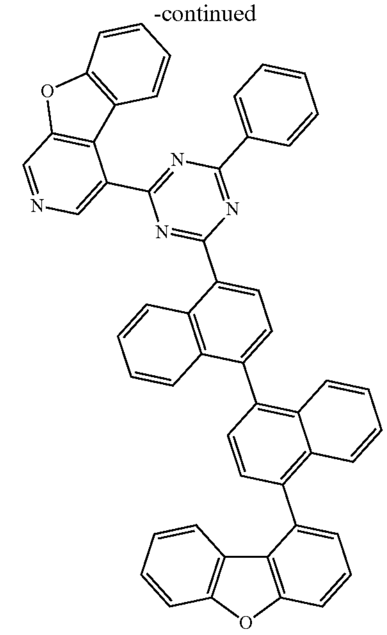
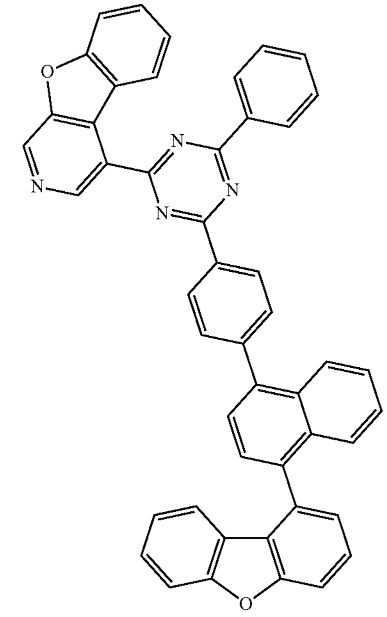
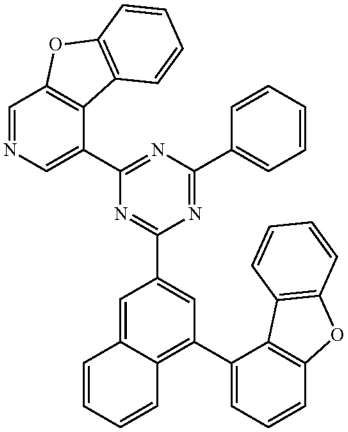
-continued
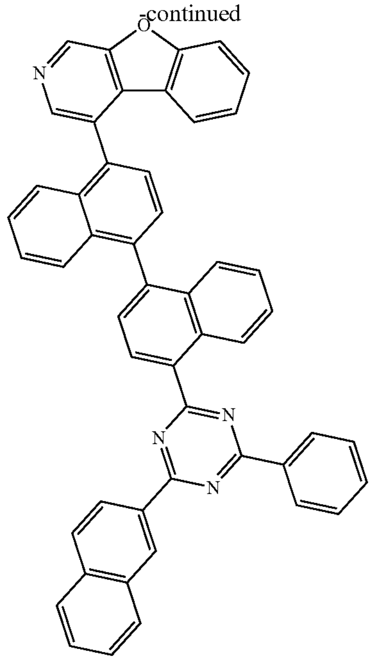
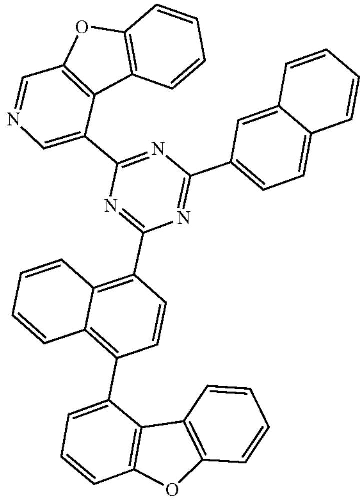
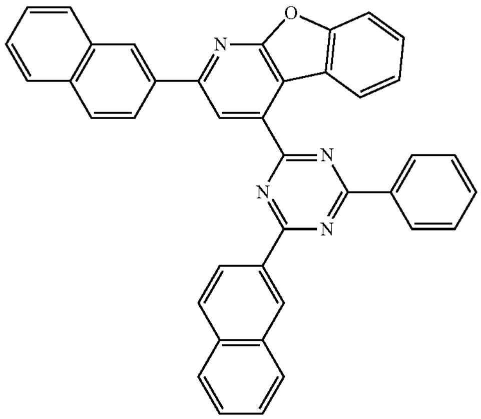

-continued
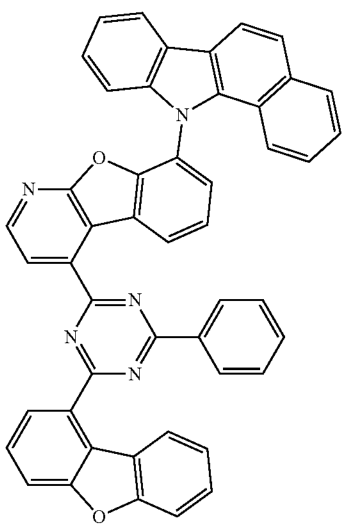
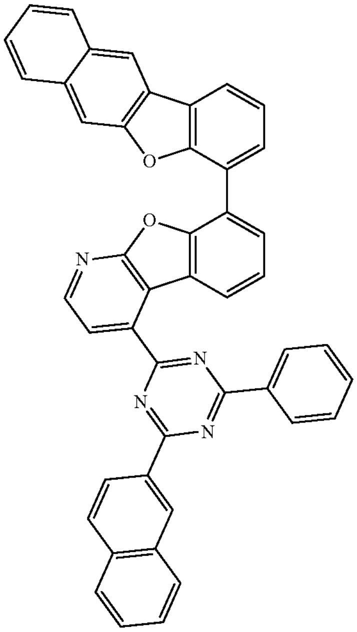
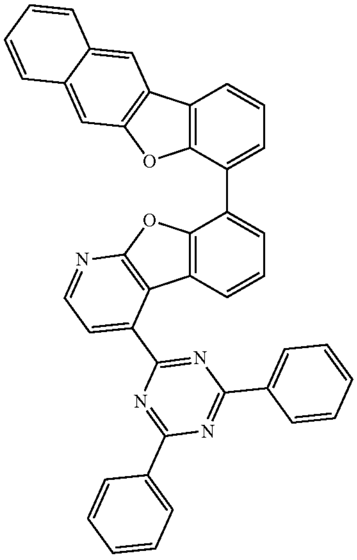
-continued
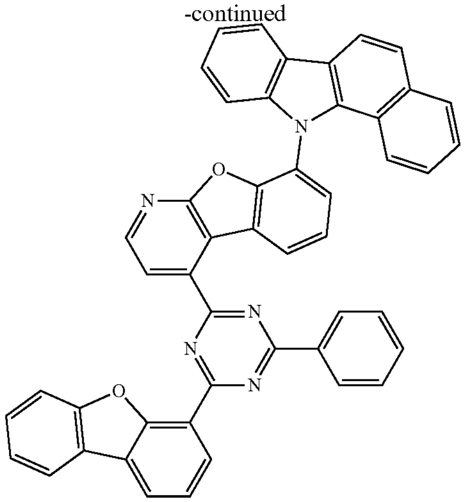
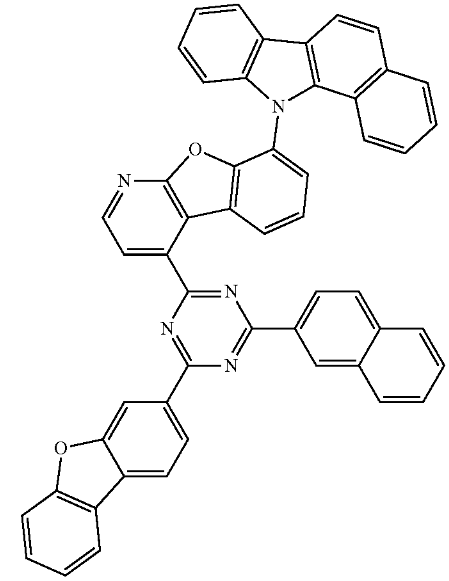
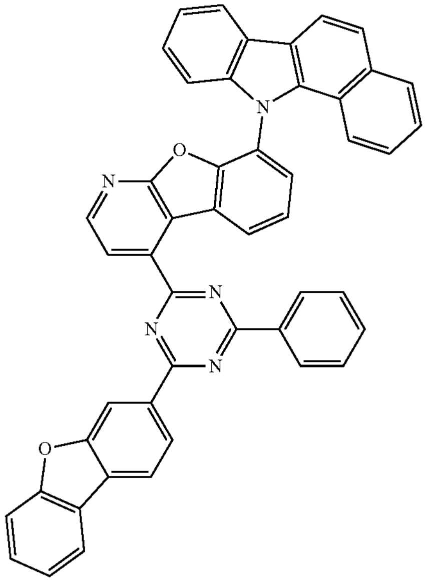

-continued
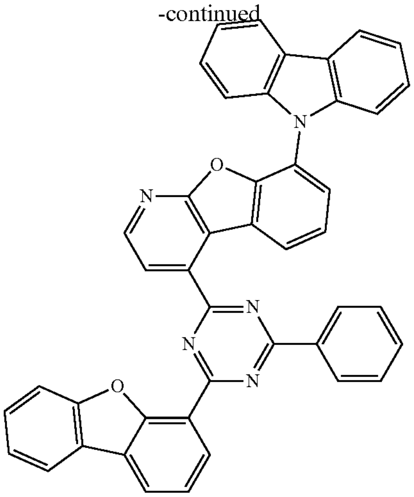
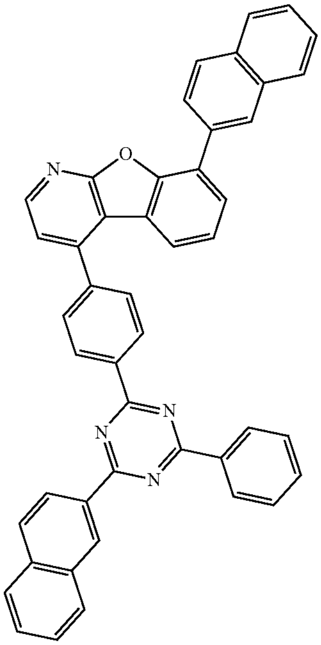
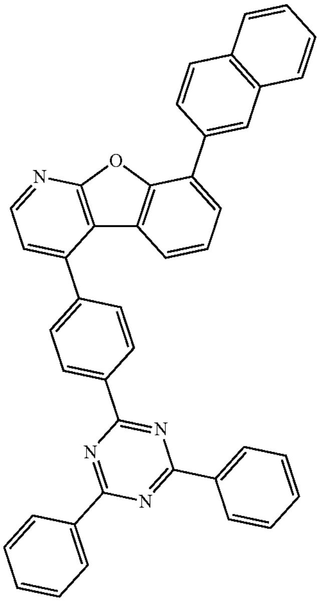
-continued
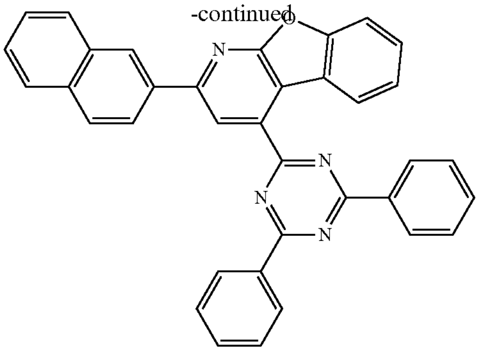
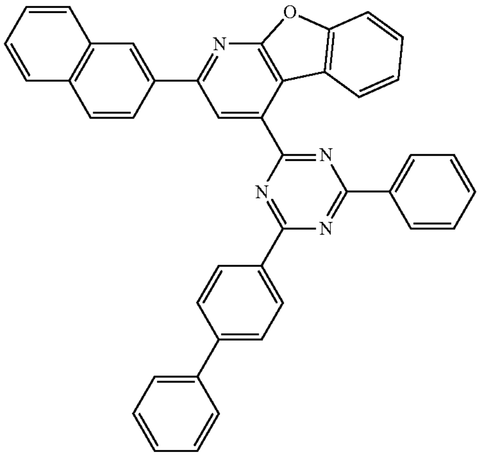
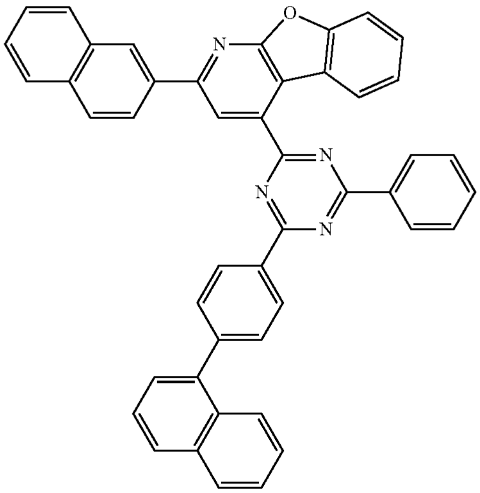

-continued
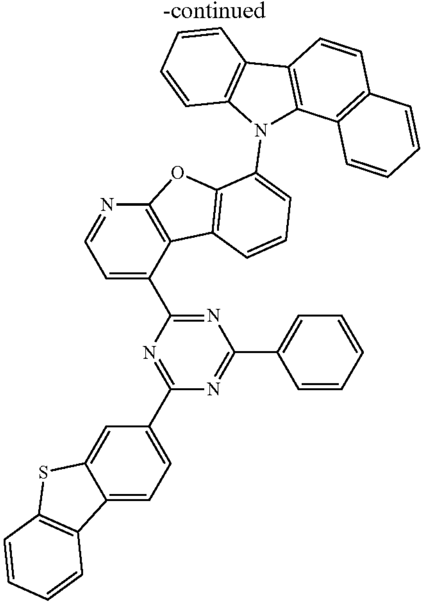
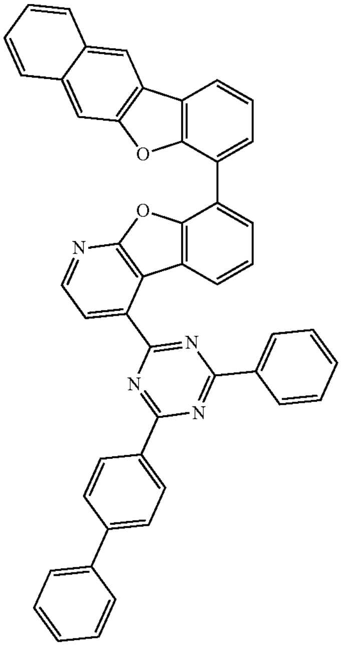
-continued
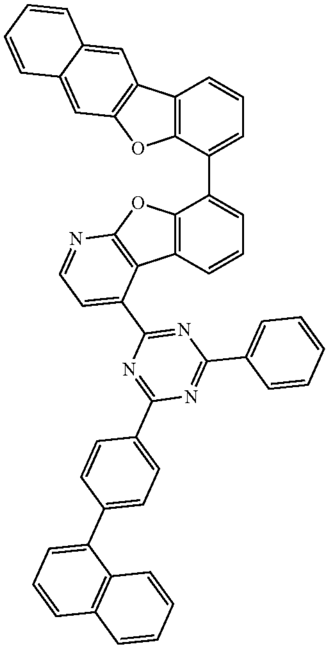
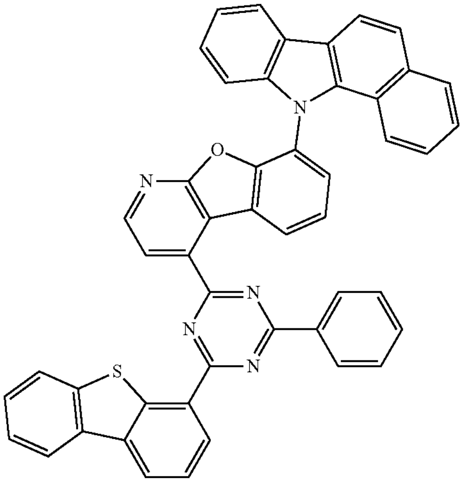
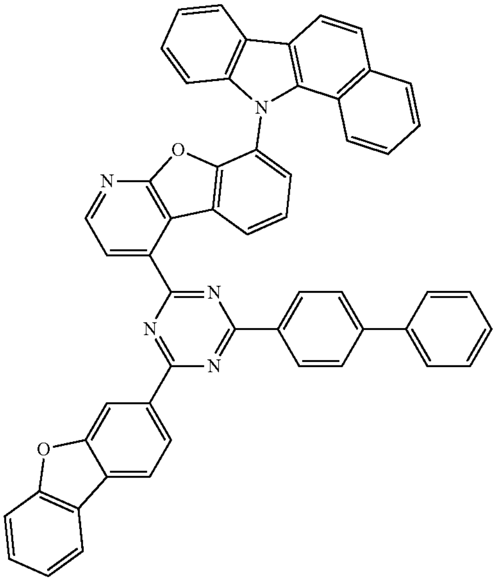

-continued
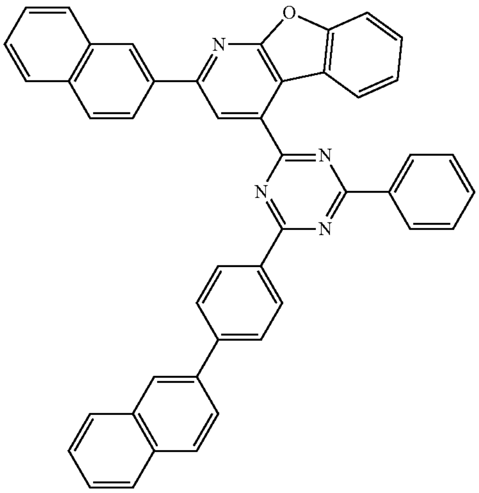
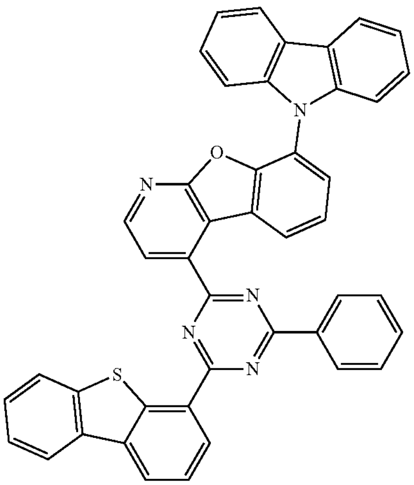
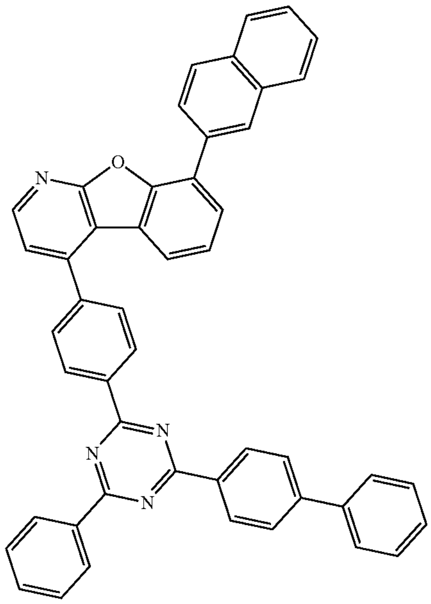
-continued
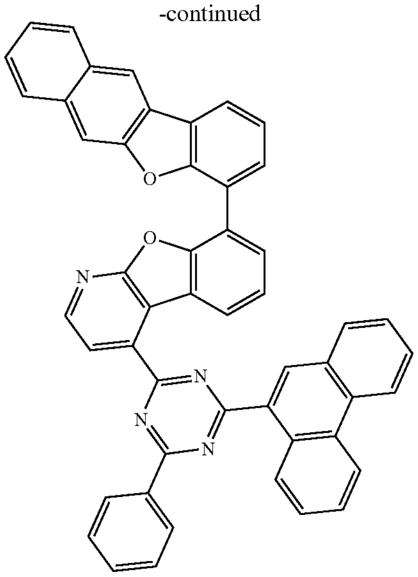
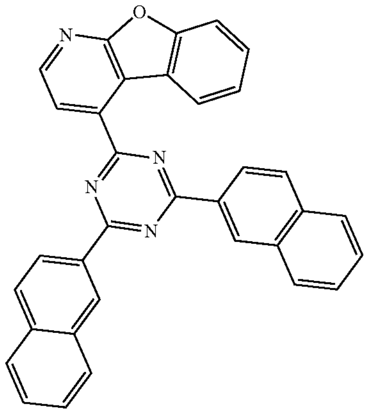
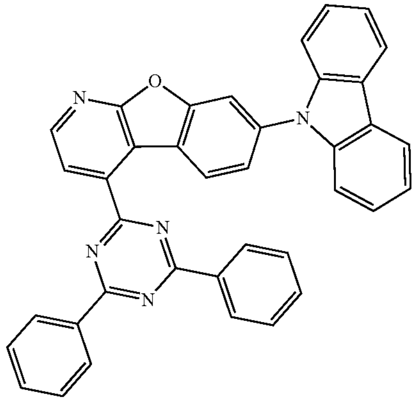

-continued
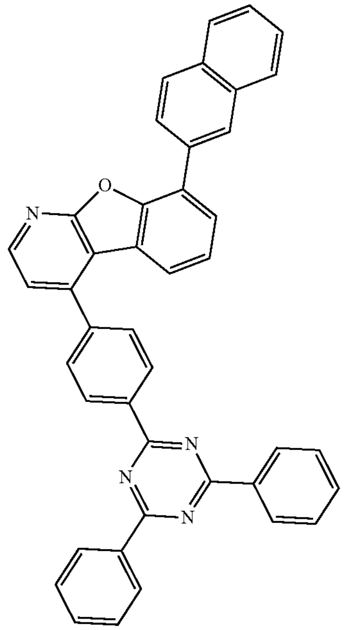
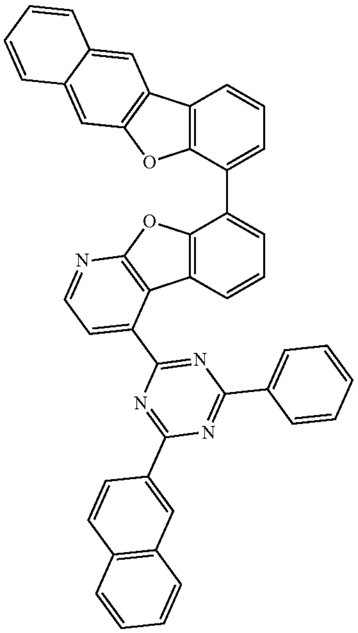
-continued
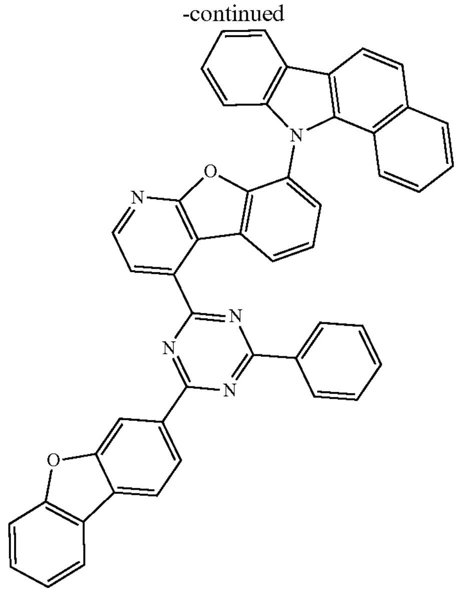
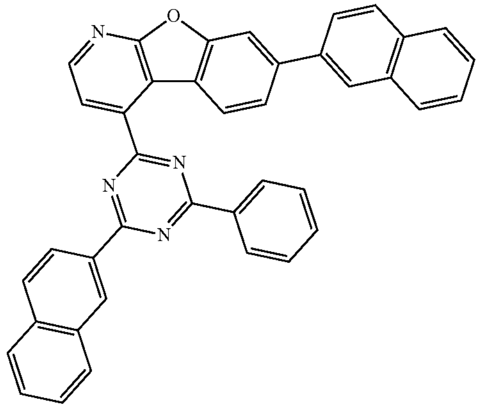
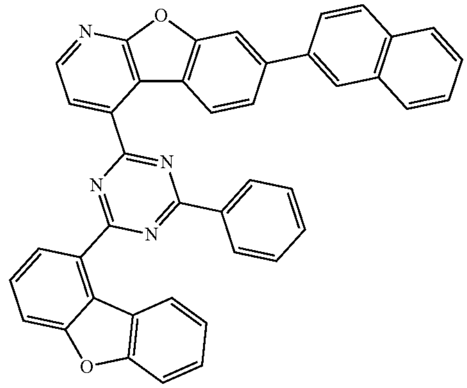

-continued
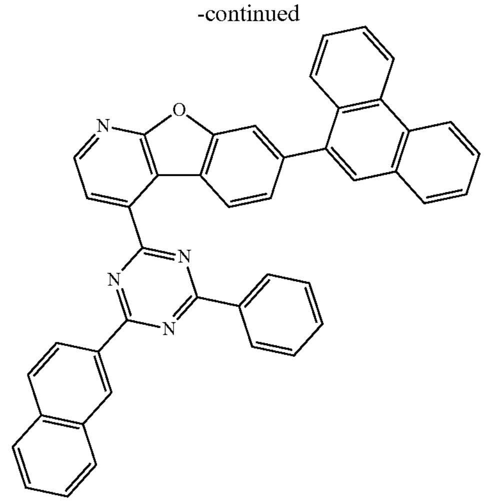
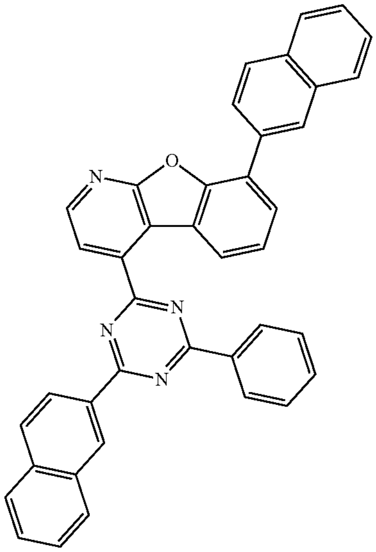
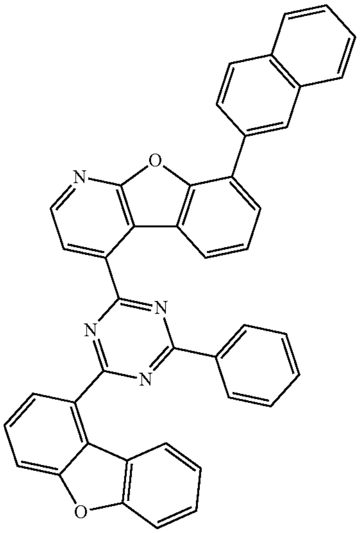
-continued
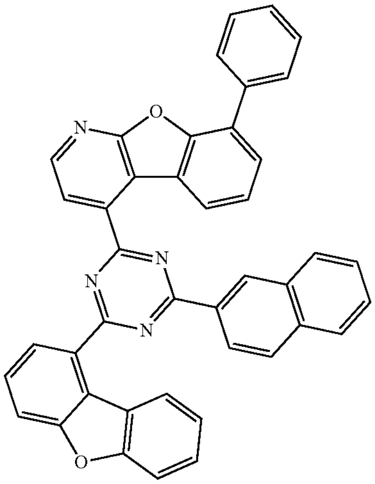
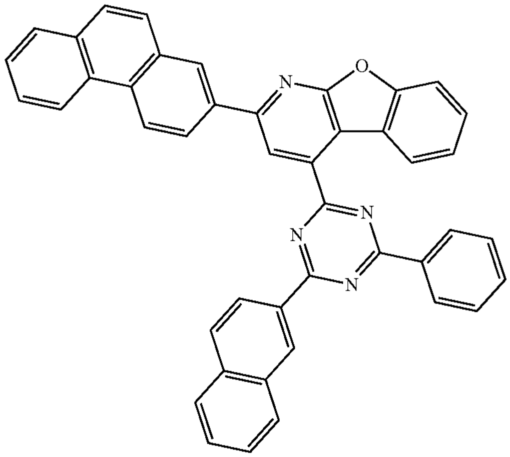
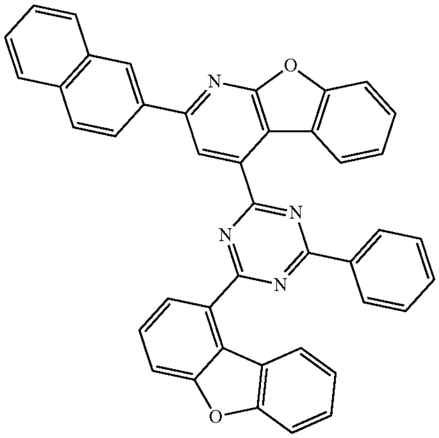

-continued
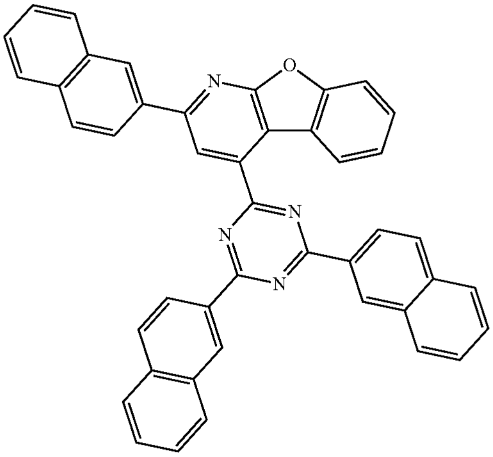
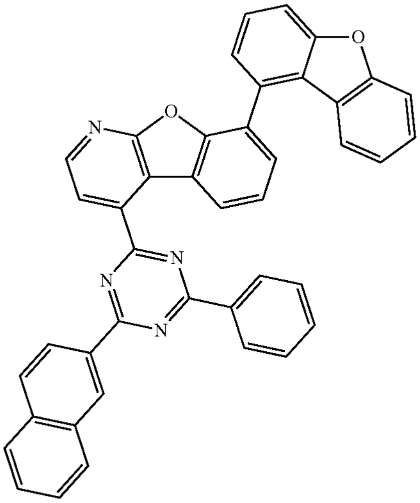
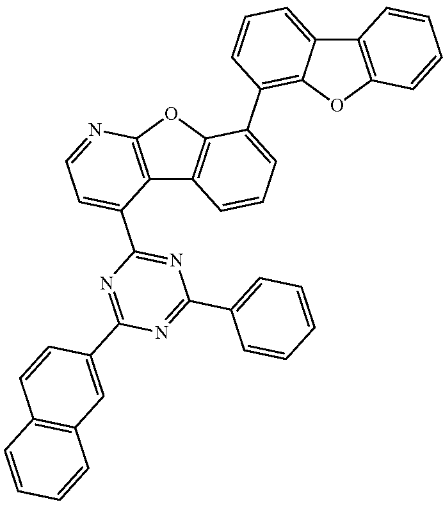
-continued
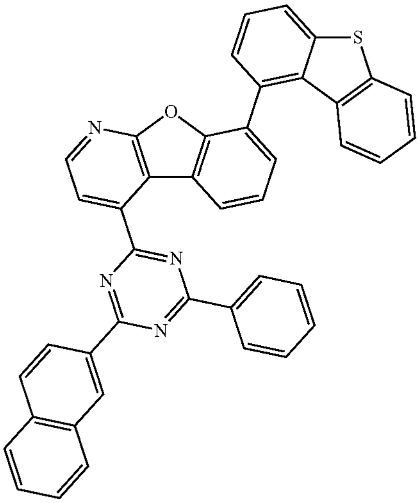
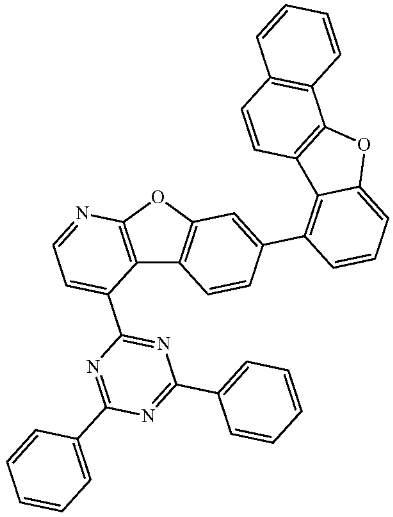
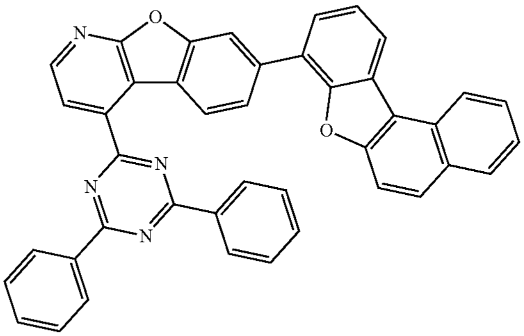

-continued
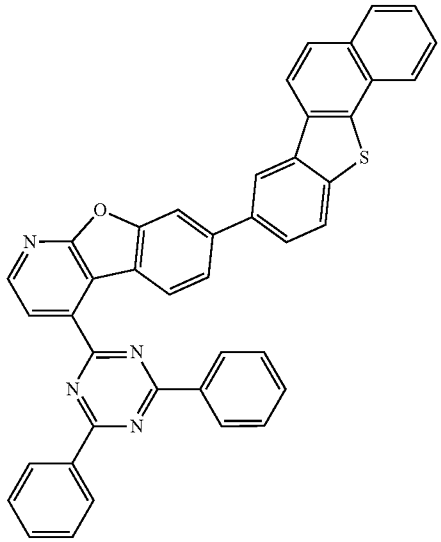
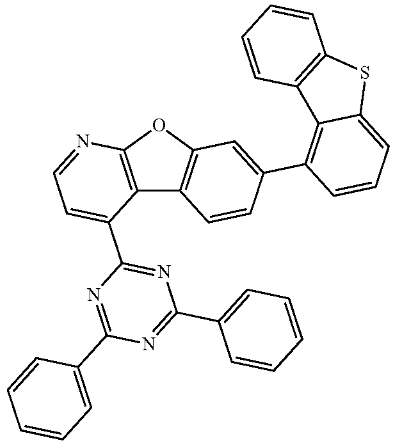
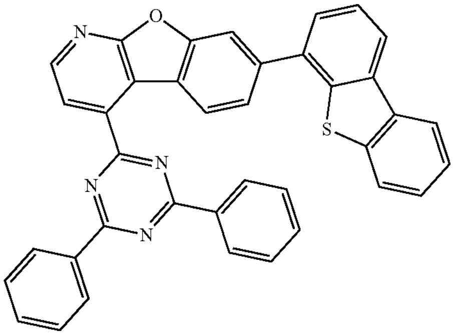
-continued
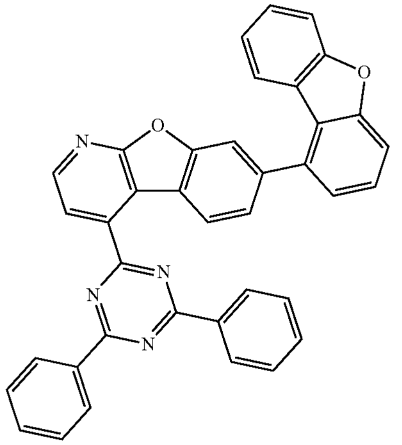
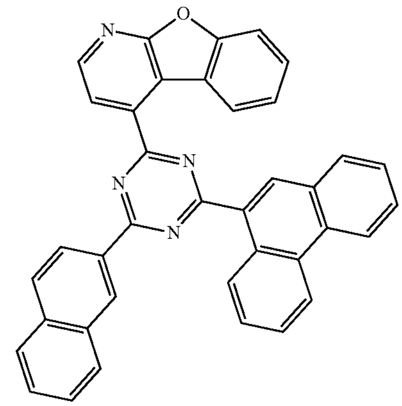
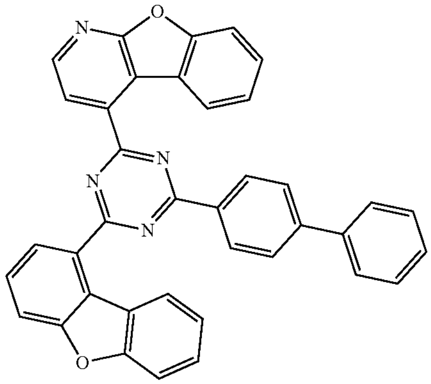
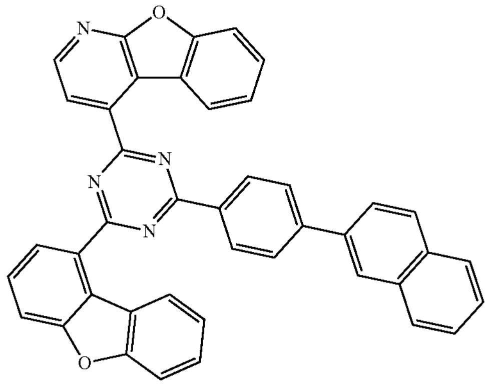

-continued
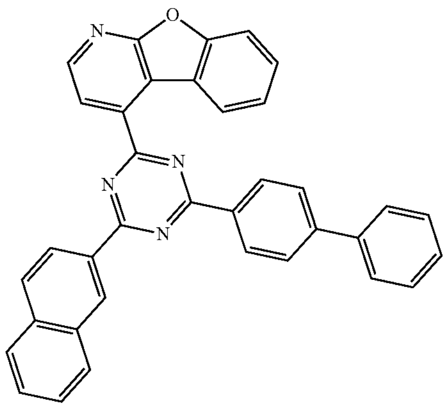
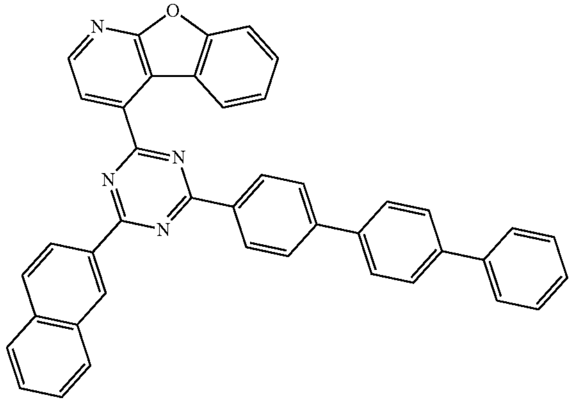
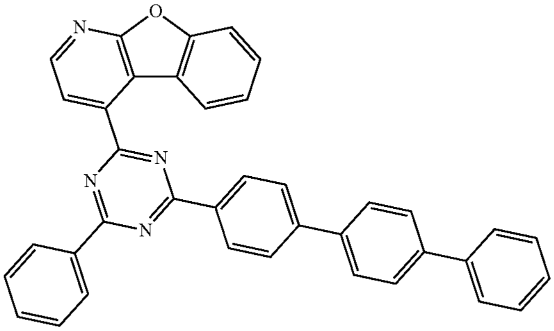
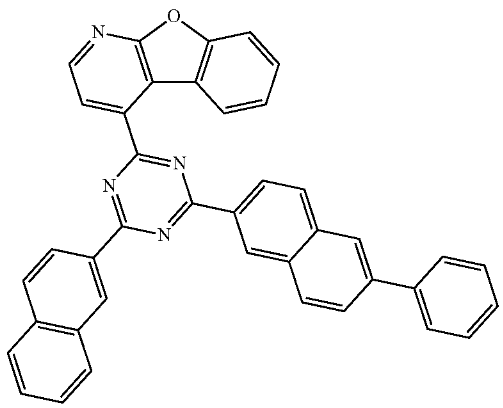
-continued
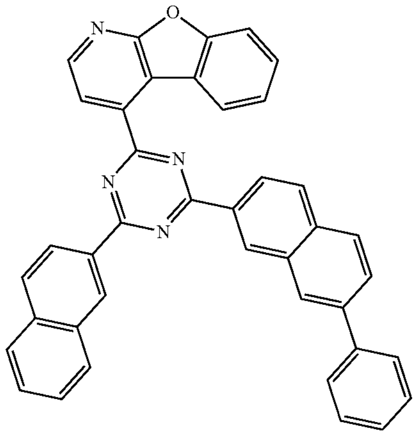
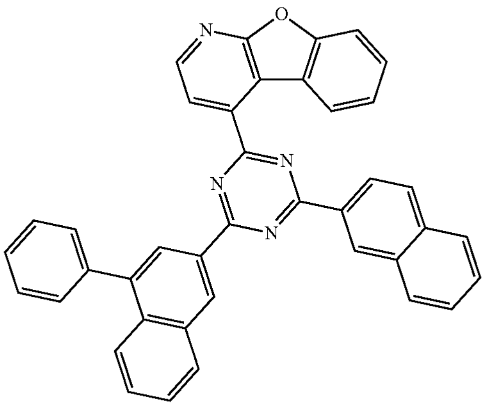
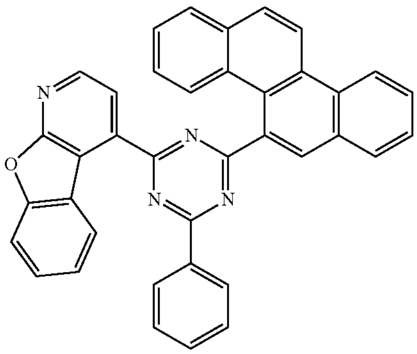
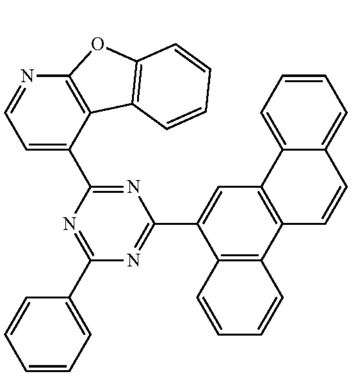

-continued
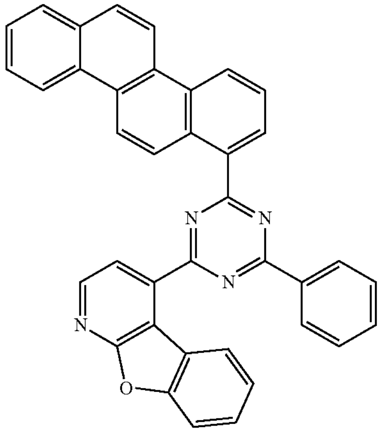
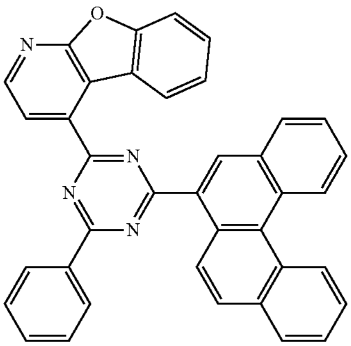
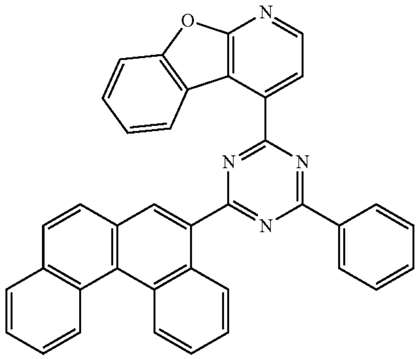
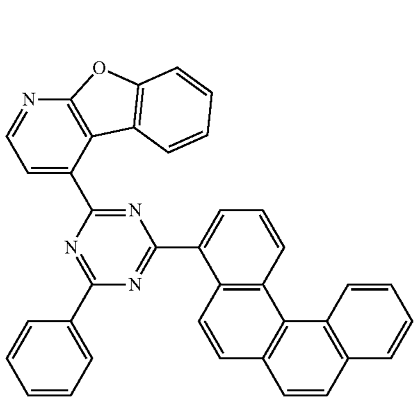
-continued
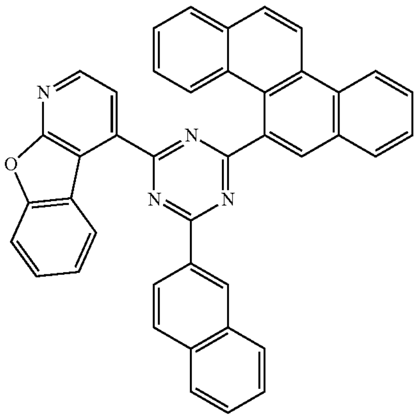
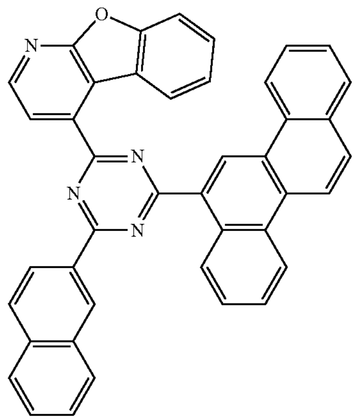
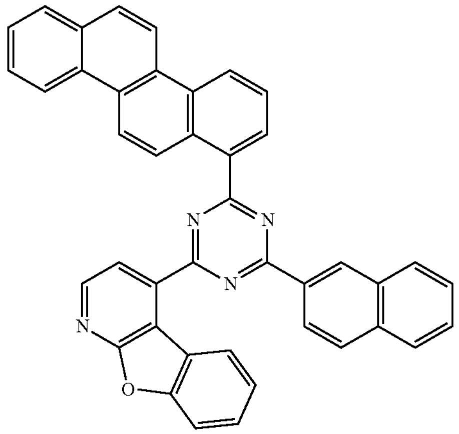
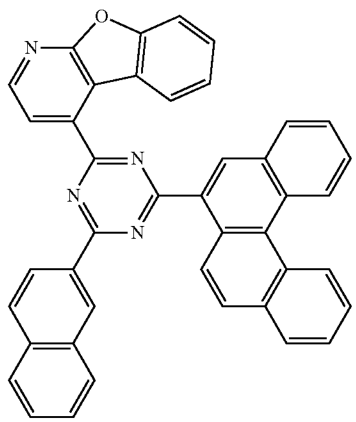

-continued
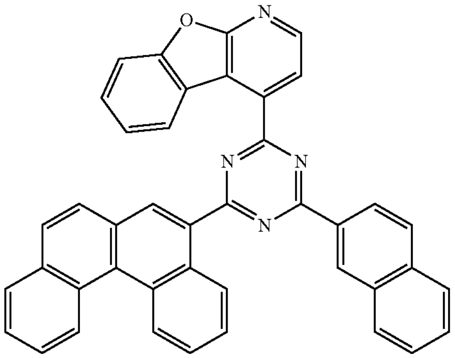
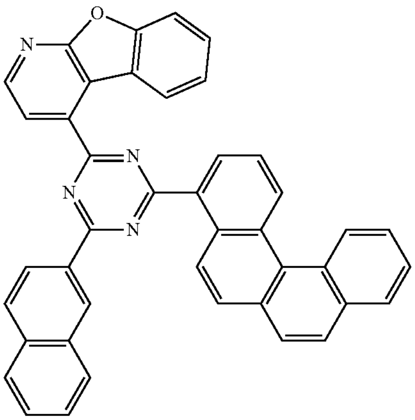
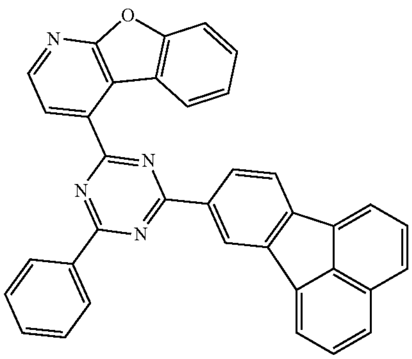
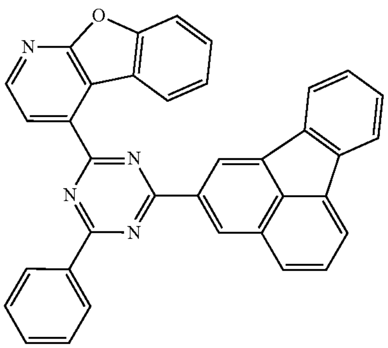
-continued
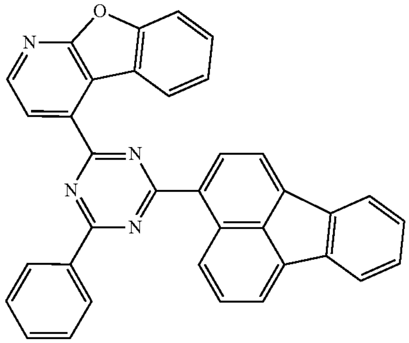
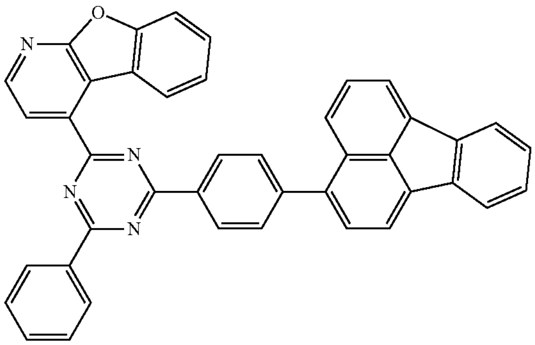
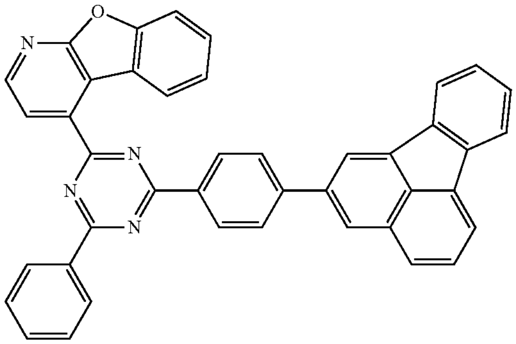
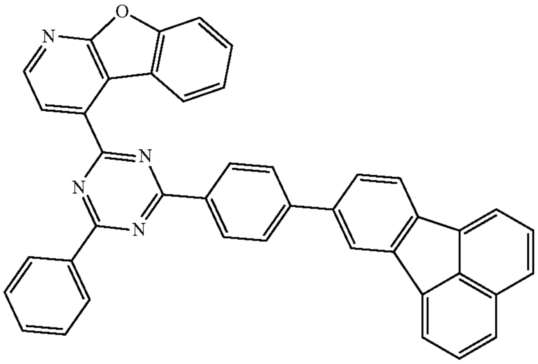

-continued
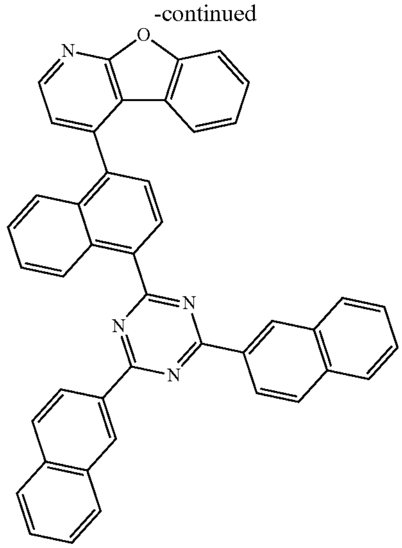
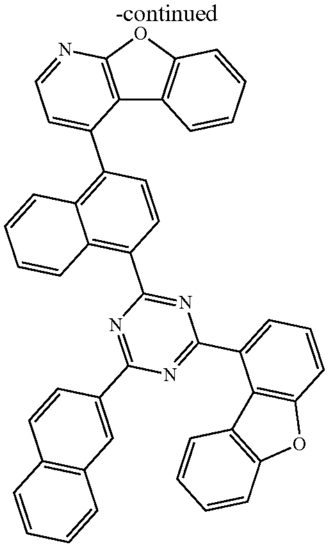
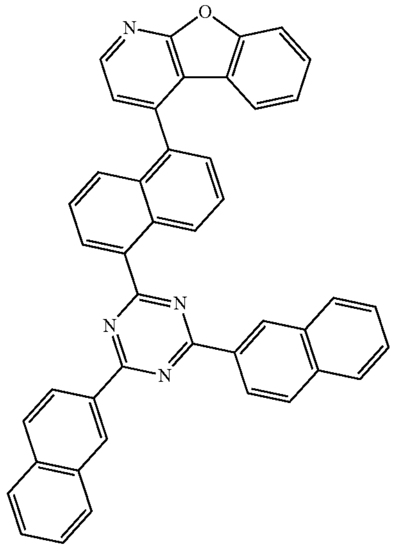
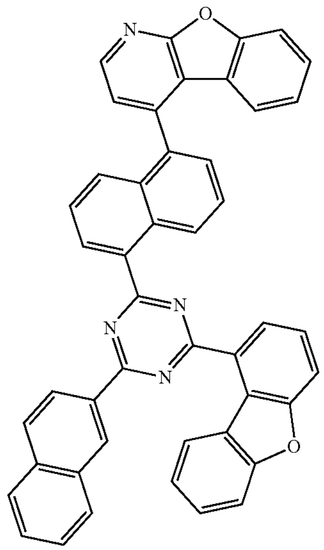
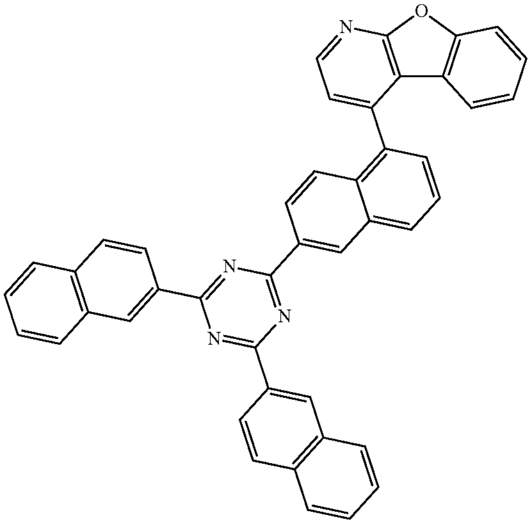
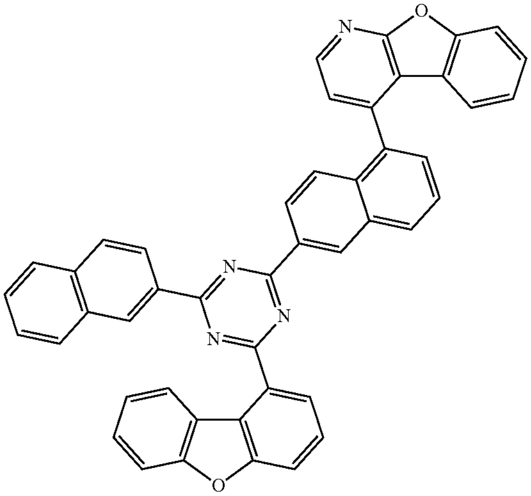

-continued
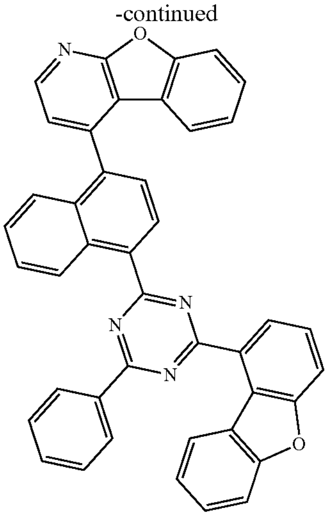
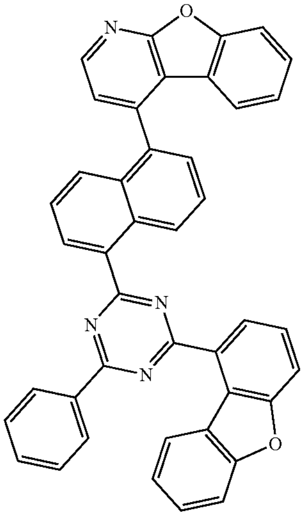
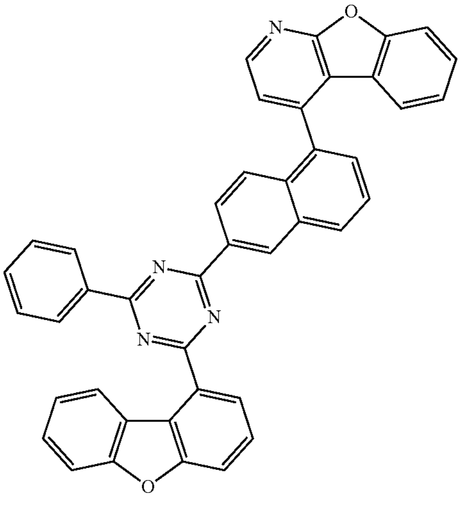
-continued
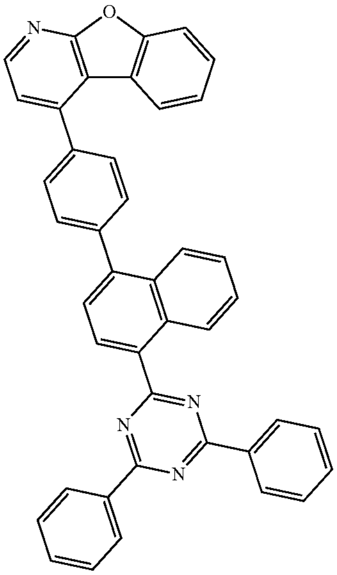
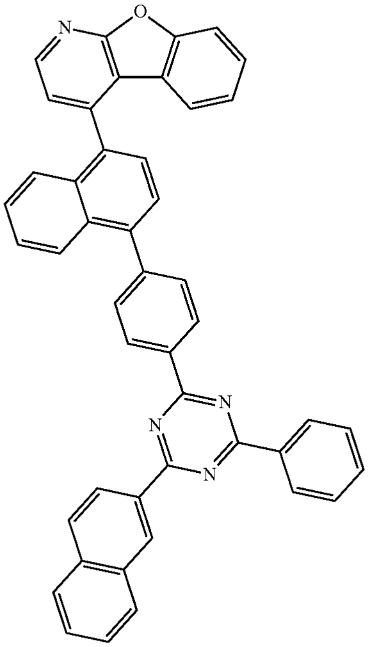
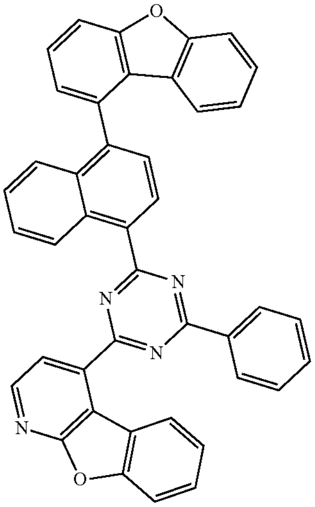

-continued
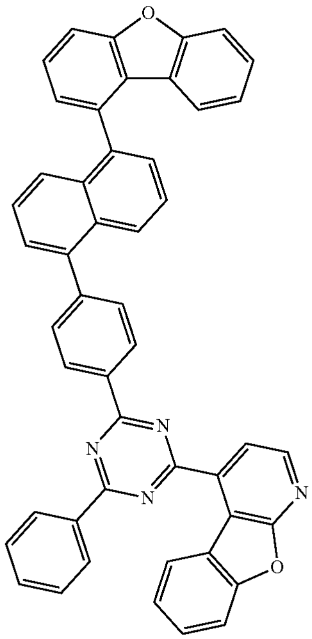
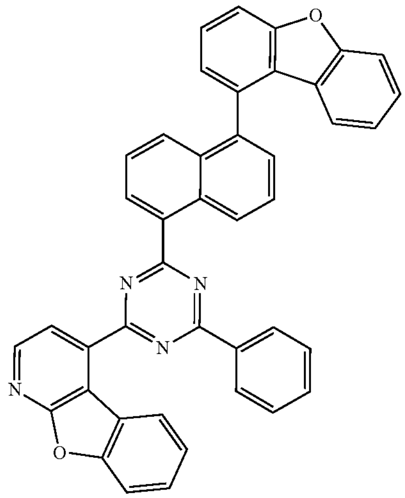
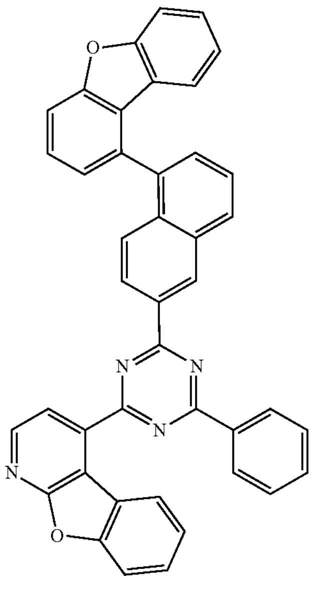
-continued
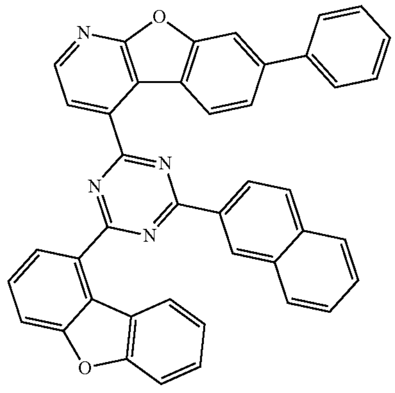
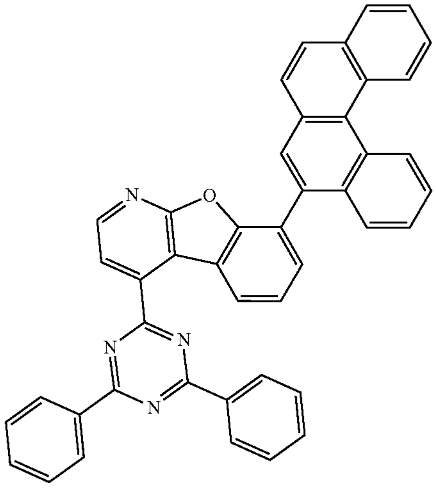
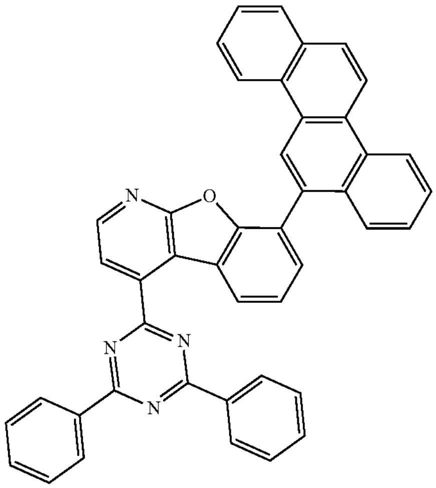

-continued
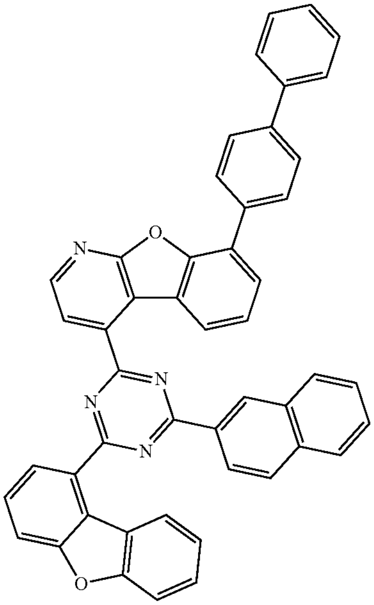
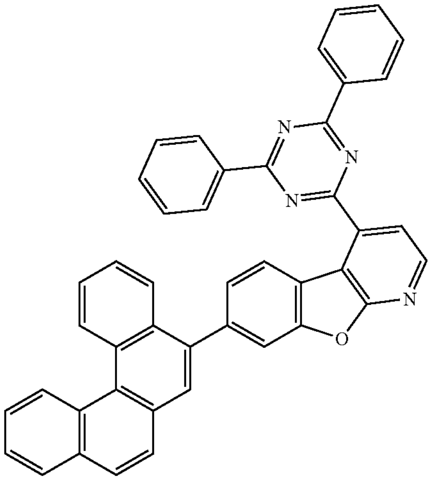
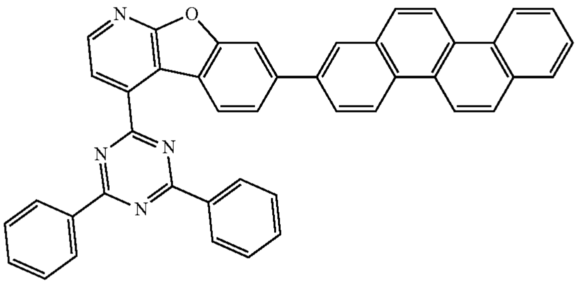
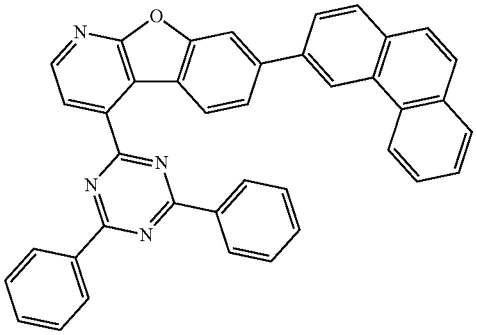
-continued
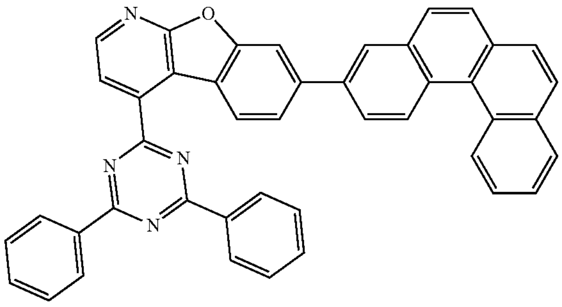
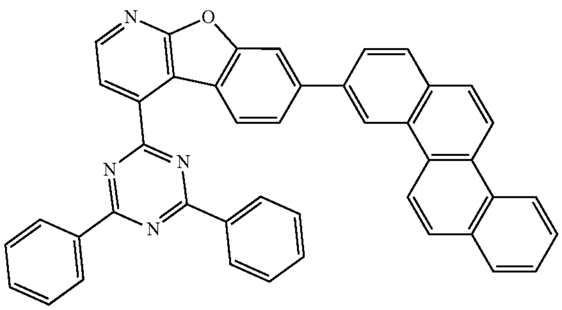
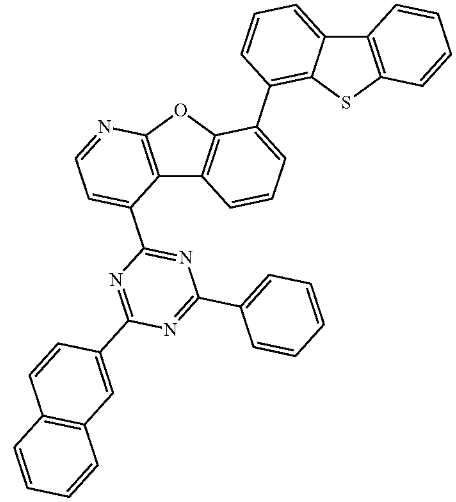
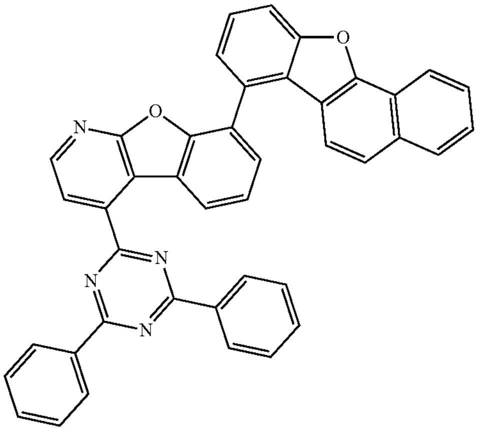

-continued
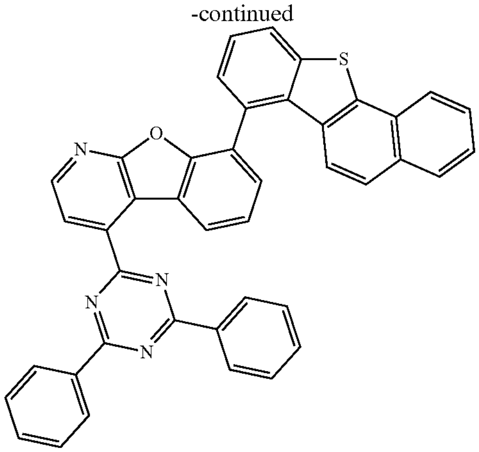
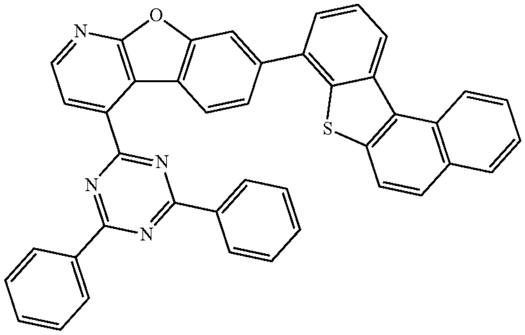
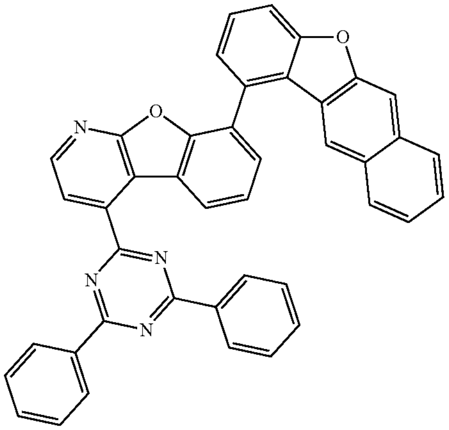
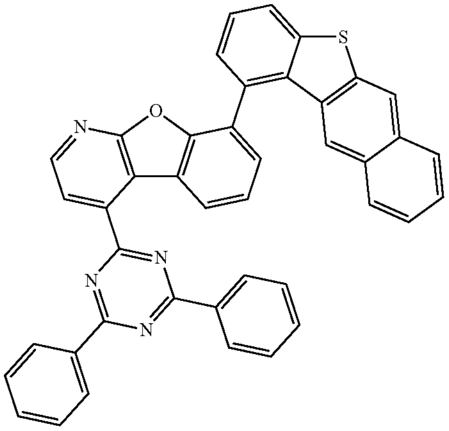
-continued
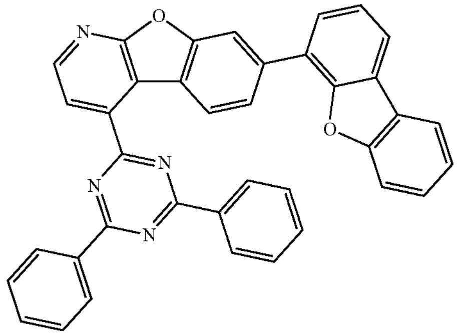
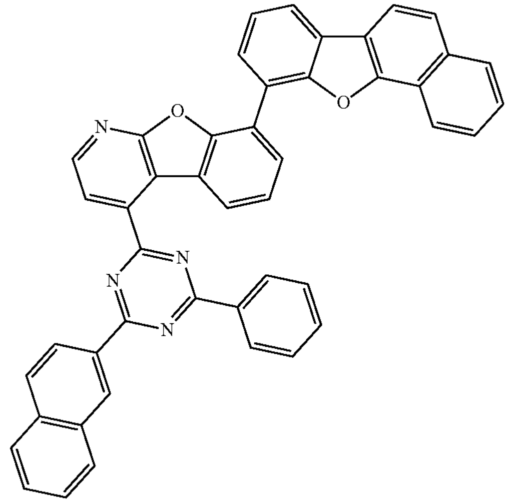
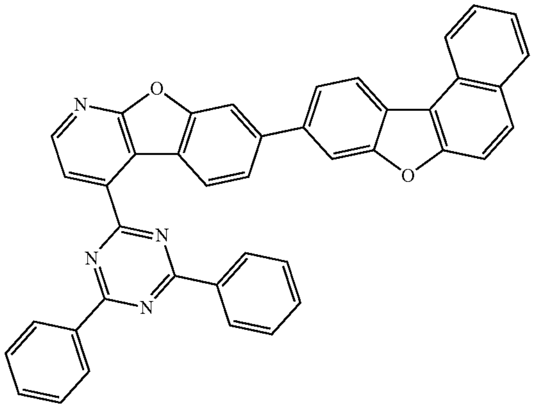
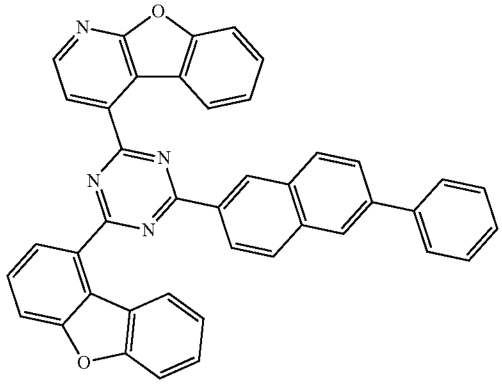

-continued
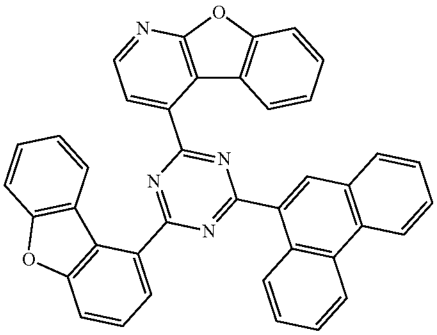
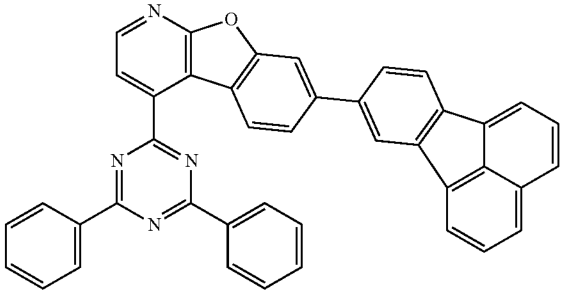
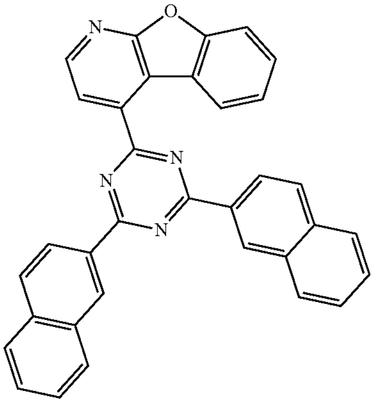
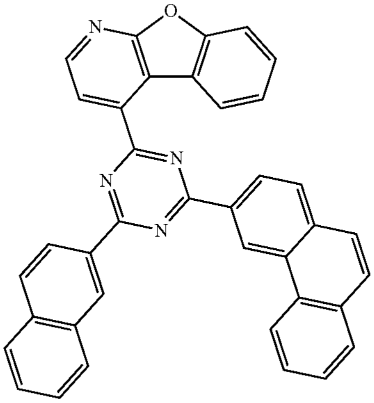
-continued
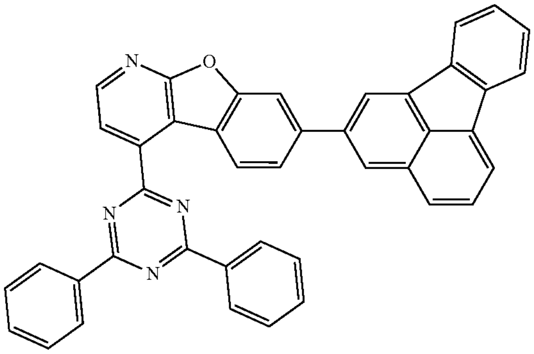
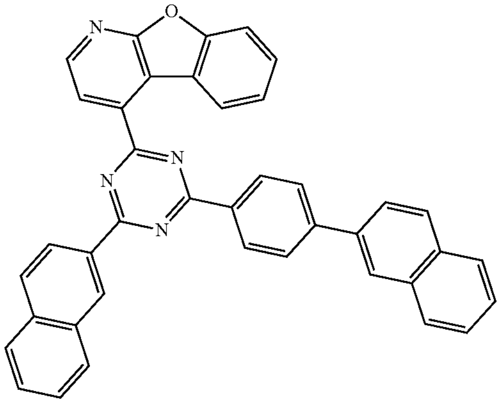
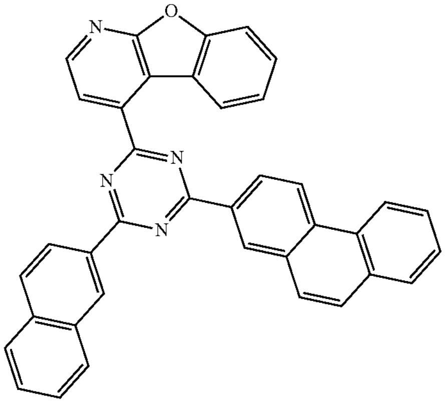
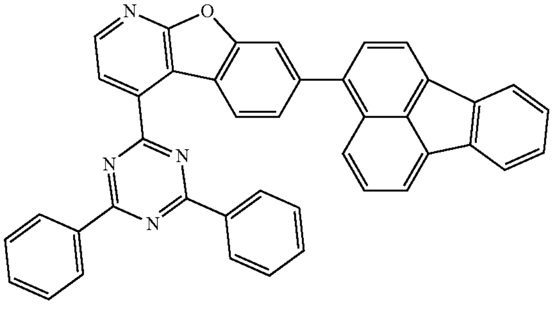

-continued
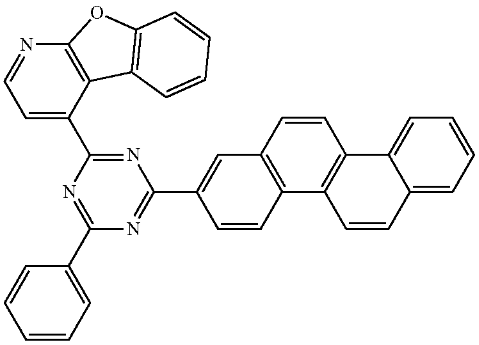
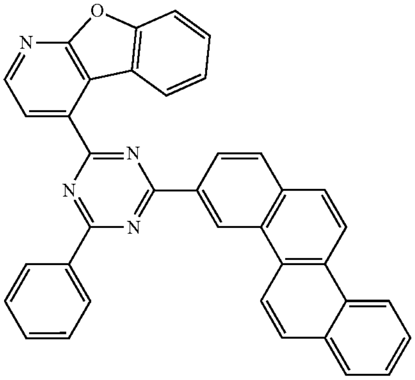
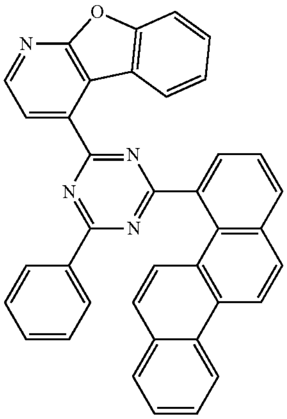
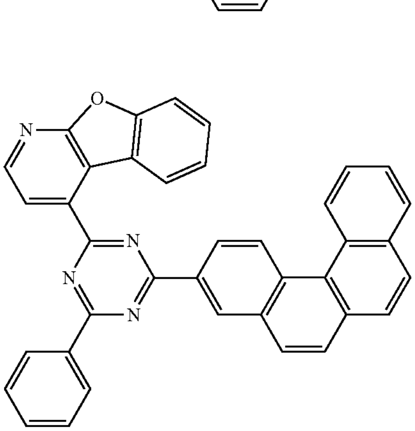
-continued
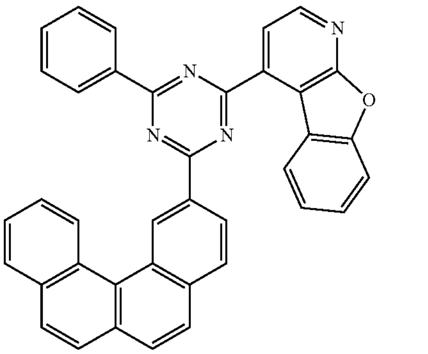
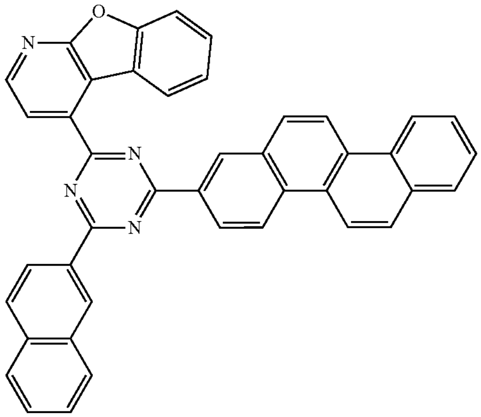
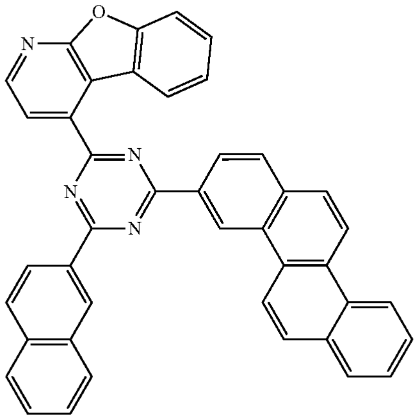
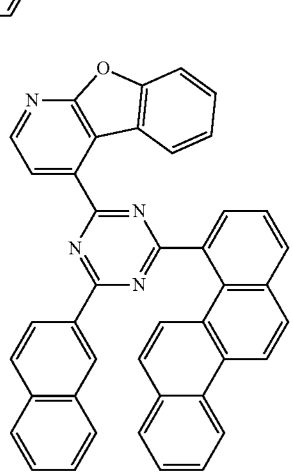

-continued
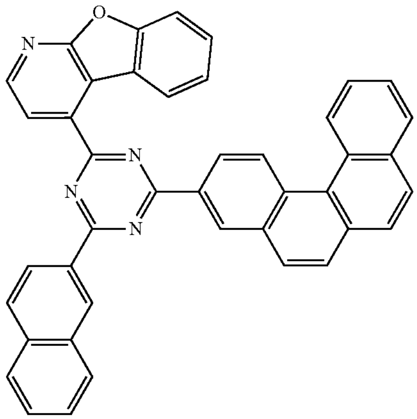
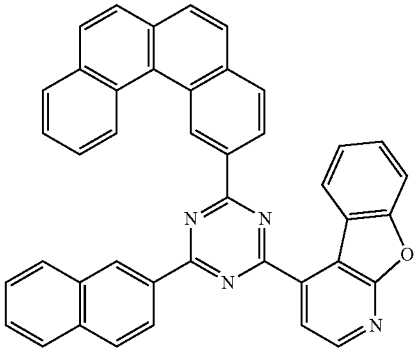
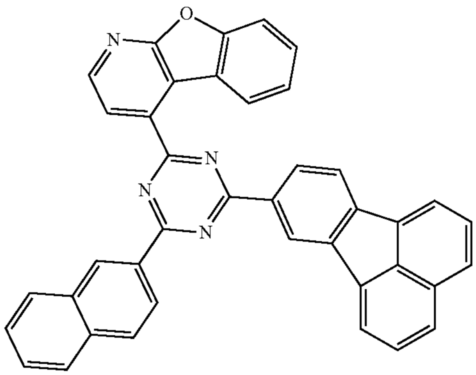
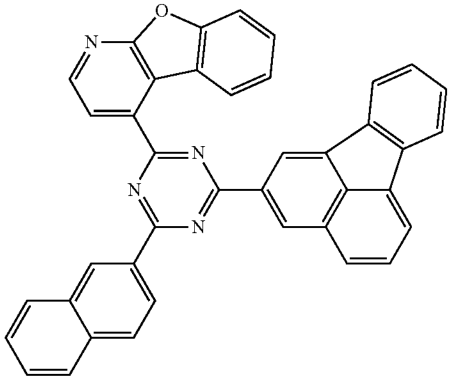
-continued
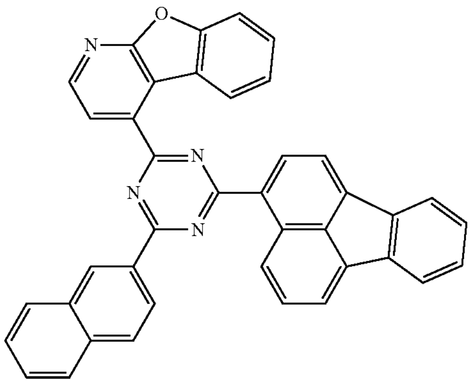
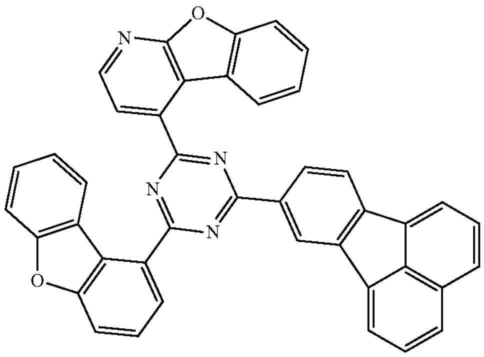
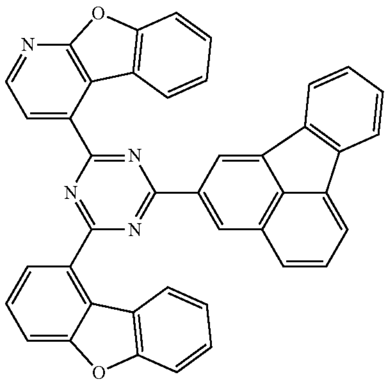
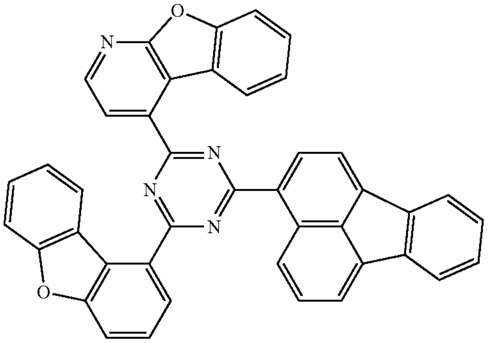

-continued
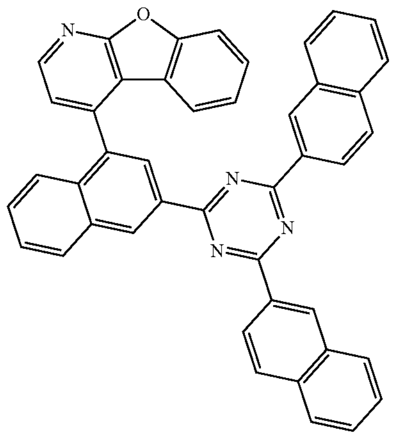
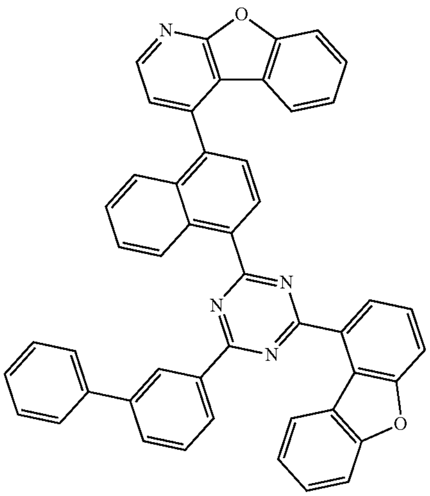
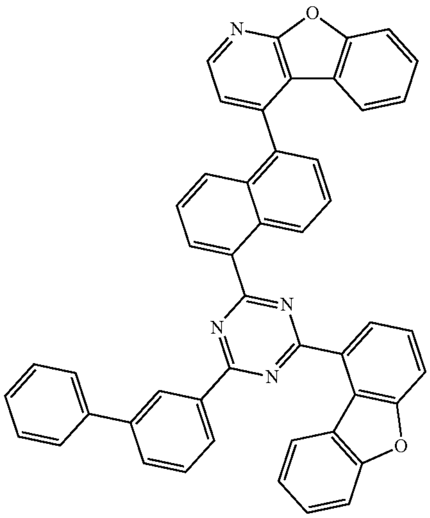
-continued
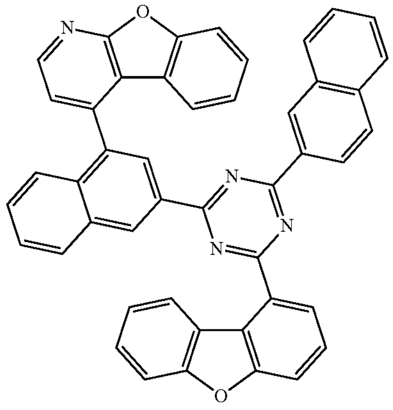
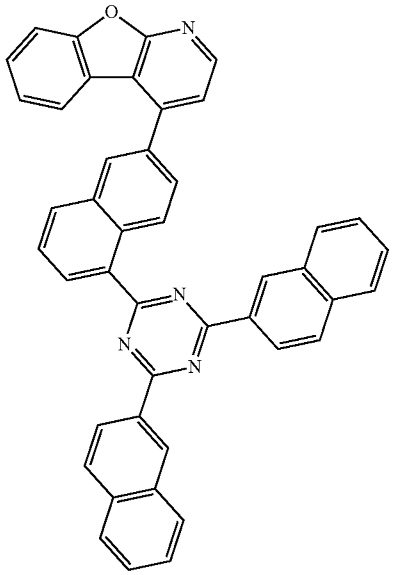
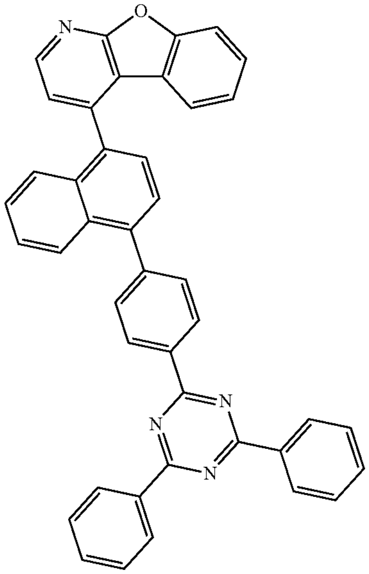

-continued
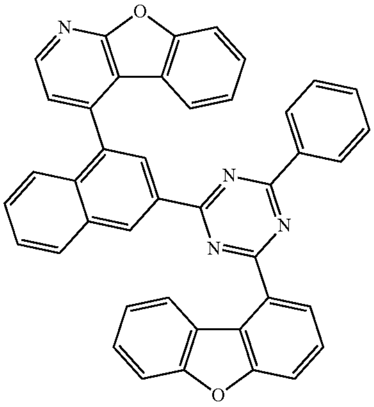
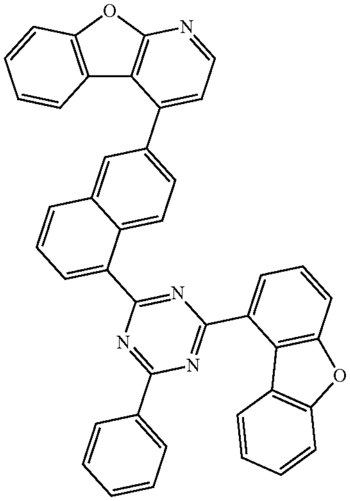
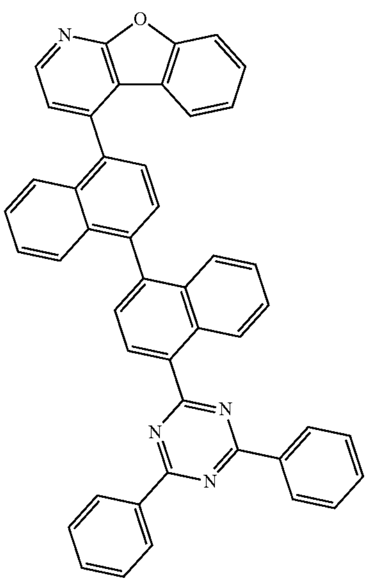
-continued
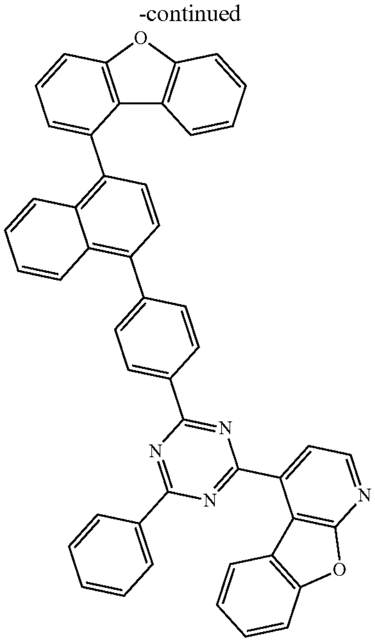
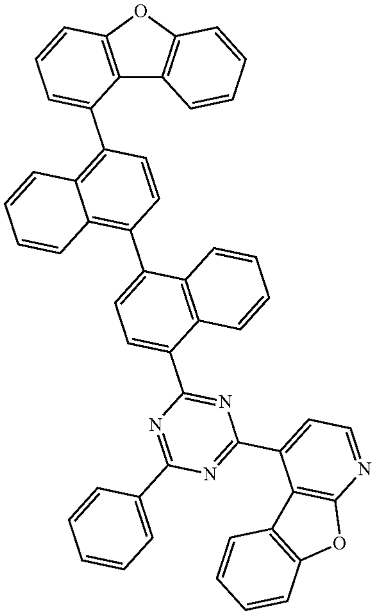

-continued
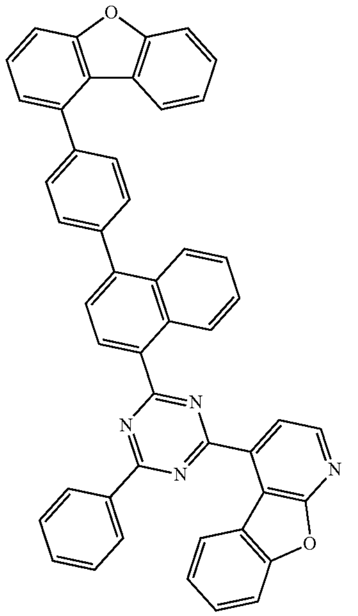
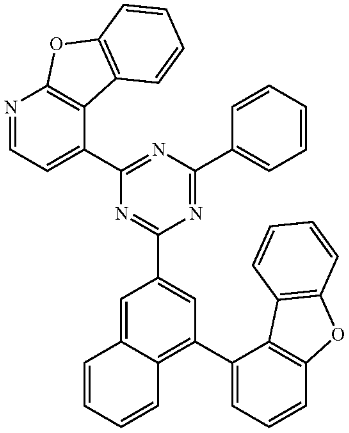
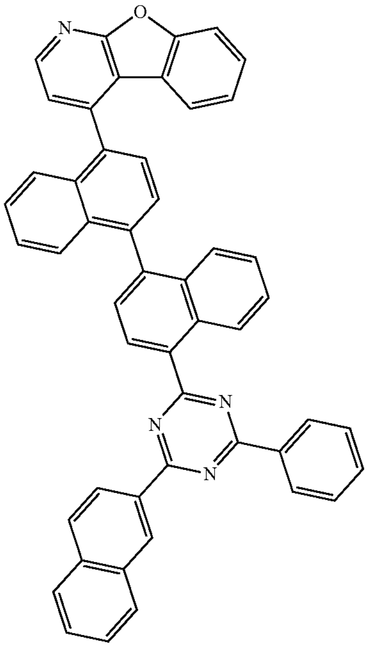
-continued
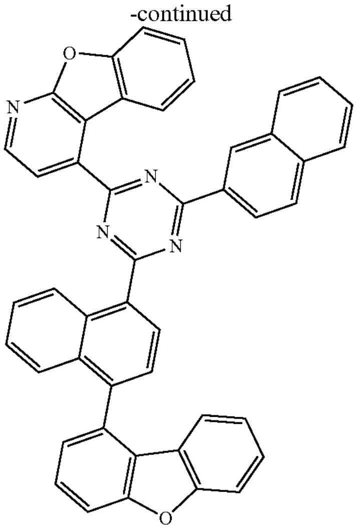
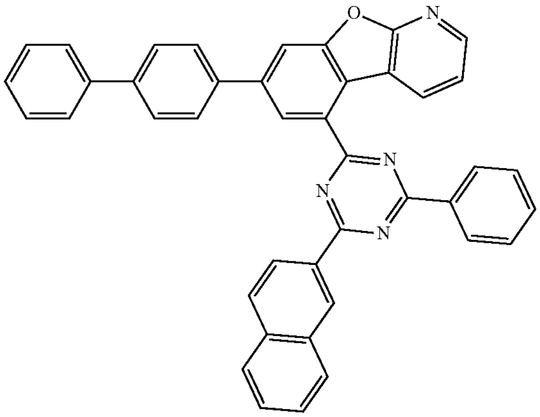
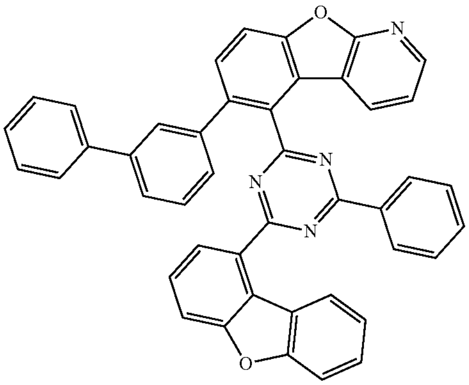

-continued
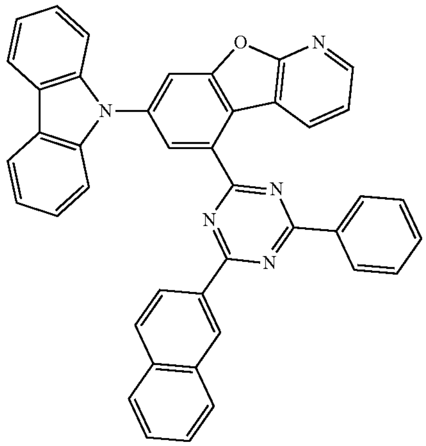
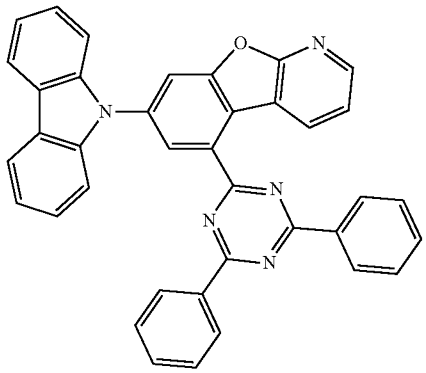
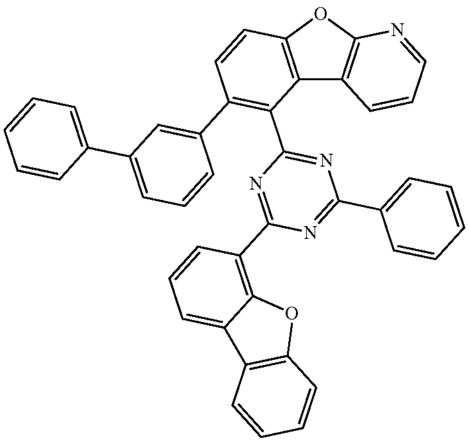
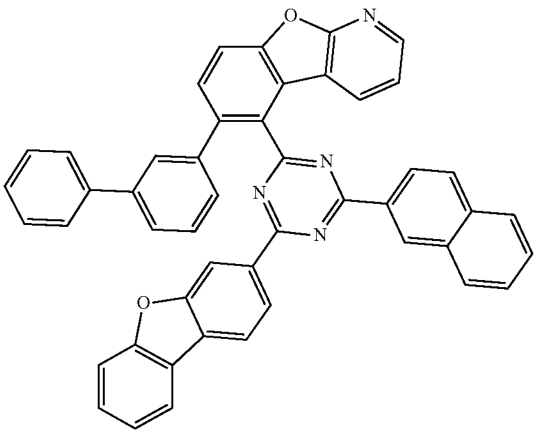
-continued
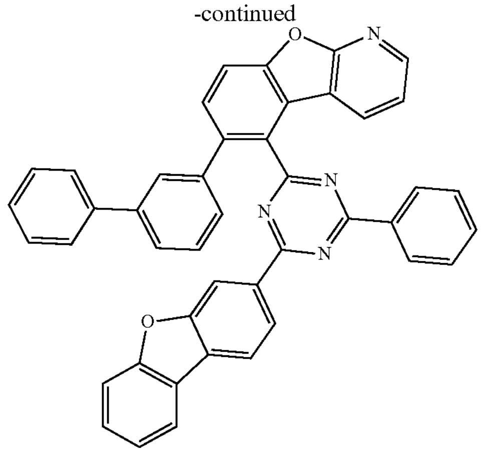
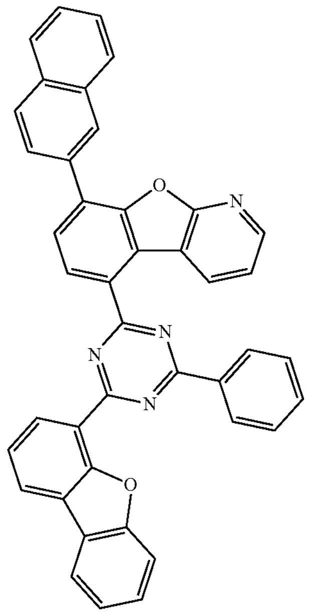
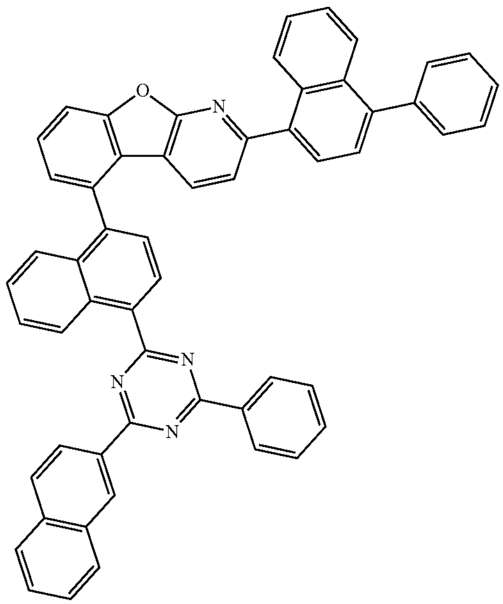

-continued
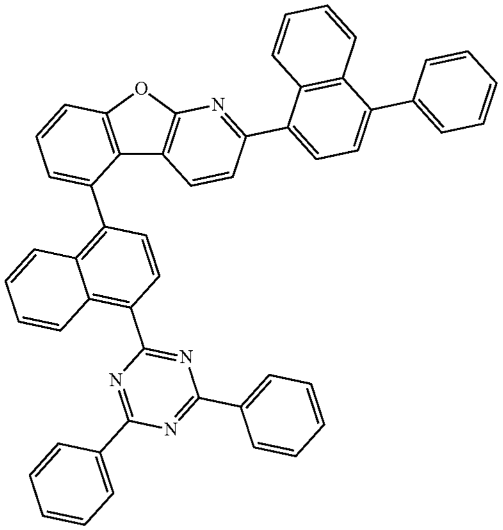
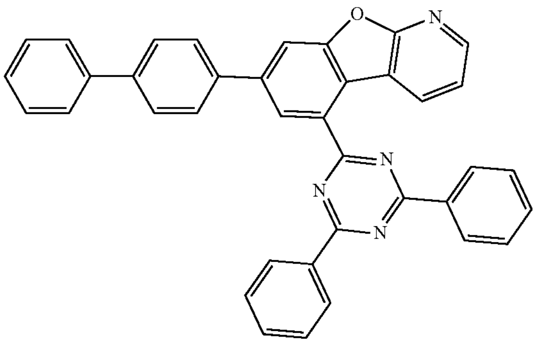
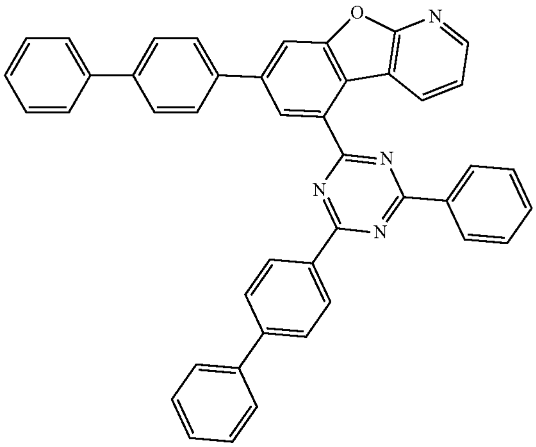
-continued
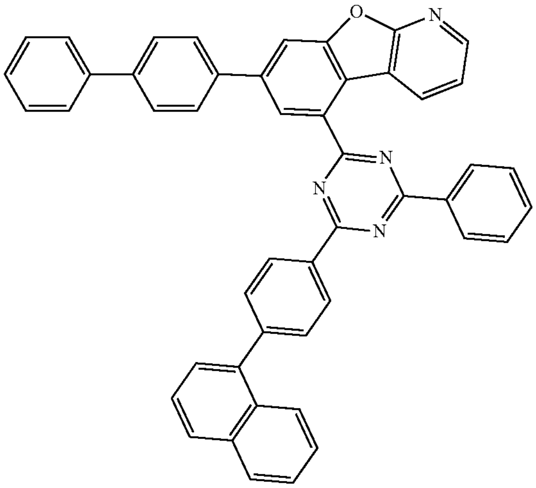
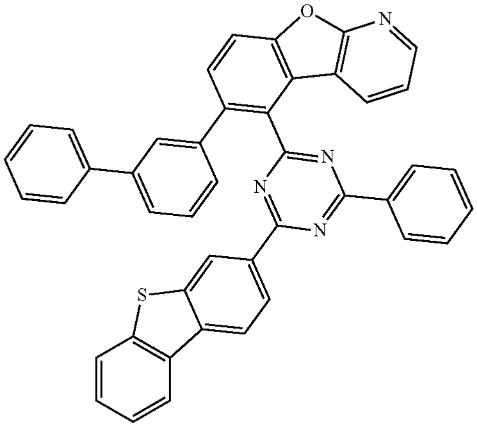
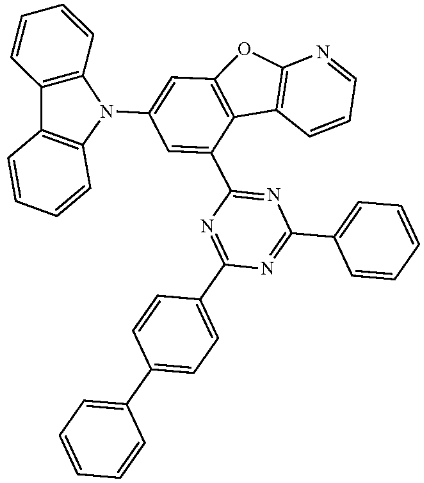

-continued
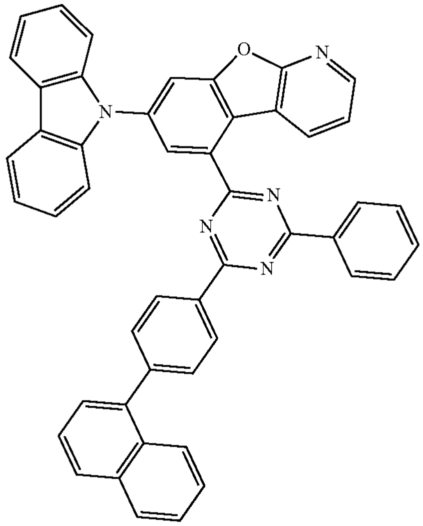
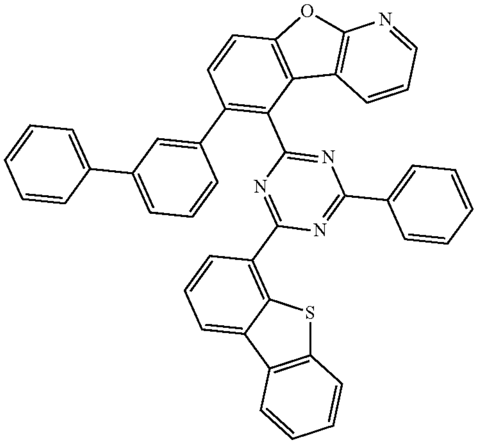
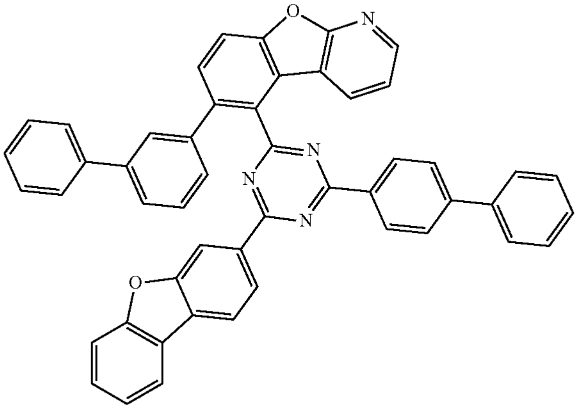
-continued
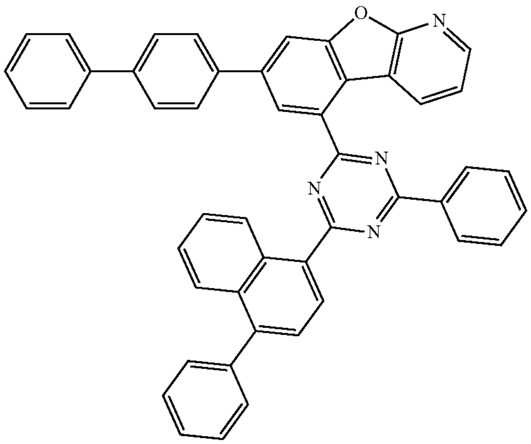
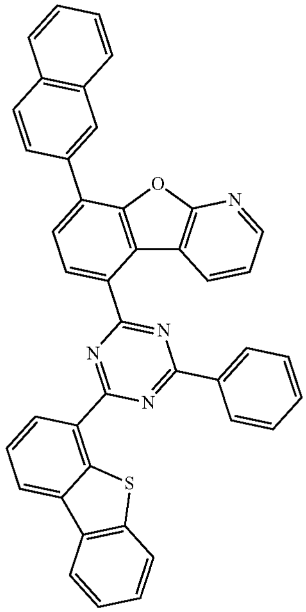
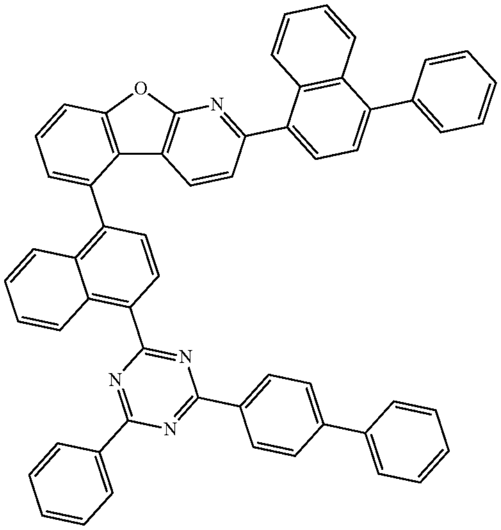

-continued
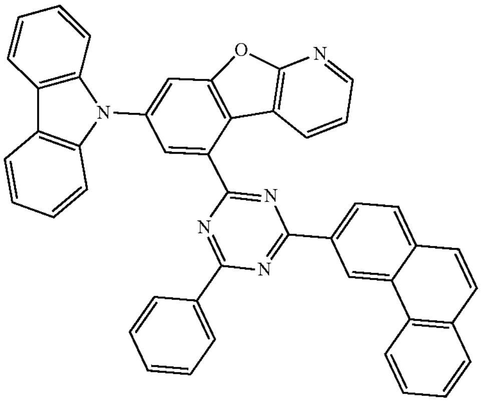
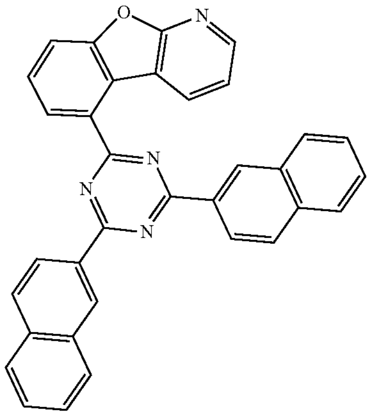
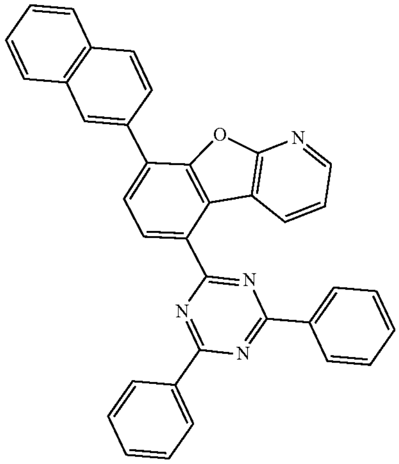
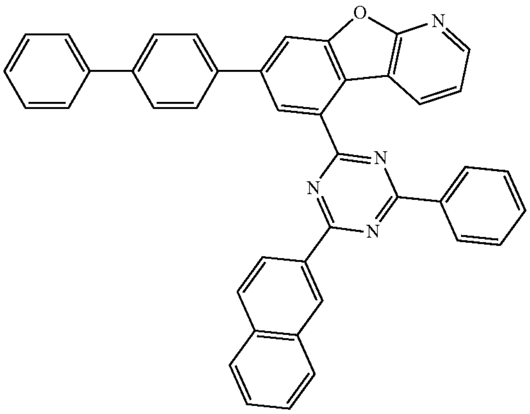
-continued
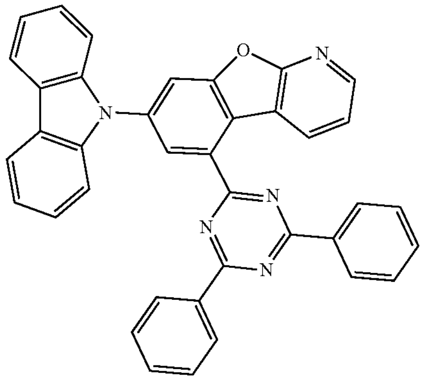
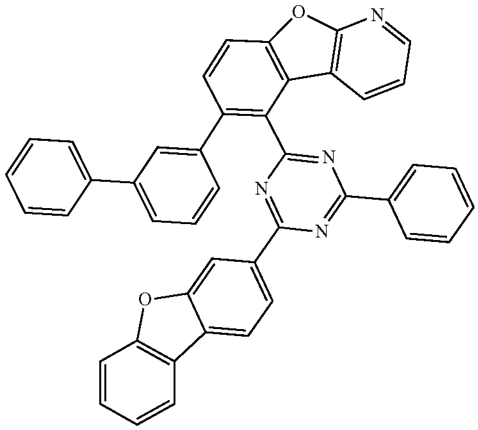
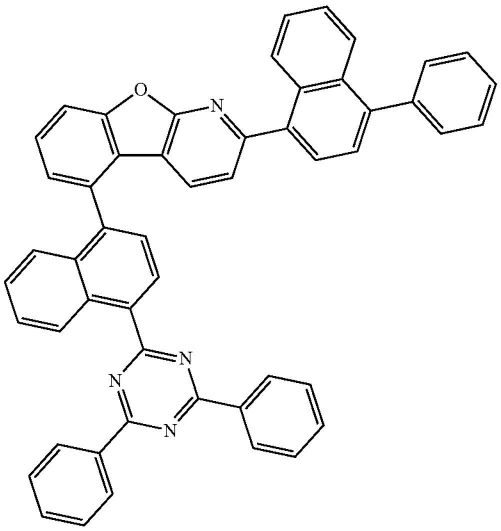

-continued
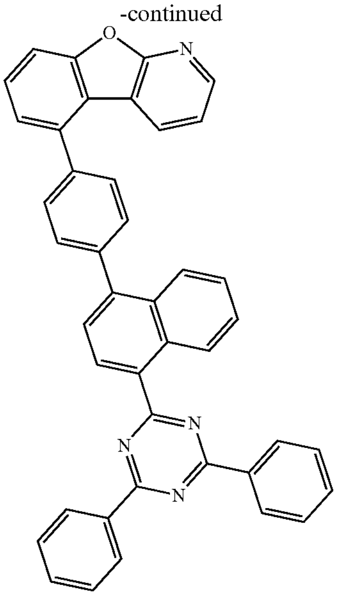
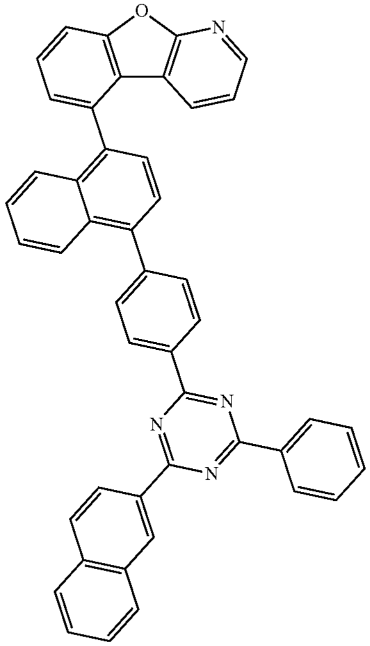
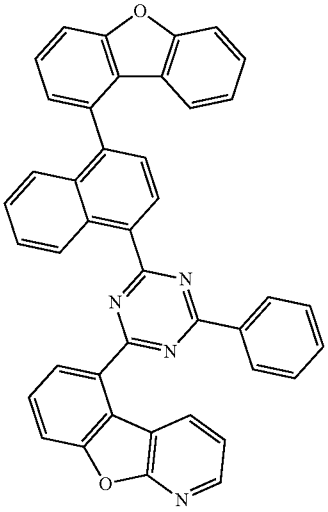
-continued
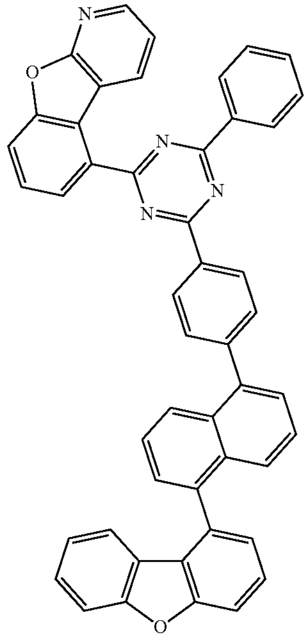
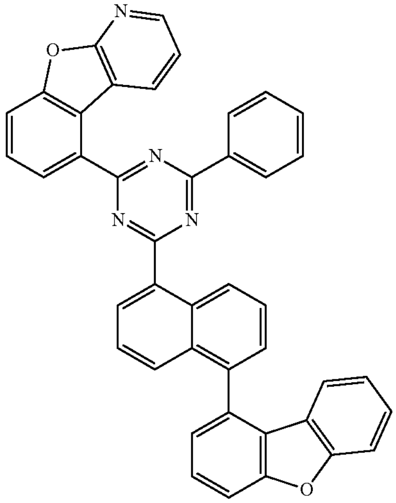
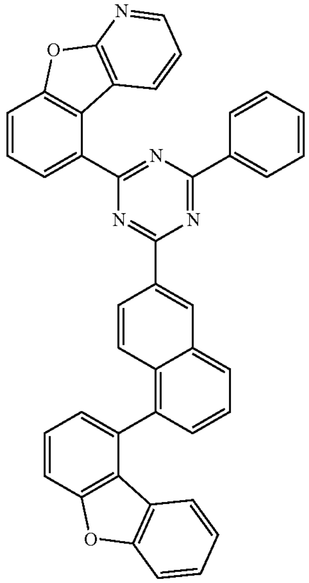

-continued
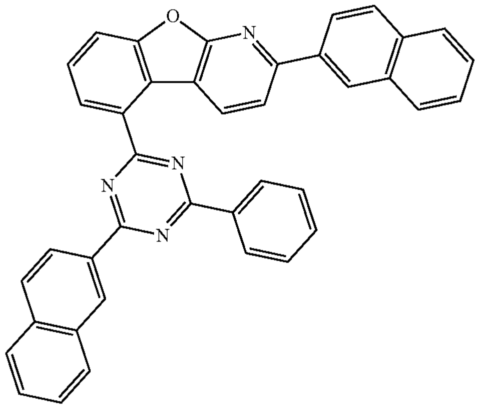
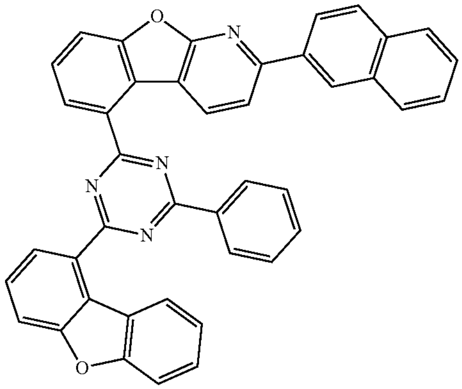
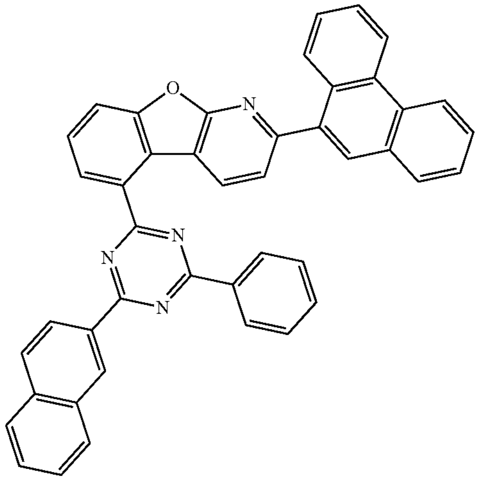
-continued
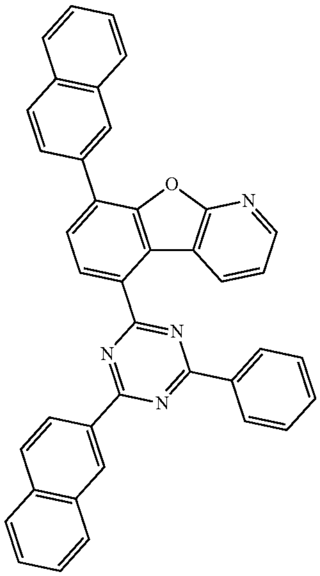
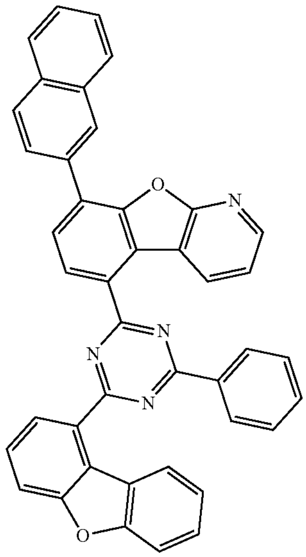
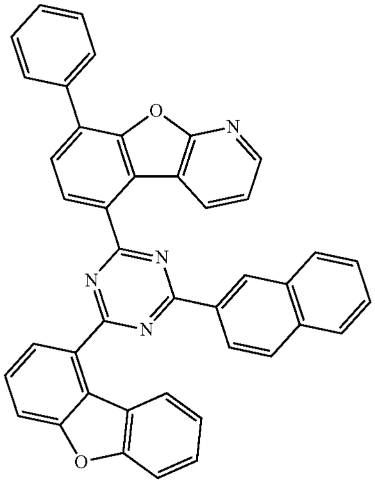

-continued
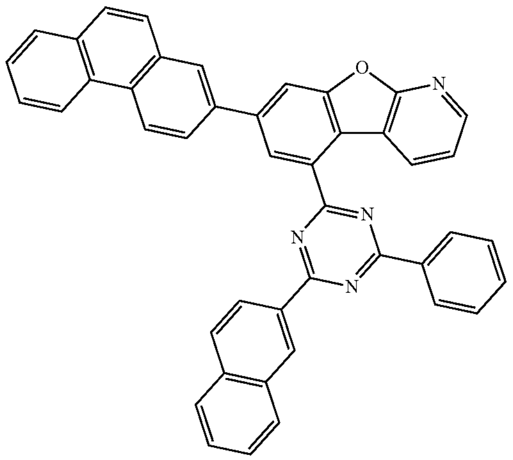
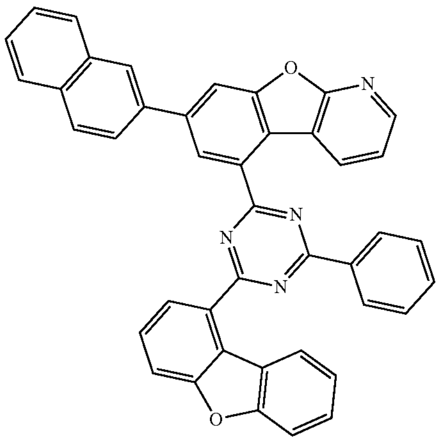
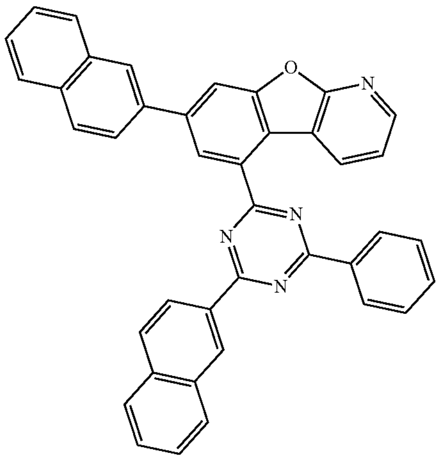
-continued
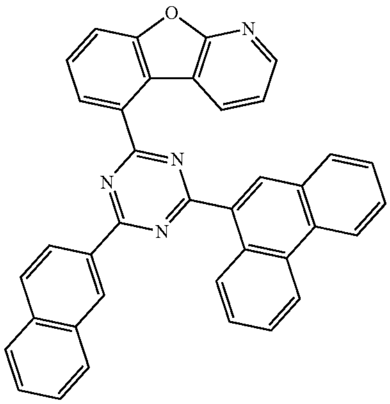
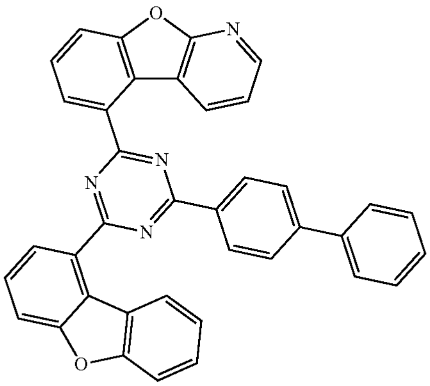
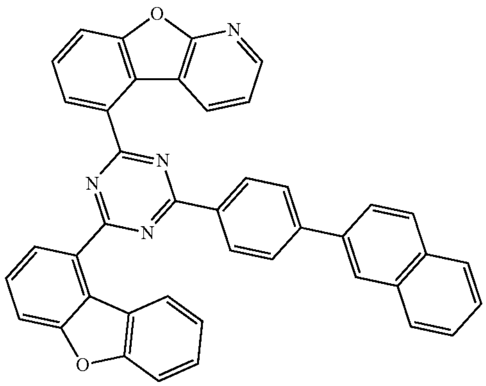
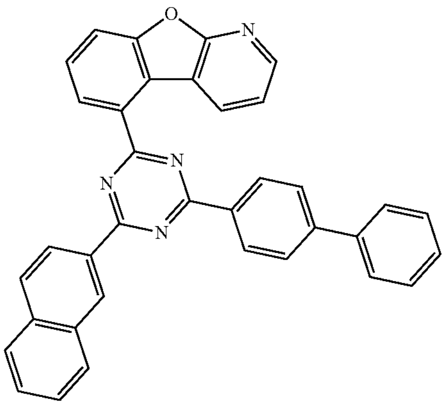

-continued
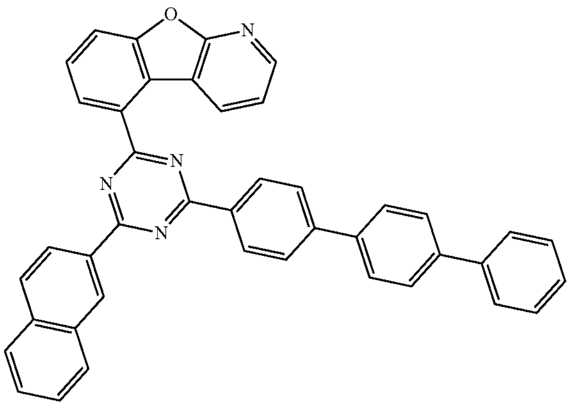
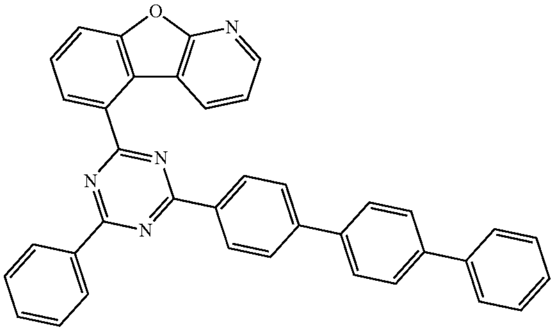
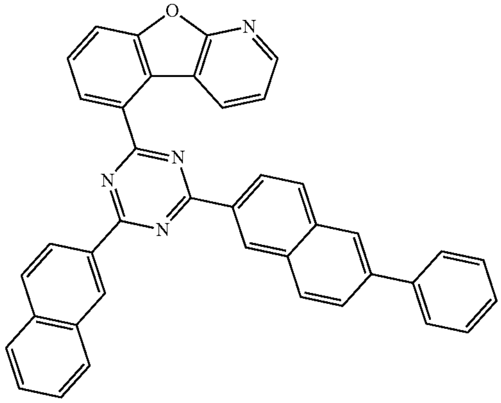
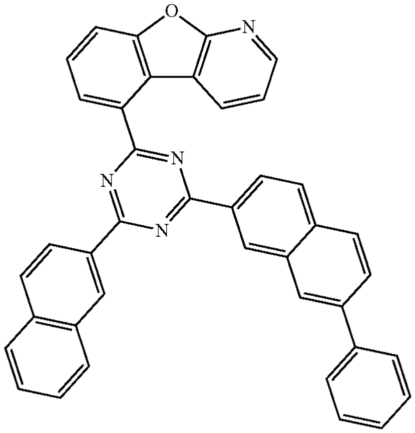
-continued
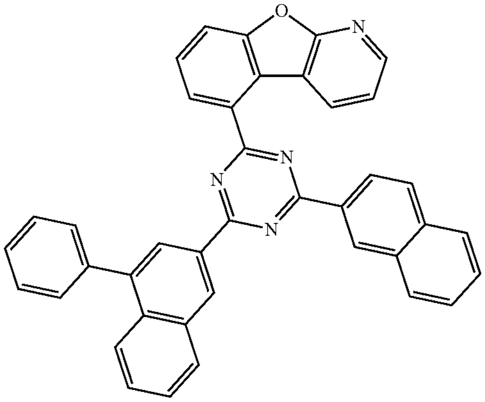
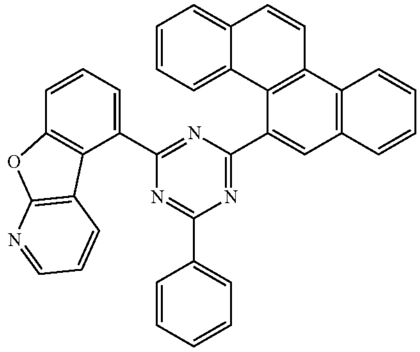
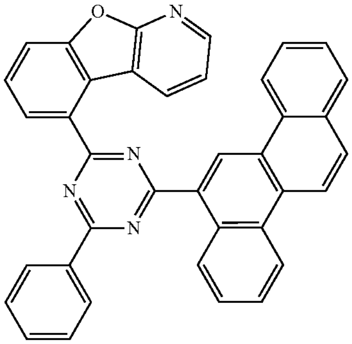
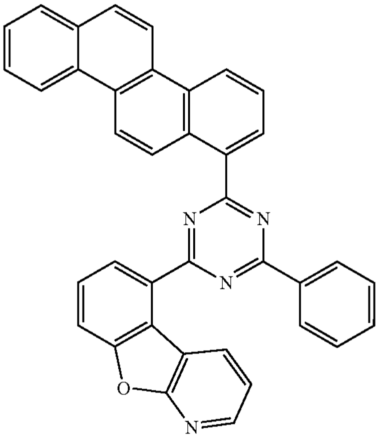

-continued
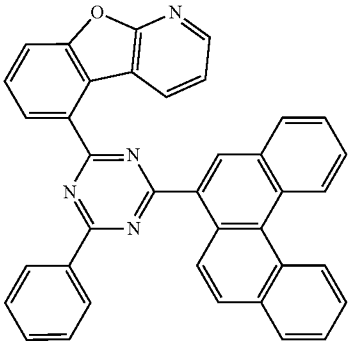
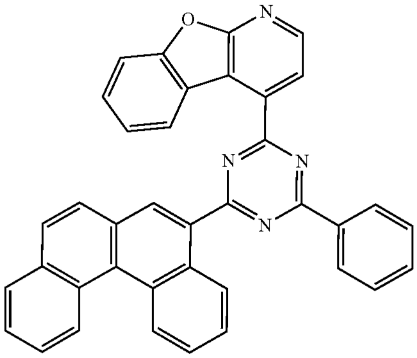
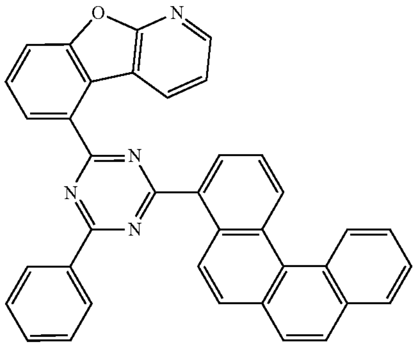
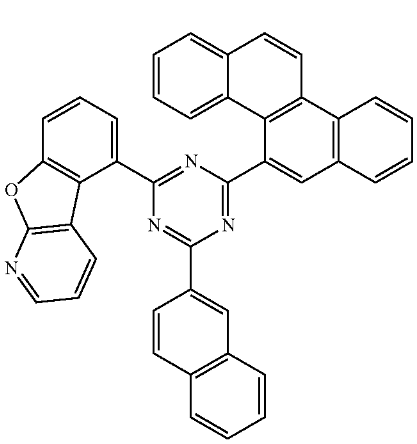
-continued
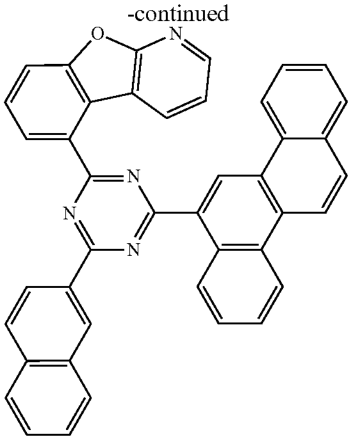
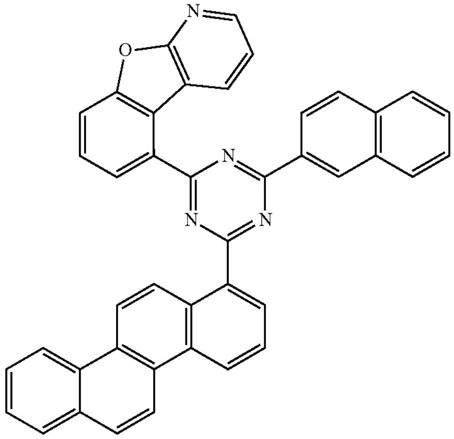
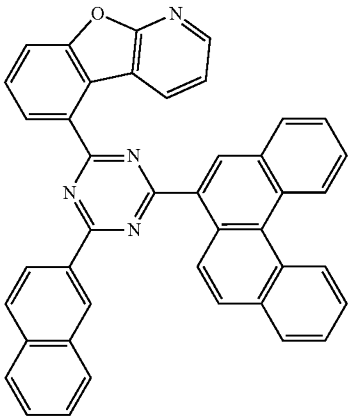
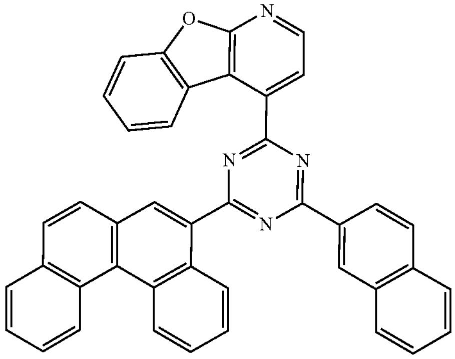

-continued
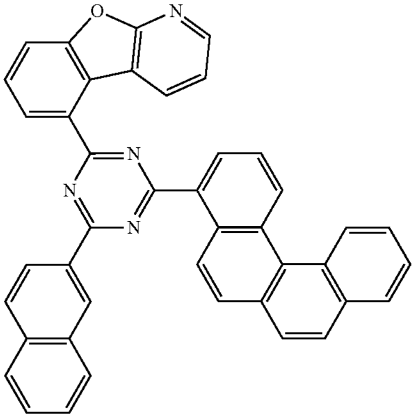
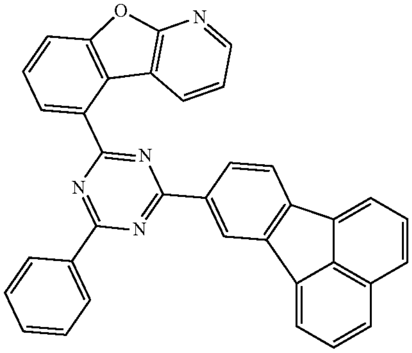
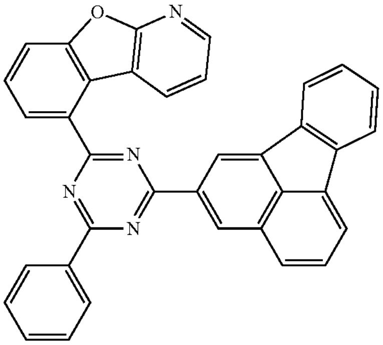
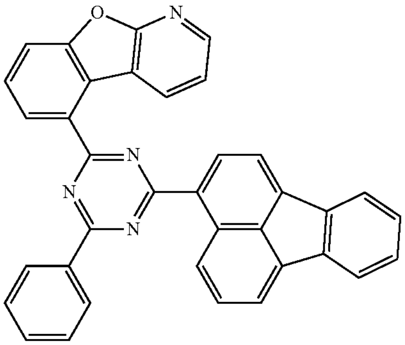
-continued
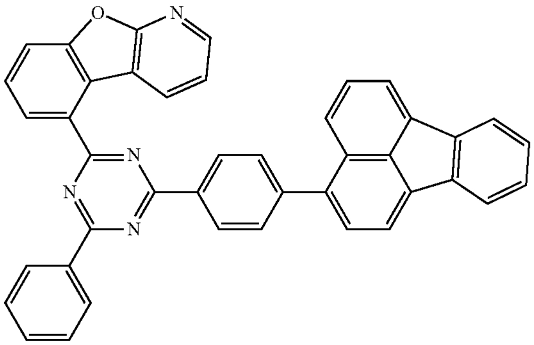
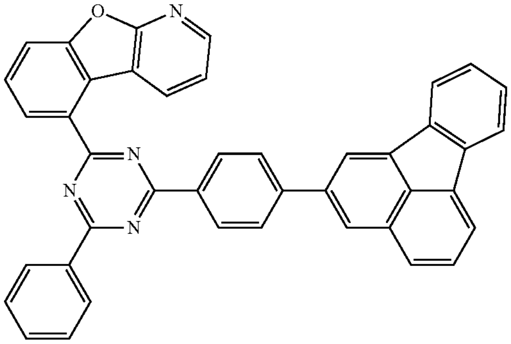
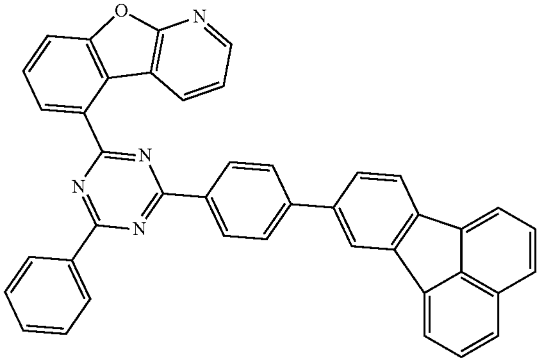
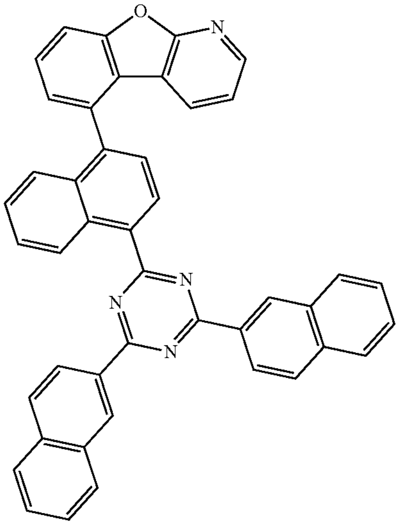

-continued
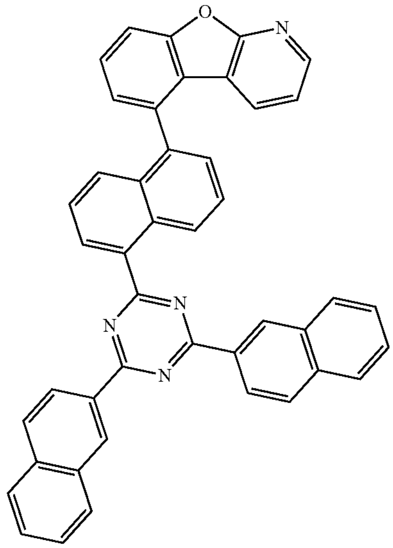
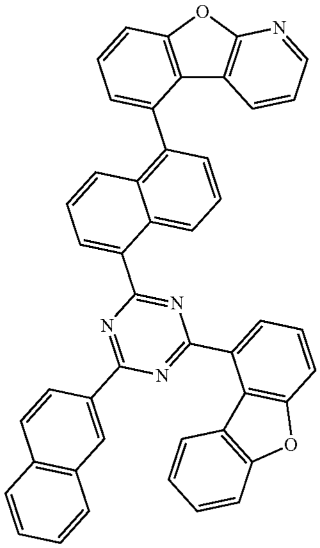
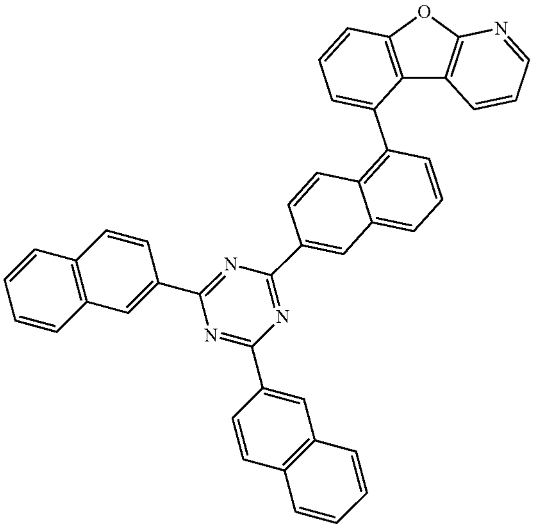
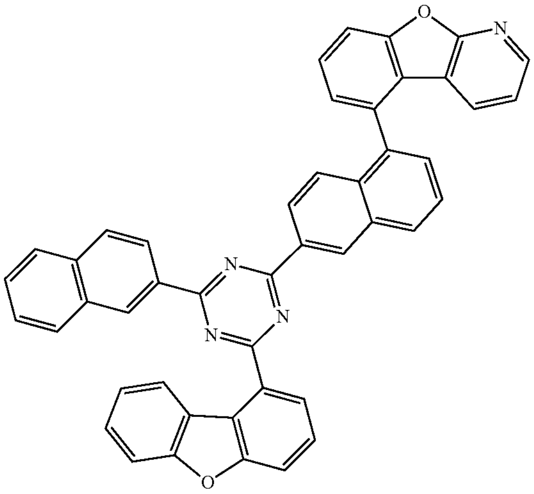
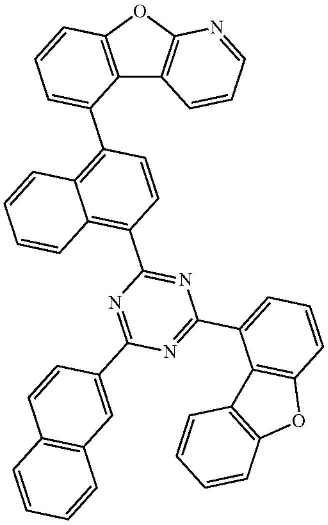
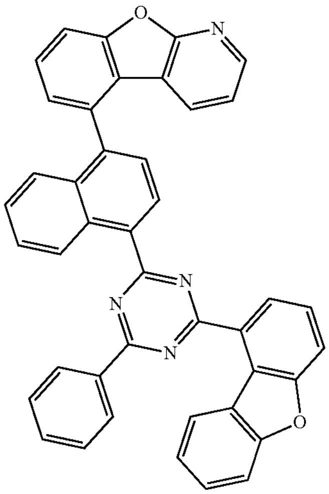
-continued -continued
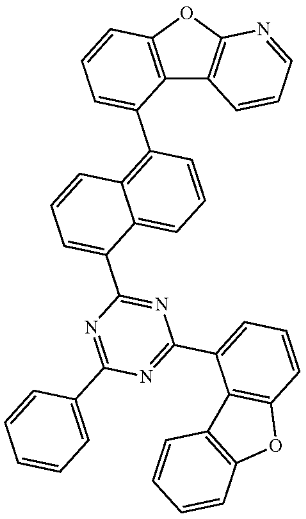
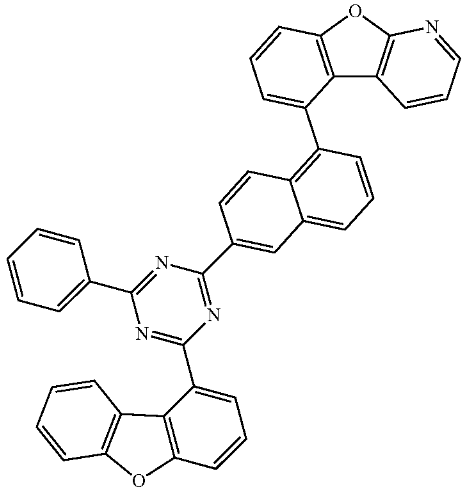
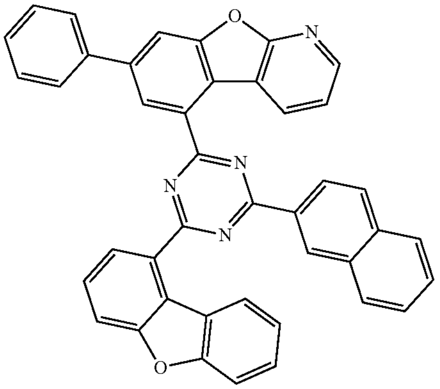
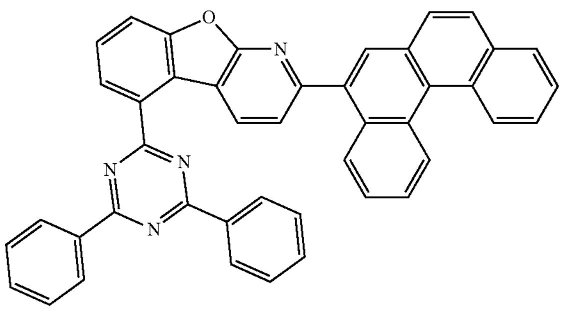
-continued
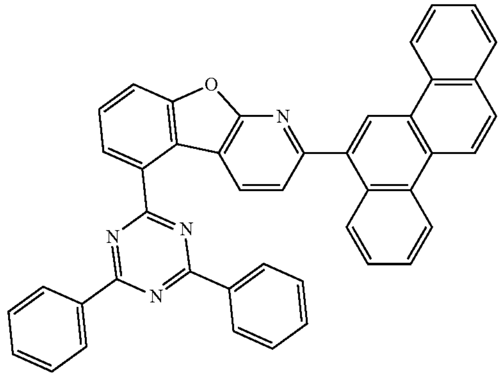
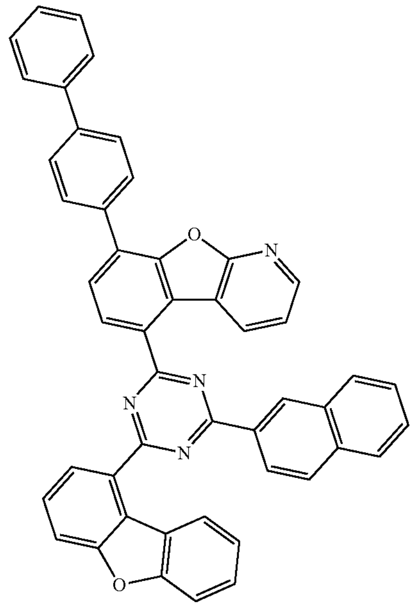
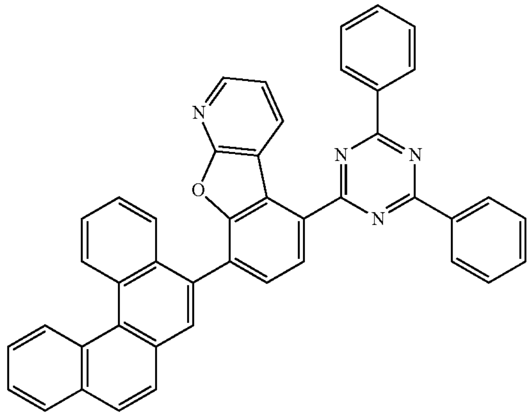

-continued
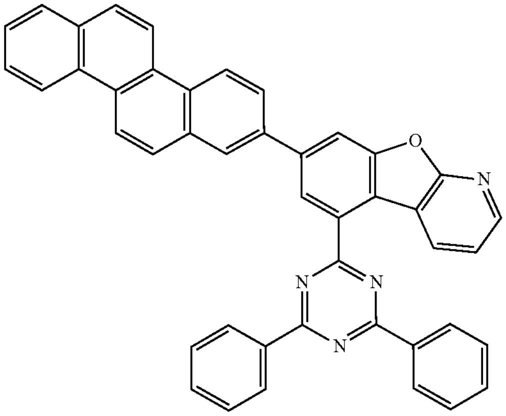
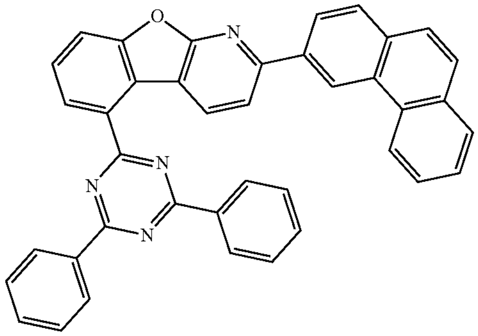
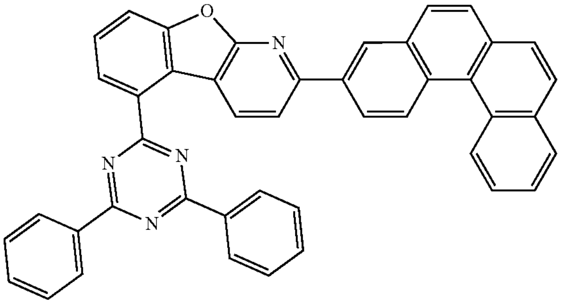
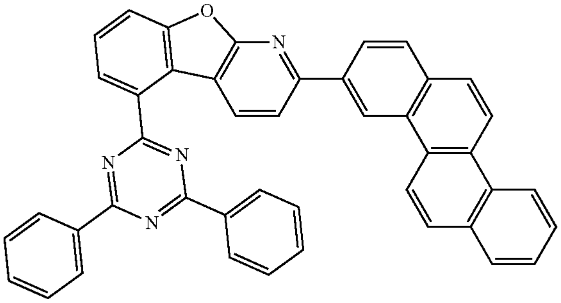
-continued
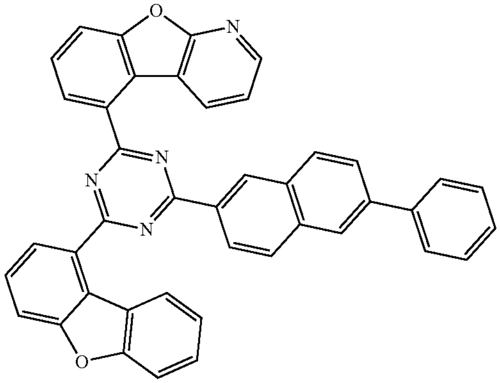
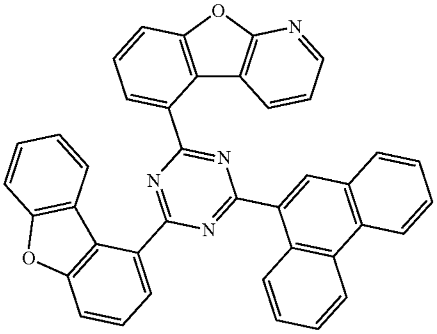
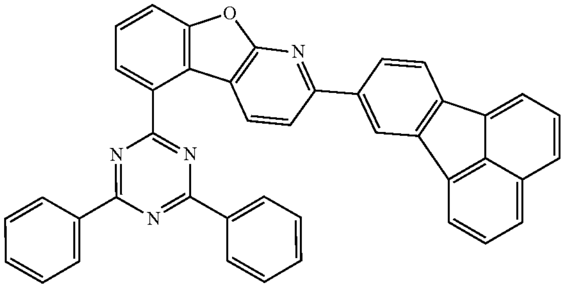
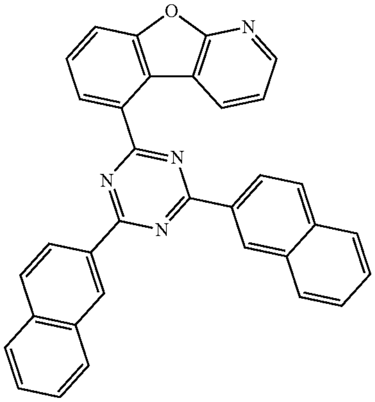

-continued
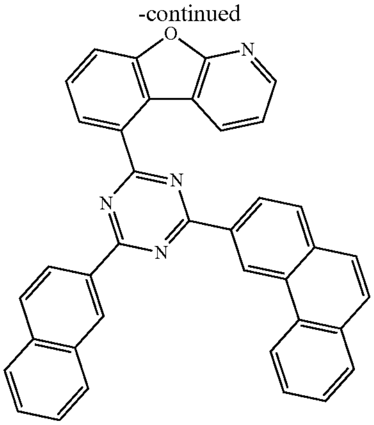
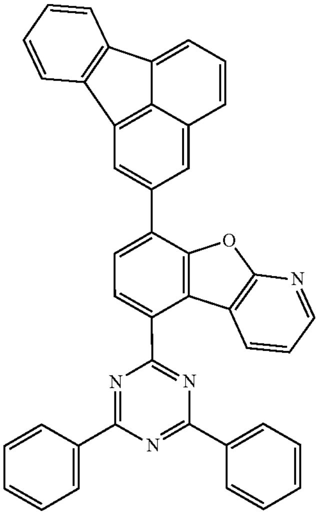
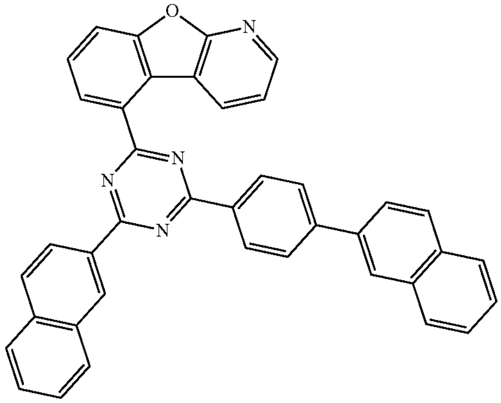
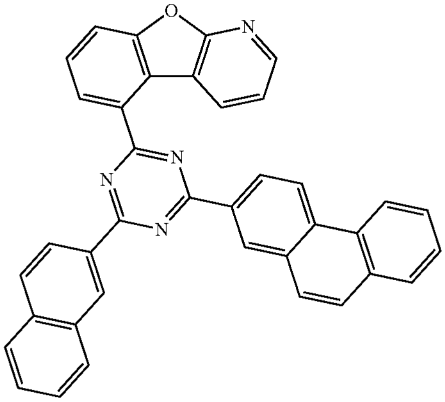
-continued
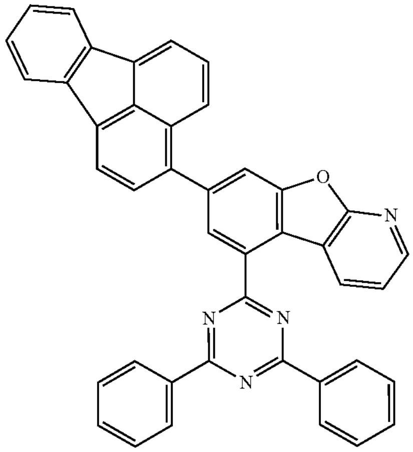
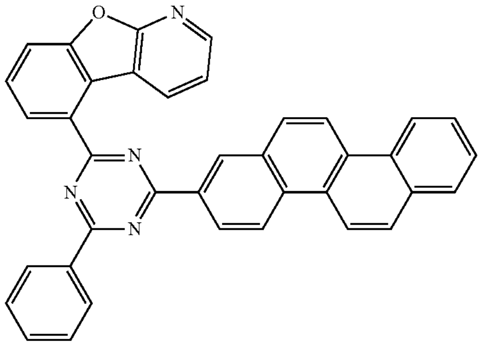
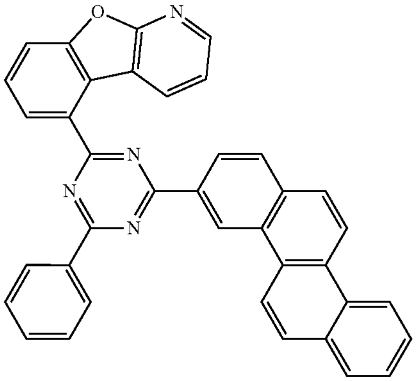
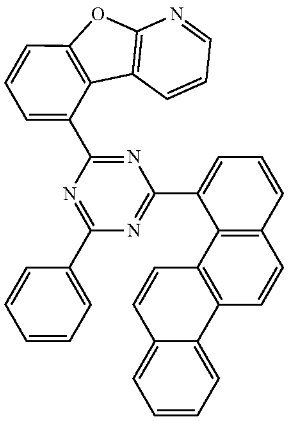

-continued
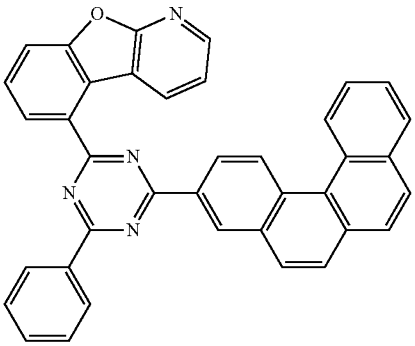
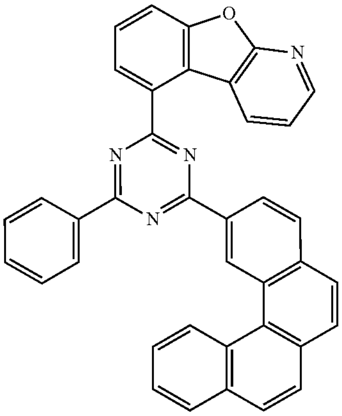
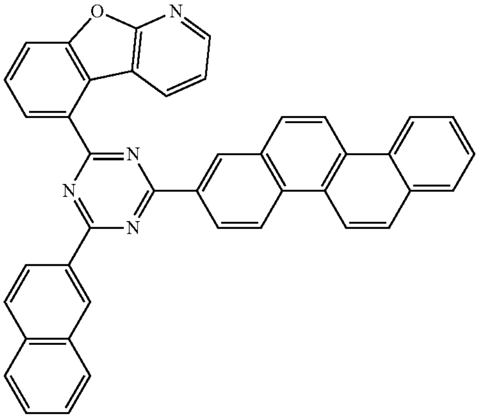
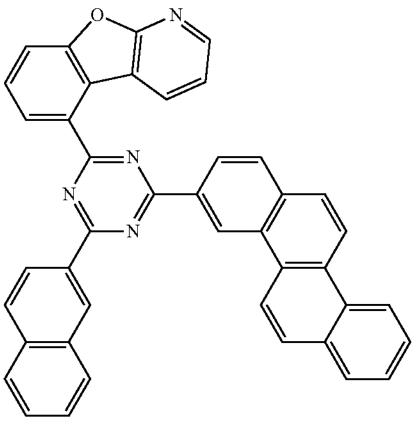
-continued
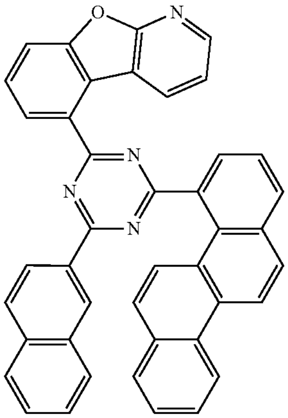
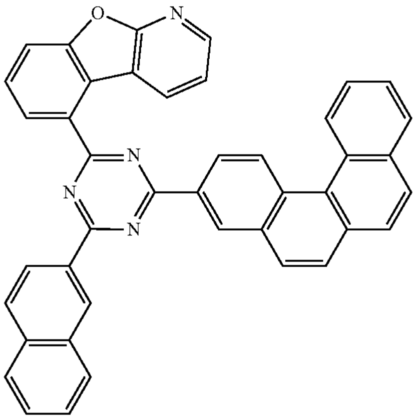
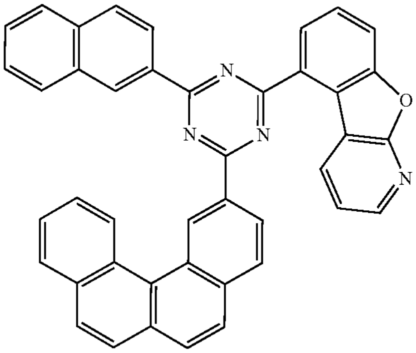
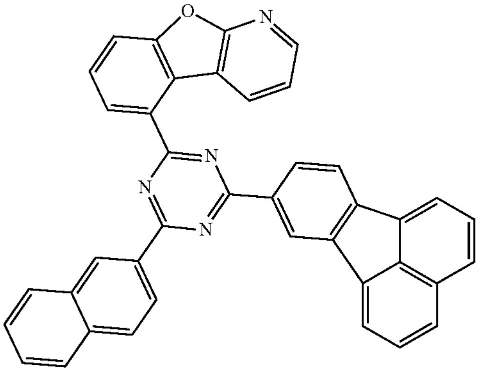

-continued
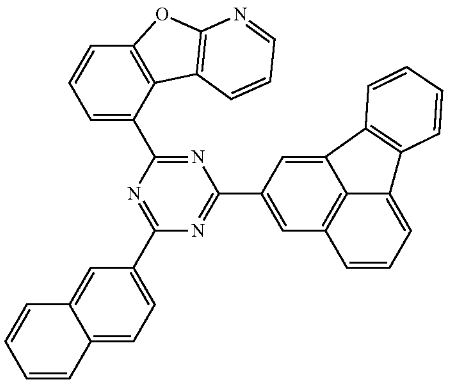
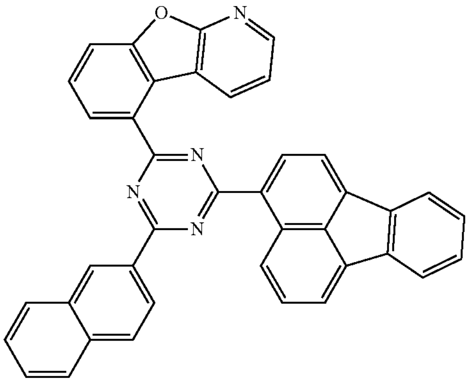
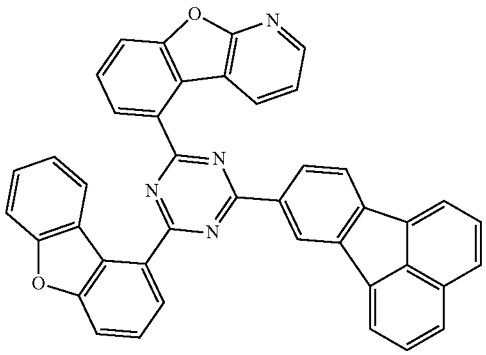
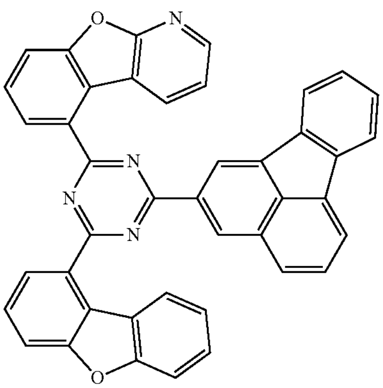
-continued
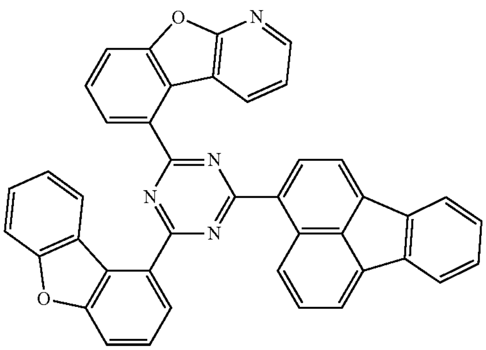
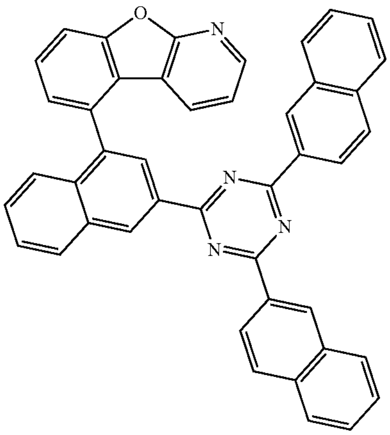
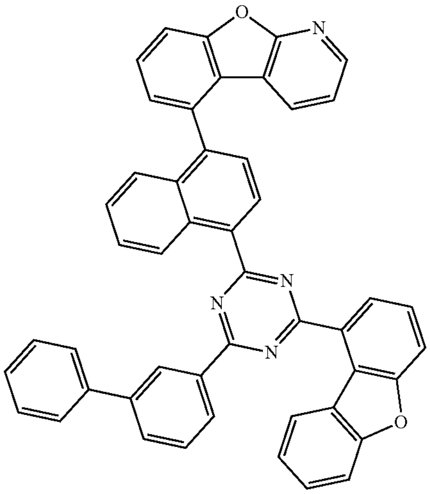

-continued
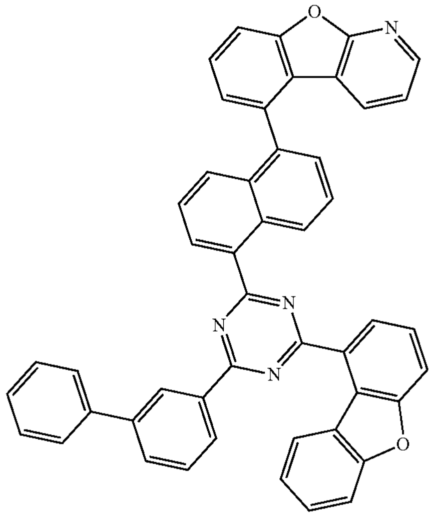
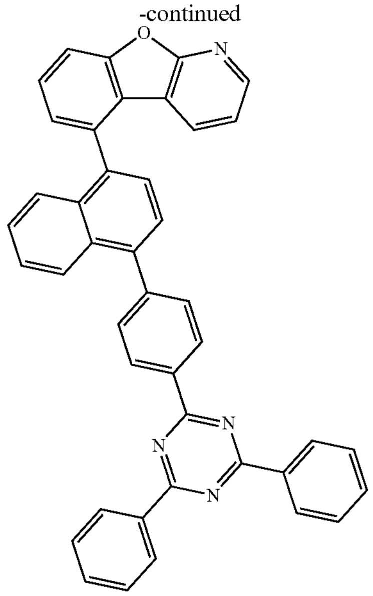
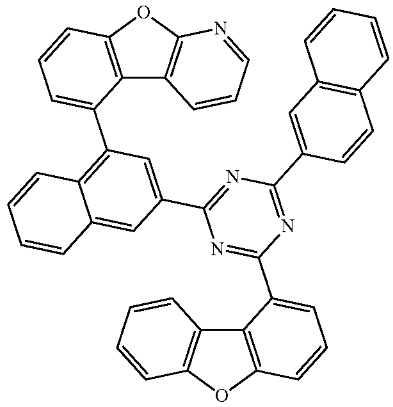
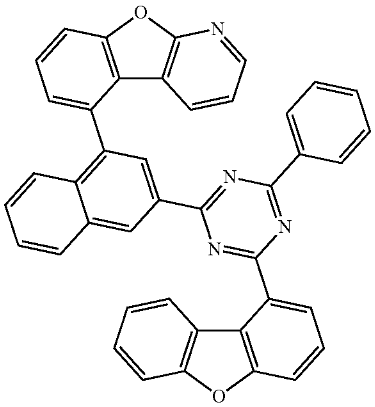
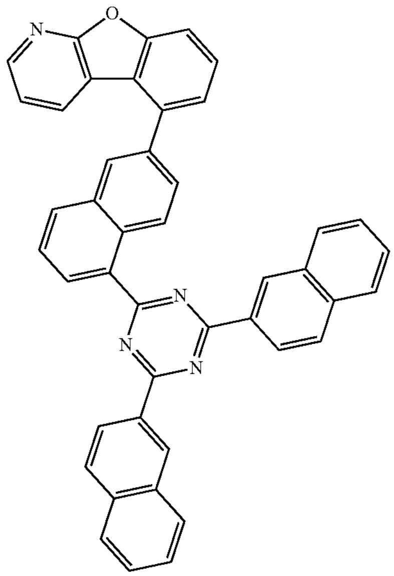
-continued
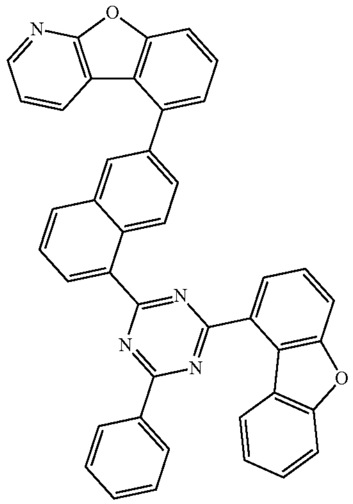

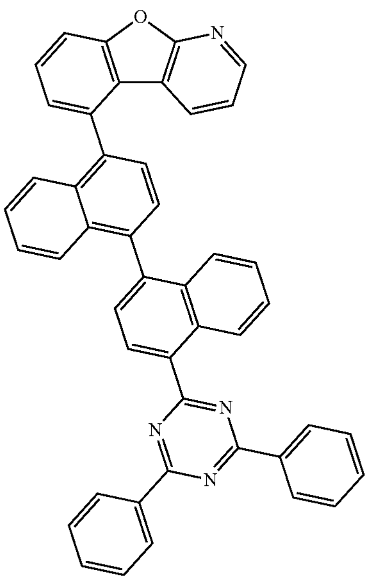
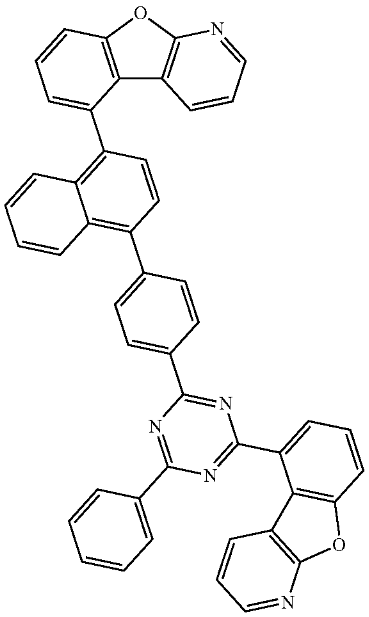
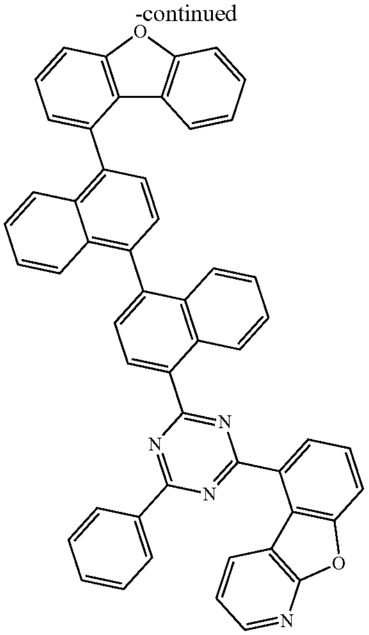
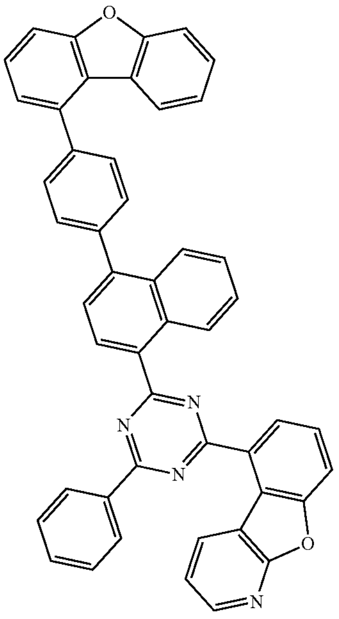
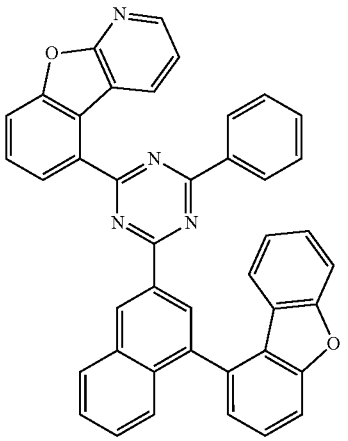

-continued
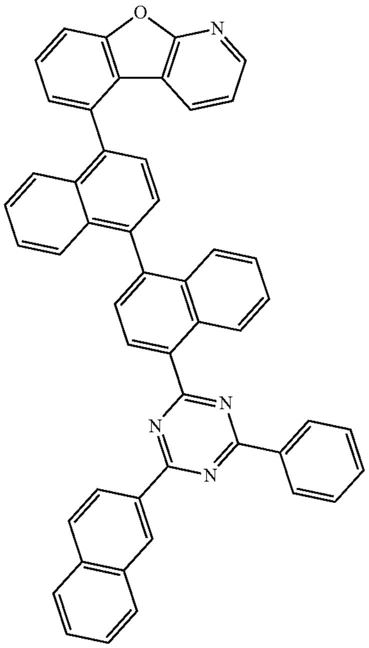
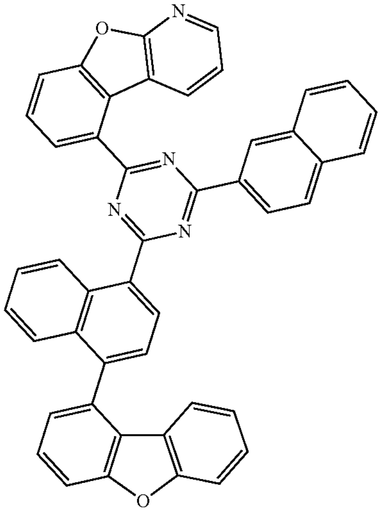
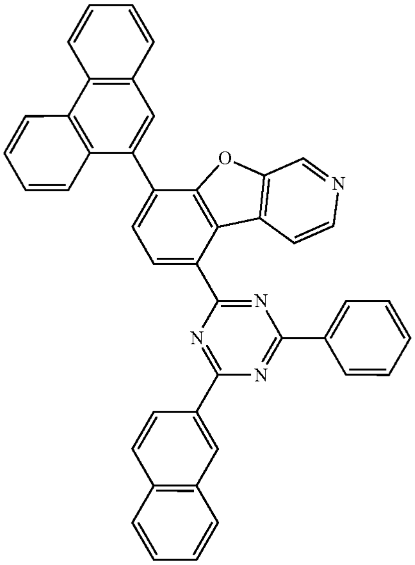
-continued
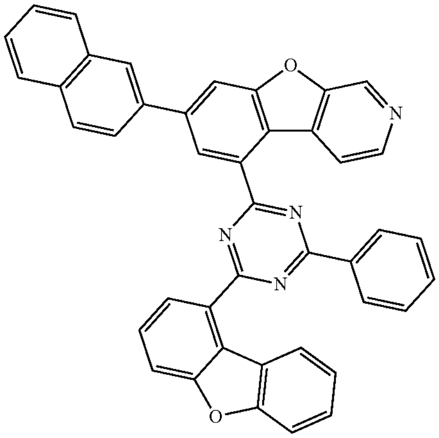
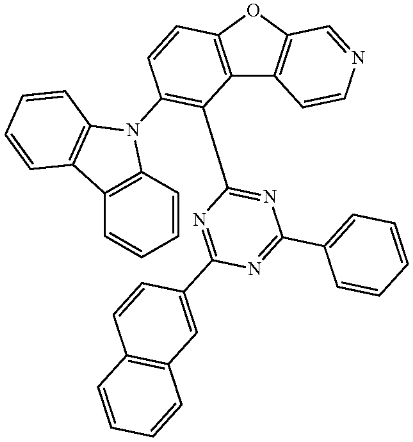
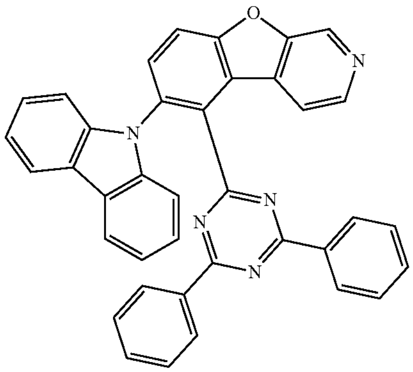
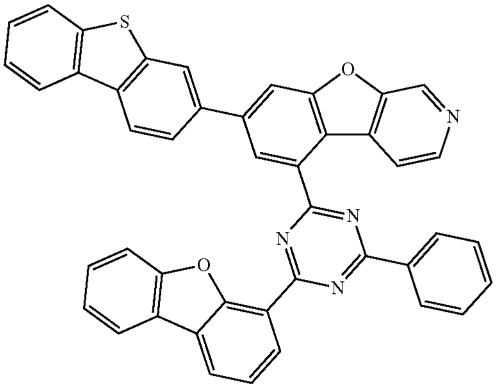

-continued
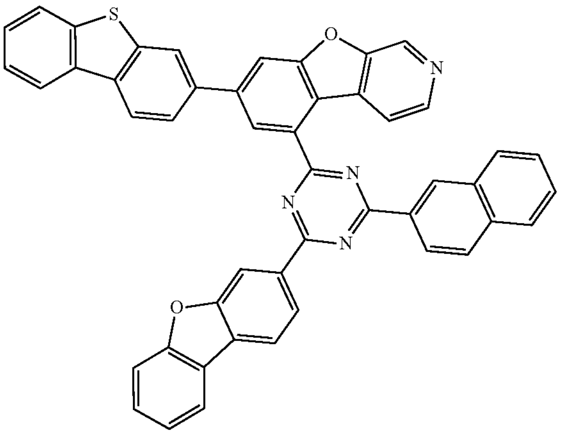
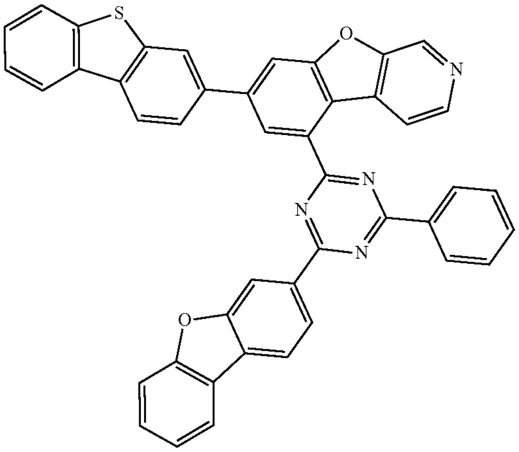
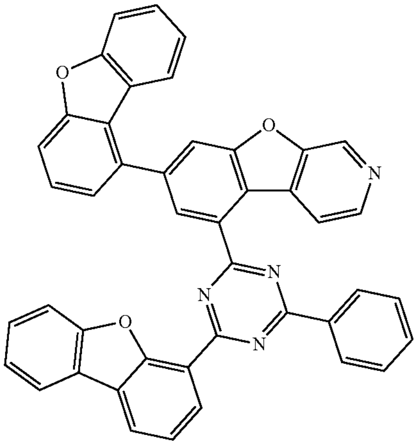
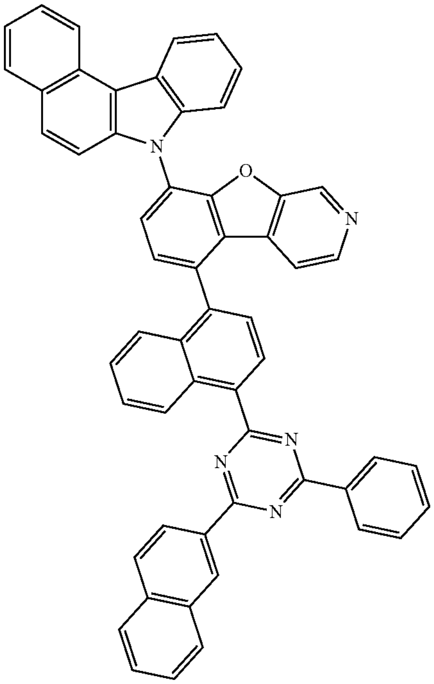
-continued
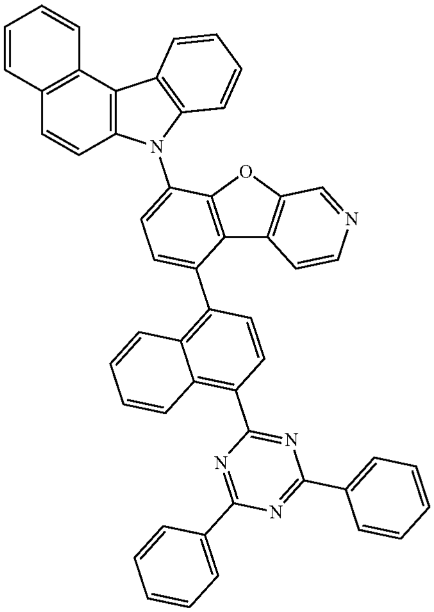

-continued
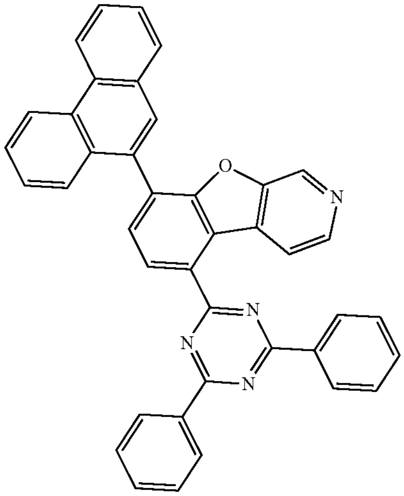
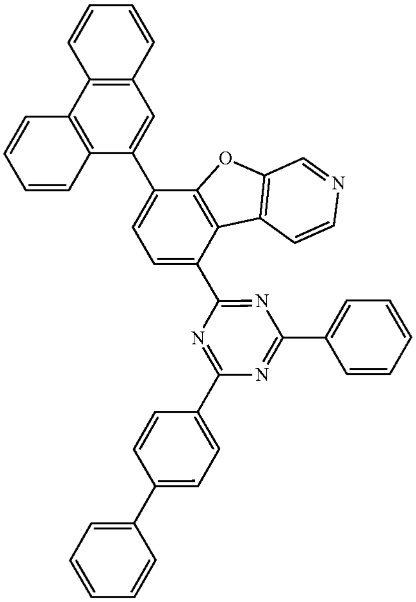
-continued
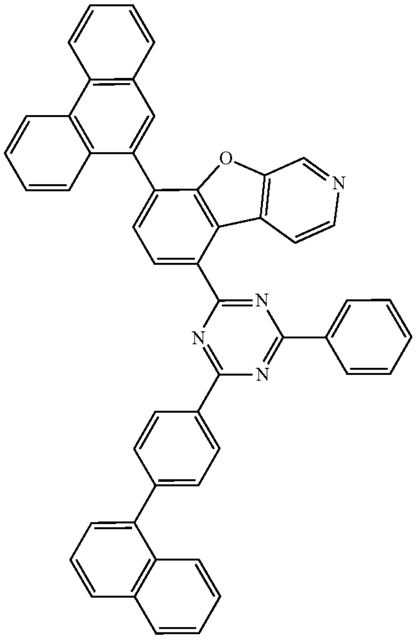
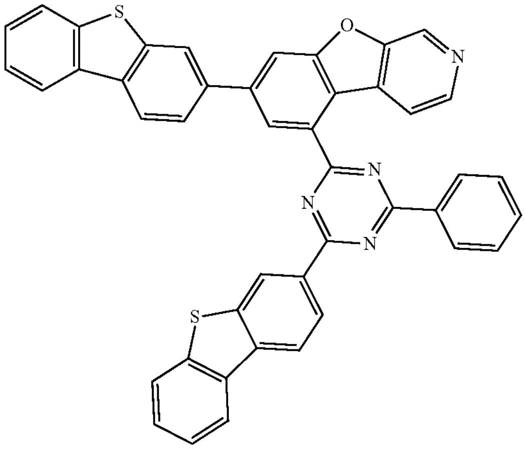
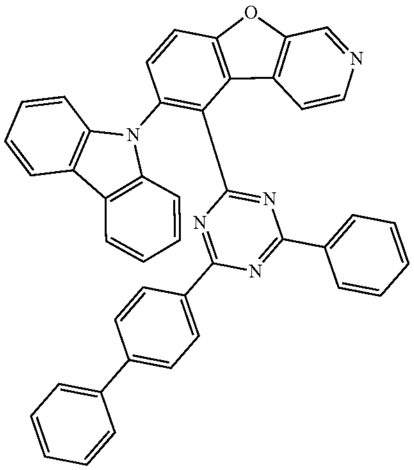

-continued
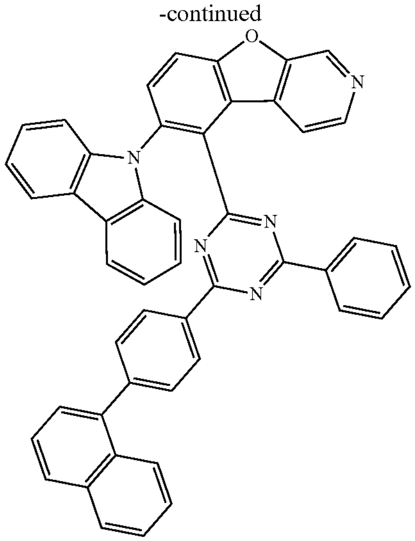
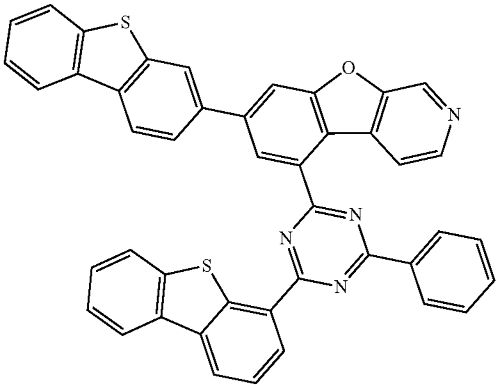
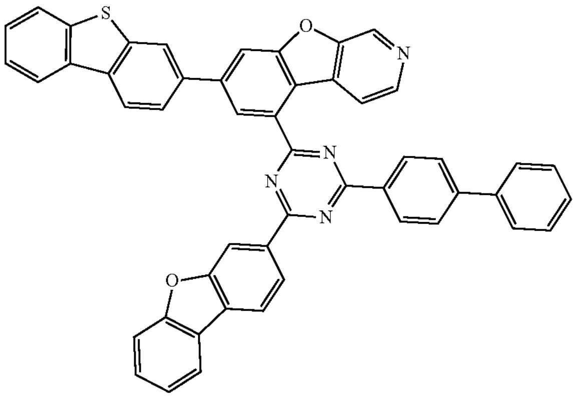
-continued
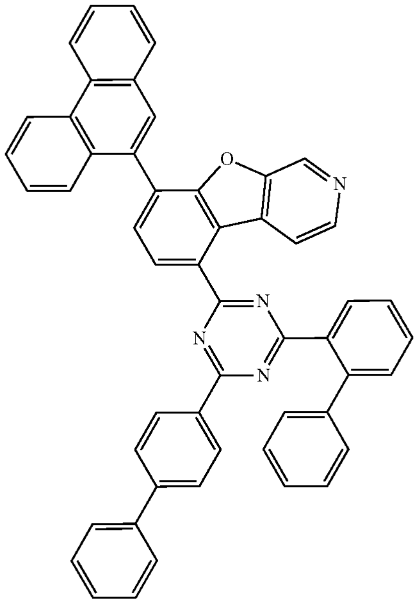
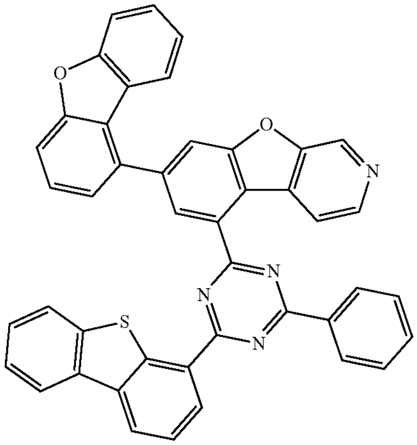

-continued
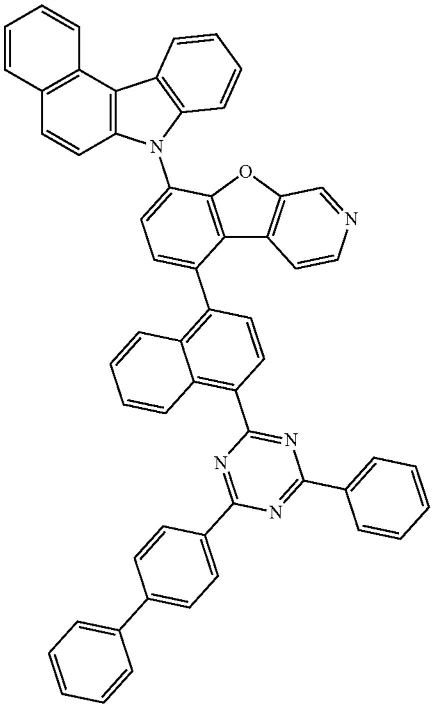
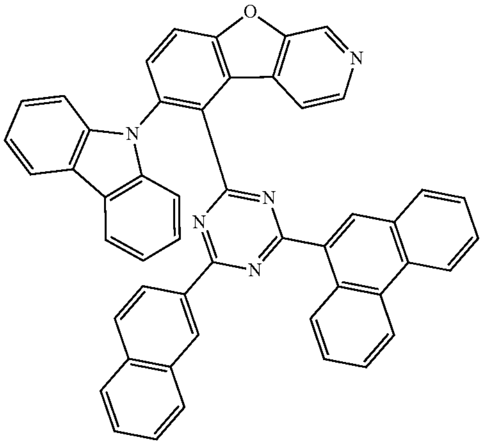
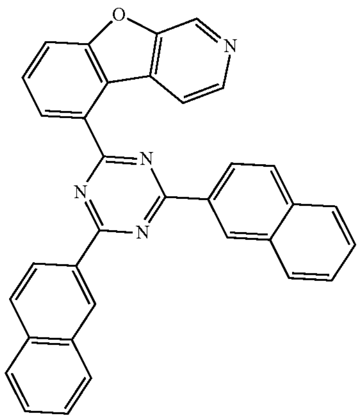
-continued
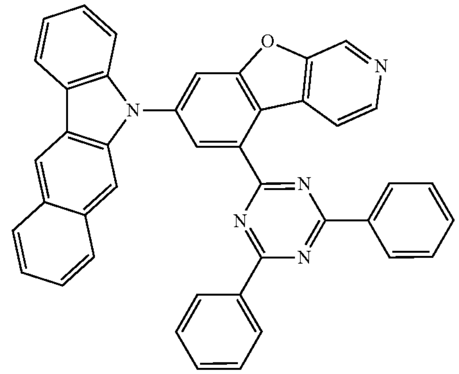
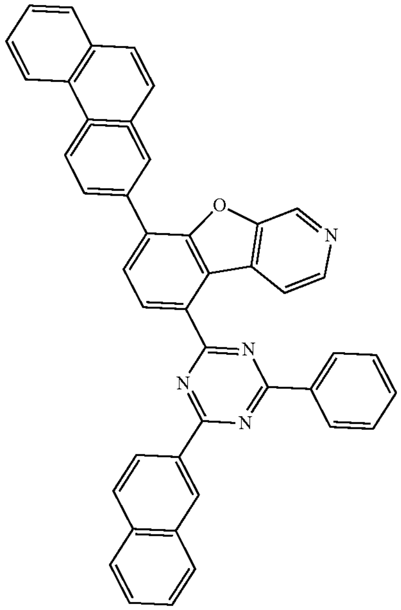
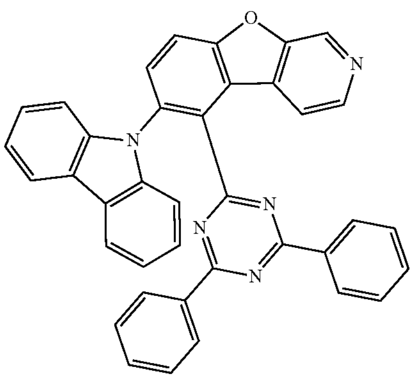

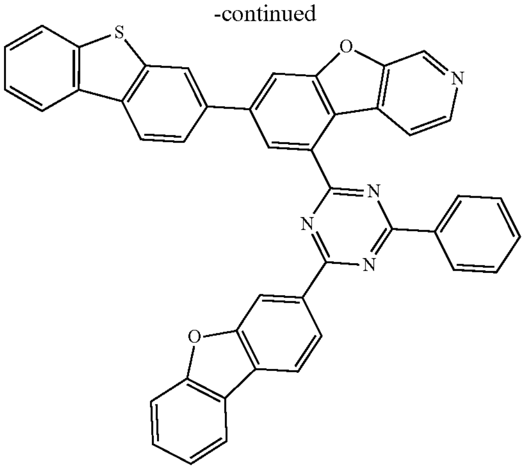
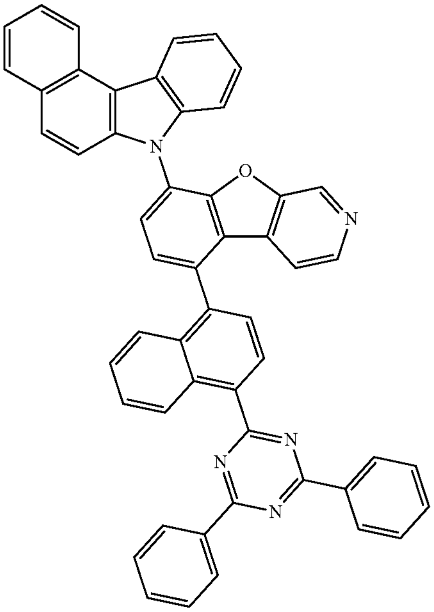
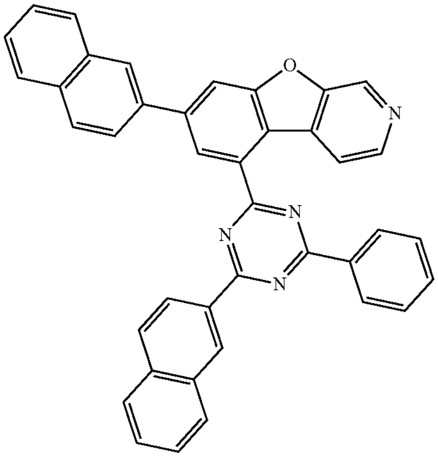
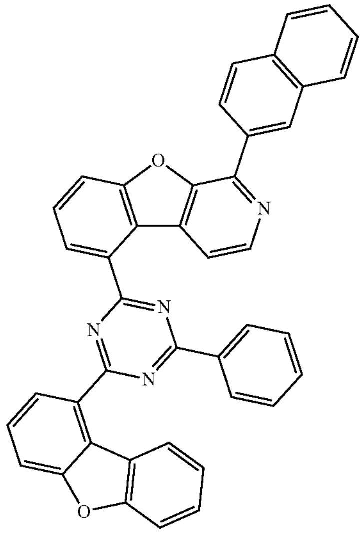
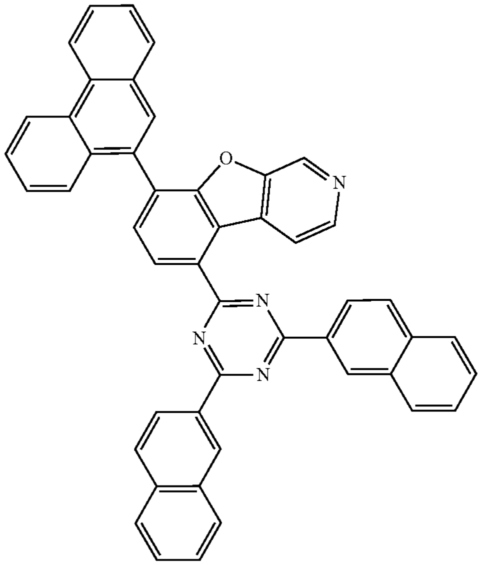
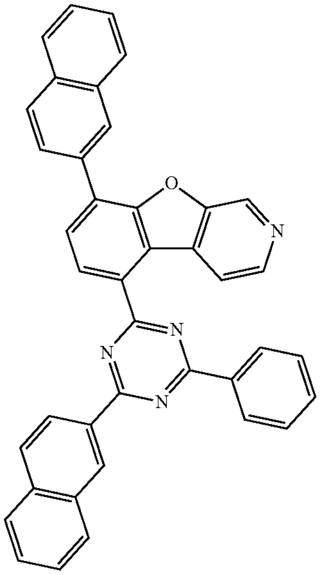

-continued
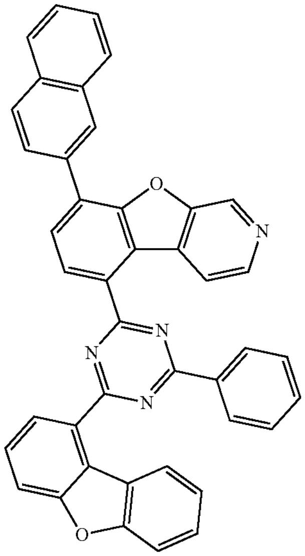
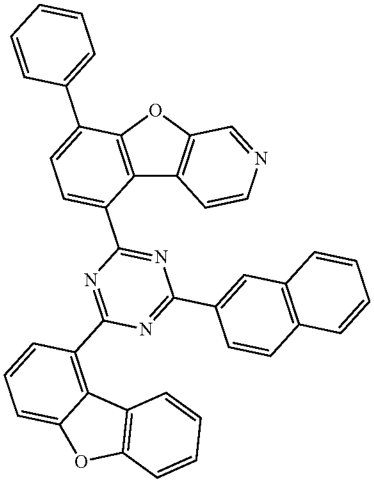
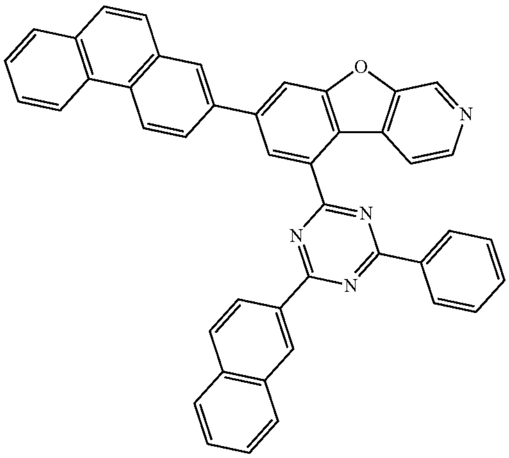
-continued
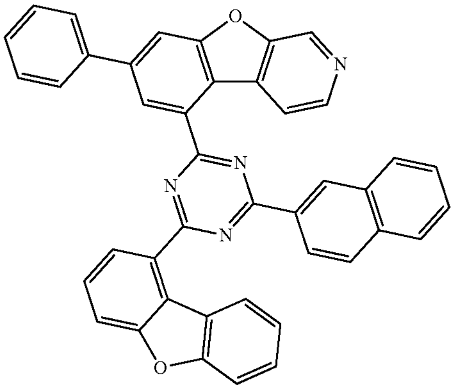
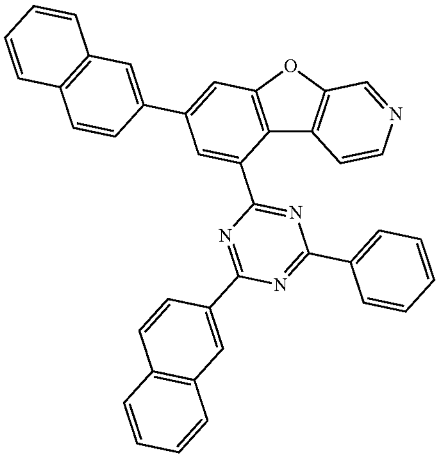
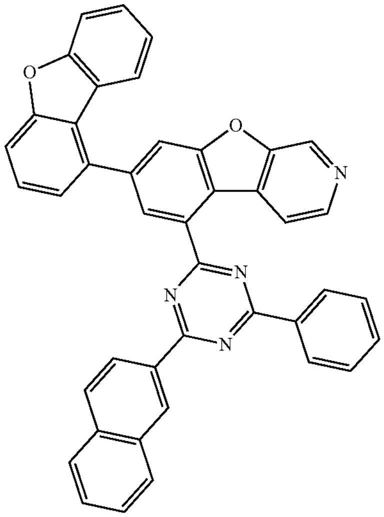

-continued
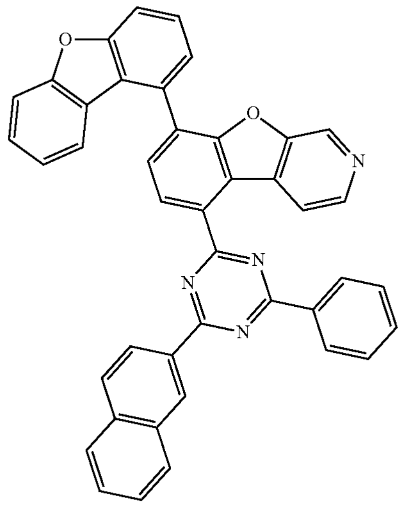
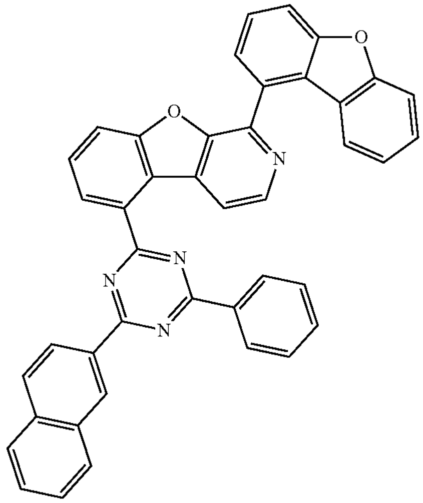
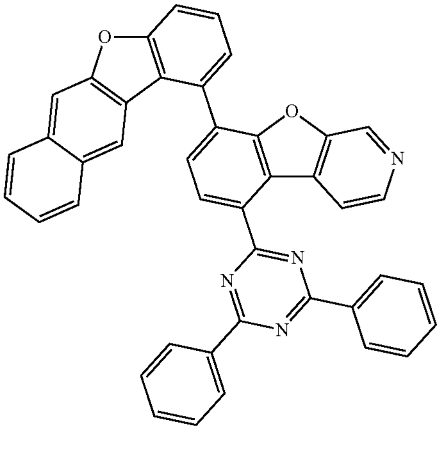
-continued
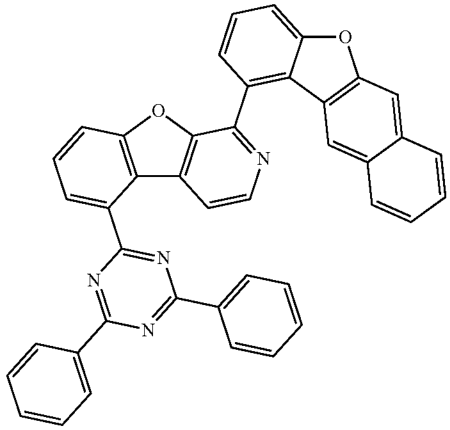
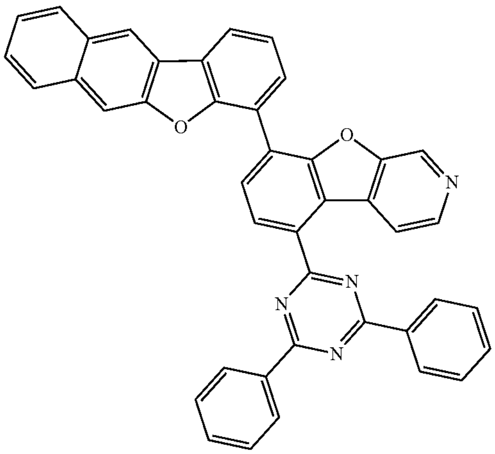
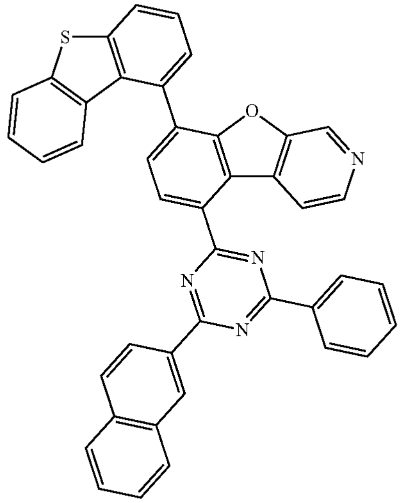

-continued
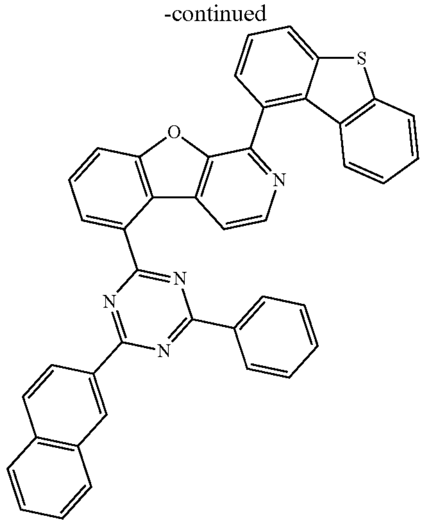
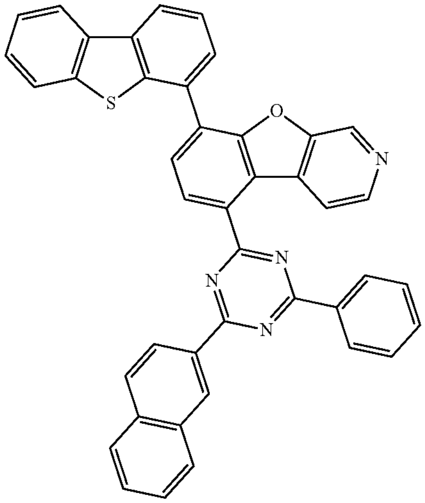
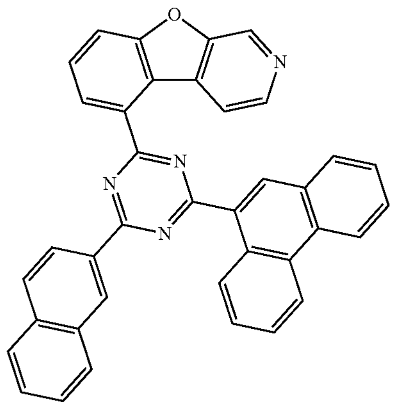
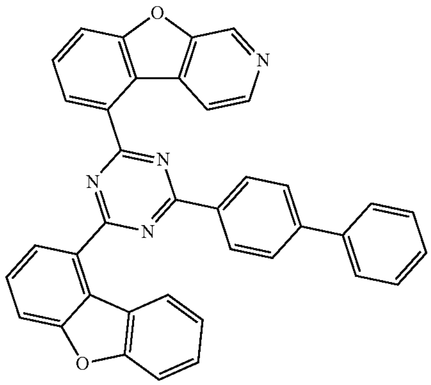
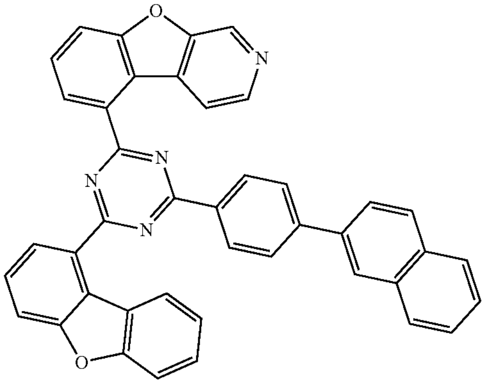
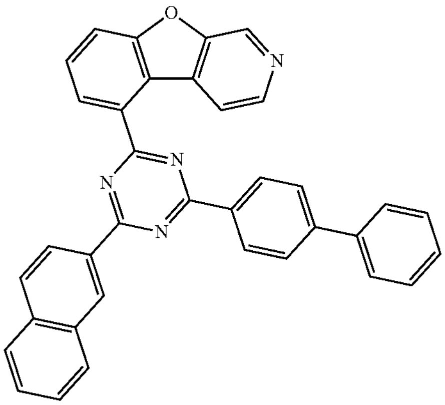
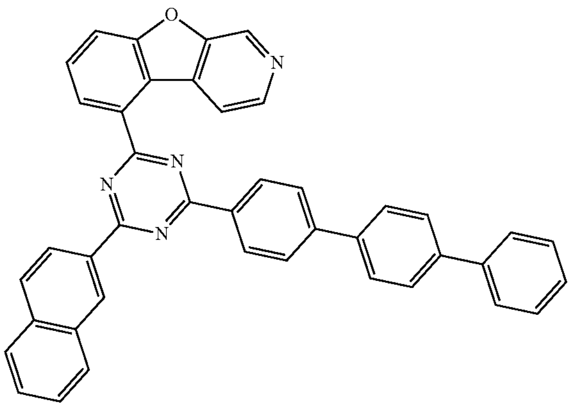
-continued -continued
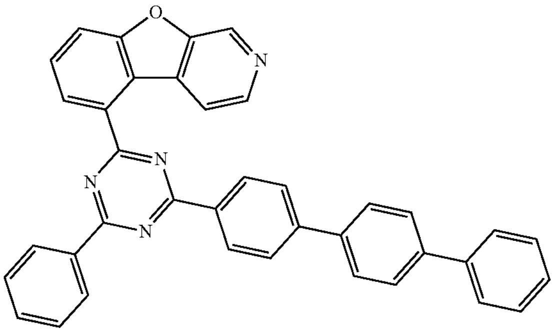
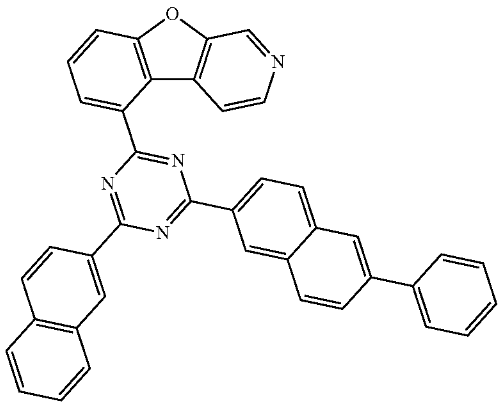
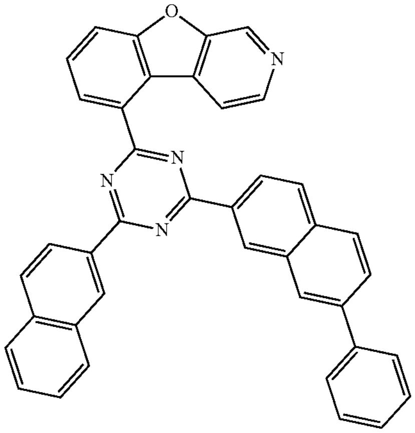
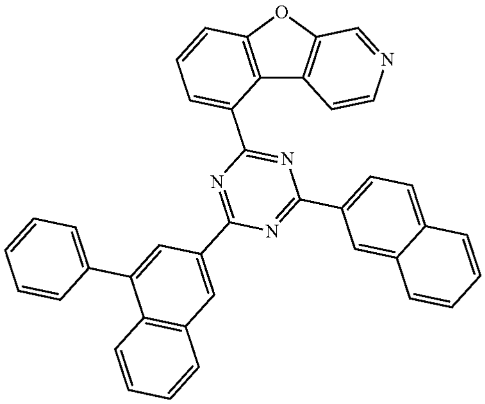
-continued
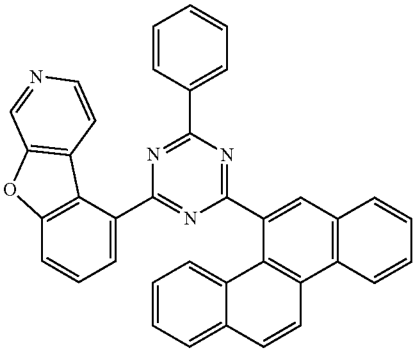
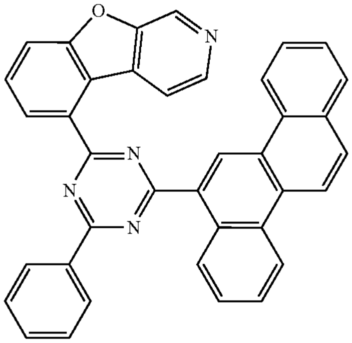
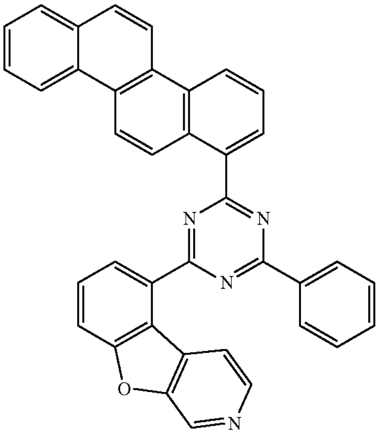
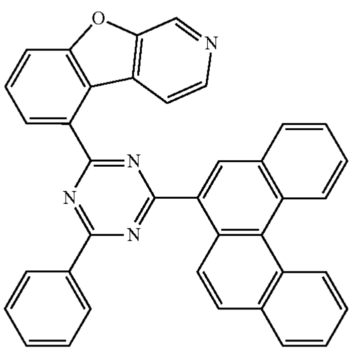

-continued
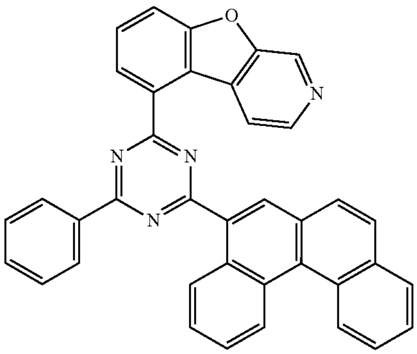
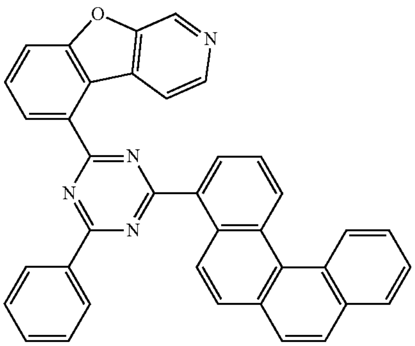
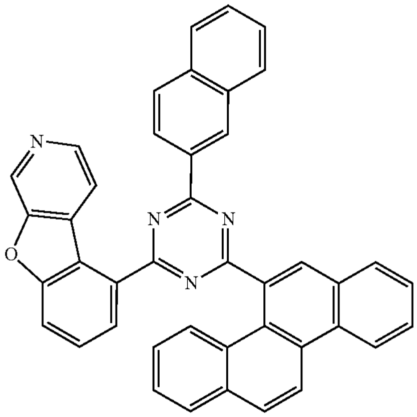
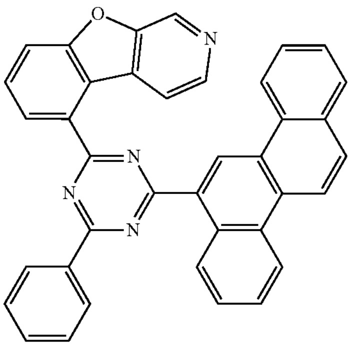
-continued
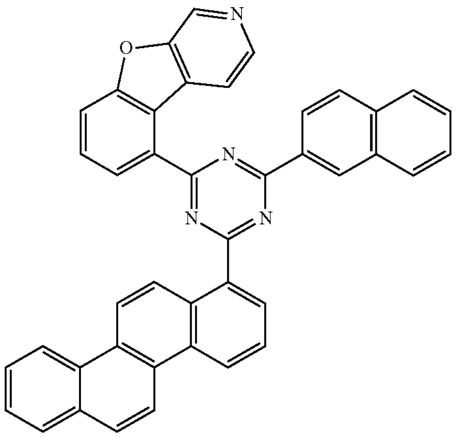
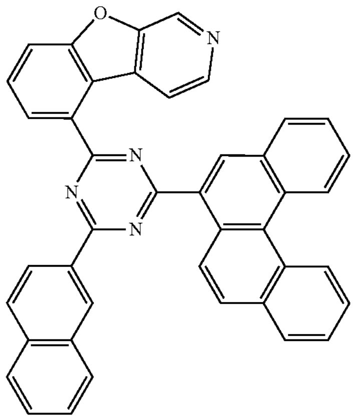
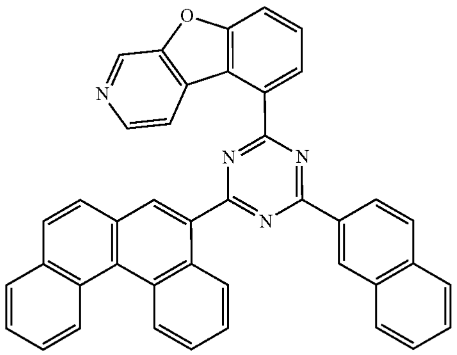
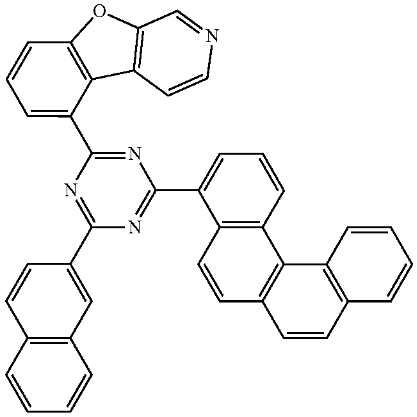

-continued
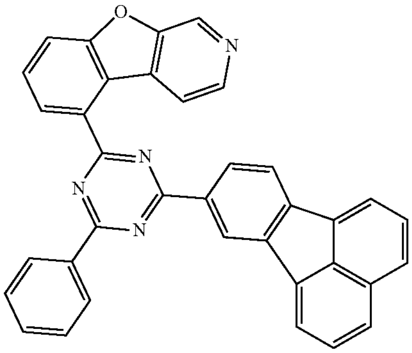
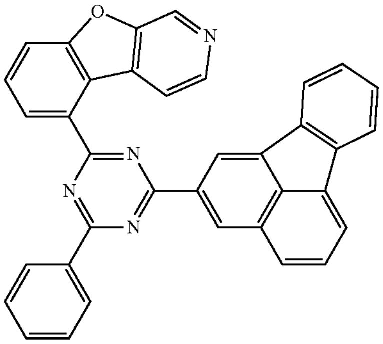
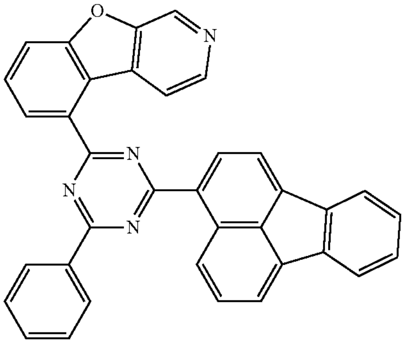
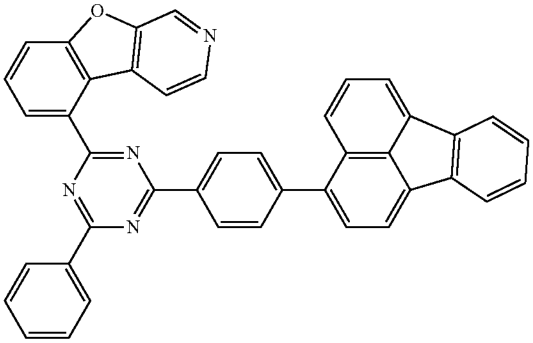
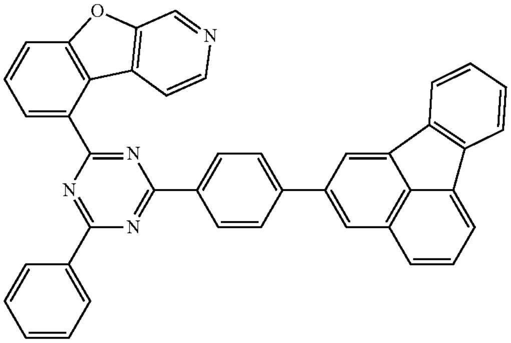
-continued
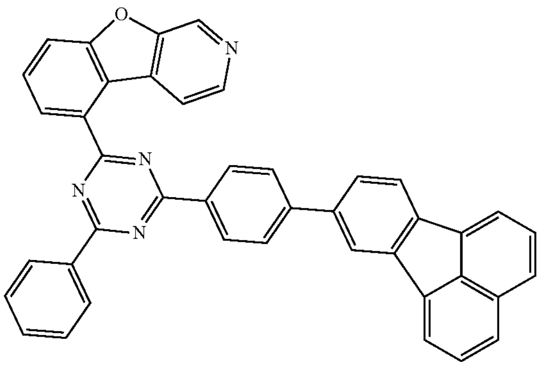
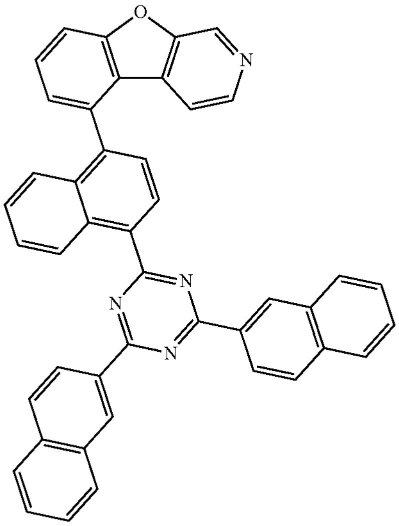
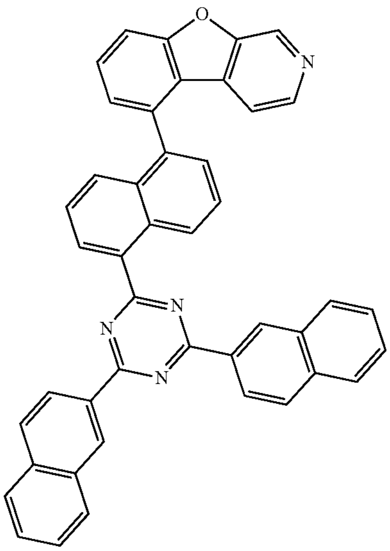

-continued
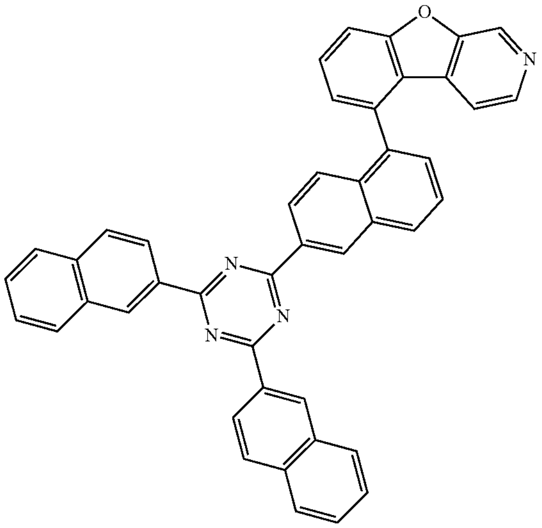
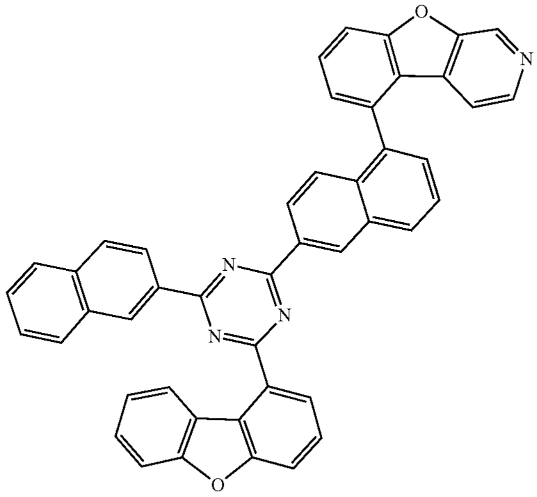
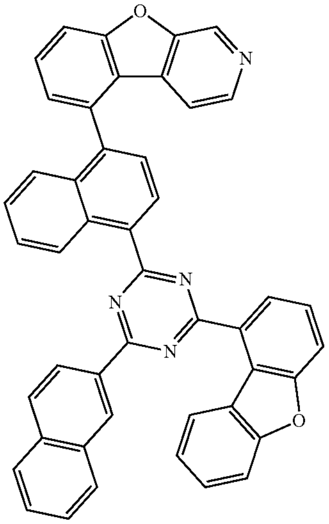
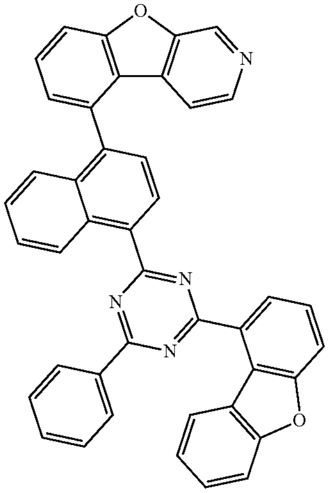
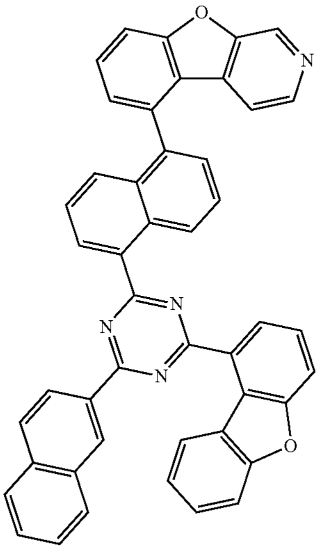
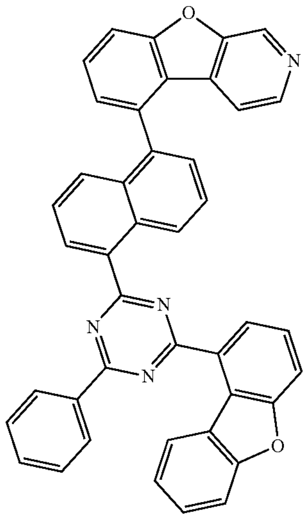

-continued
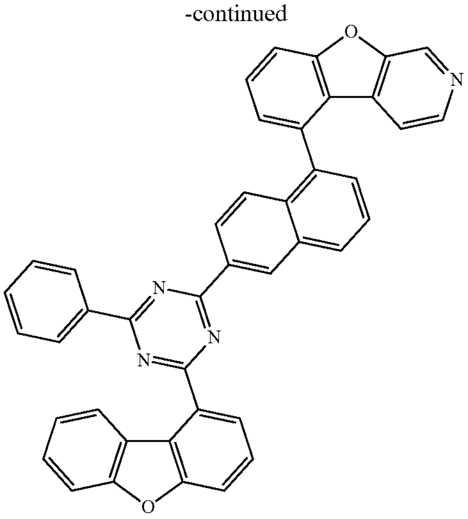
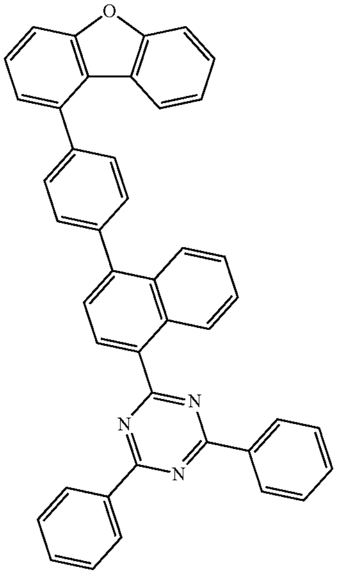
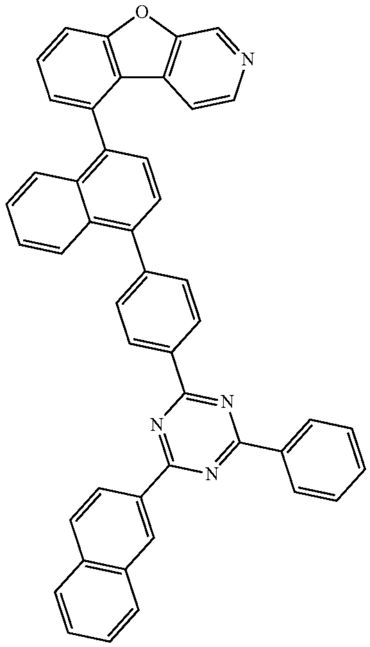
-continued
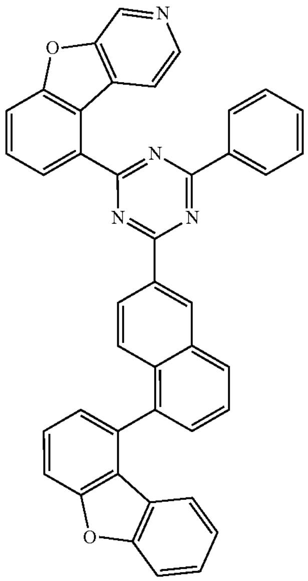
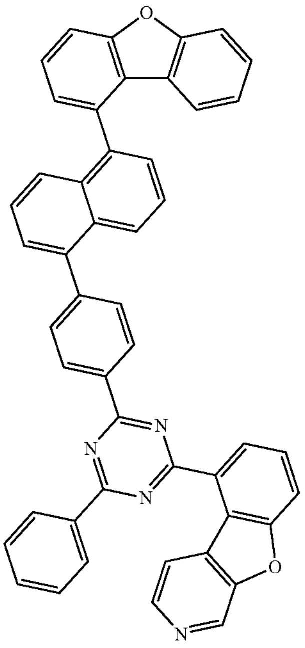
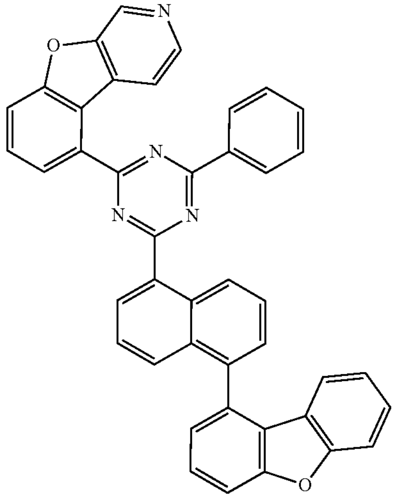

-continued
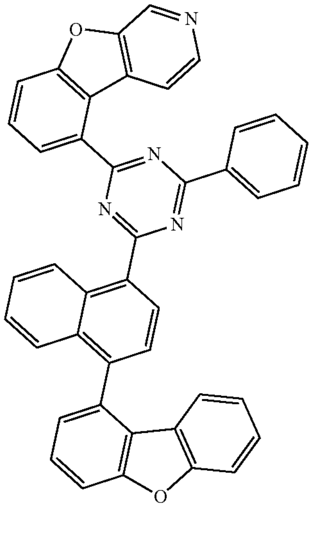
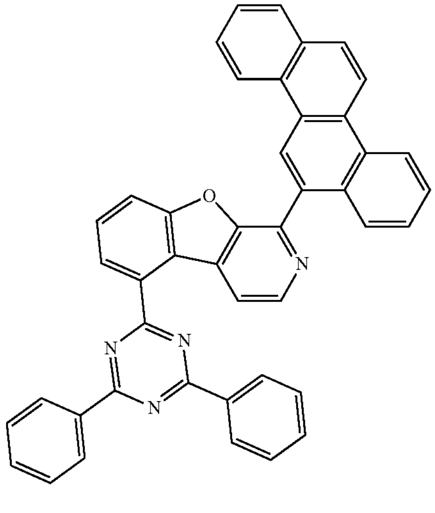
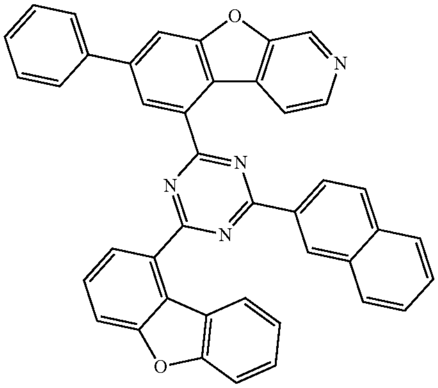
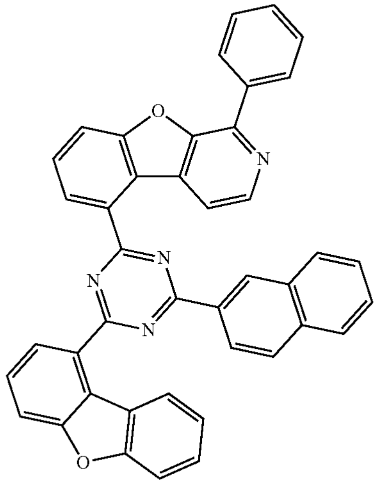
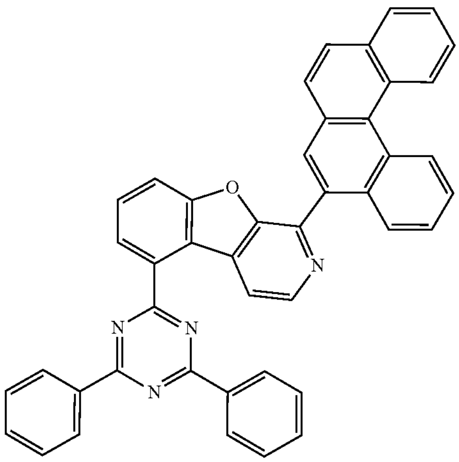
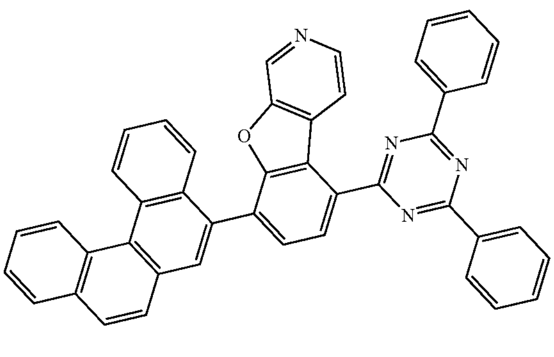
-continued -continued
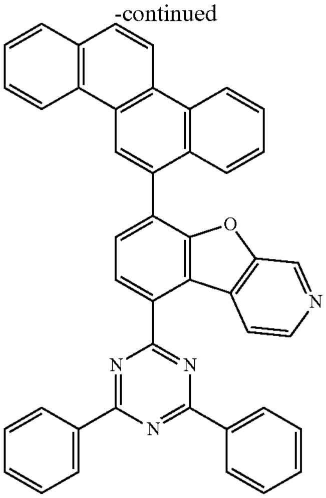
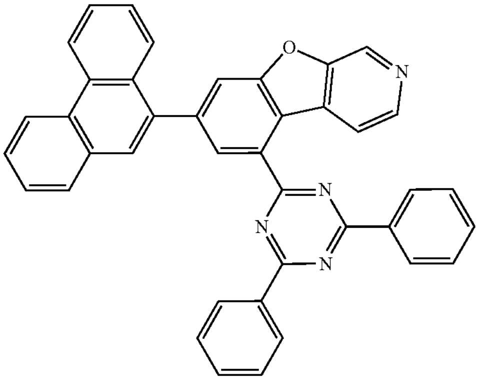
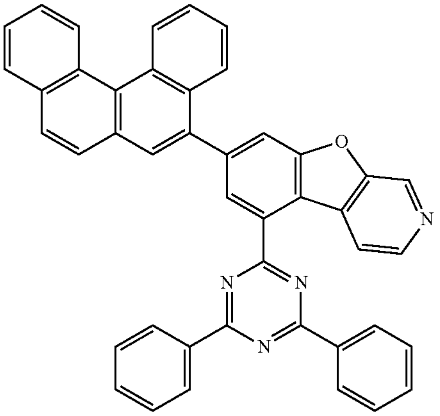
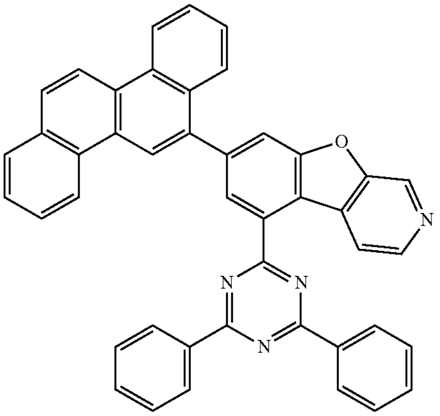
-continued
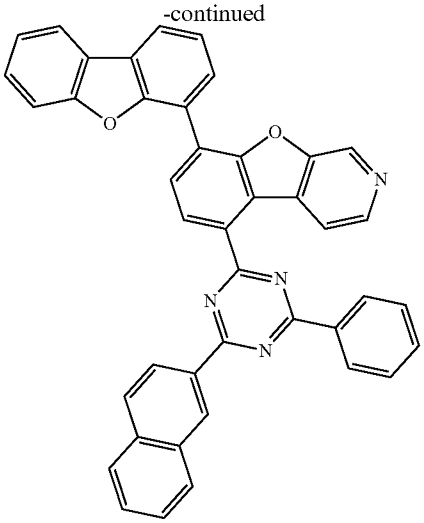
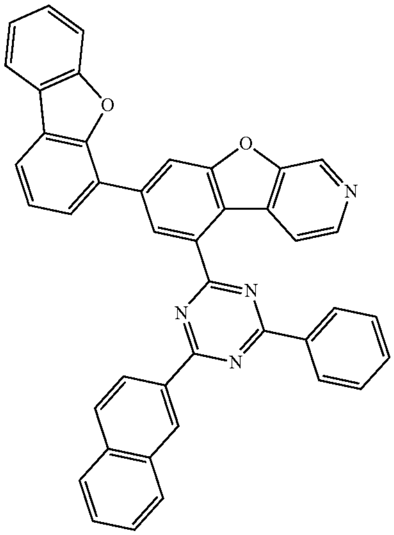
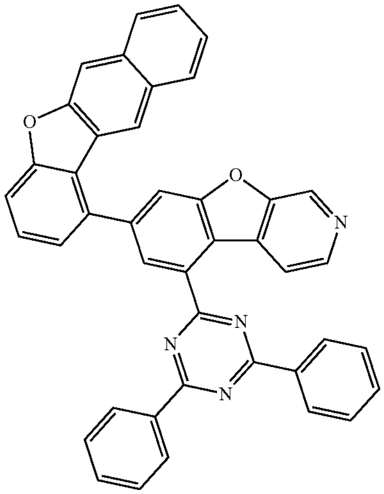

-continued
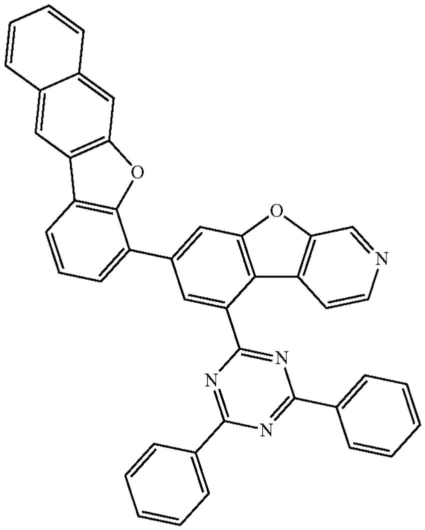
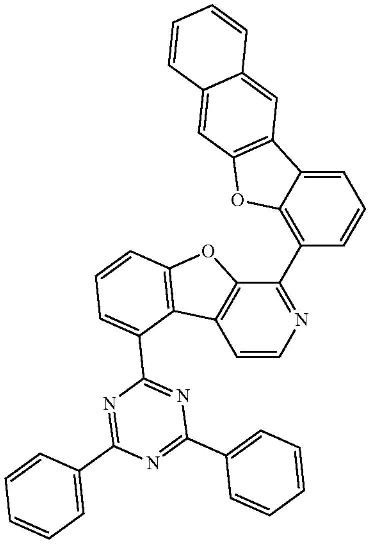
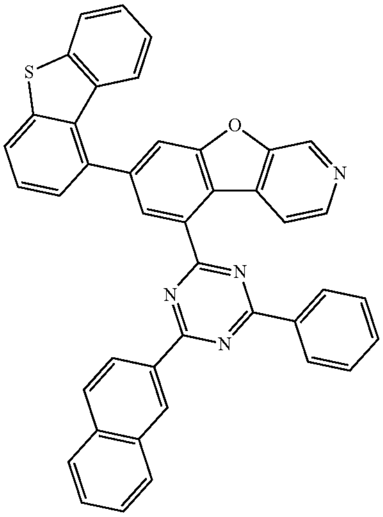
-continued
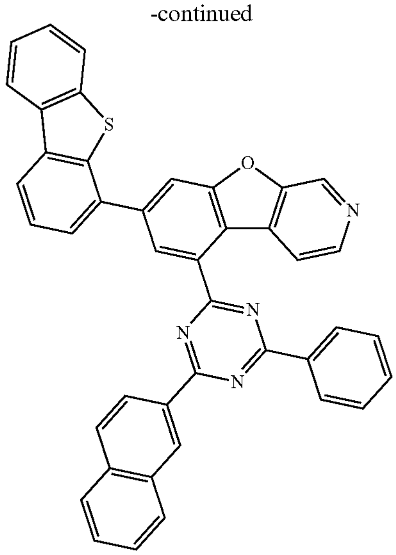
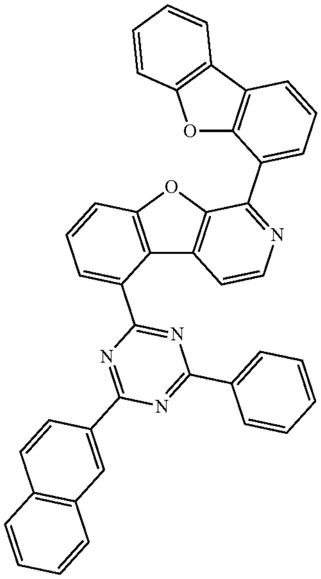
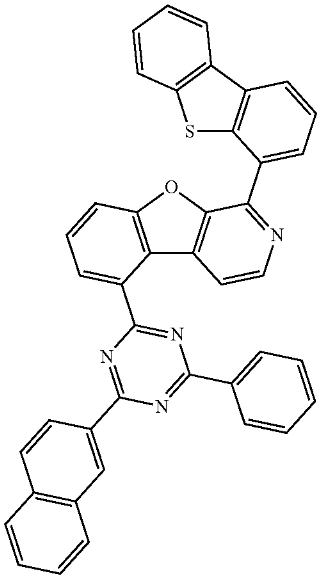

-continued
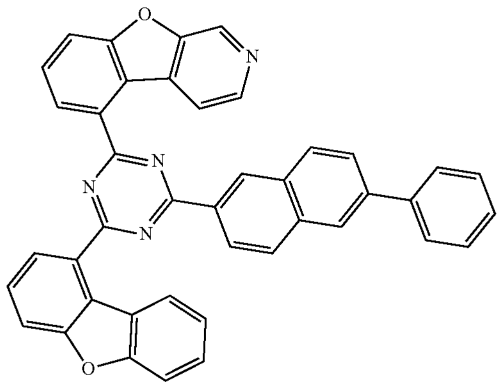
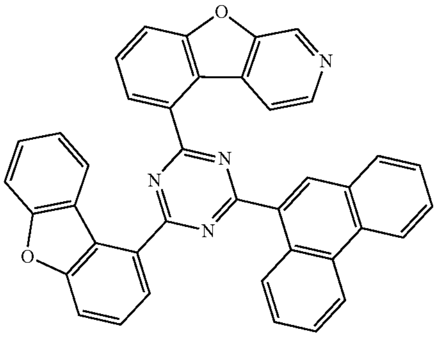
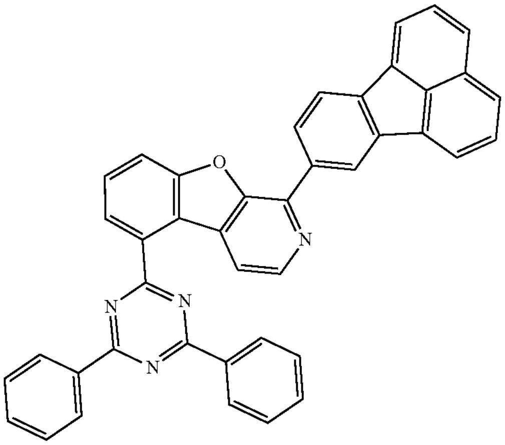
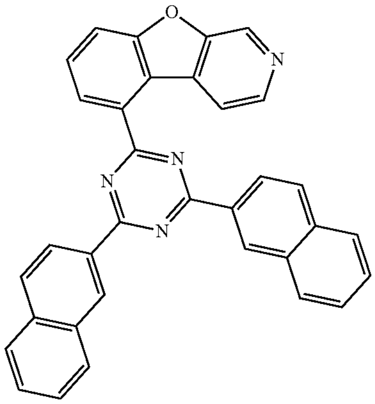
-continued
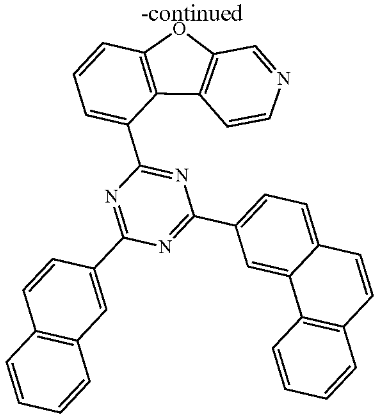
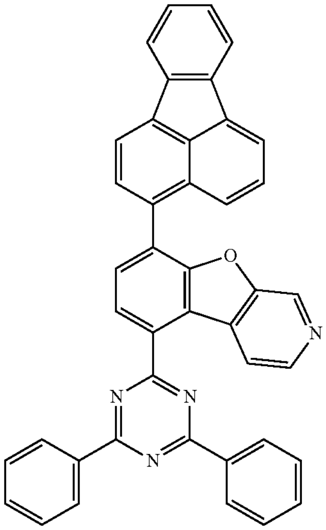
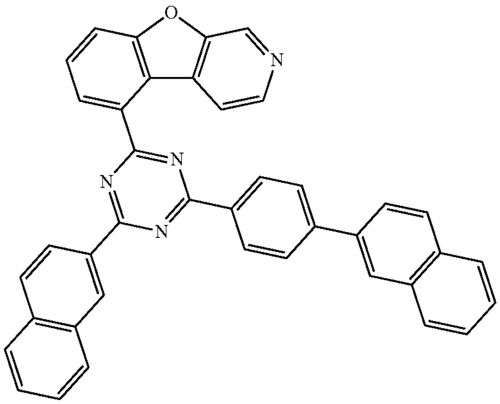
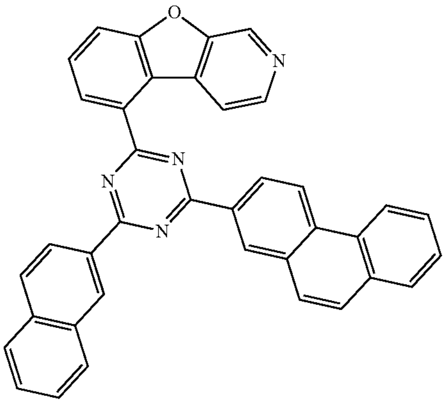

-continued
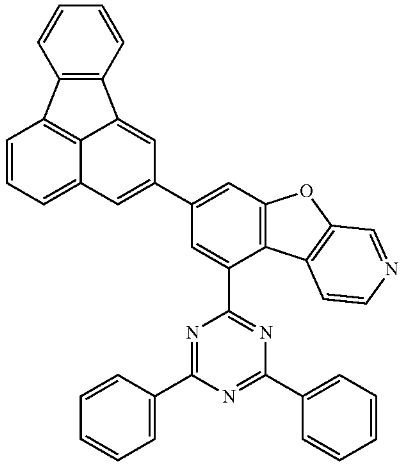
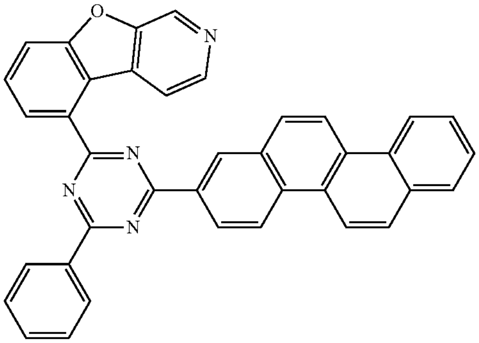
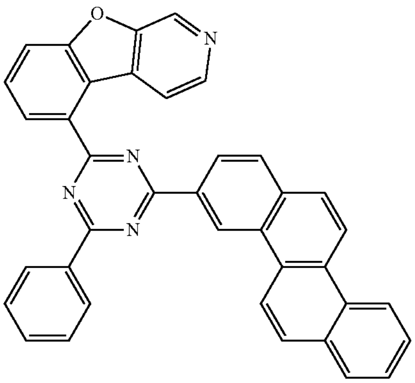
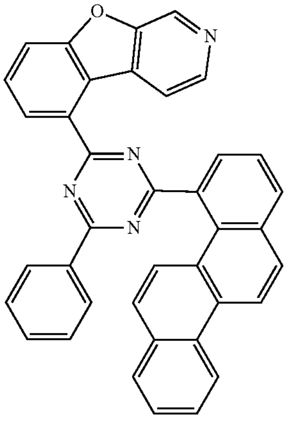
-continued
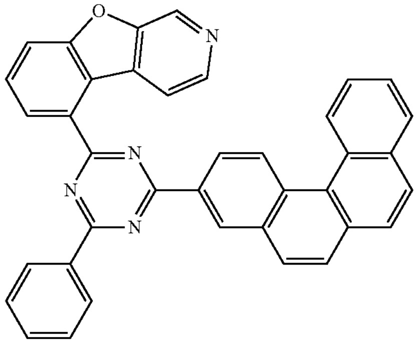
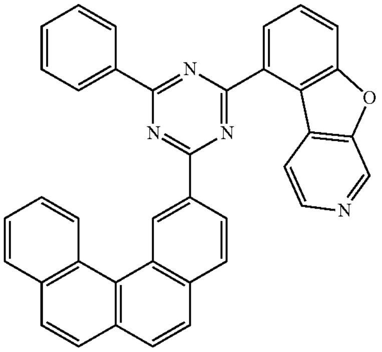
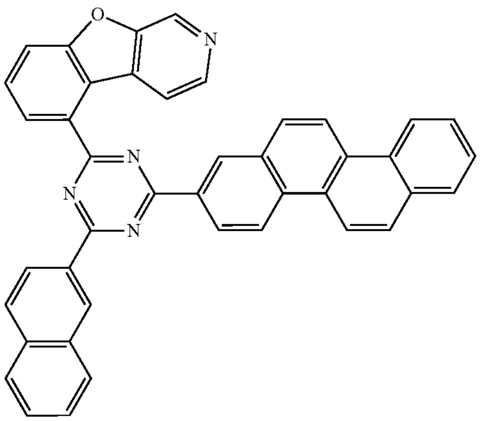
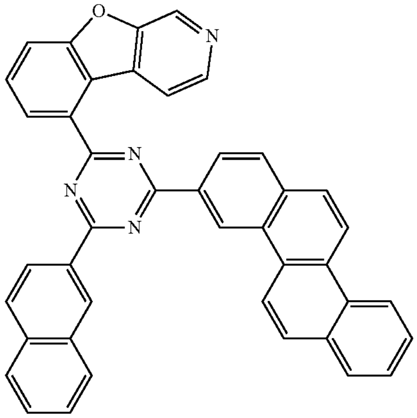

-continued
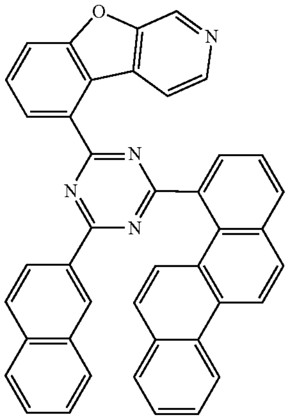
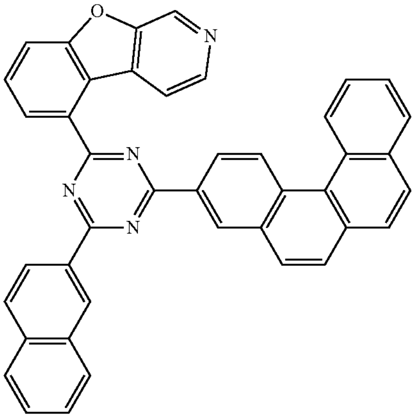
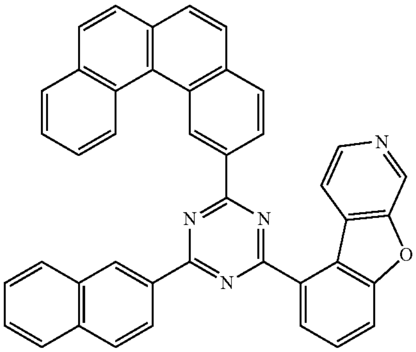
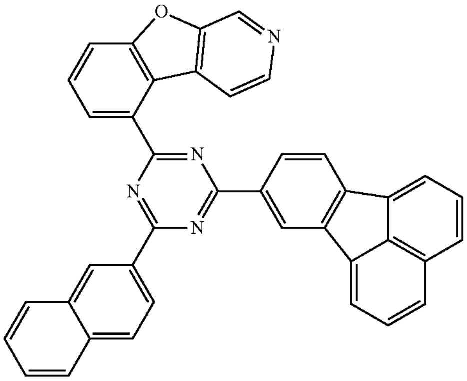
-continued
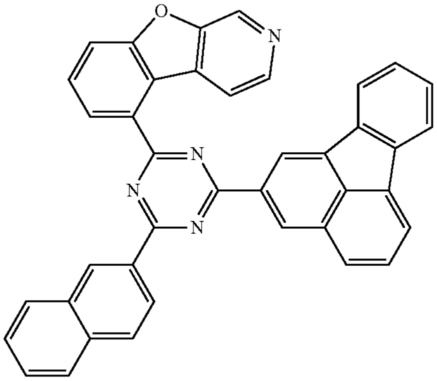
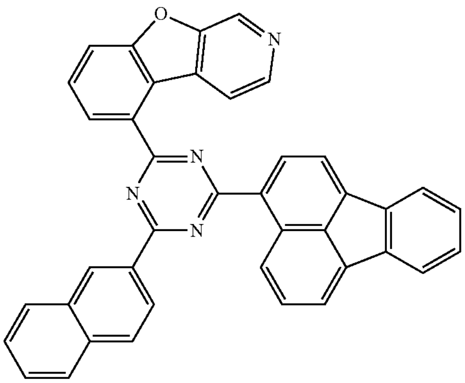
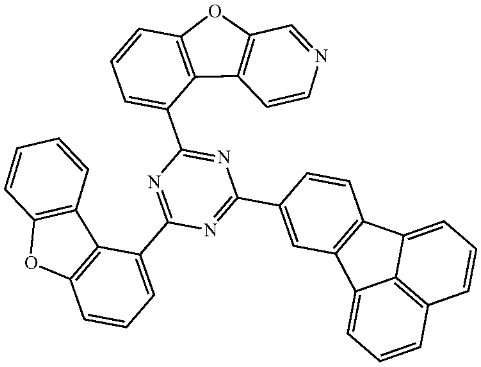
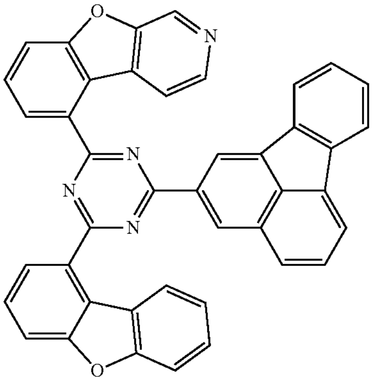

-continued
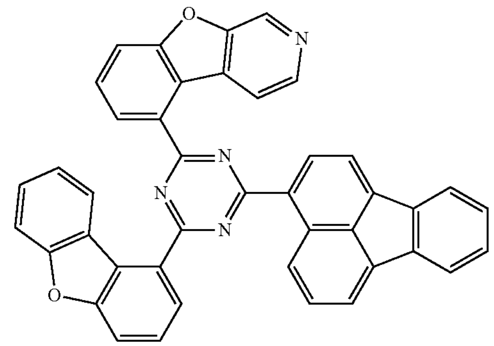
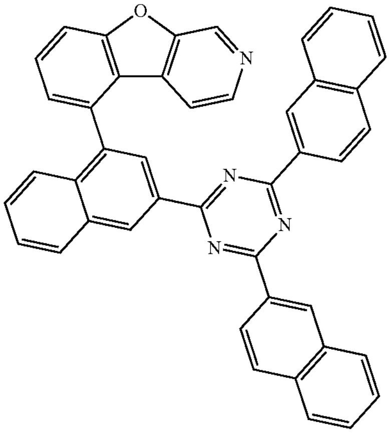
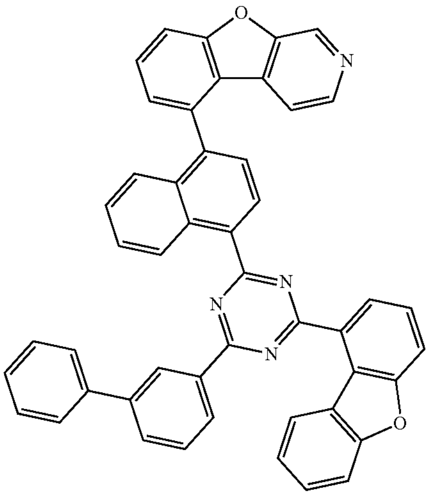
-continued
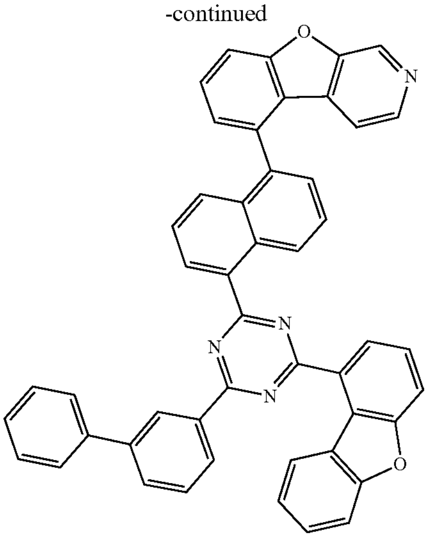
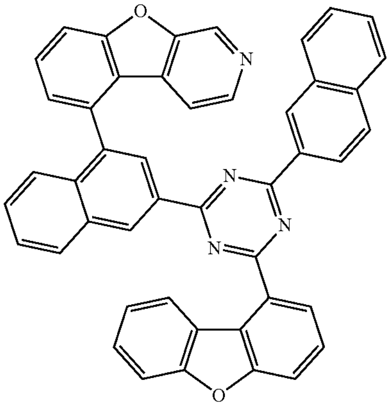
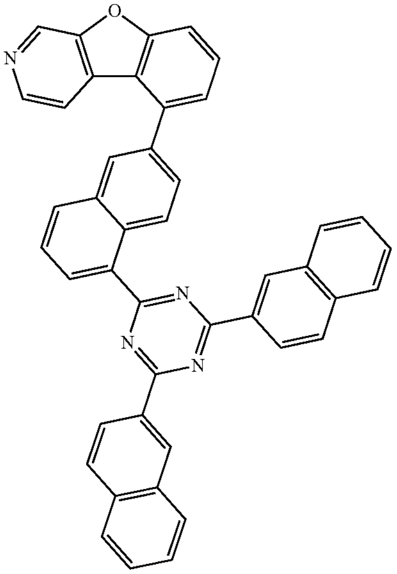

-continued
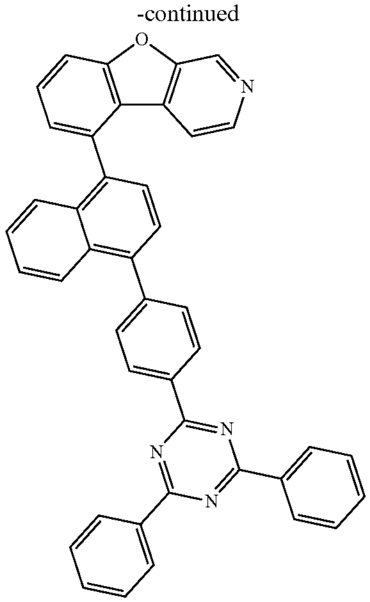
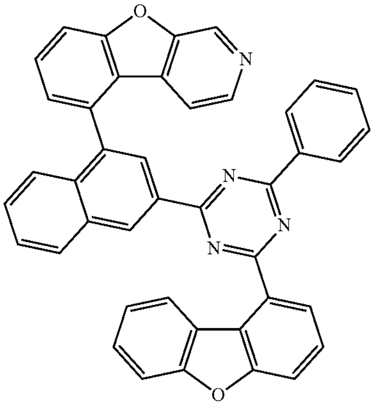
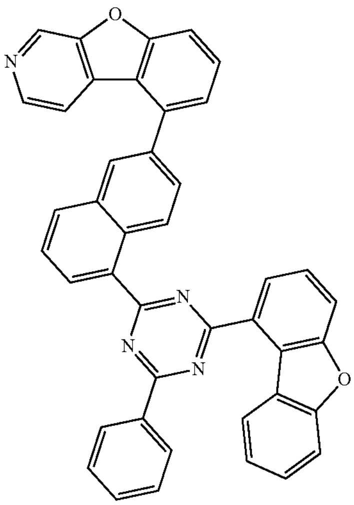
-continued
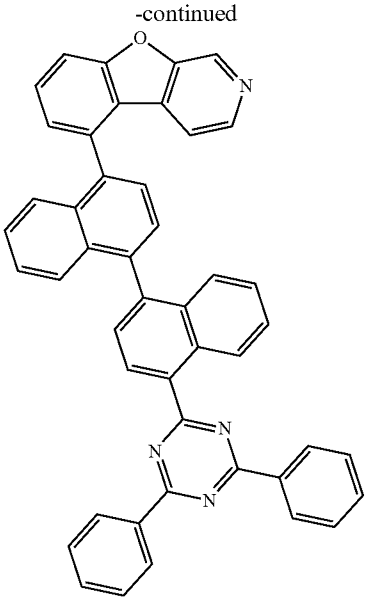
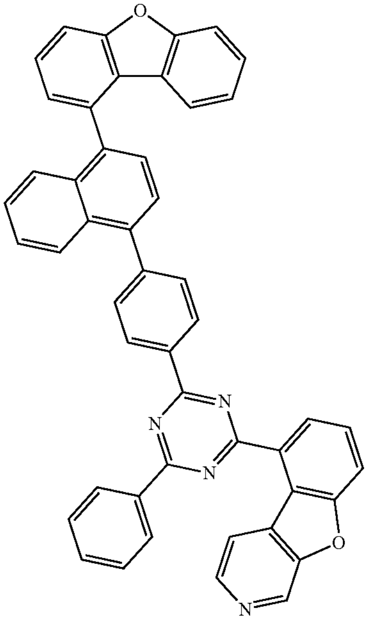

-continued
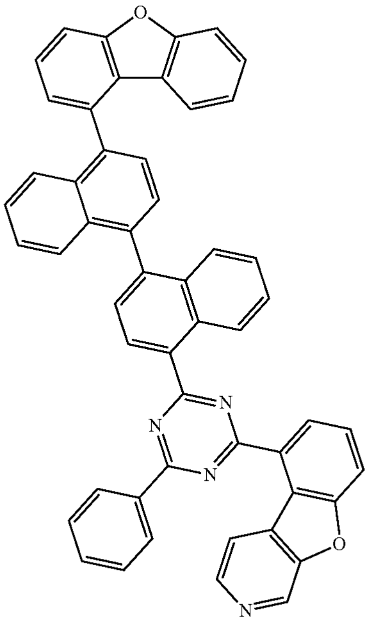
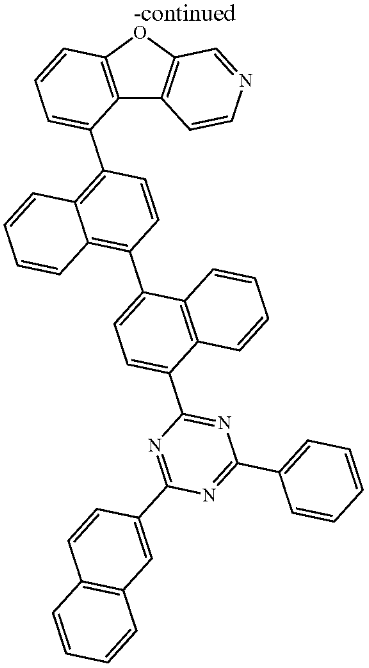
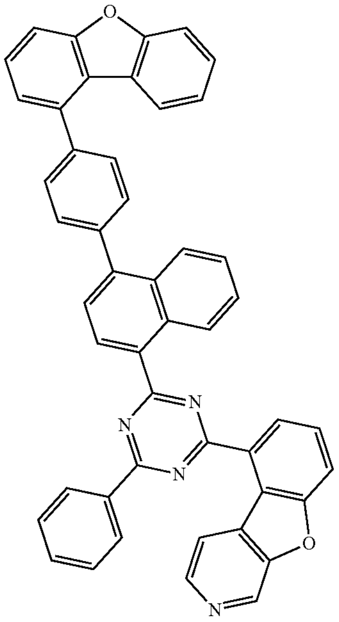
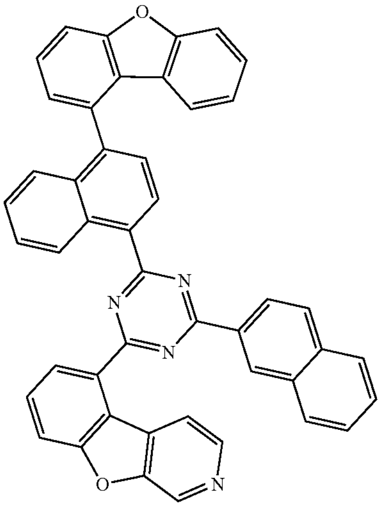
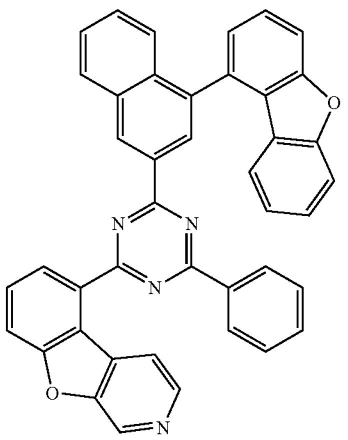
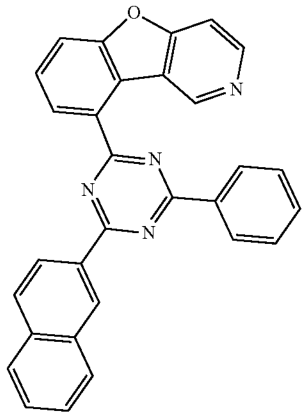
-continued -continued
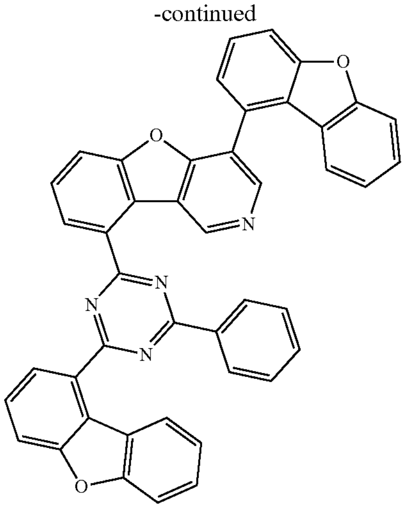
-continued
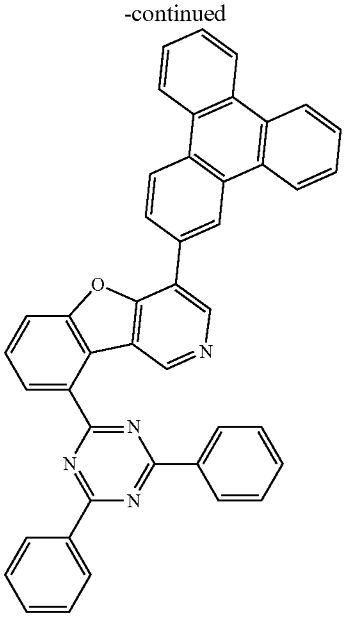
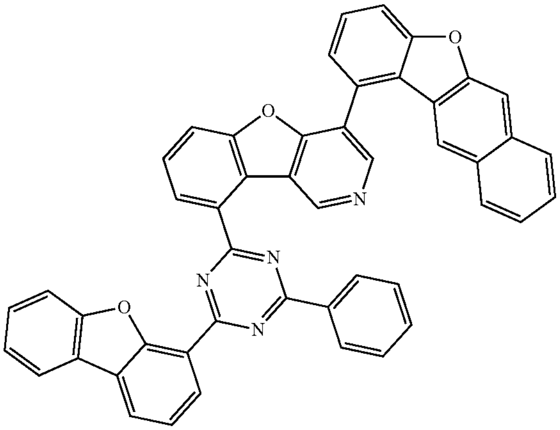
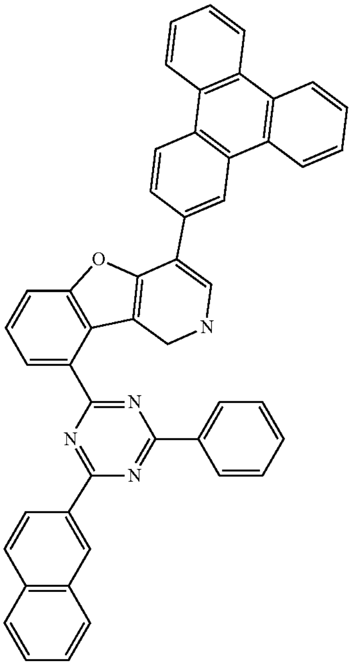
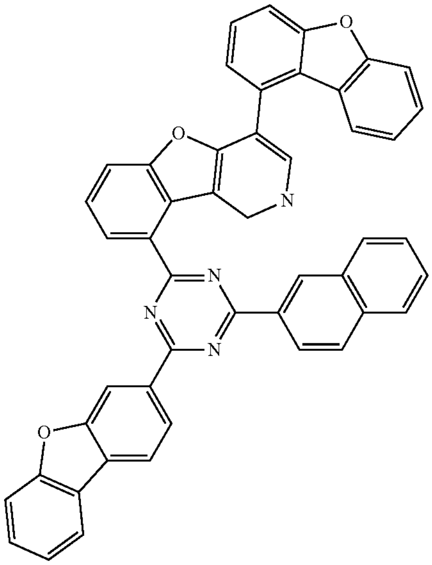

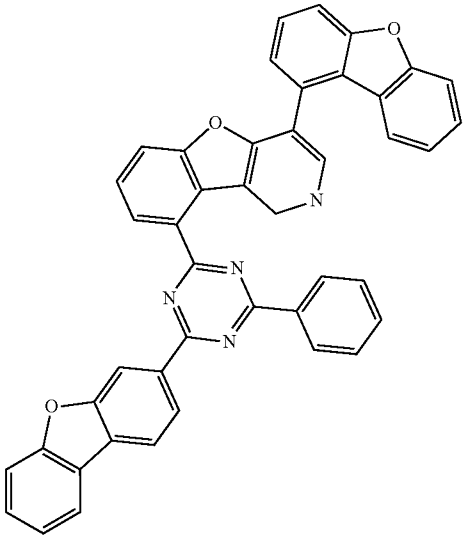
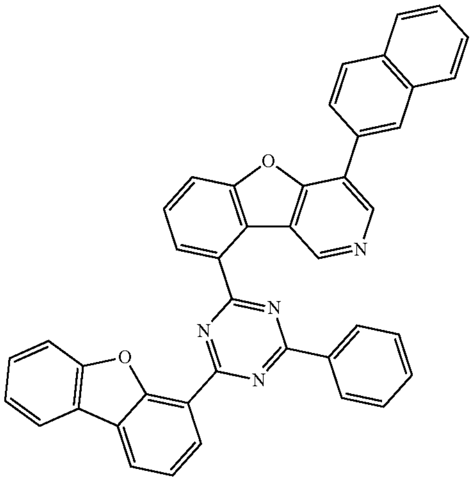
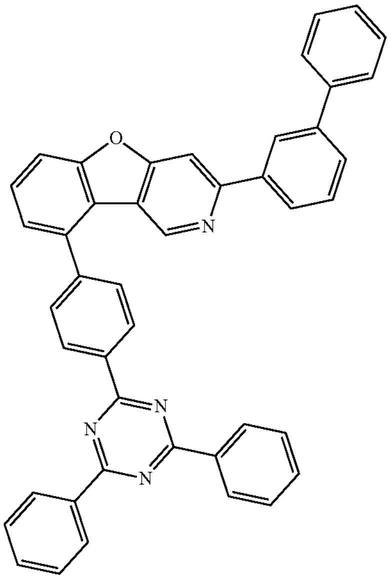
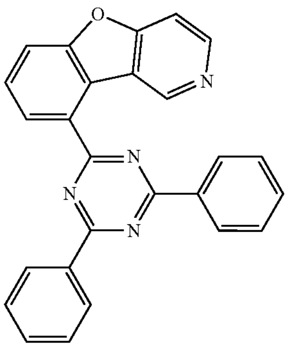
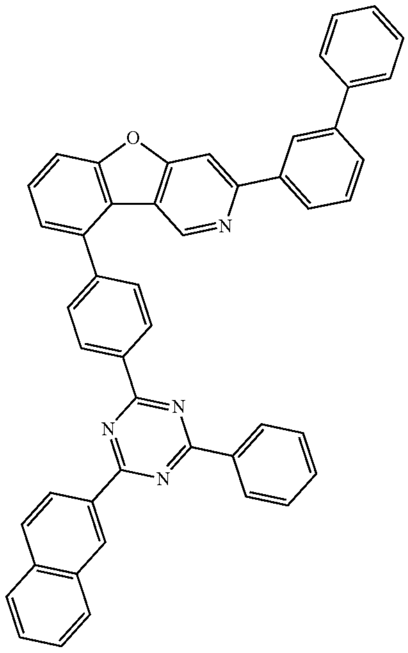
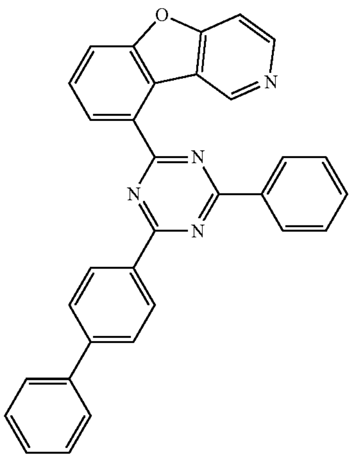

-continued
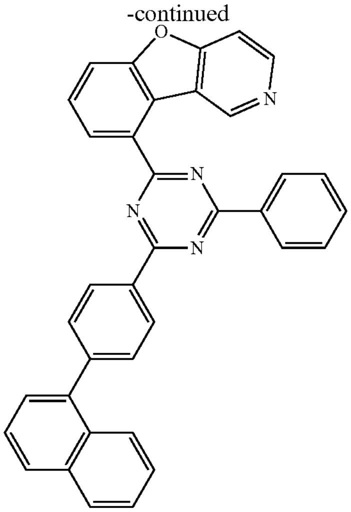
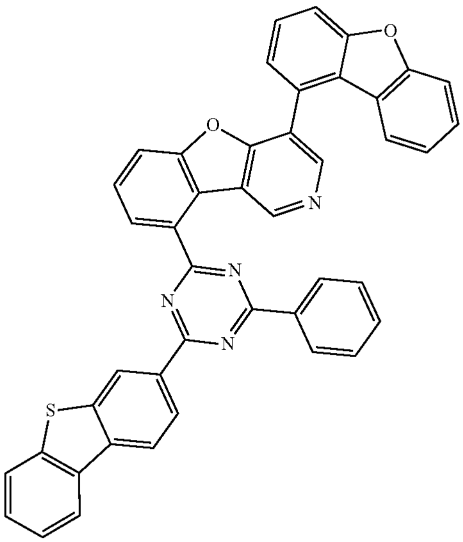
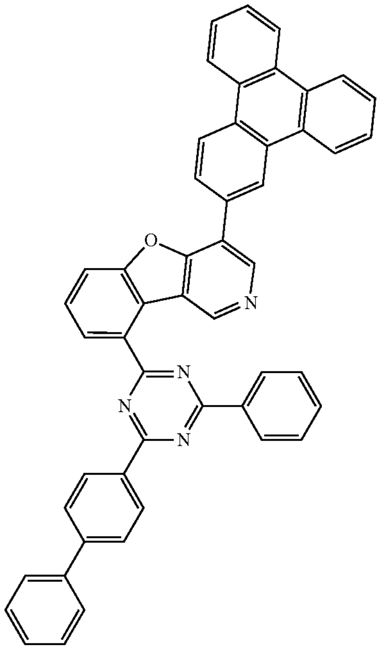
-continued
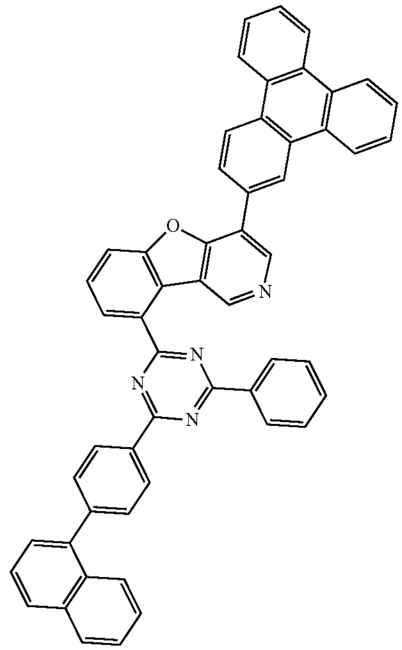
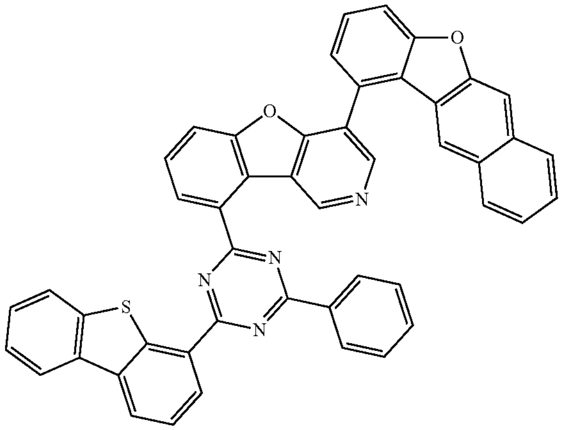
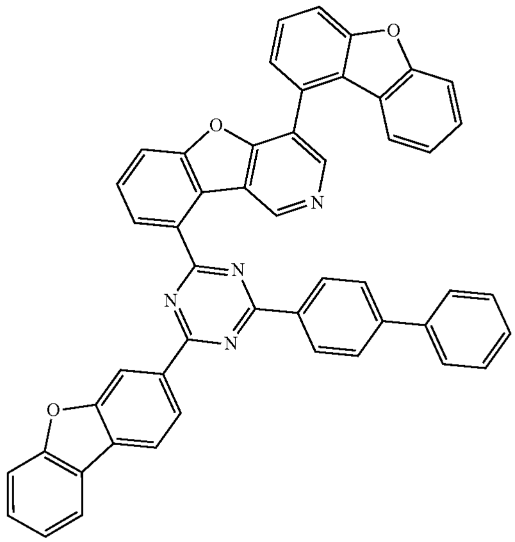

-continued
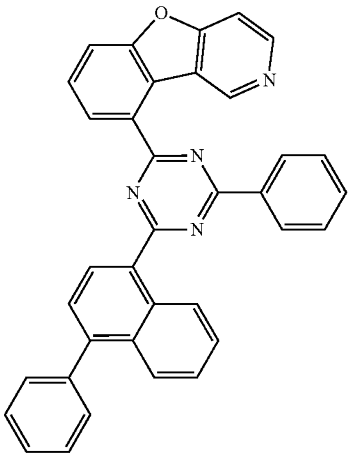
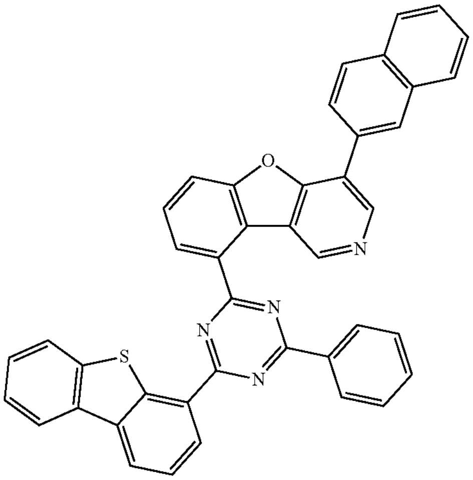
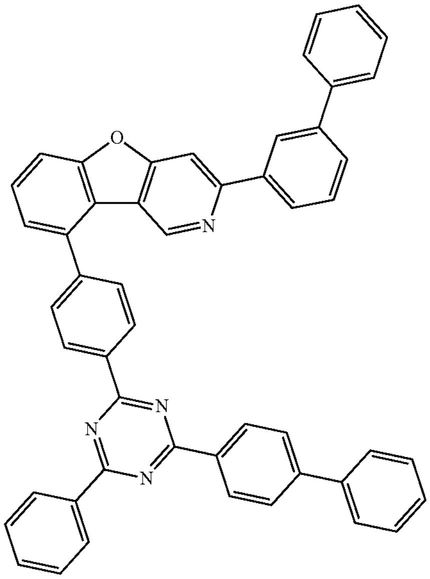
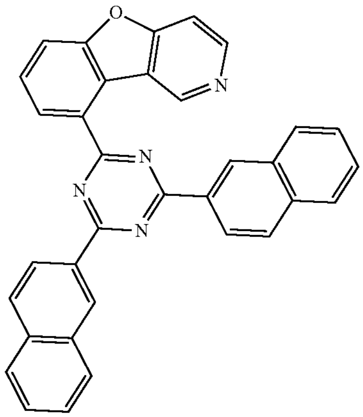
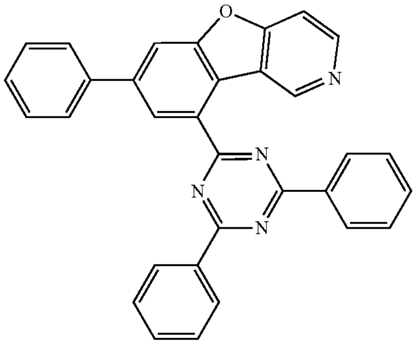
-continued
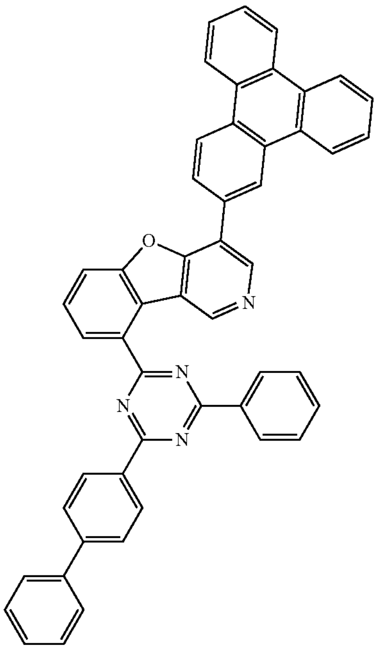

-continued
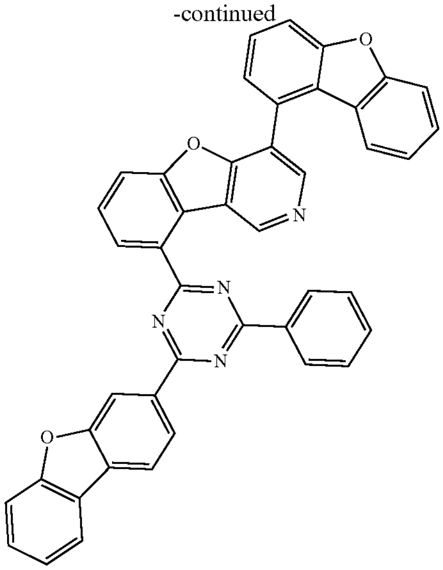
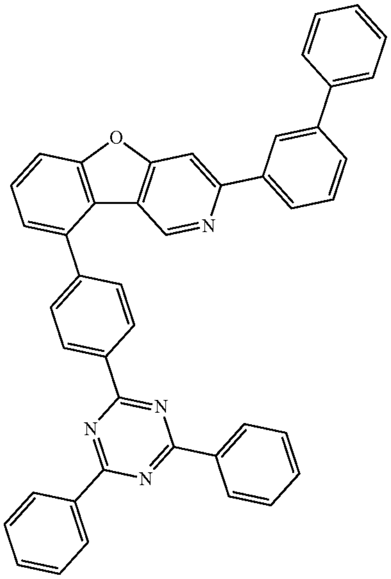
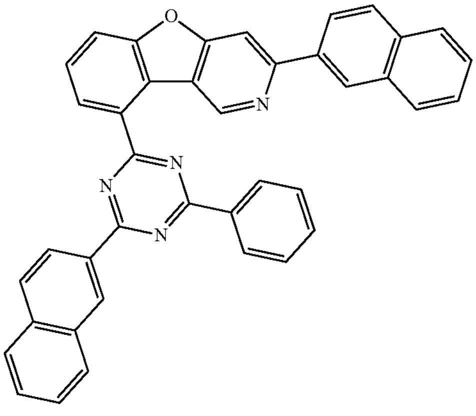
-continued
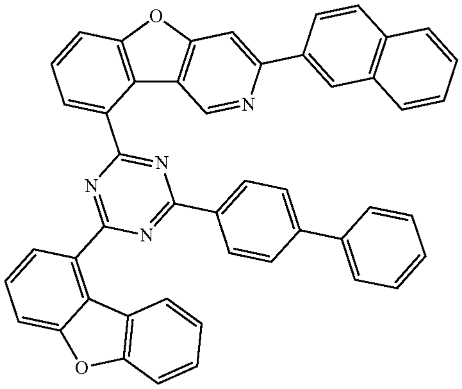
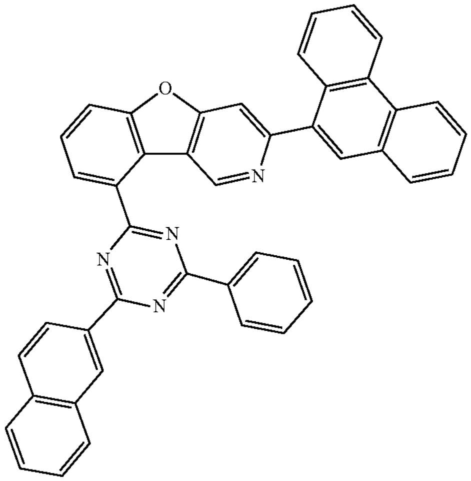
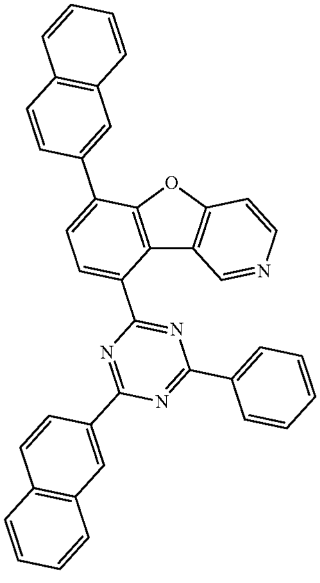

-continued
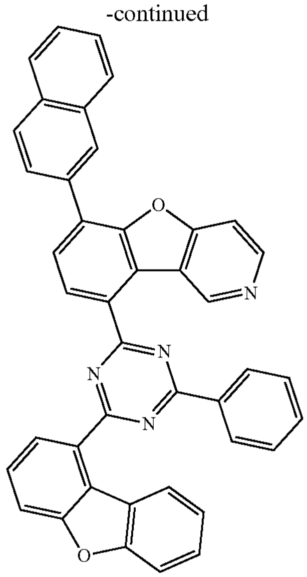
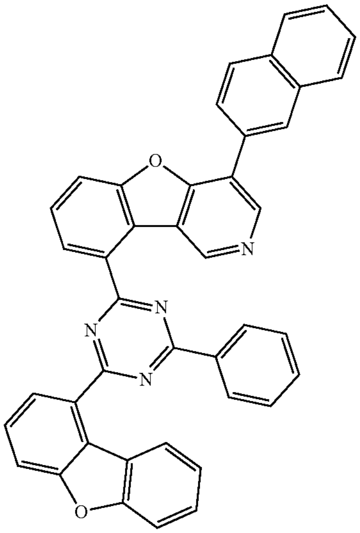
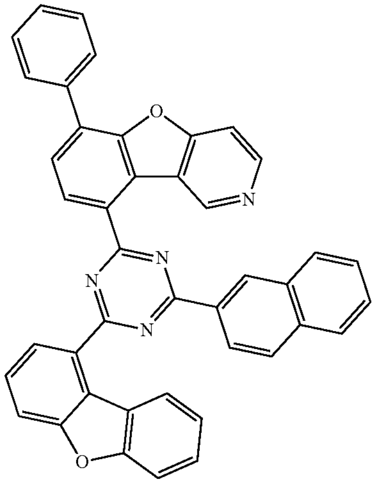
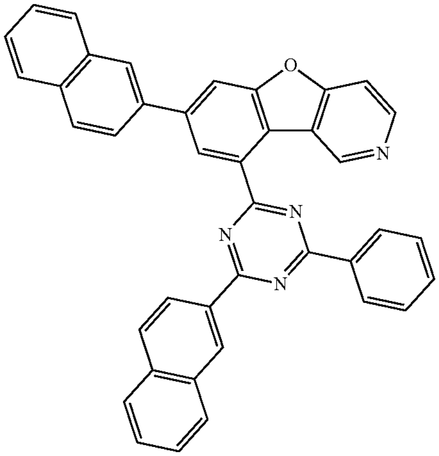
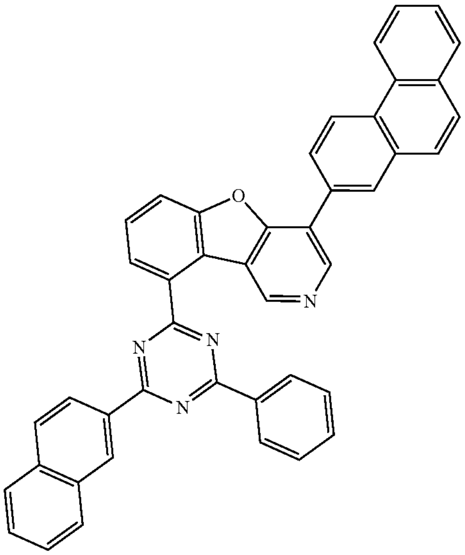
-continued
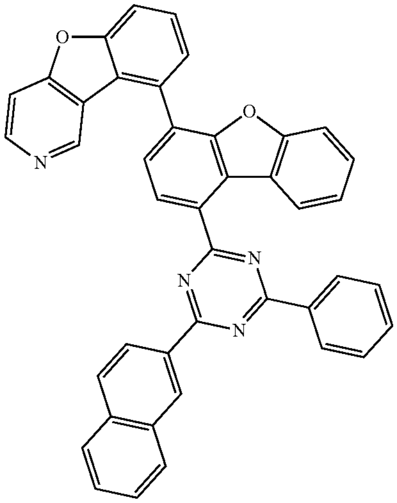

-continued
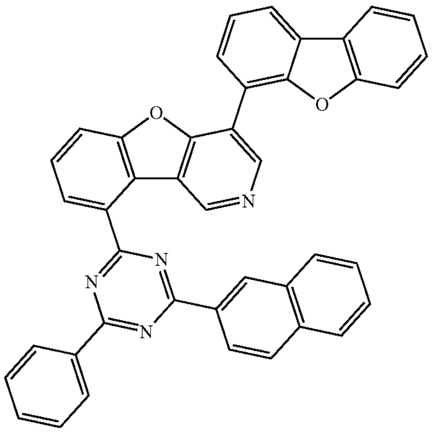
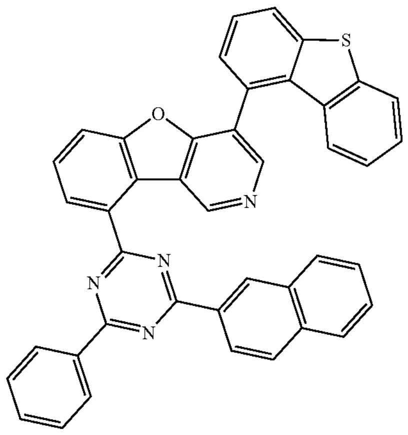
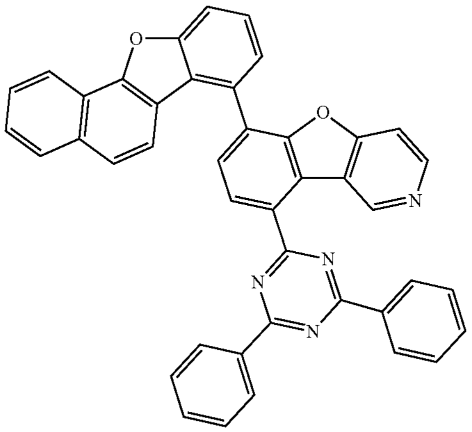
-continued
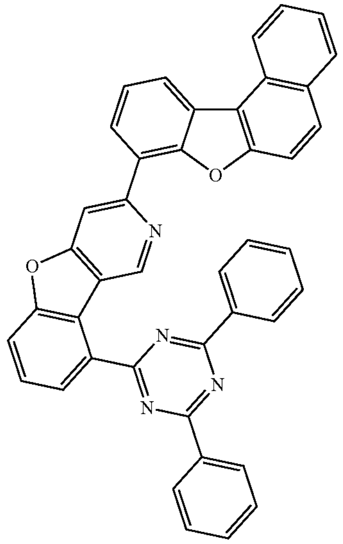
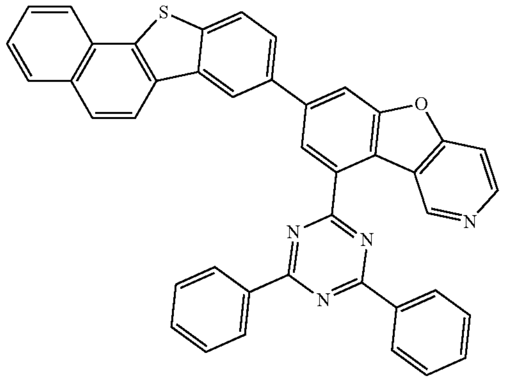
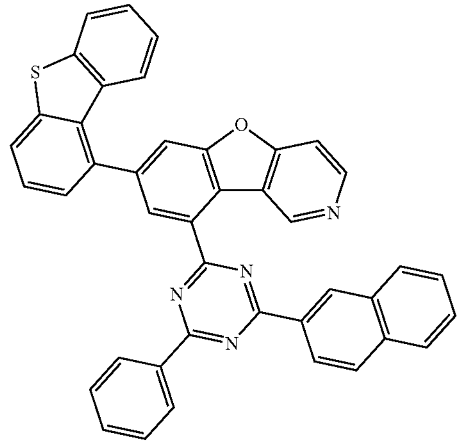
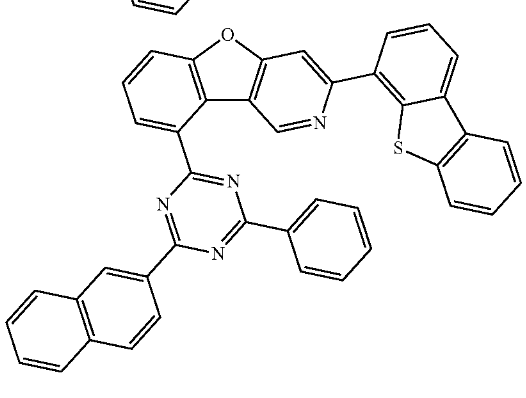

-continued
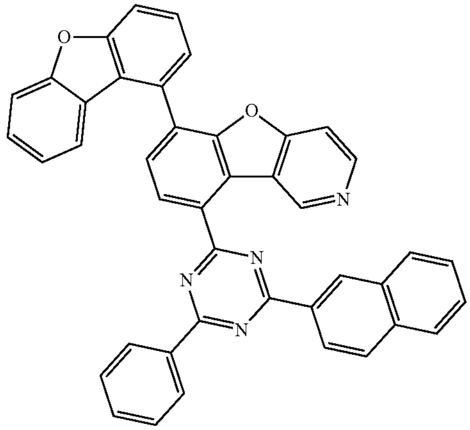
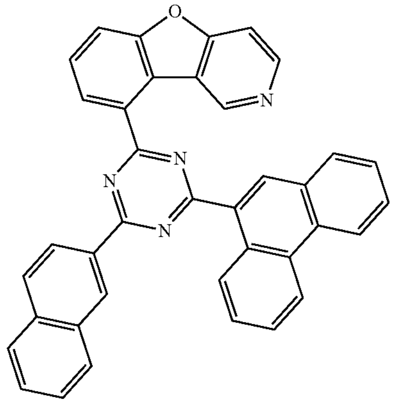
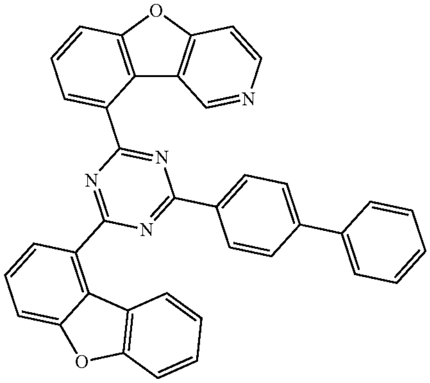
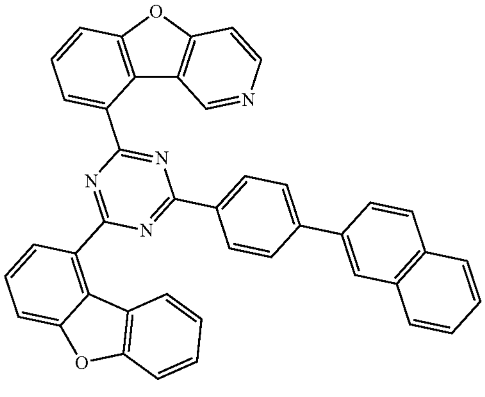
-continued
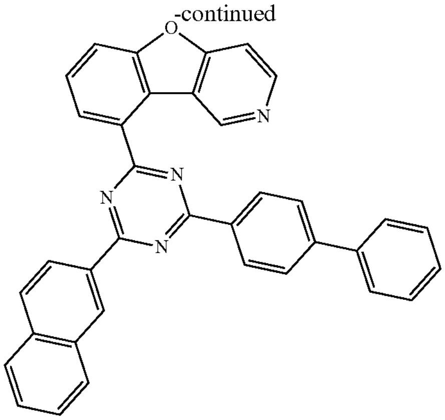
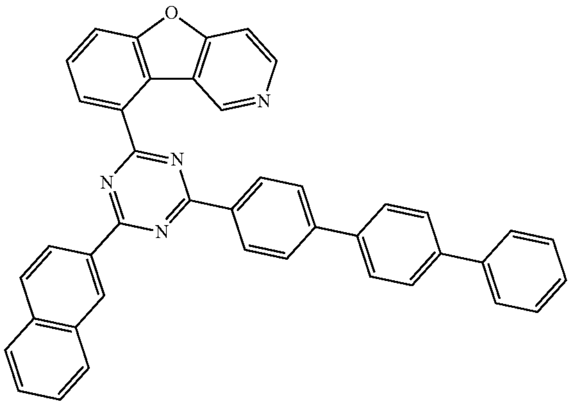
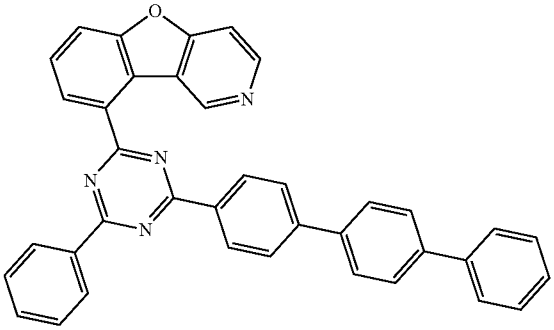
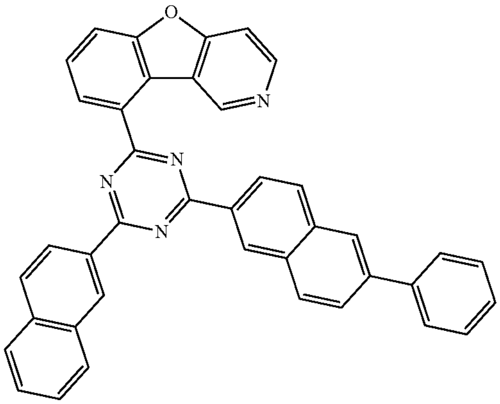

-continued
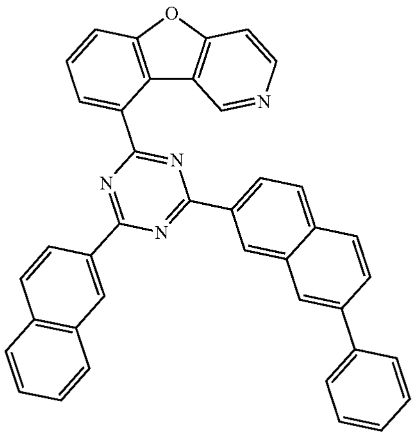
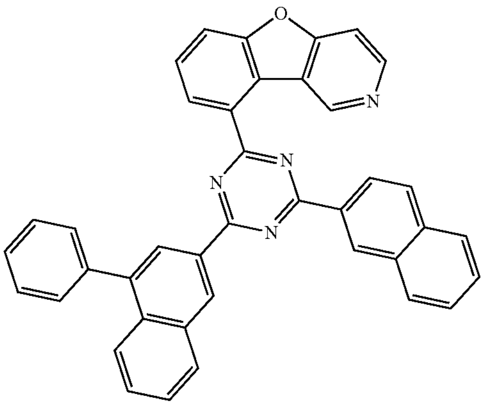
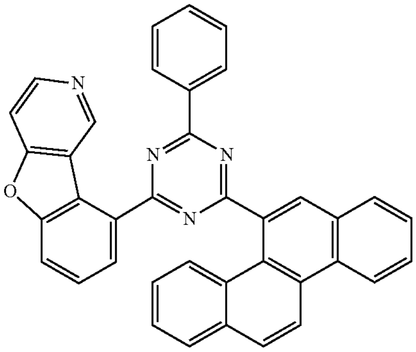
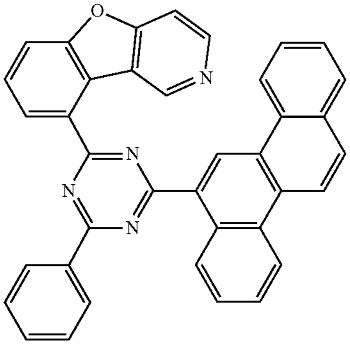
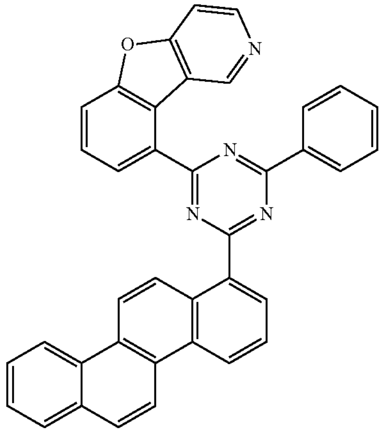
-continued
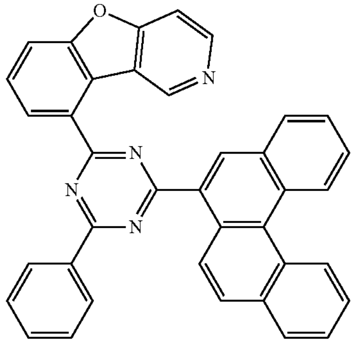
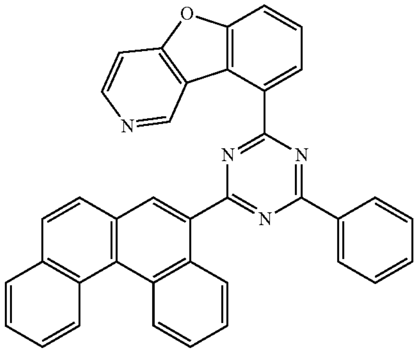
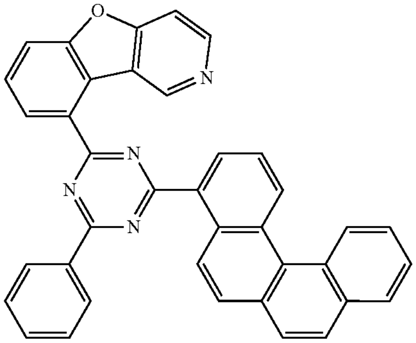

-continued
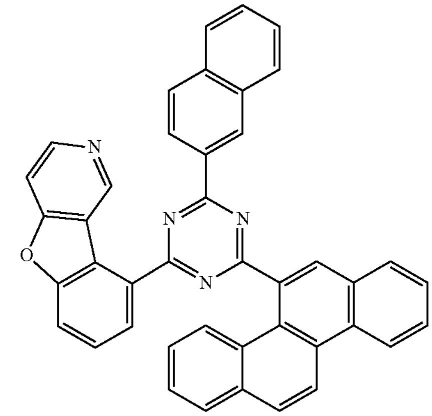
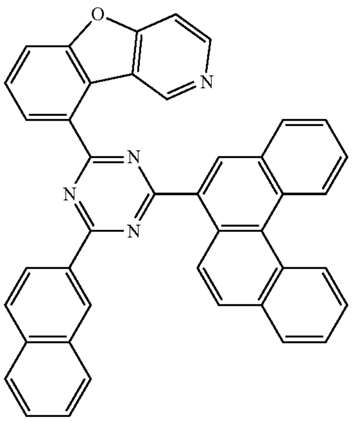
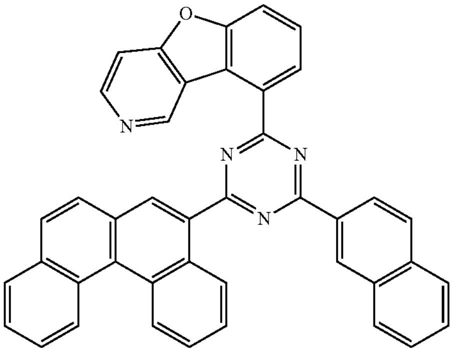
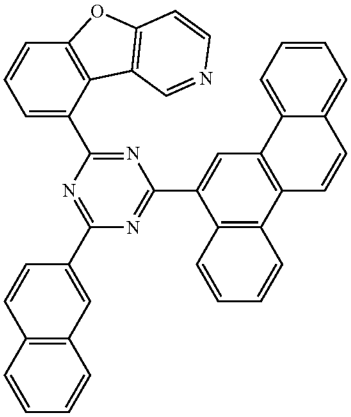
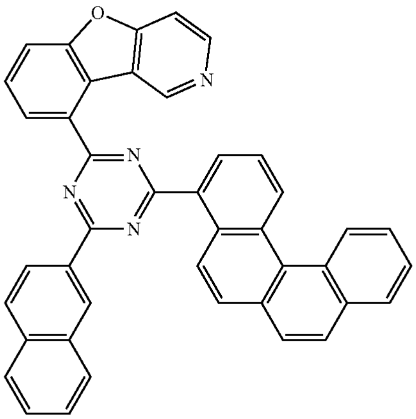
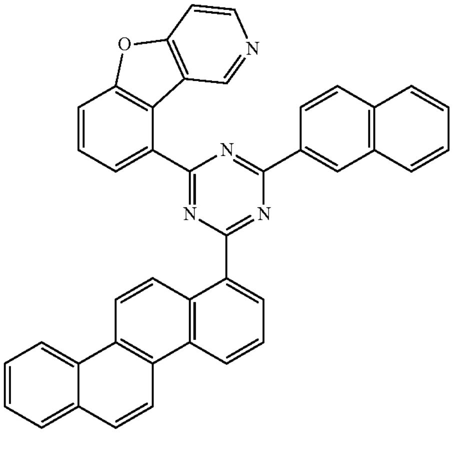
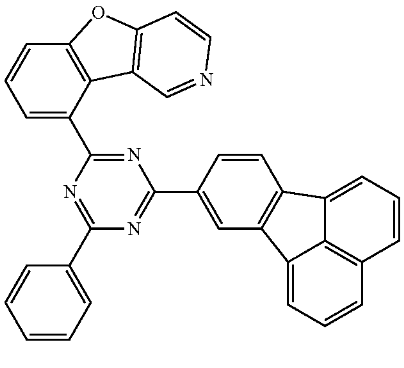

-continued
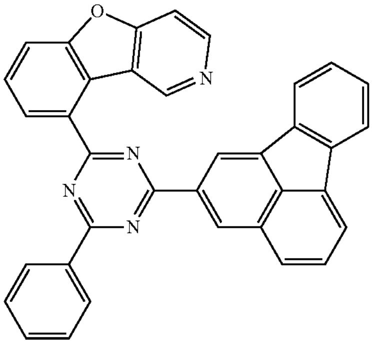
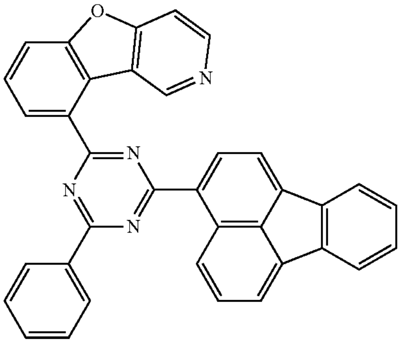
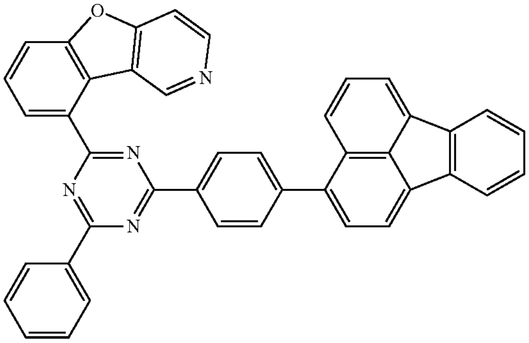
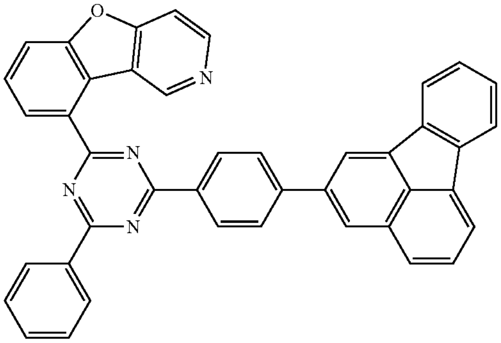
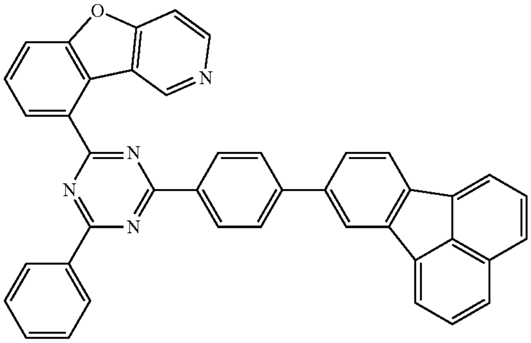
-continued
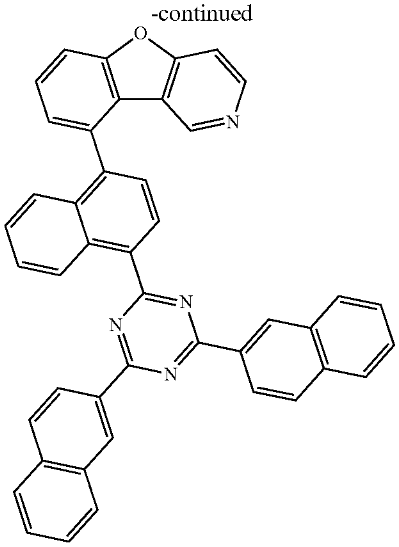
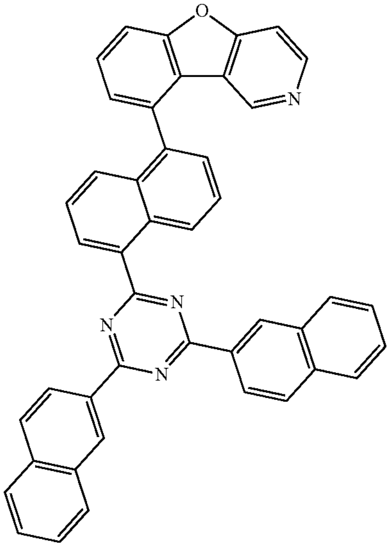
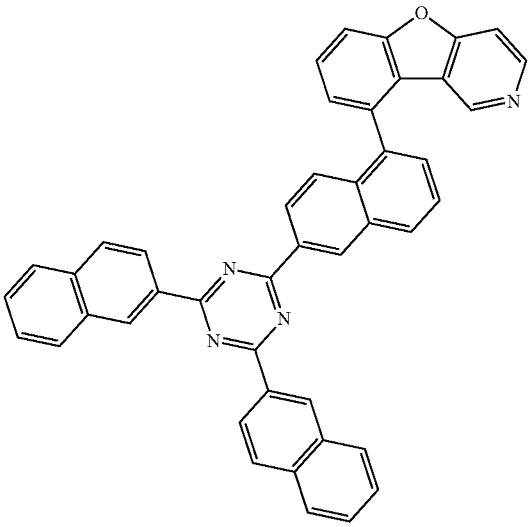

-continued
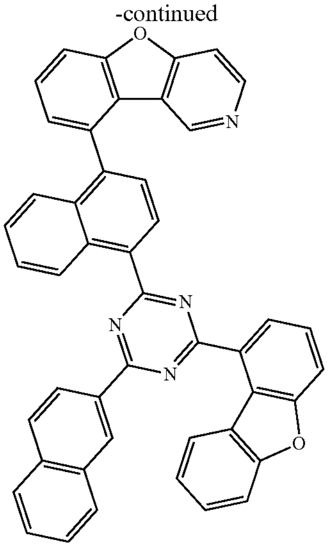
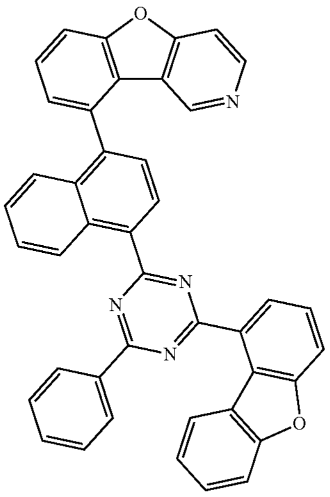
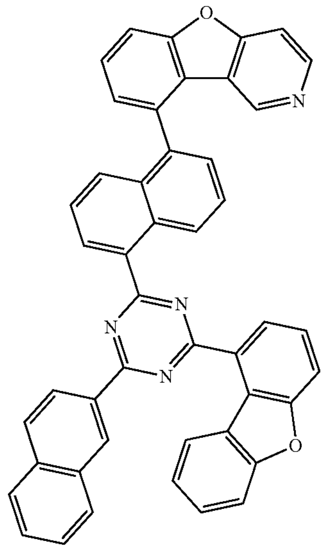
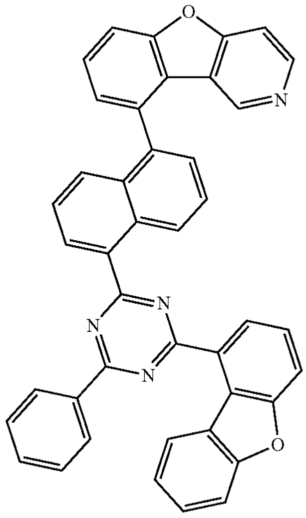
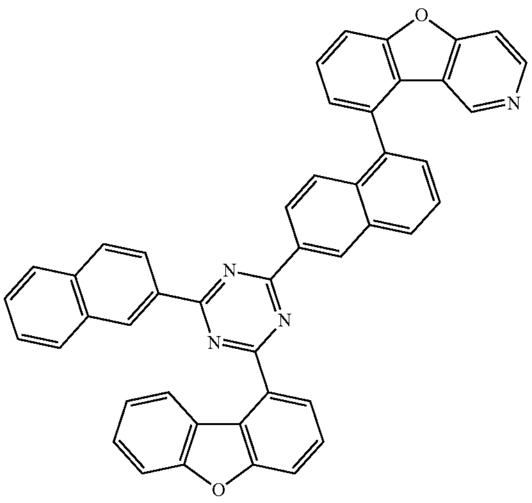
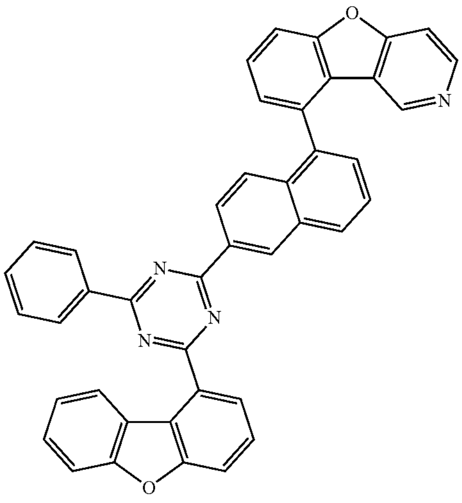
-continued -continued
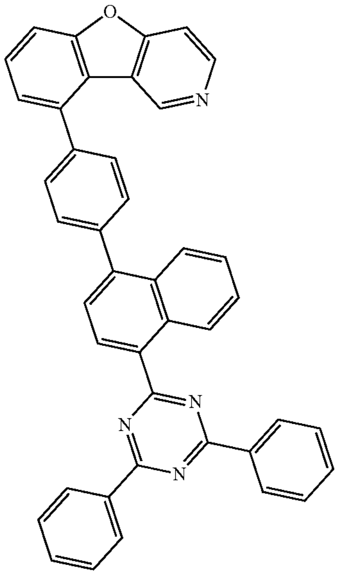
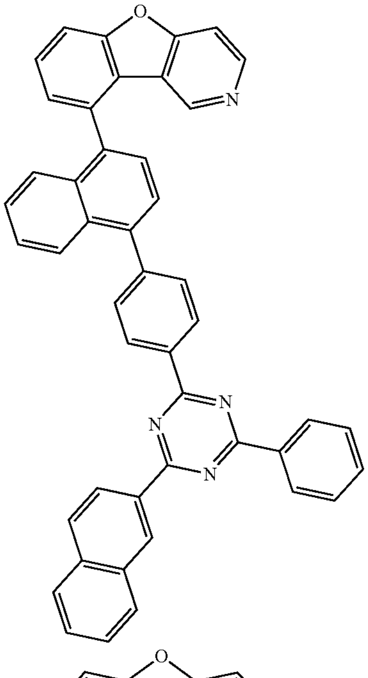
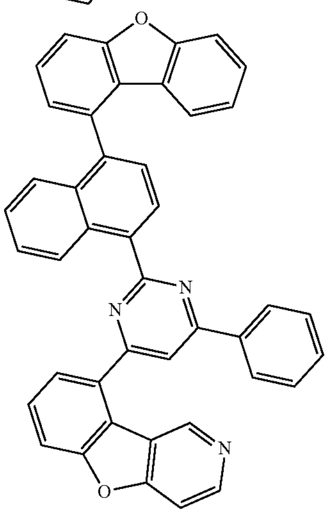
-continued
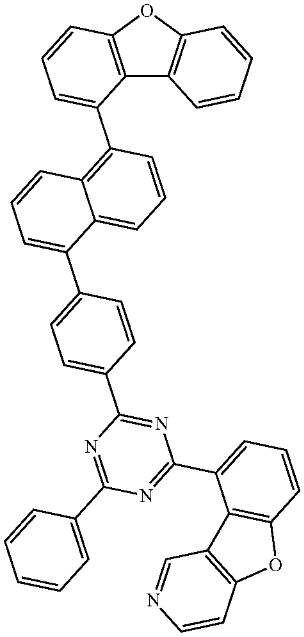
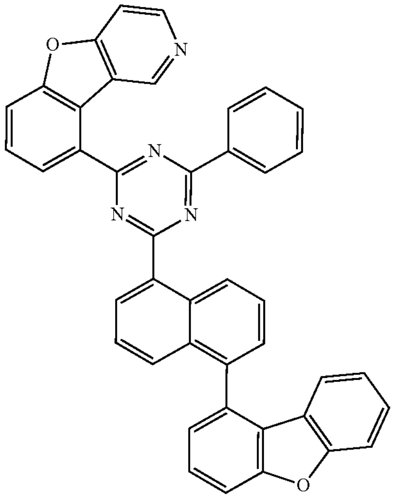
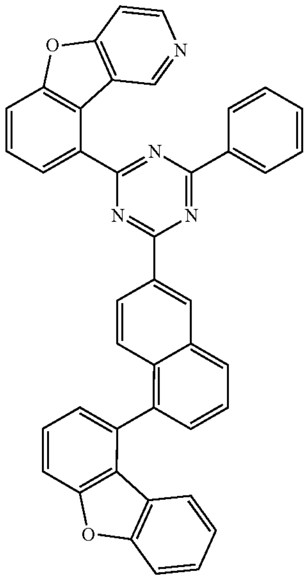

-continued
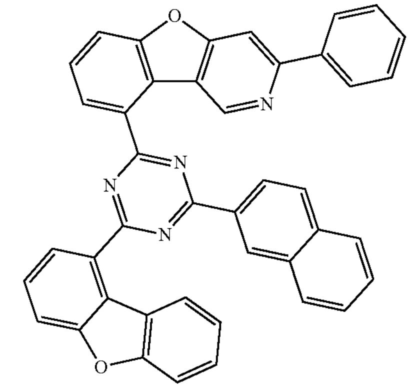
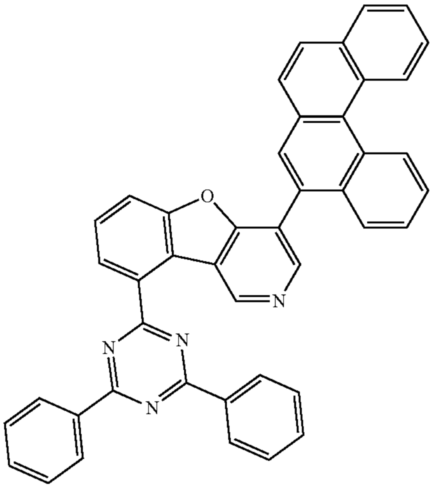
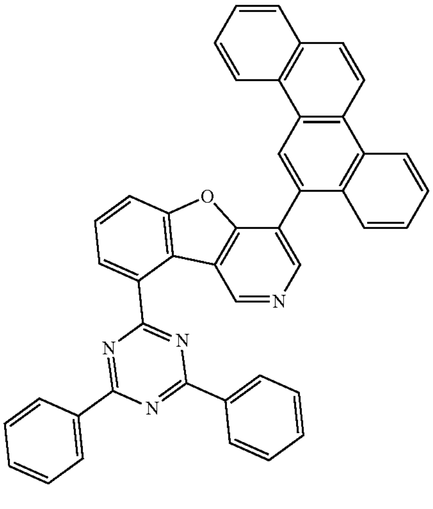
-continued
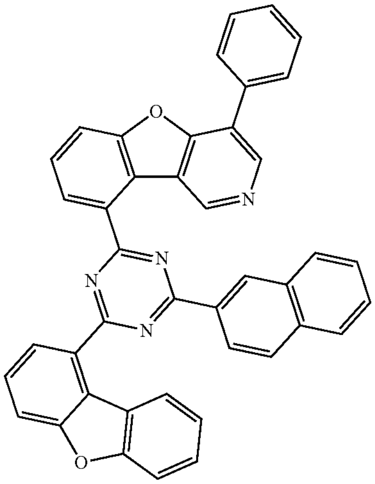
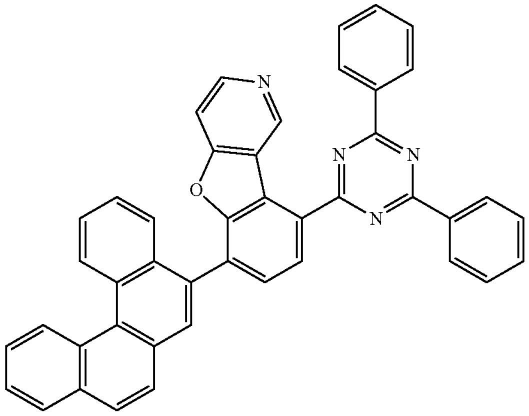
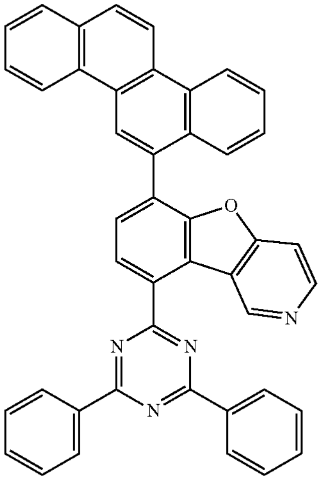

-continued
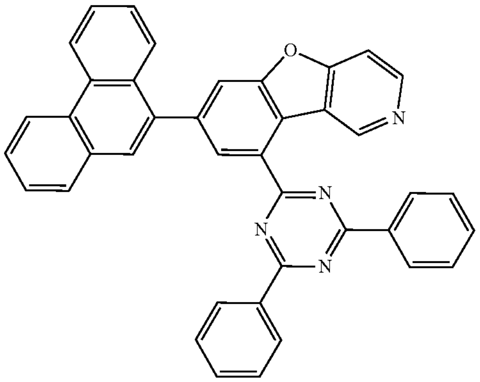
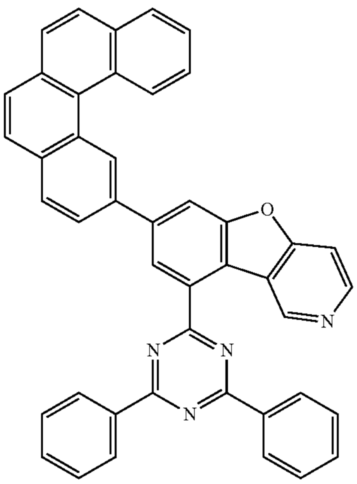
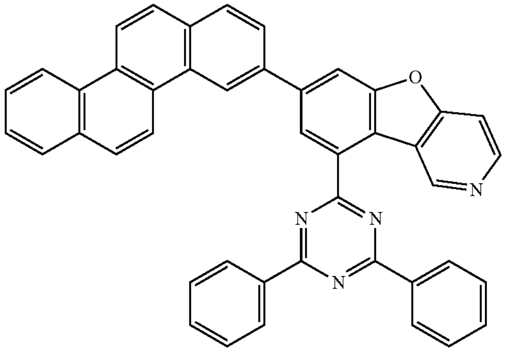
-continued
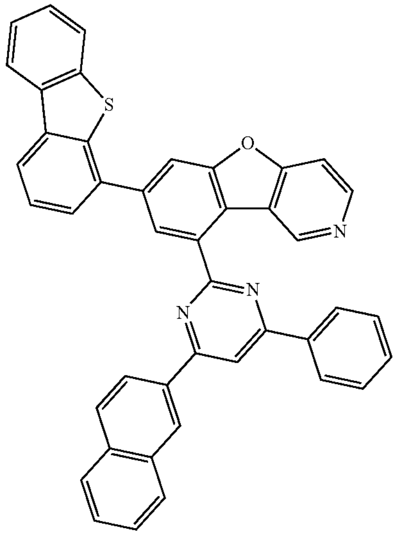
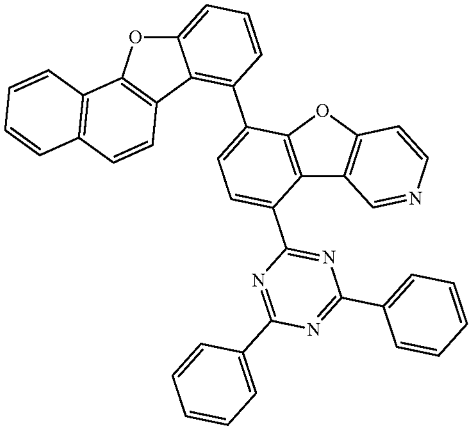
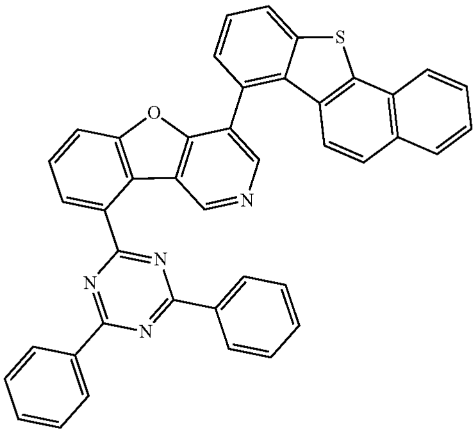

-continued
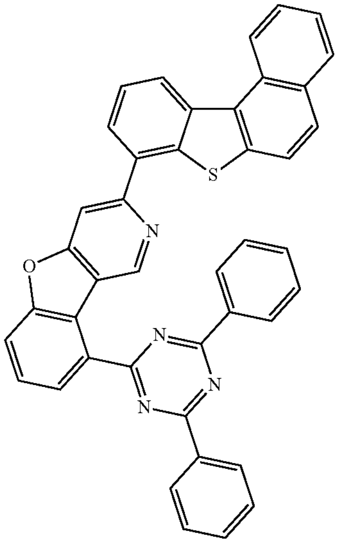
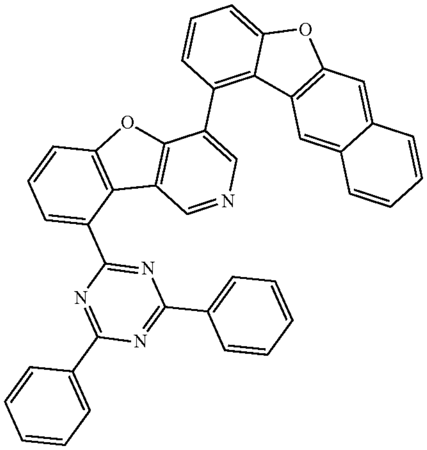
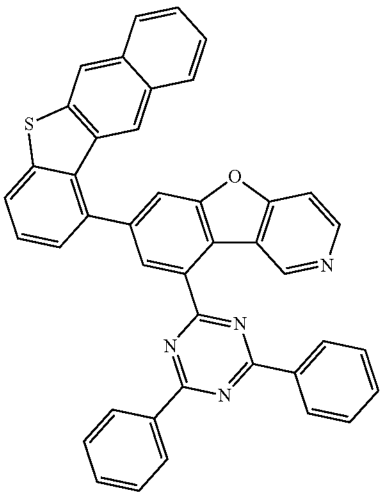
-continued
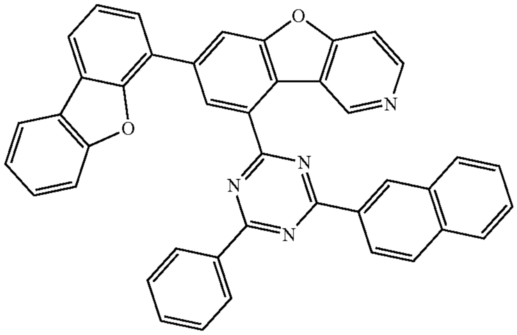
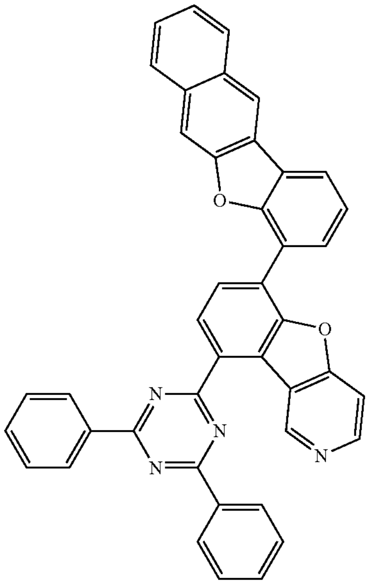
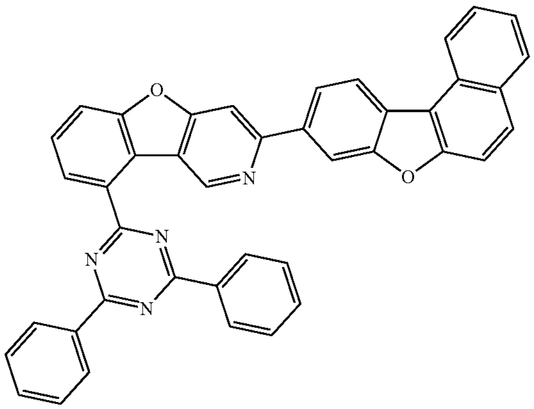
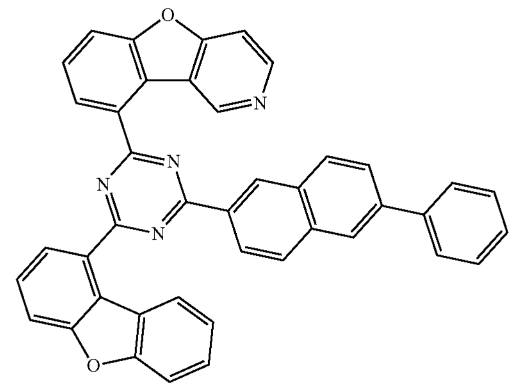

-continued
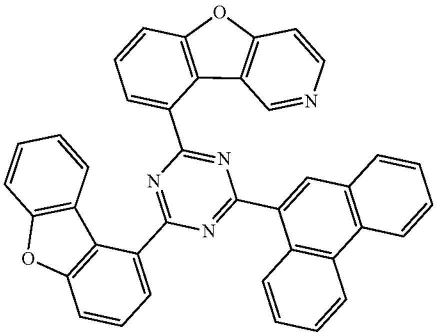
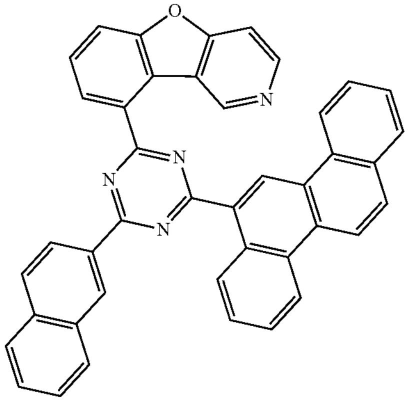
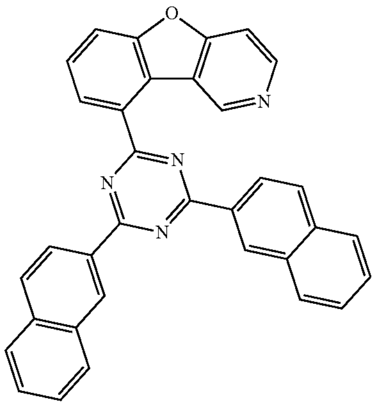
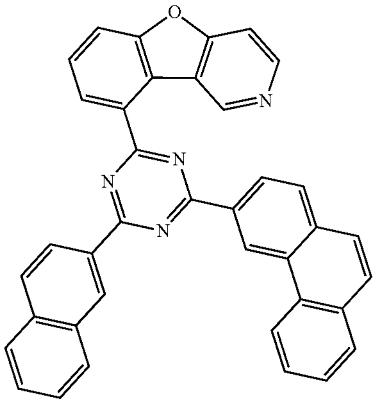
-continued
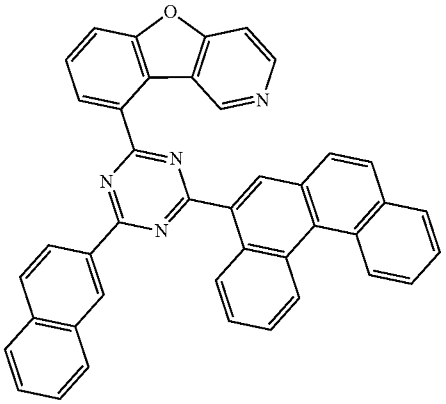
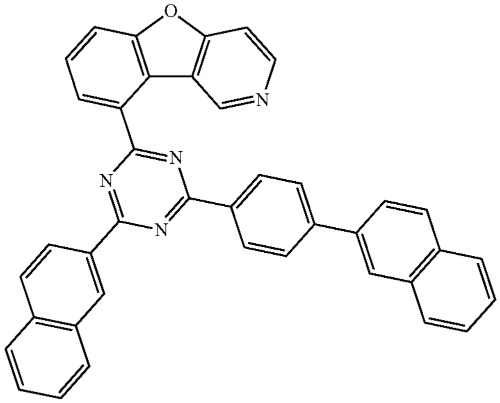
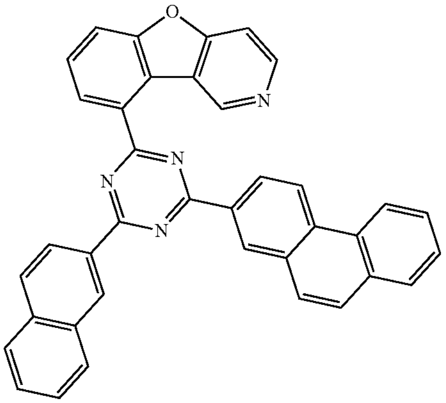
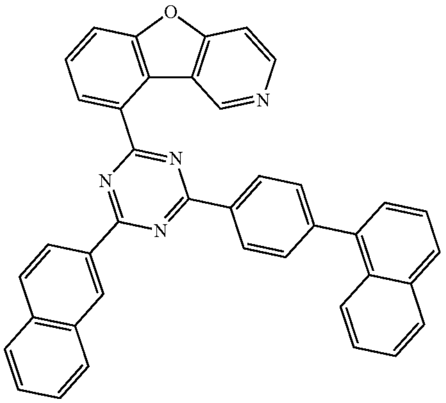

-continued
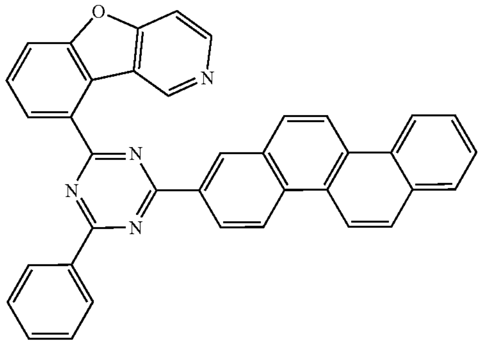
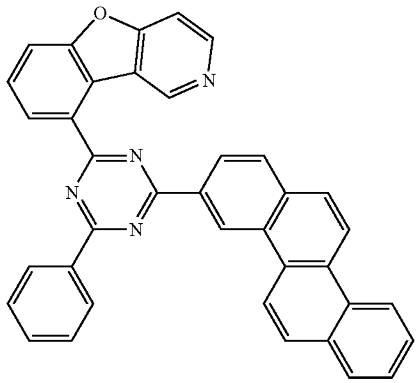
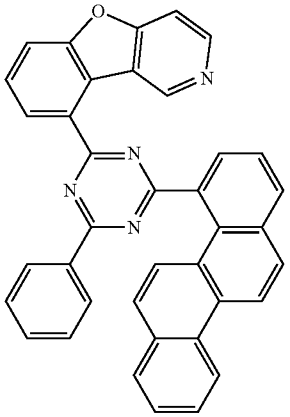
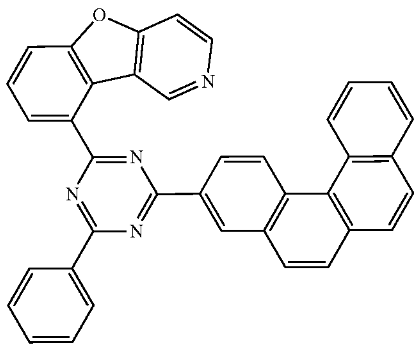
-continued
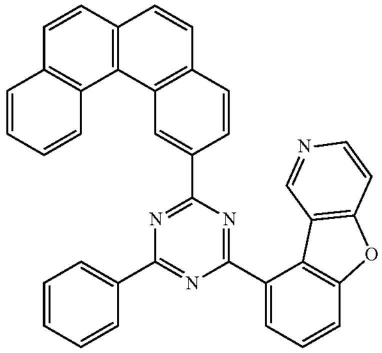
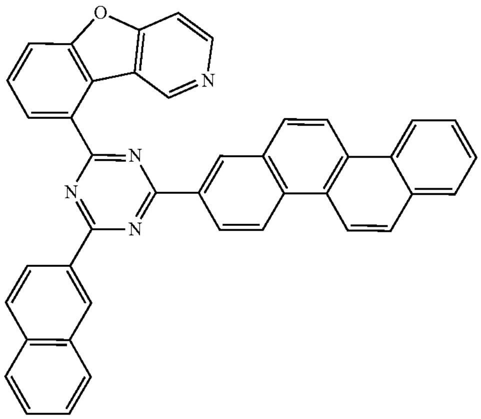
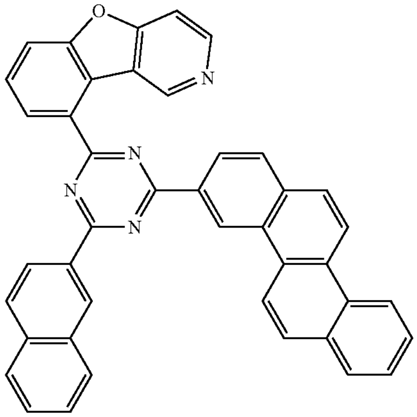
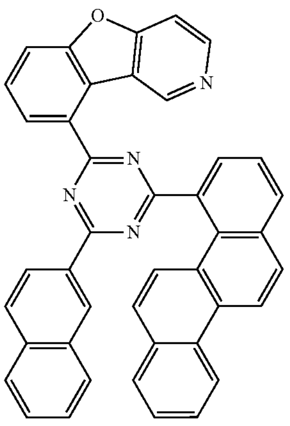

-continued
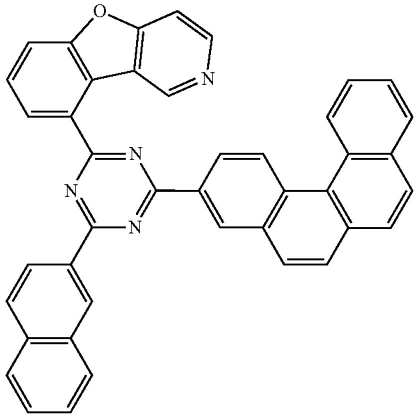
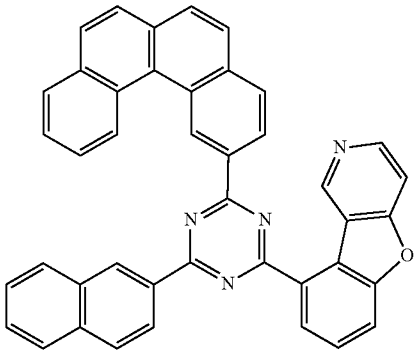
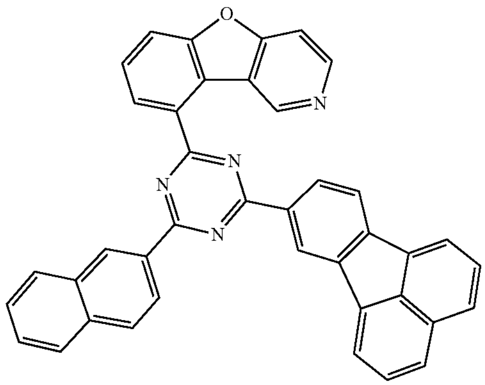
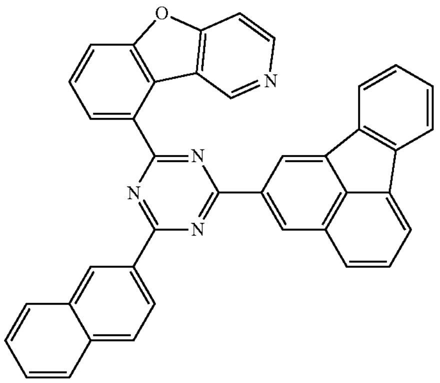
-continued
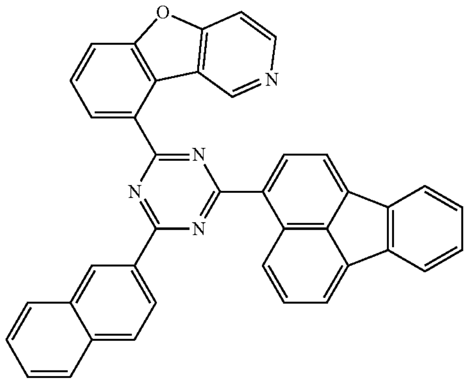
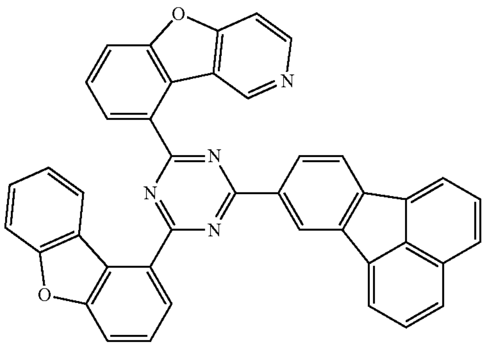
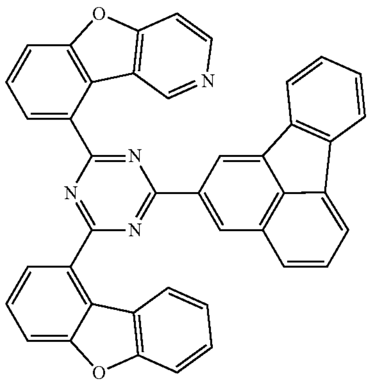
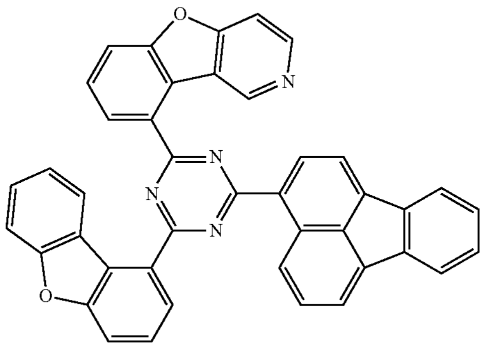

-continued
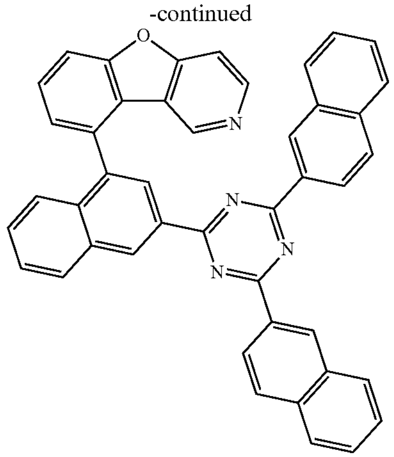
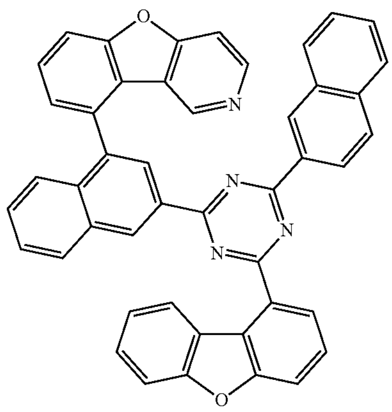
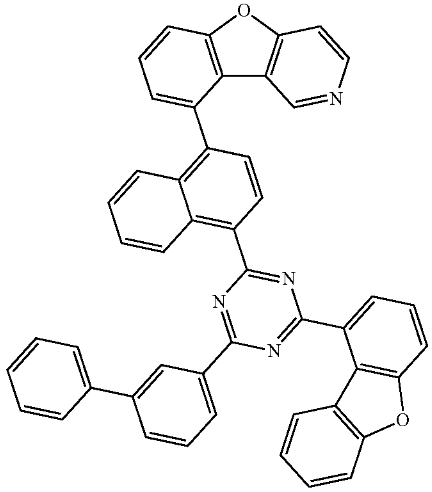
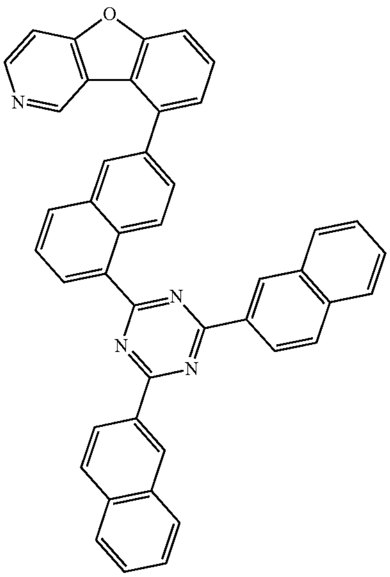
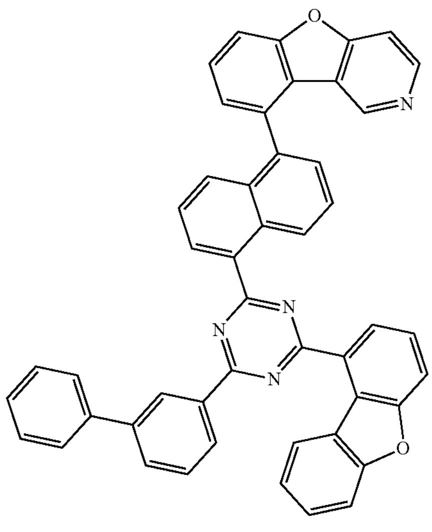
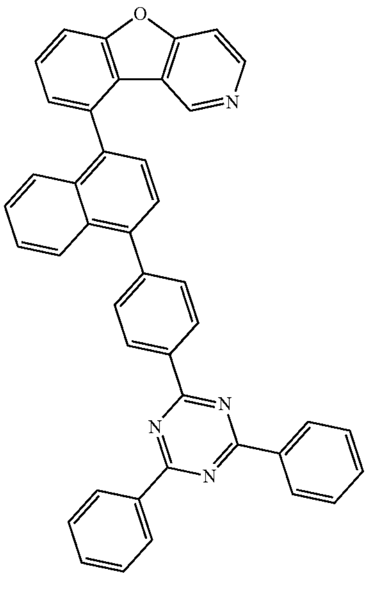

-continued
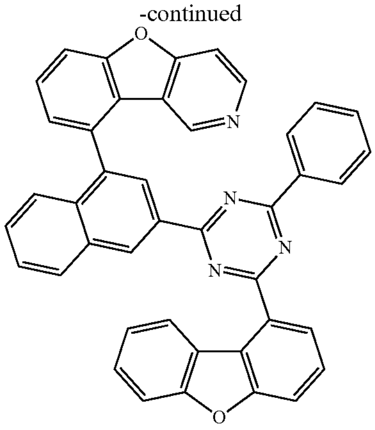
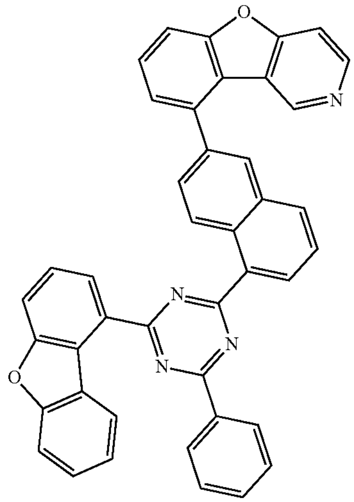
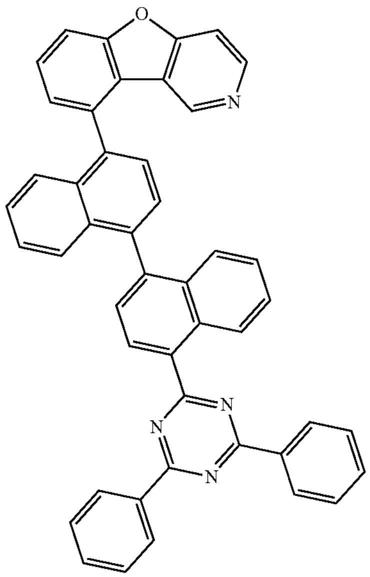
-continued
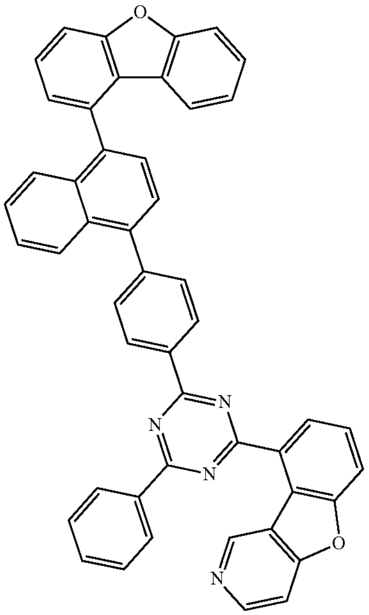
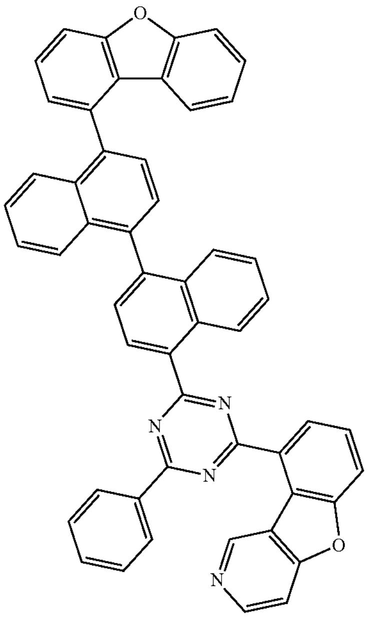

-continued
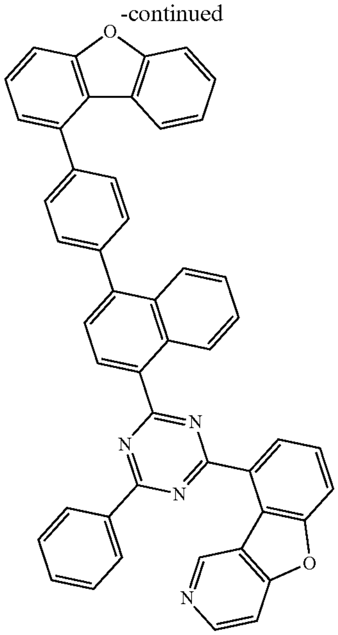
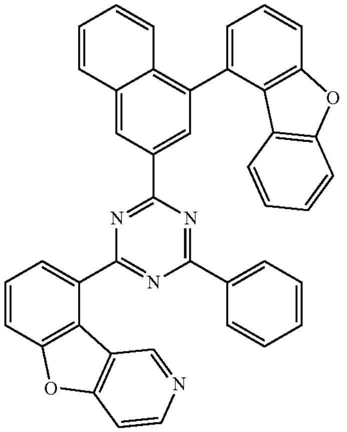
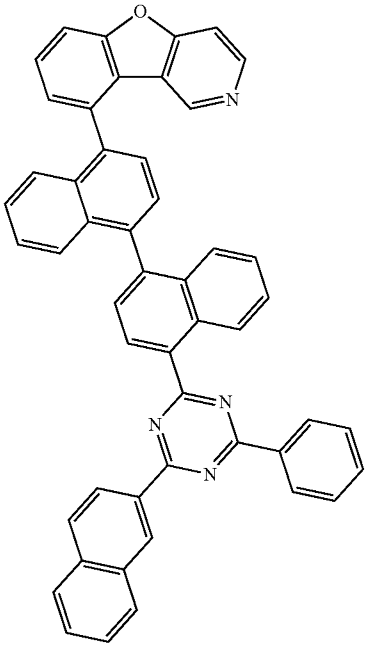
-continued
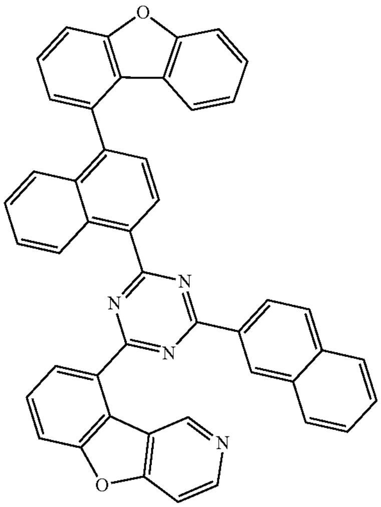
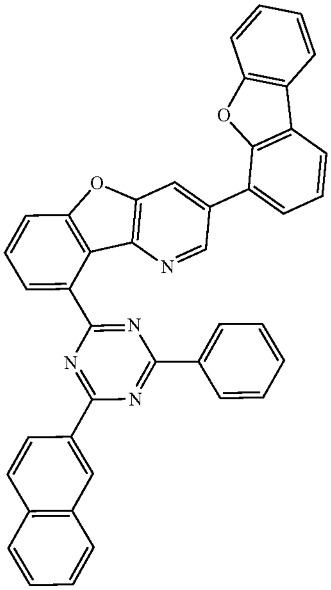
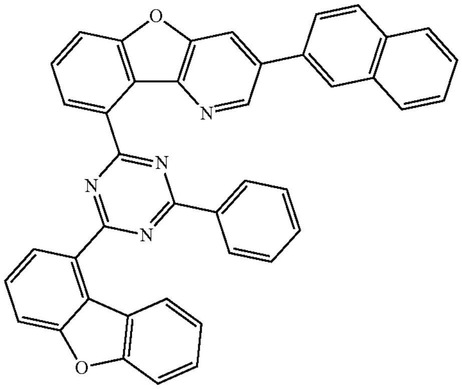

-continued
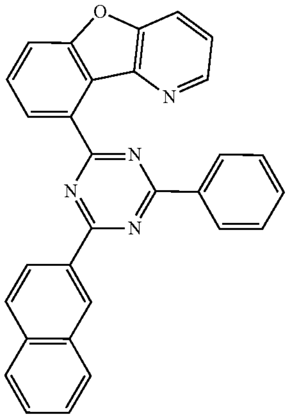
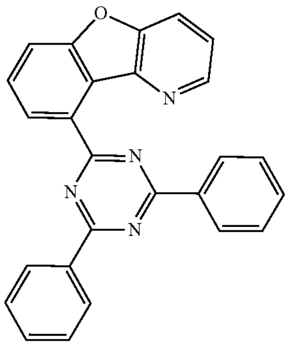
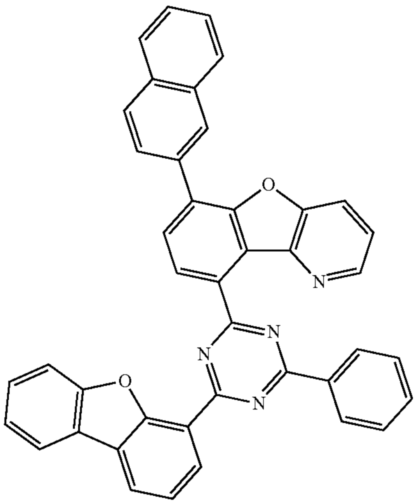
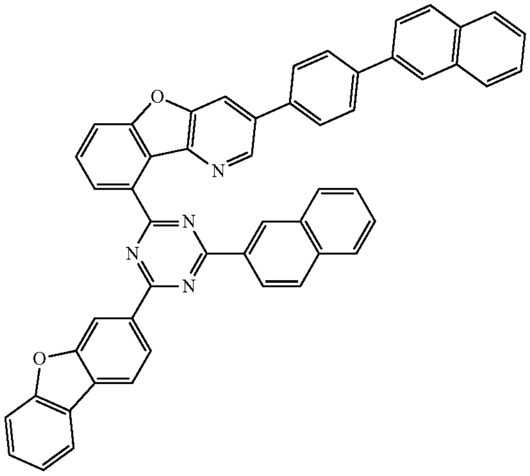
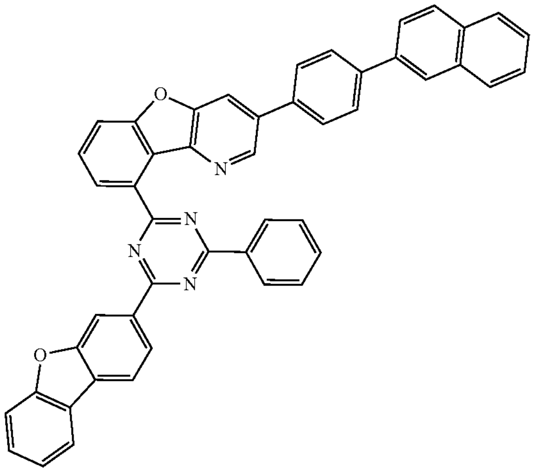
-continued
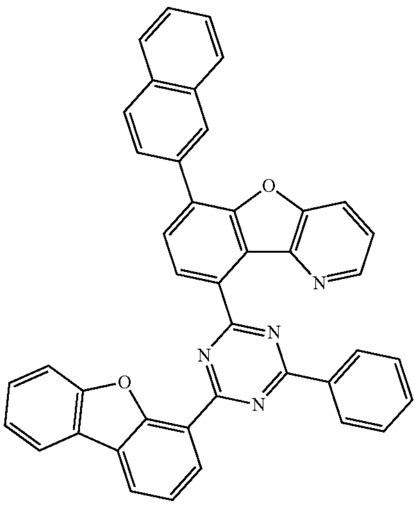

-continued
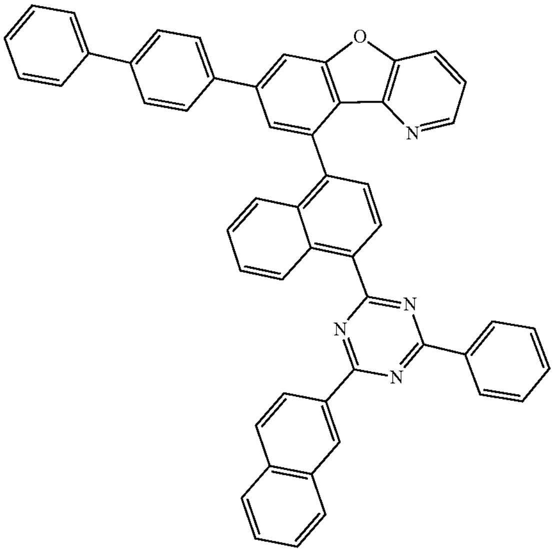
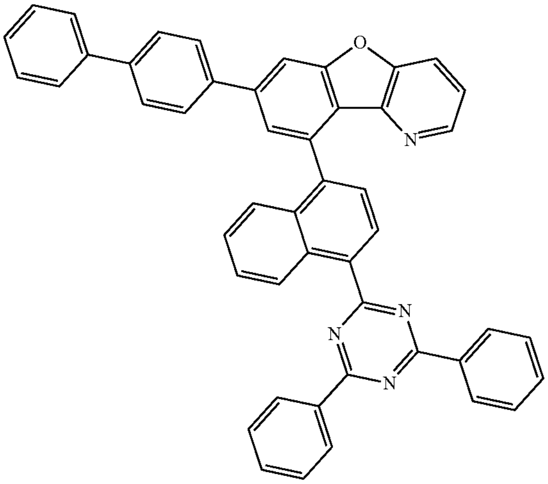
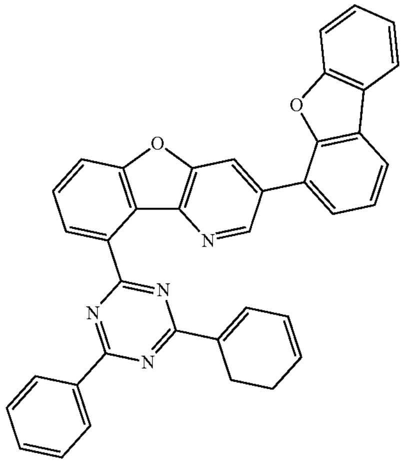
-continued
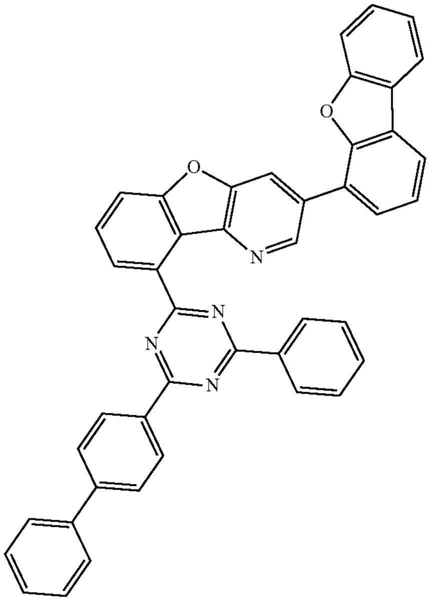
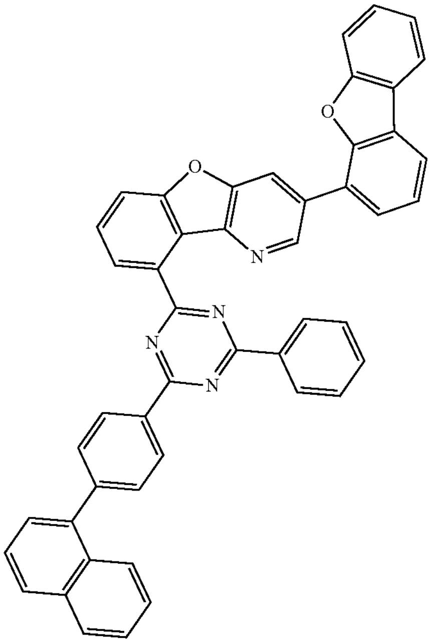
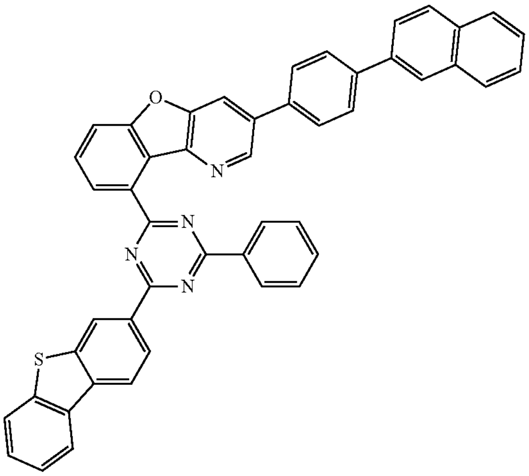

-continued
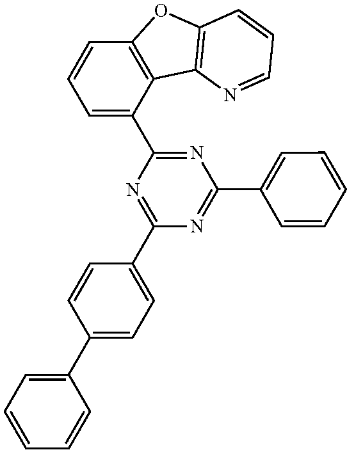
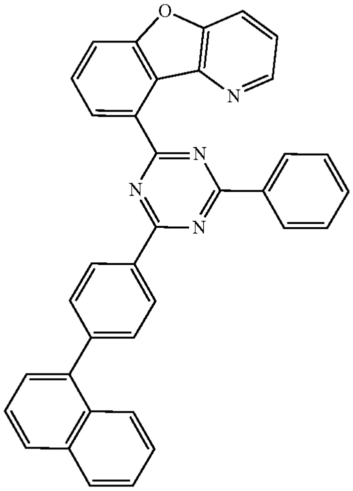
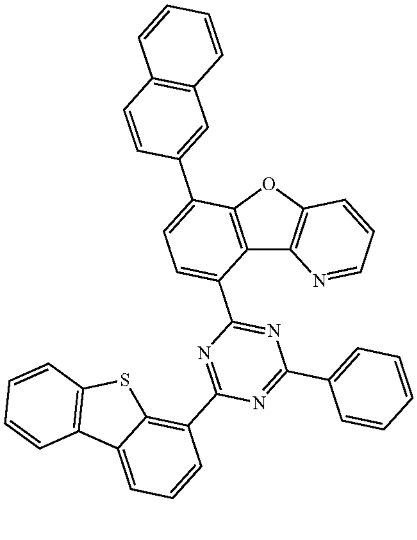
-continued
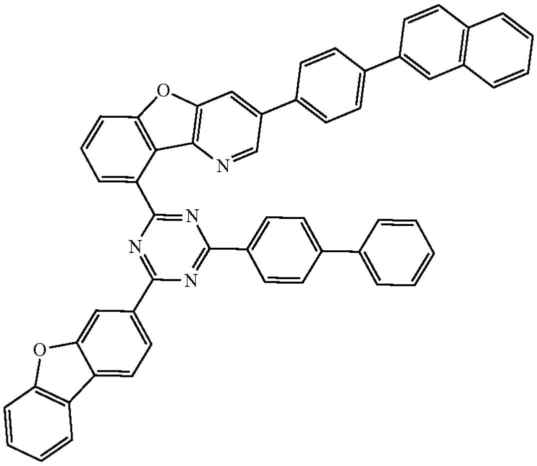
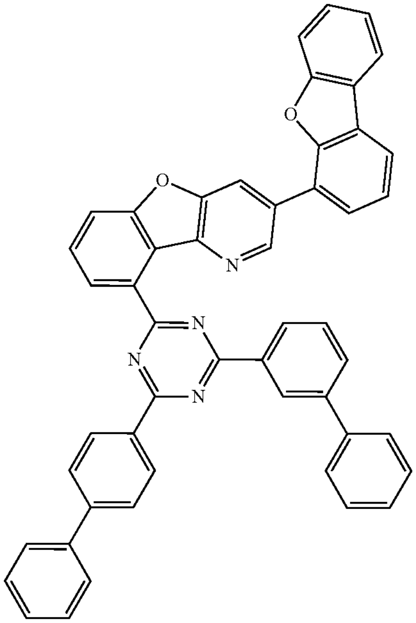
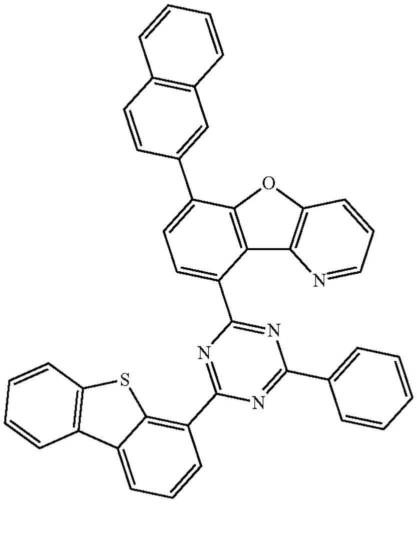

-continued
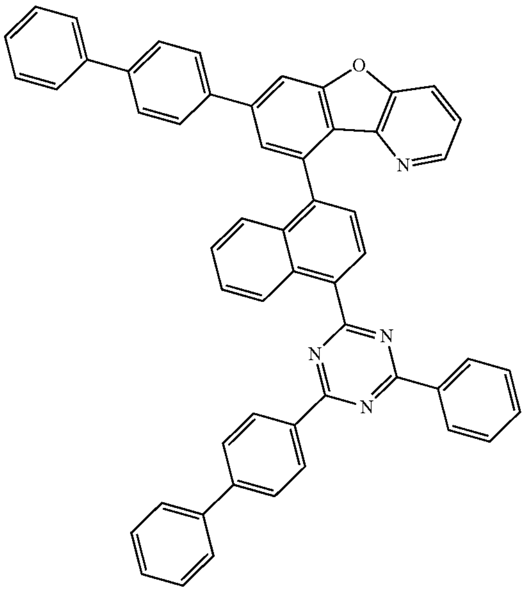
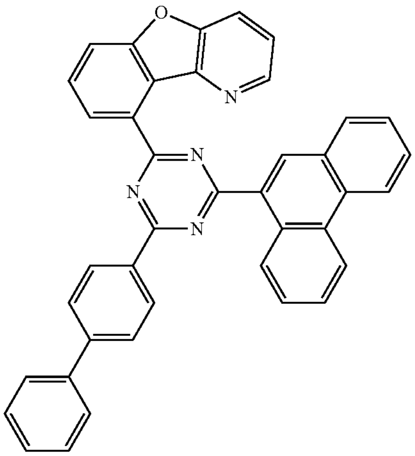
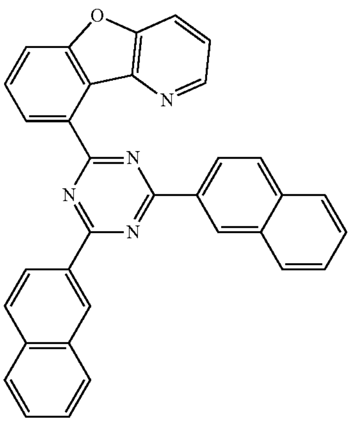
-continued
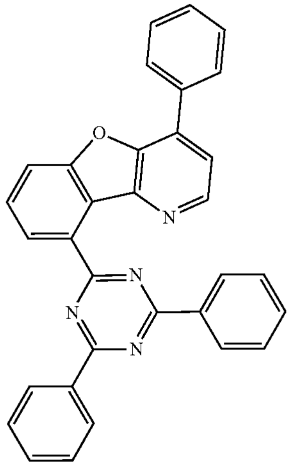
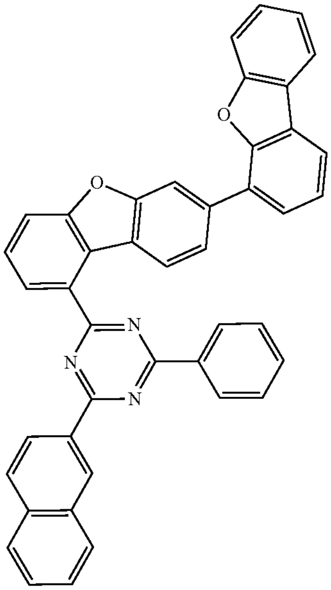
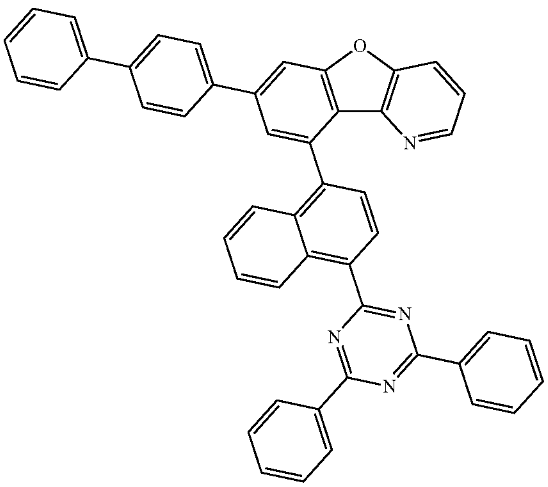

-continued
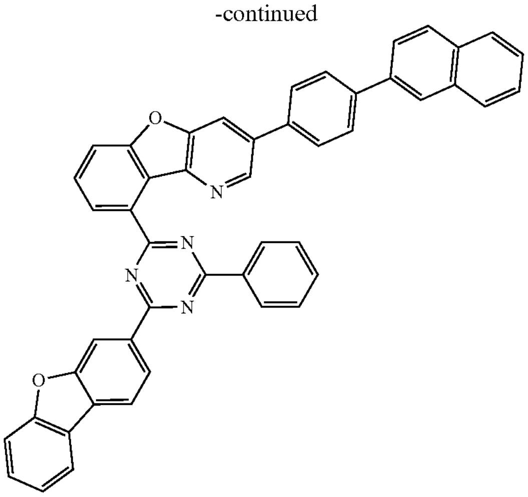
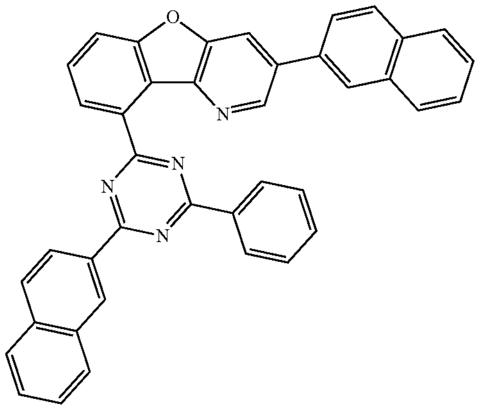
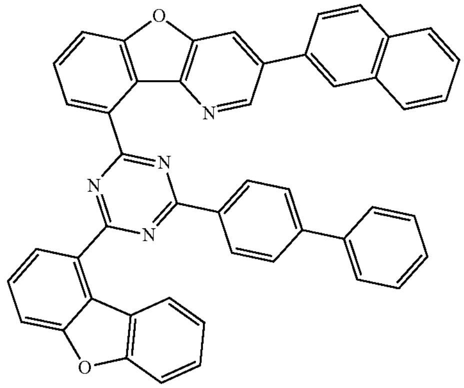
-continued
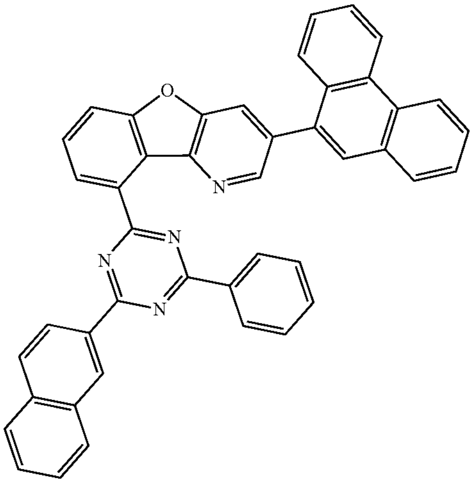
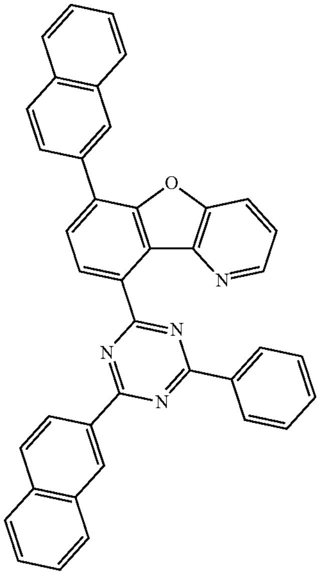
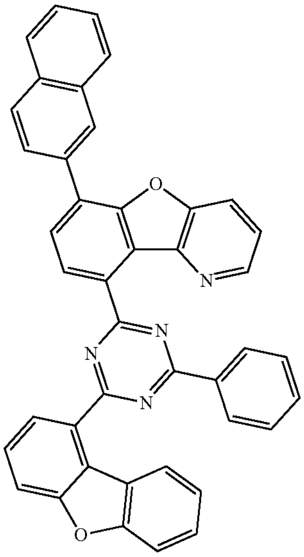

-continued
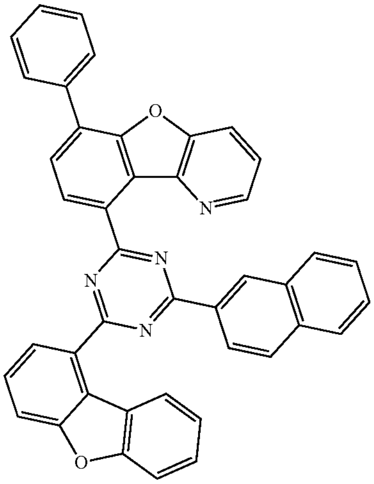
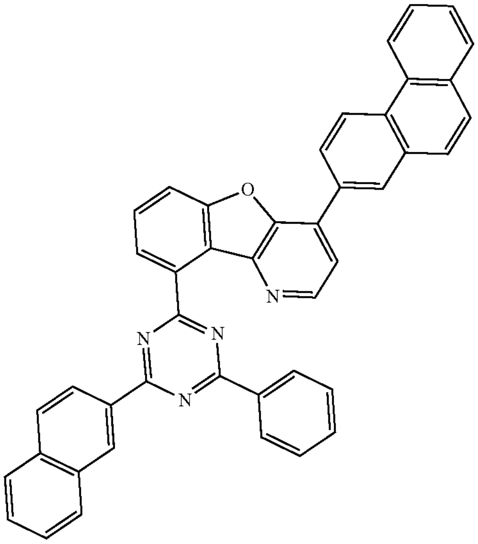
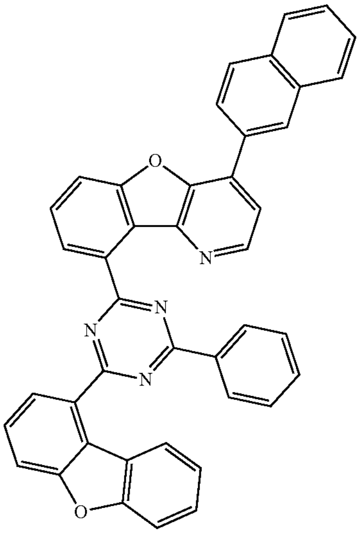
-continued
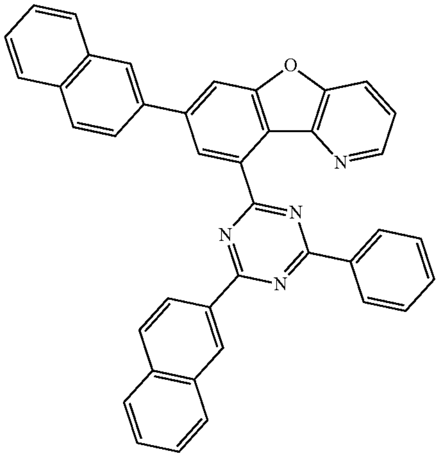
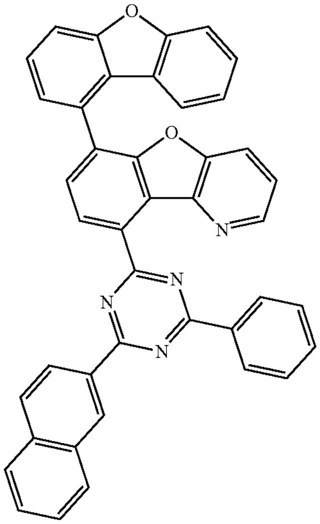
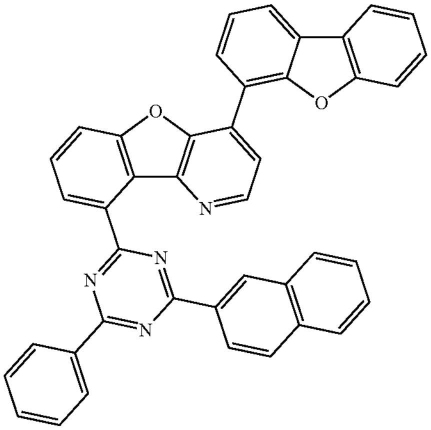

-continued
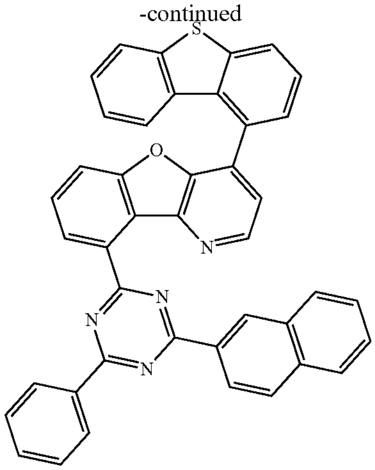
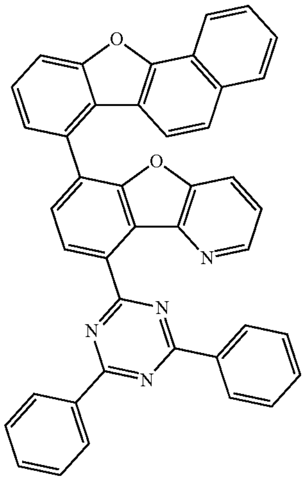
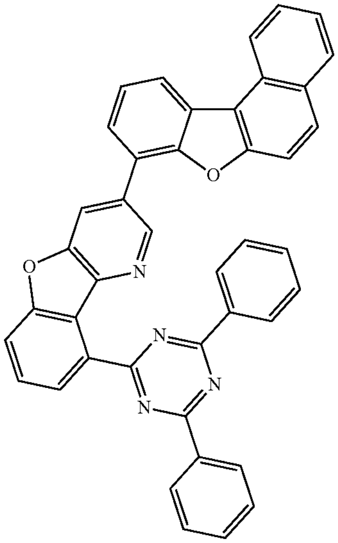
-continued
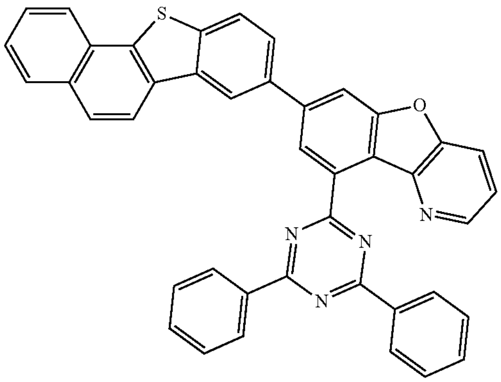
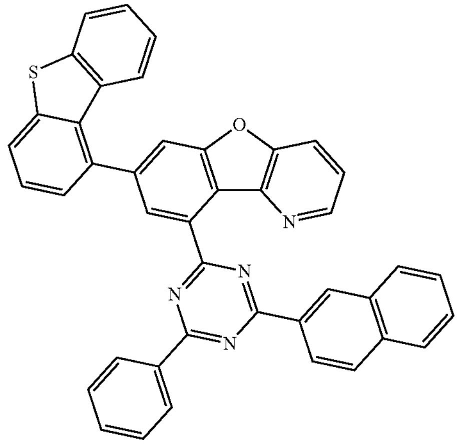
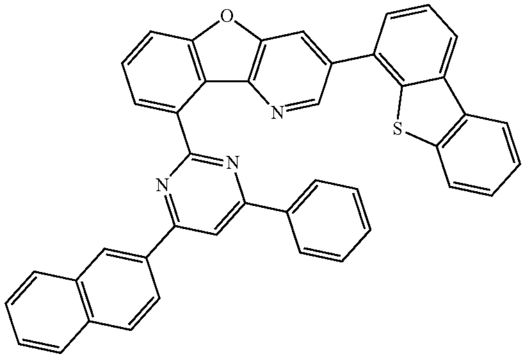
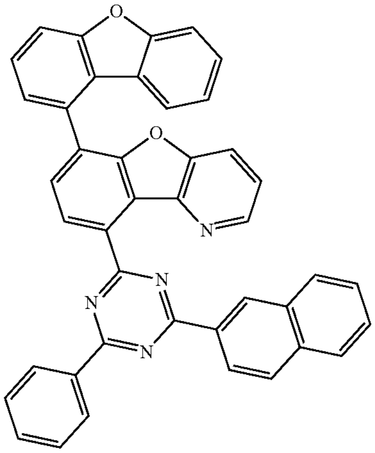

-continued
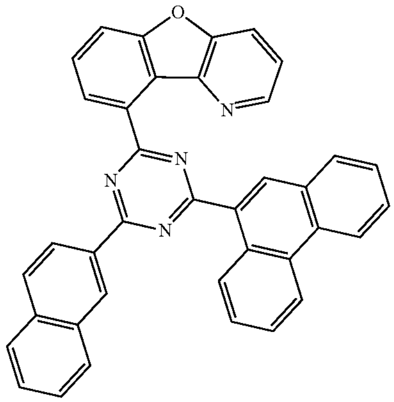
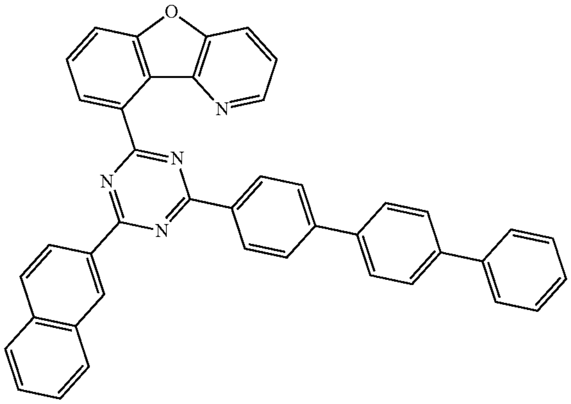
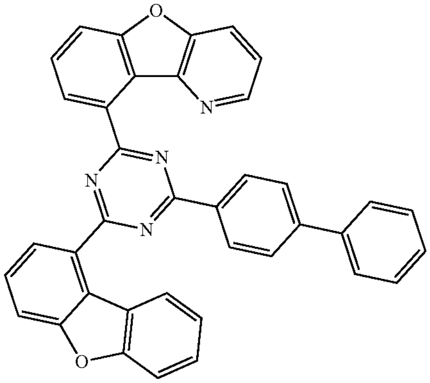
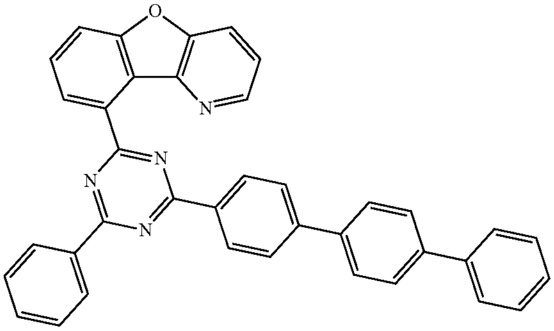
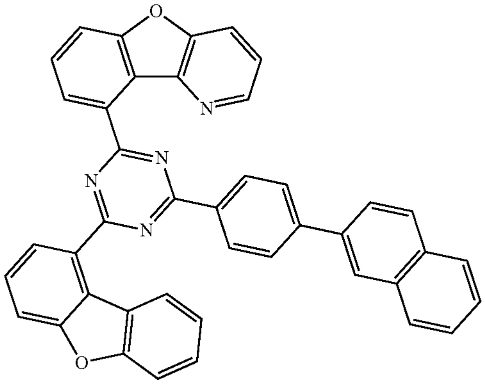
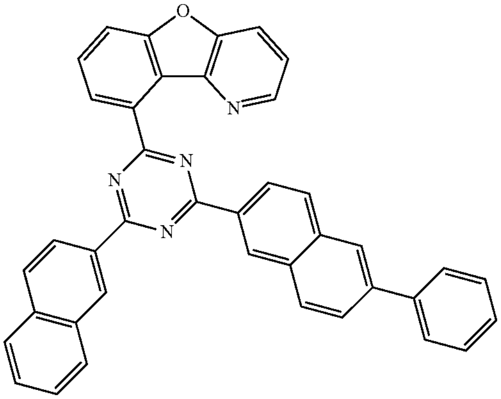
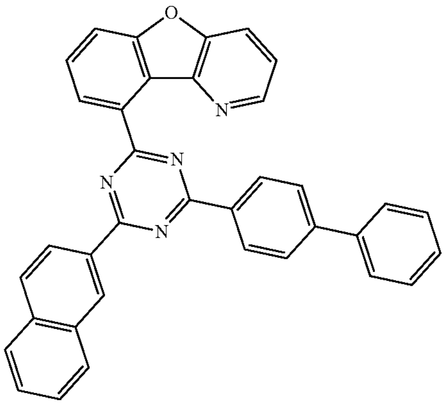
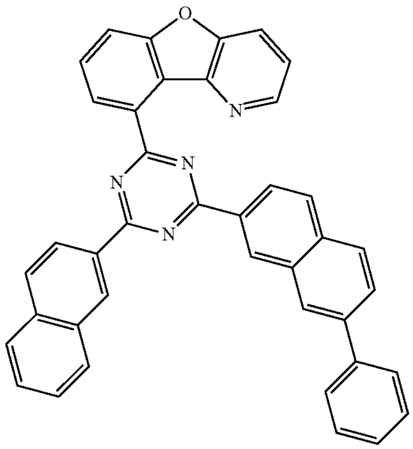

-continued
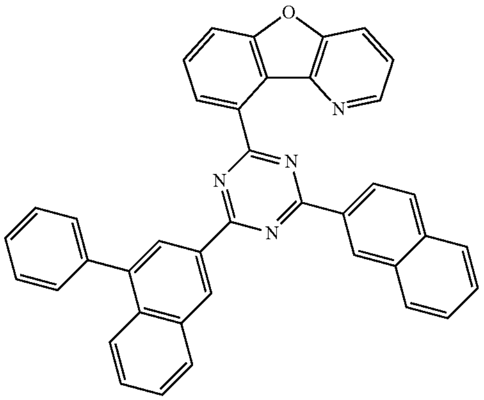
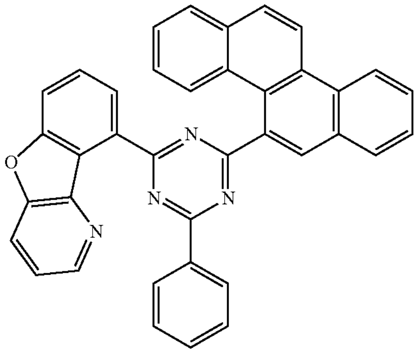
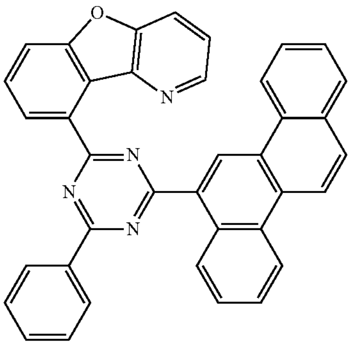
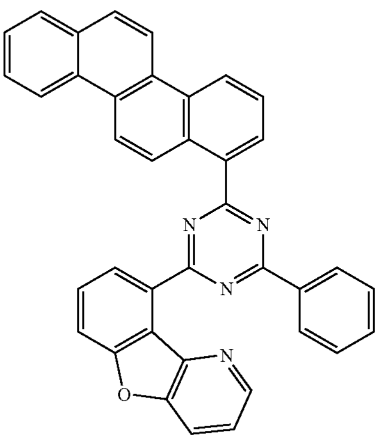
-continued
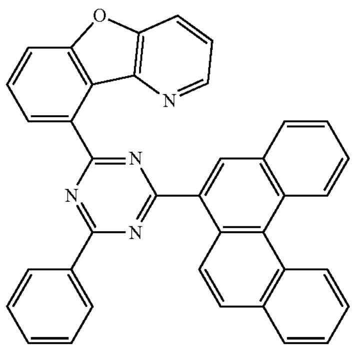
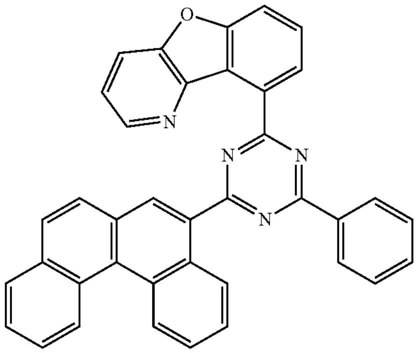
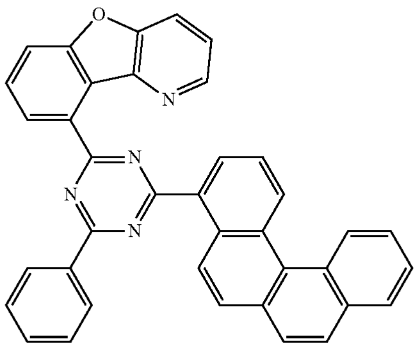
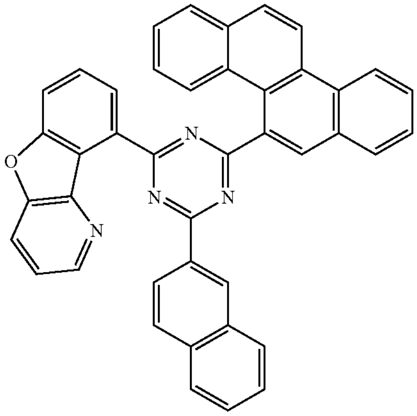

-continued
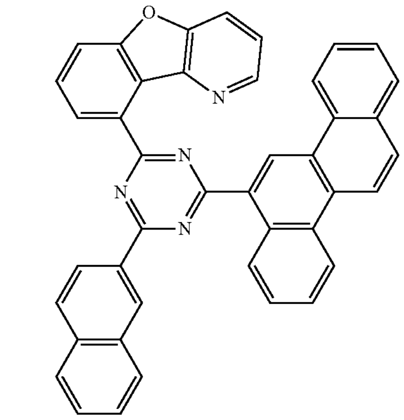
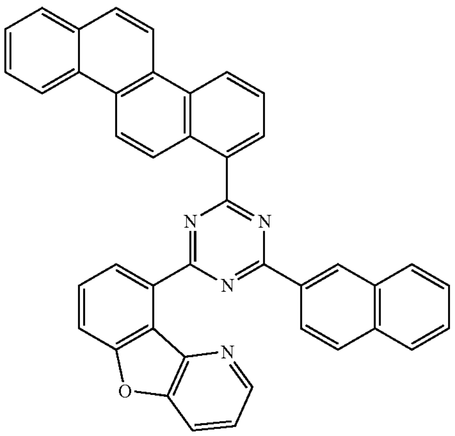
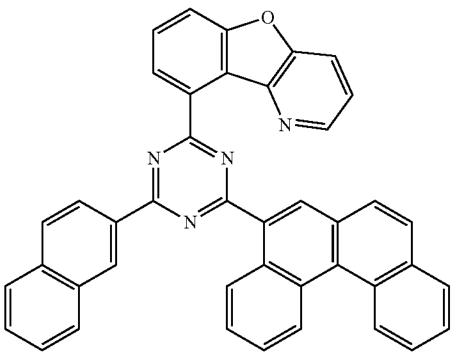
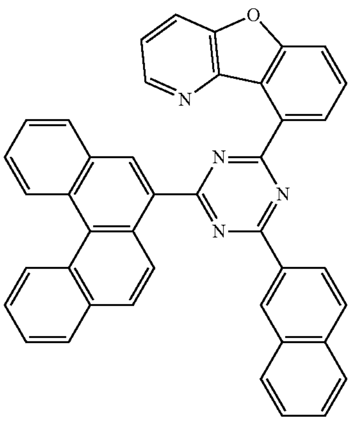
-continued
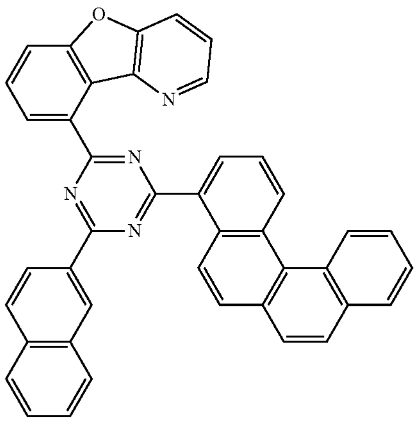
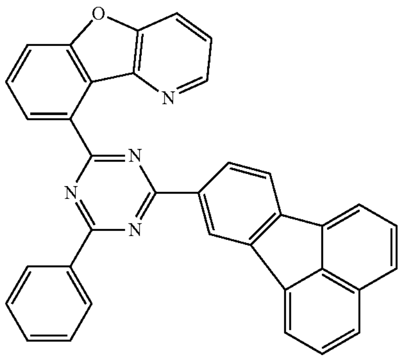
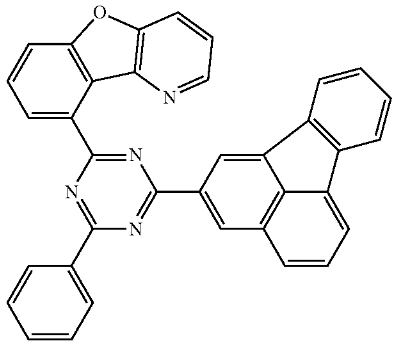
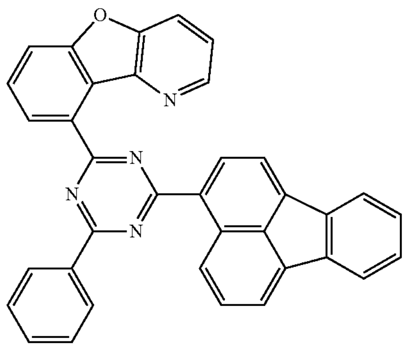

-continued
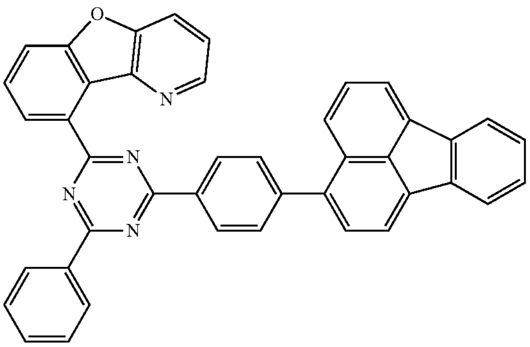
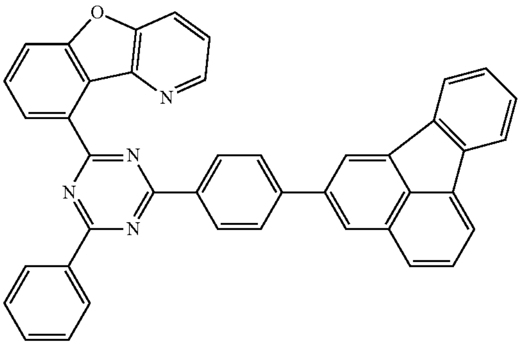
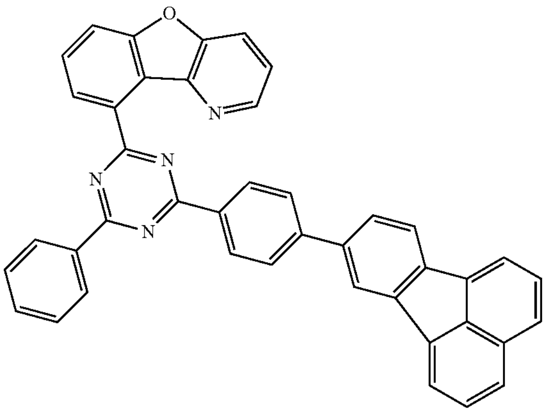
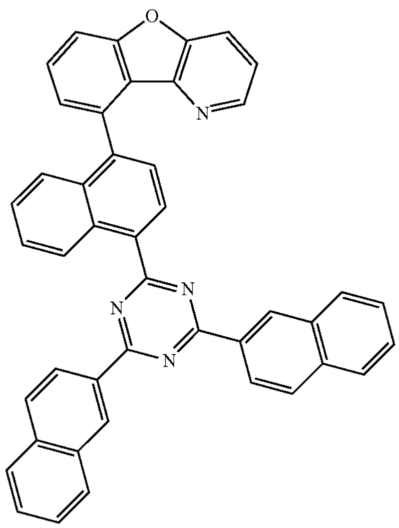
-continued
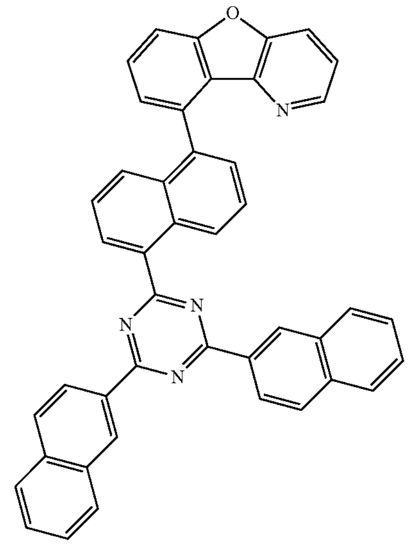
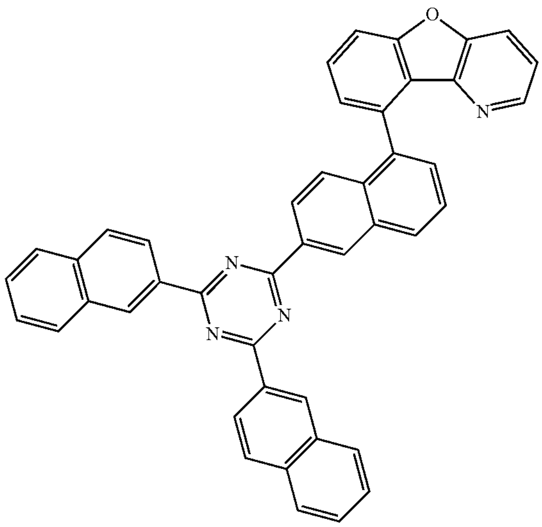
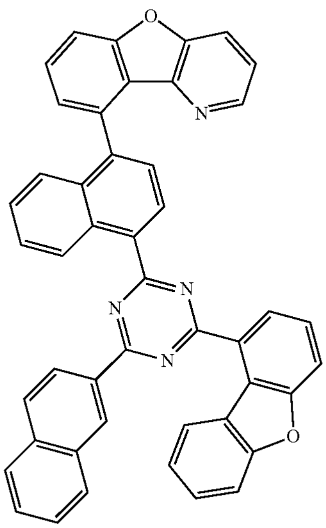

-continued
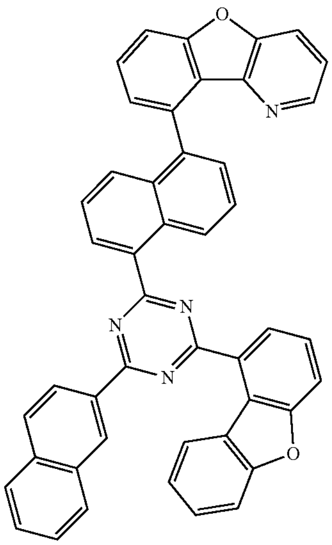
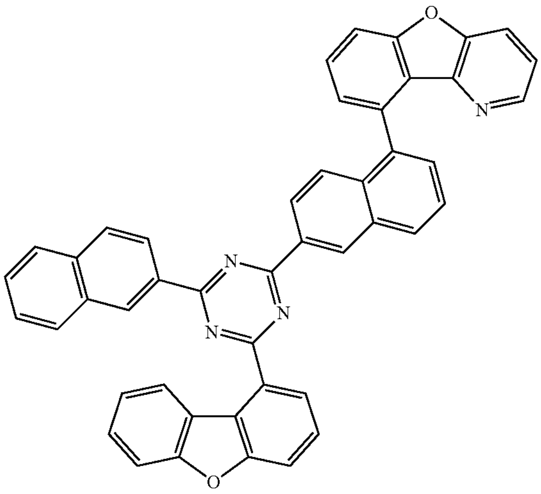
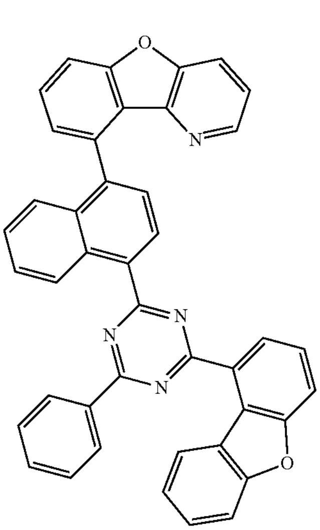
-continued
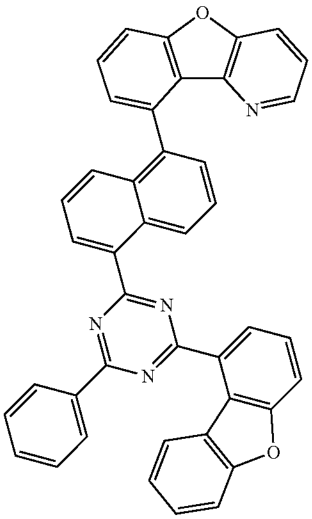
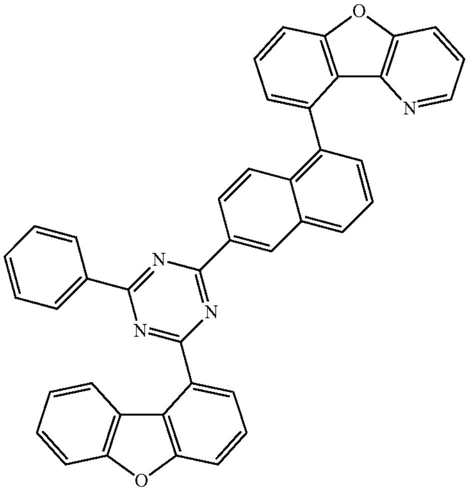
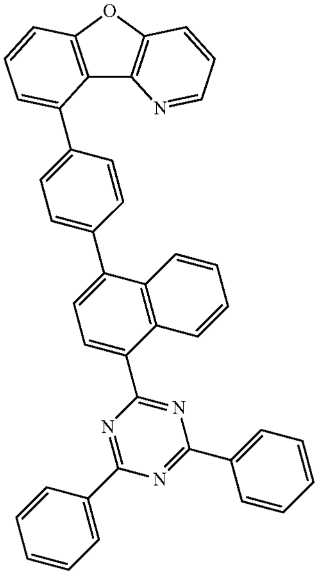

-continued
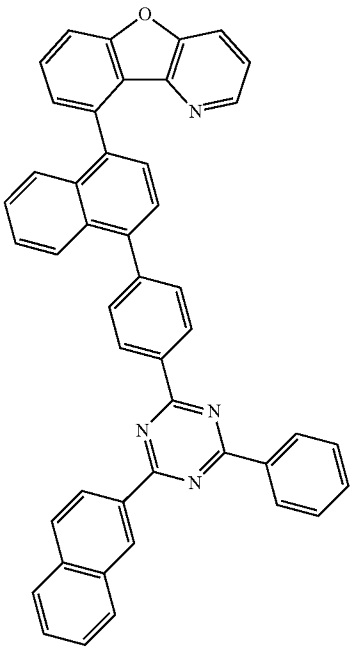
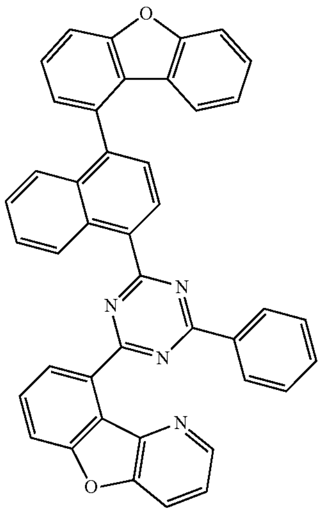
-continued
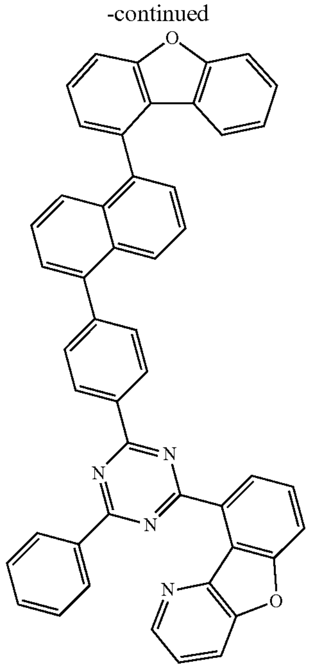
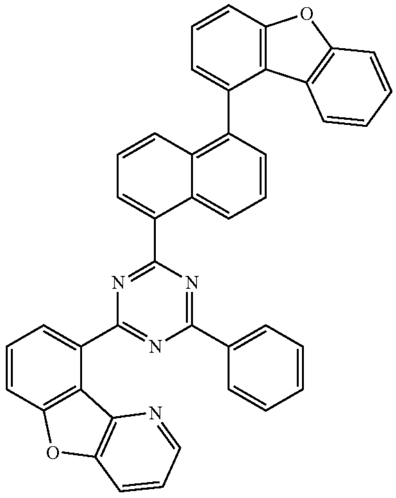
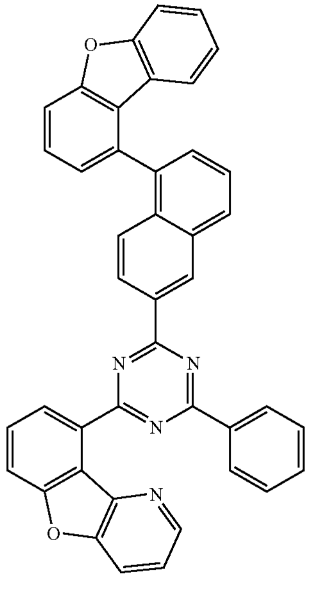

-continued
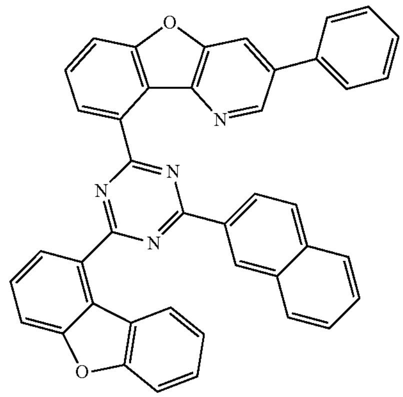
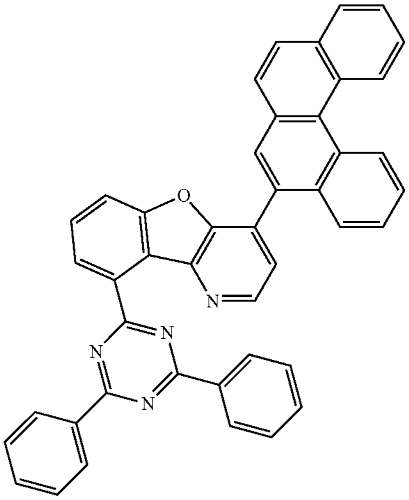
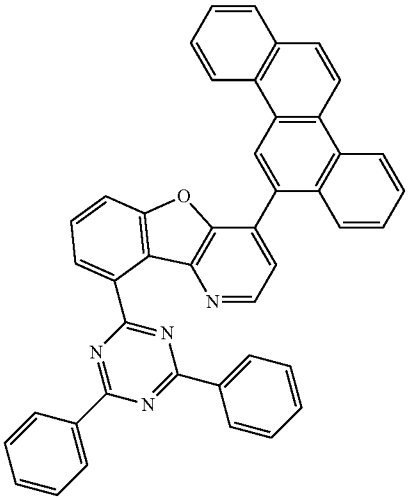
-continued
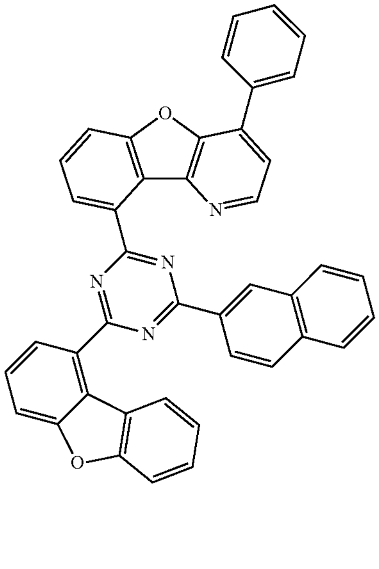
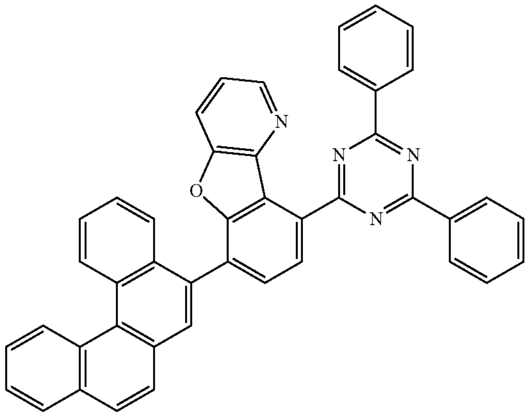
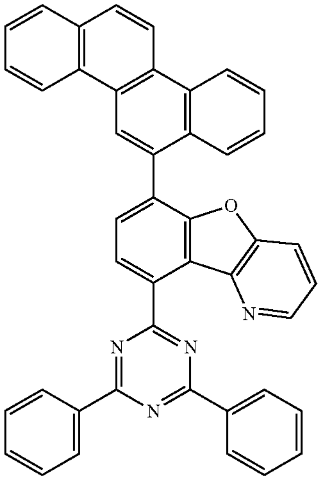

-continued
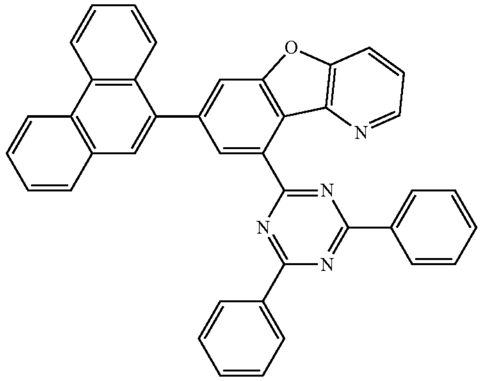
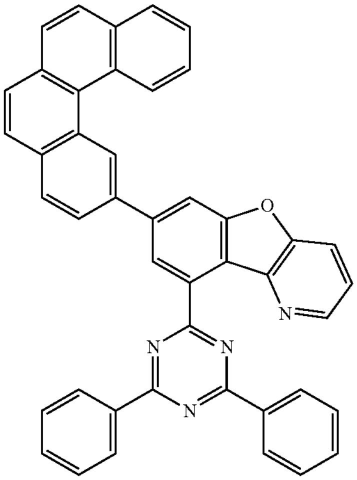
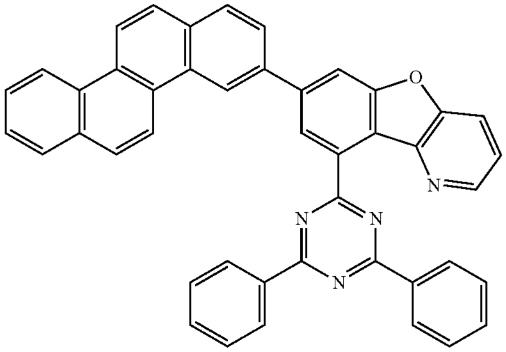
-continued
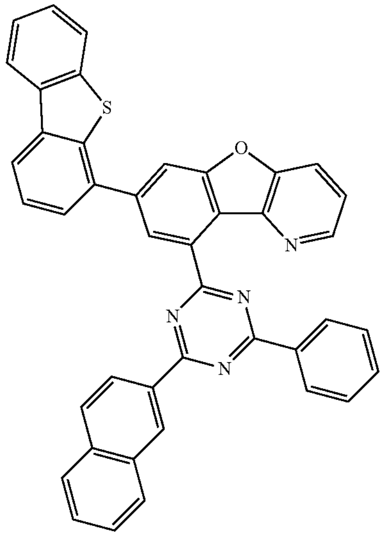
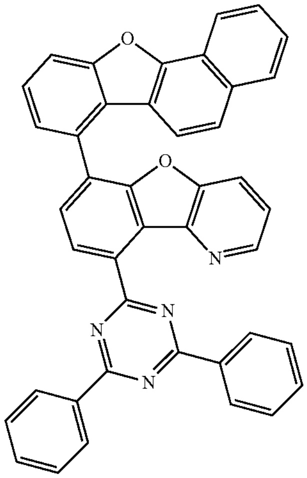
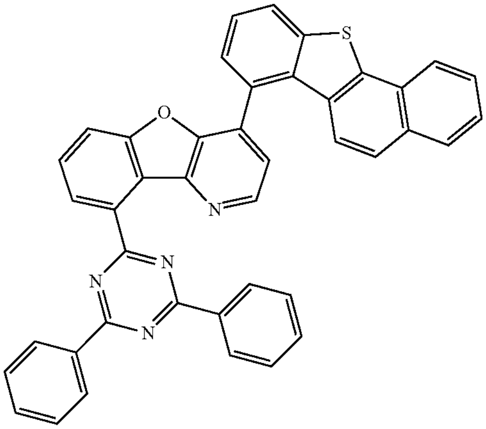

-continued
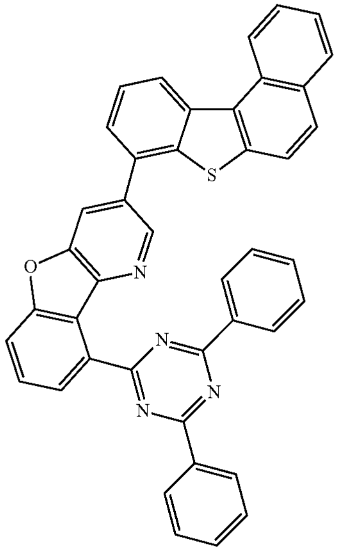
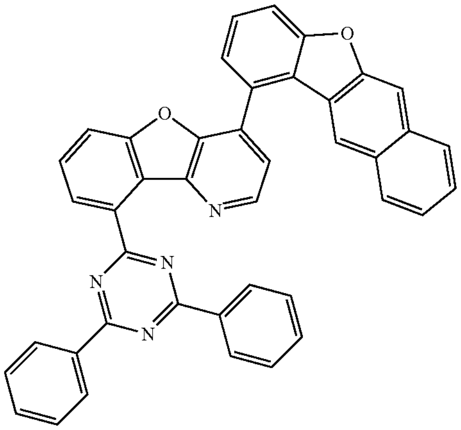
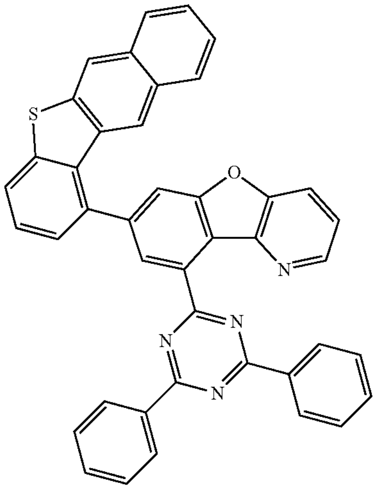
-continued
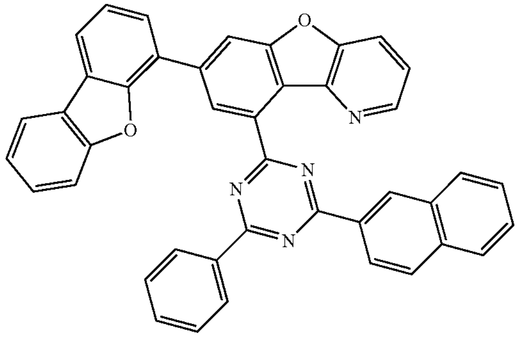
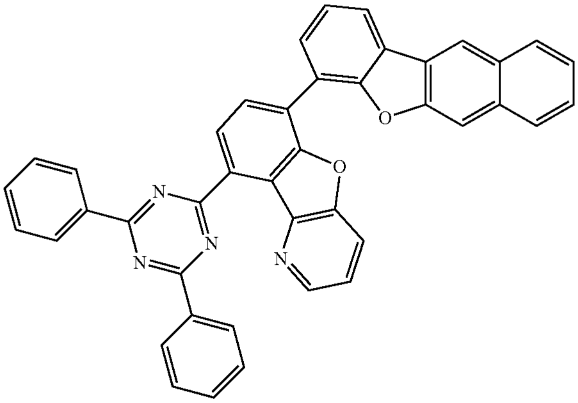
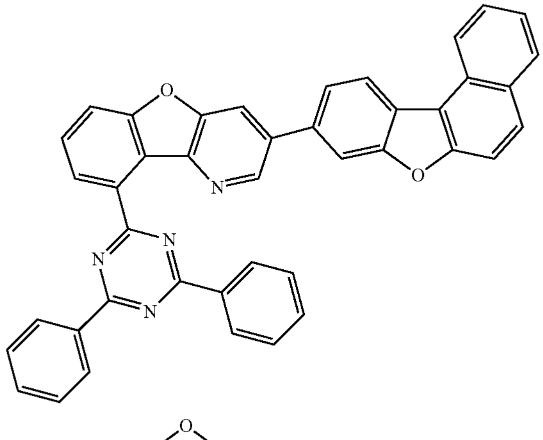
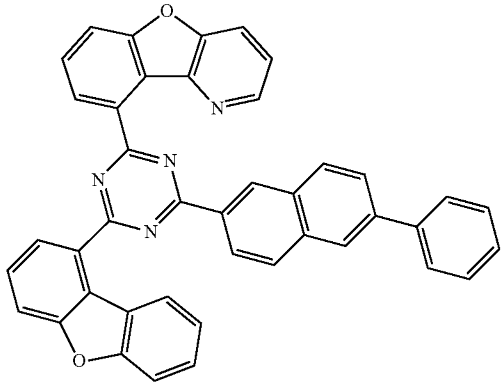

-continued
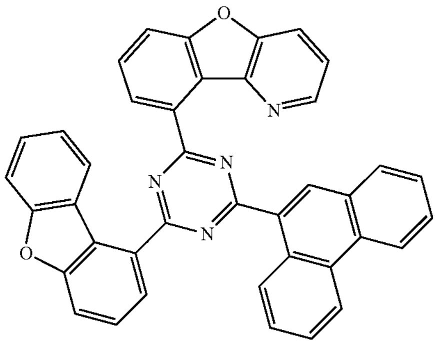
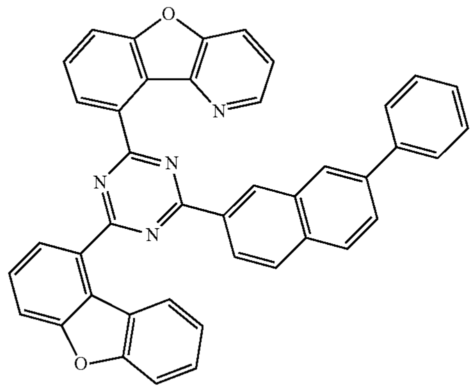
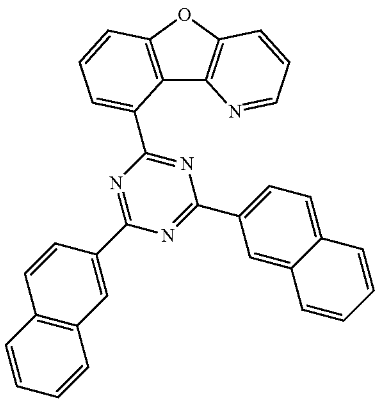
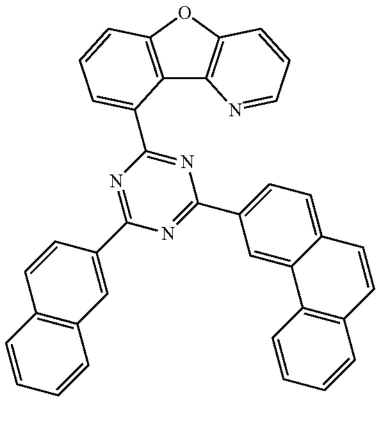
-continued
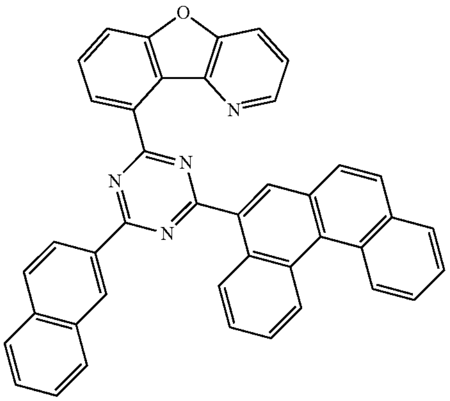
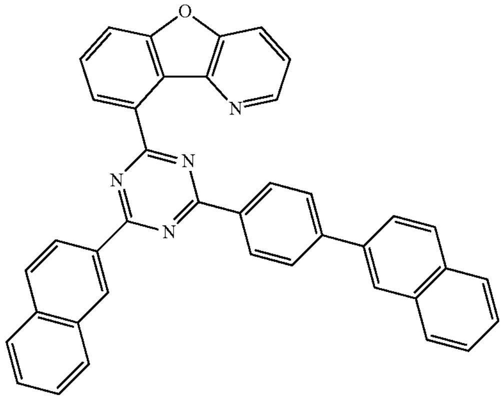
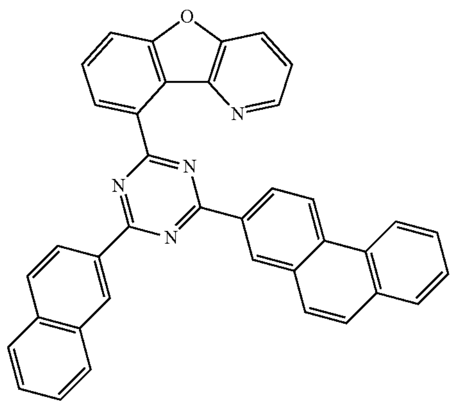
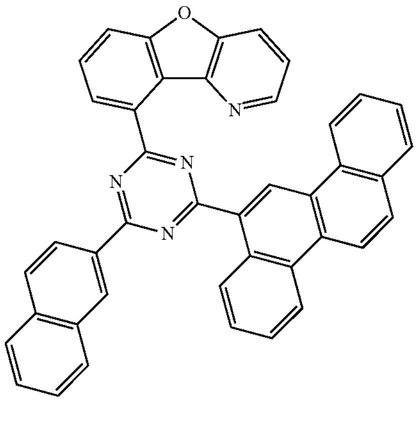

-continued
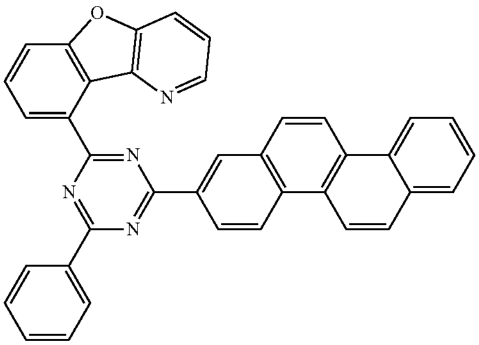
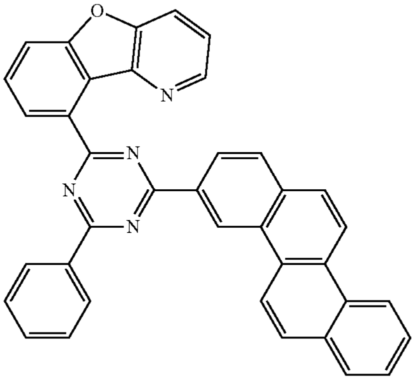
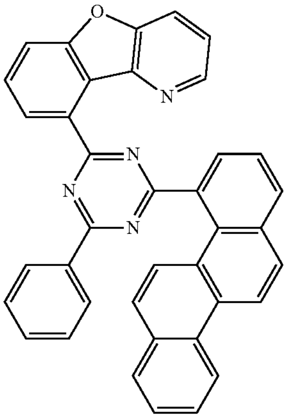
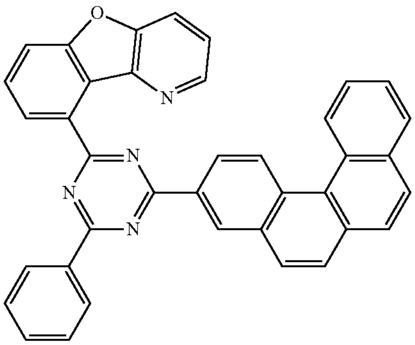
-continued
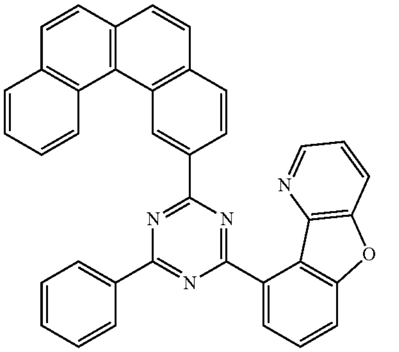
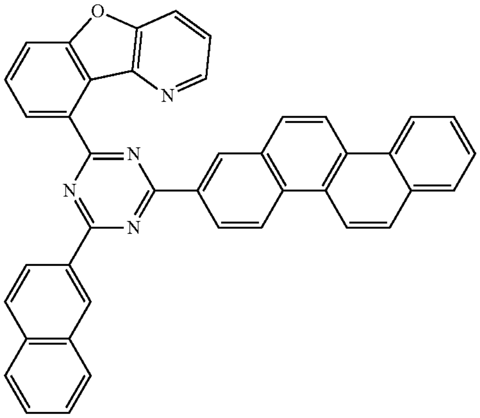
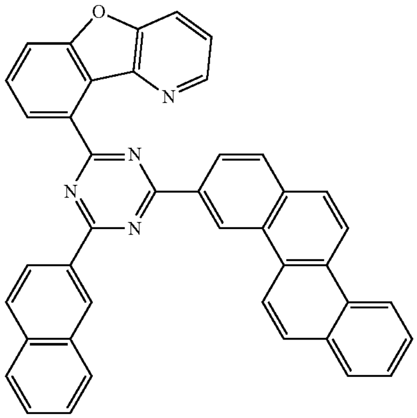
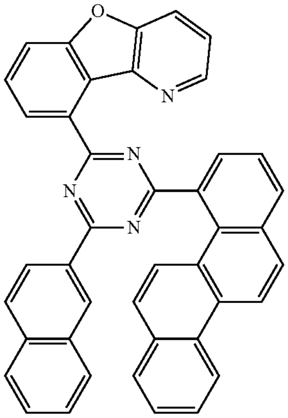

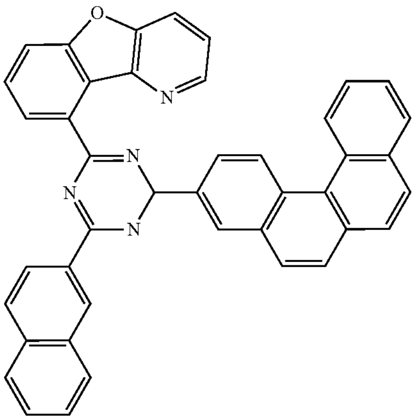
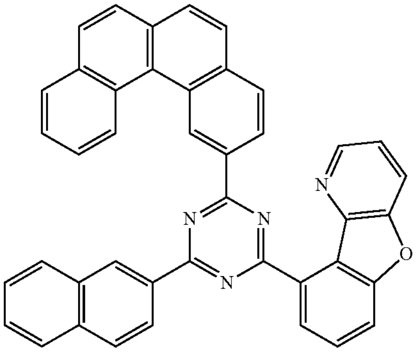
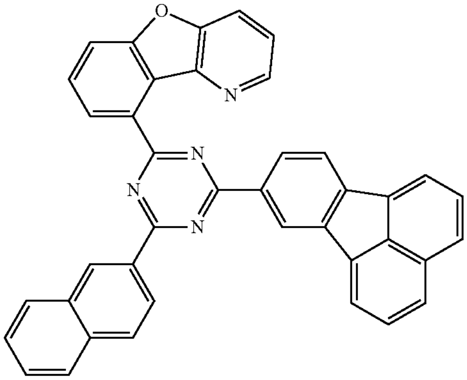
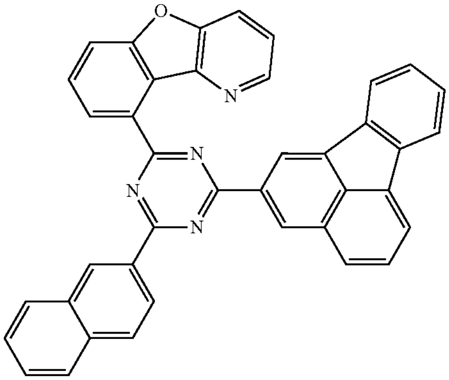
-continued
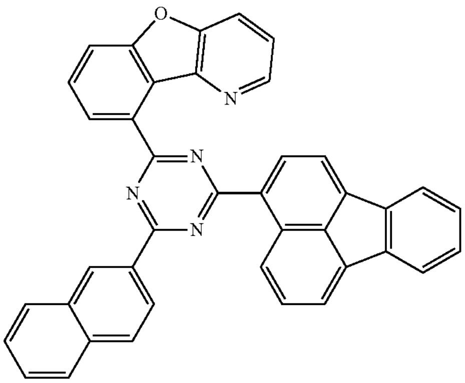
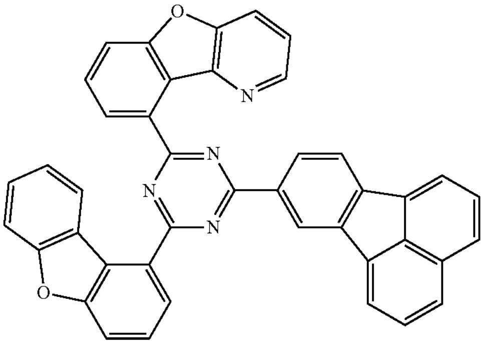
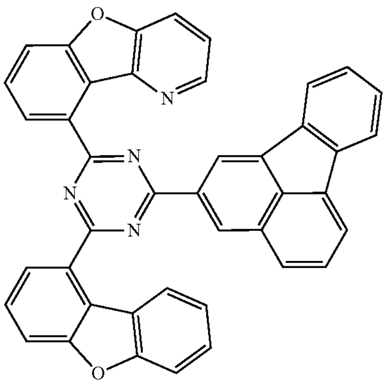
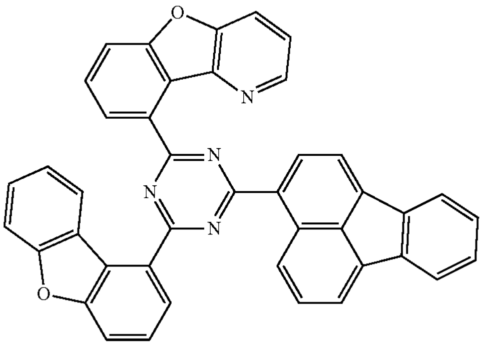

-continued
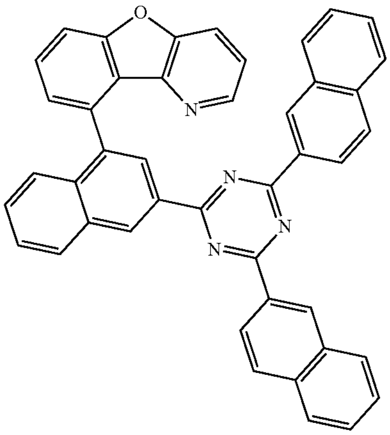
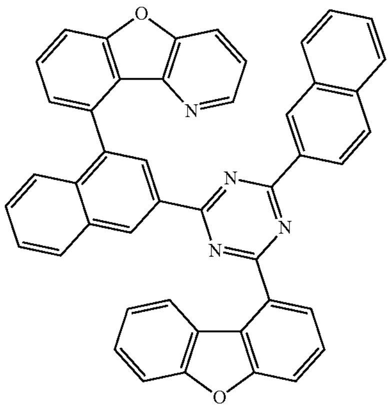
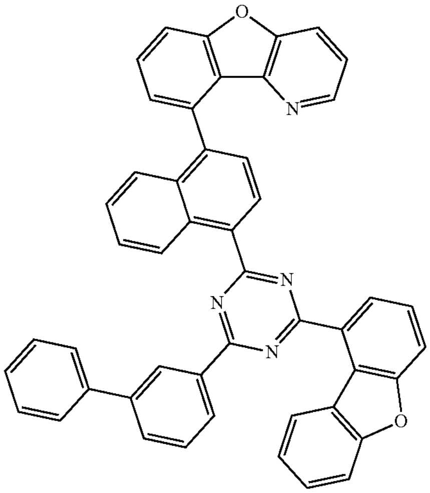
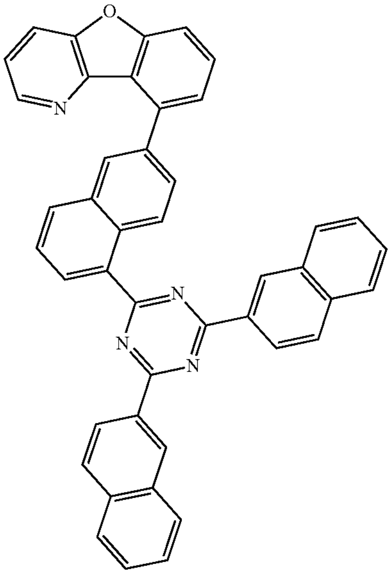
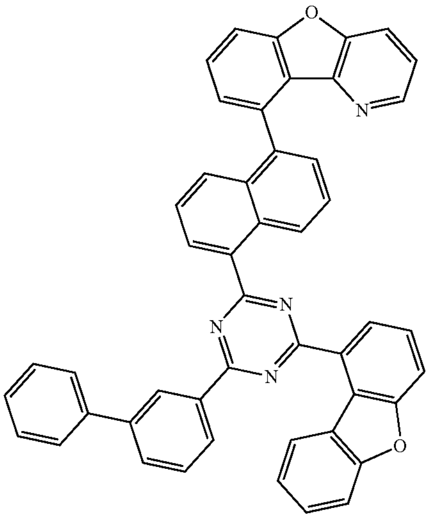
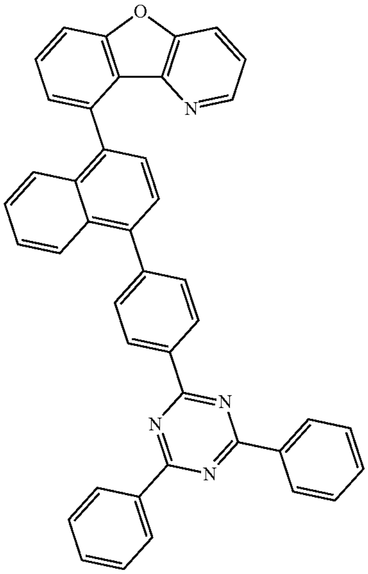
-continued -continued
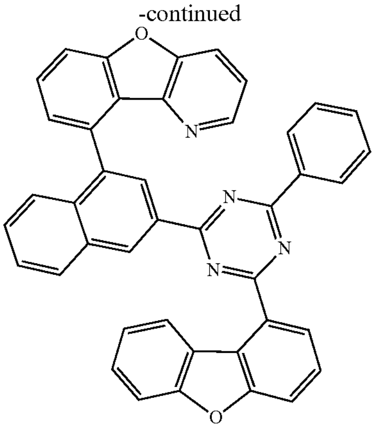
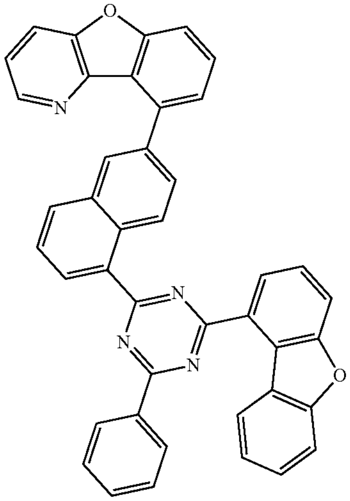
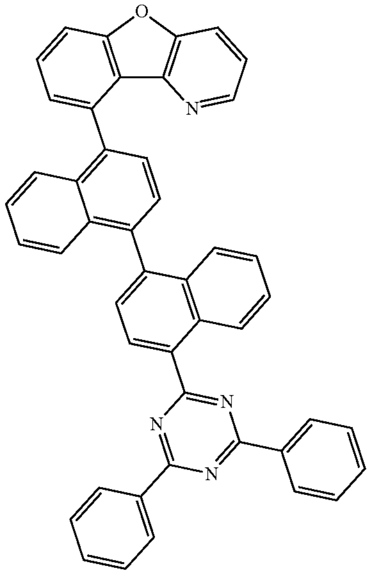
-continued
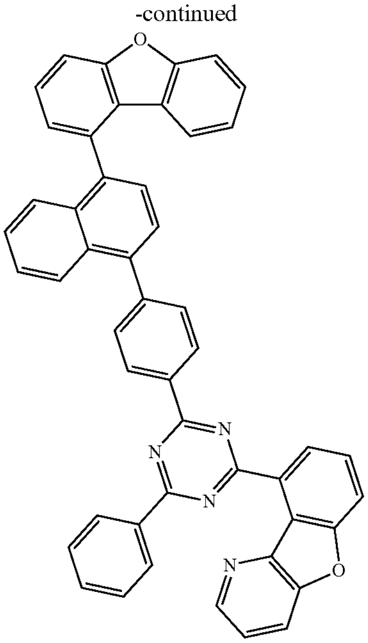
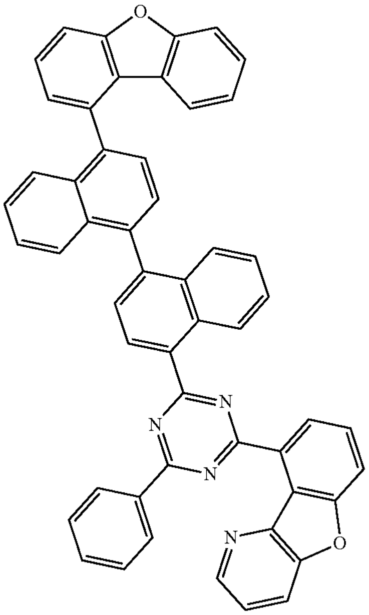

-continued

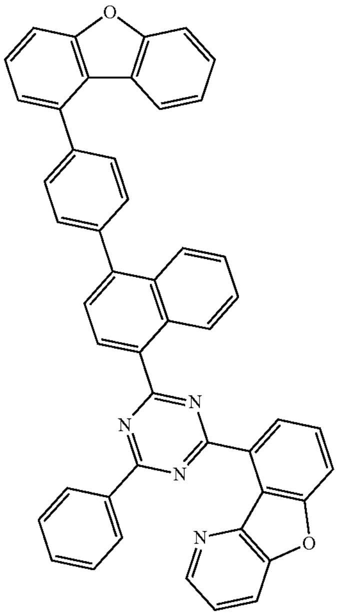

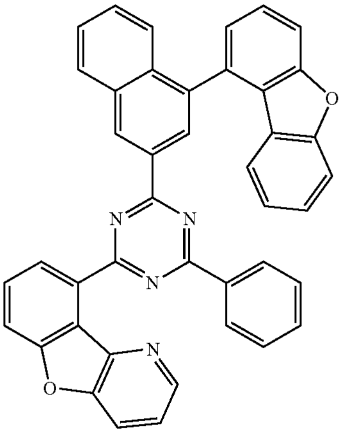

-continued

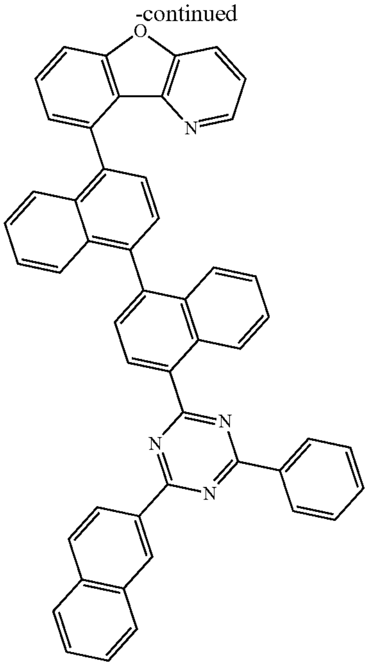

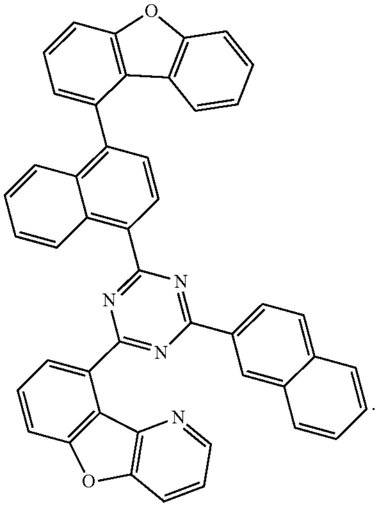

10. An organic light emitting device comprising: a first electrode; a second electrode that is provided opposite to the first electrode; and one or more organic material layers that are provided between the first electrode and the second electrode, wherein one or more layers of the organic material layers comprise the compound of claim 1.

11. The organic light emitting device of claim 10, wherein one of the organic material layers comprising the compound is a light emitting layer.

* * * * *